United States Patent
Wang

(10) Patent No.: US 10,239,832 B2
(45) Date of Patent: Mar. 26, 2019

(54) N-(1-HYDROXY-3-(PYRROLIDINYL)PROPAN-2-YL)PYRROLIDINE-3-CARBOXAMIDE DERIVATIVES AS GLUCOSYLCERAMIDE SYNTHASE INHIBITORS

(71) Applicant: BIOMARIN PHARMACEUTICAL INC., Novato, CA (US)

(72) Inventor: Bing Wang, San Jose, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 27 days.

(21) Appl. No.: 15/032,613

(22) PCT Filed: Oct. 28, 2014

(86) PCT No.: PCT/US2014/062516
§ 371 (c)(1),
(2) Date: Apr. 27, 2016

(87) PCT Pub. No.: WO2015/065937
PCT Pub. Date: May 7, 2015

(65) Prior Publication Data
US 2016/0280643 A1    Sep. 29, 2016

Related U.S. Application Data

(60) Provisional application No. 61/897,110, filed on Oct. 29, 2013.

(51) Int. Cl.
| | | |
|---|---|---|
| C07D 207/16 | (2006.01) | |
| C07D 319/16 | (2006.01) | |
| C07D 401/14 | (2006.01) | |
| C07D 405/14 | (2006.01) | |
| C07D 409/14 | (2006.01) | |
| C07D 417/14 | (2006.01) | |
| C07D 471/04 | (2006.01) | |
| C07D 401/04 | (2006.01) | |
| C07D 401/12 | (2006.01) | |
| C07D 403/12 | (2006.01) | |
| C07D 405/12 | (2006.01) | |
| C07D 409/04 | (2006.01) | |
| C07D 409/12 | (2006.01) | |

(52) U.S. Cl.
CPC ......... *C07D 207/16* (2013.01); *C07D 319/16* (2013.01); *C07D 401/04* (2013.01); *C07D 401/12* (2013.01); *C07D 401/14* (2013.01); *C07D 403/12* (2013.01); *C07D 405/12* (2013.01); *C07D 405/14* (2013.01); *C07D 409/04* (2013.01); *C07D 409/12* (2013.01); *C07D 409/14* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | |
|---|---|---|
| 6,835,831 B2 | 12/2004 | Hirth |
| 7,041,831 B2 | 5/2006 | Hirth |
| 7,763,738 B2 | 7/2010 | Hirth et al. |
| 8,389,517 B2 | 3/2013 | Ibraghimov-Beskrovnaya et al. |
| 2013/0095089 A1* | 4/2013 | Larsen ................. A61K 31/40 424/94.1 |

FOREIGN PATENT DOCUMENTS

| | | |
|---|---|---|
| EP | 1106609 A2 | 6/2001 |
| JP | 2011-529500 A | 12/2011 |
| WO | 96/39137 A1 | 12/1996 |
| WO | 02/080920 A1 | 10/2002 |
| WO | 03/008399 A1 | 1/2003 |
| WO | 03/045928 A1 | 6/2003 |
| WO | 2004/080960 A2 | 9/2004 |
| WO | 2006/053043 A2 | 5/2006 |
| WO | 2007/134086 A2 | 11/2007 |
| WO | 2008/150486 A2 | 12/2008 |
| WO | 2009/045503 A1 | 4/2009 |
| WO | 2009/117150 A2 | 9/2009 |
| WO | 2010/014554 A1 | 2/2010 |

OTHER PUBLICATIONS

Larsen et al., "Property-based design of a glucosylceramide synthase inhibitor that reduces glucosylceramide in the brain," Journal of Lipid Research, vol. 53, 282-290, 2012.

* cited by examiner

*Primary Examiner* — Sreenivasan Padmanabhan
*Assistant Examiner* — Jody L Karol
(74) *Attorney, Agent, or Firm* — Jones Day

(57) ABSTRACT

Described herein are compounds of Formula I, methods of making such compounds, pharmaceutical compositions and medicaments containing such compounds, and compounds I for use to treat or prevent diseases or conditions associated with the enzyme glucosylceramide synthase (GCS).

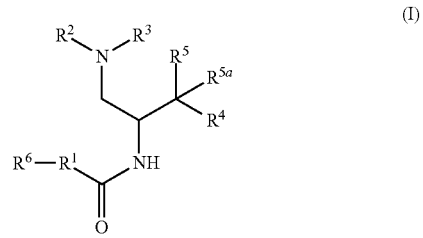

(I)

17 Claims, No Drawings

N-(1-HYDROXY-3-(PYRROLIDINYL)PROPAN-2-YL)PYRROLIDINE-3-CARBOXAMIDE DERIVATIVES AS GLUCOSYLCERAMIDE SYNTHASE INHIBITORS

CROSS REFERENCE TO RELATED APPLICATIONS

The present application is a U.S. National Stage filing under 35 U.S.C. § 371 of International Application No. PCT/US2014/062516, filed Oct. 28, 2014, which claims the benefit of priority of U.S. Provisional Application No. 61/897,110, filed Oct. 29, 2013, the contents of each of which applications are incorporated herein by reference in their entireties.

FIELD

Described herein are compounds, methods of making such compounds, pharmaceutical compositions and medicaments containing such compounds, and methods of using such compounds to treat or prevent diseases or conditions associated with the enzyme glucosylceramide synthase (GCS).

BACKGROUND

Glucosylceramide synthase (GCS) is a key enzyme which catalyzes the initial glycosylation step in the biosynthesis of glucosylceramide-based glycosphingolipids (GSLs) namely via the transfer of glucose from UDP-glucose (UDP-Glc) to ceramide to form glucosylceramide. GCS is a transmembrane, type III integral protein localized in the cis/medial golgi. Glycosphingolipids (GSLs) are believed to be integral in many cell membrane events, including cellular interactions, signaling, and trafficking. Synthesis of GSL structures has been shown (*Proc. Natl. Acad. Sci CJSA* 1999, 96(16), 9142-9147) to be essential for embryonic development and for the differentiation of some tissues. Ceramide plays a central role in sphingolipid metabolism, and downregulation of GCS activity has been shown to have marked effects on the sphingolipid pattern with diminished expression of glycosphingolipids. Sphingolipids have a role in physiological as well as pathological cardiovascular conditions. In particular, sphingolipids and their regulating enzymes appear to play a role in adaptive responses to chronic hypoxia in the neonatal rat heart (*Prostaglandins & Other Lipid Mediators* 2005, 78(1-4), 249-263).

GCS inhibitors have been proposed for the treatment of a variety of diseases (see, for example, WO2005068426). Such diseases include glycolipid storage diseases (e.g., Tay Sachs, Sandhoffs, GM1 gangliosidosis, Niemanns-Pick, and Fabry diseases), diseases associated with glycolipid accumulation (e.g., Gaucher disease), diseases that cause renal hypertrophy or hyperplasia such as diabetic nephropathy, diseases that cause hyperglycemia or hyperinsulinemia, cancers in which glycolipid synthesis is abnormal, infectious diseases caused by organisms which use cell surface glycolipids as receptors, infectious diseases in which synthesis of glucosylceramide is essential or important, diseases in which excessive glycolipid synthesis occurs (e.g., atherosclerosis, polycystic kidney disease, and renal hypertrophy), neuronal disorders, neuronal injury, inflammatory diseases or disorders associated with macrophage recruitment and activation (e.g., rheumatoid arthritis, Crohn's disease, asthma and sepsis), pain (see WO2008011483—neuropathic pain, inflammatory pain, headache pain, somatic pain, visceral pain, referred pain), cognitive disorders (see WO2008/109286—agnosia; amnesia; aphasia; an apraxia; delirium; dementia including AIDS dementia complex, Binswanger's disease, dementia with Lewy Bodies, frontotemporal dementia, mild cognitive impairment, multi-infarct dementia, Pick's disease, semantic dementia, senile dementia, and vascular dementia; and learning disorders including Asperger's syndrome, attention deficit disorder, attention deficit hyperactivity disorder, autism, childhood disintegrative disorder, and Rett syndrome), neurodegenerative disorders (such as Alzheimer's disease, corticobasal degeneration, Creutzfeldt-Jacob disease, frontotemporal lobar degeneration, Huntington disease, multiple sclerosis, normal pressure hydrocephalus, organic chronic brain syndrome, Parkinson's disease, Pick disease, progressive supranuclear palsy, and senile dementia (Alzheimer type), glomerular disease, and diabetes mellitus and obesity (see WO 2006053043). Renal hypertrophy induced by diabetes is associated with enhanced synthesis of glycosphingolipids such as glucosylceramide and ganglioside GM$_3$ which accumulate in the kidney of rats (*J. Clin. Invest.* 1993, 91(3), 797).

It has been shown that overexpression of GCS is implicated in multi-drug resistance and disrupts ceramide-induced apoptosis. For example, Turzanski et al. (*Experimental Hematology* 2005, 33(1), 62-72) have shown that ceramide induces apoptosis in acute myeloid leukemia (AML) cells and that P-glycoprotein (p-gp) confers resistance to ceramide-induced apoptosis, with modulation of the ceramide-glucosylceramide pathway making a marked contribution to this resistance in TF-I cells. Thus, GCS inhibitors can be useful for treatment of proliferative disorders (such as cancer) by inducing apoptosis in diseased cells.

Sandhoff (or type 2 GM2 gangliosidosis) is caused by a deficiency in β-hexosaminidase A and B activity which leads to an accumulation of the ganglioside GM$_2$ and other glycolipids causing damage to the central nervous system and eventually is lethal (*PLoS One* 2011, 6(6), e21758). Tay-Sachs disease (or GM$_2$ gangliosidosis) is caused by a deficiency in β-hexosaminidase A which lead to an accumulation of gangliosides in the brain's nerve cells eventually leading to their premature death. Intravenous injection of the missing enzyme(s) is not a viable option as of the enzymes does cross the blood-brain barrier (*Genetics in Medicine* 2009, 1(6), 425). Glucosylceramide synthase is a key enzyme in the synthesis of glucosylceramide and other glycosphingolipids. Its inhibition can decrease the amount of the glycosphingolipids which accumulate in Sandhoff disease.

Fabry disease is caused by loss of activity of the lysosomal hydrolase α-galactosidase which leads to an accumulation of glycosphingolipids (particularly globotriaosylceramide) causing pain, renal disease and failure, cerebral vascular disease, and myocardial infarction (*Kidney International* 2000, 57, 446). One treatment strategy is to provide the defective enzyme to the patient; however, enzyme replacement therapy can only slow the progression of the disease and is not a cure. An alternative or complementary strategy is one where glucosylceramide synthase, a key enzyme in the synthesis of glycosphingolipids, is inhibited with a small molecule thus decreasing the amount of globotriaosylceramide and other glucosylceramide-based lipids that need to be broken down by hydrolase α-galactosidase.

Gaucher disease is caused by a defect in the enzyme lysosomal glucocerebrosidase which is responsible for catalyzing the breakdown of glucosylceramide which then accumulates in tissues of affected people (*J. Org. Chem.* 2007, 72(4), 1088) causing liver malfunction, skeletal disorders, painful bone lesions, hypersplenism, pancytopenia, and neurological symptoms (convulsions, hypertonia, mental retardation, apnea, dementia, and ocular muscle apraxia). One treatment strategy is to provide the defective enzyme to the patient; however, enzyme replacement therapy is not suitable for all patients and does not address the neurological manifestations of the disease for those with type 2 and type 3. An alternative or complementary strategy is one where glucosylceramide synthase is inhibited with small molecules thus decreasing the amount of glucosylceramide that needs to be broken down by glucocerebrosidase.

Nonalcoholic fatty liver disease (NALD) is a disease where fat accumulates in the liver of people who drink little or no alcohol and results in inflammation and scarring of the liver which can progress to liver failure. Inhibition of glucosylceramide synthase in ob/ob mice lowered glucose levels, lowered liver/body weight ratio, decreased the accumulation of triglycerides, and prevented and reversed steatosis (*Hepatology* 2009, 50(1), 85-93). Thus GCS inhibitors are useful for the prevention and treatment of NALD.

Polycystic kidney disease (PKD) is a genetic disease characterized by noncancerous cysts which are filled with fluid and cause the kidneys to enlarge which can result in a decrease in quality of life (e.g., headaches, high blood pressure, back and side pain, colon problems, mitral valve prolapsed, and kidney stones) and can be life-threatening (e.g. kidney failure, aneurysm in the brain, and high blood pressure which can lead to heart disease and stroke). PKD can also damage the liver, spleen, pancreas, vasculature, testes, seminal vesicles, and intestines. Glucosylceramide and ganglioside $GM_3$ levels in the kidney are higher than in normal tissue (*Nat Med* 2010, 16(7), 788). Thus, blocking the synthesis of glucosylceramide with an inhibitor of GCS can be useful in the treatment of PKD to reduce new cyst formation (partial or complete inhibition of cystogenesis), reduce cyst mass, reduce the size and number of cysts, and/or reduce the severity of the symptoms associated. All current treatments for PKD address symptoms and do not treat the underlying cause of the disease (*Nat Med* 2010, 16(7), 788).

SUMMARY OF THE INVENTION

In one aspect, provided is a compound of Formula I:

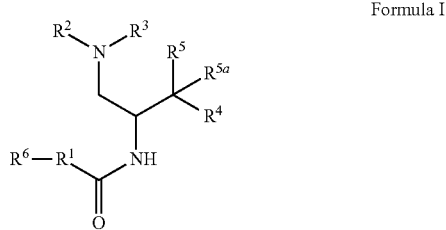

Formula I where
$R^1$ is cycloalkyl or heterocycloalkyl; wherein the heterocycloalkyl is attached to the C(O) group by a carbon atom and is optionally substituted with hydroxy;
$R^2$ is hydrogen, hydroxy, or alkyl; and $R^3$ is alkyl, aminoalkyl, alkylaminoalkyl, or dialkylaminoalkyl; or $R^2$ and $R^3$ together with the nitrogen to which they are attached form a 3-10 membered heterocycloalkyl ring which is optionally substituted with 1, 2, 3, or 4 $R^8$; and wherein the —$NR^2R^3$ heterocycloalkyl is not morpholinyl;
$R^4$ is aryl or heteroaryl each of which is optionally substituted with 1, 2, or 3 $R^9$ groups;
$R^5$ is halo, hydroxy, —$N_3$, —$NH_2$, —$NHC(O)CH_3$, —$NH(OCH_3)$, or —$NHC(O)H$ and $R^{5a}$ is hydrogen, halo, alkyl, or deuterium; or $R^5$ and $R^{5a}$ together with the carbon to which they are attached form C(O) or C(NOH);
$R^6$ is alkyl, alkoxycarbonyl, aryl, arylalkyl, arylcarbonyl, cycloalkyl, cycloalkylalkyl, heterocylcoalkyl, heterocycloalkylalkyl, heteroaryl, heteroarylalkyl, or —$C(O)NR^{6a}R^{6b}$; wherein each aryl and heteroaryl, whether alone or as part of another group, is optionally substituted with 1 or 2 $R^{10}$ groups; and wherein each heterocycloalkyl and cycloalkyl, whether alone or as part of another group, is optionally substituted with 1 or 2 groups independently selected from hydroxy, halo, haloalkyl, alkoxy, alkyl, alkylcarbonyl, and alkoxycarbonyl;
$R^{6a}$ is hydrogen or alkyl and $R^{6b}$ is aryl or heteroaryl each of which is optionally substituted with 1 or 2 halo; or $R^{6a}$ and $R^{6b}$ together with the nitrogen to which they are attached form a heterocycloalkyl optionally substituted with alkyl, hydroxy, alkylcarbonyl, or alkoxycarbonyl;
each $R^8$, when present, is independently deuterium, amino, alkylamino, dialkylamino, alkyl, hydroxy, alkoxy, halo, haloalkyl, or cycloalkyl;
each $R^9$, when present, is independently cyano, nitro, amino, alkylamino, dialkylamino, halo, haloalkyl, alkyl, —$NR^{11}C(O)NR^{11a}R^{11b}$, hydroxy, alkoxy, haloalkoxy, hydroxyalkoxy, alkenyloxy, cycloalkyloxy, cycloalkylalkyloxy, cycloalkylthio, heterocycloalkyl, heterocycloalkyloxy, heterocycloalkylalkyloxy, or phenyl; where the phenyl is optionally substituted with 1 or 2 $R^{9a}$; where each heterocycloalkyl, either alone or as part of another group, is optionally substituted with 1 or 2 groups independently selected from alkyl, hydroxy, alkylcarbonyl, and alkoxycarbonyl;
each $R^{9a}$, when present, is independently selected from alkyl, hydroxy, alkoxy, halo, haloalkyl, haloalkoxy, alkoxycarbonyl, amino, alkylamino, and dialkylamino;
each $R^{10}$, when present, is independently cyano, nitro, amino, alkylamino, dialkylamino, halo, haloalkyl, alkyl, alkenyl, alkynyl, —$NR^{11}C(O)NR^{11a}R^{11b}$, alkoxycarbonyl, aminocarbonyl, alkylaminocarbonyl, dialkylaminocarbonyl, cycloalkyl, hydroxy, alkoxy, haloalkoxy, hydroxyalkoxy, alkenyloxy, cycloalkyloxy, cycloalkylalkyloxy, cycloalkylthio, aryl, arylalkyl, aryloxy, heteroaryl, heteroarylalkyl, heteroaryloxy, heterocycloalkyl, heterocycloalkyloxy, or heterocycloalkylalkyloxy; where each aryl or heteroaryl either alone or as part of another group, are independently optionally substituted with 1, 2 or 3 $R^{10a}$; and each heterocycloalkyl, either alone or as part of another group, is optionally substituted with 1 or 2 groups independently selected from alkyl, hydroxy, alkylcarbonyl, and alkoxycarbonyl groups;
each $R^{10a}$, when present, is independently selected from cyano, halo, alkyl, alkenyl, haloalkyl, hydroxyalkyl, and cycloalkyl; and
$R^{11}$, $R^{11a}$, and $R^{11b}$ are independently hydrogen, alkyl, or cycloalkyl;
provided that when $R^1$ is cycloalkyl and $R^6$ is phenyl then the phenyl is substituted with 1 or 2 groups independently selected from cyano, nitro, amino, alkylamino, dialkylamino, haloalkyl, alkyl, —$NR^{11}C(O)NR^{11a}R^{11b}$, haloalkoxy, cycloalkyloxy, cycloalkylalkyloxy, heterocycloalkyl which is optionally substituted with 1 or 2 alkyl, heterocycloalkyloxy which is optionally substituted with 1 or 2 alkyl, or heterocycloalkylalkyloxy which is optionally substituted with 1 or 2 hydroxy; and optionally a tautomer, a single stereoisomer or mixture of stereoisomers thereof and additionally optionally a pharmaceutically acceptable salt thereof.

In a further aspect, provided is a pharmaceutical composition comprising 1) a Compound of Formula I optionally as a tautomer, a single stereoisomer or mixture of stereoisomers thereof and additionally optionally as a pharmaceutically acceptable salt thereof, and 2) a pharmaceutically acceptable excipient or pharmaceutically acceptable carrier.

In a further aspect, provided is a method of treating a disease or disorder comprising administering a Compound of Formula I, optionally as a tautomer, a single stereoisomer or mixture of stereoisomers thereof and additionally optionally as a pharmaceutically acceptable salt thereof, or the pharmaceutical composition thereof additionally comprising a pharmaceutically acceptable excipient or pharmaceutically acceptable carrier.

In a further aspect, it is provided a method of making a compound of Formula I, comprising:

a) treating an intermediate of formula 100

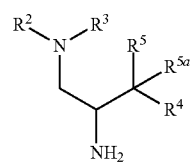

or a salt thereof, where $R^2$, $R^3$, $R^4$, $R^5$, and $R^{5a}$ and all other groups are as defined in the Summary of the Invention or as in any of the embodiments described herein; with an intermediate of formula $R^6$—$R^1C(O)$OH using standard amide coupling conditions to yield a Compound of Formula I where $R^1$ and $R^6$ are as defined in the Summary of the Invention or as in any of the embodiments described herein; and b) optionally separating individual isomers.

DETAILED DESCRIPTION

Abbreviations

| Abbreviation | Meaning |
|---|---|
| ACN | acetonitrile |
| aq | aqueous |
| Boc | tert-butoxycarbonyl |
| CBz | |
| conc | concentrated |
| DAST | diethylaminosulfur trifluoride |
| DCM | dichlorormethane |
| DIBAL | diisobutylaluminum hydride |
| DIPEA | diisoproylethylamine |
| DMF | dimethylformamide |
| DMP | Dess-Martin periodinane |
| DMSO | dimethyl sulfoxide |
| DPPA | Diphenylphosphoryl azide |
| EDCI | 1-ethyl-3-(3-dimethylaminopropyl)carbodiimide |
| h | hours |
| HATU | O-(7-azabenzotriazol-1-yl)-N,N,N',N'-tetramethyluronium hexafluorophosphate |
| HOBt | hydroxybenzotriazole |
| LDA | lithium diisopropyl amide |
| mg | milligram |
| mHz | megahertz |

| Abbreviation | Meaning |
|---|---|
| mL | milliliter |
| µL | microliter |
| MCPBA | meta-chloroperoxybenzoic acid |
| Ms | mesyl |
| NBS | N-bromosuccinimide |
| NMP | N-methyl pyrrolidone |
| NMR | nuclear magnetic resonance |
| PE | petroleum ether |
| rt or RT | room temperature |
| sat | saturated |
| TBAF | tetra-n-butylammonium fluoride |
| TBDMS | tert-butyldimethylsilyl |
| TEA | triethylamine |
| TES | triethylsilane |
| TFA | trifluoroacetic acid |
| THF | tetrahydrofuran |
| TLC | thin layer chromatography |

Definitions

To facilitate understanding of the disclosure set forth herein, a number of terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

As used throughout this application and the appended claims, the following terms have the following meanings:

"About" preceding a numerical value refers to a range of values±10% of the value specified.

"Acceptable" with respect to a formulation, composition or ingredient, as used herein, means having no persistent detrimental effect on the general health of the subject being treated.

"Alkenyl" means a straight or branched hydrocarbon radical having from 2 to 8 carbon atoms and at least one double bond and includes ethenyl, propenyl, 1-but-3-enyl, 1-pent-3-enyl, 1-hex-5-enyl and the like. "Lower alkenyl" means an alkenyl group having one to six carbon atoms.

"Alkenyloxy" means an —OR group where R is alkenyl, as defined herein.

"Alkoxy" means an —OR group where R is alkyl, as defined herein. Illustrative examples include, but are not limited to, methoxy, ethoxy, propoxy, 2-propoxy, butoxy, tert-butoxy, pentyloxy, and hexyloxy.

"Alkoxycarbonyl" means a —C(O)R group where R is alkoxy, as defined herein.

"Alkyl" means a straight or branched saturated hydrocarbon radical containing from 1-10 carbon atoms, in another example 1-6 carbon atoms. Illustrative examples include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

"Alkylamino" means a —NHR radical where R is alkyl as defined herein, or an N-oxide derivative thereof, e.g., methylamino, ethylamino, n-, iso-propylamino, n-, iso-, tert-butylamino, or methylamino-N-oxide, and the like.

"Alkylaminoalkyl" means an alkyl group substituted with one or two alkylamino groups, as defined herein.

"Alkylaminocarbonyl" means a —C(O)R group where R is alkylamino, as defined herein.

"Alkylcarbonyl" means a —C(O)R group where R is alkyl, as defined herein.

"Alkynyl" means a straight or branched hydrocarbon radical having from 2 to 8 carbon atoms and at least one triple bond and includes ethynyl, propynyl, 1-but-3-ynyl, 1-pent-3-ynyl, 1-hex-5-ynyl and the like. "Lower alkynyl" means an alkynyl group having one to six carbon atoms.

"Amino" means an —NH$_2$ group.

"Aminoalkyl" means an alkyl group substituted with at least one, for example one, two, or three, amino groups.

"Aminocarbonyl" means a —C(O)R group where R is amino, as defined herein.

"Aryl" means a monovalent six- to fourteen-membered, mono- or bi-carbocyclic ring, wherein the monocyclic ring is aromatic and at least one of the rings in the bicyclic ring is aromatic. Representative examples include phenyl, naphthyl, and indanyl, and the like.

"Arylalkyl" means an alkyl group, as defined herein, substituted with 1 or 2 aryl groups, as defined herein.

"Arylcarbonyl" means a —C(O)R group where R is aryl, as defined herein.

"Aryloxy" means an —OR group where R is aryl, as defined herein.

"Carboxy" means a —C(O)OH group.

"Cycloalkyl" means a monocyclic or fused bicyclic, saturated or partially unsaturated (but not aromatic), hydrocarbon radical of three to ten carbon ring atoms. Fused bicyclic hydrocarbon radical includes bridged rings. Cycloalkyl includes spirocycloalkyl rings. Unless stated otherwise, the valency of the group may be located on any atom of any ring within the radical, valency rules permitting. One or two ring carbon atoms may be replaced by a —C(O)—, —C(S)—, or —C(=NH)— group.

In certain embodiments, cycloalkyl groups include but are not limited to:

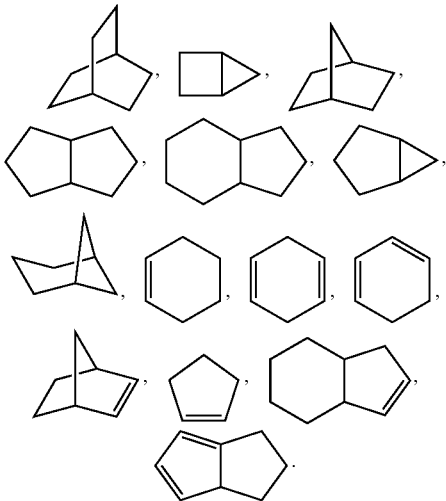

"Cycloalkylalkyl" means an alkyl group, as defined herein, substituted with at least one, in another example 1 or 2, cycloalkyl groups as defined herein.

"Cycloalkylalkyloxy" means an —OR group where R is a cycloalkylalkyl group as defined herein.

"Cycloalkyloxy" means an —OR group where R is cycloalkyl, as defined herein.

"Cycloalkylthio" means an —SR group where R is cycloalkyl, as defined herein.

"Dialkylamino" means an —NRR' radical where R and R' are independently alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with at least one, for example one or two, dialkylamino group(s), as defined herein.

"Dialkylaminocarbonyl" means a —C(O)R group where R is dialkylamino, as defined herein.

"Halo" means a fluoro, chloro, bromo, or iodo group.

"Haloalkoxy" means an alkoxy group, as defined herein, substituted with one or more halo atoms, in another example by 1, 2, or 3 halo atoms.

"Haloalkyl" means an alkyl group substituted with one or more halo atoms, in another example by 1, 2, 3, 4, 5, or 6 halo atoms, in another example by 1, 2, or 3 halo atoms. Examples include, but are not limited to, trifluoromethyl, chloromethyl, and the like.

"Heteroaryl" means monocyclic, fused bicyclic, or fused tricyclic, radical of 5 to 14 ring atoms containing one or more, in another example one, two, three, or four ring heteroatoms independently selected from —O—, —S(O)$_n$— (n is 0, 1, or 2), —N—, —N(H)—, and N-oxide, and the remaining ring atoms being carbon, wherein the ring comprising a monocyclic radical is aromatic and wherein at least one of the fused rings comprising a bicyclic or tricyclic radical is aromatic (but does not have to be a ring which contains a heteroatom, e.g. 2,3-dihydrobenzo[b][1,4]dioxin-6-yl). One or two ring carbon atoms of any nonaromatic rings comprising a bicyclic or tricyclic radical may be replaced by a —C(O)—, —C(S)—, or —C(=NH)— group. Fused bicyclic radical includes bridged ring systems. Unless stated otherwise, the valency may be located on any atom of any ring of the heteroaryl group, valency rules permitting.

In certain embodiments, heteroaryl includes, but is not limited to, triazolyl, tetrazolyl, pyrrolyl, imidazolyl, thienyl, furanyl, pyrazolyl, oxazolyl, isooxazolyl, oxadiazolyl, thiadiazolyl, indolyl, 2,3-dihydro-1H-indolyl (including, for example, 2,3-dihydro-1H-indol-2-yl or 2,3-dihydro-1H-indol-5-yl, and the like), indazolyl, phthalimidyl, benzimidazolyl, benzoxazolyl, benzofuranyl, benzothienyl, benzopyranyl, benzothiazolyl, pyridinyl, pyrazinyl, pyrimidinyl, pyridazinyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), pyrrolo[1,2-b]pyridazinyl, imidazo[1,2-a]pyridinyl, thiazolyl, benzo[d][1,3]dioxolyl, 2,3-dihydrobenzo[b][1,4]dioxinyl, furo[2,3-d]thiazolyl, thieno[2,3-d]oxazolyl, thieno[3,2-b]furanyl, furo[2,3-d]pyrimidinyl, furo[3,2-b]pyridinyl, furo[3,2-c]pyridinyl, 6,7-dihydro-5H-cyclopenta[b]pyridinyl, and 7,8-dihydro-6H-cyclopenta[g]quinoxalinyl; and derivatives, N-oxide and protected derivatives thereof.

"Heteroarylalkyl" means an alkyl group, as defined herein, substituted with 1 or 2 heteroaryl groups, as defined herein.

"Heteroaryloxy" means an —OR group where R is heteroaryl, as defined herein.

"Heterocycloalkyl" means a saturated or partially unsaturated (but not aromatic) monovalent monocyclic group of 3 to 9 ring atoms or a saturated or partially unsaturated (but not aromatic) monovalent fused bicyclic group of 5 to 12 ring atoms in which one or more heteroatoms, for example one, two, three, or four ring heteroatoms, independently selected from —O—, —S(O)$_n$— (n is 0, 1, or 2), —N=, —NH—, and N-oxide, the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting.

In certain embodiments, heterocycloalkyl includes, but is not limited to, azetidinyl, pyrrolidinyl, 2-oxopyrrolidinyl, 2,5-dihydro-1H-pyrrolinyl, 2,5-dioxo-1H-pyrrolyl, 2,5-dioxo-pyrrolidinyl, 2,5-dihydro-1H-pyrrolyl, piperidinyl, 2-oxopiperidinyl, 4-piperidonyl, morpholinyl, piperazinyl, 2-oxopiperazinyl, dioxopiperazinyl, pyranyl, tetrahydropyranyl, tetrahydrothiopyranyl, 1,3-dioxinyl, 1,3-dioxanyl, 1,4-dioxinyl, 1,4-dioxanyl, thiomorpholinyl, thiamorpholinyl, perhydroazepinyl, pyrazolidinyl, imidazolinyl, imidazolidinyl, 2,4-dioxo-imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, 2-azaspiro[3.3]heptanyl, 7-azabicyclo[2.2.1]heptanyl, and 8-azabicyclo[3.2.1]octanyl, and the derivatives thereof and N-oxide (for example 1-oxido-pyrrolidin-1-yl) or a protected derivative thereof.

"Heterocycloalkylalkyl" means an alkyl group substituted with at least one, in another example 1 or 2, heterocycloalkyl groups, as defined herein.

"Heterocycloalkylalkyloxy" means an —OR group where R is an heterocycloalkylalkyl group, as defined herein.

"Heterocycloalkyloxy" means an —OR group where R is heterocycloalkyl, as defined herein.

"Hydroxyalkoxy" means an alkoxy group, as defined herein, substituted with at least one, or in other embodiments 1, 2, or 3, hydroxy groups.

The term "protecting group" refers to a removable group which modifies the reactivity of a functional group, for example, a hydroxyl, ketone or amine, against undesirable reaction during synthetic procedures and to be later removed. Examples of hydroxy-protecting groups include, but not limited to, methylthiomethyl, tert-dimethylsilyl, tert-butyldiphenylsilyl, ethers such as methoxymethyl, and esters including acetyl, benzoyl, and the like. Examples of ketone protecting groups include, but not limited to, ketals, oximes, O-substituted oximes for example O-benzyl oxime, O-phenylthiomethyl oxime, 1-isopropoxycyclohexyl oxime, and the like. Examples of amine protecting groups include, but are not limited to, tert-butoxycarbonyl (Boc) and carbobenzyloxy (Cbz).

"Stereoisomers" include (but are not limited to) geometric isomers, enantiomers, diastereomers, and mixtures of geometric isomers, enantiomers or diastereomers. In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic column.

As used herein, "amelioration" of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "carrier" includes pharmaceutically inert, inorganic or organic carriers for the production of pharmaceutical compositions. Lactose, corn starch, or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The term "diluent" refers to chemical compounds that are used to dilute the compound of interest prior to delivery. Diluents include chemicals used to stabilize compounds because they provide a more stable environment. Salts dissolved in buffered solutions (which also can provide pH control or maintenance) are utilized as diluents in some or any embodiments, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

"Excipient" or "pharmaceutically acceptable excipient" means a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

"Pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compound of the present invention forms with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

"Subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

"Treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition.

Embodiments

The following paragraphs present a number of embodiments of the compounds disclosed herein. In each instance the embodiment includes both the recited compound(s) as well as a single stereoisomer or mixture of stereoisomers thereof, as well as a pharmaceutically acceptable salt thereof. The compounds include the N-oxides or pharmaceutically acceptable salts thereof. In some situations, the compounds exist as tautomers. All tautomers are included within the scope of the compounds presented herein.

The compounds described herein, as well as their corresponding pharmaceutically acceptable salts thereof, can exist in isotopically-labeled form, in which one or more atoms of the compounds are replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorous, sulfur, fluorine, and chloride, such as $^2$H (deuterium), $^3$H (tritium), $^{13}$C, $^{14}$C, $^{15}$N, $^{17}$O, $^{18}$O, $^{31}$P, $^{32}$P, $^{35}$S, $^{18}$F, and $^{36}$Cl, respectively. Isotopically labeled compounds of the present invention, as well as pharmaceutically acceptable salts thereof, generally can be prepared by carrying out the procedures disclosed in the Schemes and/or in the Examples and Preparations herein, by substituting a readily available isotopically labeled reagent for a non-isotopically labeled reagent.

In the compounds of the invention, unless otherwise stated, any atom not specifically designated as a particular isotope is meant to represent any stable isotope of that atom at is natural abundance. When a position is designated as "H" or "hydrogen," the position is to be understood to have hydrogen at is naturally abundant isotopic composition, with the understanding that some variation of natural isotopic abundance occurs in a synthesized compound depending upon the origin of chemical materials used in the synthesis. When a particular position is designated as "D" or "deuterium," it is to be understood that the abundance of deuterium at that position is substantially greater than the natural abundance of deuterium, with is 0.015%, and typically has at least 50% deuterium incorporation at that position.

The methods disclosed herein also include methods of treating diseases by administering deuterated compounds of the invention or other isotopically-labeled compounds of the invention alone or as pharmaceutical compositions. In some of these situations, substitution of hydrogen atoms with heavier isotopes such as deuterium can afford certain therapeutic advantages resulting from greater metabolic stability (for example, increased in vivo half-life or reduced dosage requirements). Moreover, certain isotopically-labeled compounds, for example those into which radioactive isotopes such as $^3$H and $^{14}$C are incorporated, are useful in drug and/or substrate tissue distribution assays such as positron emission tomography (PET). Tritiated ($^3$H) and carbon-14 ($^{14}$C) isotopes are useful for these embodiments.

In embodiment, provided is a compound of Formula I:

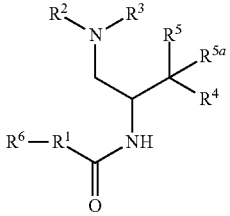

Formula I where
R$^1$ is cycloalkyl or R$^1$ is heterocycloalkyl; wherein the heterocycloalkyl is attached to the C(O) group by a carbon atom and is optionally substituted with hydroxy;
R$^2$ is hydrogen, hydroxy, or alkyl; and R$^3$ is alkyl, aminoalkyl, alkylaminoalkyl, or dialkylaminoalkyl; or R$^2$ and R$^3$ together with the nitrogen to which they are attached form a 3-10 membered heterocycloalkyl ring which is optionally substituted with 1, 2, 3, or 4 R$^8$; and wherein the —NR$^2$R$^3$ heterocycloalkyl is not morpholinyl;
R$^4$ is aryl or heteroaryl each of which is optionally substituted with 1, 2, or 3 R$^9$ groups;

$R^5$ is halo, —OH, —N$_3$, —NH$_2$, —NHC(O)CH$_3$, —NH(OCH$_3$), or —NHC(O)H and $R^{5a}$ is hydrogen, halo, alkyl, or deuterium; or $R^5$ and $R^{5a}$ together with the carbon to which they are attached form C(O) or C(NOH);

$R^6$ is alkyl, alkoxycarbonyl, aryl, arylalkyl, arylcarbonyl, cycloalkyl, cycloalkylalkyl, heterocylcoalkyl, heterocycloalkylalkyl, heteroaryl, heteroarylalkyl, or —C(O)NR$^{6a}$R$^{6b}$; wherein the aryl and the heteroaryl, whether alone or as part of arylalkyl or heteroarylalkyl, are optionally substituted with 1 or 2 R$^{10}$ groups; and wherein the heterocycloalkyl and cycloalkyl, whether alone or as part of cycloalkylalkyl or heterocycloalkylalkyl, are optionally substituted with 1 or 2 groups independently selected from hydroxy, halo, haloalkyl, alkoxy, alkyl, alkylcarbonyl, and alkoxycarbonyl;

$R^{6a}$ is hydrogen or alkyl and $R^{6b}$ is aryl or heteroaryl each of which is optionally substituted with 1 or 2 halo; or $R^{6a}$ and $R^{6b}$ together with the nitrogen to which they are attached form a heterocycloalkyl optionally substituted with alkyl, hydroxy, alkylcarbonyl, or alkoxycarbonyl;

each $R^8$, when present, is independently deuterium, amino, alkylamino, dialkylamino, alkyl, hydroxy, alkoxy, halo, haloalkyl, or cycloalkyl;

each $R^9$, when present, is independently cyano, nitro, amino, alkylamino, dialkylamino, halo, haloalkyl, alkyl, —NR$^{11}$C(O)NR$^{11a}$R$^{11b}$, hydroxy, alkoxy, haloalkoxy, hydroxyalkoxy, alkenyloxy, cycloalkyloxy, cycloalkylalkyloxy, cycloalkylthio, heterocycloalkyl, heterocycloalkyloxy, or heterocycloalkylalkyloxy; where each heterocycloalkyl, either alone or as part of another group, is optionally substituted with 1 or 2 groups independently selected from alkyl, hydroxy, alkylcarbonyl, and alkoxycarbonyl groups;

each $R^{10}$, when present, is independently is cyano, nitro, amino, alkylamino, dialkylamino, halo, haloalkyl, alkyl, —NR$^{11}$C(O)NR$^{11a}$R$^{11b}$, hydroxy, alkoxy, haloalkoxy, cycloalkyloxy, cycloalkylalkyloxy, aryl, aryloxy, heteroaryloxy, heterocycloalkyl, heterocycloalkyloxy, or heterocycloalkylalkyloxy; where each aryl or heteroaryl either alone or as part of another group, are independently optionally substituted with 1 or 2 halo or alkyl; and each heterocycloalkyl, either alone or as part of another group, is optionally substituted with 1 or 2 groups independently selected from alkyl, hydroxy, alkylcarbonyl, and alkoxycarbonyl groups;

$R^{11}$, $R^{11a}$, and $R^{11b}$ are independently hydrogen, alkyl, or cycloalkyl;

provided that when $R^1$ is cycloalkyl and $R^6$ is phenyl then the phenyl is substituted with 1 or 2 groups independently selected from cyano, nitro, amino, alkylamino, dialkylamino, haloalkyl, alkyl, —NR$^{11}$C(O)NR$^{11a}$R$^{11b}$, haloalkoxy, cycloalkyloxy, cycloalkylalkyloxy, heterocycloalkyl which is optionally substituted with 1 or 2 alkyl, heterocycloalkyloxy which is optionally substituted with 1 or 2 alkyl, or heterocycloalkylalkyloxy which is optionally substituted with 1 or 2 hydroxy; and optionally a tautomer, a single stereoisomer or mixture of stereoisomers thereof and additionally optionally a pharmaceutically acceptable salt thereof.

In one embodiment, provided is a compound of Formula I:

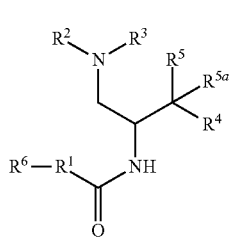

Formula I where
$R^1$ is cycloalkyl or $R^1$ is heterocycloalkyl attached to the C(O) group by a carbon atom;
$R^2$ is hydrogen, hydroxy, or alkyl; and $R^3$ is alkyl, aminoalkyl, alkylaminoalkyl, or dialkylaminoalkyl; or $R^2$ and $R^3$ together with the nitrogen to which they are attached form a 3-10 membered heterocycloalkyl ring which is optionally substituted with 1, 2, 3, or 4 R$^8$; and wherein the —NR$^2$R$^3$ heterocycloalkyl is not morpholinyl;
$R^4$ is aryl or heteroaryl each of which is optionally substituted with 1, 2, or 3 R$^9$ groups;
$R^5$ is halo, —OH, —N$_3$, —NH$_2$, —NHC(O)CH$_3$, —NH(OCH$_3$), or —NHC(O)H and $R^{5a}$ is hydrogen, halo, alkyl, or deuterium; or $R^5$ and $R^{5a}$ together with the carbon to which they are attached form C(O) or C(NOH);
$R^6$ is alkoxycarbonyl, aryl, arylalkyl, cycloalkyl, cycloalkylalkyl, heterocylcoalkyl, heterocycloalkylalkyl, heteroaryl, heteroarylalkyl, or —C(O)NR$^{6a}$R$^{6b}$; wherein the aryl and the heteroaryl, whether alone or as part of arylalkyl or heteroarylalkyl, are optionally substituted with 1 or 2 R$^{10}$ groups; and wherein the heterocycloalkyl and cycloalkyl, whether alone or as part of cycloalkylalkyl or heterocycloalkylalkyl, are optionally substituted with 1 or 2 groups independently selected from hydroxy, halo, haloalkyl, alkoxy, alkyl, alkylcarbonyl, and alkoxycarbonyl;
$R^{6a}$ is hydrogen or alkyl and $R^{6b}$ is aryl or heteroaryl each of which is optionally substituted with 1 or 2 halo; or $R^{6a}$ and $R^{6b}$ together with the nitrogen to which they are attached form a heterocycloalkyl optionally substituted with alkyl, hydroxy, alkylcarbonyl, or alkoxycarbonyl;
each $R^8$, when present, is independently deuterium, amino, alkylamino, dialkylamino, alkyl, hydroxy, alkoxy, halo, haloalkyl, or cycloalkyl;
each $R^9$, when present, is independently cyano, nitro, amino, alkylamino, dialkylamino, halo, haloalkyl, alkyl, —NR$^{11}$C(O)NR$^{11a}$R$^{11b}$, hydroxy, alkoxy, haloalkoxy, cycloalkyloxy, cycloalkylalkyloxy, heterocycloalkyl, heterocycloalkyloxy, or heterocycloalkylalkyloxy; where each heterocycloalkyl, either alone or as part of another group, is optionally substituted with 1 or 2 groups independently selected from alkyl, hydroxy, alkylcarbonyl, and alkoxycarbonyl groups;
each $R^{10}$, when present, is independently R$^9$; and
$R^{11}$, $R^{11a}$, and $R^{11b}$ are independently hydrogen, alkyl, or cycloalkyl;
provided that when $R^1$ is cycloalkyl and $R^6$ is phenyl then the phenyl is substituted with 1 or 2 groups independently selected from cyano, nitro, amino, alkylamino, dialkylamino, haloalkyl, alkyl, —NR$^{11}$C(O)NR$^{11a}$R$^{11b}$, haloalkoxy, cycloalkyloxy, cycloalkylalkyloxy, heterocycloalkyl which is optionally substituted with 1 or 2 alkyl, heterocycloalkyloxy which is optionally substituted with 1 or 2 alkyl, or heterocycloalkylalkyloxy which is optionally substituted with 1 or 2 hydroxy; and optionally a tautomer, a single stereoisomer or mixture of stereoisomers thereof and additionally optionally a pharmaceutically acceptable salt thereof.

In some or any embodiments, the compound of Formula I is that where $R^1$ is N—($R^6$)-azetidinyl, N—($R^6$)-pyrrolidinyl, or N—($R^6$)-piperidinyl, each of which is attached to the C(O) by a carbon atom, and is optionally substituted with hydroxy;

$R^2$ and $R^3$ together with the nitrogen to which they are attached form a 4-6 membered heterocycloalkyl ring with 1 or 2 nitrogen atoms, which is optionally substituted with 1 or 2 $R^8$;

$R^4$ is aryl or heteroaryl each of which is optionally substituted with 1 or 2 $R^9$ groups;

$R^5$ is —OH and $R^{5a}$ is hydrogen;

$R^6$ is alkyl, aryl, arylalkyl, arylcarbonyl, cycloalkyl, cycloalkylalkyl, heterocylcoalkyl, heterocycloalkylalkyl, heteroaryl, or heteroarylalkyl; wherein the aryl and the heteroaryl, whether alone or as part of another group, are optionally substituted with 1 or 2 $R^{10}$ groups; and wherein the heterocycloalkyl and cycloalkyl, whether alone or as part of another group, are optionally substituted with 1 or 2 groups independently selected from hydroxy, halo, haloalkyl, alkoxy, and alkyl;

each $R^8$, when present, is independently hydrogen, alkyl, hydroxy, alkoxy, halo, or haloalkyl;

each $R^9$, when present, is independently cyano, nitro, halo, haloalkyl, alkyl, hydroxy, alkoxy, haloalkoxy, hydroxyalkoxy, alkenyloxy, cycloalkyloxy, cycloalkylalkyloxy, cycloalkylthio, heterocycloalkyl, heterocycloalkyloxy, or heterocycloalkylalkyloxy; where each heterocycloalkyl, either alone or as part of another group, is optionally substituted with 1 or 2 groups independently selected from alkyl, hydroxy, alkylcarbonyl, and alkoxycarbonyl groups;

each $R^{10}$, when present, is independently is cyano, halo, haloalkyl, alkyl, hydroxy, alkoxy, haloalkoxy, cycloalkyloxy, cycloalkylalkyloxy, aryl, aryloxy, heteroaryloxy, heterocycloalkyl, heterocycloalkyloxy, or heterocycloalkylalkyloxy; where each aryl or heteroaryl either alone or as part of another group, are independently optionally substituted with 1 or 2 halo or alkyl groups; and each heterocycloalkyl, either alone or as part of another group, is optionally substituted with 1 or 2 groups independently selected from alkyl and hydroxy; and optionally a tautomer, a single stereoisomer or mixture of stereoisomers thereof and additionally optionally a pharmaceutically acceptable salt thereof.

In some or any embodiments, the compound of Formula I is that where $R^1$ is N—($R^6$)-pyrrolidinyl, attached to the C(O) by a carbon atom, and is optionally substituted with hydroxy;

$R^2$ and $R^3$ together with the nitrogen to which they are attached form a azetidinyl, pyrrolidinyl, or piperidinyl ring;

$R^4$ is aryl or heteroaryl each of which is optionally substituted with 1 or 2 $R^9$ groups;

$R^5$ is —OH and $R^{5a}$ is hydrogen;

$R^6$ is alkyl, aryl, arylalkyl, arylcarbonyl, cycloalkyl, cycloalkylalkyl, heterocylcoalkyl, heterocycloalkylalkyl, or heteroaryl; wherein the aryl and the heteroaryl, whether alone or as part of arylalkyl or heteroarylalkyl, are optionally substituted with 1 or 2 $R^{10}$ groups; and wherein the heterocycloalkyl is optionally substituted with hydroxy;

each $R^9$, when present, is independently halo, haloalkyl, alkyl, alkoxy, haloalkoxy, hydroxyalkoxy, alkenyloxy, cycloalkyloxy, cycloalkylthio, heterocycloalkyl, heterocycloalkyloxy, or heterocycloalkylalkyloxy; where each heterocycloalkyl, either alone or as part of another group, is optionally substituted with an alkyl group;

each $R^{10}$, when present, is independently is cyano, halo, haloalkyl, alkyl, haloalkoxy, cycloalkyloxy, aryl, aryloxy, or heteroaryloxy; where each aryl or heteroaryl either alone or as part of another group, are independently optionally substituted with 1 or 2 halo or alkyl; and optionally a tautomer, a single stereoisomer or mixture of stereoisomers thereof and additionally optionally a pharmaceutically acceptable salt thereof.

In some or any embodiments, the compound of Formula I is that where $R^1$ is cycloalkyl or $R^1$ is heterocycloalkyl attached to the C(O) group by a carbon atom;

$R^2$ and $R^3$ together with the nitrogen to which they are attached form a 4-7 membered heterocycloalkyl ring which is optionally substituted with 1, 2, 3, or 4 $R^8$;

$R^4$ is aryl or heteroaryl each of which is optionally substituted with 1, 2, or 3 $R^9$ groups;

$R^5$ is —OH and $R^{5a}$ is hydrogen;

$R^6$ is alkoxycarbonyl, aryl arylalkyl; cycloalkyl; heterocylcoalkyl; heterocycloalkylalkyl optionally substituted with 1 or 2 hydroxy; heteroaryl; or —C(O)N$R^{6a}R^{6b}$; wherein the aryl and the heteroaryl, whether alone or as part of arylalkyl or heteroarylalkyl, are optionally substituted with 1 or 2 $R^{10}$ groups; and wherein the heterocycloalkyl, heterocycloalkylalkyl, and cycloalkyl are optionally substituted with 1 or 2 groups independently selected from hydroxy and alkyl;

$R^{6a}$ is hydrogen or alkyl and $R^{6b}$ is aryl optionally substituted with halo;

each $R^8$, when present, is independently deuterium or alkyl;

each $R^9$, when present, is independently halo, alkyl, alkoxy, cycloalkyloxy, heterocycloalkyl which is optionally substituted with 1 or 2 alkyl, heterocycloalkyloxy which is optionally substituted with 1 or 2 alkyl, or heterocycloalkylalkyloxy which is optionally substituted with 1 or 2 hydroxy;

each $R^{10}$, when present, is independently; and provided that when $R^1$ is cycloalkyl and $R^6$ is aryl then the aryl is substituted with 1 or 2 groups independently selected from haloalkyl, haloalkoxy, cycloalkyloxy; and optionally a tautomer, a single stereoisomer or mixture of stereoisomers thereof and additionally optionally a pharmaceutically acceptable salt thereof.

In some or any embodiments, the compound of Formula I is that where $R^1$ is cycloalkyl; and all groups are as defined in the Summary of the Invention or as defined in any of the embodiments described herein. In some or any embodiments, the compound of Formula I is that where $R^1$ is cyclopropyl, cyclobutyl, cyclopentyl, cyclohexyl, or bicyclo[1.1.1]pentyl; and all groups are as defined in the Summary of the Invention or as defined in any of the embodiments described herein.

In some or any embodiments, the compound of Formula I is that where $R^1$ is heterocycloalkyl attached to the C(O) group by a carbon atom; and all groups are as defined in the Summary of the Invention or as defined in any of the embodiments described herein. In some or any embodiments, the compound of Formula I is that where $R^1$ is heterocycloalkyl attached to the C(O) group by a carbon atom and attached to $R^6$ via a nitrogen atom; and all groups are as defined in the Summary of the Invention or as defined in any of the embodiments described herein. In some or any embodiments, the compound of Formula I is that where $R^1$ is azetidinyl, pyrrolidinyl, or piperidinyl, each of which is attached to the C(O) by a carbon atom; and all groups are as defined in the Summary of the Invention or as defined in any of the embodiments described herein. In some or any embodiments, the compound of Formula I is that where $R^1$ is N—($R^6$)-azetidinyl, N—($R^6$)-pyrrolidinyl, or N—($R^6$)-piperidinyl, each of which is attached to the C(O) by a carbon atom; and all groups are as defined in the Summary of the Invention or as defined in any of the embodiments described herein. In some or any embodiments, the compound of Formula I is that where $R^1$ is N—($R^6$)-pyrrolidinyl attached to the C(O) by a carbon atom; and all groups are as defined in the Summary of the Invention or as defined in any of the embodiments described herein. In some or any embodiments, the compound of Formula I is that where $R^1$ is N—($R^6$)-azetidin-3-yl, N—($R^6$)-pyrrolidin-3-yl, or N—($R^6$)-piperidin-3-yl, each of which is attached to the C(O) by a carbon atom; and all groups are as defined in the Summary of the Invention or as defined in any of the embodiments described herein. In some or any embodiments, the compound of Formula I is that where $R^1$ is N—($R^6$)-azetidin-3-yl attached to the C(O) by a carbon atom; and all groups are as defined in the Summary of the Invention or as defined in any of the embodiments described herein.

In some or any embodiments, the compound of Formula I is that where $R^2$ and $R^3$ together with the nitrogen to which they are attached form a 3-10 membered heterocycloalkyl ring which is optionally substituted with 1, 2, 3, or 4 $R^8$; and all groups are as defined in the Summary of the Invention or as defined in any of the embodiments described herein. In some or any embodiments, the compound of Formula I is that where $R^2$ and $R^3$ together with the nitrogen to which they are attached form a 4-7 membered heterocycloalkyl ring which is optionally substituted with 1, 2, 3, or 4 $R^8$; and all groups are as defined in the Summary of the Invention or as defined in any of the embodiments described herein. In some or any embodiments, the compound of Formula I is that where $R^2$ and $R^3$ together with the nitrogen to which they are attached form azetidinyl, pyrrolidinyl, or piperidinyl, each of which is optionally substituted with 1, 2, 3, or 4 $R^8$; and all groups are as defined in the Summary of the Invention or as defined in any of the embodiments described herein. In some or any embodiments, the compound of Formula I is that where $R^2$ and $R^3$ together with the nitrogen to which they are attached form azetidinyl or pyrrolidinyl group, each of which is optionally substituted with 1, 2, 3, or 4 $R^8$; and all groups are as defined in the Summary of the Invention or as defined in any of the embodiments described herein.

In some or any embodiments, the compound of Formula I is that where $R^4$ is aryl optionally independently substituted with 1 or 2 halo, alkoxy, cycloalkyloxy, heterocycloalkyloxy, hydroxyalkoxy, hetercycloalkyl, or heterocycloalkylalkoxy; or heteroaryl optionally independently substituted with halo or haloalkyl; and all groups are as defined in the Summary of the Invention or as defined in any of the embodiments described herein. In some or any embodiments, the compound of Formula I is that where $R^4$ is aryl optionally independently substituted with 1 or 2 halo, cycloalkyloxy, or heterocycloalkyloxy; or heteroaryl optionally independently substituted with halo; and all groups are as defined in the Summary of the Invention or as defined in any of the embodiments described herein.

In some or any embodiments, the compound of Formula I is that where $R^4$ is phenyl or 2,3-dihydrobenzo[b][1,4]dioxin-6-yl, where the phenyl is optionally independently substituted with 1 or 2 halo, alkoxy, cycloalkyloxy, heterocycloalkyloxy, hydroxyalkoxy, hetercycloalkyl, or heterocycloalkylalkoxy, and the 2,3-dihydrobenzo[b][1,4]dioxin-6-yl is optionally substituted with halo or haloalkyl; and all groups are as defined in the Summary of the Invention or as defined in any of the embodiments described herein. In some or any embodiments, the compound of Formula I is that where $R^4$ is phenyl or 2,3-dihydrobenzo[b][1,4]dioxin-6-yl, where the phenyl is optionally independently substituted with 1 or 2 halo, cycloalkyloxy, or heterocycloalkyloxy, and the 2,3-dihydrobenzo[b][1,4]dioxin-6-yl is optionally substituted with halo; and all groups are as defined in the Summary of the Invention or as defined in any of the embodiments described herein.

In some or any embodiments, the compound of Formula I is that where $R^4$ is aryl optionally substituted with 1, 2, or 3 $R^9$ groups; and all groups are as defined in the Summary of the Invention or as defined in any of the embodiments described herein. In some or any embodiments, the compound of Formula I is that where $R^4$ is phenyl optionally substituted with 1, 2, or 3 $R^9$ groups; and all groups are as defined in the Summary of the Invention or as defined in any of the embodiments described herein. In some or any embodiments, the compound of Formula I is that where $R^4$ is phenyl optionally substituted with 1, 2, or 3 $R^9$ groups where each $R^9$, when present, is independently halo, alkoxy, cycloalkyloxy, heterocycloalkyl, heterocycloalkyloxy optionally substituted with alkyl, heterocycloalkylalkyloxy optionally substituted with hydroxy; and all groups are as defined in the Summary of the Invention or as defined in any of the embodiments described herein.

In some or any embodiments, the compound of Formula I is that where $R^4$ is heteroaryl optionally substituted with 1, 2, or 3 $R^9$ groups; and all groups are as defined in the Summary of the Invention or as defined in any of the embodiments described herein. In some or any embodiments, the compound of Formula I is that where $R^4$ is pyridinyl or 2,3-dihydrobenzo[b][1,4]dioxin-6-yl, optionally substituted with 1 or 2 $R^9$ groups; and all groups are as defined in the Summary of the Invention or as defined in any of the embodiments described herein. In some or any embodiments, the compound of Formula I is that where $R^4$ is pyridinyl or 2,3-dihydrobenzo[b][1,4]dioxin-6-yl, optionally substituted with 1 or 2 $R^9$ groups where each $R^9$, when present, is independently selected from halo, alkyl, alkoxy, cycloalkyloxy; and all groups are as defined in the Summary of the Invention or as defined in any of the embodiments described herein.

In some or any embodiments, the compound of Formula I is that where $R^5$ and $R^{5a}$ are halo; and all groups are as defined in the Summary of the Invention or as defined in any of the embodiments described herein.

In some or any embodiments, the compound of Formula I is that where $R^5$ is —OH and $R^{5a}$ is hydrogen; and all groups are as defined in the Summary of the Invention or as defined in any of the embodiments described herein.

In some or any embodiments, the compound of Formula I is that where $R^6$ is alkyl, aryl, arylalkyl, arylcarbonyl, cycloalkyl, cycloalkylalkyl, heterocylcoalkyl, heterocycloalkylalkyl, heteroaryl, or heteroarylalkyl; wherein the aryl and the heteroaryl, whether alone or as part of another group, are optionally substituted with 1 or 2 $R^{10}$ groups; and wherein the heterocycloalkyl and cycloalkyl, whether alone or as part of another group, are optionally substituted with 1 or 2 groups independently selected from hydroxy, halo, haloalkyl, alkoxy, and alkyl; and all groups are as defined in the Summary of the Invention or as defined in any of the embodiments described herein. In some or any embodiments, the compound of Formula I is that where $R^6$ is aryl, arylalkyl, arylcarbonyl, heterocylcoalkyl, heterocycloalkylalkyl, or heteroaryl; wherein the aryl and the heteroaryl, whether alone or as part of arylalkyl or heteroarylalkyl, are optionally substituted with 1 or 2 $R^{10}$ groups; and wherein the heterocycloalkyl is optionally substituted with hydroxy; and all groups are as defined in the Summary of the Invention or as defined in any of the embodiments described herein. In some or any embodiments, the compound of Formula I is that where $R^6$ is aryl or heteroaryl, wherein the aryl is optionally independently substituted with 1 or 2 halo, alkyl, cycloalkyloxy, or heterocycloalkyloxy; and the heteroaryl is optionally independently substituted with 1 or 2 halo, alkyl, or cycloalkyloxy; and all groups are as defined in the Summary of the Invention or as defined in any of the embodiments described herein.

In some or any embodiments, the compound of Formula I is that where $R^6$ is alkoxycarbonyl; and all groups are as defined in the Summary of the Invention or as defined in any of the embodiments described herein. In some or any embodiments, the compound of Formula I is that where $R^6$ is tert-butoxycarbonyl; and all groups are as defined in the Summary of the Invention or as defined in any of the embodiments described herein.

In some or any embodiments, the compound of Formula I is that where $R^6$ is aryl optionally substituted with 1 or 2 $R^{10}$ groups; and all groups are as defined in the Summary of the Invention or as defined in any of the embodiments described herein. In some or any embodiments, the compound of Formula I is that where $R^6$ is phenyl or napthyl optionally substituted with 1 or 2 $R^{10}$ groups; and all groups are as defined in the Summary of the Invention or as defined in any of the embodiments described herein. In some or any embodiments, the compound of Formula I is that where $R^6$ is phenyl optionally substituted with 1 or 2 $R^{10}$ groups; and all groups are as defined in the Summary of the Invention or as defined in any of the embodiments described herein. In some or any embodiments, the compound of Formula I is that where $R^6$ is phenyl optionally substituted with 1 or 2 $R^{10}$ groups where each $R^{10}$, when present, is independently selected from halo, haloalkyl, haloalkoxy, and cycloalkyloxy; and all groups are as defined in the Summary of the Invention or as defined in any of the embodiments described herein. In some or any embodiments, the compound of Formula I is that where $R^6$ is napthyl optionally substituted with 1 or 2 halo; and all groups are as defined in the Summary of the Invention or as defined in any of the embodiments described herein.

In some or any embodiments, the compound of Formula I is that where $R^6$ is heteroaryl optionally substituted with 1 or 2 $R^{10}$ groups; and all groups are as defined in the Summary of the Invention or as defined in any of the embodiments described herein. In some or any embodiments, the compound of Formula I is that where $R^6$ is pyridinyl, thiazolyl, benzothiazolyl, or 4,5,6,7-tetrahydrobenzo[d]thiazolyl, each of which is optionally substituted with 1 or 2 $R^{10}$ groups; and all groups are as defined in the Summary of the Invention or as defined in any of the embodiments described herein. In some or any embodiments, the compound of Formula I is that where $R^6$ is pyridinyl, thiazolyl, benzothiazolyl, or 4,5,6,7-tetrahydrobenzo[d]thiazolyl, each of which is optionally substituted with 1 or 2 halo; and all groups are as defined in the Summary of the Invention or as defined in any of the embodiments described herein.

In some or any embodiments, the compound of Formula I is that where $R^6$ is arylalkyl where the aryl is optionally substituted with 1 or 2 $R^{10}$ groups; and all groups are as defined in the Summary of the Invention or as defined in any of the embodiments described herein. In some or any embodiments, the compound of Formula I is that where $R^6$ is phenylalkyl where the phenyl is optionally substituted with 1 or 2 $R^{10}$ groups; and all groups are as defined in the Summary of the Invention or as defined in any of the embodiments described herein. In some or any embodiments, the compound of Formula I is that where $R^6$ is phenylalkyl where the phenyl is optionally substituted with 1 or 2 halo; and all groups are as defined in the Summary of the Invention or as defined in any of the embodiments described herein. In some or any embodiments, the compound of Formula I is that where $R^6$ is naphthylmethyl, phenylmethyl or phenethyl where the phenyl is optionally substituted with 1 or 2 $R^{10}$ groups; and all groups are as defined in the Summary of the Invention or as defined in any of the embodiments described herein. In some or any embodiments, the compound of Formula I is that where $R^6$ is phenylmethyl where the phenyl is optionally substituted with 1 or 2 $R^{10}$ groups; and all groups are as defined in the Summary of the Invention or as defined in any of the embodiments described herein.

In some or any embodiments, the compound of Formula I is that where $R^6$ is heteroarylalkyl where the heteroaryl is optionally substituted with 1 or 2 $R^{10}$ groups; and all groups are as defined in the Summary of the Invention or as defined in any of the embodiments described herein. In some or any embodiments, the compound of Formula I is that where $R^6$ is pyridinylalkyl where the heteroaryl is optionally substituted with 1 or 2 $R^{10}$ groups; and all groups are as defined in the Summary of the Invention or as defined in any of the embodiments described herein. In some or any embodiments, the compound of Formula I is that where $R^6$ is pyridinylmethyl where the heteroaryl is optionally substituted with 1 or 2 $R^{10}$ groups; and all groups are as defined in the Summary of the Invention or as defined in any of the embodiments described herein.

In some or any embodiments, the compound of Formula I is that where $R^6$ is cycloalkyl where the cycloalkyl is optionally substituted with 1 or 2 groups independently selected from hydroxy, halo, haloalkyl, alkoxy, alkyl, alkylcarbonyl, and alkoxycarbonyl; and all groups are as defined in the Summary of the Invention or as defined in any of the embodiments described herein. In some or any embodiments, the compound of Formula I is that where $R^6$ is cyclopropyl, cyclobutyl, cyclopentyl, or cyclohexyl each of which is optionally substituted with 1 or 2 groups independently selected from hydroxy, halo, haloalkyl, alkoxy, alkyl, alkylcarbonyl, and alkoxycarbonyl; and all groups are as defined in the Summary of the Invention or as defined in any of the embodiments described herein. In some or any embodiments, the compound of Formula I is that where $R^6$ is cyclopentyl or cyclohexyl each of which is optionally substituted with 1 or 2 groups independently selected from hydroxy, halo, haloalkyl, alkoxy, alkyl, alkylcarbonyl, and alkoxycarbonyl; and all groups are as defined in the Summary of the Invention or as defined in any of the embodiments described herein. In some or any embodiments, the compound of Formula I is that where $R^6$ is unsubstituted cyclopropyl, unsubstituted cyclobutyl, unsubstituted cyclopentyl, or unsubstituted cyclohexyl; and all groups are as defined in the Summary of the Invention or as defined in any of the embodiments described herein. In some or any embodiments, the compound of Formula I is that where $R^6$ is unsubstituted cyclopentyl or unsubstituted cyclohexyl;

and all groups are as defined in the Summary of the Invention or as defined in any of the embodiments described herein.

In some or any embodiments, the compound of Formula I is that where $R^6$ is cycloalkylalkyl where the cycloalkyl is optionally substituted with 1 or 2 groups independently selected from hydroxy, halo, haloalkyl, alkoxy, alkyl, alkylcarbonyl, and alkoxycarbonyl; and all groups are as defined in the Summary of the Invention or as defined in any of the embodiments described herein. In some or any embodiments, the compound of Formula I is that where $R^6$ is cycloalkylmethyl where the cycloalkyl is optionally substituted with 1 or 2 groups independently selected from hydroxy, halo, haloalkyl, alkoxy, alkyl, alkylcarbonyl, and alkoxycarbonyl; and all groups are as defined in the Summary of the Invention or as defined in any of the embodiments described herein. In some or any embodiments, the compound of Formula I is that where $R^6$ is unsubstituted cyclopropylmethyl, unsubstituted cyclobutylmethyl, unsubstituted cyclopentylmethyl, or unsubstituted cyclohexylmethyl; and all groups are as defined in the Summary of the Invention or as defined in any of the embodiments described herein. In some or any embodiments, the compound of Formula I is that where $R^6$ is unsubstituted cyclopentylmethyl or unsubstituted cyclohexylmethyl; and all groups are as defined in the Summary of the Invention or as defined in any of the embodiments described herein.

In some or any embodiments, the compound of Formula I is that where $R^6$ is heterocycloalkyl where the heterocycloalkyl is optionally substituted with 1 or 2 groups independently selected from hydroxy, halo, haloalkyl, alkoxy, alkyl, alkylcarbonyl, and alkoxycarbonyl; and all groups are as defined in the Summary of the Invention or as defined in any of the embodiments described herein. In some or any embodiments, the compound of Formula I is that where $R^6$ is unsubstituted tetrahydropyranyl; and all groups are as defined in the Summary of the Invention or as defined in any of the embodiments described herein.

In some or any embodiments, the compound of Formula I is that where $R^6$ is heterocycloalkylalkyl where the heterocycloalkyl is optionally substituted with 1 or 2 groups independently selected from hydroxy, halo, haloalkyl, alkoxy, alkyl, alkylcarbonyl, and alkoxycarbonyl; and all groups are as defined in the Summary of the Invention or as defined in any of the embodiments described herein. In some or any embodiments, the compound of Formula I is that where $R^6$ is heterocycloalkylmethyl where the heterocycloalkyl is optionally substituted with 1 or 2 groups independently selected from hydroxy, halo, haloalkyl, alkoxy, alkyl, alkylcarbonyl, and alkoxycarbonyl; and all groups are as defined in the Summary of the Invention or as defined in any of the embodiments described herein. In some or any embodiments, the compound of Formula I is that where $R^6$ is tetrahydropyranylmethyl optionally substituted with 1 or 2 groups independently selected from hydroxy, halo, haloalkyl, alkoxy, alkyl, alkylcarbonyl, and alkoxycarbonyl; and all groups are as defined in the Summary of the Invention or as defined in any of the embodiments described herein. In some or any embodiments, the compound of Formula I is that where $R^6$ is tetrahydropyranylmethyl optionally substituted with 1 or 2 hydroxy; and all groups are as defined in the Summary of the Invention or as defined in any of the embodiments described herein.

In some or any embodiments, the compound of Formula I is that where $R^6$ is $-C(O)NR^{6a}R^{6b}$; and all groups are as defined in the Summary of the Invention or as defined in any of the embodiments described herein. In some or any embodiments, the compound of Formula I is that where $R^6$ is $-C(O)NR^{6a}R^{6b}$ where $R^{6a}$ is hydrogen; and all groups are as defined in the Summary of the Invention or as defined in any of the embodiments described herein. In some or any embodiments, the compound of Formula I is that where $R^6$ is $-C(O)NR^{6a}R^{6b}$ where $R^{6a}$ is hydrogen and $R^{6b}$ is aryl or heteroaryl each of which is optionally substituted with halo; and all groups are as defined in the Summary of the Invention or as defined in any of the embodiments described herein. In some or any embodiments, the compound of Formula I is that where $R^6$ is $-C(O)NR^{6a}R^{6b}$ where $R^{6a}$ is hydrogen and $R^{6b}$ is phenyl optionally substituted with 1 or 2 halo; and all groups are as defined in the Summary of the Invention or as defined in any of the embodiments described herein.

In some or any embodiments, the compound of Formula I is according to Formula I(a):

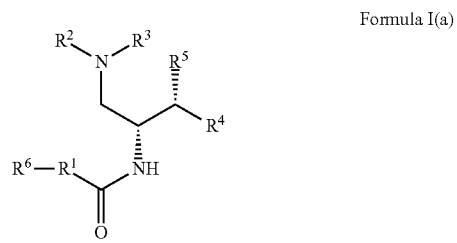

Formula I(a)

where all groups are as defined in the Summary of the Invention or as defined in any of the embodiments described herein.

In some or any embodiments, the compound of Formula I is according to Formula I(b):

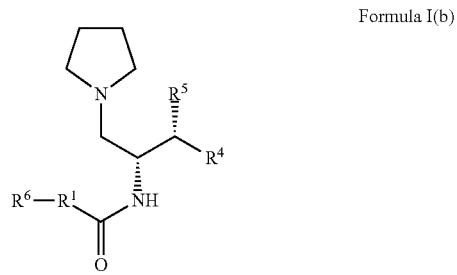

Formula I(b)

where all groups are as defined in the Summary of the Invention or as defined in any of the embodiments described herein.

In some or any embodiments, the compound of Formula I is according to Formula I(c):

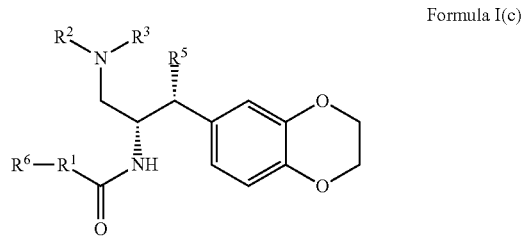

Formula I(c)

where all groups are as defined in the Summary of the Invention or as defined in any of the embodiments described herein. In some or any embodiments, the compound of Formula I is according to Formula I(c) where:

$R^1$ is pyrrolidinyl attached to the C(O) by a carbon atom, and is optionally substituted with hydroxy;

$R^2$ and $R^3$ together with the nitrogen to which they are attached form a azetidinyl, pyrrolidinyl, or piperidinyl ring, which is optionally substituted with 1 or 2 $R^8$;

$R^5$ is —OH and $R^{5a}$ is hydrogen;

$R^6$ is aryl, arylalkyl, arylcarbonyl, cycloalkyl, cycloalkylalkyl, heterocylcoalkyl, heterocycloalkylalkyl, heteroaryl, or heteroarylalkyl; wherein the aryl and the heteroaryl, whether alone or as part of another group, are optionally substituted with 1 or 2 $R^{10}$ groups; and wherein the heterocycloalkyl and cycloalkyl, whether alone or as part of another group, are optionally substituted with 1 or 2 groups independently selected from hydroxy, halo, haloalkyl, alkoxy, and alkyl; or $R^2$ and $R^3$ together with the nitrogen to which they are attached form a azetidinyl or pyrrolidinyl ring; and $R^6$ is phenyl or naphthyl optionally substituted with chloro or fluoro.

In some or any embodiments, the compound of Formula I is according to Formula I(a) or I(c) and $R^2$ and $R^3$ together with the nitrogen to which they are attached form a 3-10 membered heterocycloalkyl ring which is optionally substituted with 1, 2, 3, or 4 $R^8$; and all groups are as defined in the Summary of the Invention or as defined in any of the embodiments described herein.

In some or any embodiments, the compound of Formula I is according to Formula I(a), I(b), or I(c) and $R^5$ is hydroxy; and all groups are as defined in the Summary of the Invention or as defined in any of the embodiments described herein.

In some or any embodiments, the compound of Formula I is according to Formula I(a), I(b), or I(c) and $R^1$ is cycloalkyl; and all groups are as defined in the Summary of the Invention or as defined in any of the embodiments described herein.

In some or any embodiments, the compound of Formula I is according to Formula I(a), I(b), or I(c) and $R^1$ is heterocycloalkyl attached to the C(O) by a carbon atom; and all groups are as defined in the Summary of the Invention or as defined in any of the embodiments described herein.

In some or any embodiments, the compound of Formula I is according to Formula I(a) or I(c) and $R^2$ and $R^3$ together with the nitrogen to which they are attached form a 3-10 membered heterocycloalkyl ring which is optionally substituted with 1, 2, 3, or 4 $R^8$; $R^1$ is heterocycloalkyl attached to the C(O) by a carbon atom; and all groups are as defined in the Summary of the Invention or as defined in any of the embodiments described herein.

In some or any embodiments, the compound of Formula I is according to Formula I(a) or I(c) and $R^2$ and $R^3$ together with the nitrogen to which they are attached form a 3-10 membered heterocycloalkyl ring which is optionally substituted with 1, 2, 3, or 4 $R^8$; $R^1$ is heterocycloalkyl attached to the C(O) by a carbon atom; $R^5$ is hydroxy; and all groups are as defined in the Summary of the Invention or as defined in any of the embodiments described herein.

In some or any embodiments, the compound of Formula I is according to Formula I(b) and $R^5$ is hydroxy; and all groups are as defined in the Summary of the Invention or as defined in any of the embodiments described herein.

In some or any embodiments, the compound of Formula I is according to Formula I(b) and $R^1$ is heterocycloalkyl attached to the C(O) by a carbon atom, $R^5$ is hydroxy, and all groups are as defined in the Summary of the Invention or as defined in any of the embodiments described herein.

In some or any embodiments, the compound of Formula I is according to Formula I(a) or I(c) and $R^2$ and $R^3$ together with the nitrogen to which they are attached form a 3-10 membered heterocycloalkyl ring which is optionally substituted with 1, 2, 3, or 4 $R^8$; $R^5$ is hydroxy; and all groups are as defined in the Summary of the Invention or as defined in any of the embodiments described herein.

In some or any embodiments, the compound of Formula I is according to Formula I(d):

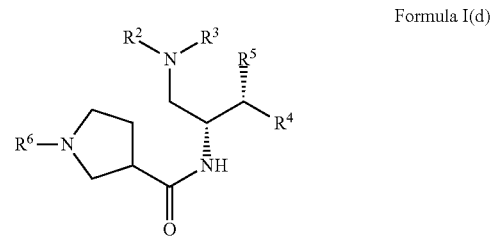

Formula I(d)

where all groups are as defined in the Summary of the Invention or as defined in any of the embodiments described herein. In some or any embodiments, the compound of Formula I is according to Formula I(d) where:

$R^2$ and $R^3$ together with the nitrogen to which they are attached form a azetidinyl, pyrrolidinyl, or piperidinyl ring;

$R^4$ is aryl or heteroaryl each of which is optionally substituted with 1 or 2 $R^9$ groups;

$R^5$ is —OH and $R^{5a}$ is hydrogen;

$R^6$ is alkyl, aryl, arylalkyl, arylcarbonyl, cycloalkyl, cycloalkylalkyl, heterocylcoalkyl, heterocycloalkylalkyl, or heteroaryl; wherein the aryl and the heteroaryl, whether alone or as part of arylalkyl or heteroarylalkyl, are optionally substituted with 1 or 2 $R^{10}$ groups; and wherein the heterocycloalkyl is optionally substituted with hydroxy;

each $R^9$, when present, is independently halo, haloalkyl, alkyl, alkoxy, haloalkoxy, hydroxyalkoxy, alkenyloxy, cycloalkyloxy, cycloalkylthio, heterocycloalkyl, heterocycloalkyloxy, or heterocycloalkylalkyloxy; where each heterocycloalkyl, either alone or as part of another group, is optionally substituted with an alkyl group;

each $R^{10}$, when present, is independently is cyano, halo, haloalkyl, alkyl, haloalkoxy, cycloalkyloxy, aryl, aryloxy, or heteroaryloxy; where each aryl or heteroaryl either alone or as part of another group, are independently optionally substituted with 1 or 2 halo or alkyl; and optionally a tautomer, a single stereoisomer or mixture of stereoisomers thereof and additionally optionally a pharmaceutically acceptable salt thereof.

In some or any embodiments, the compound of Formula I is according to Formula I(d) where $R^2$ and $R^3$ together with the nitrogen to which they are attached form a azetidinyl or pyrrolidinyl ring; $R^4$ is phenyl or 2,3-dihydrobenzo[b][1,4]dioxin-6-yl, where the phenyl is optionally independently substituted with 1 or 2 halo, cycloalkyloxy, or heterocycloalkyloxy, and the 2,3-dihydrobenzo[b][1,4]dioxin-6-yl is optionally substituted with halo; and $R^6$ is aryl or heteroaryl, each optionally substituted with chloro, fluoro, or alkyl; or $R^6$ is phenyl or naphthyl optionally independently substituted with chloro or fluoro.

In some or any embodiments, the compound of Formula I(d) is that where $R^2$ and $R^3$ together with the nitrogen to which they are attached form a 3-10 membered heterocycloalkyl ring which is optionally substituted with 1, 2, 3, or 4 $R^8$; and all groups are as defined in the Summary of the Invention or as defined in any of the embodiments described herein. In some or any embodiments, the compound of Formula I(d) is that where $R^5$ is hydroxy; and all groups are as defined in the Summary of the Invention or as defined in any of the embodiments described herein. In some or any embodiments, the compound of Formula I(d) is that where $R^4$ is 2,3-dihydrobenzo[b][1,4]dioxin-6-yl; and all groups are as defined in the Summary of the Invention or as defined in any of the embodiments described herein.

In some or any embodiments, the compound of Formula I is according to Formula I(d1):

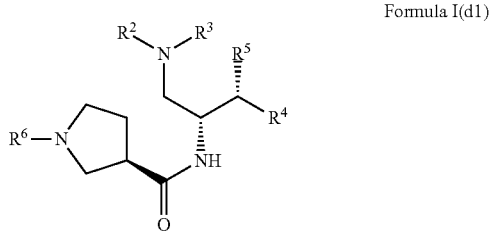

Formula I(d1)

where all groups are as defined in the Summary of the Invention or as defined in any of the embodiments described herein. In some or any embodiments, the compound of Formula I(d1) is that where $R^2$ and $R^3$ together with the nitrogen to which they are attached form a 3-10 membered heterocycloalkyl ring which is optionally substituted with 1, 2, 3, or 4 $R^8$; and all groups are as defined in the Summary of the Invention or as defined in any of the embodiments described herein. In some or any embodiments, the compound of Formula I(d1) is that where $R^5$ is hydroxy; and all groups are as defined in the Summary of the Invention or as defined in any of the embodiments described herein. In some or any embodiments, the compound of Formula I(d1) is that where $R^4$ is 2,3-dihydrobenzo[b][1,4]dioxin-6-yl; and all groups are as defined in the Summary of the Invention or as defined in any of the embodiments described herein.

In some or any embodiments, the compound of Formula I is according to Formula I(d2):

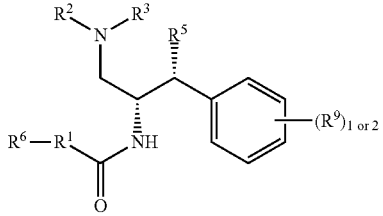

Formula I(d2)

where all groups are as defined in the Summary of the Invention or as defined in any of the embodiments described herein. In some or any embodiments, the compound of Formula I(d2) is that where $R^1$ is pyrrolidinyl attached to the C(O) by a carbon atom, and is optionally substituted with hydroxy; $R^2$ and $R^3$ together with the nitrogen to which they are attached form azetidinyl or pyrrolidinyl; $R^5$ is —OH and $R^{5a}$ is hydrogen; and each $R^9$ is independently halo, hydroxyalkoxy, cycloalkyloxy, heterocycloalkyloxy, or heterocycloalkylalkyloxy; and $R^6$ is aryl or heteroaryl, each optionally substituted with chloro, fluoro, or alkyl; or $R^6$ is phenyl optionally independently substituted with chloro or fluoro. In some or any embodiments, the compound of Formula I(d2) is that where:

$R^1$ is N—($R^6$)-azetidinyl, N—($R^6$)-pyrrolidinyl, or N—($R^6$)-piperidinyl, each of which is attached to the C(O) by a carbon atom, and is optionally substituted with hydroxy;

$R^2$ and $R^3$ together with the nitrogen to which they are attached form a 4-6 membered heterocycloalkyl ring with 1 or 2 nitrogen atoms;

$R^5$ is —OH and $R^{5a}$ is hydrogen;

$R^6$ is alkyl, aryl, arylalkyl, arylcarbonyl, cycloalkyl, cycloalkylalkyl, heterocylcoalkyl, heterocycloalkylalkyl, heteroaryl, or heteroarylalkyl; wherein the aryl and the heteroaryl, whether alone or as part of another group, are optionally substituted with 1 or 2 $R^{10}$ groups; and wherein the heterocycloalkyl and cycloalkyl, whether alone or as part of another group, are optionally substituted with 1 or 2 groups independently selected from hydroxy, halo, haloalkyl, alkoxy, and alkyl;

each $R^9$, when present, is independently cyano, nitro, halo, haloalkyl, alkyl, hydroxy, alkoxy, haloalkoxy, hydroxyalkoxy, alkenyloxy, cycloalkyloxy, cycloalkylalkyloxy, cycloalkylthio, heterocycloalkyl, heterocycloalkyloxy, or heterocycloalkylalkyloxy; where each heterocycloalkyl, either alone or as part of another group, is optionally substituted with 1 or 2 groups independently selected from alkyl, hydroxy, alkylcarbonyl, and alkoxycarbonyl groups;

each $R^{10}$, when present, is independently is cyano, halo, haloalkyl, alkyl, hydroxy, alkoxy, haloalkoxy, cycloalkyloxy, cycloalkylalkyloxy, aryl, aryloxy, heteroaryloxy, heterocycloalkyl, heterocycloalkyloxy, or heterocycloalkylalkyloxy; where each aryl or heteroaryl either alone or as part of another group, are independently optionally substituted with 1 or 2 halo or alkyl groups; and each heterocycloalkyl, either alone or as part of another group, is optionally substituted with 1 or 2 groups independently selected from alkyl and hydroxy; and optionally a tautomer, a single stereoisomer or mixture of stereoisomers thereof and additionally optionally a pharmaceutically acceptable salt thereof.

In some or any embodiments, the compound of Formula I is according to Formula I(e), Formula I(e1), or Formula I(e2):

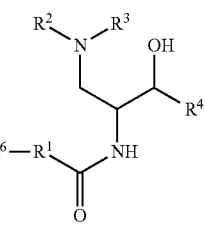

Formula I(e)

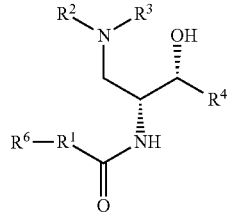

Formula I(e1)

-continued

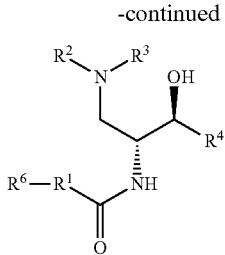

Formula I(e2)

where all groups are as defined in the Summary of the Invention or as defined in any of the embodiments described herein. In some or any embodiments, the compound of Formula I is according to Formula I(c) where:

$R^1$ is pyrrolidinyl attached to the C(O) by a carbon atom, and is optionally substituted with hydroxy;

$R^2$ and $R^3$ together with the nitrogen to which they are attached form a azetidinyl, pyrrolidinyl, or piperidinyl ring, which is optionally substituted with 1 or 2 $R^8$;

$R^6$ is aryl, arylalkyl, arylcarbonyl, cycloalkyl, cycloalkylalkyl, heterocylcoalkyl, heterocycloalkylalkyl, heteroaryl, or heteroarylalkyl; wherein the aryl and the heteroaryl, whether alone or as part of another group, are optionally substituted with 1 or 2 $R^{10}$ groups; and wherein the heterocycloalkyl and cycloalkyl, whether alone or as part of another group, are optionally substituted with 1 or 2 groups independently selected from hydroxy, halo, haloalkyl, alkoxy, and alkyl; or $R^2$ and $R^3$ together with the nitrogen to which they are attached form a azetidinyl or pyrrolidinyl ring; and $R^6$ is phenyl or naphthyl optionally substituted with chloro or fluoro.

In some or any embodiments, the compound of Formula I is according to Formula I(f), Formula I(f1), or Formula I(f2):

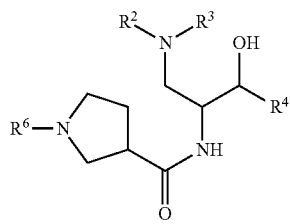

Formula I(f)

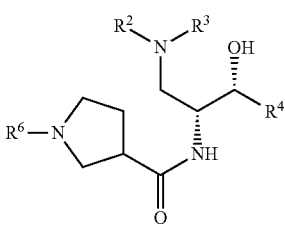

Formula I(f1)

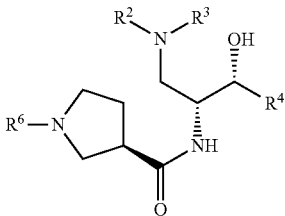

Formula I(f2)

where all groups are as defined in the Summary of the Invention or as defined in any of the embodiments described herein.

In some or any embodiments, the compound of Formula I is according to Formula I(g), Formula I(g1), Formula I(h), or Formula I(h1):

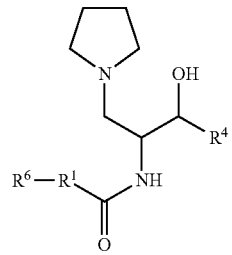

Formula I(g)

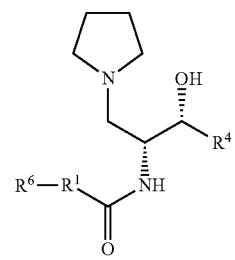

Formula I(g1)

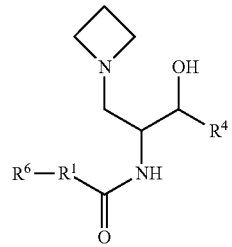

Formula I(h)

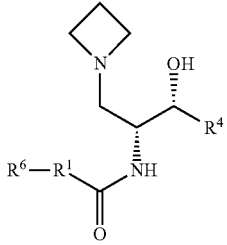

Formula I(h1)

where all groups are as defined in the Summary of the Invention or as defined in any of the embodiments described herein.

In some or any embodiments, the compound of Formula I is according to the compounds in Table 1:

TABLE 1

| Example No. | Name | Structure |
|---|---|---|
| 1C | 1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 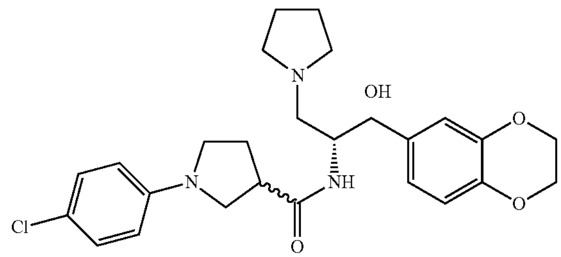 |
| 2A | 1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 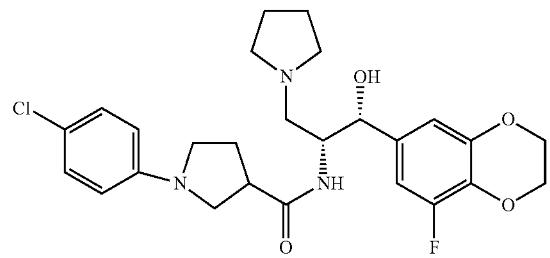 [SMILES: O=C(N[C@H](CN1CCCC1)[C@H](O)c1cc(F)c2c(c1)OCCO2)C1CCN(c2ccc(Cl)cc2)C1] |
| 3A | N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide | 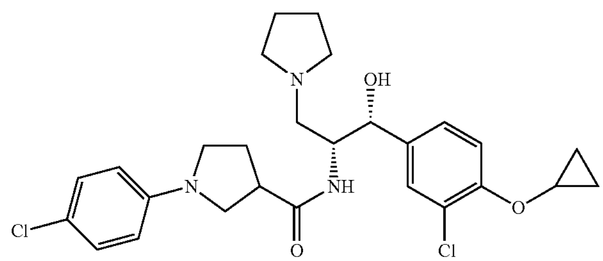 [SMILES: O=C(N[C@H](CN1CCCC1)[C@H](O)c1ccc(OC2CC2)c(Cl)c1)C1CCN(c2ccc(Cl)cc2)C1] |
| 1 | (R)-1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 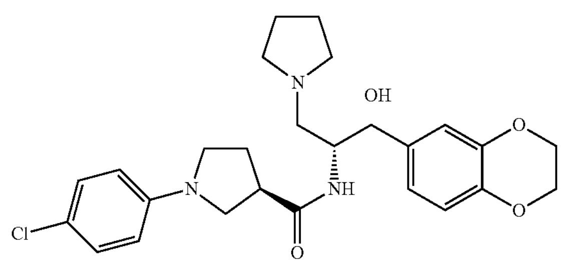 |
| 1D | (S)-1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 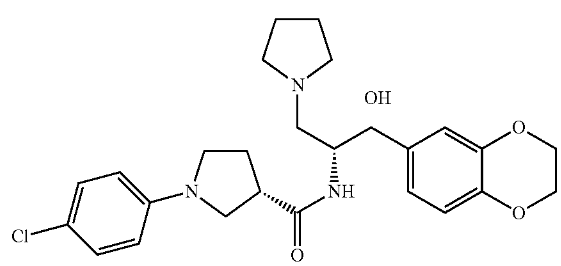 |

TABLE 1-continued

| Example No. | Name | Structure |
|---|---|---|
| 5D | N-((1R,2R)-1-(2,3-dihydrobenzo[b][1,4]dioxin-6-yl)-1-hydroxy-3-(pyrrolidin-1-yl)propan-2-yl)-1-((4-hydroxytetrahydro-2H-pyran-4-yl)methyl)pyrrolidine-3-carboxamide | 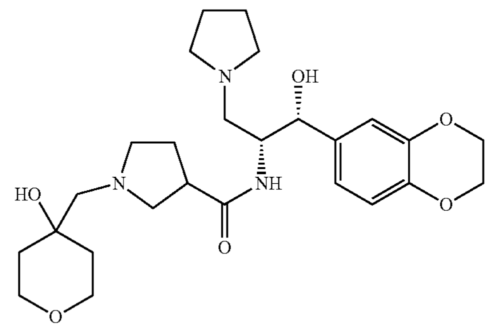 [SMILES: O=C(N[C@H](CN1CCCC1)[C@H](O)c1ccc2c(c1)OCCO2)C1CCN(CC2(O)CCOCC2)C1] |
| 6 | N-((1R,2R)-1-(3-chloro-4-cyclopropoxyphenyl)-1-hydroxy-3-(pyrrolidin-1-yl)propan-2-yl)-1-(4-(trifluoromethyl)phenyl)pyrrolidine-3-carboxamide | 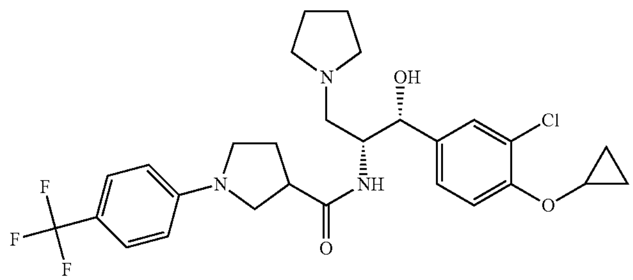 [SMILES: O=C(N[C@H](CN1CCCC1)[C@H](O)c1ccc(OC2CC2)c(Cl)c1)C1CCN(c2ccc(C(F)(F)F)cc2)C1] |
| 8D | (S)-1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 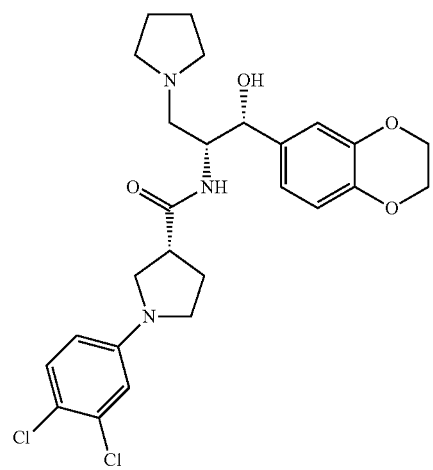 [SMILES: O=C(N[C@H](CN1CCCC1)[C@H](O)c1ccc2c(c1)OCCO2)[C@@H]1CCN(c2ccc(Cl)c(Cl)c2)C1] |
| 8 | (R)-1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 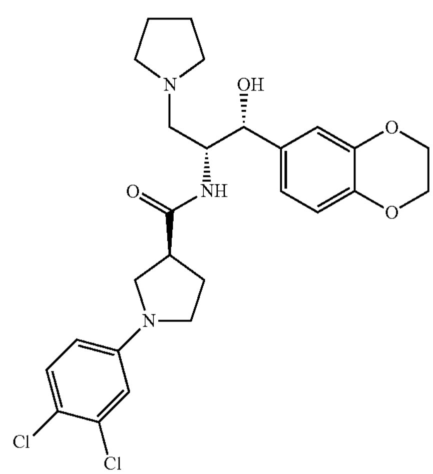 [SMILES: O=C(N[C@H](CN1CCCC1)[C@H](O)c1ccc2c(c1)OCCO2)[C@H]1CCN(c2ccc(Cl)c(Cl)c2)C1] |

TABLE 1-continued

| Example No. | Name | Structure |
|---|---|---|
| 9D | N-((1R,2R)-1-(2,3-dihydrobenzo[b][1,4]dioxin-6-yl)-1-hydroxy-3-(pyrrolidin-1-yl)propan-2-yl)-1-(tetrahydro-2H-pyran-4-yl)pyrrolidine-3-carboxamide | 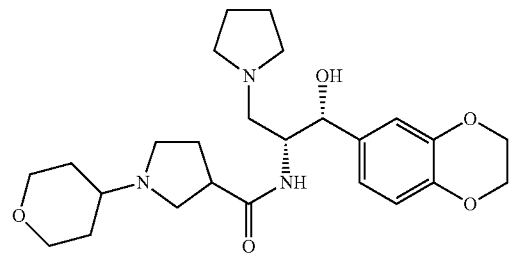 |
| 10 | N-((1R,2R)-1-(3-chloro-4-cyclopropoxyphenyl)-1-hydroxy-3-(pyrrolidin-1-yl)propan-2-yl)-1-(4-(trifluoromethoxy)phenyl)pyrrolidine-3-carboxamide | 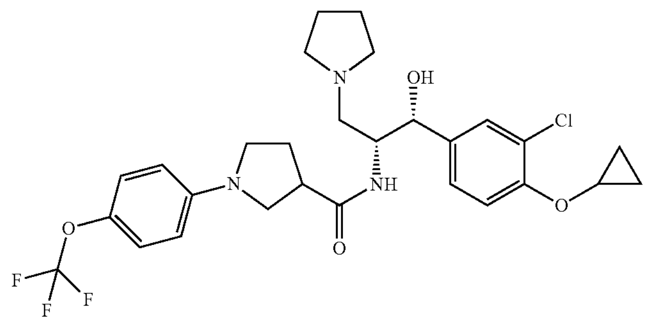 [SMILES: O=C(N[C@H](CN1CCCC1)[C@H](O)c1ccc(OC2CC2)c(Cl)c1)C1CCN(c2ccc(OC(F)(F)F)cc2)C1] |
| 5 | (R)-N-((1R,2R)-1-(2,3-dihydrobenzo[b][1,4]dioxin-6-yl)-1-hydroxy-3-(pyrrolidin-1-yl)propan-2-yl)-1-((4-hydroxytetrahydro-2H-pyran-4-yl)methyl)pyrrolidine-3-carboxamide | 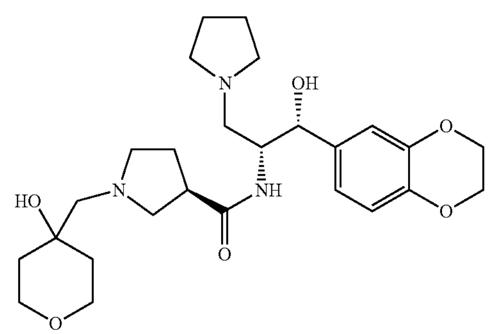 [SMILES: O=C(N[C@H](CN1CCCC1)[C@H](O)c1ccc2c(c1)OCCO2)[C@@H]1CCN(CC2(O)CCOCC2)C1] |
| 5E | (S)-N-((1R,2R)-1-(2,3-dihydrobenzo[b][1,4]dioxin-6-yl)-1-hydroxy-3-(pyrrolidin-1-yl)propan-2-yl)-1-((4-hydroxytetrahydro-2H-pyran-4-yl)methyl)pyrrolidine-3-carboxamide | 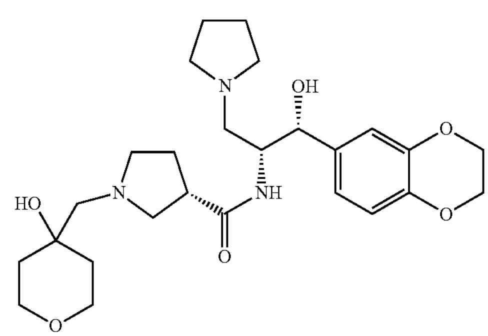 [SMILES: O=C(N[C@H](CN1CCCC1)[C@H](O)c1ccc2c(c1)OCCO2)[C@H]1CCN(CC2(O)CCOCC2)C1] |

TABLE 1-continued

| Example No. | Name | Structure |
|---|---|---|
| 11 | 1-cyclopentyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 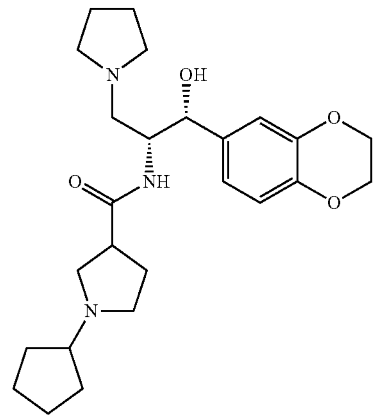 [SMILES: O=C(N[C@H](CN1CCCC1)[C@H](O)c1ccc2c(c1)OCCO2)C1CCN(C2CCCC2)C1] |
| 12D | (S)-1-(2,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 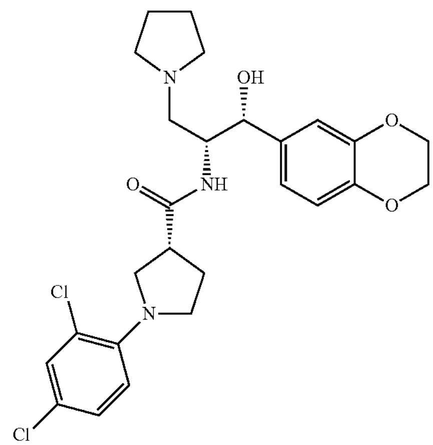 [SMILES: O=C(N[C@H](CN1CCCC1)[C@H](O)c1ccc2c(c1)OCCO2)[C@@H]1CCN(c2ccc(Cl)cc2Cl)C1] |
| 12 | (R)-1-(2,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 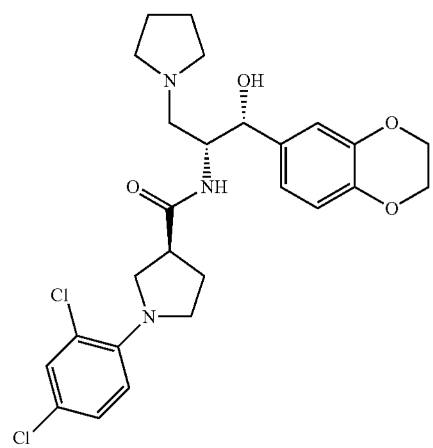 [SMILES: O=C(N[C@H](CN1CCCC1)[C@H](O)c1ccc2c(c1)OCCO2)[C@H]1CCN(c2ccc(Cl)cc2Cl)C1] |
| 13 | (R)-1-(4-chlorophenyl)-N-((1R,2R)-1-(6-cyclopropoxypyridin-3-yl)-1-hydroxy-3-(pyrrolidin-1-yl)propan-2-yl)pyrrolidine-3-carboxamide | 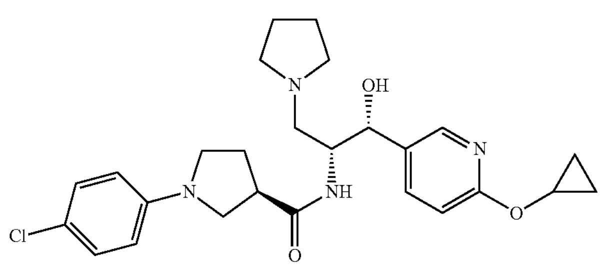 [SMILES: O=C(N[C@H](CN1CCCC1)[C@H](O)c1ccc(OC2CC2)nc1)[C@@H]1CCN(c2ccc(Cl)cc2)C1] |

TABLE 1-continued

| Example No. | Name | Structure |
|---|---|---|
| 13C | (S)-1-(4-chlorophenyl)-N-((1R,2R)-1-(6-cyclopropoxypyridin-3-yl)-1-hydroxy-3-(pyrrolidin-1-yl)propan-2-yl)pyrrolidine-3-carboxamide | 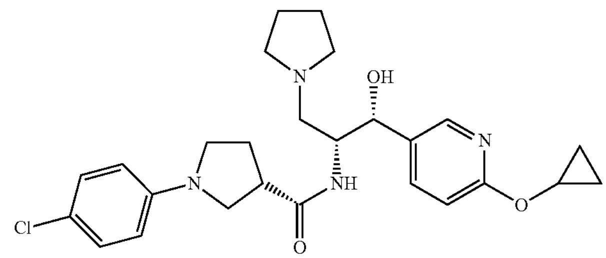 |
| 14C | N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide | 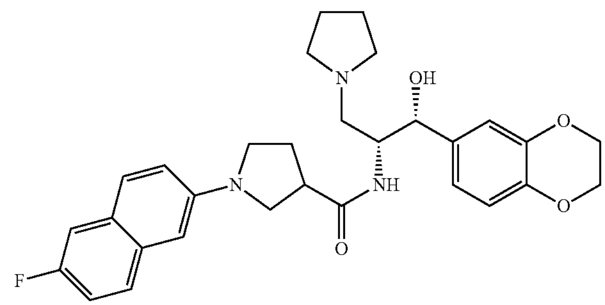 [SMILES: O=C(N[C@H](CN1CCCC1)[C@H](O)c1ccc2c(c1)OCCO2)C1CCN(c2ccc3cc(F)ccc3c2)C1] |
| 2 | (R)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 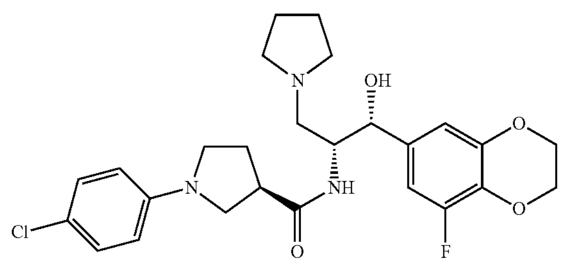 [SMILES: O=C(N[C@H](CN1CCCC1)[C@H](O)c1cc(F)c2c(c1)OCCO2)[C@@H]1CCN(c2ccc(Cl)cc2)C1] |
| 2B | (S)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 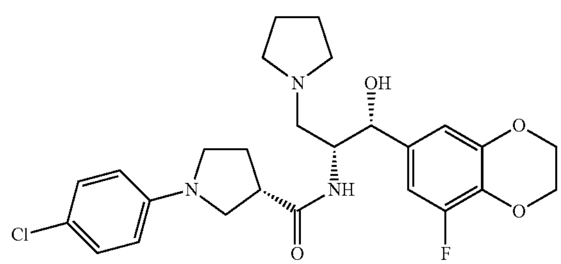 [SMILES: O=C(N[C@H](CN1CCCC1)[C@H](O)c1cc(F)c2c(c1)OCCO2)[C@H]1CCN(c2ccc(Cl)cc2)C1] |
| 3 | (S)-N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide | 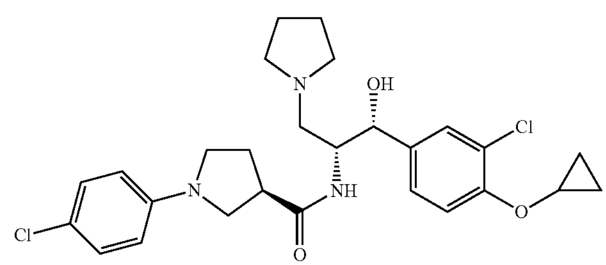 [SMILES: O=C(N[C@H](CN1CCCC1)[C@H](O)c1ccc(OC2CC2)c(Cl)c1)[C@@H]1CCN(c2ccc(Cl)cc2)C1] |

TABLE 1-continued

| Example No. | Name | Structure |
|---|---|---|
| 3B | (R)-N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide | 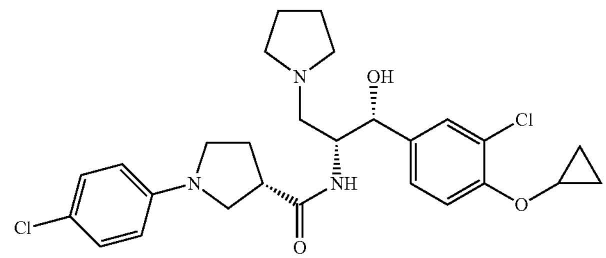 [SMILES: O=C(N[C@H](CN1CCCC1)[C@H](O)c1ccc(OC2CC2)c(Cl)c1)[C@H]1CCN(c2ccc(Cl)cc2)C1] |
| 9 | (R)-N-((1R,2R)-1-(2,3-dihydrobenzo[b][1,4]dioxin-6-yl)-1-hydroxy-3-(pyrrolidin-1-yl)propan-2-yl)-1-(tetrahydro-2H-pyran-4-yl)pyrrolidine-3-carboxamide | 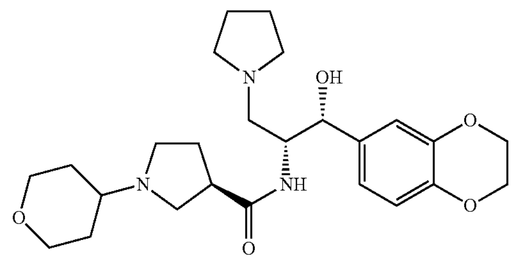 [SMILES: O=C(N[C@H](CN1CCCC1)[C@H](O)c1ccc2c(c1)OCCO2)[C@@H]1CCN(C2CCOCC2)C1] |
| 9E | (S)-N-((1R,2R)-1-(2,3-dihydrobenzo[b][1,4]dioxin-6-yl)-1-hydroxy-3-(pyrrolidin-1-yl)propan-2-yl)-1-(tetrahydro-2H-pyran-4-yl)pyrrolidine-3-carboxamide | 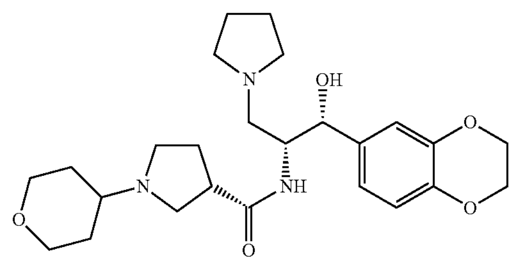 |
| 15C | 1-(4-chlorobenzyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 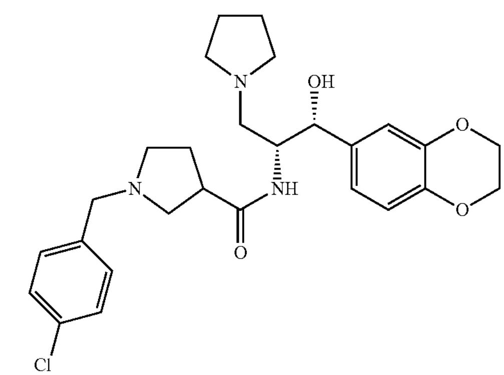 [SMILES: O=C(N[C@H](CN1CCCC1)[C@H](O)c1ccc2c(c1)OCCO2)C1CCN(Cc2ccc(Cl)cc2)C1] |
| 14D | (R)-N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide | 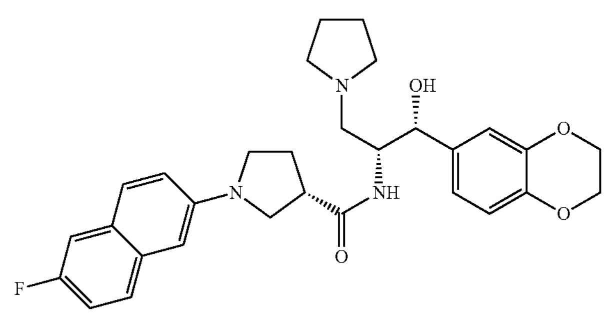 [SMILES: O=C(N[C@H](CN1CCCC1)[C@H](O)c1ccc2c(c1)OCCO2)[C@H]1CCN(c2ccc3cc(F)ccc3c2)C1] |

TABLE 1-continued

| Example No. | Name | Structure |
|---|---|---|
| 14 | (S)-N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide | 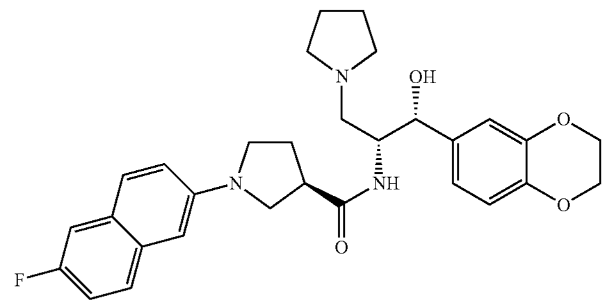 [SMILES: O=C(N[C@H](CN1CCCC1)[C@H](O)c1ccc2c(c1)OCCO2)[C@@H]1CCN(c2ccc3cc(F)ccc3c2)C1] |
| 36F | N-((1R,2R)-1-(2,3-dihydrobenzo[b][1,4]dioxin-6-yl)-1-hydroxy-3-(pyrrolidin-1-yl)propan-2-yl)-1-(4,5,6,7-tetrahydrobenzo[d]thiazol-2-yl)pyrrolidine-3-carboxamide | 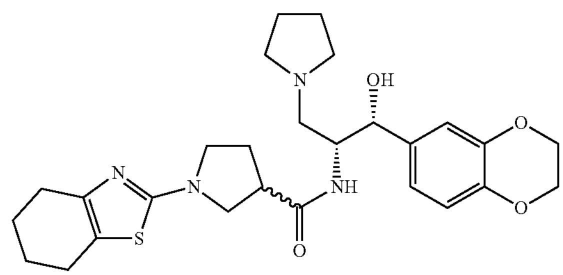 [SMILES: O=C(N[C@H](CN1CCCC1)[C@H](O)c1ccc2c(c1)OCCO2)C1CCN(c2nc3c(s2)CCCC3)C1] |
| 17D | (S)-N-((1R,2R)-1-(2,3-dihydrobenzo[b][1,4]dioxin-6-yl)-1-hydroxy-3-(pyrrolidin-1-yl)propan-2-yl)-1-(thiazol-2-yl)pyrrolidine-3-carboxamide | 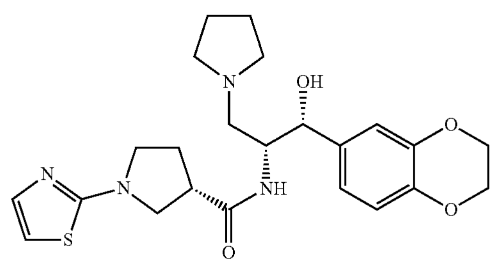 [SMILES: O=C(N[C@H](CN1CCCC1)[C@H](O)c1ccc2c(c1)OCCO2)[C@H]1CCN(c2nccs2)C1] |
| 19 | 1-(4-chloro-3-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 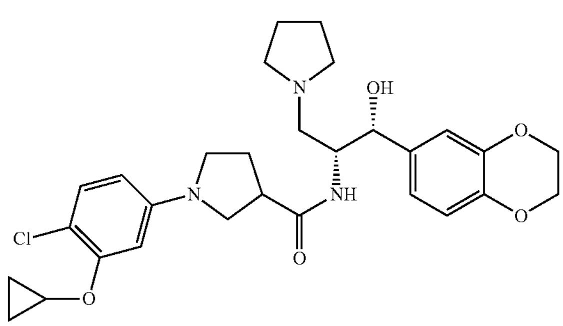 [SMILES: O=C(N[C@H](CN1CCCC1)[C@H](O)c1ccc2c(c1)OCCO2)C1CCN(c2ccc(Cl)c(OC3CC3)c2)C1] |

TABLE 1-continued

| Example No. | Name | Structure |
|---|---|---|
| 20D | 1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 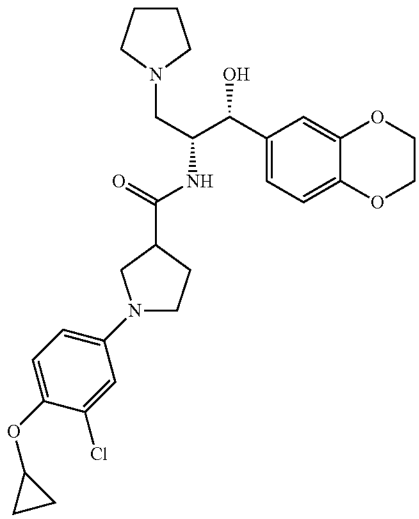 [SMILES: O=C(N[C@H](CN1CCCC1)[C@H](O)c1ccc2c(c1)OCCO2)C1CCN(c2ccc(OC3CC3)c(Cl)c2)C1] |
| 22C | N-((1R,2R)-1-(2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | 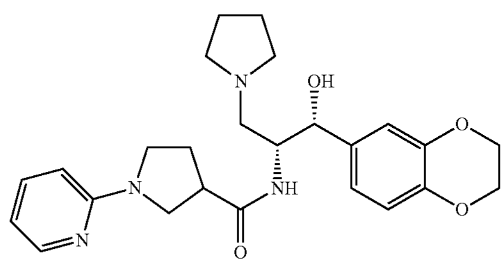 [SMILES: O=C(N[C@H](CN1CCCC1)[C@H](O)c1ccc2c(c1)OCCO2)C1CCN(c2ccccn2)C1] |
| 17 | (R)-N-((1R,2R)-1-(2,3-dihydrobenzo[b][1,4]dioxin-6-yl)-1-hydroxy-3-(pyrrolidin-1-yl)propan-2-yl)-1-(thiazol-2-yl)pyrrolidine-3-carboxamide | 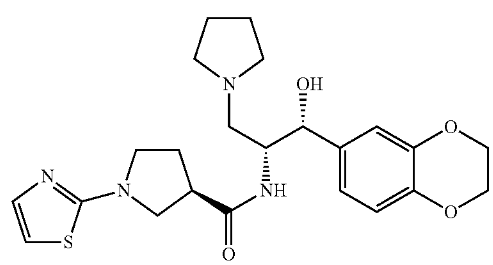 [SMILES: O=C(N[C@H](CN1CCCC1)[C@H](O)c1ccc2c(c1)OCCO2)[C@@H]1CCN(c2nccs2)C1] |
| 21E | 1-(4-chlorophenethyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 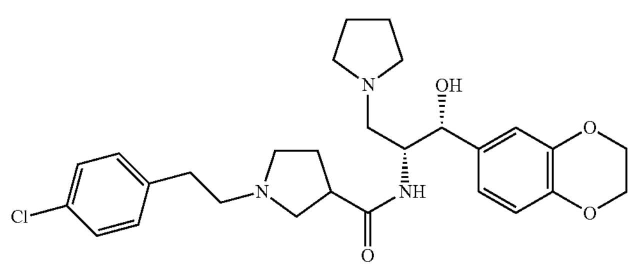 [SMILES: O=C(N[C@H](CN1CCCC1)[C@H](O)c1ccc2c(c1)OCCO2)C1CCN(CCc2ccc(Cl)cc2)C1] |

TABLE 1-continued

| Example No. | Name | Structure |
|---|---|---|
| 15 | (R)-1-(4-chlorobenzyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 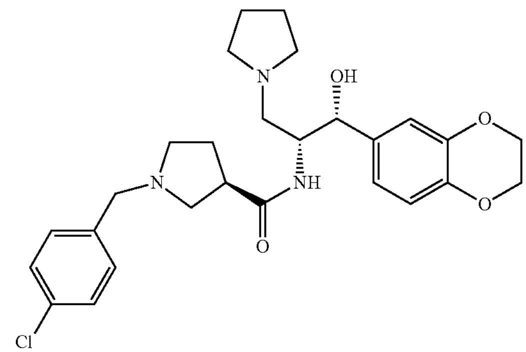 [SMILES: O=C(N[C@H](CN1CCCC1)[C@H](O)c1ccc2c(c1)OCCO2)[C@@H]1CCN(Cc2ccc(Cl)cc2)C1] |
| 15D | (S)-1-(4-chlorobenzyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 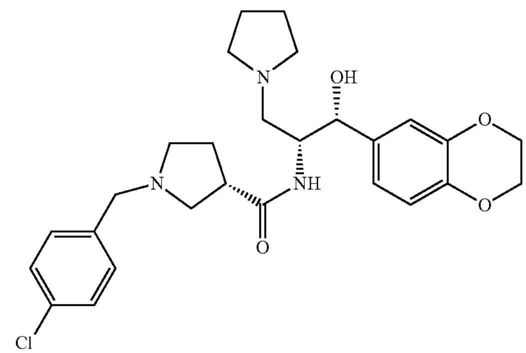 [SMILES: O=C(N[C@H](CN1CCCC1)[C@H](O)c1ccc2c(c1)OCCO2)[C@H]1CCN(Cc2ccc(Cl)cc2)C1] |
| 36 | (R)-N-((1R,2R)-1-(2,3-dihydrobenzo[b][1,4]dioxin-6-yl)-1-hydroxy-3-(pyrrolidin-1-yl)propan-2-yl)-1-(4,5,6,7-tetrahydrobenzo[d]thiazol-2-yl)pyrrolidine-3-carboxamide | 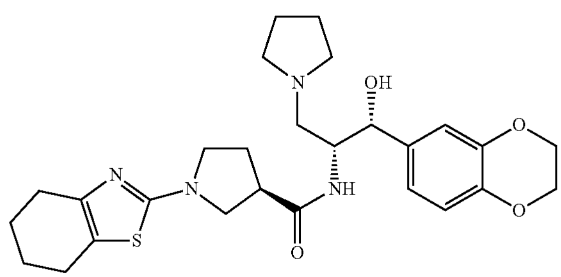 [SMILES: O=C(N[C@H](CN1CCCC1)[C@H](O)c1ccc2c(c1)OCCO2)[C@@H]1CCN(c2nc3c(s2)CCCC3)C1] |
| 36G | (S)-N-((1R,2R)-1-(2,3-dihydrobenzo[b][1,4]dioxin-6-yl)-1-hydroxy-3-(pyrrolidin-1-yl)propan-2-yl)-1-(4,5,6,7-tetrahydrobenzo[d]thiazol-2-yl)pyrrolidine-3-carboxamide | 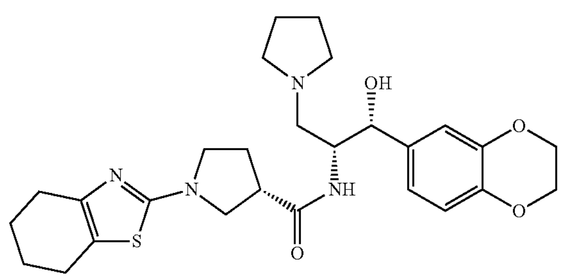 [SMILES: O=C(N[C@H](CN1CCCC1)[C@H](O)c1ccc2c(c1)OCCO2)[C@H]1CCN(c2nc3c(s2)CCCC3)C1] |
| 20 | (R)-1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 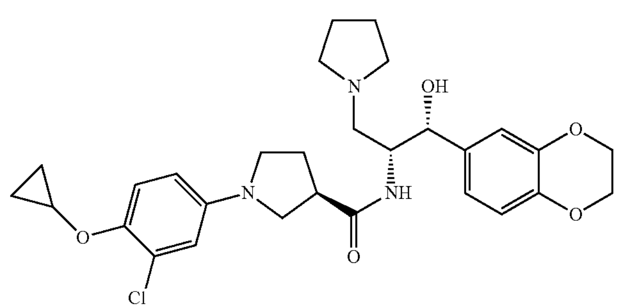 [SMILES: O=C(N[C@H](CN1CCCC1)[C@H](O)c1ccc2c(c1)OCCO2)[C@@H]1CCN(c2ccc(OC3CC3)c(Cl)c2)C1] |

TABLE 1-continued

| Example No. | Name | Structure |
|---|---|---|
| 20E | (S)-1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 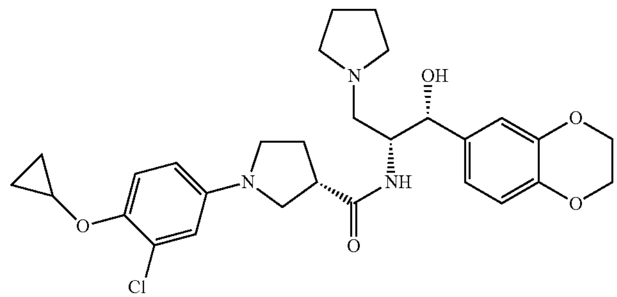 [SMILES: O=C(N[C@H](CN1CCCC1)[C@H](O)c1ccc2c(c1)OCCO2)[C@H]1CCN(c2ccc(OC3CC3)c(Cl)c2)C1] |
| 23 | (R)-N-((1R,2R)-1-(3-chloro-4-isopropoxyphenyl)-1-hydroxy-3-(pyrrolidin-1-yl)propan-2-yl)-1-(4-chlorophenyl)pyrrolidine-3-carboxamide | 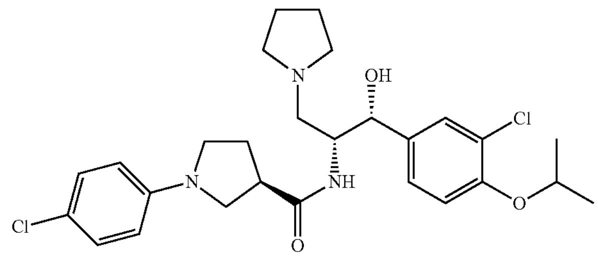 [SMILES: CC(C)Oc1ccc([C@@H](O)[C@@H](CN2CCCC2)NC(=O)[C@@H]2CCN(c3ccc(Cl)cc3)C2)cc1Cl] |
| 23B | (S)-N-((1R,2R)-1-(3-chloro-4-isopropoxyphenyl)-1-hydroxy-3-(pyrrolidin-1-yl)propan-2-yl)-1-(4-chlorophenyl)pyrrolidine-3-carboxamide | 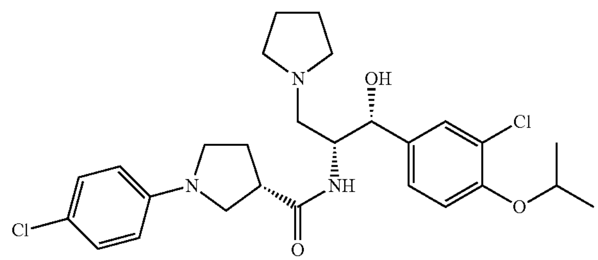 [SMILES: CC(C)Oc1ccc([C@@H](O)[C@@H](CN2CCCC2)NC(=O)[C@H]2CCN(c3ccc(Cl)cc3)C2)cc1Cl] |
| 24B | N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | 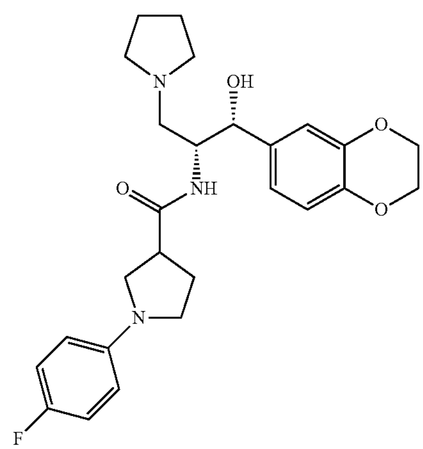 [SMILES: O=C(N[C@H](CN1CCCC1)[C@H](O)c1ccc2c(c1)OCCO2)C1CCN(c2ccc(F)cc2)C1] |
| 25 | (R)-N-((1R,2R)-3-(azetidin-1-yl)-1-(8-fluoro-2,3-dihydrobenzo[b][1,4]dioxin-6-yl)-1-hydroxypropan-2-yl)-1-(4-chlorophenyl)pyrrolidine-3-carboxamide | 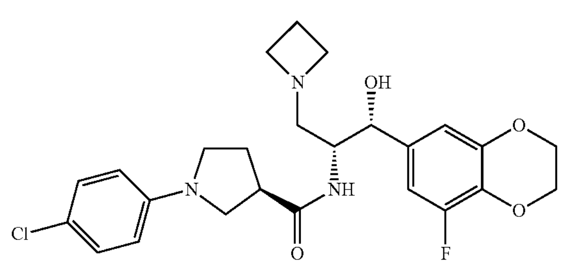 [SMILES: O=C(N[C@H](CN1CCC1)[C@H](O)c1cc(F)c2c(c1)OCCO2)[C@@H]1CCN(c2ccc(Cl)cc2)C1] |

TABLE 1-continued

| Example No. | Name | Structure |
|---|---|---|
| 25B | (S)-N-((1R,2R)-3-(azetidin-1-yl)-1-(8-fluoro-2,3-dihydrobenzo[b][1,4]dioxin-6-yl)-1-hydroxypropan-2-yl)-1-(4-chlorophenyl)pyrrolidine-3-carboxamide | 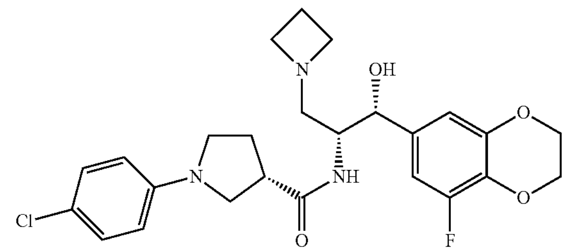 [SMILES: O=C(N[C@H](CN1CCC1)[C@H](O)c1cc(F)c2c(c1)OCCO2)[C@H]1CCN(c2ccc(Cl)cc2)C1] |
| 26 | 1-cyclohexyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 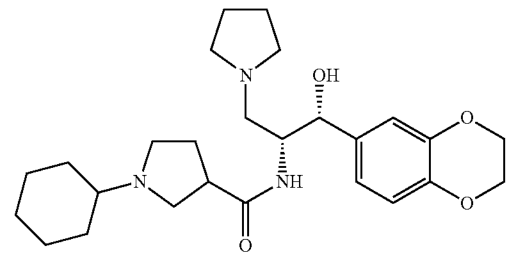 [SMILES: O=C(N[C@H](CN1CCCC1)[C@H](O)c1ccc2c(c1)OCCO2)C1CCN(C2CCCCC2)C1] |
| 27 | (R)-N-((1R,2R)-1-(6-cyclopropoxypyridin-3-yl)-1-hydroxy-3-(pyrrolidin-1-yl)propan-2-yl)-1-(4-fluorophenyl)pyrrolidine-3-carboxamide | 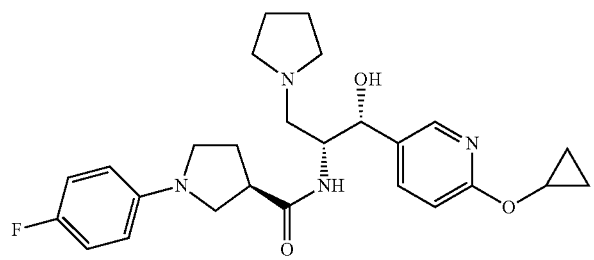 [SMILES: O=C(N[C@H](CN1CCCC1)[C@H](O)c1ccc(OC2CC2)nc1)[C@@H]1CCN(c2ccc(F)cc2)C1] |
| 27C | (S)-N-((1R,2R)-1-(6-cyclopropoxypyridin-3-yl)-1-hydroxy-3-(pyrrolidin-1-yl)propan-2-yl)-1-(4-fluorophenyl)pyrrolidine-3-carboxamide | 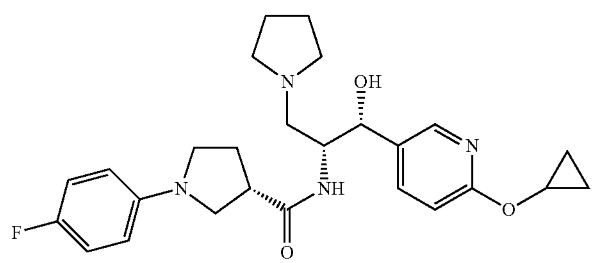 [SMILES: O=C(N[C@H](CN1CCCC1)[C@H](O)c1ccc(OC2CC2)nc1)[C@H]1CCN(c2ccc(F)cc2)C1] |
| 28C | 1-(5-chloropyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 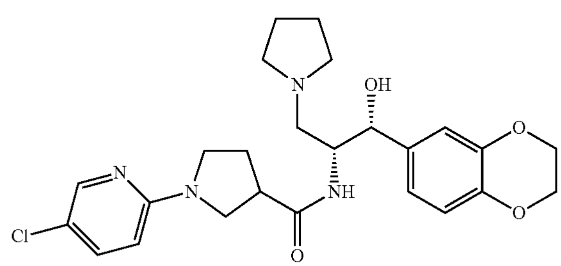 [SMILES: O=C(N[C@H](CN1CCCC1)[C@H](O)c1ccc2c(c1)OCCO2)C1CCN(c2ccc(Cl)cn2)C1] |
| 22 | (R)-N-((1R,2R)-1-(2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | 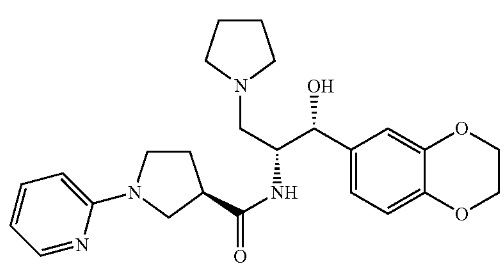 [SMILES: O=C(N[C@H](CN1CCCC1)[C@H](O)c1ccc2c(c1)OCCO2)[C@@H]1CCN(c2ccccn2)C1] |

TABLE 1-continued

| Example No. | Name | Structure |
|---|---|---|
| 22D | (S)-N-((1R,2R)-1-(2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | 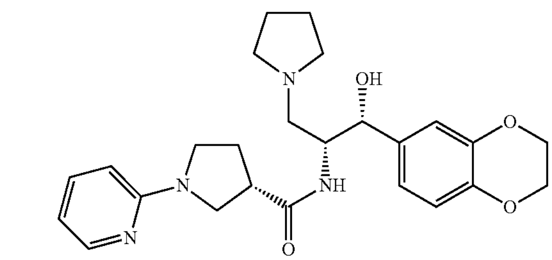 [SMILES: O=C(N[C@H](CN1CCCC1)[C@H](O)c1ccc2c(c1)OCCO2)[C@H]1CCN(c2ccccn2)C1] |
| 29 | (R)-1-(4-chlorophenyl)-N-((1R,2R)-1-hydroxy-1-(6-isopropoxypyridin-3-yl)-3-(pyrrolidin-1-yl)propan-2-yl)pyrrolidine-3-carboxamide | 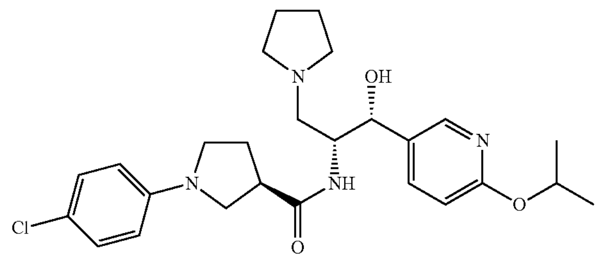 [SMILES: CC(C)Oc1ccc([C@@H](O)[C@@H](CN2CCCC2)NC(=O)[C@@H]2CCN(c3ccc(Cl)cc3)C2)cn1] |
| 29B | (S)-1-(4-chlorophenyl)-N-((1R,2R)-1-hydroxy-1-(6-isopropoxypyridin-3-yl)-3-(pyrrolidin-1-yl)propan-2-yl)pyrrolidine-3-carboxamide | 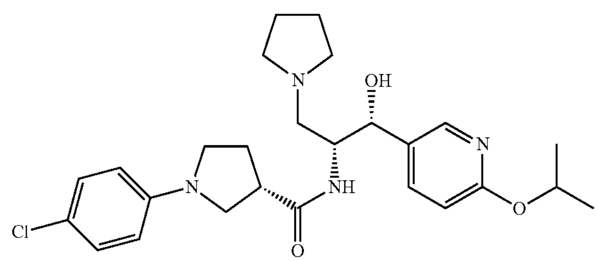 [SMILES: CC(C)Oc1ccc([C@@H](O)[C@@H](CN2CCCC2)NC(=O)[C@H]2CCN(c3ccc(Cl)cc3)C2)cn1] |
| 30 | 1-butyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 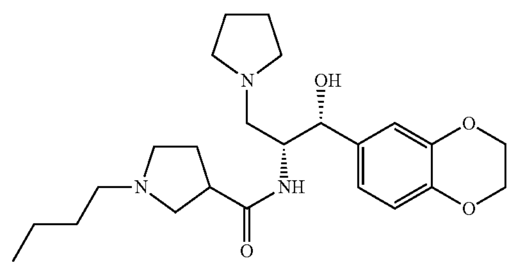 [SMILES: CCCCN1CCC(C(=O)N[C@H](CN2CCCC2)[C@H](O)c2ccc3c(c2)OCCO3)C1] |
| 31 | (R)-1-(4-fluorophenyl)-N-((1R,2R)-1-hydroxy-1-(6-isopropoxypyridin-3-yl)-3-(pyrrolidin-1-yl)propan-2-yl)pyrrolidine-3-carboxamide | 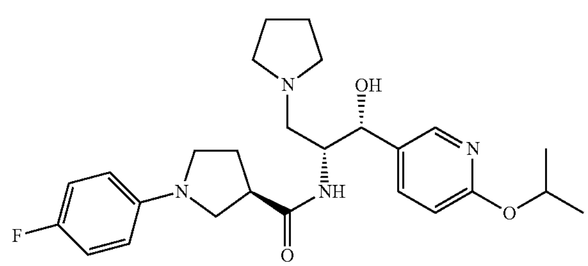 [SMILES: CC(C)Oc1ccc([C@@H](O)[C@@H](CN2CCCC2)NC(=O)[C@@H]2CCN(c3ccc(F)cc3)C2)cn1] |
| 31B | (S)-1-(4-fluorophenyl)-N-((1S,2R)-1-hydroxy-1-(6-isopropoxypyridin-3-yl)-3-(pyrrolidin-1-yl)propan-2-yl)pyrrolidine-3-carboxamide | 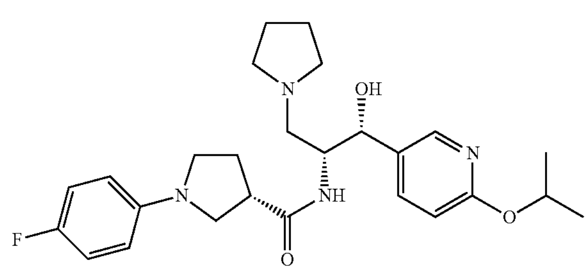 [SMILES: CC(C)Oc1ccc([C@@H](O)[C@@H](CN2CCCC2)NC(=O)[C@H]2CCN(c3ccc(F)cc3)C2)cn1] |

TABLE 1-continued

| Example No. | Name |
|---|---|
| 32 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(4-fluorophenyl)pyrrolidine-3-carboxamide |
| 32A | (S)-N-((1R,2R)-1-(3-chloro-4-((tetrahydro-2H-pyran-4-yl)oxy)phenyl)-1-hydroxy-3-(pyrrolidin-1-yl)propan-2-yl)-1-(4-fluorophenyl)pyrrolidine-3-carboxamide |
| 21 | (R)-1-(4-chlorophenethyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide |
| 21F | (S)-1-(4-chlorophenethyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide |
| 28 | (R)-1-(5-chloropyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide |
| 28D | (S)-1-(5-chloropyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide |

TABLE 1-continued

| Example No. | Name | Structure |
|---|---|---|
| 54 | (R)-N-((1R,2R)-1-(3-chloro-4-cyclopropoxyphenyl)-1-hydroxy-3-(pyrrolidin-1-yl)propan-2-yl)-1-(pyridin-2-yl)pyrrolidine-3-carboxamide | 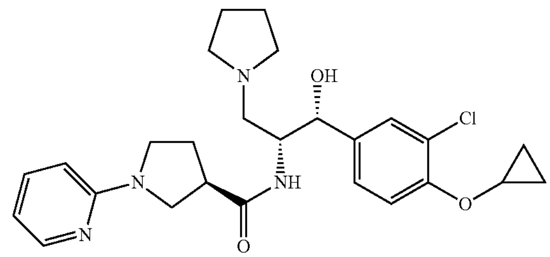 [SMILES: O=C(N[C@H](CN1CCCC1)[C@H](O)c1ccc(OC2CC2)c(Cl)c1)[C@@H]1CCN(c2ccccn2)C1] |
| 33 | (R)-1-(4-chlorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide | 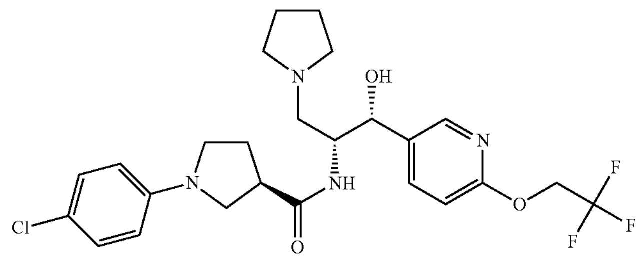 [SMILES: O=C(N[C@H](CN1CCCC1)[C@H](O)c1ccc(OCC(F)(F)F)nc1)[C@@H]1CCN(c2ccc(Cl)cc2)C1] |
| 33A | (S)-1-(4-chlorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide | 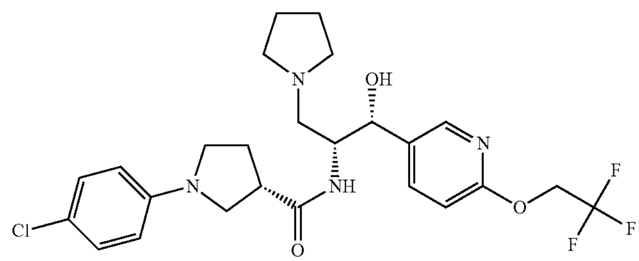 [SMILES: O=C(N[C@H](CN1CCCC1)[C@H](O)c1ccc(OCC(F)(F)F)nc1)[C@H]1CCN(c2ccc(Cl)cc2)C1] |
| 34 | (R)-1-(4-fluorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide | 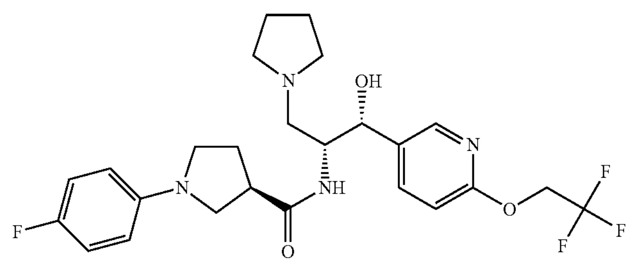 [SMILES: O=C(N[C@H](CN1CCCC1)[C@H](O)c1ccc(OCC(F)(F)F)nc1)[C@@H]1CCN(c2ccc(F)cc2)C1] |
| 34A | (S)-1-(4-fluorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide | 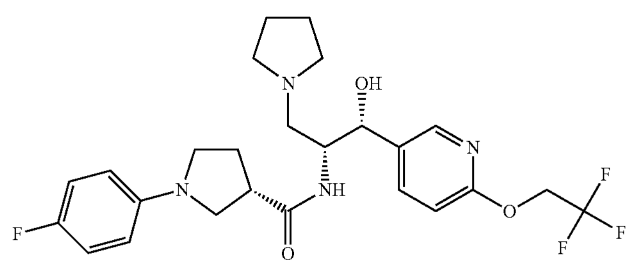 [SMILES: O=C(N[C@H](CN1CCCC1)[C@H](O)c1ccc(OCC(F)(F)F)nc1)[C@H]1CCN(c2ccc(F)cc2)C1] |
| 24 | (R)-N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | 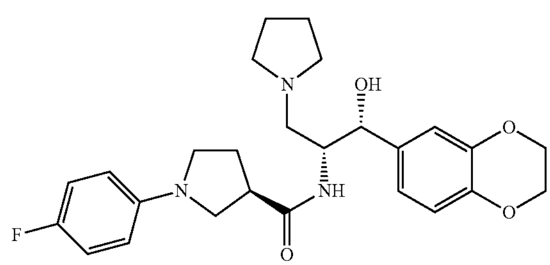 [SMILES: O=C(N[C@H](CN1CCCC1)[C@H](O)c1ccc2c(c1)OCCO2)[C@@H]1CCN(c2ccc(F)cc2)C1] |

TABLE 1-continued

| Example No. | Name | Structure |
|---|---|---|
| 24C | (S)-N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | 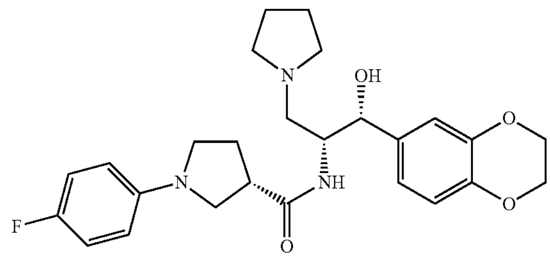 [SMILES: O=C(N[C@H](CN1CCCC1)[C@H](O)c1ccc2c(c1)OCCO2)[C@H]1CCN(c2ccc(F)cc2)C1] |
| 35 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | 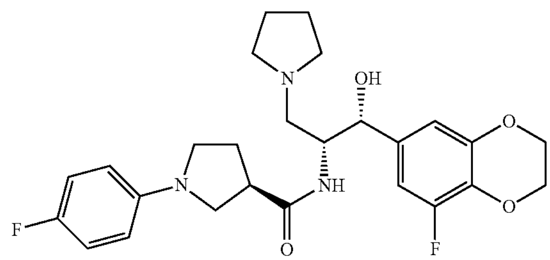 [SMILES: O=C(N[C@H](CN1CCCC1)[C@H](O)c1cc(F)c2c(c1)OCCO2)[C@@H]1CCN(c2ccc(F)cc2)C1] |
| 35A | (S)-N-((1R,2R)-1-(8-fluoro-2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | 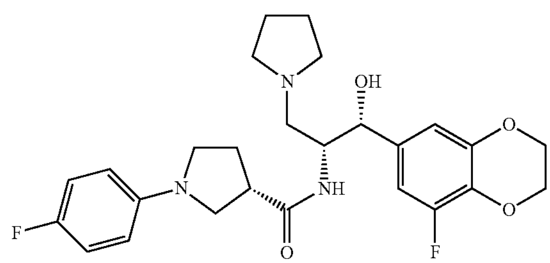 [SMILES: O=C(N[C@H](CN1CCCC1)[C@H](O)c1cc(F)c2c(c1)OCCO2)[C@H]1CCN(c2ccc(F)cc2)C1] |
| 44C | (S)-1-(4-chlorophenyl)-N-((1R,2R)-1-(8-fluoro-2,3-dihydrobenzo[b][1,4]dioxin-6-yl)-1-hydroxy-3-(piperidin-1-yl)propan-2-yl)pyrrolidine-3-carboxamide | 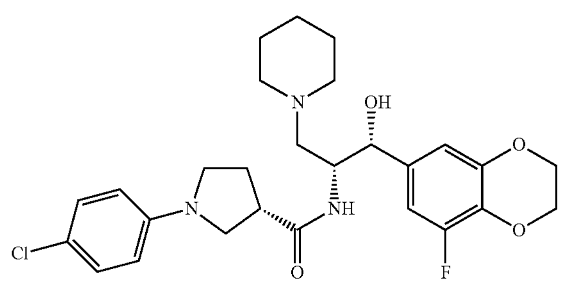 [SMILES: O=C(N[C@H](CN1CCCCC1)[C@H](O)c1cc(F)c2c(c1)OCCO2)[C@H]1CCN(c2ccc(Cl)cc2)C1] |
| 44 | (R)-1-(4-chlorophenyl)-N-((1R,2R)-1-(8-fluoro-2,3-dihydrobenzo[b][1,4]dioxin-6-yl)-1-hydroxy-3-(piperidin-1-yl)propan-2-yl)pyrrolidine-3-carboxamide | 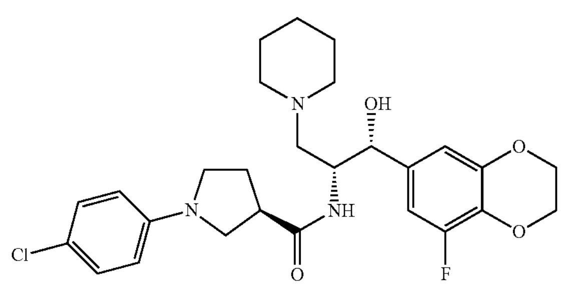 [SMILES: O=C(N[C@H](CN1CCCCC1)[C@H](O)c1cc(F)c2c(c1)OCCO2)[C@@H]1CCN(c2ccc(Cl)cc2)C1] |

TABLE 1-continued

| Example No. | Name | Structure |
|---|---|---|
| 43D | 1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide | 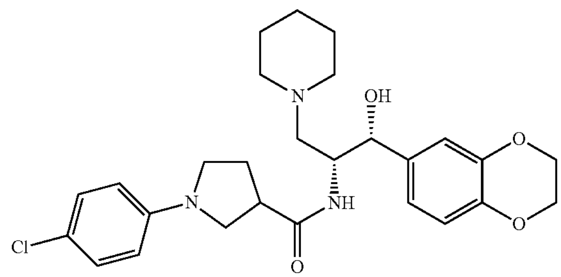 |
| 54A | (S)-N-((1R,2R)-1-(3-chloro-4-cyclopropoxyphenyl)-1-hydroxy-3-(pyrrolidin-1-yl)propan-2-yl)-1-(pyridin-2-yl)pyrrolidine-3-carboxamide | 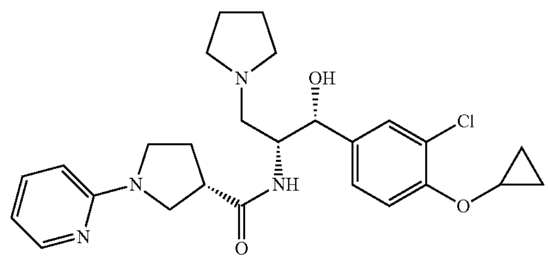 [SMILES: O=C(N[C@H](CN1CCCC1)[C@H](O)c1ccc(OC2CC2)c(Cl)c1)[C@H]1CCN(c2ccccn2)C1] |
| 45 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(4-chlorophenyl)pyrrolidine-3-carboxamide | 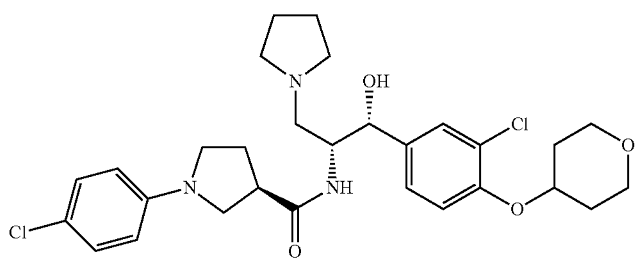 [SMILES: O=C(N[C@H](CN1CCCC1)[C@H](O)c1ccc(OC2CCOCC2)c(Cl)c1)[C@@H]1CCN(c2ccc(Cl)cc2)C1] |
| 45A | (S)-N-((1R,2R)-1-(3-chloro-4-((tetrahydro-2H-pyran-4-yl)oxy)phenyl)-1-hydroxy-3-(pyrrolidin-1-yl)propan-2-yl)-1-(4-chlorophenyl)pyrrolidine-3-carboxamide | 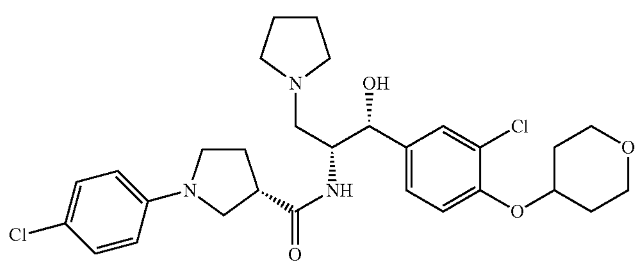 [SMILES: O=C(N[C@H](CN1CCCC1)[C@H](O)c1ccc(OC2CCOCC2)c(Cl)c1)[C@H]1CCN(c2ccc(Cl)cc2)C1] |
| 55A | 1-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 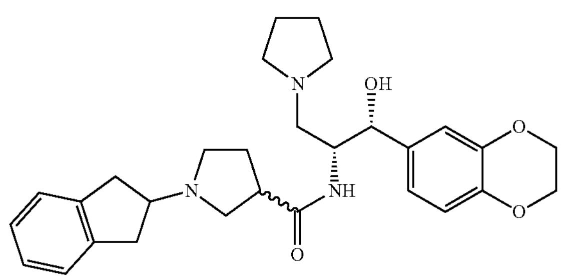 [SMILES: O=C(N[C@H](CN1CCCC1)[C@H](O)c1ccc2c(c1)OCCO2)C1CCN(C2Cc3ccccc3C2)C1] |

TABLE 1-continued

| Example No. | Name | Structure |
|---|---|---|
| 56D | 1-(2-cyclopropoxypyridin-4-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 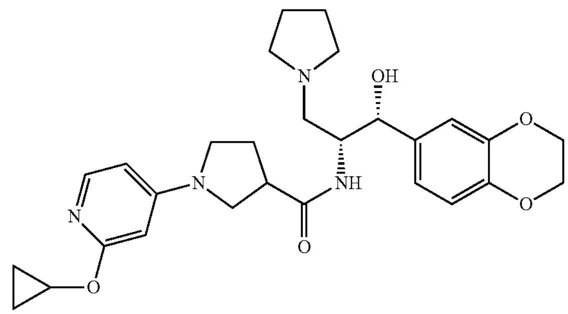 [SMILES: O=C(N[C@H](CN1CCCC1)[C@H](O)c1ccc2c(c1)OCCO2)C1CCN(c2ccnc(OC3CC3)c2)C1] |
| 46A | N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide | 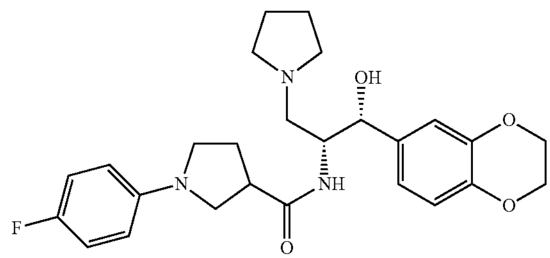 [SMILES: O=C(N[C@H](CN1CCCC1)[C@H](O)c1ccc2c(c1)OCCO2)C1CCN(c2ccc(F)cc2)C1] |
| 47A | N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide | 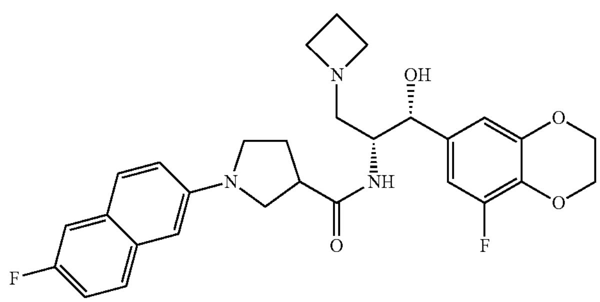 [SMILES: O=C(N[C@H](CN1CCC1)[C@H](O)c1cc(F)c2c(c1)OCCO2)C1CCN(c2ccc3cc(F)ccc3c2)C1] |
| 48 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | 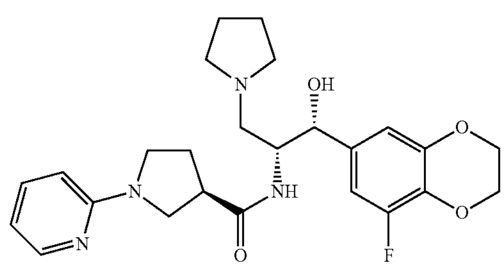 [SMILES: O=C(N[C@H](CN1CCCC1)[C@H](O)c1cc(F)c2c(c1)OCCO2)[C@@H]1CCN(c2ccccn2)C1] |
| 48A | (S)-N-((1R,2R)-1-(8-fluoro-2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | 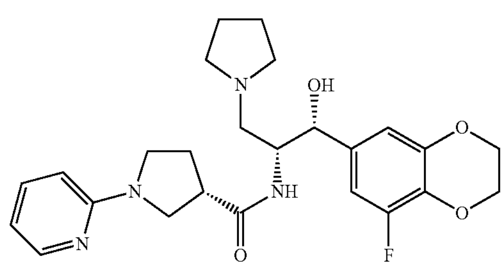 [SMILES: O=C(N[C@H](CN1CCCC1)[C@H](O)c1cc(F)c2c(c1)OCCO2)[C@H]1CCN(c2ccccn2)C1] |

TABLE 1-continued

| Example No. | Name | Structure |
|---|---|---|
| 49 | (R)-N-((1R,2R)-1-(3-chloro-4-((1-methylpiperidin-4-yl)oxy)phenyl)-1-hydroxy-3-(pyrrolidin-1-yl)propan-2-yl)-1-(4-chlorophenyl)pyrrolidine-3-carboxamide | 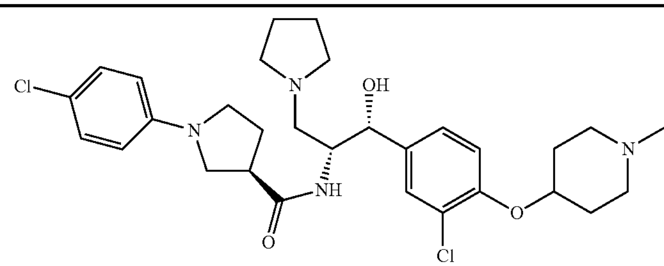 |
| 49A | (S)-N-((1R,2R)-1-(3-chloro-4-((1-methylpiperidin-4-yl)oxy)phenyl)-1-hydroxy-3-(pyrrolidin-1-yl)propan-2-yl)-1-(4-chlorophenyl)pyrrolidine-3-carboxamide | 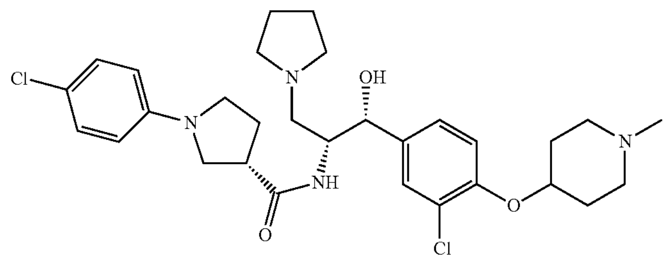 [SMILES: CN1CCC(Oc2ccc([C@@H](O)[C@@H](CN3CCCC3)NC(=O)[C@H]3CCN(c4ccc(Cl)cc4)C3)cc2Cl)CC1] |
| 50 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(6-fluoronaphthalen-2-yl)pyrrolidine-3-carboxamide | 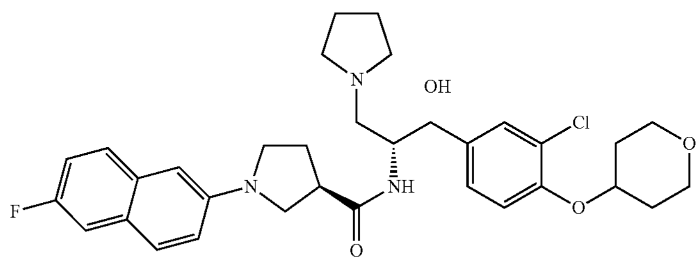 |
| 50A | (S)-N-((1R,2R)-1-(3-chloro-4-((tetrahydro-2H-pyran-4-yl)oxy)phenyl)-1-hydroxy-3-(pyrrolidin-1-yl)propan-2-yl)-1-(6-fluoronaphthalen-2-yl)pyrrolidine-3-carboxamide | 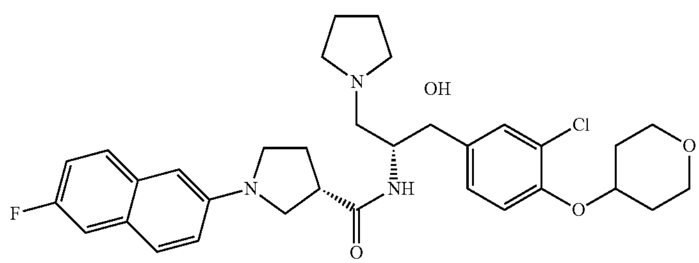 |
| 51 | (R)-1-(4-chlorophenyl)-N-((1R,2R)-1-(2,2-dimethylchroman-6-yl)-1-hydroxy-3-(pyrrolidin-1-yl)propan-2-yl)pyrrolidine-3-carboxamide | 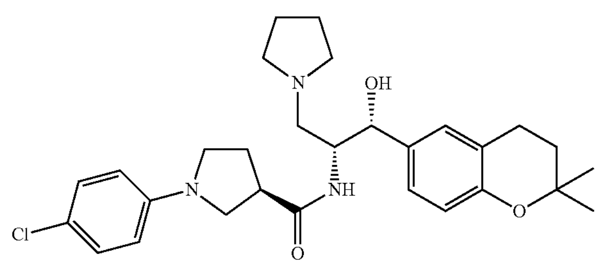 [SMILES: CC1(C)CCc2cc([C@@H](O)[C@@H](CN3CCCC3)NC(=O)[C@@H]3CCN(c4ccc(Cl)cc4)C3)ccc2O1] |
| 51A | (S)-1-(4-chlorophenyl)-N-((1R,2R)-1-(2,2-dimethylchroman-6-yl)-1-hydroxy-3-(pyrrolidin-1-yl)propan-2-yl)pyrrolidine-3-carboxamide | 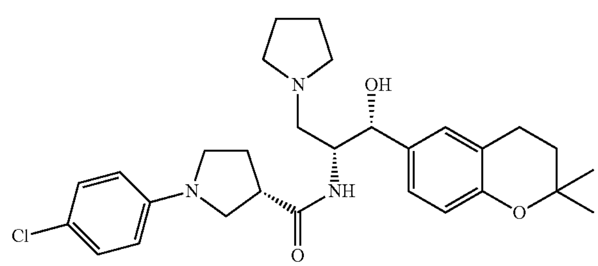 [SMILES: CC1(C)CCc2cc([C@@H](O)[C@@H](CN3CCCC3)NC(=O)[C@H]3CCN(c4ccc(Cl)cc4)C3)ccc2O1] |

TABLE 1-continued

| Example No. | Name | Structure |
|---|---|---|
| 43 | (R)-1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide | 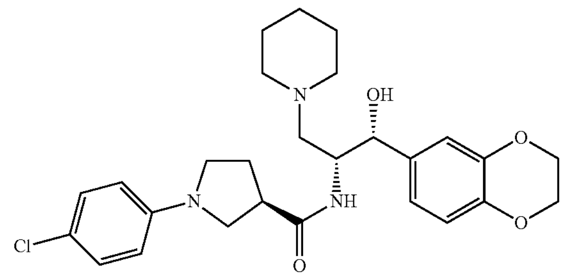 [SMILES: O=C(N[C@H](CN1CCCCC1)[C@H](O)c1ccc2c(c1)OCCO2)[C@@H]1CCN(c2ccc(Cl)cc2)C1] |
| 43E | (S)-1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide | 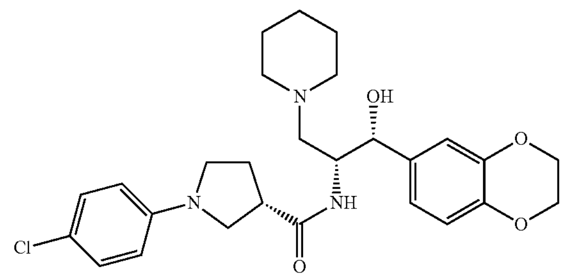 [SMILES: O=C(N[C@H](CN1CCCCC1)[C@H](O)c1ccc2c(c1)OCCO2)[C@H]1CCN(c2ccc(Cl)cc2)C1] |
| 56 | (R)-1-(2-cyclopropoxypyridin-4-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 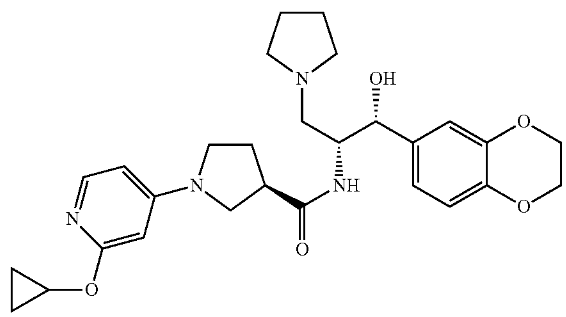 [SMILES: O=C(N[C@H](CN1CCCC1)[C@H](O)c1ccc2c(c1)OCCO2)[C@@H]1CCN(c2ccnc(OC3CC3)c2)C1] |
| 56E | (S)-1-(2-cyclopropoxypyridin-4-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 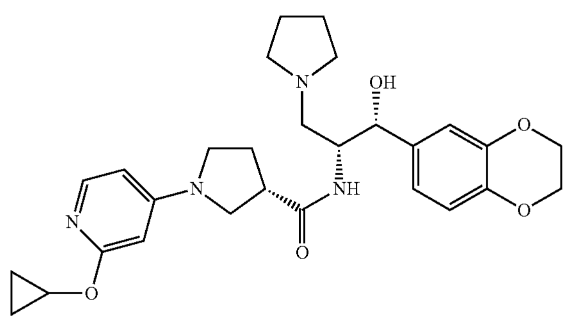 [SMILES: O=C(N[C@H](CN1CCCC1)[C@H](O)c1ccc2c(c1)OCCO2)[C@H]1CCN(c2ccnc(OC3CC3)c2)C1] |
| 52 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide | 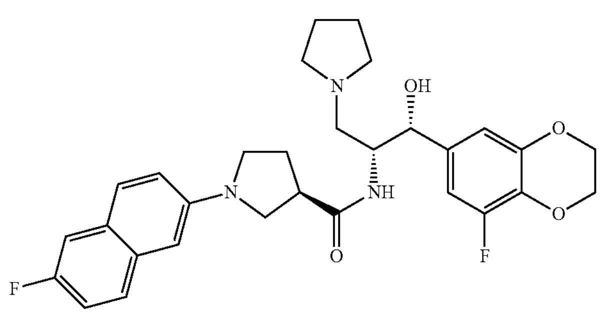 [SMILES: O=C(N[C@H](CN1CCCC1)[C@H](O)c1cc(F)c2c(c1)OCCO2)[C@@H]1CCN(c2ccc3cc(F)ccc3c2)C1] |

TABLE 1-continued

| Example No. | Name |
|---|---|
| 52A | (S)-N-((1R,2R)-1-(8-fluoro-2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide |
| 55 | (R)-1-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide |
| 55B | (S)-1-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide |
| 46 | (R)-N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide |
| 46B | (S)-N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide |

TABLE 1-continued

| Example No. | Name | Structure |
|---|---|---|
| 53C | 1-(benzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 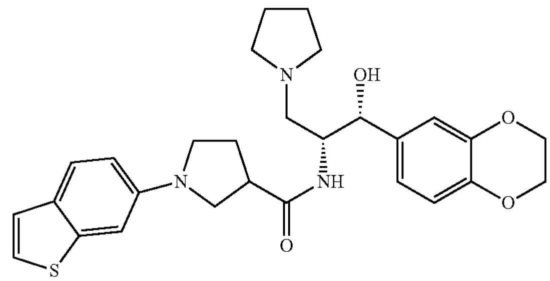 [SMILES: O=C(N[C@H](CN1CCCC1)[C@H](O)c1ccc2c(c1)OCCO2)C1CCN(c2ccc3ccsc3c2)C1] |
| 47 | (R)-N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide | 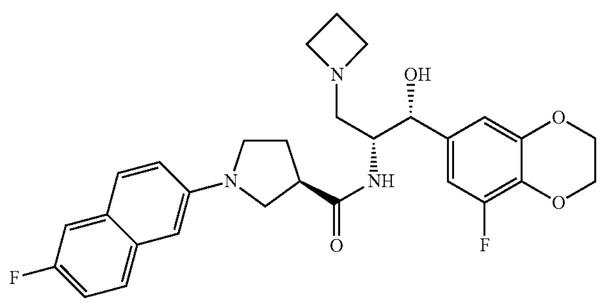 [SMILES: O=C(N[C@H](CN1CCC1)[C@H](O)c1cc(F)c2c(c1)OCCO2)[C@@H]1CCN(c2ccc3cc(F)ccc3c2)C1] |
| 47B | (S)-N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide | 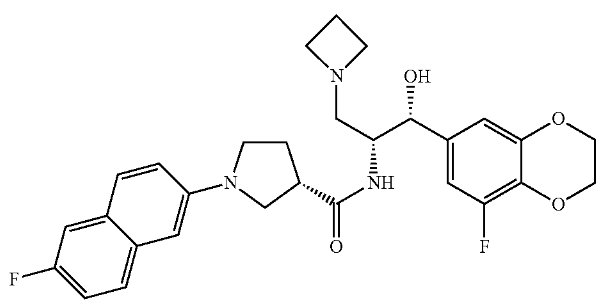 [SMILES: O=C(N[C@H](CN1CCC1)[C@H](O)c1cc(F)c2c(c1)OCCO2)[C@H]1CCN(c2ccc3cc(F)ccc3c2)C1] |
| 57A | (S)-N-((1R,2R)-1-(3-chloro-4-cyclopropoxyphenyl)-1-hydroxy-3-(pyrrolidin-1-yl)propan-2-yl)-1-(5-chloropyridin-2-yl)pyrrolidine-3-carboxamide | 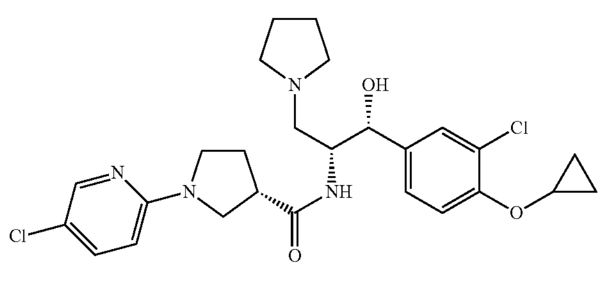 [SMILES: O=C(N[C@H](CN1CCCC1)[C@H](O)c1ccc(OC2CC2)c(Cl)c1)[C@H]1CCN(c2ccc(Cl)cn2)C1] |
| 57 | (R)-N-((1R,2R)-1-(3-chloro-4-cyclopropoxyphenyl)-1-hydroxy-3-(pyrrolidin-1-yl)propan-2-yl)-1-(5-chloropyridin-2-yl)pyrrolidine-3-carboxamide | 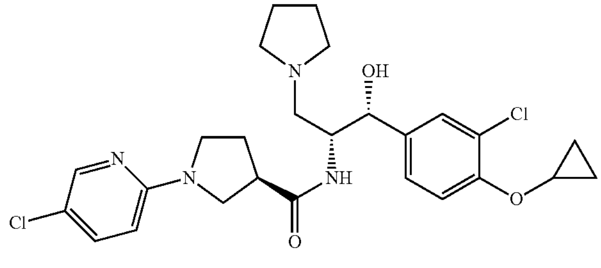 [SMILES: O=C(N[C@H](CN1CCCC1)[C@H](O)c1ccc(OC2CC2)c(Cl)c1)[C@@H]1CCN(c2ccc(Cl)cn2)C1] |

TABLE 1-continued

| Example No. | Name | Structure |
|---|---|---|
| 58 | (R)-1-(6-cyclopropoxypyridin-3-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 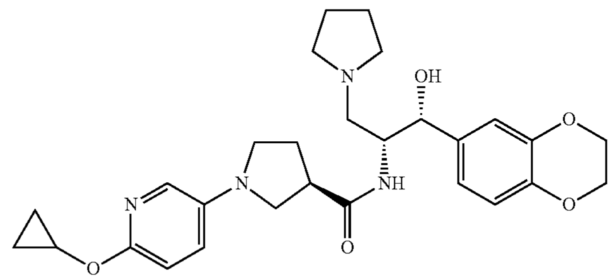 [SMILES: O=C(N[C@H](CN1CCCC1)[C@H](O)c1ccc2c(c1)OCCO2)[C@@H]1CCN(c2ccc(OC3CC3)nc2)C1] |
| 58D | (S)-1-(6-cyclopropoxypyridin-3-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 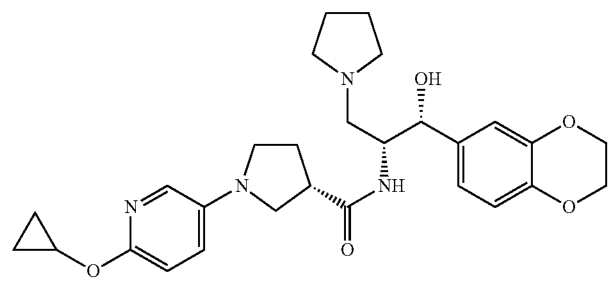 [SMILES: O=C(N[C@H](CN1CCCC1)[C@H](O)c1ccc2c(c1)OCCO2)[C@H]1CCN(c2ccc(OC3CC3)nc2)C1] |
| 59 | (R)-N-((1R,2R)-1-(3-chloro-4-(oxetan-3-yloxy)phenyl)-1-hydroxy-3-(pyrrolidin-1-yl)propan-2-yl)-1-(4-chlorophenyl)pyrrolidine-3-carboxamide | 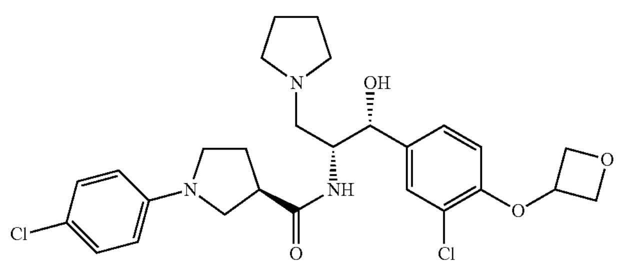 [SMILES: O=C(N[C@H](CN1CCCC1)[C@H](O)c1ccc(OC2COC2)c(Cl)c1)[C@@H]1CCN(c2ccc(Cl)cc2)C1] |
| 60 | (R)-N-((1R,2R)-1-(4-(2-(azetidin-1-yl)ethoxy)-3-chlorophenyl)-1-hydroxy-3-(pyrrolidin-1-yl)propan-2-yl)-1-(4-chlorophenyl)pyrrolidine-3-carboxamide | 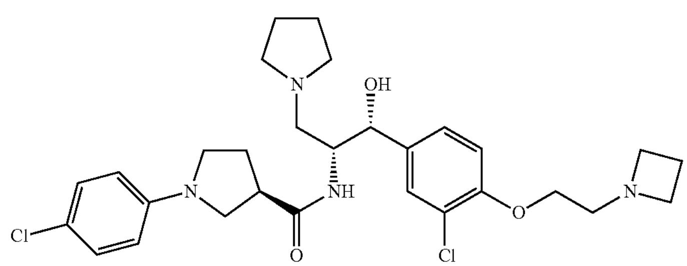 [SMILES: O=C(N[C@H](CN1CCCC1)[C@H](O)c1ccc(OCCN2CCC2)c(Cl)c1)[C@@H]1CCN(c2ccc(Cl)cc2)C1] |
| 60A | (S)-N-((1R,2R)-1-(4-(2-(azetidin-1-yl)ethoxy)-3-chlorophenyl)-1-hydroxy-3-(pyrrolidin-1-yl)propan-2-yl)-1-(4-chlorophenyl)pyrrolidine-3-carboxamide | 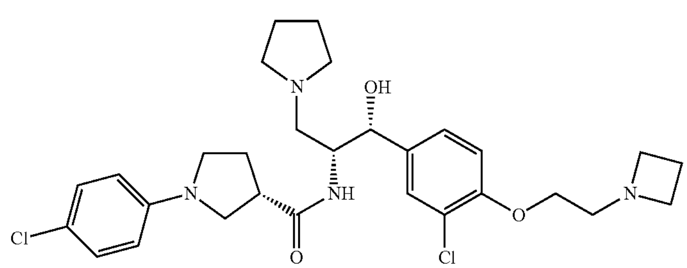 [SMILES: O=C(N[C@H](CN1CCCC1)[C@H](O)c1ccc(OCCN2CCC2)c(Cl)c1)[C@H]1CCN(c2ccc(Cl)cc2)C1] |

TABLE 1-continued

| Example No. | Name | Structure |
|---|---|---|
| 61C | N-((1R,2R)-1-(2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide | 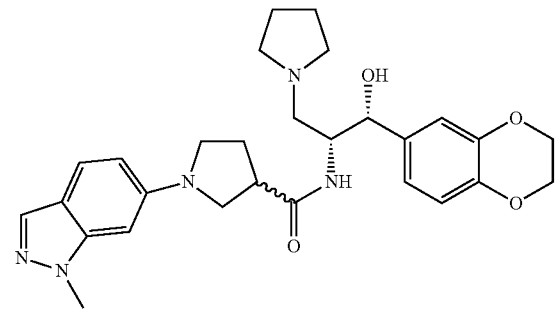 |
| 62 | (R)-1-(4-chlorophenyl)-N-((1R,2R)-1-hydroxy-1-(6-(oxetan-3-yloxy)pyridin-3-yl)-3-(pyrrolidin-1-yl)propan-2-yl)pyrrolidine-3-carboxamide | 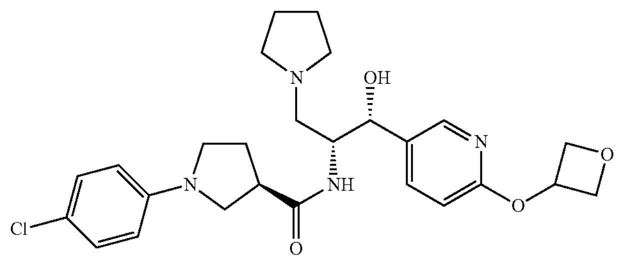 [SMILES: O=C(N[C@H](CN1CCCC1)[C@H](O)c1ccc(OC2COC2)nc1)[C@@H]1CCN(c2ccc(Cl)cc2)C1] |
| 63C | N-((1R,2R)-1-(2,3-dihydrobenzo[b][1,4]dioxin-6-yl)-1-hydroxy-3-(pyrrolidin-1-yl)propan-2-yl)-1-(2-methyl-1,2,3,4-tetrahydroisoquinolin-7-yl)pyrrolidine-3-carboxamide | 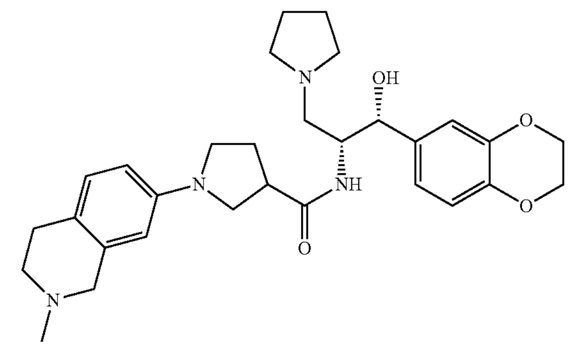 [SMILES: CN1CCc2ccc(N3CCC(C(=O)N[C@H](CN4CCCC4)[C@H](O)c4ccc5c(c4)OCCO5)C3)cc2C1] |
| 64 | N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-6-yl)pyrrolidine-3-carboxamide | 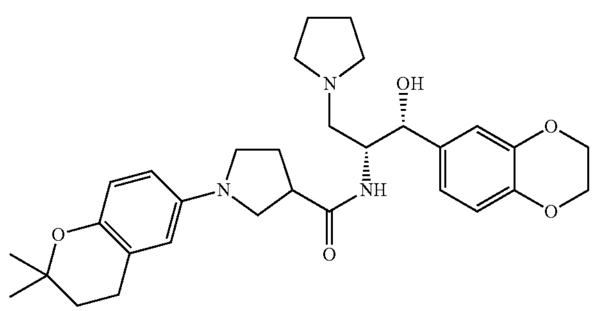 [SMILES: CC1(C)CCc2cc(N3CCC(C(=O)N[C@H](CN4CCCC4)[C@H](O)c4ccc5c(c4)OCCO5)C3)ccc2O1] |
| 65 | (R)-1-(4-chlorophenyl)-N-((1R,2R)-1-(4-cyclopropoxy-3-fluorophenyl)-1-hydroxy-3-(pyrrolidin-1-yl)propan-2-yl)pyrrolidine-3-carboxamide | 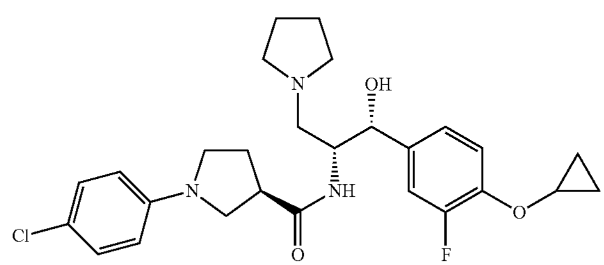 [SMILES: O=C(N[C@H](CN1CCCC1)[C@H](O)c1ccc(OC2CC2)c(F)c1)[C@@H]1CCN(c2ccc(Cl)cc2)C1] |

TABLE 1-continued

| Example No. | Name | Structure |
|---|---|---|
| 66 | (R)-N-((1R,2R)-1-(3-chloro-4-cyclopropoxyphenyl)-1-hydroxy-3-(piperidin-1-yl)propan-2-yl)-1-(4-chlorophenyl)pyrrolidine-3-carboxamide | 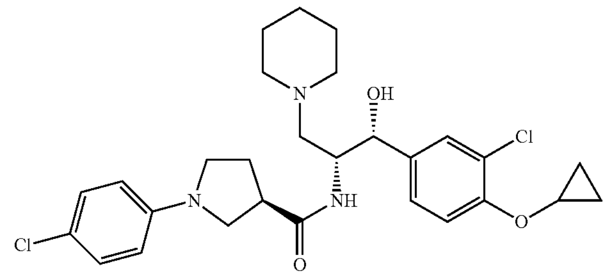 [SMILES: O=C(N[C@H](CN1CCCCC1)[C@H](O)c1ccc(OC2CC2)c(Cl)c1)[C@@H]1CCN(c2ccc(Cl)cc2)C1] |
| 67C | (S)-N-((1R,2R)-1-(3-chloro-4-cyclopropoxyphenyl)-1-hydroxy-3-(pyrrolidin-1-yl)propan-2-yl)-1-(naphthalen-2-yl)pyrrolidine-3-carboxamide | 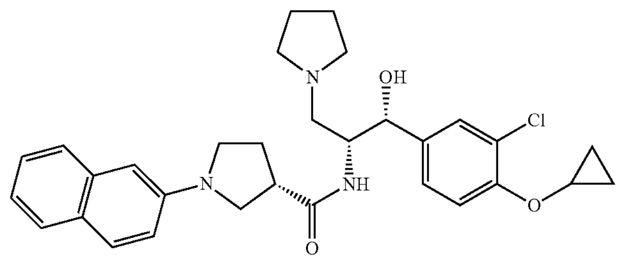 [SMILES: O=C(N[C@H](CN1CCCC1)[C@H](O)c1ccc(OC2CC2)c(Cl)c1)[C@H]1CCN(c2ccc3ccccc3c2)C1] |
| 68C | (S)-N-((1R,2S)-1-(8-fluoro-2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | 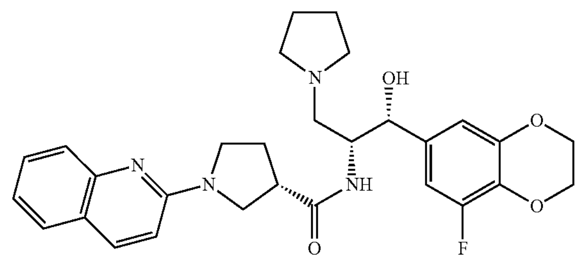 [SMILES: O=C(N[C@H](CN1CCCC1)[C@H](O)c1cc(F)c2c(c1)OCCO2)[C@H]1CCN(c2ccc3ccccc3n2)C1] |
| 61 | (R)-N-((1R,2R)-1-(2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide | 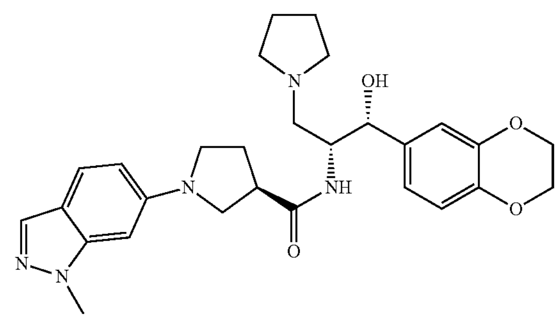 [SMILES: Cn1ncc2ccc(N3CC[C@@H](C(=O)N[C@H](CN4CCCC4)[C@H](O)c4ccc5c(c4)OCCO5)C3)cc21] |
| 61D | (S)-N-((1R,2R)-1-(2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide | 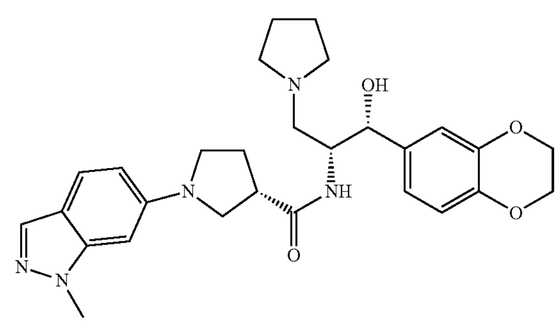 [SMILES: Cn1ncc2ccc(N3CC[C@H](C(=O)N[C@H](CN4CCCC4)[C@H](O)c4ccc5c(c4)OCCO5)C3)cc21] |

TABLE 1-continued

| Example No. | Name | Structure |
|---|---|---|
| 69 | (R)-N-((1R,2R)-1-(4-cyclopropoxy-3-fluorophenyl)-1-hydroxy-3-(pyrrolidin-1-yl)propan-2-yl)-1-(4-fluorophenyl)pyrrolidine-3-carboxamide | 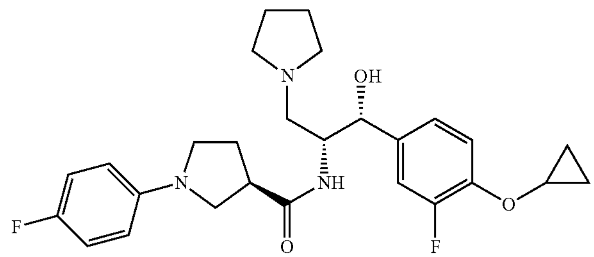 [SMILES: O=C(N[C@H](CN1CCCC1)[C@H](O)c1ccc(OC2CC2)c(F)c1)[C@@H]1CCN(c2ccc(F)cc2)C1] |
| 69A | (S)-N-((1R,2R)-1-(4-cyclopropoxy-3-fluorophenyl)-1-hydroxy-3-(pyrrolidin-1-yl)propan-2-yl)-1-(4-fluorophenyl)pyrrolidine-3-carboxamide | 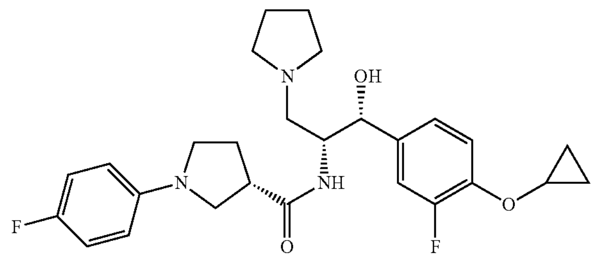 [SMILES: O=C(N[C@H](CN1CCCC1)[C@H](O)c1ccc(OC2CC2)c(F)c1)[C@H]1CCN(c2ccc(F)cc2)C1] |
| 70 | (R)-N-((1R,2R)-1-(2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide | 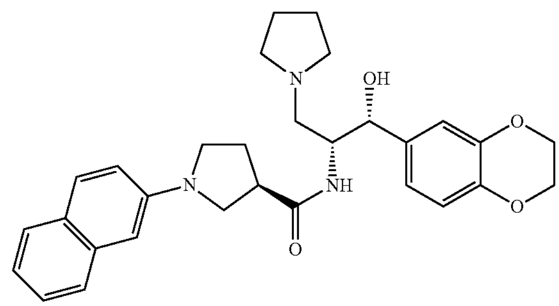 [SMILES: O=C(N[C@H](CN1CCCC1)[C@H](O)c1ccc2c(c1)OCCO2)[C@@H]1CCN(c2ccc3ccccc3c2)C1] |
| 70A | (S)-N-((1R,2R)-1-(2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide | 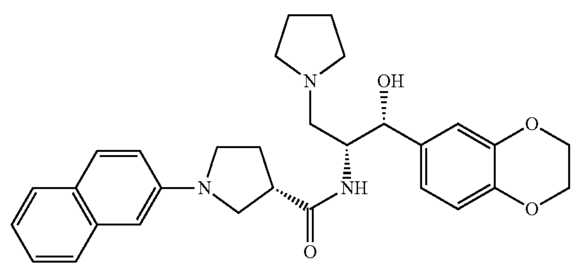 |
| 71E | N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-7-yl)pyrrolidine-3-carboxamide | 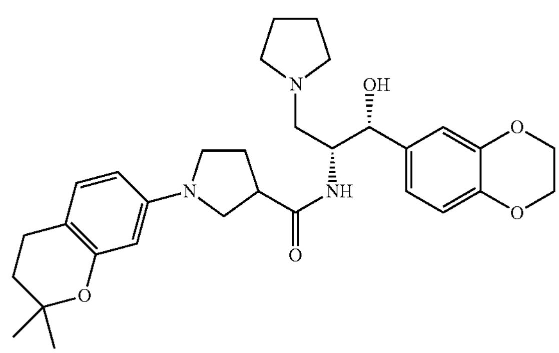 [SMILES: CC1(C)CCc2ccc(N3CCC(C(=O)N[C@H](CN4CCCC4)[C@H](O)c4ccc5c(c4)OCCO5)C3)cc2O1] |

TABLE 1-continued

| Example No. | Name | Structure |
|---|---|---|
| 72A | N-((1R,2R)-1-(2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | 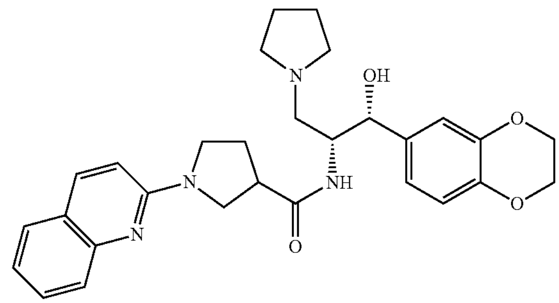 [SMILES: O=C(N[C@H](CN1CCCC1)[C@H](O)c1ccc2c(c1)OCCO2)C1CCN(c2ccc3ccccc3n2)C1] |
| 73 | (R)-N-((1R,2R)-3-(azetidin-1-yl)-1-(3-chloro-4-cyclopropoxyphenyl)-1-hydroxypropan-2-yl)-1-(4-chlorophenyl)pyrrolidine-3-carboxamide | 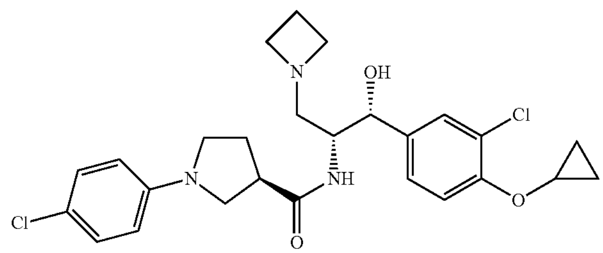 [SMILES: O=C(N[C@H](CN1CCC1)[C@H](O)c1ccc(OC2CC2)c(Cl)c1)[C@@H]1CCN(c2ccc(Cl)cc2)C1] |
| 67 | (R)-N-((1R,2R)-1-(3-chloro-4-cyclopropoxyphenyl)-1-hydroxy-3-(pyrrolidin-1-yl)propan-2-yl)-1-(naphthalen-2-yl)pyrrolidine-3-carboxamide | 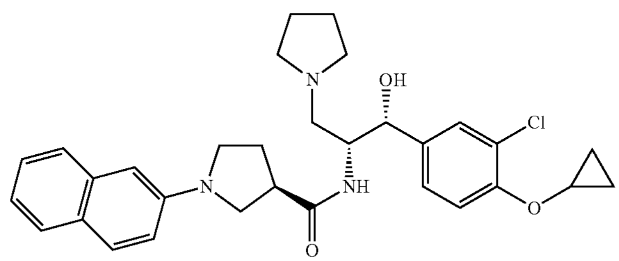 [SMILES: O=C(N[C@H](CN1CCCC1)[C@H](O)c1ccc(OC2CC2)c(Cl)c1)[C@@H]1CCN(c2ccc3ccccc3c2)C1] |
| 53 | (R)-1-(benzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 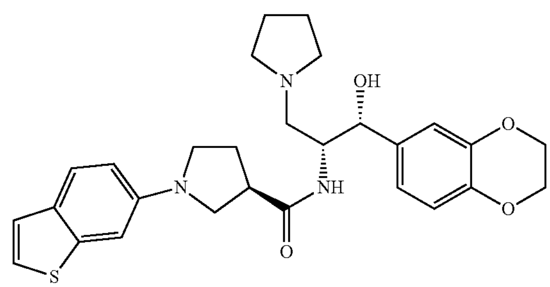 [SMILES: O=C(N[C@H](CN1CCCC1)[C@H](O)c1ccc2c(c1)OCCO2)[C@@H]1CCN(c2ccc3ccsc3c2)C1] |
| 53D | (S)-1-(benzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 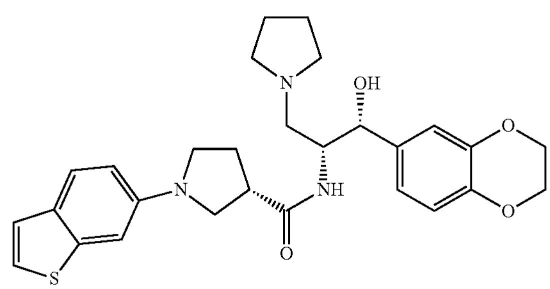 [SMILES: O=C(N[C@H](CN1CCCC1)[C@H](O)c1ccc2c(c1)OCCO2)[C@H]1CCN(c2ccc3ccsc3c2)C1] |

TABLE 1-continued

| Example No. | Name | Structure |
|---|---|---|
| 74 | (R)-N-((1R,2R)-1-(3-chloro-4-morpholinophenyl)-1-hydroxy-3-(pyrrolidin-1-yl)propan-2-yl)-1-(4-chlorophenyl)pyrrolidine-3-carboxamide | 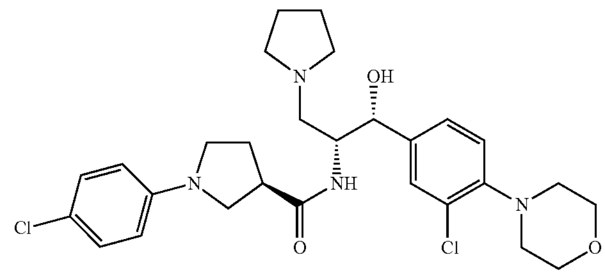 [SMILES: O=C(N[C@H](CN1CCCC1)[C@H](O)c1ccc(N2CCOCC2)c(Cl)c1)[C@@H]1CCN(c2ccc(Cl)cc2)C1] |
| 74C | (S)-N-((1R,2R)-1-(3-chloro-4-morpholinophenyl)-1-hydroxy-3-(pyrrolidin-1-yl)propan-2-yl)-1-(4-chlorophenyl)pyrrolidine-3-carboxamide | 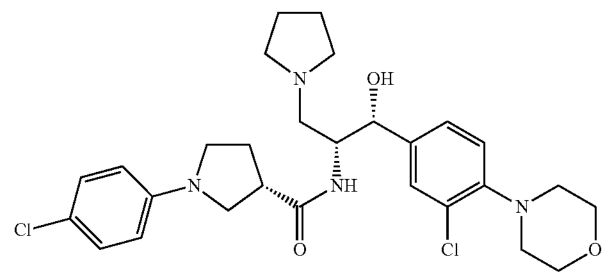 [SMILES: O=C(N[C@H](CN1CCCC1)[C@H](O)c1ccc(N2CCOCC2)c(Cl)c1)[C@H]1CCN(c2ccc(Cl)cc2)C1] |
| 75 | (R)-N-((1R,2R)-1-(3-chloro-4-cyclopropoxyphenyl)-1-hydroxy-3-(pyrrolidin-1-yl)propan-2-yl)-1-(3-(pyridin-2-yloxy)phenyl)pyrrolidine-3-carboxamide | 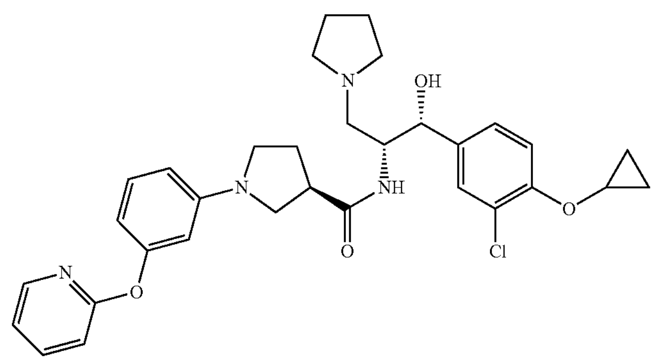 [SMILES: O=C(N[C@H](CN1CCCC1)[C@H](O)c1ccc(OC2CC2)c(Cl)c1)[C@@H]1CCN(c2cccc(Oc3ccccn3)c2)C1] |
| 75E | (S)-N-((1R,2R)-1-(3-chloro-4-cyclopropoxyphenyl)-1-hydroxy-3-(pyrrolidin-1-yl)propan-2-yl)-1-(3-(pyridin-2-yloxy)phenyl)pyrrolidine-3-carboxamide | 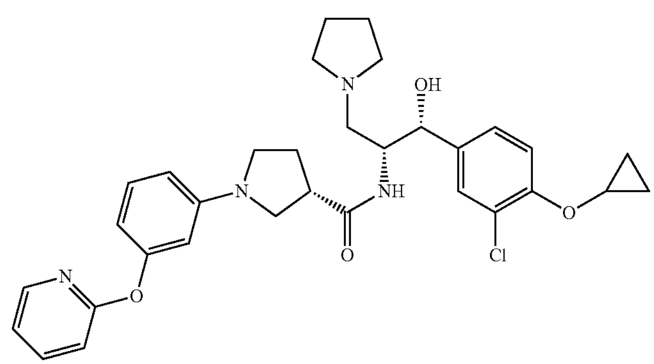 [SMILES: O=C(N[C@H](CN1CCCC1)[C@H](O)c1ccc(OC2CC2)c(Cl)c1)[C@H]1CCN(c2cccc(Oc3ccccn3)c2)C1] |
| 76D | 1-(2-chlorobenzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 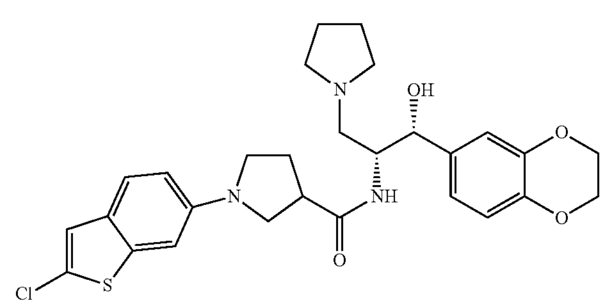 [SMILES: O=C(N[C@H](CN1CCCC1)[C@H](O)c1ccc2c(c1)OCCO2)C1CCN(c2ccc3cc(Cl)sc3c2)C1] |

TABLE 1-continued

| Example No. | Name | Structure |
|---|---|---|
| 77 | N-[2-(2H,3H-benzo[e]1,4-dioxan-6-yl)(1R,2R)-2-hydroxy-1-(pyrrolidinylmethyl)ethyl][1-(4-chlorophenyl)pyrrolidin-3-yl]carboxamide | 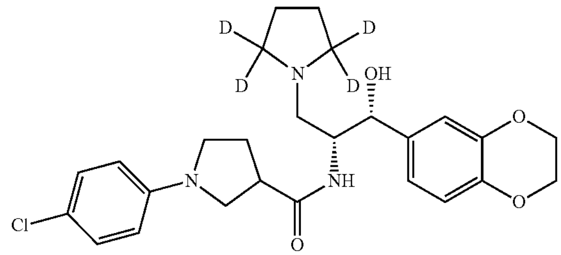 [SMILES: [2H]C1([2H])CCC([2H])([2H])N1C[C@@H](NC(=O)C1CCN(c2ccc(Cl)cc2)C1)[C@H](O)c1ccc2c(c1)OCCO2] |
| 78 | (R)-N-((1R,2R)-3-(azetidin-1-yl)-1-(2,3-dihydrobenzo[b][1,4]dioxin-6-yl)-1-hydroxypropan-2-yl)-1-(4-chlorophenyl)pyrrolidine-3-carboxamide | 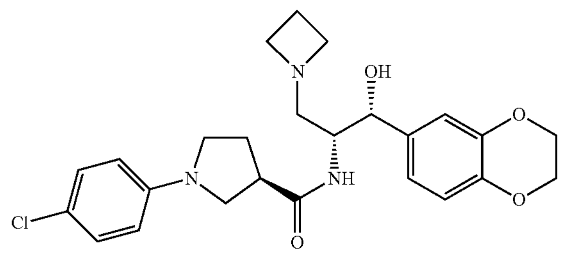 [SMILES: O=C(N[C@H](CN1CCC1)[C@H](O)c1ccc2c(c1)OCCO2)[C@@H]1CCN(c2ccc(Cl)cc2)C1] |
| 72 | (R)-N-((1R,2R)-1-(2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | 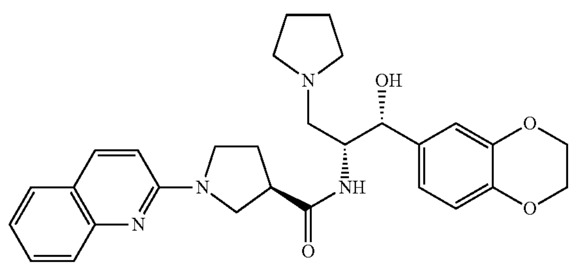 [SMILES: O=C(N[C@H](CN1CCCC1)[C@H](O)c1ccc2c(c1)OCCO2)[C@@H]1CCN(c2ccc3ccccc3n2)C1] |
| 72B | (S)-N-((1R,2R)-1-(2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | 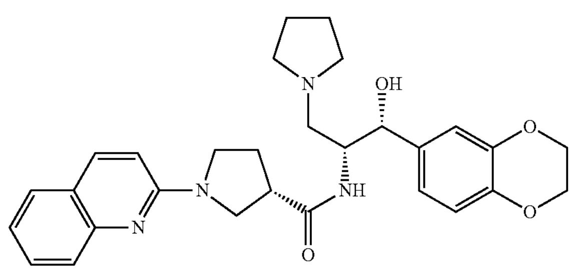 |
| 71 | (R)-N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-7-yl)pyrrolidine-3-carboxamide | 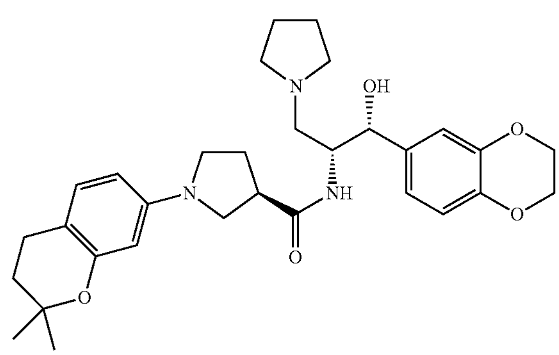 [SMILES: CC1(C)CCc2ccc(N3CC[C@@H](C(=O)N[C@H](CN4CCCC4)[C@H](O)c4ccc5c(c4)OCCO5)C3)cc2O1] |

TABLE 1-continued

| Example No. | Name | Structure |
|---|---|---|
| 71F | (S)-N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-7-yl)pyrrolidine-3-carboxamide | 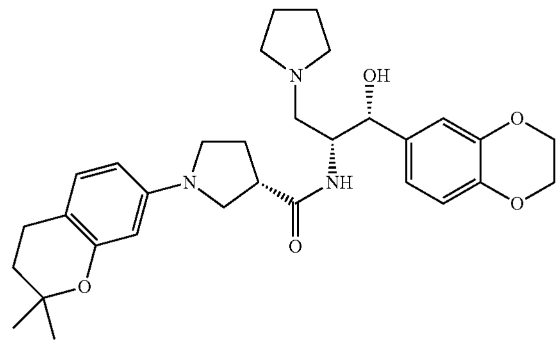 [SMILES: CC1(C)CCc2ccc(N3CC[C@H](C(=O)N[C@H](CN4CCCC4)[C@H](O)c4ccc5c(c4)OCCO5)C3)cc2O1] |
| 79A | N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide | 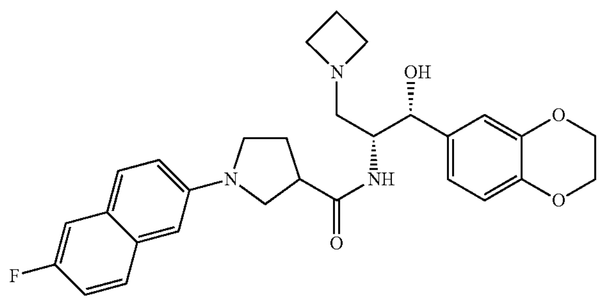 [SMILES: O=C(N[C@H](CN1CCC1)[C@H](O)c1ccc2c(c1)OCCO2)C1CCN(c2ccc3cc(F)ccc3c2)C1] |
| 80G | N-((1R,2R)-1-(2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | 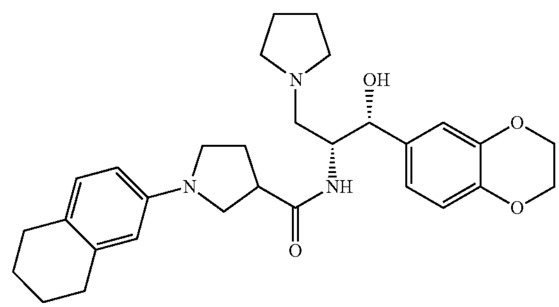 [SMILES: O=C(N[C@H](CN1CCCC1)[C@H](O)c1ccc2c(c1)OCCO2)C1CCN(c2ccc3c(c2)CCCC3)C1] |
| 68 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | 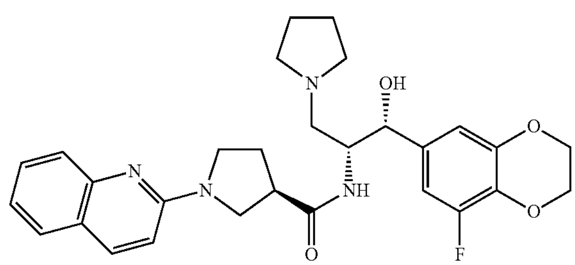 [SMILES: O=C(N[C@H](CN1CCCC1)[C@H](O)c1cc(F)c2c(c1)OCCO2)[C@@H]1CCN(c2ccc3ccccc3n2)C1] |
| 63 | (R)-N-((1R,2R)-1-(2,3-dihydrobenzo[b][1,4]dioxin-6-yl)-1-hydroxy-3-(pyrrolidin-1-yl)propan-2-yl)-1-(2-methyl-1,2,3,4-tetrahydroisoquinolin-7-yl)pyrrolidine-3-carboxamide | 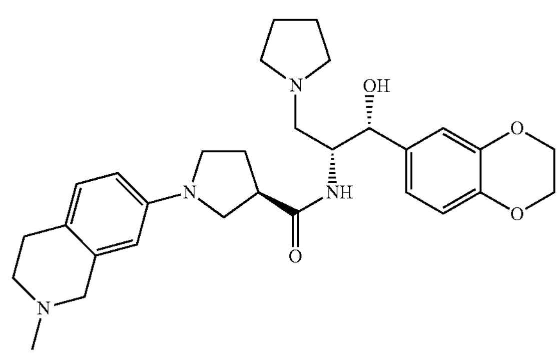 [SMILES: CN1CCc2ccc(N3CC[C@@H](C(=O)N[C@H](CN4CCCC4)[C@H](O)c4ccc5c(c4)OCCO5)C3)cc2C1] |

TABLE 1-continued

| Example No. | Name | Structure |
|---|---|---|
| 63D | (S)-N-((1R,2R)-1-(2,3-dihydrobenzo[b][1,4]dioxin-6-yl)-1-hydroxy-3-(pyrrolidin-1-yl)propan-2-yl)-1-(2-methyl-1,2,3,4-tetrahydroisoquinolin-7-yl)pyrrolidine-3-carboxamide | 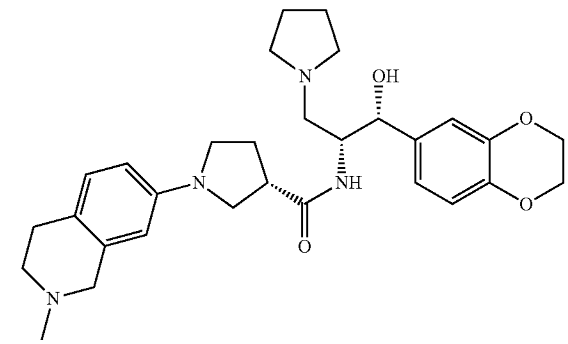 |
| 76E | (S)-1-(2-chlorobenzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 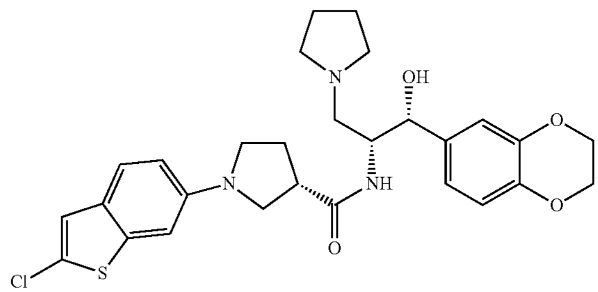 |
| 76 | (R)-1-(2-chlorobenzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 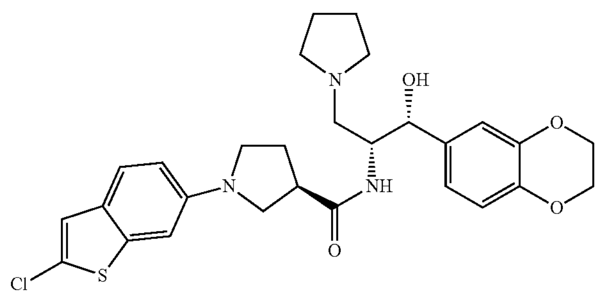 [SMILES: O=C(N[C@H](CN1CCCC1)[C@H](O)c1ccc2c(c1)OCCO2)[C@@H]1CCN(c2ccc3cc(Cl)sc3c2)C1] |
| 81 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide | 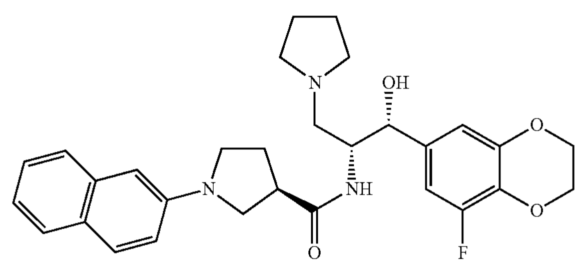 [SMILES: O=C(N[C@H](CN1CCCC1)[C@H](O)c1cc(F)c2c(c1)OCCO2)[C@@H]1CCN(c2ccc3ccccc3c2)C1] |
| 82 | (R)-N-(1R,2R)-1-(2,3-dihydrobenzo[b][1,4]dioxin-6-yl)-1-hydroxy-3-(pyrrolidin-1-yl)propan-2-yl)-1-(2,6-dimethylpyridin-4-yl)pyrrolidine-3-carboxamide | 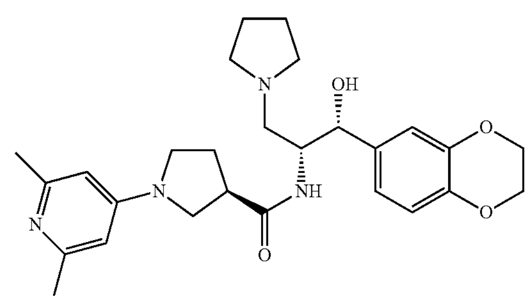 [SMILES: Cc1cc(N2CC[C@@H](C(=O)N[C@H](CN3CCCC3)[C@H](O)c3ccc4c(c3)OCCO4)C2)cc(C)n1] |

TABLE 1-continued

| Example No. | Name | Structure |
|---|---|---|
| 82E | (S)-N-((1R,2R)-1-(2,3-dihydrobenzo[b][1,4]dioxin-6-yl)-1-hydroxy-3-(pyrrolidin-1-yl)propan-2-yl)-1-(2,6-dimethylpyridin-4-yl)pyrrolidine-3-carboxamide | 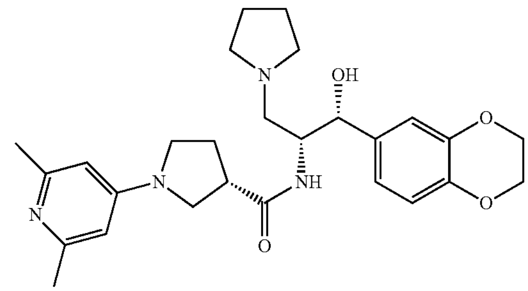 [SMILES: Cc1cc(N2CC[C@H](C(=O)N[C@H](CN3CCCC3)[C@H](O)c3ccc4c(c3)OCCO4)C2)cc(C)n1] |
| 83C | N-((1R,2R)-1-(2,3-dihydrobenzo[b][1,4]dioxin-6-yl)-1-hydroxy-3-(pyrrolidin-1-yl)propan-2-yl)-1-(quinoxalin-6-yl)pyrrolidine-3-carboxamide | 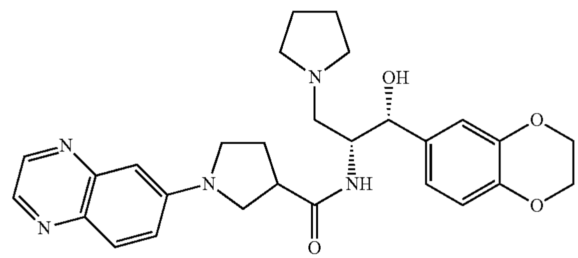 [SMILES: O=C(N[C@H](CN1CCCC1)[C@H](O)c1ccc2c(c1)OCCO2)C1CCN(c2ccc3nccnc3c2)C1] |
| 84 | (R)-N-((1R,2R)-1-(3-chloro-4-cyclopropoxyphenyl)-1-hydroxy-3-(pyrrolidin-1-yl)propan-2-yl)-1-(6-fluoronaphthalen-2-yl)pyrrolidine-3-carboxamide | 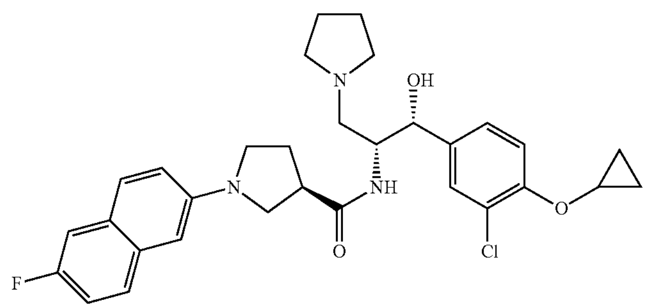 [SMILES: O=C(N[C@H](CN1CCCC1)[C@H](O)c1ccc(OC2CC2)c(Cl)c1)[C@@H]1CCN(c2ccc3cc(F)ccc3c2)C1] |
| 84A | (S)-N-((1R,2R)-1-(3-chloro-4-cyclopropoxyphenyl)-1-hydroxy-3-(pyrrolidin-1-yl)propan-2-yl)-1-(6-fluoronaphthalen-2-yl)pyrrolidine-3-carboxamide | 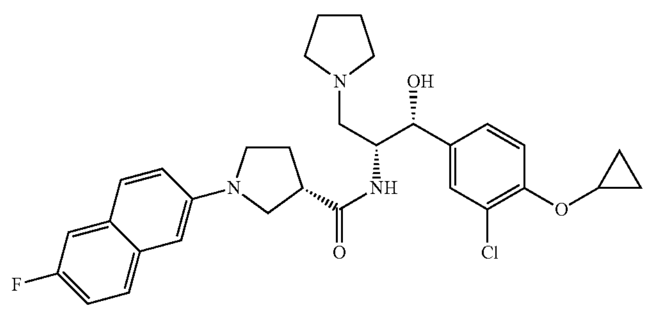 [SMILES: O=C(N[C@H](CN1CCCC1)[C@H](O)c1ccc(OC2CC2)c(Cl)c1)[C@H]1CCN(c2ccc3cc(F)ccc3c2)C1] |
| 79 | (R)-N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide | 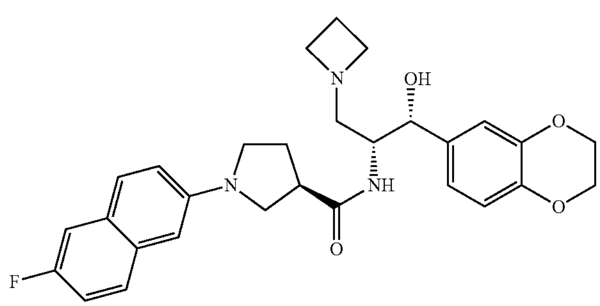 [SMILES: O=C(N[C@H](CN1CCC1)[C@H](O)c1ccc2c(c1)OCCO2)[C@@H]1CCN(c2ccc3cc(F)ccc3c2)C1] |

TABLE 1-continued

| Example No. | Name | Structure |
|---|---|---|
| 79B | (S)-N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide | 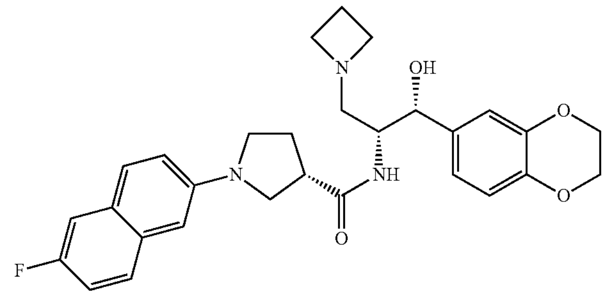 [SMILES: O=C(N[C@H](CN1CCC1)[C@H](O)c1ccc2c(c1)OCCO2)[C@H]1CCN(c2ccc3cc(F)ccc3c2)C1] |
| 80 | (R)-N-((1R,2R)-1-(2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | 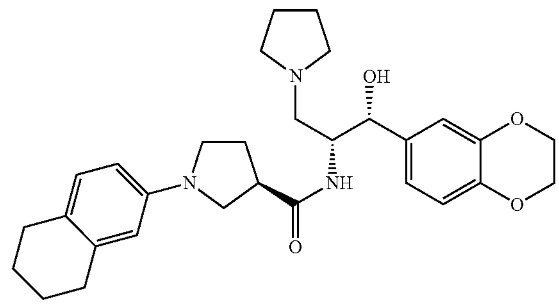 [SMILES: O=C(N[C@H](CN1CCCC1)[C@H](O)c1ccc2c(c1)OCCO2)[C@@H]1CCN(c2ccc3c(c2)CCCC3)C1] |
| 80H | (S)-N-((1R,2R)-1-(2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | 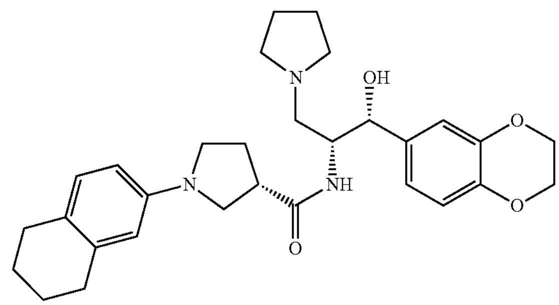 [SMILES: O=C(N[C@H](CN1CCCC1)[C@H](O)c1ccc2c(c1)OCCO2)[C@H]1CCN(c2ccc3c(c2)CCCC3)C1] |
| 85 | (R)-N-((1R,2R)-3-(azetidin-1-yl)-1-(8-fluoro-2,3-dihydrobenzo[b][1,4]dioxin-6-yl)-1-hydroxypropan-2-yl)-1-(naphthalen-2-yl)pyrrolidine-3-carboxamide | 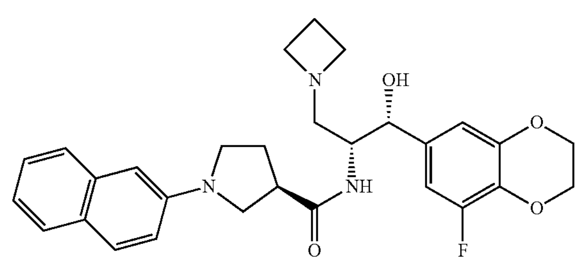 [SMILES: O=C(N[C@H](CN1CCC1)[C@H](O)c1cc(F)c2c(c1)OCCO2)[C@@H]1CCN(c2ccc3ccccc3c2)C1] |
| 86 | (R)-N-((1R,2R)-3-(azetidin-1-yl)-1-(3-chloro-4-cyclopropoxyphenyl)-1-hydroxypropan-2-yl)-1-(naphthalen-2-yl)pyrrolidine-3-carboxamide | 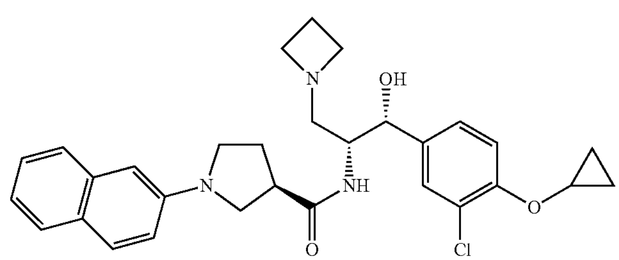 [SMILES: O=C(N[C@H](CN1CCC1)[C@H](O)c1ccc(OC2CC2)c(Cl)c1)[C@@H]1CCN(c2ccc3ccccc3c2)C1] |

TABLE 1-continued

| Example No. | Name | Structure |
|---|---|---|
| 87 | (R)-N-((1R,2R)-1-(3-chloro-4-(2-hydroxy-2-methylpropoxy)phenyl)-1-hydroxy-3-(pyrrolidin-1-yl)propan-2-yl)-1-(4-chlorophenyl)pyrrolidine-3-carboxamide | 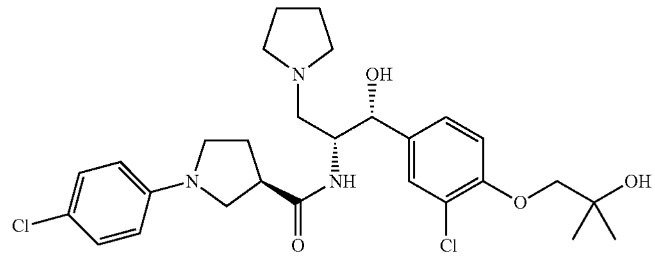 [SMILES: CC(C)(O)COc1ccc([C@@H](O)[C@@H](CN2CCCC2)NC(=O)[C@@H]2CCN(c3ccc(Cl)cc3)C2)cc1Cl] |
| 88C | 1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 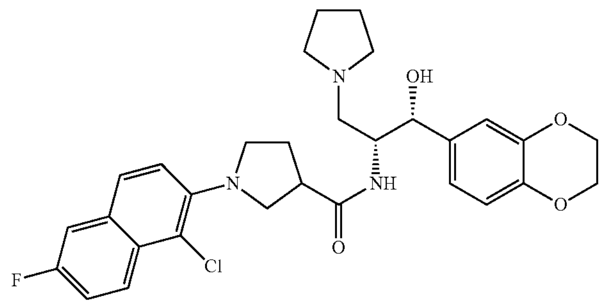 [SMILES: O=C(N[C@H](CN1CCCC1)[C@H](O)c1ccc2c(c1)OCCO2)C1CCN(c2ccc3cc(F)ccc3c2Cl)C1] |
| 89F | N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide | 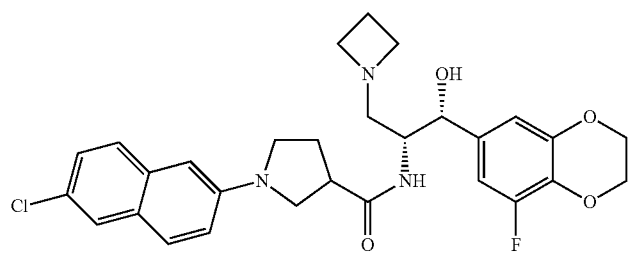 [SMILES: O=C(N[C@H](CN1CCC1)[C@H](O)c1cc(F)c2c(c1)OCCO2)C1CCN(c2ccc3cc(Cl)ccc3c2)C1] |
| 90 | (R)-N-((1R,2R)-1-(2,3-dihydrobenzo[b][1,4]dioxin-6-yl)-1-hydroxy-3-(pyrrolidin-1-yl)propan-2-yl)-1-(1,5-naphthyridin-3-yl)pyrrolidine-3-carboxamide | 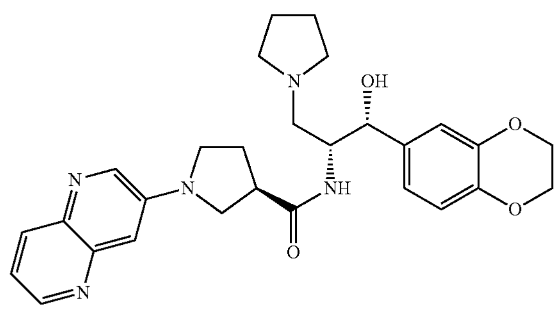 [SMILES: O=C(N[C@H](CN1CCCC1)[C@H](O)c1ccc2c(c1)OCCO2)[C@@H]1CCN(c2cnc3cccnc3c2)C1] |
| 90D | (S)-N-((1R,2R)-1-(2,3-dihydrobenzo[b][1,4]dioxin-6-yl)-1-hydroxy-3-(pyrrolidin-1-yl)propan-2-yl)-1-(1,5-naphthyridin-3-yl)pyrrolidine-3-carboxamide | 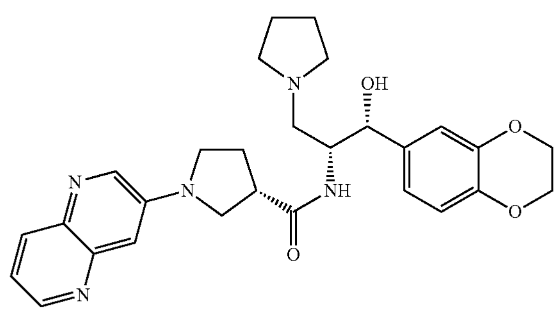 [SMILES: O=C(N[C@H](CN1CCCC1)[C@H](O)c1ccc2c(c1)OCCO2)[C@H]1CCN(c2cnc3cccnc3c2)C1] |

TABLE 1-continued

| Example No. | Name | Structure |
|---|---|---|
| 92 | (R)-1-(benzo[b]thiophen-6-yl)-N-((1R,2R)-1-(3-chloro-4-((tetrahydro-2H-pyran-4-yl)oxy)phenyl)-1-hydroxy-3-(pyrrolidin-1-yl)propan-2-yl)pyrrolidine-3-carboxamide | 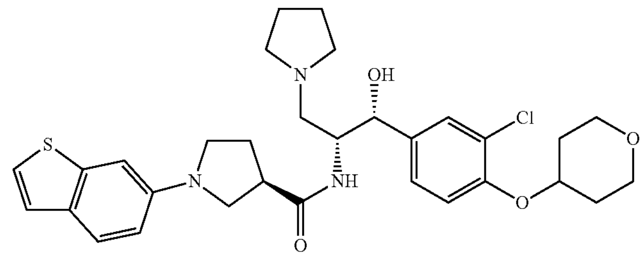 [SMILES: O=C(N[C@H](CN1CCCC1)[C@H](O)c1ccc(OC2CCOCC2)c(Cl)c1)[C@@H]1CCN(c2ccc3ccsc3c2)C1] |
| 83 | (R)-N-((1R,2R)-1-(2,3-dihydrobenzo[b][1,4]dioxin-6-yl)-1-hydroxy-3-(pyrrolidin-1-yl)propan-2-yl)-1-(quinoxalin-6-yl)pyrrolidine-3-carboxamide | 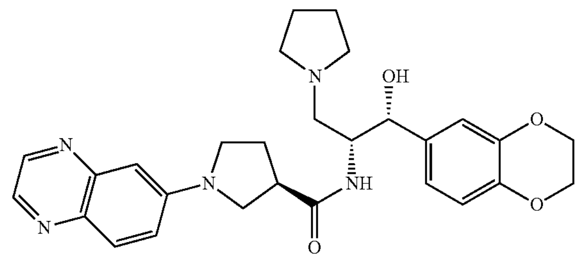 [SMILES: O=C(N[C@H](CN1CCCC1)[C@H](O)c1ccc2c(c1)OCCO2)[C@@H]1CCN(c2ccc3nccnc3c2)C1] |
| 83D | (S)-N-((1R,2R)-1-(2,3-dihydrobenzo[b][1,4]dioxin-6-yl)-1-hydroxy-3-(pyrrolidin-1-yl)propan-2-yl)-1-(quinoxalin-6-yl)pyrrolidine-3-carboxamide | 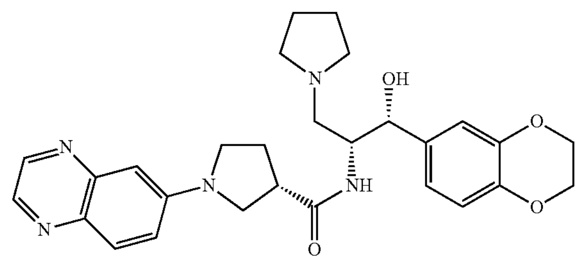 [SMILES: O=C(N[C@H](CN1CCCC1)[C@H](O)c1ccc2c(c1)OCCO2)[C@H]1CCN(c2ccc3nccnc3c2)C1] |
| 88 | (R)-1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 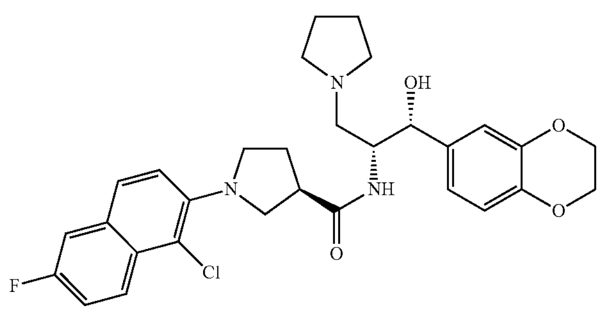 [SMILES: O=C(N[C@H](CN1CCCC1)[C@H](O)c1ccc2c(c1)OCCO2)[C@@H]1CCN(c2ccc3cc(F)ccc3c2Cl)C1] |
| 88D | (S)-1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 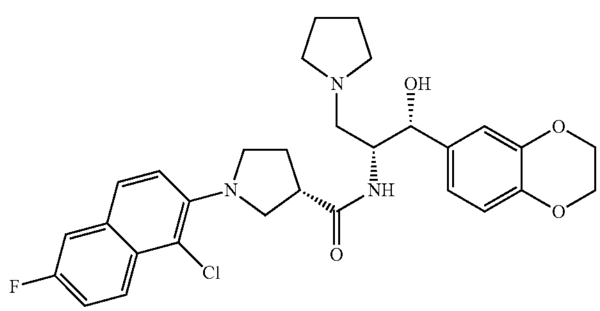 [SMILES: O=C(N[C@H](CN1CCCC1)[C@H](O)c1ccc2c(c1)OCCO2)[C@H]1CCN(c2ccc3cc(F)ccc3c2Cl)C1] |

TABLE 1-continued

| Example No. | Name | Structure |
|---|---|---|
| 89 | (R)-N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide | 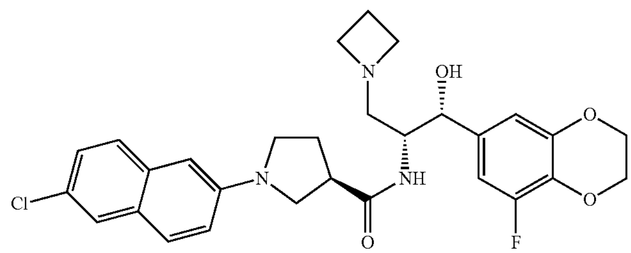 [SMILES: O=C(N[C@H](CN1CCC1)[C@H](O)c1cc(F)c2c(c1)OCCO2)[C@@H]1CCN(c2ccc3cc(Cl)ccc3c2)C1] |
| 89G | (S)-N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide | 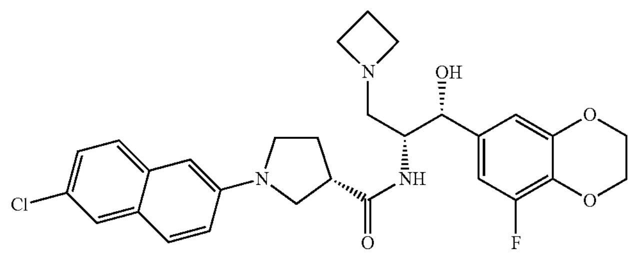 |
| 93 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | 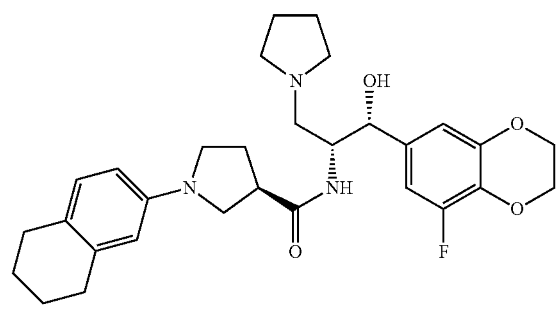 [SMILES: O=C(N[C@H](CN1CCCC1)[C@H](O)c1cc(F)c2c(c1)OCCO2)[C@@H]1CCN(c2ccc3c(c2)CCCC3)C1] |
| 93A | (S)-N-((1R,2R)-1-(8-fluoro-2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | 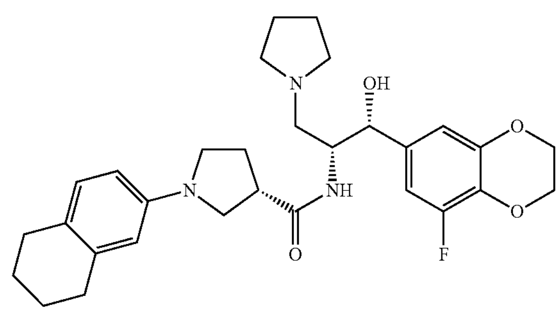 [SMILES: O=C(N[C@H](CN1CCCC1)[C@H](O)c1cc(F)c2c(c1)OCCO2)[C@H]1CCN(c2ccc3c(c2)CCCC3)C1] |
| 91 | (R)-1-(benzo[b]thiophen-6-yl)-N-((1R,2R)-1-(3-chloro-4-cyclopropoxyphenyl)-1-hydroxy-3-(pyrrolidin-1-yl)propan-2-yl)pyrrolidine-3-carboxamide | 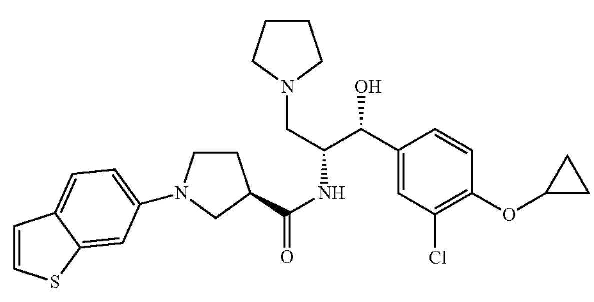 [SMILES: O=C(N[C@H](CN1CCCC1)[C@H](O)c1ccc(OC2CC2)c(Cl)c1)[C@@H]1CCN(c2ccc3ccsc3c2)C1] |

TABLE 1-continued

| Example No. | Name | Structure |
|---|---|---|
| 94 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(naphthalen-2-yl)pyrrolidine-3-carboxamide | 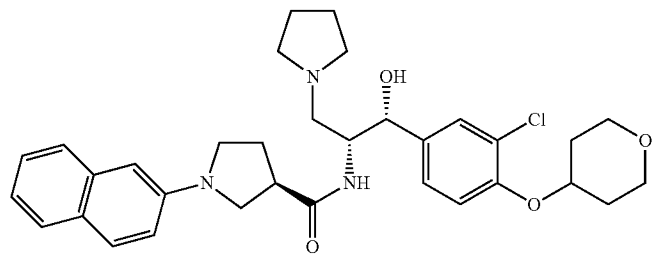 [SMILES: O=C(N[C@H](CN1CCCC1)[C@H](O)c1ccc(OC2CCOCC2)c(Cl)c1)[C@@H]1CCN(c2ccc3ccccc3c2)C1] |
| 95 | (R)-N-((1R,2R)-3-(azetidin-1-yl)-1-(3-chloro-4-cyclopropoxyphenyl)-1-hydroxypropan-2-yl)-1-(6-fluoronaphthalen-2-yl)pyrrolidine-3-carboxamide | 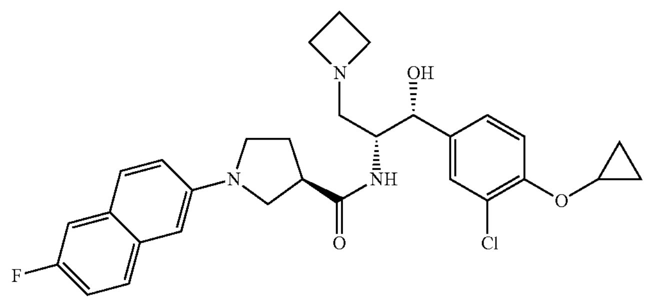 [SMILES: O=C(N[C@H](CN1CCC1)[C@H](O)c1ccc(OC2CC2)c(Cl)c1)[C@@H]1CCN(c2ccc3cc(F)ccc3c2)C1] |
| 96 | (R)-N-((1R,2R)-1-(3-chloro-4-cyclopropoxyphenyl)-1-hydroxy-3-(pyrrolidin-1-yl)propan-2-yl)-1-(4-fluorophenyl)pyrrolidine-3-carboxamide | 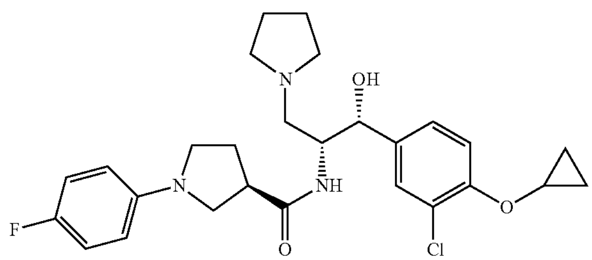 [SMILES: O=C(N[C@H](CN1CCCC1)[C@H](O)c1ccc(OC2CC2)c(Cl)c1)[C@@H]1CCN(c2ccc(F)cc2)C1] |
| 97 | (R)-1-(benzo[b]thiophen-6-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 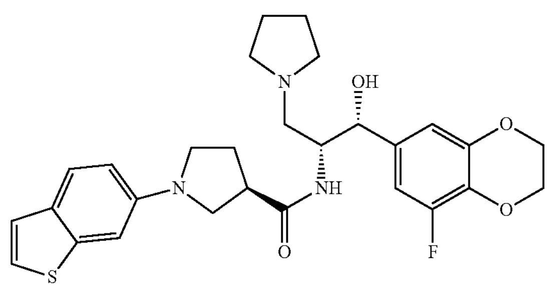 [SMILES: O=C(N[C@H](CN1CCCC1)[C@H](O)c1cc(F)c2c(c1)OCCO2)[C@@H]1CCN(c2ccc3ccsc3c2)C1] |
| 97C | (S)-1-(benzo[b]thiophen-6-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 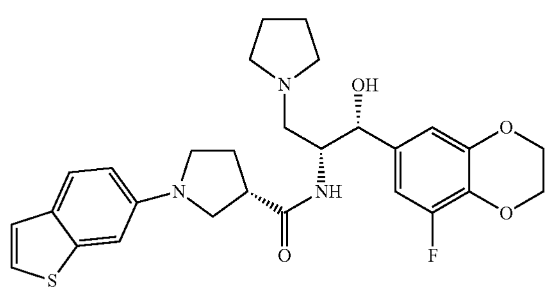 [SMILES: O=C(N[C@H](CN1CCCC1)[C@H](O)c1cc(F)c2c(c1)OCCO2)[C@H]1CCN(c2ccc3ccsc3c2)C1] |

TABLE 1-continued

| Example No. | Name | Structure |
|---|---|---|
| 98 | (R)-N-((1R,2R)-1-(3-chloro-4-cyclopropoxyphenyl)-1-hydroxy-3-(pyrrolidin-1-yl)propan-2-yl)-1-(5,6,7,8-tetrahydronaphthalen-2-yl)pyrrolidine-3-carboxamide | 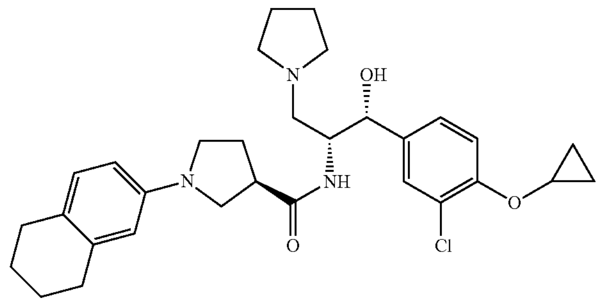 [SMILES: O=C(N[C@H](CN1CCCC1)[C@H](O)c1ccc(OC2CC2)c(Cl)c1)[C@@H]1CCN(c2ccc3c(c2)CCCC3)C1] |
| 98A | (S)-N-((1R,2R)-1-(3-chloro-4-cyclopropoxyphenyl)-1-hydroxy-3-(pyrrolidin-1-yl)propan-2-yl)-1-(5,6,7,8-tetrahydronaphthalen-2-yl)pyrrolidine-3-carboxamide | 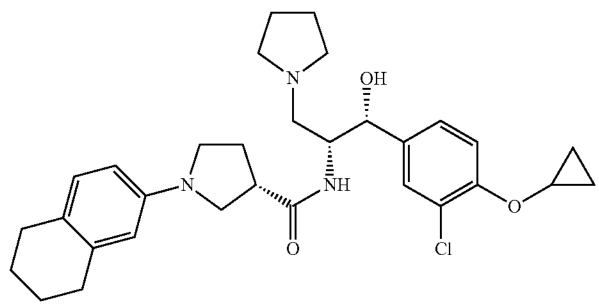 [SMILES: O=C(N[C@H](CN1CCCC1)[C@H](O)c1ccc(OC2CC2)c(Cl)c1)[C@H]1CCN(c2ccc3c(c2)CCCC3)C1] |
| 99C | 1-(6-chloroquinolin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 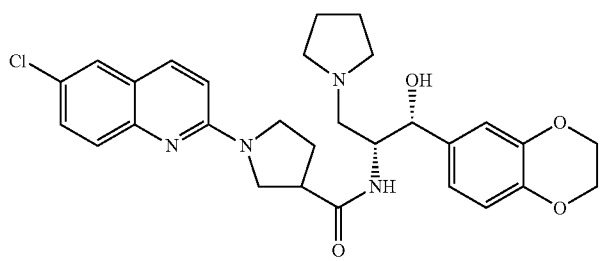 [SMILES: O=C(N[C@H](CN1CCCC1)[C@H](O)c1ccc2c(c1)OCCO2)C1CCN(c2ccc3cc(Cl)ccc3n2)C1] |
| 100 | (R)-N-((1R,2R)-1-(3-chloro-4-cyclopropoxyphenyl)-1-hydroxy-3-(pyrrolidin-1-yl)propan-2-yl)-1-(6-chloroquinolin-2-yl)pyrrolidine-3-carboxamide | 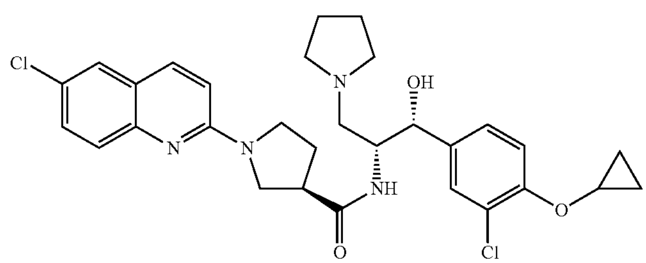 [SMILES: O=C(N[C@H](CN1CCCC1)[C@H](O)c1ccc(OC2CC2)c(Cl)c1)[C@@H]1CCN(c2ccc3cc(Cl)ccc3n2)C1] |
| 101 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(2-chlorobenzo[b]thiophen-6-yl)pyrrolidine-3-carboxamide | 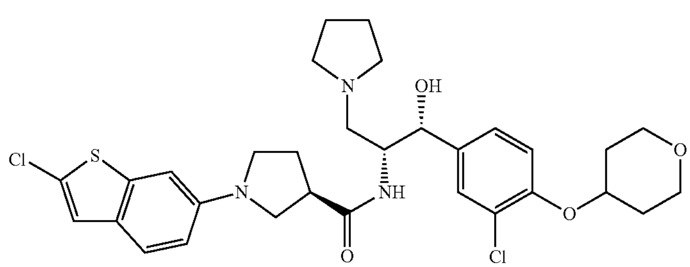 [SMILES: O=C(N[C@H](CN1CCCC1)[C@H](O)c1ccc(OC2CCOCC2)c(Cl)c1)[C@@H]1CCN(c2ccc3cc(Cl)sc3c2)C1] |

TABLE 1-continued

| Example No. | Name | Structure |
|---|---|---|
| 102 | (R)-N-((1R,2R)-1-(3-chloro-4-(2-hydroxy-2-methylpropoxy)phenyl)-1-hydroxy-3-(pyrrolidin-1-yl)propan-2-yl)-1-(6-fluoronaphthalen-2-yl)pyrrolidine-3-carboxamide | 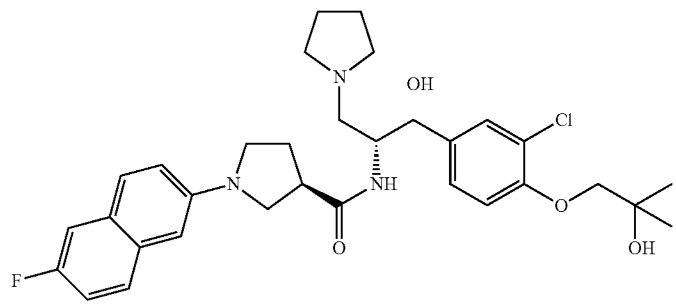 |
| 103 | (R)-1-(4-chloro-3-(pyridin-2-yloxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide | 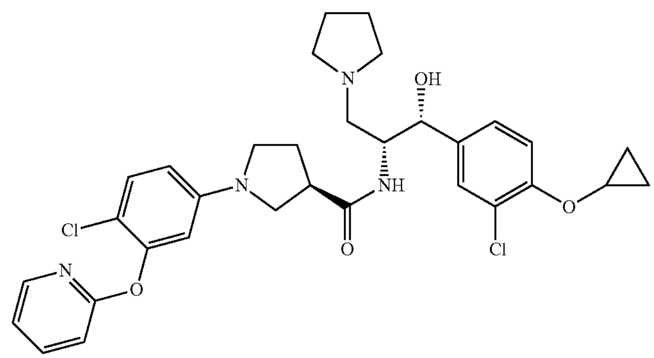 [SMILES: O=C(N[C@H](CN1CCCC1)[C@H](O)c1ccc(OC2CC2)c(Cl)c1)[C@@H]1CCN(c2ccc(Cl)c(Oc3ccccn3)c2)C1] |
| 104 | (R)-1-(6-chloroquinolin-2-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 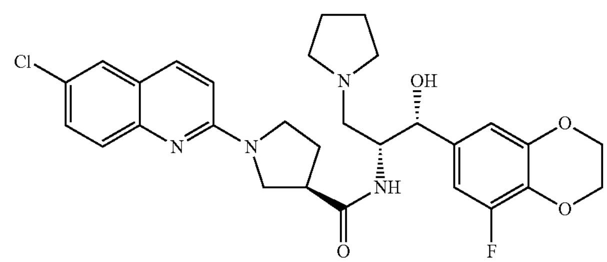 [SMILES: O=C(N[C@H](CN1CCCC1)[C@H](O)c1cc(F)c2c(c1)OCCO2)[C@@H]1CCN(c2ccc3cc(Cl)ccc3n2)C1] |
| 105 | (R)-1-(4-chloro-3-(pyridin-2-yloxy)phenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 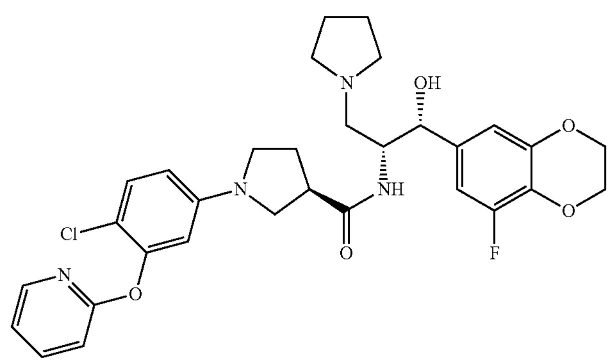 [SMILES: O=C(N[C@H](CN1CCCC1)[C@H](O)c1cc(F)c2c(c1)OCCO2)[C@@H]1CCN(c2ccc(Cl)c(Oc3ccccn3)c2)C1] |
| 106 | (R)-N-(1R,2R)-1-(2,3-dihydrobenzo[b][1,4]dioxin-6-yl)-1-hydroxy-3-(pyrrolidin-1-yl)propan-2-yl)-1-(quinolin-7-yl)pyrrolidine-3-carboxamide | 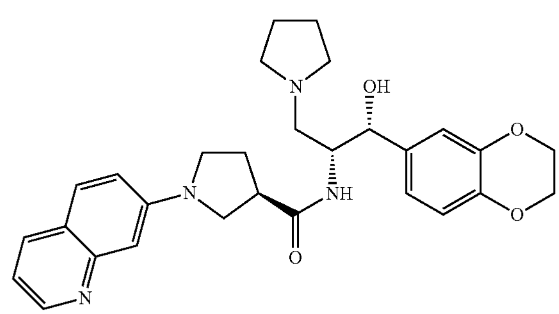 [SMILES: O=C(N[C@H](CN1CCCC1)[C@H](O)c1ccc2c(c1)OCCO2)[C@@H]1CCN(c2ccc3cccnc3c2)C1] |

TABLE 1-continued

| Example No. | Name | Structure |
|---|---|---|
| 107 | (R)-N-((1R,2R)-1-(3-chloro-4-(2-hydroxy-2-methylpropoxy)phenyl)-1-hydroxy-3-(pyrrolidin-1-yl)propan-2-yl)-1-(naphthalen-2-yl)pyrrolidine-3-carboxamide | 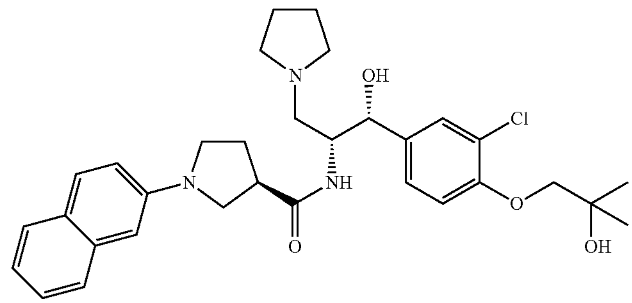 [SMILES: CC(C)(O)COc1ccc([C@@H](O)[C@@H](CN2CCCC2)NC(=O)[C@@H]2CCN(c3ccc4ccccc4c3)C2)cc1Cl] |
| 99 | (R)-1-(6-chloroquinolin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 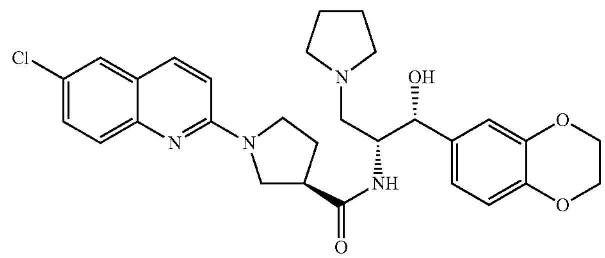 [SMILES: O=C(N[C@H](CN1CCCC1)[C@H](O)c1ccc2c(c1)OCCO2)[C@@H]1CCN(c2ccc3cc(Cl)ccc3n2)C1] |
| 99D | (S)-1-(6-chloroquinolin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 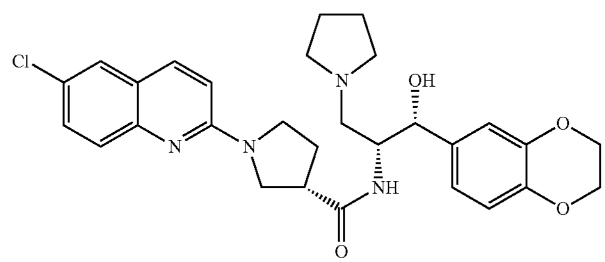 [SMILES: O=C(N[C@H](CN1CCCC1)[C@H](O)c1ccc2c(c1)OCCO2)[C@H]1CCN(c2ccc3cc(Cl)ccc3n2)C1] |
| 108 | (R)-N-((1R,2R)-3-(azetidin-1-yl)-1-(8-fluoro-2,3-dihydrobenzo[b][1,4]dioxin-6-yl)-1-hydroxypropan-2-yl)-1-(2-chlorobenzo[b]thiophen-6-yl)pyrrolidine-3-carboxamide | 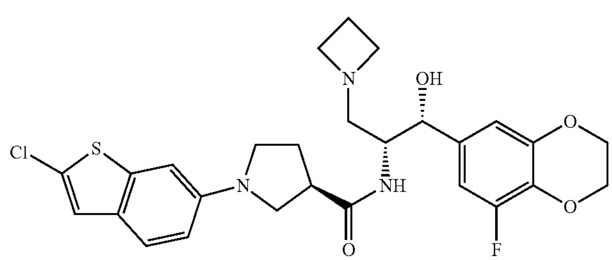 [SMILES: O=C(N[C@H](CN1CCC1)[C@H](O)c1cc(F)c2c(c1)OCCO2)[C@@H]1CCN(c2ccc3cc(Cl)sc3c2)C1] |
| 109 | (R)-N-((1R,2R)-1-(3-chloro-4-cyclopropoxyphenyl)-1-hydroxy-3-(pyrrolidin-1-yl)propan-2-yl)-1-(2-chlorobenzo[b]thiophen-6-yl)pyrrolidine-3-carboxamide | 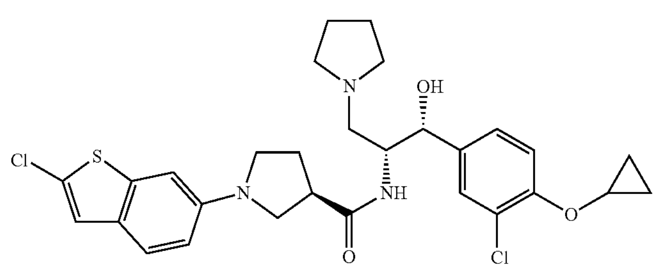 [SMILES: O=C(N[C@H](CN1CCCC1)[C@H](O)c1ccc(OC2CC2)c(Cl)c1)[C@@H]1CCN(c2ccc3cc(Cl)sc3c2)C1] |

TABLE 1-continued

| Example No. | Name | Structure |
|---|---|---|
| 110 | (R)-1-(4-chloro-3-(pyridin-2-yloxy)phenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 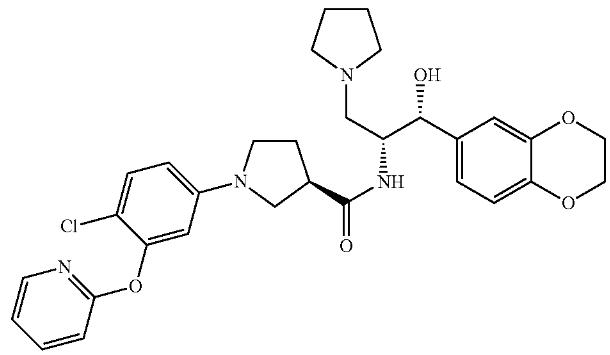 [SMILES: O=C(N[C@H](CN1CCCC1)[C@H](O)c1ccc2c(c1)OCCO2)[C@@H]1CCN(c2ccc(Cl)c(Oc3ccccn3)c2)C1] |
| 111 | (R)-1-(2-chlorobenzo[b]thiophen-6-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 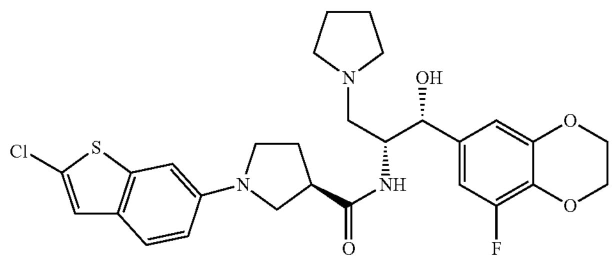 [SMILES: O=C(N[C@H](CN1CCCC1)[C@H](O)c1cc(F)c2c(c1)OCCO2)[C@@H]1CCN(c2ccc3cc(Cl)sc3c2)C1] |
| 112 | (R)-N-((1R,2R)-1-(3-chloro-4-cyclopropoxyphenyl)-1-hydroxy-3-(pyrrolidin-1-yl)propan-2-yl)-1-(6-(4-chlorophenoxy)pyridin-2-yl)pyrrolidine-3-carboxamide | 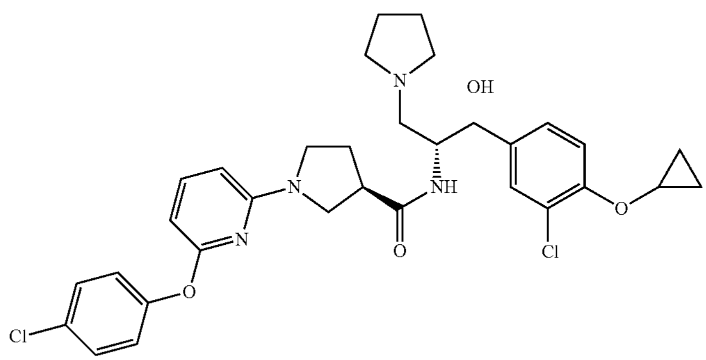 |
| 113 | (R)-1-(6-(4-chlorophenoxy)pyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 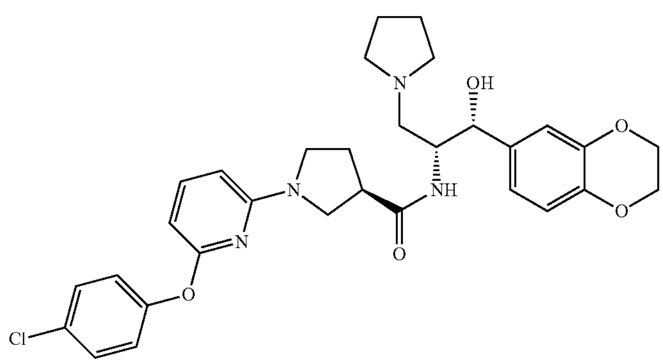 [SMILES: O=C(N[C@H](CN1CCCC1)[C@H](O)c1ccc2c(c1)OCCO2)[C@@H]1CCN(c2cccc(Oc3ccc(Cl)cc3)n2)C1] |

TABLE 1-continued

| Example No. | Name | Structure |
|---|---|---|
| 114 | (R)-1-(6-(4-chlorophenoxy)pyridin-2-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 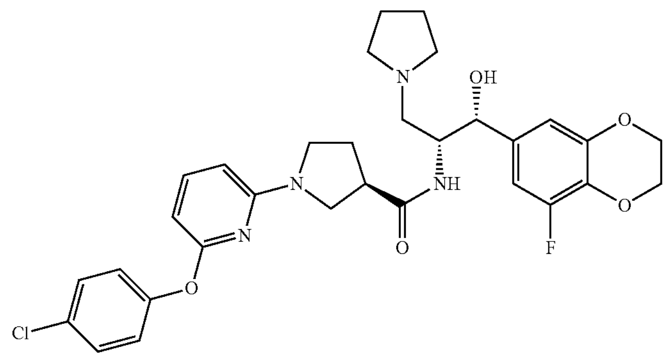 [SMILES: O=C(N[C@H](CN1CCCC1)[C@H](O)c1cc(F)c2c(c1)OCCO2)[C@@H]1CCN(c2cccc(Oc3ccc(Cl)cc3)n2)C1] |
| 115 | (R)-N-((1R,2R)-1-(3-chloro-4-cyclopropoxyphenyl)-1-hydroxy-3-(pyrrolidin-1-yl)propan-2-yl)-1-(6-(4-fluorophenoxy)pyridin-2-yl)pyrrolidine-3-carboxamide | 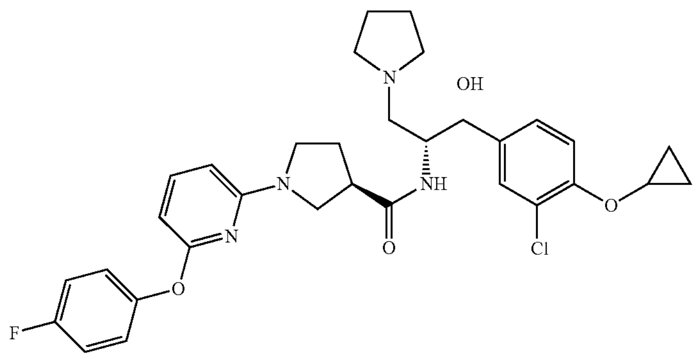 |
| 116 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(6-(4-fluorophenoxy)pyridin-2-yl)pyrrolidine-3-carboxamide | 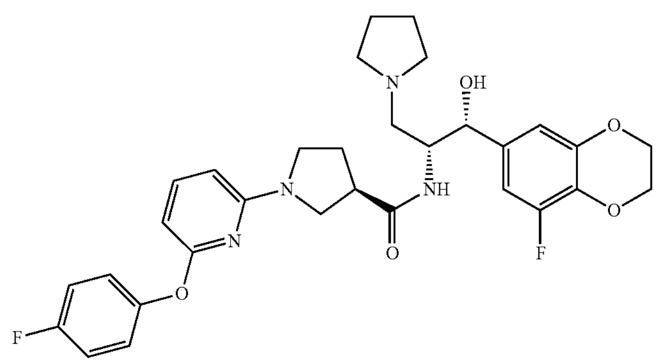 [SMILES: O=C(N[C@H](CN1CCCC1)[C@H](O)c1cc(F)c2c(c1)OCCO2)[C@@H]1CCN(c2cccc(Oc3ccc(F)cc3)n2)C1] |
| 117 | (R)-N-((1R,2R)-1-(3-chloro-4-(oxetan-3-yloxy)phenyl)-1-hydroxy-3-(pyrrolidin-1-yl)propan-2-yl)-1-(6-fluoronaphthalen-2-yl)pyrrolidine-3-carboxamide | 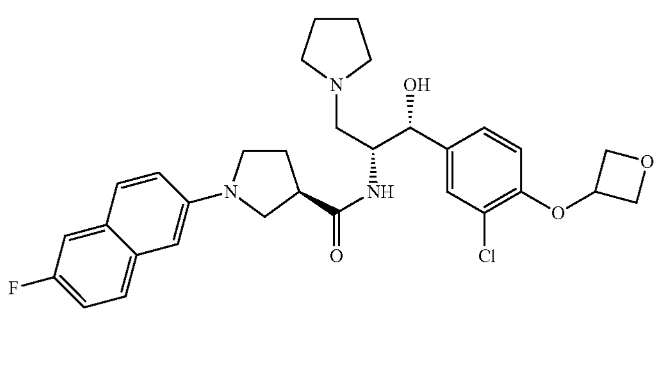 [SMILES: O=C(N[C@H](CN1CCCC1)[C@H](O)c1ccc(OC2COC2)c(Cl)c1)[C@@H]1CCN(c2ccc3cc(F)ccc3c2)C1] |

TABLE 1-continued

| Example No. | Name | Structure |
|---|---|---|
| 118 | (R)-N-((1R,2R)-1-(3-chloro-4-cyclopropoxyphenyl)-1-hydroxy-3-(pyrrolidin-1-yl)propan-2-yl)-1-(2-chloro-5-(pyridin-2-yloxy)phenyl)pyrrolidine-3-carboxamide | 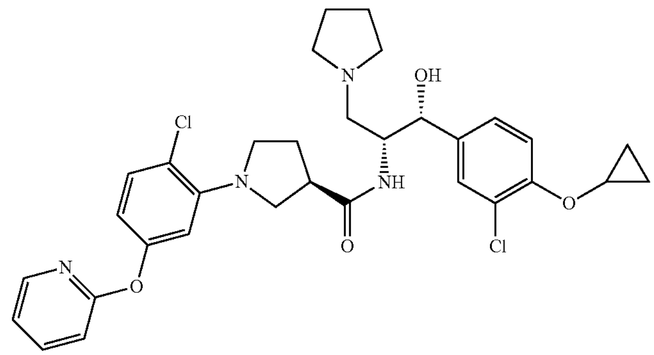 [SMILES: O=C(N[C@H](CN1CCCC1)[C@H](O)c1ccc(OC2CC2)c(Cl)c1)[C@@H]1CCN(c2cc(Oc3ccccn3)ccc2Cl)C1] |
| 119 | (R)-N-((1R,2R)-1-(2,3-dihydrobenzo[b][1,4]dioxin-6-yl)-1-hydroxy-3-(pyrrolidin-1-yl)propan-2-yl)-1-(6-(4-fluorophenoxy)pyridin-2-yl)pyrrolidine-3-carboxamide | 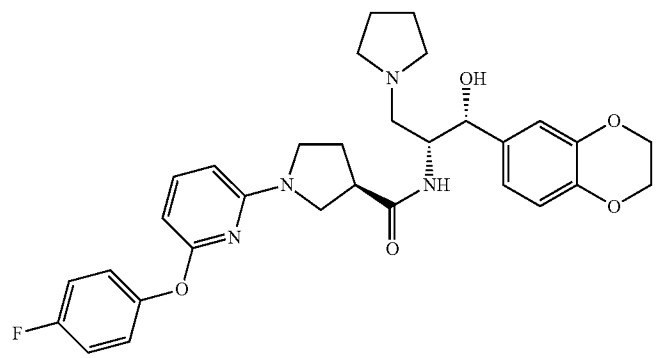 [SMILES: O=C(N[C@H](CN1CCCC1)[C@H](O)c1ccc2c(c1)OCCO2)[C@@H]1CCN(c2cccc(Oc3ccc(F)cc3)n2)C1] |
| 121 | (R)-1-benzoyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | 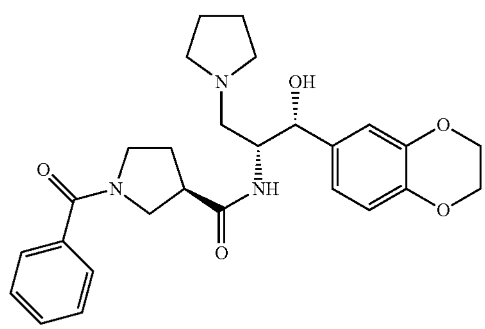 [SMILES: O=C(N[C@H](CN1CCCC1)[C@H](O)c1ccc2c(c1)OCCO2)[C@@H]1CCN(C(=O)c2ccccc2)C1] |
| 120 | (R)-1-benzoyl-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 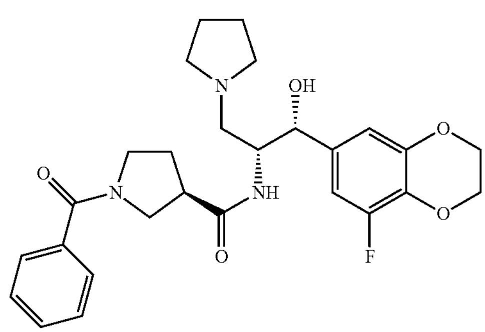 [SMILES: O=C(N[C@H](CN1CCCC1)[C@H](O)c1cc(F)c2c(c1)OCCO2)[C@@H]1CCN(C(=O)c2ccccc2)C1] |

TABLE 1-continued

| Example No. | Name | Structure |
|---|---|---|
| 122 | (R)-N-((1R,2R)-3-(azetidin-1-yl)-1-(3-chloro-4-(oxetan-3-yloxy)phenyl)-1-hydroxypropan-2-yl)-1-(6-fluoronaphthalen-2-yl)pyrrolidine-3-carboxamide | 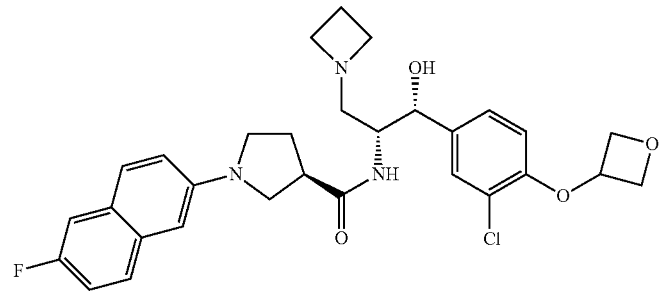 [SMILES: O=C(N[C@H](CN1CCC1)[C@H](O)c1ccc(OC2COC2)c(Cl)c1)[C@@H]1CCN(c2ccc3cc(F)ccc3c2)C1] |
| 123 | (R)-N-((1R,2R)-1-(2,3-dihydrobenzo[b][1,4]dioxin-6-yl)-1-hydroxy-3-(pyrrolidin-1-yl)propan-2-yl)-1-(6-(4-fluorophenyl)pyridin-2-yl)pyrrolidine-3-carboxamide | 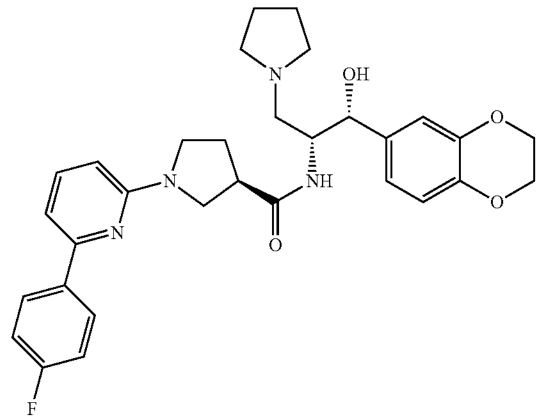 [SMILES: O=C(N[C@H](CN1CCCC1)[C@H](O)c1ccc2c(c1)OCCO2)[C@@H]1CCN(c2cccc(-c3ccc(F)cc3)n2)C1] |
| 124 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(6-(4-fluorophenyl)pyridin-2-yl)pyrrolidine-3-carboxamide | 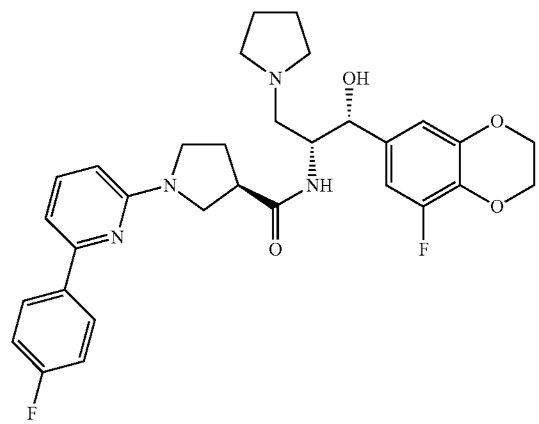 [SMILES: O=C(N[C@H](CN1CCCC1)[C@H](O)c1cc(F)c2c(c1)OCCO2)[C@@H]1CCN(c2cccc(-c3ccc(F)cc3)n2)C1] |
| 125 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(1-methyl-1H-indazol-5-yl)pyrrolidine-3-carboxamide | 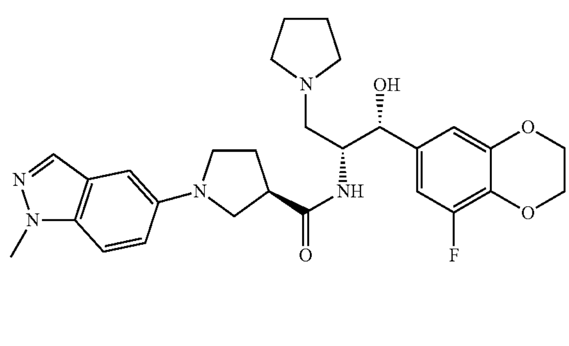 [SMILES: Cn1ncc2cc(N3CC[C@@H](C(=O)N[C@H](CN4CCCC4)[C@H](O)c4cc(F)c5c(c4)OCCO5)C3)ccc21] |

TABLE 1-continued

| Example No. | Name | Structure |
|---|---|---|
| 127 | (R)-N-((1R,2R)-1-(3-chloro-4-cyclopropoxyphenyl)-1-hydroxy-3-(pyrrolidin-1-yl)propan-2-yl)-1-(1-methyl-1H-indazol-5-yl)pyrrolidine-3-carboxamide | 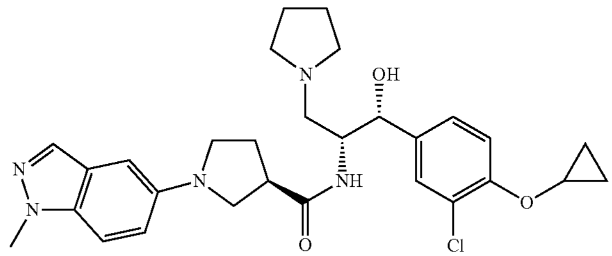 [SMILES: Cn1ncc2cc(N3CC[C@@H](C(=O)N[C@H](CN4CCCC4)[C@H](O)c4ccc(OC5CC5)c(Cl)c4)C3)ccc21] |
| 128 | (R)-1-(4-chloro-3-(4-fluorophenoxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide | 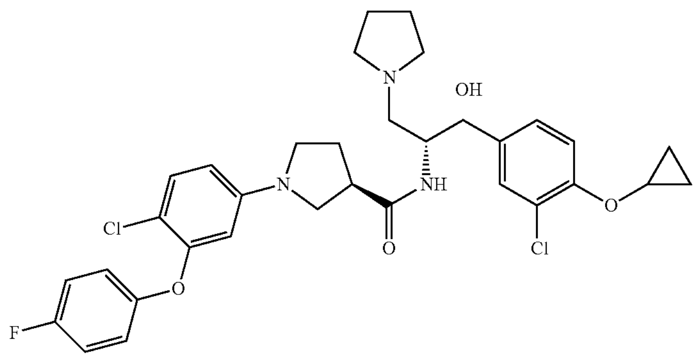 |
| 129 | (R)-1-benzoyl-N-((1R,2R)-1-(3-chloro-4-cyclopropoxyphenyl)-1-hydroxy-3-(pyrrolidin-1-yl)propan-2-yl)pyrrolidine-3-carboxamide | 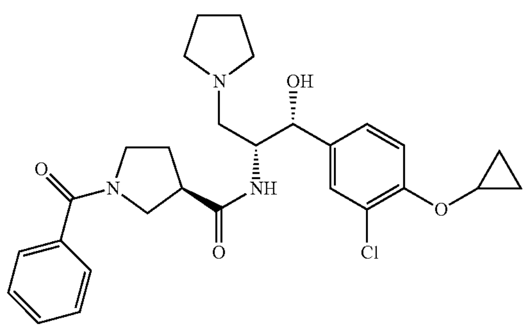 [SMILES: O=C(N[C@H](CN1CCCC1)[C@H](O)c1ccc(OC2CC2)c(Cl)c1)[C@@H]1CCN(C(=O)c2ccccc2)C1] |
| 126 | (R)-N-((1R,2R)-1-(3-chloro-4-cyclopropoxyphenyl)-1-hydroxy-3-(pyrrolidin-1-yl)propan-2-yl)-1-(6-(4-fluorophenyl)pyridin-2-yl)pyrrolidine-3-carboxamide | 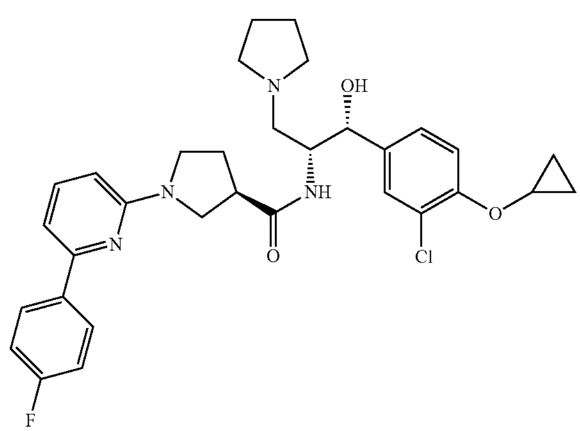 [SMILES: O=C(N[C@H](CN1CCCC1)[C@H](O)c1ccc(OC2CC2)c(Cl)c1)[C@@H]1CCN(c2cccc(-c3ccc(F)cc3)n2)C1] |

TABLE 1-continued

| Example No. | Name | Structure |
|---|---|---|
| 130 | (R)-1-(4-chlorophenyl)-N-((1R,2R)-1-(5-fluoro-2,3-dihydrobenzo[b][1,4]dioxin-6-yl)-1-hydroxy-3-(pyrrolidin-1-yl)propan-2-yl)pyrrolidine-3-carboxamide | 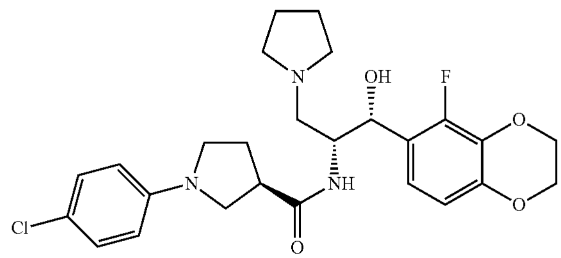 [SMILES: O=C(N[C@H](CN1CCCC1)[C@H](O)c1ccc2c(c1F)OCCO2)[C@@H]1CCN(c2ccc(Cl)cc2)C1] |
| 131 | (R)-1-(4-chloro-3-((6-methylpyridin-2-yl)oxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide | 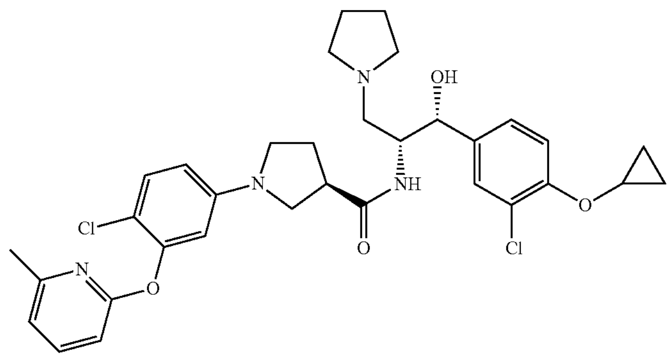 [SMILES: Cc1cccc(Oc2cc(N3CC[C@@H](C(=O)N[C@H](CN4CCCC4)[C@H](O)c4ccc(OC5CC5)c(Cl)c4)C3)ccc2Cl)n1] |
| 132 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide | 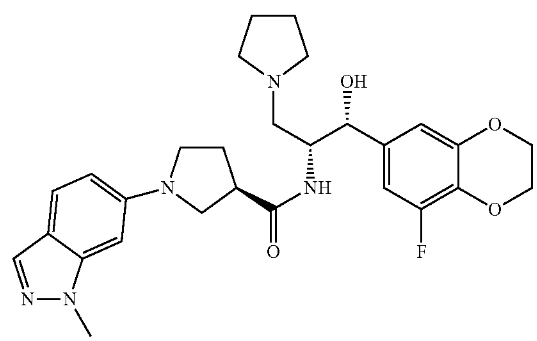 [SMILES: Cn1ncc2ccc(N3CC[C@@H](C(=O)N[C@H](CN4CCCC4)[C@H](O)c4cc(F)c5c(c4)OCCO5)C3)cc21] |
| 133 | (R)-N-((1R,2R)-1-(3-chloro-4-cyclopropoxyphenyl)-1-hydroxy-3-(pyrrolidin-1-yl)propan-2-yl)-1-(1-methyl-1H-indazol-6-yl)pyrrolidine-3-carboxamide | 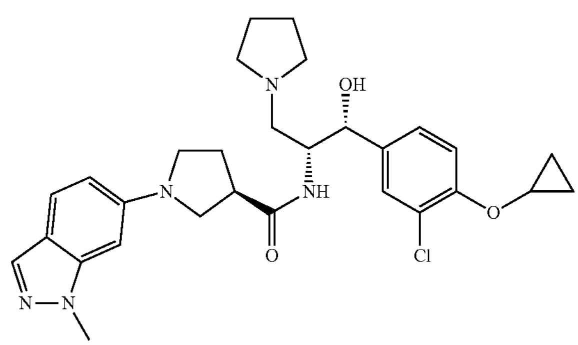 [SMILES: Cn1ncc2ccc(N3CC[C@@H](C(=O)N[C@H](CN4CCCC4)[C@H](O)c4ccc(OC5CC5)c(Cl)c4)C3)cc21] |

TABLE 1-continued

| Example No. | Name | Structure |
|---|---|---|
| 134 | (R)-N-((1R,2R)-3-(azetidin-1-yl)-1-(8-fluoro-2,3-dihydrobenzo[b][1,4]dioxin-6-yl)-1-hydroxypropan-2-yl)-1-(1-methyl-1H-indazol-6-yl)pyrrolidine-3-carboxamide | 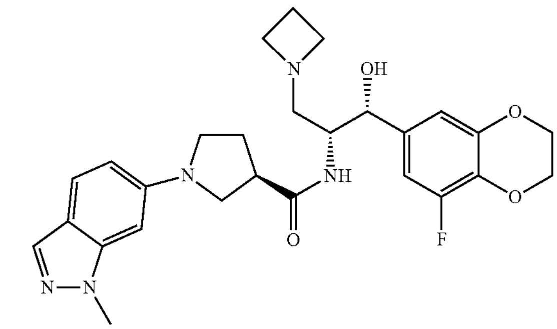 [SMILES: Cn1ncc2ccc(N3CC[C@@H](C(=O)N[C@H](CN4CCC4)[C@H](O)c4cc(F)c5c(c4)OCCO5)C3)cc21] |
| 135 | (R)-N-((1R,2R)-1-(4-(tert-butoxy)-3-chlorophenyl)-1-hydroxy-3-(pyrrolidin-1-yl)propan-2-yl)-1-(4-chlorophenyl)pyrrolidine-3-carboxamide | 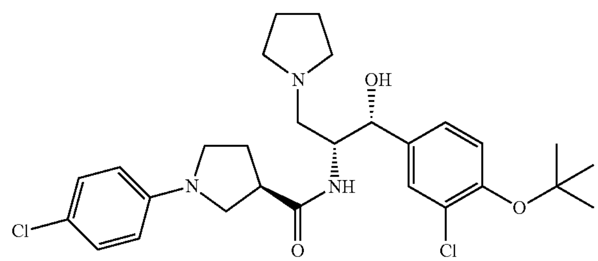 [SMILES: CC(C)(C)Oc1ccc([C@@H](O)[C@@H](CN2CCCC2)NC(=O)[C@@H]2CCN(c3ccc(Cl)cc3)C2)cc1Cl] |
| 136 | (R)-1-(4-chloro-3-(cyclohexyloxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide | 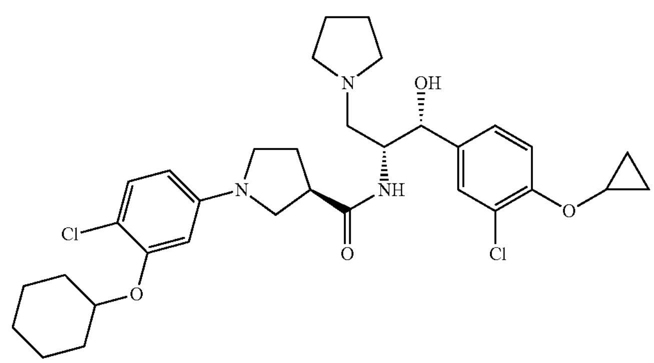 [SMILES: O=C(N[C@H](CN1CCCC1)[C@H](O)c1ccc(OC2CC2)c(Cl)c1)[C@@H]1CCN(c2ccc(Cl)c(OC3CCCCC3)c2)C1] |
| 137 | (R)-1-(4-chlorophenyl)-N-((1R,2R)-1-hydroxy-3-(pyrrolidin-1-yl)-1-(8-(trifluoromethyl)-2,3-dihydrobenzo[b][1,4]dioxin-6-yl)propan-2-yl)pyrrolidine-3-carboxamide | 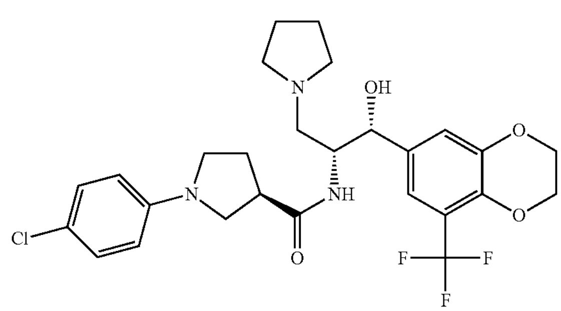 [SMILES: O=C(N[C@H](CN1CCCC1)[C@H](O)c1cc2c(c(C(F)(F)F)c1)OCCO2)[C@@H]1CCN(c2ccc(Cl)cc2)C1] |

TABLE 1-continued

| Example No. | Name |
|---|---|
| 138 | (R)-1-(6-chloro-4'-fluoro-[1,1'-biphenyl]-3-yl)-N-((1R,2R)-1-(3-chloro-4-cyclopropoxyphenyl)-1-hydroxy-3-(pyrrolidin-1-yl)propan-2-yl)pyrrolidine-3-carboxamide |
| 139 | (R)-1-(4-(tert-butyl)phenyl)-N-((1R,2R)-1-(3-chloro-4-cyclopropoxyphenyl)-1-hydroxy-3-(pyrrolidin-1-yl)propan-2-yl)pyrrolidine-3-carboxamide |
| 140 | (R)-N-((1R,2R)-1-(3-chloro-4-cyclobutoxyphenyl)-1-hydroxy-3-(pyrrolidin-1-yl)propan-2-yl)-1-(4-chlorophenyl)pyrrolidine-3-carboxamide |
| 141 | (R)-N-((2R,2R)-1-(3-chloro-4-(cyclopentyloxy)phenyl)-1-hydroxy-3-(pyrrolidin-1-yl)propan-2-yl)-1-(4-chlorophenyl)pyrrolidine-3-carboxamide |
| 142 | (R)-1-(4-(tert-butyl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide |

TABLE 1-continued

| Example No. | Name | Structure |
|---|---|---|
| 143 | (R)-N-((1R,2R)-1-(benzo[b][1,4]dioxin-6-yl)-1-hydroxy-3-(pyrrolidin-1-yl)propan-2-yl)-1-(4-chlorophenyl)pyrrolidine-3-carboxamide | 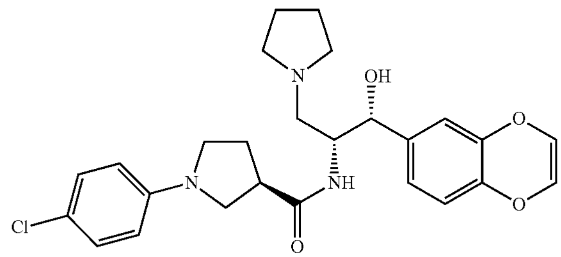 [SMILES: O=C(N[C@H](CN1CCCC1)[C@H](O)c1ccc2c(c1)OC=CO2)[C@@H]1CCN(c2ccc(Cl)cc2)C1] |
| 144 | (R)-1-(5-chloro-6-(4-fluorophenyl)pyridin-2-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | 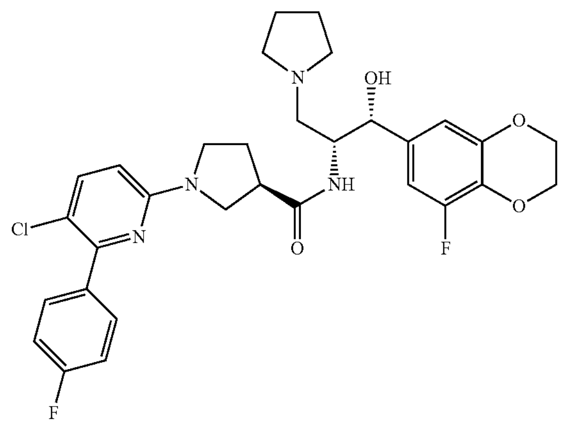 [SMILES: O=C(N[C@H](CN1CCCC1)[C@H](O)c1cc(F)c2c(c1)OCCO2)[C@@H]1CCN(c2ccc(Cl)c(-c3ccc(F)cc3)n2)C1] |
| 145 | (R)-N-((1R,2R)-1-(3-chloro-4-(cyclopropylthio)phenyl)-1-hydroxy-3-(pyrrolidin-1-yl)propan-2-yl)-1-(4-chlorophenyl)pyrrolidine-3-carboxamide | 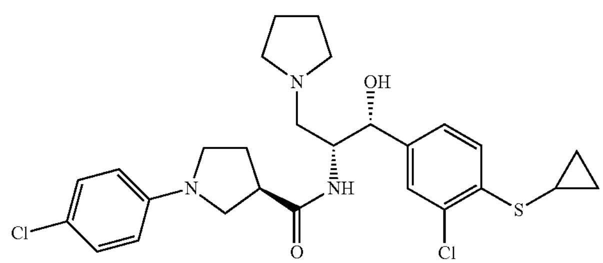 |
| 146 | (R)-N-((1R,2R)-1-(3-chloro-4-cyclopropoxyphenyl)-1-hydroxy-3-(pyrrolidin-1-yl)propan-2-yl)-1-(5-chloro-6-(4-fluorophenyl)pyridin-2-yl)pyrrolidine-3-carboxamide | 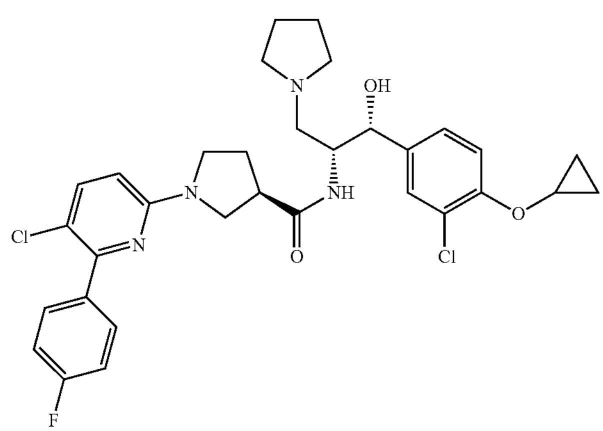 [SMILES: O=C(N[C@H](CN1CCCC1)[C@H](O)c1ccc(OC2CC2)c(Cl)c1)[C@@H]1CCN(c2ccc(Cl)c(-c3ccc(F)cc3)n2)C1] |

TABLE 1-continued

| Example No. | Name | Structure |
|---|---|---|
| 147 | (R)-N-((1R,2R)-1-(3-chloro-4-(vinyloxy(phenyl)-1-hydroxy-3-(pyrrolidin-1-yl)propan-2-yl)-1-(4-chlorophenyl)pyrrolidine-3-carboxamide | 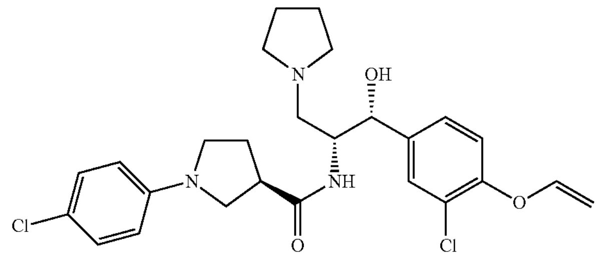 [SMILES: C=COc1ccc([C@@H](O)[C@@H](CN2CCCC2)NC(=O)[C@@H]2CCN(c3ccc(Cl)cc3)C2)cc1Cl] |
| 148 | (R)-N-((1R,2R)-1-(4-cyclopropoxyphenyl)-1-hydroxy-3-(pyrrolidin-1-yl)propan-2-yl)-1-(4-fluorophenyl)pyrrolidine-3-carboxamide | 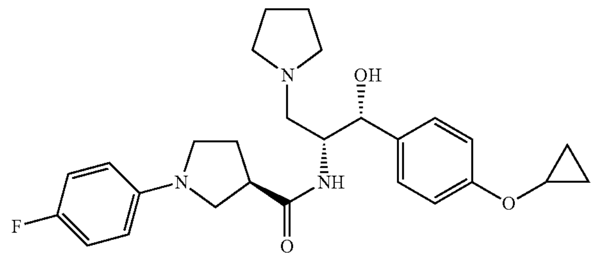 |
| 149 | (R)-N-((1R,2R)-1-(4-cyclopropoxyphenyl)-1-hydroxy-3-(pyrrolidin-1-yl)propan-2-yl)-1-phenylpyrrolidine-3-carboxamide | 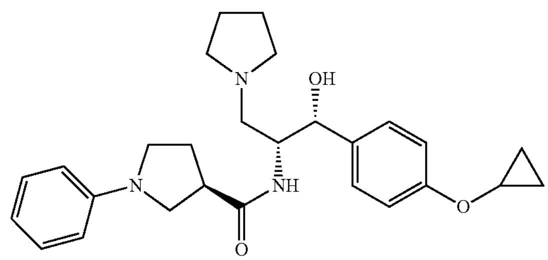 [SMILES: O=C(N[C@H](CN1CCCC1)[C@H](O)c1ccc(OC2CC2)cc1)[C@@H]1CCN(c2ccccc2)C1] |
| 150 | (R)-N-((1R,2R)-1-(3-chloro-4-cyclopropoxyphenyl)-1-hydroxy-3-(pyrrolidin-1-yl)propan-2-yl)-1-phenylpyrrolidine-3-carboxamide | 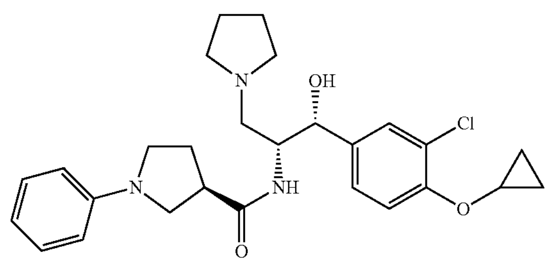 [SMILES: O=C(N[C@H](CN1CCCC1)[C@H](O)c1ccc(OC2CC2)c(Cl)c1)[C@@H]1CCN(c2ccccc2)C1] |
| 151 | (R)-N-((1R,2R)-1-(4-cyclopropoxy-3-fluorophenyl)-1-hydroxy-3-(pyrrolidin-1-yl)propan-2-yl)-1-phenylpyrrolidine-3-carboxamide | 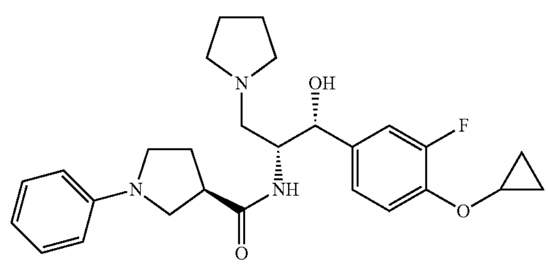 [SMILES: O=C(N[C@H](CN1CCCC1)[C@H](O)c1ccc(OC2CC2)c(F)c1)[C@@H]1CCN(c2ccccc2)C1] |
| 152 | (R)-N-((1R,2R)-1-(3-chloro-4-cyclopropoxyphenyl)-1-hydroxy-3-(pyrrolidin-1-yl)propan-2-yl)-1-(4-cyanophenyl)pyrrolidine-3-carboxamide | 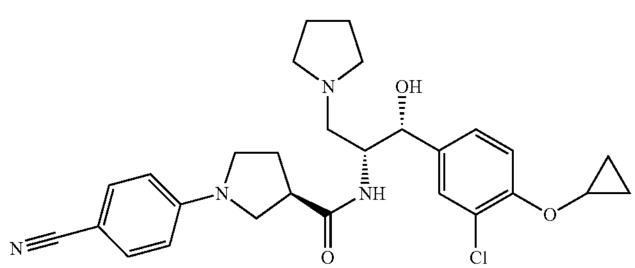 [SMILES: N#Cc1ccc(N2CC[C@@H](C(=O)N[C@H](CN3CCCC3)[C@H](O)c3ccc(OC4CC4)c(Cl)c3)C2)cc1] |

TABLE 1-continued

| Example No. | Name | Structure |
|---|---|---|
| 152C | (R)-N-((1S,2R)-1-(3-chloro-4-cyclopropoxyphenyl)-1-hydroxy-3-(pyrrolidin-1-yl)propan-2-yl)-1-(4-cyanophenyl)pyrrolidine-3-carboxamide | 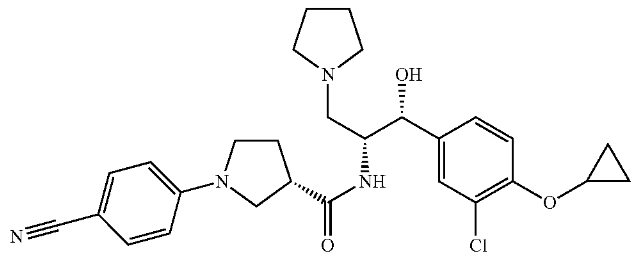 [SMILES: N#Cc1ccc(N2CC[C@H](C(=O)N[C@H](CN3CCCC3)[C@H](O)c3ccc(OC4CC4)c(Cl)c3)C2)cc1] |
| 153 | (R)-N-((1R,2R)-1-(3-chloro-4-cyclopropoxyphenyl)-1-hydroxy-3-(pyrrolidin-1-yl)propan-2-yl)-1-(p-tolyl)pyrrolidine-3-carboxamide | 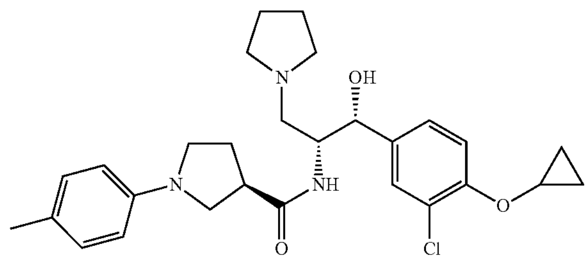 [SMILES: Cc1ccc(N2CC[C@@H](C(=O)N[C@H](CN3CCCC3)[C@H](O)c3ccc(OC4CC4)c(Cl)c3)C2)cc1] |
| 154 | (S)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)-3-hydroxypyrrolidine-3-carboxamide | 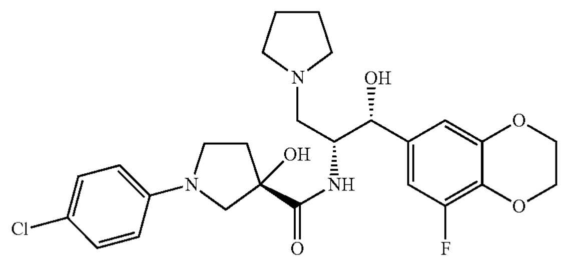 [SMILES: O=C(N[C@H](CN1CCCC1)[C@H](O)c1cc(F)c2c(c1)OCCO2)[C@]1(O)CCN(c2ccc(Cl)cc2)C1] |
| 154C | (R)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)-3-hydroxypyrrolidine-3-carboxamide | 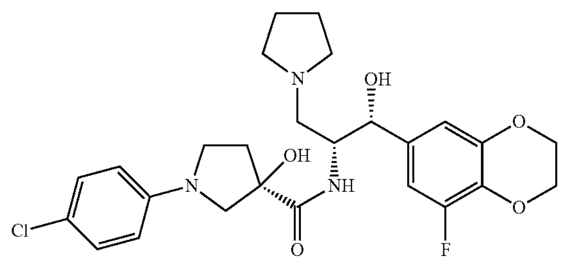 [SMILES: O=C(N[C@H](CN1CCCC1)[C@H](O)c1cc(F)c2c(c1)OCCO2)[C@@]1(O)CCN(c2ccc(Cl)cc2)C1] |
| 155 | (R)-1-(4-chlorophenyl)-N-((1R,2R)-1-(4-cyclopropoxyphenyl)-1-hydroxy-3-(pyrrolidin-1-yl)propan-2-yl)pyrrolidine-3-carboxamide | 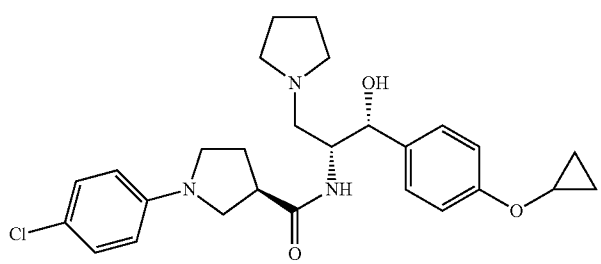 [SMILES: O=C(N[C@H](CN1CCCC1)[C@H](O)c1ccc(OC2CC2)cc1)[C@@H]1CCN(c2ccc(Cl)cc2)C1] |
| 156 | (R)-1-(4-chlorophenyl)-N-((1R,2R)-1-(4-chlorophenyl)-1-hydroxy-3-(pyrrolidin-1-yl)propan-2-yl)pyrrolidine-3-carboxamide | 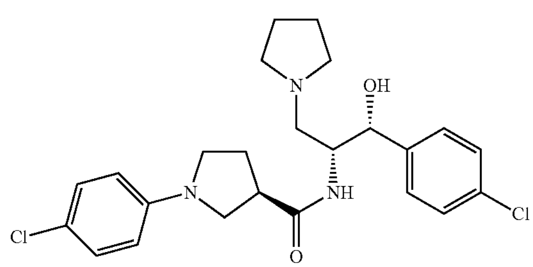 [SMILES: O=C(N[C@H](CN1CCCC1)[C@H](O)c1ccc(Cl)cc1)[C@@H]1CCN(c2ccc(Cl)cc2)C1] |

TABLE 1-continued

| Example No. | Name | Structure |
|---|---|---|
| 157 | (R)-1-(benzo[b]thiophen-6-yl)-N-((1R,2R)-1-(4-cyclopropoxyphenyl)-1-hydroxy-3-(pyrrolidin-1-yl)propan-2-yl)pyrrolidine-3-carboxamide | 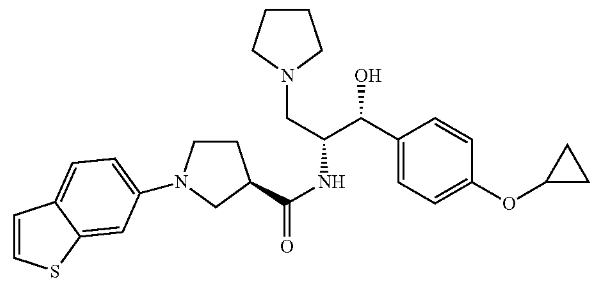 [SMILES: O=C(N[C@H](CN1CCCC1)[C@H](O)c1ccc(OC2CC2)cc1)[C@@H]1CCN(c2ccc3ccsc3c2)C1] |
| 158 | (R)-N-((1R,2R)-3-(azetidin-1-yl)-1-(4-cyclopropoxyphenyl)-1-hydroxypropan-2-yl)-1-(benzo[b]thiophen-6-yl)pyrrolidine-3-carboxamide | 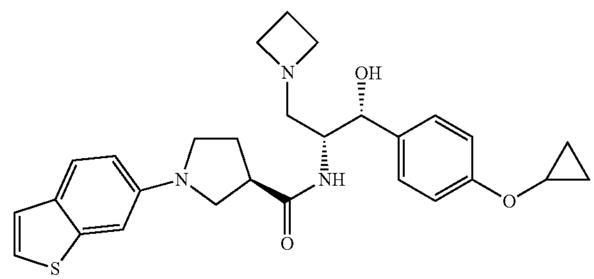 [SMILES: O=C(N[C@H](CN1CCC1)[C@H](O)c1ccc(OC2CC2)cc1)[C@@H]1CCN(c2ccc3ccsc3c2)C1] |
| 159 | (R)-N-((1R,2R)-3-(azetidin-1-yl)-1-(4-cyclopropoxyphenyl)-1-hydroxypropan-2-yl)-1-(6-fluoronaphthalen-2-yl)pyrrolidine-3-carboxamide | 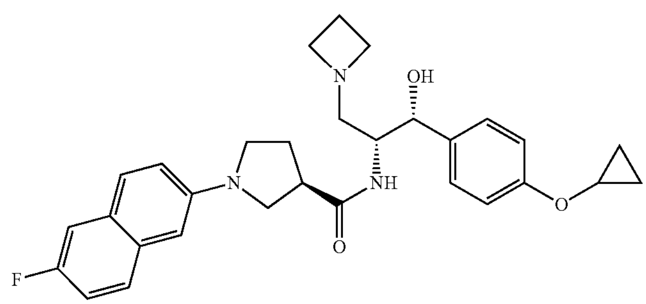 [SMILES: O=C(N[C@H](CN1CCC1)[C@H](O)c1ccc(OC2CC2)cc1)[C@@H]1CCN(c2ccc3cc(F)ccc3c2)C1] |
| 159C | (S)-N-((1R,2R)-3-(azetidin-1-yl)-1-(4-cyclopropoxyphenyl)-1-hydroxypropan-2-yl)-1-(6-fluoronaphthalen-2-yl)pyrrolidine-3-carboxamide | 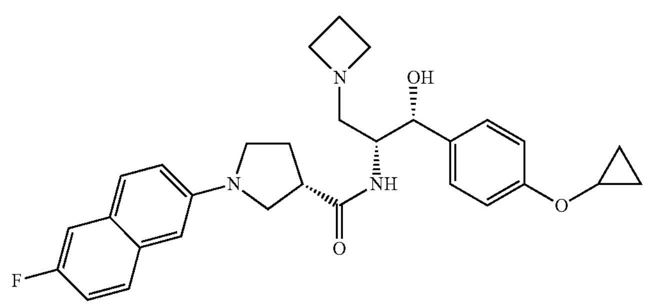 [SMILES: O=C(N[C@H](CN1CCC1)[C@H](O)c1ccc(OC2CC2)cc1)[C@H]1CCN(c2ccc3cc(F)ccc3c2)C1] |
| 160 | (R)-1-(4-chlorophenyl)-N-((1R,2R)-1-(4-(difluoromethoxy)phenyl)-1-hydroxy-3-(pyrrolidin-1-yl)propan-2-yl)pyrrolidine-3-carboxamide | 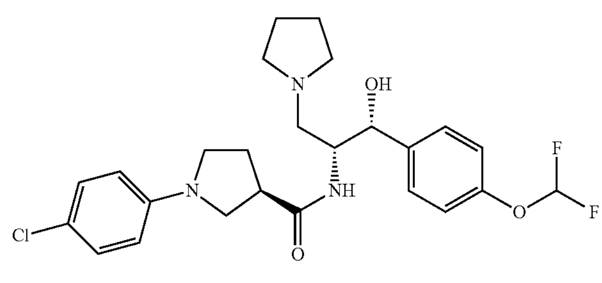 [SMILES: O=C(N[C@H](CN1CCCC1)[C@H](O)c1ccc(OC(F)F)cc1)[C@@H]1CCN(c2ccc(Cl)cc2)C1] |

TABLE 1-continued

| Example No. | Name | Structure |
|---|---|---|
| 161 | (R)-N-((1R,2R)-1-(4-(difluoromethoxy)phenyl)-1-hydroxy-3-(pyrrolidin-1-yl)propan-2-yl)-1-phenylpyrrolidine-3-carboxamide | 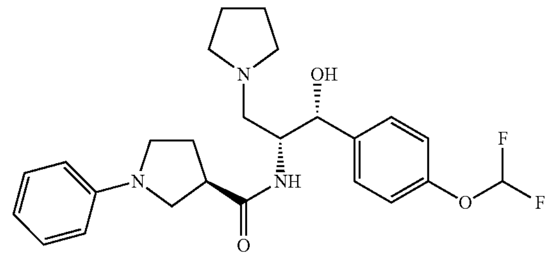 [SMILES: O=C(N[C@H](CN1CCCC1)[C@H](O)c1ccc(OC(F)F)cc1)[C@@H]1CCN(c2ccccc2)C1] |
| 162 | (R)-N-((1R,2R)-1-(4-cyclopropoxyphenyl)-1-hydroxy-3-(pyrrolidin-1-yl)propan-2-yl)-1-(6-fluoronaphthalen-2-yl)pyrrolidine-3-carboxamide | 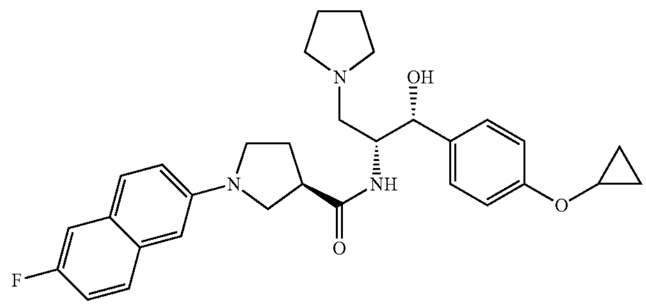 [SMILES: O=C(N[C@H](CN1CCCC1)[C@H](O)c1ccc(OC2CC2)cc1)[C@@H]1CCN(c2ccc3cc(F)ccc3c2)C1] |

In some or any embodiments, the compound is selected from Table 1.

In some or any embodiments, the compound is selected from the group consisting of the compounds of Examples 1, 1C, 1D, 2, 2A, 2B, 5, 5D, 5E, 8, 8C, 8D, 9, 9D, 9E, 11, 12, 12D, 14, 14C, 14D, 15, 15C, 15D, 17, 17D, 19, 20, 20D, 20E, 21, 21E, 21F, 22, 22C, 22D, 24, 24B, 24C, 25, 25B, 26, 28, 28C, 28D, 30, 35, 35A, 36, 36F, 36G, 43, 43D, 43E, 44, 44C, 46, 46A, 46B, 47, 47A, 47B, 48, 48A, 52, 52A, 53, 53C, 53D, 55, 55A, 55B, 56, 56D, 56E, 58, 58D, 61, 61C, 61D, 63, 63C, 63D, 64, 68, 68C, 70, 70A, 71, 71E, 71F, 72, 72A, 72B, 76, 76D, 76E, 77, 78, 79, 79A, 79B, 80, 80G, 80H, 81, 82, 82E, 83, 83C, 83D, 85, 88, 88C, 88D, 89, 89F, 89G, 90, 90D, 93, 93A, 97, 97C, 99, 99C, 99D, 104, 105, 106, 108, 110, 111, 113, 114, 116, 119, 120, 121, 123, 124, 125, 130, 132, 134, 137, 142, 144, 154, and 154C.

In some or any embodiments, the compound is selected from the group consisting of the compounds of Examples 3, 3A, 3B, 6, 10, 23, 23B, 32, 32A, 45, 45A, 49, 49A, 50, 50A, 54, 54A, 57, 57A, 59, 60, 60A, 65, 66, 67, 67C, 69, 69A, 73, 74, 74C, 75, 75E, 84, 84A, 86, 87, 91, 92, 94, 95, 96, 98, 98A, 100, 101, 102, 103, 107, 109, 112, 115, 117, 118, 122, 126, 127, 128, 129, 131, 133, 135, 136, 138, 139, 140, 141, 145, 146, 147, 148, 149, 150, 151, 152, 152C, 153, 155, 156, 157, 158, 159, 159A, 160, 161, and 162.

In some or any embodiments, the compound is selected from the group consisting of the compounds of Examples 1, 1C, 1D, 2, 2A, 2B, 3, 3A, 3B, 6, 8, 8C, 8D, 10, 12, 12D, 13, 13C, 14, 14C, 14D, 19, 20, 20D, 20E, 23, 23B, 24, 24B, 24C, 25, 25B, 27, 27C, 29, 29B, 31, 31B, 32, 32A, 33, 33A, 34, 34A, 35, 35A, 43, 43D, 43E, 44, 44C, 45, 45A, 46, 46A, 46B, 47, 47A, 47B, 49, 49A, 50, 50A, 51, 51A, 52, 52A, 59, 60, 60A, 62, 65, 66, 67, 67C, 69, 69A, 70, 70A, 73, 74, 74C, 75, 75E, 77, 78, 79, 79A, 79B, 81, 84, 84A, 85, 86, 87, 88, 88C, 88D, 89, 89F, 89G, 94, 95, 96, 102, 103, 105, 107, 110, 117, 118, 122, 128, 130, 131, 135, 136, 137, 138, 139, 140, 141, 142, 143, 145, 147, 148, 149, 150, 151, 152, 152C, 153, 154, 154C, 155, 156, 159, 159A, 160, 161, and 162.

In some or any embodiments, the compound is selected from the group consisting of the compounds of Examples 17, 17D, 22, 22C, 22D, 28, 28C, 28D, 48, 48A, 53, 53C, 53D, 54, 54A, 56, 56D, 56E, 57, 57A, 58, 58D, 61, 61C, 61D, 68, 68C, 72, 72A, 72B, 76, 76D, 76E, 82, 82E, 83, 83C, 83D, 90, 90D, 91, 92, 97, 97C, 99, 99C, 99D, 100, 101, 104, 106, 108, 109, 111, 112, 113, 114, 115, 116, 119, 123, 124, 125, 126, 127, 132, 133, 134, 144, 146, 157, and 158.

In some or any embodiments, the compound is selected from the group consisting of the compounds of Examples 5, 5D, 5E, 9, 9D, 9E, 11, 26, 30, 36, 36F, 36G, 55, 55A, 55B, 63, 63C, 63D, 64, 71, 71E, 71F, 80, 80G, 80H, 93, 93A, 98, and 98A.

In some or any embodiments, the compound is selected from the group consisting of the compounds of Examples 13, 13C, 27, 27C, 29, 29B, 31, 31B, 33, 33A, 34, 34A, and 62.

In some or any embodiments, the compound is selected from the group consisting of the compounds of Examples 15, 15C, 15D, 21, 21E, 21F, 120, 121, and 129.4.

In some or any embodiments, provided is a pharmaceutical composition comprising 1) a Compound of Formula I, (b), I(c), or a compound in Table 1 optionally as a tautomer, a single stereoisomer or mixture of stereoisomers thereof and additionally optionally as a pharmaceutically acceptable salt thereof, and 2) a pharmaceutically acceptable excipient or pharmaceutically acceptable carrier.

Pharmaceutical Composition/Formulation

In some or any embodiments, optionally in combination with any or all of the above various embodiments, provided herein is a pharmaceutical composition comprising of a compound of Formula I, I(a), I(b), I(c), I(d), I(d1), I(d2), I(e), I(e1), I(e2), I(f), I(f1), I(f2), I(g), I(g1), I(h), I(h1), or a compound of Table 1 or stereoisomers, or a pharmaceutically acceptable salt, and one or more pharmaceutically acceptable carrier(s), excipient(s), binder(s) or diluent(s). The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants.

In some or any embodiments, disclosed herein is a pharmaceutical composition comprising a compound, pharmaceutically acceptable salt, pharmaceutically acceptable N-oxide, pharmaceutically active metabolite, pharmaceutically acceptable prodrug, or pharmaceutically acceptable solvate of any of the compounds disclosed herein. In some embodiments, the pharmaceutical compositions further comprises a pharmaceutically acceptable diluent, excipient or binder.

In some or any embodiments, pharmaceutical compositions are formulated in any manner, including using one or more physiologically acceptable carriers comprising excipients and/or auxiliaries which facilitate processing of the active compounds into pharmaceutical preparations. In some embodiments, proper formulation is dependent upon the route of administration chosen. In various embodiments, any techniques, carriers, and excipients are used as suitable.

A pharmaceutical composition, as used herein, refers to a mixture of a compound described herein with other chemical components, such as carriers, stabilizers, diluents, dispersing agents, suspending agents, thickening agents, and/or excipients. In some or any embodiments, a pharmaceutical composition facilitates administration of the compound to an organism. In some embodiments, practicing the methods of treatment or use provided herein, includes administering or using a pharmaceutical composition comprising a therapeutically effective amount of a compound provided herein. In specific embodiments, the methods of treatment provided for herein include administering such a pharmaceutical composition to a mammal having a disease or condition to be treated. In one embodiment, the mammal is a human. In some embodiments, the therapeutically effective amount varies widely depending on the severity of the disease, the age and relative health of the subject, the potency of the compound used and other factors. In various embodiments, the compounds described herein are used singly or in combination with one or more therapeutic agents as components of mixtures.

In a some or any embodiment, it is provided a method of forming a composition, comprising providing a compound and forming the composition. In some embodiments, the composition further comprises a pharmaceutically acceptable carrier. In some embodiments of the composition, optionally in combination with any or all of the above various embodiments, the composition is formulated in a formulation for local or systemic delivery. Examples of such formulations are formulations for oral administration, injection, topical administration, pulmonary administration, or implant. In some or any embodiments, the compound is according to any of the various embodiments described above or below.

In some or any embodiments, the pharmaceutical compositions provided herein are formulated for intravenous injections. In certain aspects, the intravenous injection formulations provided herein are formulated as aqueous solutions, and, in some embodiments, in physiologically compatible buffers such as Hank's solution, Ringer's solution, or physiological saline buffer. In certain embodiments, the pharmaceutical compositions provided herein are formulated for transmucosal administration. In some aspects, transmucosal formulations include penetrants appropriate to the barrier to be permeated. In certain embodiments, the pharmaceutical compositions provided herein are formulated for other parenteral injections, appropriate formulations include aqueous or nonaqueous solutions, and in one embodiment, with physiologically compatible buffers or excipients.

In some or any embodiments, the pharmaceutical compositions provided herein are formulated for oral administration. In certain aspects, the oral formulations provided herein comprise compounds described herein that are formulated with pharmaceutically acceptable carriers or excipients. Such carriers enable the compounds described herein to be formulated as tablets, powders, pills, dragees, capsules, liquids, gels, syrups, elixirs, slurries, suspensions and the like, for oral ingestion by a patient to be treated.

In some or any embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are optionally added, such as the cross-linked croscarmellose sodium, polyvinylpyrrolidone, agar, or alginic acid or a salt thereof such as sodium alginate.

In some or any embodiments, provided herein is a pharmaceutical composition formulated as dragee cores with suitable coatings. In some or any embodiments, concentrated sugar solutions are used in forming the suitable coating, and optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs and/or pigments are added to tablets, dragees and/or the coatings thereof for, e.g., identification or to characterize different combinations of active compound doses.

In some or any embodiments, pharmaceutical preparations which are used include orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In some or any embodiments, in soft capsules, the active compounds are dissolved or suspended in suitable liquids, such as fatty oils, liquid paraffin, or liquid polyethylene glycols. In addition, stabilizers are optionally added. In some or any embodiments, the formulations for oral administration are in dosages suitable for such administration.

In some or any embodiments, the pharmaceutical compositions provided herein are formulated for buccal or sublingual administration. In some or any embodiments, buccal or sublingual compositions take the form of tablets, lozenges, or gels formulated in a conventional manner. In some or any embodiments, parenteral injections involve bolus injection or continuous infusion. In some embodiments, formulations for injection are presented in unit dosage form, e.g., in ampoules or in multi-dose containers, with an added preservative. In some embodiments, the pharmaceutical composition described herein is in a form suitable for parenteral injection as a sterile suspensions, solutions or emulsions in oily or aqueous vehicles, and optionally contains formulatory agents such as suspending, stabilizing and/or dispersing agents. Pharmaceutical formulations for parenteral administration include aqueous solutions of the active compounds in water-soluble form. In some embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In some or any embodiments, aqueous injection suspensions contain substances which increase the viscosity of the suspension, such as sodium carboxymethyl cellulose, sorbitol, or dextran. Optionally, the suspensions also contain suitable stabilizers or agents which increase the solubility of the compounds to allow for the preparation of highly concentrated solutions. In alternative embodiments, the active ingredient is in powder form for constitution with a suitable vehicle, e.g., sterile pyrogen-free water, before use.

In some embodiments, the compounds described herein are administered topically. In specific embodiments, the compounds described herein are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and/or preservatives.

In some or any embodiments, the pharmaceutical compositions provided herein are formulated for transdermal administration of compounds described herein. In some embodiments, administration of such compositions employs transdermal delivery devices and transdermal delivery patches. In some or any embodiments, the compositions are lipophilic emulsions or buffered, aqueous solutions, dissolved and/or dispersed in a polymer or an adhesive. Such patches include those constructed for continuous, pulsatile, or on demand delivery of pharmaceutical agents. In some embodiments, transdermal delivery of the compounds described herein is accomplished by use of iontophoretic patches and the like. In some or any embodiments, transdermal patches provide controlled delivery of the compounds provided herein, such as, for example, compounds of Formula (I). In some or any embodiments, the rate of absorption is slowed by using rate-controlling membranes or by trapping the compound within a polymer matrix or gel. Conversely, absorption enhancers are optionally used to increase absorption. Absorption enhancer and carrier include absorbable pharmaceutically acceptable solvents that assist in passage of the compound through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In some or any embodiments, the pharmaceutical compositions provided herein are formulated for administration by inhalation. In some or any embodiments, in such pharmaceutical compositions formulated for inhalation, the compounds described herein are in a form as an aerosol, a mist or a powder. In some embodiments, pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In certain aspects of a pressurized aerosol, the dosage unit is determined by providing a valve to deliver a metered amount. In some or any embodiments, capsules and cartridges of, such as, by way of example only, gelatin for use in an inhaler or insufflator is formulated containing a powder mix of the compound described herein and a suitable powder base such as lactose or starch.

In some embodiments, the compounds described herein are formulated in rectal compositions such as enemas, rectal gels, rectal foams, rectal aerosols, suppositories, jelly suppositories, or retention enemas. In some or any embodiments, rectal compositions optionally contain conventional suppository bases such as cocoa butter or other glycerides, as well as synthetic polymers such as polyvinylpyrrolidone, PEG, and the like. In some or any suppository forms of the compositions, a low-melting wax such as, but not limited to, a mixture of fatty acid glycerides, optionally in combination with cocoa butter is first melted.

In various embodiments provided herein, the pharmaceutical compositions are formulated in a conventional manner using one or more physiologically acceptable carriers comprising excipients and auxiliaries which facilitate processing of the active compounds into pharmaceutically acceptable preparations. In some or any embodiments, proper formulation is dependent upon the route of administration chosen. In various embodiments, any of the techniques, carriers, and excipients is used as suitable. In some embodiments, pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

In some or any embodiments, the pharmaceutical compositions include at least one pharmaceutically acceptable carrier, diluent or excipient and a compound described herein described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds described herein exist as tautomers. All tautomers are included within the scope of the compounds presented herein. Additionally, included herein are the solvated and unsolvated forms of the compounds described herein. Solvated compounds include those that are solvated with pharmaceutically acceptable solvents such as water, ethanol, and the like. The solvated forms of the compounds presented herein are also considered to be disclosed herein. In some embodiments, the pharmaceutical compositions described herein include other medicinal or pharmaceutical agents, carriers, adjuvants, such as preserving, stabilizing, wetting or emulsifying agents, solution promoters, salts for regulating the osmotic pressure, and/or buffers. In additional embodiments, the pharmaceutical compositions described herein also contain other therapeutically valuable substances.

Methods for the preparation of compositions containing the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. In various embodiments, the compositions are in liquid solutions or suspensions, solid forms suitable for solution or suspension in a liquid prior to use, or as emulsions. These compositions optionally contain minor amounts of nontoxic, auxiliary substances, such as wetting or emulsifying agents, pH buffering agents, and so forth.

In some embodiments, a composition comprising a compound described herein takes the form of a liquid where the agents are present in solution, in suspension or both. In some embodiments, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

Useful aqueous suspension optionally contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions optionally comprise an mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful compositions optionally include solubilizing agents to aid in the solubility of a compound described herein. The term "solubilizing agent" generally includes agents that result in formation of a micellar solution or a true solution of the agent. Solubilizing agents include certain acceptable nonionic surfactants, for example polysorbate 80, and ophthalmically acceptable glycols, polyglycols, e.g., polyethylene glycol 400, and glycol ethers.

Useful compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Certain useful compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Some useful compositions optionally include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Certain useful compositions optionally one or more antioxidants to enhance chemical stability where required. Suitable antioxidants include, by way of example only, ascorbic acid and sodium metabisulfite.

In some embodiments, aqueous suspension compositions are packaged in single-dose non-reclosable containers. In alternative embodiments, multiple-dose reclosable containers are used, in which case it is typical to include a preservative in the composition.

In various embodiments, any delivery system for hydrophobic pharmaceutical compounds is employed. Liposomes and emulsions are examples of delivery vehicles or carriers for hydrophobic drugs. In some or any embodiments, certain organic solvents such as N-methylpyrrolidone are employed. In some embodiments, the compounds are delivered using a sustained-release system, such as semipermeable matrices of solid hydrophobic polymers containing the therapeutic agent. Various sustained-release materials are utilized in the embodiments herein. In some or any embodiments, sustained-release capsules release the compounds for a few weeks up to over 100 days. In some embodiments, depending on the chemical nature and the biological stability of the therapeutic reagent, additional strategies for protein stabilization are employed.

In some or any embodiments, the formulations or compositions described herein benefit from and/or optionally comprise antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Dosing and Treatment Regimens

In some or any embodiments, the method can be conducted in living bodies of mammals. In such a case, the compounds may be administered to the mammals.

In some or any embodiments, the compounds described herein are used in the preparation or manufacture of medicaments for the treatment of diseases or conditions that are mediated by the enzyme GCS or in which inhibition of the enzyme GCS ameliorates the disease or condition. In some embodiments, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

In some or any embodiments, provided is a method of treating or ameliorating a medical condition, comprising administering to a subject in need thereof a compound according to any of the various embodiments described herein or a pharmaceutical composition according to any of the various embodiments described herein.

In some or any embodiments, provided herein is a method of treating or ameliorating a disease ameliorated by the inhibition of GCS comprising administering to a subject in need of treatment a therapeutically-effective amount of a compound of Formula I, I(a), I(b), I(c), I(d), I(d1), I(d2), I(e), I(e1), I(e2), I(f), I(f1), I(f2), I(g), I(g1), I(h), I(h1), or a compound in Table 1 optionally as a tautomer, a single stereoisomer or mixture of stereoisomers thereof and additionally optionally as a pharmaceutically acceptable salt thereof. In some or any embodiments, the disease is selected from glycolipid storage diseases (e.g., Tay Sachs, Sandhoffs, GM1 gangliosidosis—including type, type 2 and type 3, Niemanns-Pick, and Fabry diseases); diseases associated with glycolipid accumulation (e.g., Gaucher disease); diseases that cause renal hypertrophy or hyperplasia such as diabetic nephropathy; diseases that cause hyperglycemia or hyperinsulemia; cancers in which glycolipid synthesis is abnormal; infectious diseases caused by organisms which use cell surface glycolipids as receptors or in which synthesis of glucosylceramide is essential or important; a metabolic disorder such as atherosclerosis, polycystic kidney disease, renal hypertrophy, diabetes mellitus, and obesity; cancer such as breast cancer, renal adenocarcinoma, brain cancer, neuroblastoma, lung cancer, intestinal cancer, pancreas and prostrate cancer; neuronal disorders; neuronal injury; inflammatory diseases or disorders (e.g., rheumatoid arthritis, Crohn's disease, asthma and sepsis), and diabetes mellitus and obesity. In another embodiment, the disease is a gangliosidosis with central nervous system involvement, e.g. Gaucher's type 2, Gaucher's type 3, Gaucher's type 1 in which patients are at a higher risk for peripheral neuropathy and parkinsonian features, Sandhoff, infantile Sandhoff with peripheral neuropathy, GM1 gangliosidosis type 1, GM1 gangliosidosis type 2, GM1 gangliosidosis type, Tay-Sachs, and GM2 gangliosidosis, AB variant. In another embodiment the compounds of Formula I, I(a), I(b), I(c), I(d), I(d1), I(d2), I(e), I(e1), I(e2), I(f), I(f1), I(f2), I(g), I(g1), I(h), I(h1), or a compound in Table 1 optionally as a tautomer, a single stereoisomer or mixture of stereoisomers thereof and additionally optionally as a pharmaceutically acceptable salt thereof is one which crosses the blood brain barrier.

In any of the aforementioned embodiments are further embodiments that include single administrations of the effective amount of the compound, including further embodiments in which the compound is administered to the subject (i) once; (ii) multiple times over the span of one day; (iii) continually; or (iv) continuously.

In any of the aforementioned embodiments are further embodiments in which administration is enteral, parenteral, or both, and wherein:

(a) the effective amount of the compound is systemically administered to the subject;

(b) the effective amount of the compound is administered orally to the subject;

(c) the effective amount of the compound is intravenously administered to the subject;

(d) the effective amount of the compound is administered by inhalation;

(e) the effective amount of the compound is administered by nasal administration;

(f) the effective amount of the compound is administered by injection to the subject;

(g) the effective amount of the compound is administered topically (dermal) to the subject;

(h) the effective amount of the compound is administered by ophthalmic administration; and/or (i) the effective amount of the compound is administered rectally to the subject.

In some or any embodiments, the compositions containing the compound(s) described herein are administered for prophylactic and/or therapeutic treatments. In some or any therapeutic applications, the compositions are administered to a patient already suffering from a disease or condition, in an amount sufficient to cure or at least partially arrest the symptoms of the disease or condition. In some embodiments, amounts effective for this use will depend on the severity and course of the disease or condition, previous therapy, the patient's health status, weight, and response to the drugs, and the judgment of the treating physician. In certain instances, it is considered appropriate for the caregiver to determine such therapeutically effective amounts by routine experimentation (including, but not limited to, a dose escalation clinical trial).

In some or any prophylactic applications, compositions containing the compounds described herein are administered to a patient susceptible to or otherwise at risk of a particular disease, disorder or condition. In some embodiments, the amount administered is defined to be a "prophylactically effective amount or dose." In some or any embodiments of this use, the precise amounts of compound administered depend on the patient's state of health, weight, and the like. In some embodiments, it is considered appropriate for the caregiver to determine such prophylactically effective amounts by routine experimentation (e.g., a dose escalation clinical trial). In some or any embodiments, when used in a patient, effective amounts for this use will depend on the severity and course of the disease, disorder or condition, previous therapy, the patient's health status and response to the drugs, and the judgment of the treating physician.

In some or any embodiments are further embodiments that include multiple administrations of the effective amount of the compound, including further embodiments wherein:

(i) the compound is administered in a single dose;

(ii) the time between multiple administrations is every 6 hours;

(iii) the compound is administered to the subject every 8 hours.

In further or alternative embodiments, the method includes a drug holiday, wherein the administration of the compound is temporarily suspended or the dose of the compound being administered is temporarily reduced; at the end of the drug holiday, dosing of the compound is resumed. In some embodiments, the length of the drug holiday varies from 2 days to 1 year.

In certain instances, a patient's condition does not improve or does not significantly improve following administration of a compound or composition described herein and, upon the doctor's discretion the administration of the compounds is optionally administered chronically, that is, for an extended period of time, including throughout the duration of the patient's life in order to ameliorate or otherwise control or limit the symptoms of the patient's disease or condition.

In certain cases wherein the patient's status does improve or does not substantially improve, upon the doctor's discretion the administration of the compounds are optionally given continuously; alternatively, the dose of drug being administered is optionally temporarily reduced or temporarily suspended for a certain length of time (i.e., a "drug holiday"). In some or any embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes a reduction from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some or any embodiments, once improvement of the patient's conditions has occurred, a maintenance dose is administered if necessary. In some embodiments, the dosage, e.g., of the maintenance dose, or the frequency of administration, or both, are reduced, as a function of the symptoms, to a level at which the improved disease, disorder or condition is retained. In some or any embodiments, however, patients are optionally given intermittent treatment on a long-term basis upon any recurrence of symptoms.

In some or any embodiments, the amount of a given agent that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In some or any embodiments, however, doses employed for adult human treatment is in the range of about 0.02 to about 5000 mg per day, in a specific embodiment about 1 to about 1500 mg per day. In various embodiments, the desired dose is conveniently presented in a single dose or as divided doses administered simultaneously (or over a short period of time) or at appropriate intervals, for example as two, three, four or more sub-doses per day.

In some or any embodiments, the pharmaceutical compositions described herein are in a unit dosage form suitable for single administration of precise dosages. In some instances, in unit dosage form, the formulation is divided into unit doses containing appropriate quantities of one or more compound. In some or any embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In alternative embodiments, multiple-dose reclosable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In some or any embodiments, the daily dosages appropriate for the compounds described herein described herein are from about 0.01 to about 2.5 mg/kg per body weight. In some embodiments, an indicated daily dosage in the larger subject, including, but not limited to, humans, is in the range from about 0.5 mg to about 100 mg, conveniently administered in divided doses, including, but not limited to, up to four times a day or in extended release form. In some or any embodiments, suitable unit dosage forms for oral administration comprise from about 1 to about 50 mg active ingredient. The foregoing ranges are merely suggestive, as the number of variables in regard to an individual treatment regime is large, and considerable excursions from these recommended values are not uncommon. In some or any embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

In some or any embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. In some or any embodiments, compounds exhibiting high therapeutic indices are preferred. In some embodiments, the data obtained from cell culture assays and animal studies is used in formulating a range of dosage for use in human. In specific embodiments, the dosage of such compounds lies within a range of circulating concentrations that include the $ED_{50}$ with minimal toxicity. In some or any embodiments, the dosage varies within this range depending upon the dosage form employed and the route of administration utilized.

Articles of manufacture, comprising packaging material, a compound provided herein that is effective for modulating the activity of the enzyme GCS, or for treatment, prevention or amelioration of one or more symptoms of a GCS-mediated disease or condition, within the packaging material, and a label that indicates that the compound or composition, or pharmaceutically acceptable salt, pharmaceutically acceptable N-oxide, pharmaceutically active metabolite, pharmaceutically acceptable prodrug, or pharmaceutically acceptable solvate thereof, is used for modulating the activity of GCS, or for treatment, prevention or amelioration of one or more symptoms of GCS-mediated disease or condition, are provided.

For use in the therapeutic applications described herein, kits and articles of manufacture are also described herein. In various embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some embodiments, the containers are formed from a variety of materials such as glass or plastic.

In some embodiments, the articles of manufacture provided herein contain packaging materials. Packaging materials for use in packaging pharmaceutical products include, but are not limited to, blister packs, bottles, tubes, inhalers, pumps, bags, vials, containers, syringes, bottles, and any packaging material suitable for a selected formulation and intended mode of administration and treatment.

In some embodiments, the container(s) described herein comprise one or more compounds described herein, optionally in a composition or in combination with another agent as disclosed herein. The container(s) optionally have a sterile access port (for example in some embodiments the container is an intravenous solution bag or a vial having a stopper pierceable by a hypodermic injection needle). Such kits optionally comprise a compound with an identifying description or label or instructions relating to its use in the methods described herein.

In some embodiments, a kit will comprises one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions is optionally included.

In some or any embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In some or any embodiments, a label indicates that the contents are to be used for a specific therapeutic application. In some embodiments, the label indicates directions for use of the contents, such as in the methods described herein.

In some or any embodiments, the pharmaceutical compositions are presented in a pack or dispenser device which contains one or more unit dosage forms containing a compound provided herein. In some embodiments, the pack contains a metal or plastic foil, such as a blister pack. The pack or dispenser device is optionally accompanied by instructions for administration. In some embodiments, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. In some or any embodiments, such notice is, for example, the labeling approved by the U.S. Food and Drug Administration for prescription drugs, or the approved product insert. In some embodiments, compositions containing a compound provided herein are formulated in a compatible pharmaceutical carrier and are placed in an appropriate container labeled for treatment of an indicated condition.

Any combination of the groups described above for the various variables is contemplated herein.

Preparation of Compounds

The following are illustrative examples of how the compounds can be prepared and tested. Although the examples can represent only some embodiments, it should be understood that the following examples are illustrative and not limiting.

In a further aspect, it is provided a method of making a compound, comprising synthesizing a compound as any of the various embodiments described above or below. Examples of the method are further described in the Examples.

Compounds disclosed herein are commercially available or can be readily prepared from commercially available starting materials according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Synthesis of some of the compounds are exemplified in detail below.

In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral axillary, separation of the resulting mixture of diastereomers by recrystallization or chromatography and liberation of the optically pure product from the auxiliary or (2) direct separation of the mixture of optical enantiomers on chiral chromatographic column.

Materials were obtained from commercial suppliers and were used without further purification. Air or moisture sensitive reactions were conducted under argon atmosphere using oven-dried glassware and standard syringe/septa techniques. $^1$H NMR spectra were measured at 400 MHz unless stated otherwise and data were reported as follows in ppm (δ) from the internal standard (TMS, 0.0 ppm): chemical shift (multiplicity, integration, coupling constant in Hz).

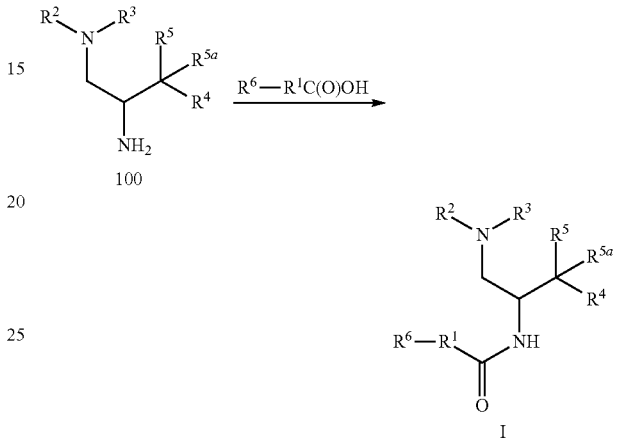

A Compound of Formula I (where all groups are as defined in the Summary of the Invention for a compound of Formula I or according to any of the embodiments disclosed herein) can be prepared according to General Scheme 1.

A Compound of Formula I can be prepared using standard amide coupling conditions. More specifically, an intermediate of formula 100, which can be prepared using procedures disclosed herein or are known to one of ordinary skill in the art, is treated with $R^6$—$R^1$—C(O)OH in a solvent such as DMF, DCM or THF, optionally in the presence of a base such as DIPEA or TEA, and in the presence of a coupling agent such as EDCI and/or HOBt to yield a compound of Formula I. The mixture can optionally be purified using procedures known to one of ordinary skill in the art. Alternatively, the intermediate of formula $R^6$—$R^1$C(O)OH can be treated with a chlorinating agent such as oxalyl chloride in a solvent such as DMF followed by treatment with the intermediate of formula 100 to yield a compound of Formula I. The mixture can optionally be purified (or individual isomers optionally resolved) using procedures known to one of ordinary skill in the art.

When $R^6$ is alkoxycarbonyl, the Compound of Formula I can be treated with an acid such as TFA in a solvent such as DCM. Reductive akylation on the free amine can done in a solvent such as DCM and/or MeOH in the presence of a reducing agent such as NaBH(OAc)$_3$. The mixture can optionally be purified (or individual isomers optionally resolved) using procedures known to one of ordinary skill in the art.

General Scheme 2

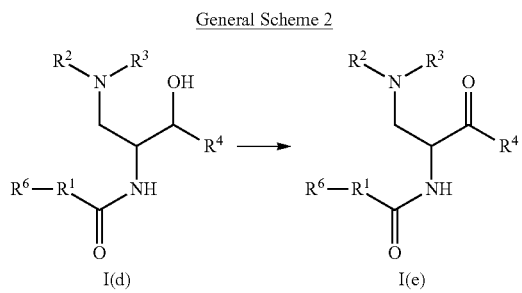

A Compound of Formula I(e) (where all groups are as defined in the Summary of the Invention for a compound of Formula I or according to any of the embodiments disclosed herein) can be prepared according to General Scheme 2. A Compound of Formula I(d) is treated with a base such as NMP, in the presence of $NHCO_3$, and in a solvent such as DCM to yield a Compound of Formula I(e). The mixture can optionally be purified (or individual isomers optionally resolved) using procedures known to one of ordinary skill in the art.

General Scheme 3

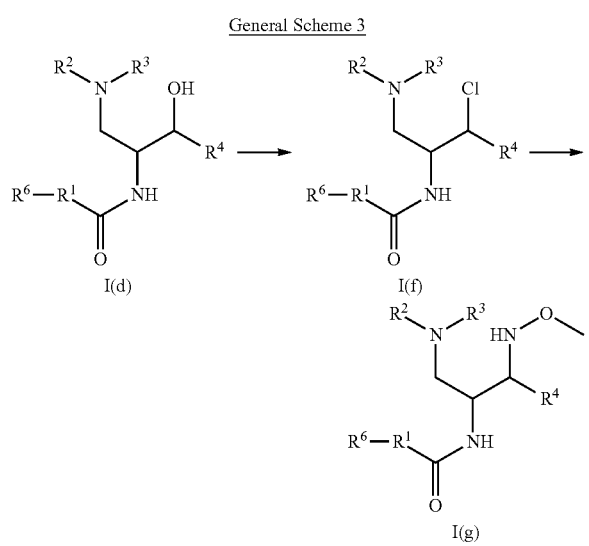

A Compound of Formula I(f) or I(g) (where all groups are as defined in the Summary of the Invention for a compound of Formula I or according to any of the embodiments disclosed herein) can be prepared according to General Scheme 3. A Compound of Formula I(d) is treated with a chlorinating agent such as $SOCl_2$ in a solvent such as DCM to yield a Compound of Formula I(f). A Compound of Formula I(g) is prepared by treating a Compound of Formula I(f) with $NH_2OCH_3$ in a solvent such as MeOH. The mixture can optionally be purified (or individual isomers optionally resolved) using procedures known to one of ordinary skill in the art.

General Scheme 4

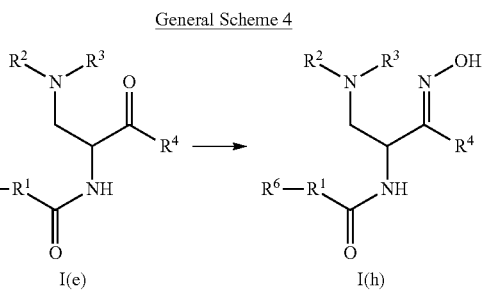

A Compound of Formula I(h) (where all groups are as defined in the Summary of the Invention for a compound of Formula I or according to any of the embodiments disclosed herein) can be prepared according to General Scheme 4. A Compound of Formula I(e) is treated with hydroxylamine in a solvent such as MeOH to yield a Compound of Formula I(h). The mixture can optionally be purified (or individual isomers optionally resolved) using procedures known to one of ordinary skill in the art.

General Scheme 5

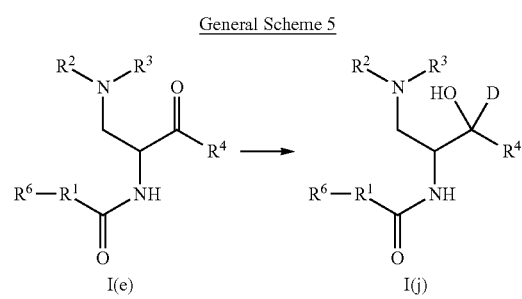

A Compound of Formula I(j) (where all groups are as defined in the Summary of the Invention for a compound of Formula I or according to any of the embodiments disclosed herein) can be prepared according to General Scheme 5. A Compound of Formula I(e) is treated with $NaBD_4$ in a deuterated solvent such as $CD_3OD$ to yield a Compound of Formula I(j). The mixture can optionally be purified (or individual isomers optionally resolved) using procedures known to one of ordinary skill in the art.

General Scheme 6

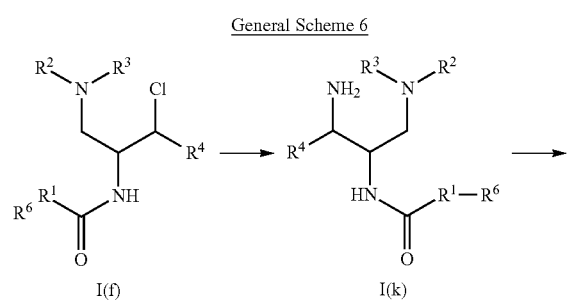

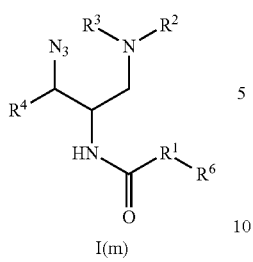

I(m)

A Compound of Formula I(k) or I(m) (where all groups are as defined in the Summary of the Invention for a compound of Formula I or according to any of the embodiments disclosed herein) can be prepared according to General Scheme 6. A Compound of Formula I(f) is treated with $NaN_3$ in a solvent such as DMF and heated to about 50° C. to yield a Compound of Formula I(k) which can be optionally worked up before proceeding to the next step. The Compound of Formula I(k) is then treated with $PPh_3$ in a solvent such as THF to yield the Compound of Formula I(m). The mixture can optionally be purified (or individual isomers optionally resolved) using procedures known to one of ordinary skill in the art.

In some or any embodiments of General Schemes 1-6, intermediate of formula 100 or the Compound of Formula I(d), I(e), or I(f) is that where $R^2$ and $R^3$ together with the nitrogen to which they are attached form a 3-10-membered ring which is optionally substituted with 1, 2, or 3 $R^8$ groups.

SYNTHETIC EXAMPLES

Intermediate A

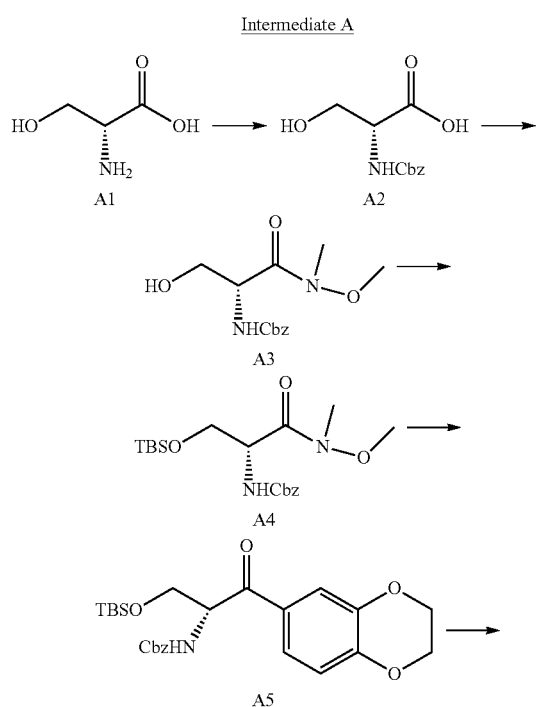

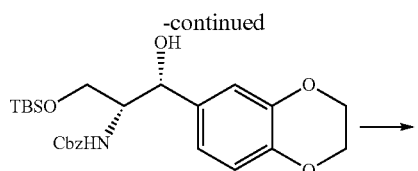
A6

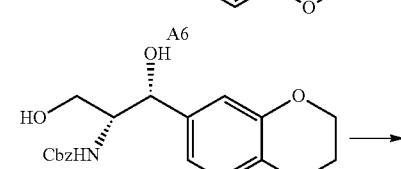
A7

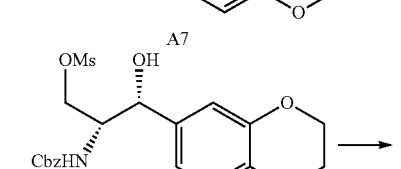
A8

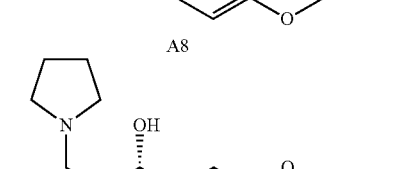
A9

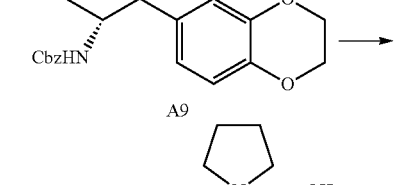
A

Benzyl chloroformate (50 mL, 50 w.t. % solution in toluene, 148 mmol) was added to a solution of (R)-2-amino-3-hydroxypropanoic acid (A1, 10.5 g, 100 mmol) in sat. aq $NaHCO_3$ solution (400 mL). The mixture was stirred vigorously for 4 h at 20° C., and the aqueous solution was extracted with ether (400 mL×2). The aqueous phase was acidified with conc. hydrochloric acid to pH=2 and extracted with ethyl acetate (300 mL×3). The combined organic phase was dried with $Na_2SO_4$ and concentrated to afford crude product Compound A2. LC-MS (m/z): 240 [M+1]$^+$; $^1$H-NMR (DMSO-$d_6$, 400 MHz) peaks: δ (ppm) 3.653 (m, 2H), 4.051 (m, 1H), 4.884 (m, 1H), 5.038 (s, 2H), 7.303-7.373 (m, 6H), 12.658 (s, 1H).

To a mixture of EDCI HCl (2.4 g, 12.5 mmol), HOBt (1.7 g, 12.5 mmol), DIPEA (2.7 g, 20 mmol) in DCM (50 mL) was added Compound A2 (1 g, 4 mmol) and N,O-dimethylhydroxylamine hydrochloride (1.2 g, 12.5 mmol). The mixture was stirred at room temperature overnight. The mixture was washed with hydrochloric acid solution (1 M, 50 mL×2), saturated aqueous $NaHCO_3$ (20 mL), brine (20 mL), and dried over $Na_2SO_4$. The crude product was purified by silica gel column chromatography (ethyl acetate in petroleum, 30% v/v) to give Compound A3. LC-MS (m/z): 283 [M+1]$^+$; $^1$H-NMR (CDCl$_3$, 400 MHz) peaks: δ (ppm) 3.113 (s, 3H), 3.673 (s, 3H), 3.743 (t, J=4.8 Hz, 2H), 4.766 (m, 1H), 4.959-5.044 (m, 2H), 6.046 (d, J=8.0 Hz, 1H), 7.200-7.254 (m 5H).

TBDMS-Cl (800 mg, 5.31 mmol) in THF (10 mL) was added dropwise to a solution of Compound A3 (500 mg, 1.77 mmol) and imidazole (602 mg, 8.86 mmol) in THF (20 mL) at 0° C. The mixture was stirred at room temperature for 2 h, and then filtered. The filtrate was washed with 1N HCl (50 mL×2) and brine (50 mL), and dried over $Na_2SO_4$. The crude product was purified with silica gel column chromatography (ethyl acetate in petroleum, 13% v/v) to give Compound A4. LC-MS (m/z): 396 [M+1]$^+$; $^1$H-NMR (CDCl$_3$, 400 MHz) peaks: δ (ppm) 0.012 (s, 3H), 0.085 (s, 6H), 0.852 (s, 9H), 3.211 (s, 3H), 3.756 (s, 3H), 3.794-3.896 (m, 2H), 4.809 (m, 1H), 5.085 (q, J=11.2 Hz, 2H), 5.662 (d, J=8.8 Hz, 1H), 7.286-7.351 (m 5H).

To a solution of 6-bromo-2,3-dihydrobenzo[b][1,4]dioxine (4.9 g, 23 mmol) in THF (100 mL) was added n-BuLi (1.6 M, 15 mL) at −60° C. under $N_2$ and stirred for 0.5 h, before a solution of Compound A4 (3 g, 7.6 mmol) in THF (50 mL) was added slowly. The mixture was stirred at −60° C. for 1 h, and followed by addition of a saturated NH$_4$Cl solution. The mixture was extracted with ethyl acetate (100 mL×2), brine (100 mL), and then dried over $Na_2SO_4$. The crude product was purified by column chromatography on silica gel (ethyl acetate in petroleum, 10% v/v) to give Compound A5. LC-MS (m/z): 472 [M+1]$^+$; $^1$H-NMR (CDCl$_3$, 400 MHz) peaks: δ (ppm) 0.000 (s, 3H), 0.024 (s, 3H), 0.892 (s, 9H), 4.024-4.116 (m, 1H), 4.402-4.465 (m, 4H), 5.262 (s, 2H), 5.421 (m, 1H), 6.066 (d, J=8.0 Hz, 1H), 7.043 (d, J=8.0 Hz, 1H), 7.444-7.505 (m, 5H), 7.618-7.639 (m, 2H).

To a solution of Compound A5 (5 g, 106 mmol) in THF (25 mL) and water (25 mL) was added acetic acid (75 mL). The resulting mixture was stirred at 35° C. for 16 h, diluted with brine (150 mL), adjusted to pH 8 with saturated aqueous sodium bicarbonate solution (75 mL), extracted with ethyl acetate (100 mL×2), dried over anhydrous sodium sulfate, concentrated, and purified with flash column chromatography on silica gel (ethyl acetate in petroleum, 20% v/v) to yield Compound A6. LC-MS (ESI) (m/z): 358 [M+H]$^+$; $^1$H-NMR (CDCl$_3$, 400 MHz): δ (ppm) 2.81 (t, J=6.0 Hz, 1H), 3.83-3.88 (m, 1H), 3.99-4.05 (m, 1H), 4.26-4.33 (m, 4H), 5.13 (s, 2H), 5.30-5.32 (m, 1H), 6.16 (d, J=6.4 Hz, 1H), 6.92 (d, J=8.0 Hz, 1H), 7.31-7.36 (m, 5H), 7.52-7.55 (m, 2H).

To a solution of Compound A6 (714 mg, 2 mmol) in dry THF (20 mL) was added dropwise DIBAL-H (1.5 N, 2.7 mL, 4 mmol) under nitrogen at −80° C. The resultant mixture was stirred at −80° C. for 30 min, and then DIBAL-H (1.5 N, 2.7 mL, 4 mmol) was added dropwise again. The mixture was stirred at −80° C. for 1 h, quenched with aqueous HCl solution (2 N, 12 mL) at −20° C., extracted with ethyl acetate (50 mL×2), dried over anhydrous sodium sulfate, and purified with flash column chromatography on silica gel (ethyl acetate in petroleum, 50% v/v) to furnish Compound A7. LC-MS (ESI) (m/z): 342 [M-OH]$^+$; $^1$H-NMR (CDCl$_3$, 400 MHz): δ (ppm) 2.76 (s, 1H), 3.26 (s, 1H), 3.72-3.83 (m, 3H), 4.21 (s, 4H), 4.86 (s, 1H), 5.02 (s, 2H), 5.51 (d, J=8.0 Hz, 1H), 6.80 (s, 2H), 6.88 (s, 1H), 7.29-7.33 (m, 5H).

To a solution of the obtained Compound A7 (3.6 g, 10 mmol) in THF (50 mL) was added Et$_3$N (3 g, 30 mmol), then the mixture was cooled to −15° C. before adding MsCl (0.8 mL) slowly. The mixture was stirred at −15° C. about half an hour. The reaction mixture was taken up with water (30 mL), extracted with ETHYL ACETATE (30 mL×3), dried over anhydrous sodium sulfate, and evaporated to get Compound A8. To a solution of the resulted mesolate intermediate (A8) in THF (50 mL) was added pyrrolidine (5.7 g, 80 mmol), K$_2$CO$_3$ (11 g, 80 mmol) and NaI (3 g). The mixture was heated at 50° C. overnight. After filtration and evaporation, the crude product was purified by column chromatography on silica gel (methanol in dichloromethane, 5% v/v) to give Compound A9. LC-MS (m/z): 413 [M+1]$^+$; $^1$H-NMR (CDCl$_3$, 400 MHz): δ (ppm) 1.756 (m, 4H), 2.534 (m, 1H), 2.660 (m, 4H), 2.877 (m, 1H), 4.019 (m, 1H), 4.236 (s, 4H), 4.924 (d, J=2.8 Hz, 1H), 5.043 (s, 2H), 5.079 (m, 1H), 6.7756-6.892 (m, 3H), 7.266-7.361 (m, 5H).

To a solution of Compound A9 (2.5 g, 6.1 mmol) in methanol (20 mL) was added Pd(OH)$_2$ (250 mg), then the mixture was stirred at room temperature under H$_2$ overnight. The mixture was filtered and the filtrate was evaporated to dryness to give Intermediate A. LC-MS (m/z): 279 [M+1]$^+$; $^1$H-NMR (CDCl$_3$, 400 MHz): δ (ppm) 1.70 (m, 4H), 2.53 (m, 6H), 3.05 (m, 1H), 4.18 (s, 4H), 4.47 (d, J=3.6 Hz, 1H), 6.75 (m, 3H).

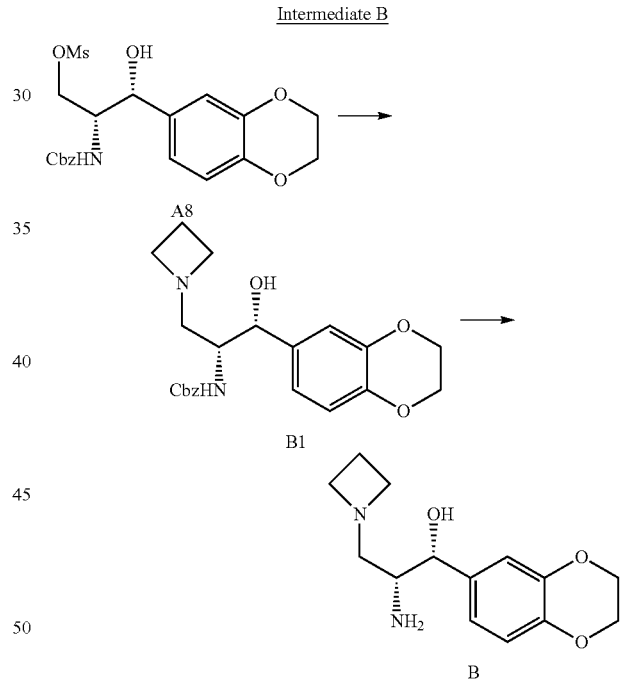

Intermediate B

Intermediates B1 and B were synthesized, by employing the procedures described for Intermediates A9 and A using azetidine and Intermediate B1 in lieu of pyrrolidine and Intermediate A9.

Intermediates B1. LC-MS (ESI) m/z: 399 [M+H]$^+$; $^1$H-NMR (CDCl$_3$, 400 MHz): δ (ppm) 2.09-2.16 (m, 2H), 2.74-2.77 (m, 1H), 2.97-3.00 (m, 1H), 3.35-3.42 (m, 4H), 3.81 (s, 1H), 4.24 (s, 4H), 4.92 (s, 1H), 4.98-5.20 (m, 3H), 6.80-6.82 (m, 3H), 7.26-7.31 (m, 5H).

Intermediate B. LC-MS (ESI) m/z: 265 [M+H]$^+$; $^1$H-NMR (CDCl$_3$, 400 MHz): δ (ppm) 2.02-2.04 (m, 2H), 2.53-2.57 (m, 2H), 3.22-3.25 (m, 4H), 4.19 (s, 5H), 4.51 (d, J=3.2 Hz, 1H), 6.72-6.80 (m, 3H).

Intermediate C

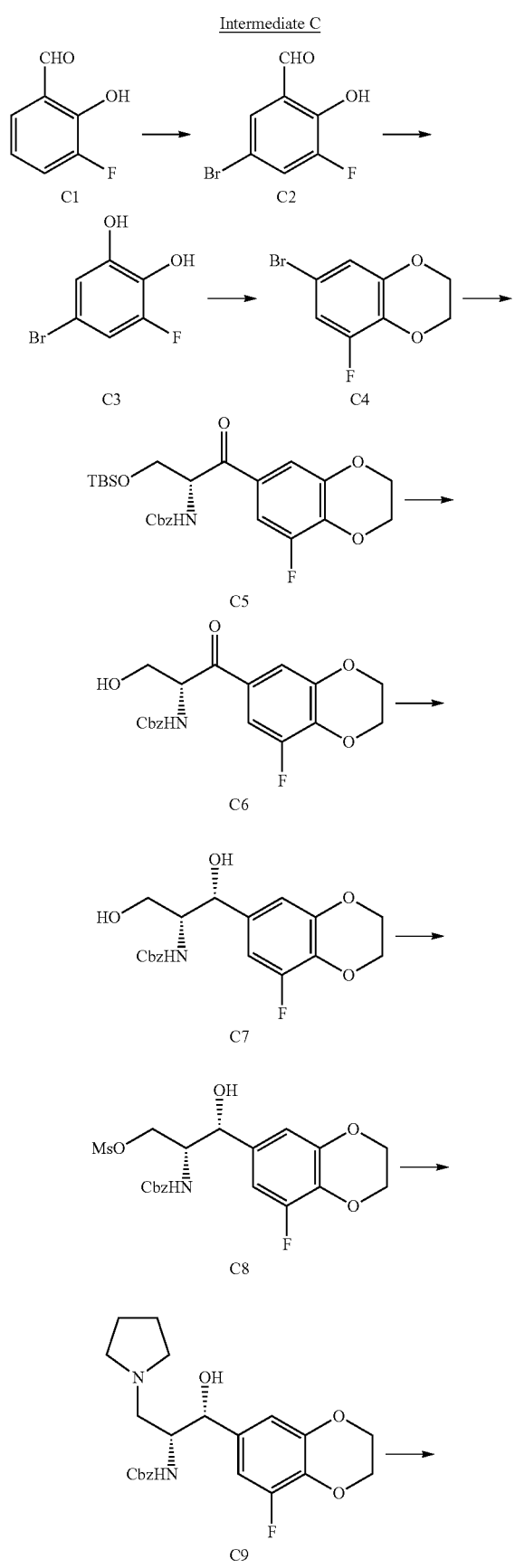
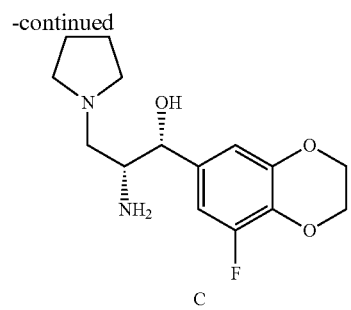

To a solution of Compound C1 (50 g, 357 mmol) in MeCN (400 mL) was added NBS (60.08 g, 360 mmol) and HCOONH$_4$ (2.47 mg, 39 mmol) at room temperature and then the mixture was stirred at room temperature for 2 h. After removal of the solvent the mixture was diluted with ethyl acetate (200 mL), then washed with brine, dried over anhydrous Na$_2$SO$_4$, and concentrated to give Compound C2. $^1$H-NMR (CDCl$_3$, 400 MHz): δ (ppm) 7.48-7.23 (m, 2H), 9.87 (s, 1H), 10.89 (s, 1H).

To a solution of Compound C2 (40 g, 183 mmol) in THF (260 mL) was added dropwise aq. NaOH solution (0.05 N, 720 mL, 37 mmol) at 0° C., then 30% H$_2$O$_2$ solution (90 mL). The mixture was stirred for 2 h at room temperature and followed by the addition of a second portion of 30% H$_2$O$_2$ (90 mL). After stirring for 4 h, it was cooled to 0° C. and aq. NaOH solution (2 N, 112 mL) was added to reach a pH 10~11. The mixture was stirred for 0.5 h and quenched with conc. HCl at 0° C. to pH 2~3. It was extracted with dichloromethane (250 mL×3) and washed with brine (300 mL×2), dried over Na$_2$SO$_4$, and concentrated to give Compound C3. LC-MS (m/z): 205 [M−1]$^-$.

To a mixture of Compound C3 (30 g, 146 mol), K$_2$CO$_3$ (60.3 g, 437 mol) in DMF (450 mL) was added 1, 2-dibromoethane (63 mL, 730 mol). The mixture was stirred at 80° C. for 4 h. After cooling to room temperature, it was filtered and the cake was washed with ethyl acetate (100 mL). The filtrate was diluted with water (900 mL) and extracted with ethyl acetate (400 mL×3). The organic layer was washed with water (900 mL×5) and brine (900 ml×1), dried, concentrated, and purified by column chromatography on silica gel (ethyl acetate in petroleum, 5% v/v) to afford Compound C4. $^1$H-NMR (CDCl$_3$, 400 MHz): δ (ppm) 4.35 (s, 4H), 6.91 (t, J=8 Hz, 1H), 7.33 (s, 1H).

Intermediates C5, C6, C7, C8, C9, and C were synthesized, by employing the procedures described correspondingly for Intermediates A5, A6, A7, A8, A9, and A using Intermediates C4, C5, C6, C7, C8, and C9 in lieu of 6-bromo-2,3-dihydrobenzo[b][1,4]dioxine, Intermediates A5, A6, A7, A8, and A9.

Intermediate C5. LC-MS (m/z): 490 [M+1]$^+$.
Intermediate C6. LC-MS (ESI) m/z: 376 [M+H]$^+$; $^1$H-NMR (CDCl$_3$, 400 MHz): δ (ppm) 2.50-2.53 (m, 1H), 3.78-3.83 (m, 1H), 3.91-3.97 (m, 1H), 4.25-4.27 (m, 2H), 4.31-4.33 (m, 2H), 5.07 (s, 2H), 6.00 (d, J=4 Hz, 1H), 7.24-7.31 (m, 7H).
Intermediate C7. LC-MS (ESI) m/z: 360 [M−OH]$^+$; $^1$H-NMR (CDCl$_3$, 400 MHz): δ (ppm) 3.45-3.59 (m, 3H), 4.23-4.24 (m, 4H), 4.84 (s, 1H), 5.00 (s, 2H), 5.54 (d, J=8 Hz, 1H), 6.69 (t, J=8 Hz, 2H), 7.27-7.35 (m, 5H).
Intermediate C8. LC-MS (m/z): 438 [M+1−18]$^+$.
Intermediate C9. LC-MS (m/z): 431 [M+1]$^+$.
Intermediate C. LC-MS (m/z): 297 [M+1]$^+$.

Intermediate D

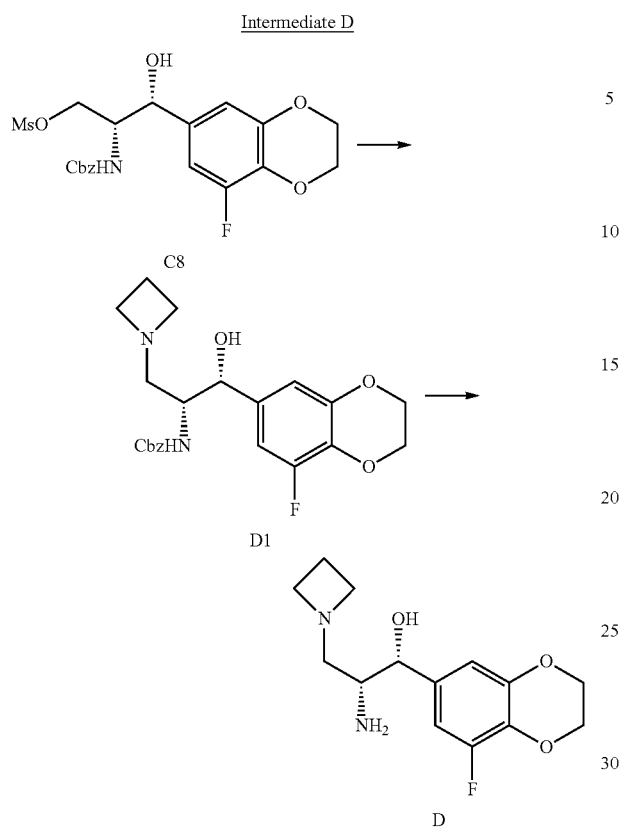

Intermediates D1 and D were synthesized, by employing the procedures described for Intermediates A9 and azetidine and Intermediate D1 in lieu of pyrrolidine and Intermediate A9.

Intermediate D1. LC-MS (ESI) m/z: 417 [M+H]$^+$; $^1$H-NMR (CDCl$_3$, 400 MHz): δ (ppm) 2.03-2.12 (m, 2H), 2.57 (d, J=8 Hz, 1H), 2.69-2.72 (d, J=12 Hz, 1H), 2.91-2.98 (m, 1H), 3.12-3.36 (m, 3H), 3.63-3.75 (m, 1H), 4.10-4.14 (m, 1H), 4.25 (s, 4H), 4.68-4.85 (m, 1H), 5.00-5.08 (m, 2H), 6.63-6.71 (m, 2H), 7.24-7.36 (m, 5H).

Intermediate D, which was directly used for the next step. LC-MS (ESI) m/z: 283 [M+H]$^+$; $^1$H-NMR (CDCl$_3$, 400 MHz) δ (ppm) 2.05-2.12 (m, 2H), 2.59-2.62 (m, 2H), 3.25-3.35 (m, 5H), 4.28 (s, 4H), 4.50 (d, J=4 Hz, 1H), 6.64-6.75 (m, 2H).

Intermediate E

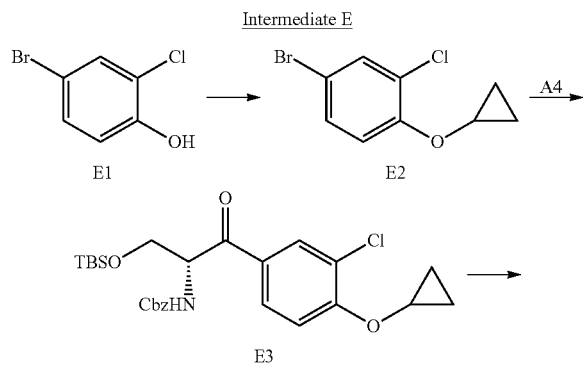

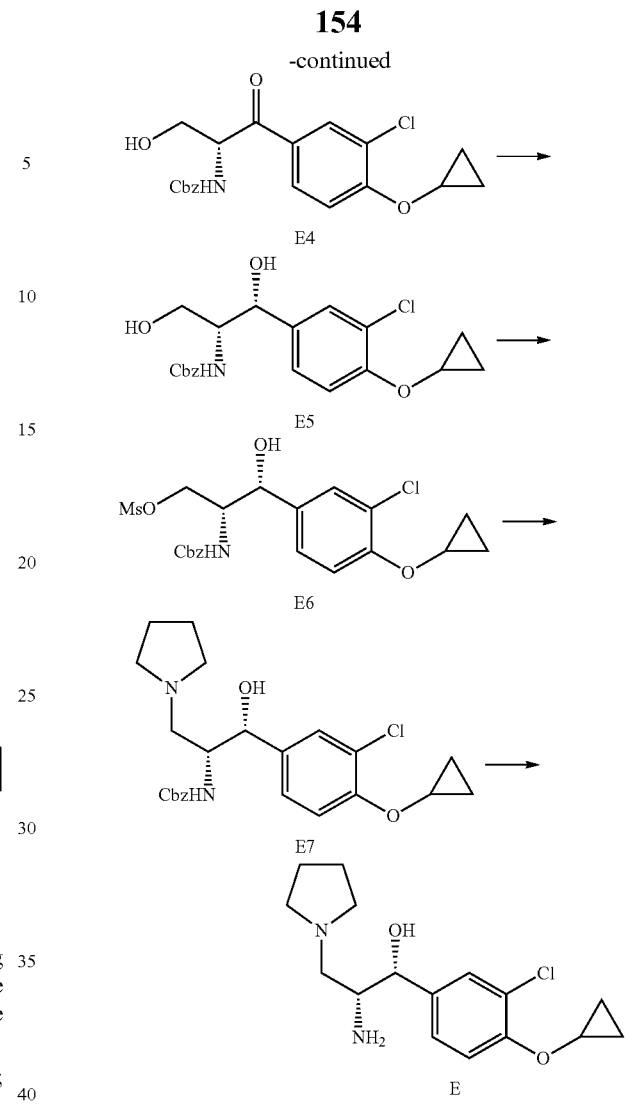

To a solution of Compound E1 (20 g, 96 mmol) in 1-methyl-2-pyrrolidinone (300 mL) was added cesium carbonate (62.8 g, 193 mmol) and bromocyclopropane (24 mL, 289 mmol). The mixture was stirred for 24 h while keeping the inner temperature between 145° C. and 155° C. After the reaction was cooled to ambient temperature, the dark solution was diluted with water (400 mL) and extracted with a mixture of ethyl acetate in petroleum ether (15% v/v) (300 mL×3). The combined organic phases were washed with brine (150 mL×4), dried over anhydrous sodium sulfate, filtered, and concentrated to afford the crude product. The crude product was purified with flash column chromatography on silica gel (petroleum ether) to furnish Compound E2. HPLC: Rt: 1.96 minute. $^1$H-NMR (CDCl$_3$, 400 MHz): δ (ppm) 0.80-0.88 (m, 4H), 3.67-3.82 (m, 1H), 7.15 (d, J=8.8 Hz, 1H), 7.32 (dd, J=8.8, 2.4 Hz, 1H), 7.47 (d, J=2.4 Hz, 1H).

Intermediates E3, E4, E5, E6, and E7, were synthesized, by employing the procedures described for Intermediates A5, A6, A7, A8, and A9 using Intermediates E2, E3, E4, E5, and E6 in lieu of 6-bromo-2,3-dihydrobenzo[b][1,4]dioxine, Intermediates A5, A6, A7, and A8.

Intermediate E3. LC-MS (ESI) m/z: 504 [M+H]$^+$; $^1$H-NMR (CDCl$_3$, 400 MHz): δ (ppm) 0.01 (d, J=6.0 Hz, 6H), 0.87 (s, 9H), 1.02 (d, J=4.8 Hz, 4H), 1.36-1.40 (m, 1H), 3.99-4.03 (m, 1H), 4.09 (dd, J=10.0, 3.6 Hz, 1H), 5.26 (s, 2H), 5.42-5.44 (m, 1H), 6.04 (d, J=8.0 Hz, 1H), 7.44-7.50 (m, 6H), 8.00 (dd, J=8.8, 1.6 Hz, 1H), 8.11 (s, 1H).

Intermediate E4. LC-MS (ESI) m/z: 390 [M+H]+, 412 [M+Na]+; 1H-NMR (CDCl3, 400 MHz): δ (ppm) 0.89 (d, J=4.5 Hz, 4H), 2.78 (s, 1H), 3.81-3.92 (m, 2H), 4.01 (d, J=9.4 Hz, 1H), 5.08-5.17 (m, 2H), 5.26-5.38 (m, 1H), 6.12 (d, J=6.9 Hz, 1H), 7.25-7.45 (m, 6H), 7.92 (d, J=8.5 Hz, 1H), 8.02 (s, 1H).

Intermediate E5. LC-MS (ESI) m/z: 374 [M-OH]+; 1H-NMR (CDCl3, 400 MHz): δ (ppm) 0.80-0.83 (m, 4H), 1.23-1.27 (m, 1H), 2.79 (s, 1H), 3.45 (d, J=2.0 Hz, 1H), 3.74-3.81 (m, 4H), 4.93-5.08 (m, 2H), 5.52-5.54 (m, 1H), 7.16-7.37 (m, 8H).

Intermediate E6, which was directly used for the next step without further purification. LC-MS (ESI) m/z: 452 [M-OH]+.

Intermediate E7, which was directly used for the next step without further purification. LC-MS (ESI) m/z: 311 [M+H]+.

To a solution of Compound E7 (520 mg, 1.17 mmol) in ethanol (12 mL) and water (2 mL) was added LiOH.H2O (197 mg, 4.68 mmol). The mixture was heated to 80° C. and stirred for 16 h. The reaction was diluted with water (15 mL) and extracted with dichloromethane (50 mL×2). The combined organic phases were washed with water (50 mL) and brine (50 mL), dried over anhydrous sodium sulfate, filtered, and concentrated to furnish Compound E, which was directly used for the next step without further purification. LC-MS (ESI) m/z: 311 [M+H]+.

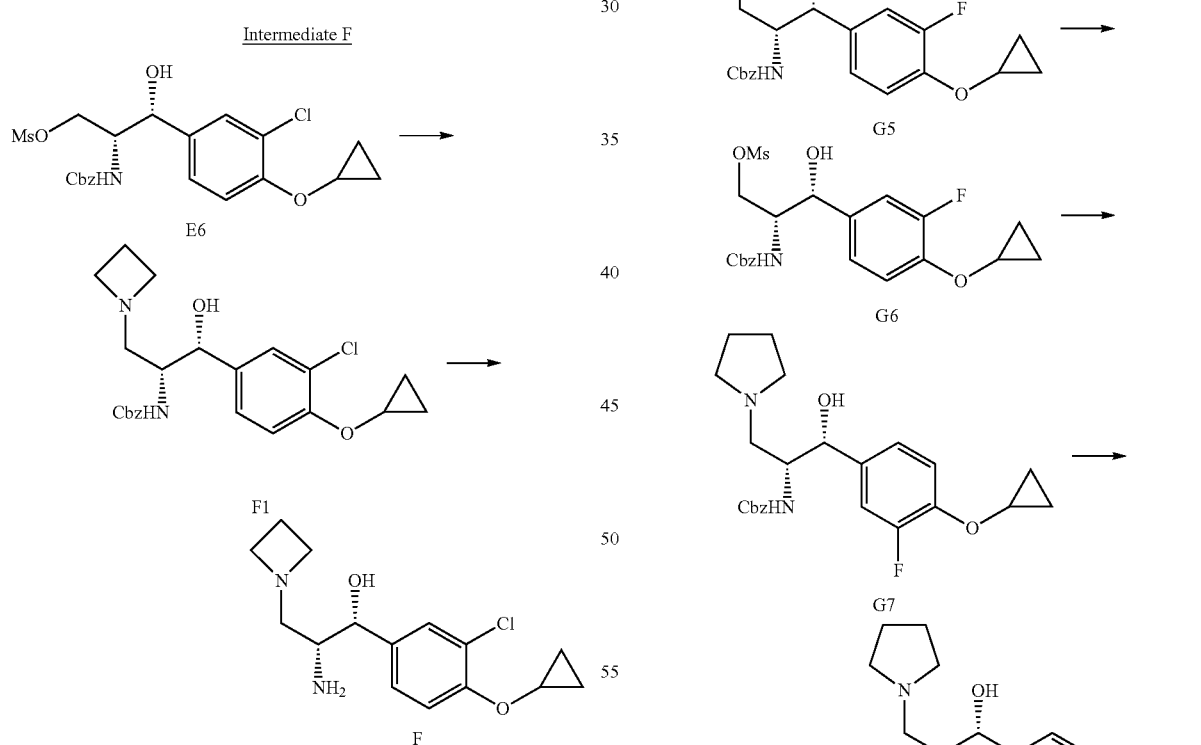

Intermediates F1 and F were synthesized, by employing the procedures described for Intermediates A9 and A using azetidine, Intermediates E6, and F1 in lieu of pyrrolidine, Intermediates A8, and A9.

Intermediates F1. LC-MS (ESI) m/z: 431 [M+H]+.

Intermediate F, which was directly used for the next step without further purification. LC-MS (ESI) m/z: 297 [M+H]+.

To a solution of Compound G1 (20 g, 105 mmol) in 1-methyl-2-pyrrolidinone (300 mL) was added cesium carbonate (68.4 g, 210 mmol) and bromocyclopropane (38 g, 316 mmol). The mixture was stirred for 24 h while keeping the inner temperature between 145° C. and 155° C. The reaction mixture was cooled down to room temperature and filtered. The filtrate was diluted with water (1500 mL) and extracted with ethyl acetate (200 mL×3). The combined organic phases were washed with water (300 mL×5) and brine (300 mL), dried over anhydrous sodium sulfate, filtered, and concentrated to afford a crude compound. The crude product was purified with flash column chromatography on silica gel (petroleum ether, 100% v/v) to furnish Compound G2. LC-MS (ESI) m/z: No. $^1$H-NMR (CDCl$_3$, 400 MHz): δ (ppm) 0.79-0.84 (m, 4H), 3.78-3.80 (m, 1H), 7.14-7.23 (m, 3H).

Intermediates G3, G4, G5, G6, G7, and G, were synthesized, by employing the procedures described for Intermediates A5, A6, A7, A8, A9, and A using Intermediates G2, G3, G4, G5, G6, and G7 in lieu of 6-bromo-2,3-dihydrobenzo[b][1,4]dioxine, Intermediates A5, A6, A7, A8, and A9.

Intermediate G3. LC-MS (ESI) m/z: 488 [M+H]$^+$; $^1$H-NMR (DMSO-d$_6$, 400 MHz): δ (ppm) −0.08 (s, 6H), 0.82 (m, 11H), 0.84-0.88 (m, 2H), 3.81-3.90 (m, 2H), 4.05-4.09 (m, 1H), 5.03 (s, 2H), 5.13-5.18 (m, 1H), 7.27-7.36 (m, 5H), 7.53 (t, J=8.4 Hz, 1H), 7.64 (d, J=8.4 Hz, 1H), 7.74 (dd, J=12.0, 2.4 Hz, 1H), 7.86 (d, J=8.4 Hz, 1H).

Intermediate G4. LC-MS (ESI) m/z: 374 [M+H]$^+$; $^1$H-NMR (DMSO-d$_6$, 400 MHz): δ (ppm) 0.75-0.89 (m, 4H), 3.62-3.78 (m, 2H), 4.07-4.09 (m, 1H), 4.91 (t, J=5.6 Hz, 1H), 5.03 (s, 2H), 5.10-5.14 (m, 1H), 7.26-7.38 (m, 5H), 7.55 (t, J=8.8 Hz, 1H), 7.60 (d, J=8.0 Hz, 1H), 7.79 (dd, J=12.0, 1.6 Hz, 1H), 7.90 (d, J=8.4 Hz, 1H).

Intermediate G5. LC-MS (ESI) m/z: 376 [M+H]$^+$; $^1$H-NMR (DMSO-d$_6$, 400 MHz): δ (ppm) 0.38-0.81 (m, 4H), 3.25-3.31 (m, 1H), 3.47-3.53 (m, 1H), 3.64-3.65 (m, 1H), 3.88-3.91 (m, 1H), 4.72-4.77 (m, 2H), 4.87-5.01 (m, 2H), 5.37 (d, J=5.2 Hz, 1H), 6.75 (d, J=10.0 Hz, 1H), 7.05-7.34 (m, 8H).

Intermediate G6, which was used for the next step without further purification. LC-MS (ESI) m/z: 436 [M-OH]$^+$.

Intermediate G7. LC-MS (ESI) m/z: 429 [M+H]$^+$; $^1$H-NMR (DMSO-d$_6$, 400 MHz): δ (ppm) 0.68-0.81 (m, 4H), 1.66 (s, 4H), 2.24-2.50 (m, 5H), 2.59-2.64 (m, 1H), 3.75-3.81 (m, 1H), 3.88-3.91 (m, 1H), 4.72 (s, 1H), 4.87-5.00 (m, 2H), 5.52 (brs, 1H), 6.79 (d, J=9.2 Hz, 1H), 7.05-7.13 (m, 2H), 7.17-7.34 (m, 6H).

Intermediate G. LC-MS (ESI) m/z: 295 [M+H]$^+$; $^1$H-NMR (DMSO-d$_6$, 400 MHz): δ (ppm) 0.67-0.79 (m, 4H), 1.23 (s, 2H), 1.65 (s, 4H), 2.16-2.20 (m, 1H), 2.29-2.36 (m, 6H), 2.86-2.89 (m, 1H), 3.89-3.93 (m, 1H), 4.38 (d, J=4.8 Hz, 1H), 7.06-7.15 (m, 2H), 7.32 (t, J=8.4 Hz, 1H).

Intermediate H

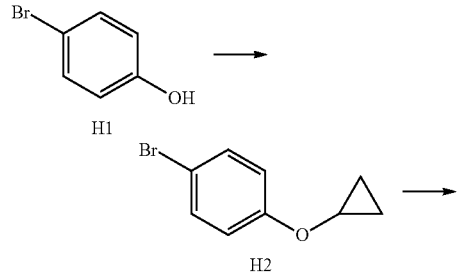

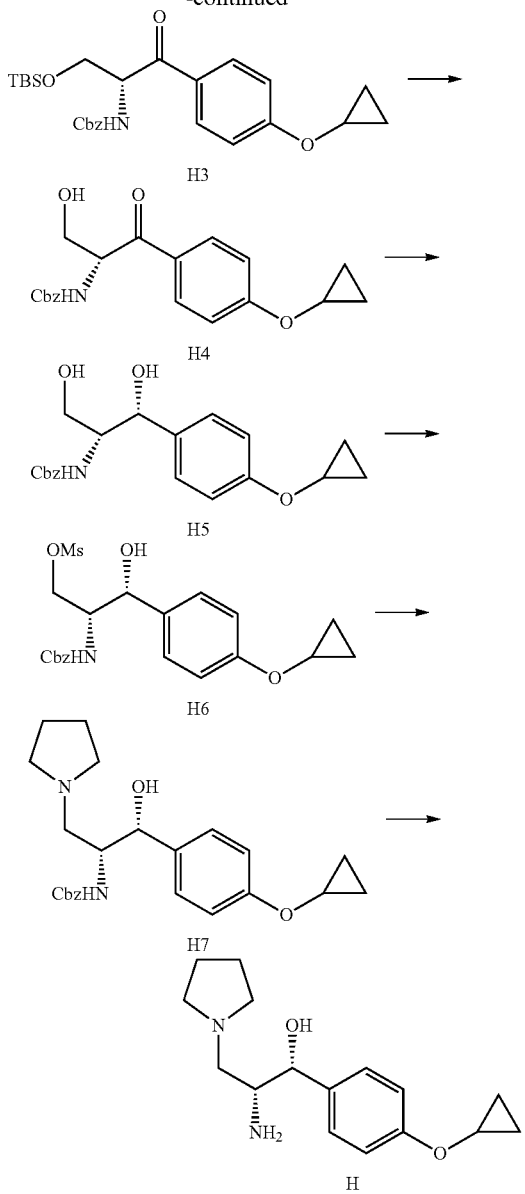

To a solution of Compound H1 (100 g, 0.58 mol) in 1-methyl-2-pyrrolidinone (1.5 L) was added cesium carbonate (377 g, 1.169 mol) and bromocyclopropane (93 mL, 1.16 mol). The mixture was stirred between 140° C. and 150° C. for 24 h. After the reaction mixture was cooled to ambient temperature, the dark solution was diluted with water (1 L) and extracted with a mixture of ethyl acetate (600 mL×3). The combined organic phases were washed with brine (200 mL×4), dried over anhydrous sodium sulfate, filtered, and concentrated to afford the crude Compound H2. The crude product was purified with flash column chromatography on silica gel (petroleum ether) to furnish Intermediate H2. Retention time: 2.19 minutes; $^1$H-NMR (CDCl$_3$, 400 MHz): δ (ppm) 0.66-0.75 (m, 4H), 3.60-3.71 (m, 1H), 6.82-7.02 (m, 2H), 7.28-7.41 (m, 2H).

Intermediates H3, H4, H5, H6, and H7, were synthesized, by employing the procedures described for Intermediates A5, A6, A7, A8, and A9 using Intermediates H2, H3, H4, H5, and H6 in lieu of 6-bromo-2,3-dihydrobenzo[b][1,4] dioxine, Intermediates A5, A6, A7, and A8.

Intermediate H3. LC-MS (ESI) m/z: 470 [M+H]⁺.

Intermediate H4. LC-MS (ESI) m/z: 356 [M+H]⁺, 378 [M+Na]⁺; ¹H NMR (DMSO-d₆, 400 MHz): δ (ppm) 0.65-0.72 (m, 2H), 0.78-0.88 (m, 2H), 3.58-3.71 (m, 1H), 3.75-3.80 (m, 1H), 3.94-3.99 (m, 1H), 4.89 (t, J=5.8 Hz, 1H), 5.04 (s, 2H), 5.16 (dd, J=13.0, 5.5 Hz, 1H), 7.17 (d, J=8.7 Hz, 2H), 7.32-7.38 (m, 4H), 7.51 (d, J=7.9 Hz, 1H), 8.00 (d, J=8.7 Hz, 2H).

Intermediate H5. LC-MS (ESI) m/z: 340 [M-OH]⁺. ¹H-NMR (CDCl₃, 400 MHz): δ (ppm) 0.74-0.77 (m, 4H), 1.81 (s, 1H), 2.76 (s, 1H), 3.23 (s, 1H), 3.65-3.90 (m, 4H), 4.92-5.08 (m, 2H), 5.51 (d, J=7.8 Hz, 1H), 6.99 (d, J=8.6 Hz, 2H), 7.27-7.38 (m, 7H).

Intermediate H6. LC-MS (ESI) m/z: 418 [M-OH]⁺, 458 [M+Na]⁺. ¹H-NMR (CDCl₃, 400 MHz): δ (ppm) 0.66-0.84 (m, 4H), 1.76 (s, 1H), 2.92-2.96 (m, 3H), 3.69-3.74 (m, 1H), 4.07-4.17 (m, 2H), 4.34-4.39 (m, 1H), 4.89 (s, 1H), 5.00-5.03 (m, 2H), 5.40 (d, J=7.1 Hz, 1H), 7.00 (d, J=8.6 Hz, 2H), 7.16-7.75 (m, 7H).

Intermediate H7. LC-MS (ESI) m/z: 411 [M+H]⁺.

Intermediate H was synthesized, by employing the procedure described for Intermediate E using Intermediate H7 in lieu of Intermediate E7, which was directly used for the next step without further purification. LC-MS (ESI) m/z: 277 [M+H]⁺; ¹H-NMR (DMSO-d₆, 400 MHz): δ (ppm) 0.60-0.64 (m, 2H), 0.74-0.78 (m, 2H), 1.23 (s, 1H), 1.65 (s, 4H), 2.10-2.14 (m, 1H), 2.28-2.49 (m, 6H), 2.87-2.90 (m, 1H), 3.77-3.82 (m, 1H), 4.33 (d, J=5.0 Hz, 1H), 6.98 (d, J=8.4 Hz, 2H), 7.22 (d, J=8.8 Hz, 2H).

Intermediate I

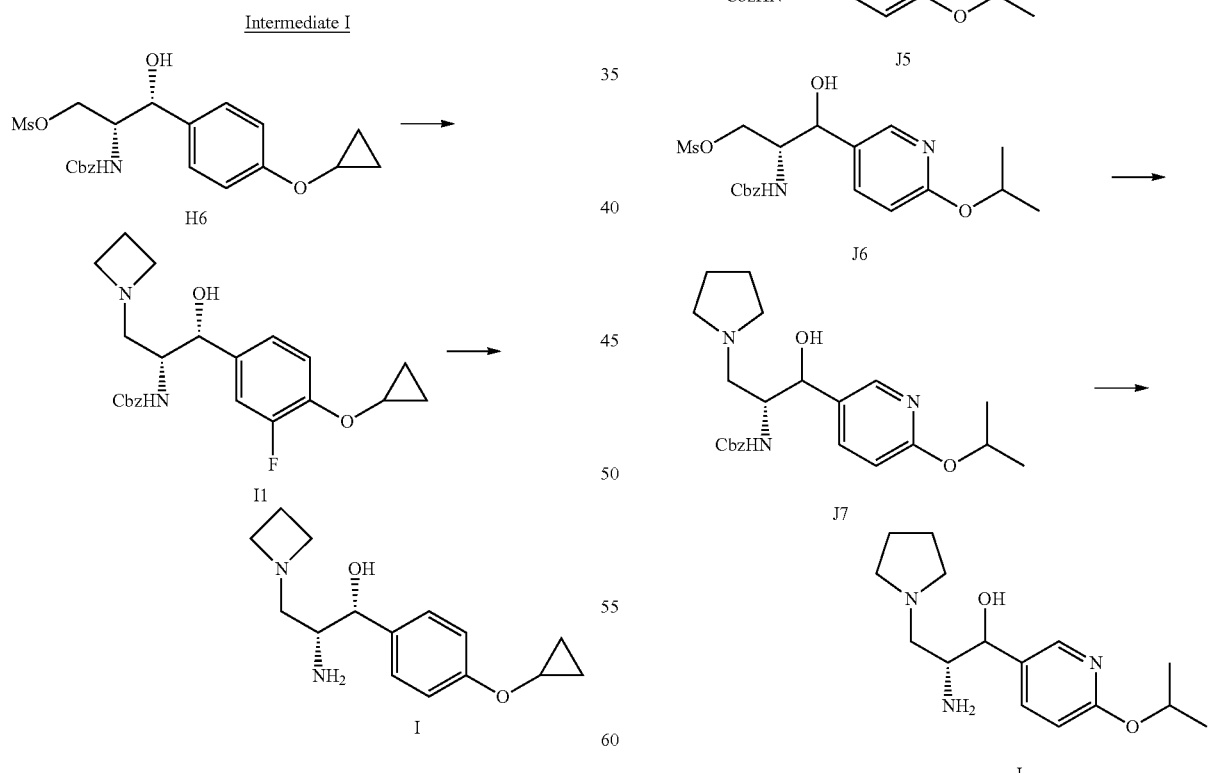

Intermediate I1 was synthesized, by employing the procedure described for Intermediate A9 using azetidine and Intermediate H6 in lieu of pyrrolidine and Intermediate A8, (yield 56%). LC-MS (ESI) m/z: 397 [M+H]⁺.

Intermediate I was synthesized, by employing the procedure described for Intermediate E using Intermediate I1 in lieu of Intermediate E7, which was directly used for the next step without further purification. LC-MS (ESI) m/z: 263 [M+H]⁺.

Intermediate J

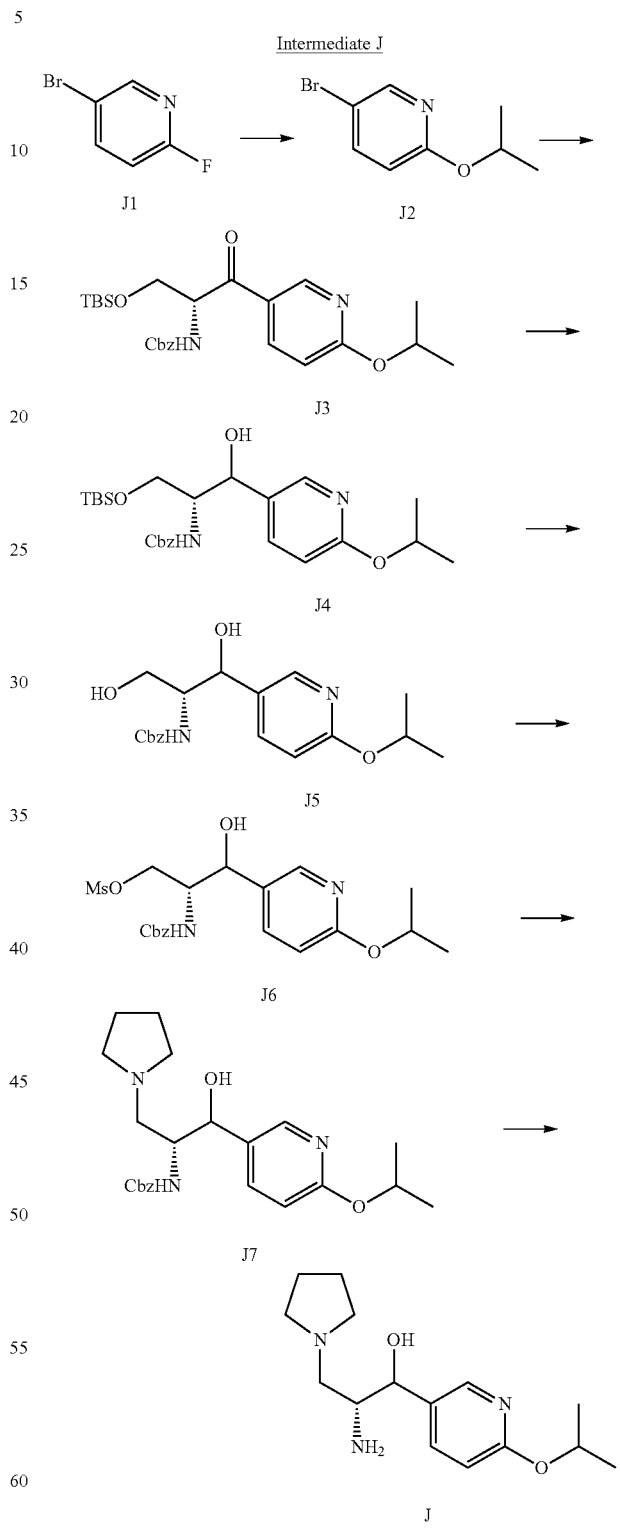

NaH (60%, 10.4 g, 0.26 mol) was added in two portions to isopropyl alcohol (300 mL) at room temperature (about 30° C.) under N₂. The mixture was stirred at 60° C. for 30 min. Compound J1 (20.0 g, 0.11 mol) was added in two portions and the mixture was stirred at reflux for 4 h, followed at 80° C. overnight. The solution was concentrated in vacuo. Water (100 mL) and ethyl acetate (200 mL) were added and the layers were separated. The aqueous layer was extracted with ethyl acetate (50 mL×3). The combined organic layers were washed with water (10 mL×2), brine (10 mL×2) and dried over anhydrous Na$_2$SO$_4$. After filtration the solvent was removed in vacuo. The crude product was subjected to flash column chromatography (silica gel, ethyl acetate in petroleum, 0-50% v/v) to provide Compound J2. LC-MS (m/z): 217 [M+1]$^+$, 219 [M+3]$^+$; $^1$H-NMR (CDCl$_3$, 400 MHz) major characteristic peaks: δ (ppm) 1.33 (d, J=6.4 Hz, 6H), 5.23 (m, 1H), 5.69 (d, J=8.8 Hz, 1H), 7.61 (dd, J=2.4, 8.8 Hz, 1H), 8.16 (d, J=2.4 Hz, 1H).

Intermediate J3 was synthesized, by employing the procedures described for Intermediates A5 using J2 in lieu of 6-bromo-2,3-dihydrobenzo[b][1,4]dioxine. LC-MS (m/z): 473 [M+1]$^+$; $^1$H-NMR (CDCl$_3$, 400 MHz) major characteristic peaks: δ (ppm) −0.11 (s, 3H), −0.10 (s, 3H), 0.75 (s, 9H), 1.37 (d, J=6.4 Hz, 6H), 3.87-3.90 (m, 1H), 3.98-4.02 (m, 1H), 5.14 (s, 2H), 5.29 (t, J=3.6 Hz, 1H), 5.42 (m, 1H), 5.92 (d, J=8.0 Hz, 1H), 6.73 (d, J=8.8 Hz, 1H), 7.36-7.38 (m, 5H), 8.11 (dd, J=2.4, 8.8 Hz, 1H), 8.79 (d, J=2.4 Hz, 1H).

Compound J3 (10.1 g, 21.4 mmol) was dissolved in anhydrous THF (200 mL) and cooled down to −70° C. under nitrogen atmosphere. L-Selectride (42.8 mL, 1M solution in THF, 42.8 mmol) was added dropwise while keeping the temperature at −70° C. Then the reaction was stirred for 0.5 h at −70° C. After the reaction was complete as monitored by TLC, the reaction was quenched with saturated NH$_4$Cl solution (30 mL) and extracted with ethyl acetate (100 mL×3). The combined organic phases were washed water (10 mL) and brine (10 mL×2), and dried over anhydrous Na$_2$SO$_4$. The crude product was purified with column chromatography on silica gel (ethyl acetate in petroleum, 20% v/v) to provide Compound J4. LC-MS (m/z): 475 [M+1]$^+$; $^1$H-NMR (CDCl$_3$, 400 MHz) major characteristic peaks: δ (ppm) 0.06 (s, 3H), 0.08 (s, 3H), 0.92 (s, 9H), 1.34 (d, J=6.4 Hz, 6H), 3.70-3.81 (m, 3H), 5.01 (s, 1H), 5.05 (d, J=4.4 Hz, 1H), 5.60 (s, 1H), 5.28 (m, 1H), 5.46 (d, J=8.0 Hz, 1H), 6.64 (d, J=8.4 Hz, 1H), 7.32-7.34 (m, 5H), 7.56 (dd, J=2.4, 8.4 Hz, 1H), 8.11 (s, 1H).

To a solution of Compound J4 (7.7 g, 16.24 mmol) in THF (150 mL) was added a solution of TBAF (2.12 g, 8.12 mmol) in THF (10 mL) at 0° C., then the mixture was stirred at 30° C. overnight. After the reaction was complete as monitored by TLC and LC-MS, it was concentrated by evaporation. Then residue was treated with water (50 mL) and extracted with ethyl acetate (100 mL×3), washed with brine (10 mL), and dried over anhydrous Na$_2$SO$_4$. The crude product was purified with flash column (silica gel, methanol in dichloromethane, 8% v/v) to furnish Compound J5. LC-MS (m/z): 361 [M+1]$^+$; $^1$H-NMR (DMSO-d$_6$, 400 MHz) major characteristic peaks: δ (ppm) 1.27 (d, J=6.4 Hz, 6H), 3.29 (m, 1H), 3.52-3.59 (m, 2H), 4.46-4.52 (m, 1H), 4.71-4.96 (m, 3H), 5.22 (m, 1H), 5.33 (d, J=4.8 Hz, 0.6H), 5.39 (d, J=4.8 Hz, 0.4H), 5.60 (s, 1H), 6.64 (d, J=8.4 Hz, 1H), 6.79 (d, J=8.4 Hz, 0.6H), 6.95 (d, J=8.4 Hz, 0.4H), 7.13-7.28 (m, 5H), 7.59 (m, 1H), 8.03 (s, 1H).

Intermediates J6, J7, and J were synthesized, by employing the procedures described for Intermediates A8, A9, and A using Intermediates J5, J6, and J7 in lieu of Intermediates A7, A8, and A9.

Intermediate J6. LC-MS (m/z): 439 [M+1]$^+$.

Intermediate J7. LC-MS (m/z): 414 [M+1]$^+$; $^1$H-NMR (CDCl$_3$, 400 MHz) major characteristic peaks: δ (ppm) 1.27 (d, J=6.0 Hz, 6H), 1.71 (m, 4H), 2.59 (m, 4H), 2.72-2.76 (m, 2H), 4.96-5.02 (m, 3H), 5.22 (m, 1H), 6.57 (d, J=8.4 Hz, 1H), 7.20-7.29 (m, 5H), 7.44 (d, J=8.4 Hz, 1H), 8.01 (s, 1H).

Intermediate J. LC-MS (m/z): 280 [M+1]$^+$.

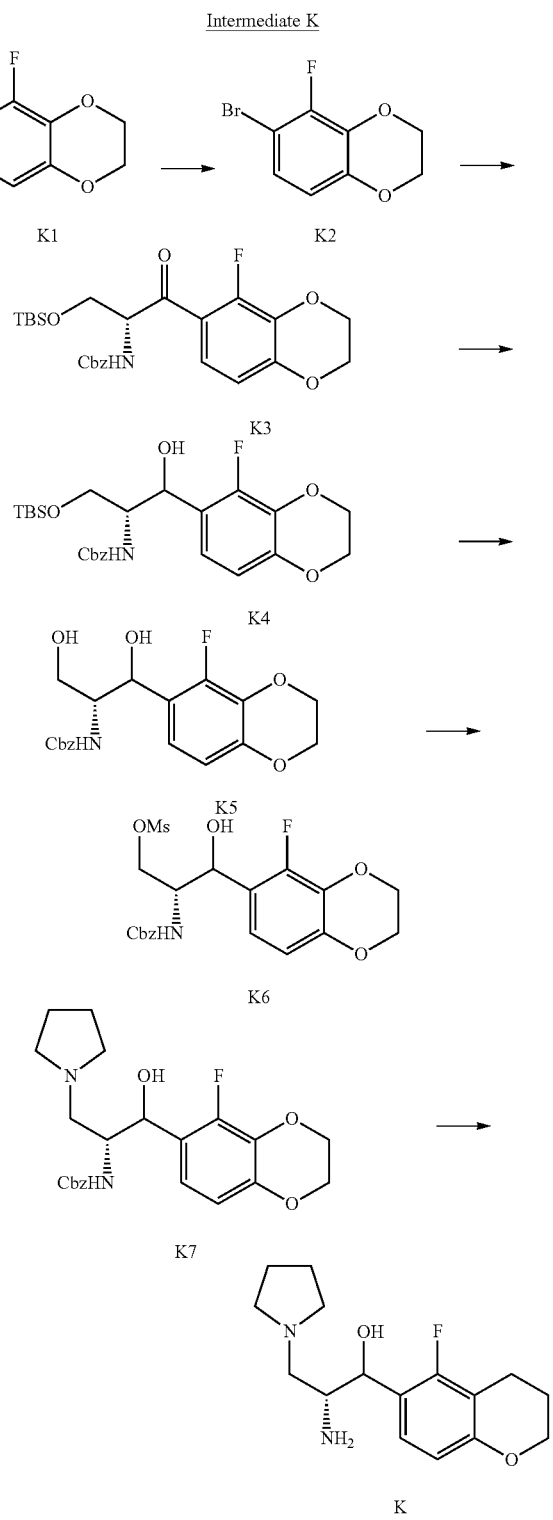

Intermediate K

To a solution of Compound K1 (3.35 g, 21.73 mmol) in methanol (10 mL) was added dropwise bromine (1.34 mL, 26.10 mmol) at −10° C. The mixture was stirred room temperature for 5 h. It was quenched with saturated aqueous Na₂S₂O₃ solution (100 mL) and filtered to remove the solid. The filtrate was evaporated and purified with flash column chromatography on silica gel (ethyl acetate in petroleum ether, from 0% to 3% v/v) to afford Intermediate K2. ¹H-NMR (CDCl₃, 400 MHz): δ (ppm) 4.26-4.33 (m, 4H), 6.58 (d, J=8.8 Hz, 1H), 6.95 (t, J=8.8 Hz, 1H).

Intermediates K3, K4, K5, K6, K7, and K, were synthesized, by employing the procedures described for Intermediates J3, J4, J5, J6, J7, and J using Intermediate K2, K3, K4, K5, K6, and K7 in lieu of Intermediate J2, J3, J4, J5, J6, and J7.

Intermediate K3. LC-MS (ESI) m/z: 490 [M+H]⁺; ¹H-NMR (CDCl₃, 400 MHz): δ (ppm) −0.07 (s, 3H), 0.06 (s, 3H), 0.86 (s, 9H), 4.04-4.13 (m, 2H), 4.42-4.47 (m, 4H), 5.24 (m, 2H), 5.33 (d, J=8.0 Hz, 1H), 6.08 (d, J=8.0 Hz, 1H), 6.85 (d, J=8.8 Hz, 1H), 7.37-7.48 (m, 6H).

Intermediate K4. LC-MS (ESI) m/z: 474 [M-OH]⁺; ¹H-NMR (CDCl₃, 400 MHz): δ (ppm) −0.06 (s, 3H), 0.09 (s, 3H), 0.85 (s, 9H), 3.76 (s, 1H), 3.90 (s, 2H), 4.28 (s, 4H), 4.95-5.21 (m, 3H), 5.46-5.56 (m, 2H), 6.61-6.71 (m, 1H), 6.88-6.93 (m, 1H), 7.29-7.36 (m, 5H).

Intermediate K5. LC-MS (ESI) m/z: 360 [M-OH]⁺; ¹H-NMR (DMSO-d₆, 400 MHz): δ (ppm) 3.33-3.57 (m, 1H), 3.66-3.94 (m, 1H), 4.20-4.28 (m, 4H), 4.68-4.98 (m, 3H), 5.28-5.46 (m, 1H), 6.63-6.78 (m, 2H), 7.14-7.32 (m, 5H).

Intermediate K6. LC-MS (ESI) m/z: 438 [M-OH]⁺; ¹H-NMR (CDCl₃, 400 MHz): δ (ppm) 2.98 (s, 3H), 4.22-4.31 (m, 5H), 4.38 (d, J=4.4 Hz, 2H), 5.31 (s, 4H), 5.60 (d, J=6.0 Hz, 1H), 6.68 (d J=8.8 Hz, 1H), 6.79 (t, J=7.6 Hz, 1H), 7.33-7.43 (m, 5H).

Intermediate K7. LC-MS (ESI) m/z: 431 [M+H]⁺.

Intermediate K. LC-MS (ESI) m/z: 297 [M+H]⁺; ¹H-NMR (CD₃OD, 400 MHz): δ (ppm) 1.71-1.81 (m, 4H), 2.56-2.68 (m, 4H), 3.08-3.17 (m, 2H), 4.17-4.21 (m, 5H), 4.76 (d, J=6.0 Hz, 1H), 6.59-6.66 (m, 1H), 6.81-6.88 (m, 1H).

Intermediate L

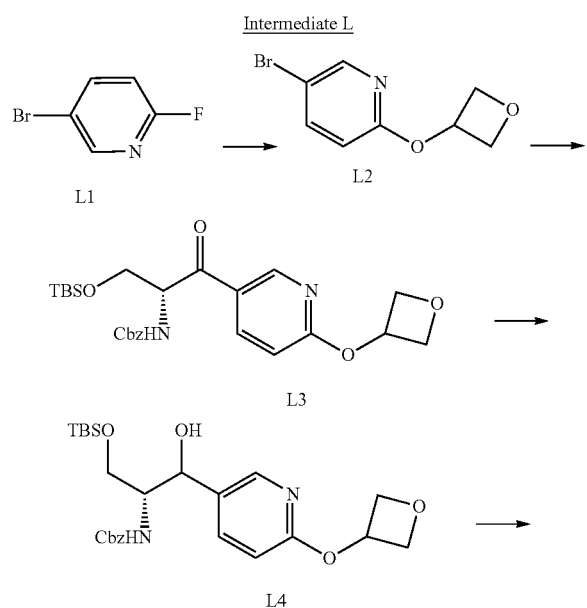

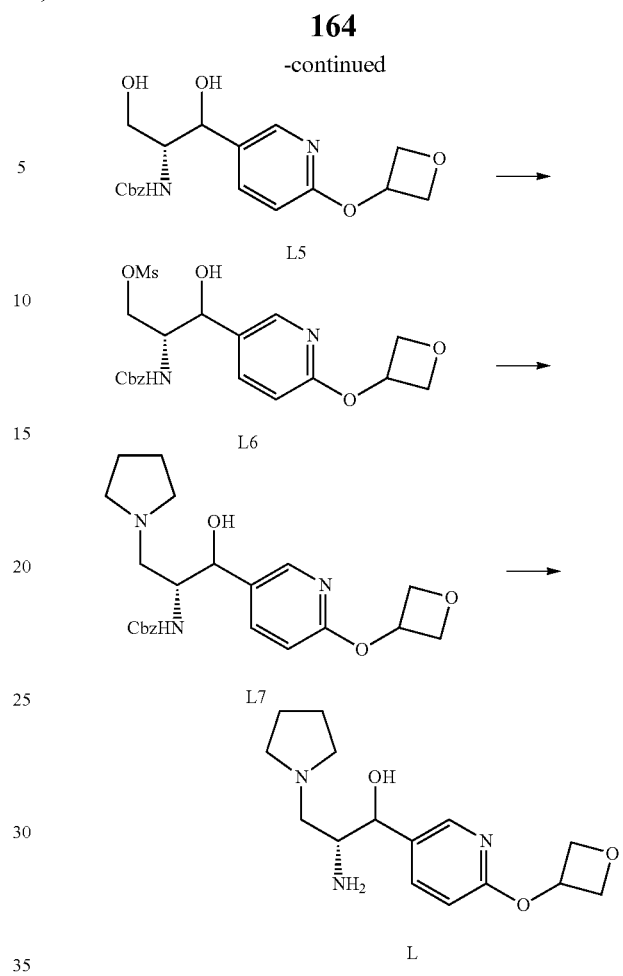

Compounds 5-bromo-2-fluoropyridine (LL 17.6 g, 0.10 mol) and oxetan-3-ol (11.1 g, 0.15 mol) were dissolved in NMP (100 mL) and treated with potassium tert-butoxide (150 mL, 1 M solution in THF, 0.15 mol) at 0° C. The solution became dark, cloudy, and warmed. After 30 min. the reaction mixture was partitioned between ethyl acetate: petroleum ether (1:1, 400 mL) and water (400 mL). The organic layer was separated, washed with water and 5% aq. LiCl, dried over sodium sulfate, filtered, and concentrated. The residue was purified with flash column chromatography on silica gel (ethyl acetate in petroleum ether, 10% v/v) to afford Compound L2. LC-MS (ESI) m/z: 232 [M+H]⁺; ¹H-NMR (CDCl₃, 400 MHz) δ (ppm) 4.69-4.72 (m, 2H), 4.97 (t, J=6.8 Hz, 2H), 5.53-5.58 (m, 1H), 6.72 (d, J=8.4 Hz, 1H), 7.68 (dd, J₁=8.4 Hz, J₂=2.4 Hz, 1H), 8.11 (d, J=2.4 Hz, 1H).

Intermediates L3, L4, L5, L6, L7, and L, were synthesized, by employing the procedures described for Intermediates J3, J4, J5, J6, J7, and J using Intermediates L2, L3, L4, L5, L6, and L7 in lieu of Intermediates J2, J3, J4, J5, J6, and J7.

Intermediate L3. LC-MS (ESI) m/z: 487 [M+H]⁺;
Intermediate L4. LC-MS (ESI) m/z: 489 [M+H]⁺; ¹H-NMR (CDCl₃, 400 MHz) δ (ppm) 0.00 (s, 6H), 0.86 (s, 9H), 3.62-3.81 (m, 4H), 4.64-4.67 (m, 2H), 4.89-5.02 (m, 5H), 5.36-5.38 (m, 1H), 5.51-5.54 (m, 1H), 6.66-6.72 (m, 1H), 7.19-7.29 (m, 5H), 7.53-7.56 (m, 1H), 7.79 (s, 1H).

Intermediate L5. LC-MS (ESI) m/z: 375 [M+H]⁺; ¹H-NMR (CDCl₃, 400 MHz) δ (ppm) 3.81-3.87 (m, 3H), 4.70-4.73 (m, 2H), 4.96-5.03 (m, 4H), 5.48-5.51 (m, 1H), 5.57-5.61 (m, 1H), 6.73-6.75 (m, 1H), 7.29-7.37 (m, 5H), 7.61-7.64 (m, 1H), 8.05-8.06 (m, 1H).

Intermediate L6. LC-MS (ESI) m/z: 453 [M+H]+.

Intermediate L7. LC-MS (ESI) m/z: 428 [M+H]+.

Intermediate L. LC-MS (ESI) m/z: 293 [M+H]+; 1H-NMR (MeOD, 400 MHz) δ (ppm) 2.26 (dd, $J_1$=11.6 Hz, $J_2$=4.4 Hz, 1H), 2.44-2.62 (m, 5H), 3.07-3.12 (m, 1H), 4.08-4.11 (m, 1H), 4.51 (d, J=5.6 Hz, 1H), 4.69-4.72 (m, 2H), 4.97 (t, J=6.8 Hz, 2H), 5.53-5.58 (m, 1H), 6.95 (d, J=8.8 Hz, 1H), 7.75 (dd, $J_1$=8.8 Hz, $J_2$=2.4 Hz, 1H), 8.11 (d, J=2.4 Hz, 1H).

Intermediate M

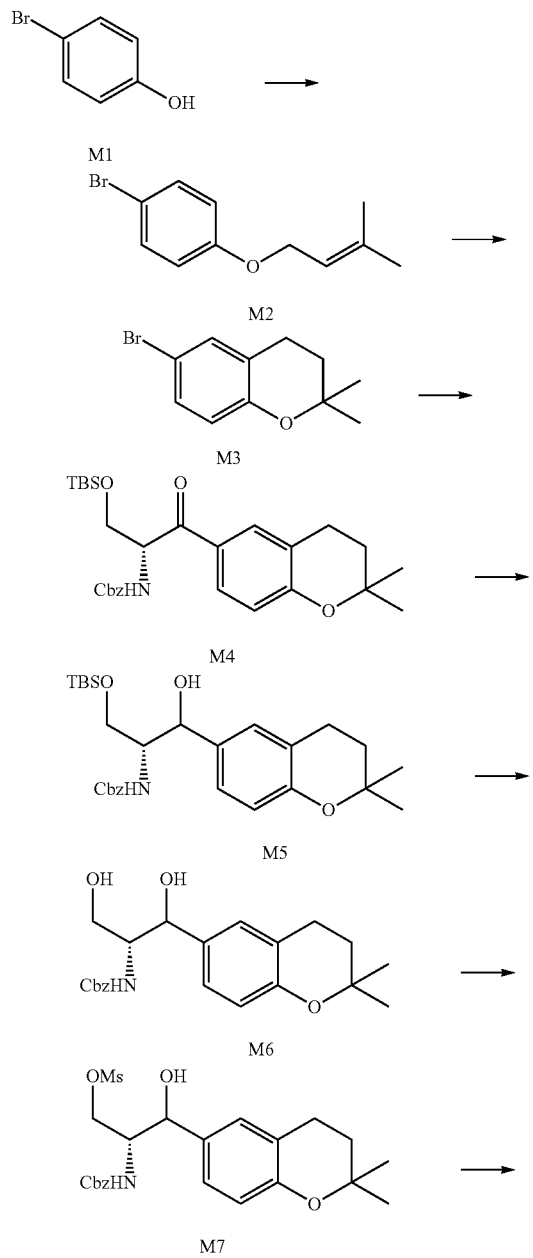

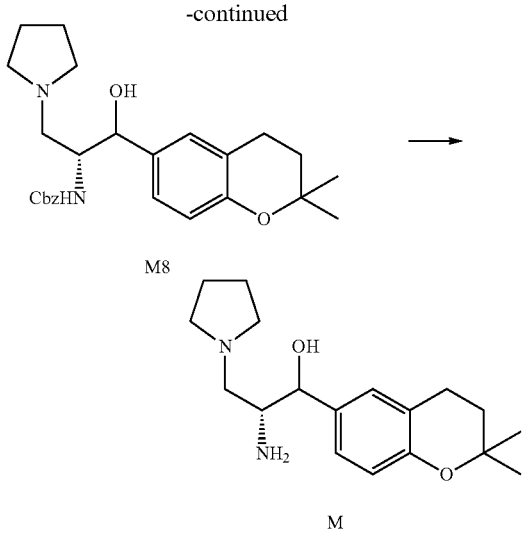

A suspension of Compound M1 (30.00 g, 0.173 mol), 1-bromo-3-methylbut-2-ene (28.42 g, 0.190 mol), $K_2CO_3$ (35.81 g, 0.360 mol) and KI (500 mg) in acetone (70 mL) was stirred at 65° C., for 16 h. The mixture was filtrated to remove solid. The filtrate was purified with silica chromatography (ethyl acetate in petroleum ether, from 0% to 2% v/v) to furnish Compound M2. 1H-NMR ($CDCl_3$, 400 MHz) δ (ppm) 1.73 (s, 3H), 1.79 (s, 3H), 4.46 (d, J=6.8 Hz, 2H), 5.46 (t, J=8.0 Hz, 1H), 7.78 (d, J=9.2 Hz, 2H), 7.36 (d, J=9.2 Hz, 2H).

To a solution of Compound M2 (20.00 g, 0.083 mmol) in DCM (200 mL) was added dropwise trifluoromethanesulfonic acid (7.4 mL) at −78° C. After addition, the mixture was stirred at 28° C. for 10 min. Then it was quenched with 15% KOH (100 mL), washed with water (50 mL×3) and brine (50 mL×2), dried over anhydrous sodium sulfate, concentrated, and purified with silica chromatography (ethyl acetate in petroleum ether, from 0% to 8% v/v) to furnish Compound M3. 1H-NMR ($CDCl_3$, 400 MHz) δ (ppm) 1.32 (s, 6H), 1.79 (t, J=6.8 Hz, 3H), 2.74 (d, J=6.8 Hz, 2H), 6.65 (d, J=8.0 Hz, 1H), 7.16 (d, J=8.8 Hz, 2H).

Intermediates M4, M5, M6, M7, and M8, were synthesized, by employing the procedures described for Intermediates J3, J4, J5, J6, and J7 using Compound M3, M4, M5, M6, and M7 in lieu of Intermediate J2, J3, J4, J5, and J6.

Intermediate M4. LC-MS (ESI) m/z: 498 [M+H]+; 1H-NMR ($CDCl_3$, 400 MHz) δ (ppm) −0.14 (s, 3H), −0.12 (s, 3H), 0.74 (s, 9H), 1.36 (s, 6H), 2.79-2.85 (m, 2H), 3.75 (t, J=6.8 Hz, 2H), 3.86-3.95 (m, 2H), 5.12 (s, 2H), 5.29-5.34 (m, 1H), 5.93 (d, J=7.6 Hz, 1H), 7.80 (d, J=8.4 Hz, 1H), 7.32-7.38 (m, 6H), 7.70-7.74 (m, 2H).

Intermediate M5. LC-MS (ESI) m/z: 482 [M-OH]+; 1H-NMR ($CDCl_3$, 400 MHz) δ (ppm) 0.90 (s, 15H), 1.32 (s, 6H), 1.76-1.80 (m, 2H), 2.74 (t, J=6.4 Hz, 2H), 3.67-3.83 (m, 3H), 4.19 (s, 1H), 4.91-5.12 (m, 3H), 5.29-5.46 (m, 1H), 6.73 (d, J=8.8 Hz, 1H), 6.97-7.05 (m, 2H), 7.27-7.38 (m, 5H).

Intermediate M6. LC-MS (ESI) m/z: 368 [M-OH]+; 1H-NMR ($CDCl_3$, 400 MHz) δ (ppm) 0.95 (s, 6H), 1.79 (t, J=6.8 Hz, 2H), 2.75 (t, J=6.8 Hz, 2H), 3.76-4.26 (m, 4H), 4.62-5.18 (m, 4H), 6.77 (d, J=8.4 Hz, 1H), 6.96-7.06 (m, 2H), 7.30-7.36 (m, 5H).

Intermediate M7. LC-MS (ESI) m/z: 446 [M-OH]+; 1H-NMR ($CDCl_3$, 400 MHz) δ (ppm) 1.02 (s, 6H), 1.82 (t, J=6.8 Hz, 2H), 2.98 (t, J=6.8 Hz, 2H), 3.16 (s, 3H), 3.80-

4.20 (m, 4H), 4.80-5.10 (m, 4H), 6.72 (d, J=8.4 Hz, 1H), 6.96-7.06 (m, 2H), 7.30-7.36 (m, 5H).

Intermediate M8. LC-MS (ESI) m/z: 439 [M-OH]$^+$; $^1$H-NMR (CDCl$_3$, 400 MHz) δ (ppm) 1.32 (s, 6H), 1.71-1.80 (m, 6H), 2.42-2.56 (m, 2H), 2.66-2.79 (m, 6H), 3.39-3.44 (m, 1H), 3.97-4.06 (m, 1H), 4.70 (s, 1H), 4.93 (s, 1H), 5.04 (s, 2H), 6.73-6.79 (m, 1H), 6.99-7.09 (m, 2H), 7.29-7.38 (m, 5H).

A solution of Compound M8 (2.10 g, 4.79 mmol) and KOH (2.68 g, 47.94 mmol) in EtOH/H$_2$O (50/5 mL) was stirred at 80° C. for 16 h. And then it was diluted with ethyl acetate (200 mL), washed with water (200 mL) and brine (200 mL), dried over anhydrous sodium sulfate, and purified with reverse phase chromatography using eluent (methanol in water, from 0% to 100% v/v) to furnish Intermediate M. LC-MS (ESI) m/z: 305 [M-OH]$^+$; $^1$H-NMR (CDCl$_3$, 400 MHz): δ (ppm) 1.32 (s, 6H), 1.76-1.81 (m, 8H), 2.47-2.68 (m, 6H), 2.78 (t, J=6.8 Hz, 2H), 3.11-3.16 (m, 1H), 3.49 (s, 1H), 4.55 (s, 1H), 6.75 (d, J=8.0 Hz, 1H), 7.02-7.12 (m, 2H).

Intermediate N

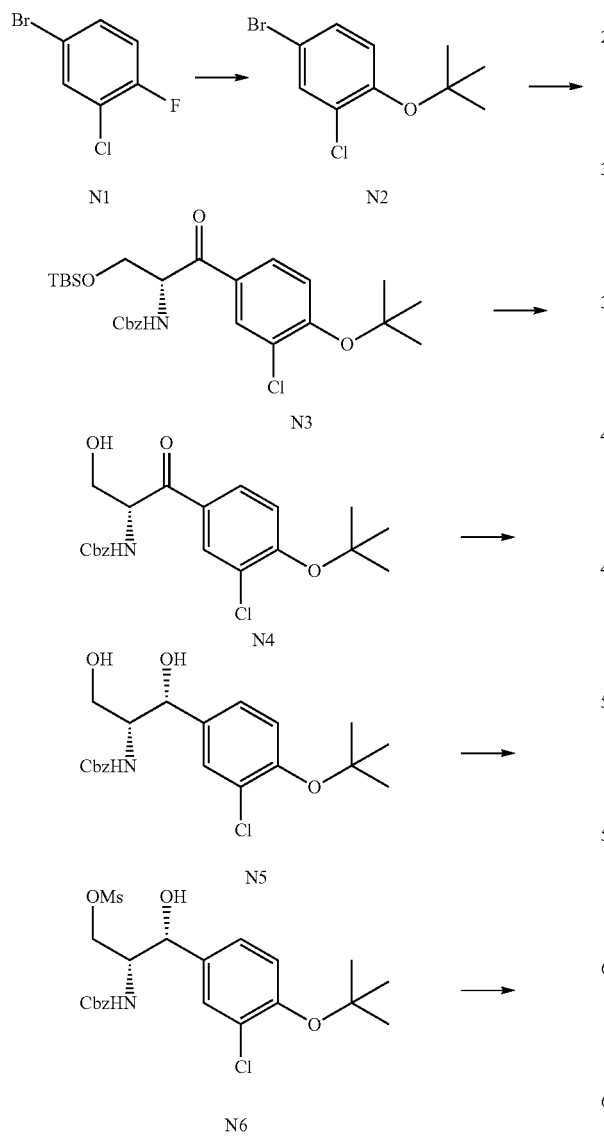

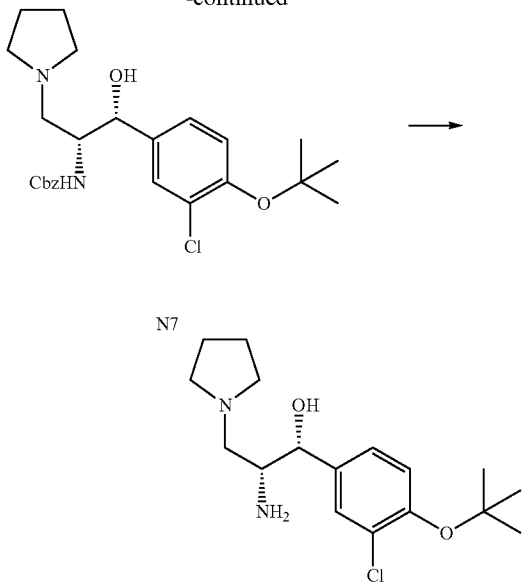

To a solution of Compound N1 (10.00 g, 47.85 mmol) in DMF (100 mL) was added t-BuOK (8.04 mL, 71.77 mmol) at room temperature. The mixture was stirred room temperature for 2 h and quenched with water (100 mL). The mixture was diluted with ethyl acetate (300 mL), washed with water (200 mL) and brine (200 mL), dried over anhydrous sodium sulfate, and purified with flash column chromatography on silica gel (ethyl acetate in petroleum ether, from 0% to 5% v/v) to afford Compound N2. $^1$H-NMR (DMSO-d$_6$, 400 MHz): δ (ppm) 1.36 (s, 9H), 7.19 (d, J=8.8 Hz, 1H), 7.45 (d, J=8.8 Hz, 1H), 7.71 (s, 1H).

Intermediates N3, N4, N5, N6, and N7, were synthesized, by employing the procedures described for Intermediate A5, A6, A7, A8, and A9 using Intermediate N2, N3, N4, N5, and N6 in lieu of 6-bromo-2,3-dihydrobenzo[b][1,4]dioxine, Intermediates A5, A6, A7, and A8.

Intermediate N3. LC-MS (ESI) m/z: 520 [M+H]$^+$; $^1$H-NMR (CDCl$_3$, 400 MHz): δ (ppm) −0.12 (s, 6H), 0.73 (s, 9H), 1.48 (s, 9H), 3.84-3.88 (m, 1H), 3.96-3.99 (m, 1H), 5.12 (s, 2H), 5.29-5.34 (m, 1H), 5.88-5.90 (m, 1H), 7.18 (d, J=8.4 Hz, 1H), 7.32-7.38 (m, 5H), 7.78 (d, J=10.8 Hz, 1H), 8.01 (m, 1H).

Intermediate N4. LC-MS (ESI) m/z: 388 [M-OH]$^+$; $^1$H-NMR (CDCl$_3$, 400 MHz): δ (ppm) 1.50 (s, 9H), 2.57-2.62 (m, 1H), 3.87-3.92 (m, 1H), 3.97-4.05 (m, 1H), 5.15 (s, 2H), 7.19 (d, J=8.4 Hz, 1H), 7.26-7.38 (m, 6H), 7.83 (d, J=7.6 Hz, 1H), 8.05 (s, 1H).

Intermediate N5. LC-MS (ESI) m/z: 390 [M-OH]$^+$; $^1$H-NMR (CDCl$_3$, 400 MHz): δ (ppm) 1.40 (s, 9H), 2.43-2.45 (m, 1H), 3.24 (s, 1H), 3.77-3.83 (m, 3H), 4.96-5.10 (m, 3H), 5.47 (s, 1H), 7.06 (d, J=8.0 Hz, 1H), 7.14 (d, J=8.8 Hz, 1H), 7.29-7.37 (m, 5H), 7.41 (s, 1H).

Intermediate N6. The target compound was directly used for the next step without further purification. LC-MS (ESI) m/z: 468 [M-OH]$^+$.

Intermediate N7. LC-MS (ESI) m/z: 461 [M+H]$^+$; $^1$H-NMR (CDCl$_3$, 400 MHz): δ (ppm) 1.40 (s, 9H), 1.76-1.81 (m, 4H), 2.65-2.89 (m, 6H), 4.01 (s, 1H), 4.98-5.06 (m, 3H), 7.08 (s, 1H), 7.29-7.41 (m, 6H), 7.41 (s, 1H).

Intermediate N was synthesized, by employing the procedure described for Intermediate E using Intermediate N7 in lieu of Intermediate E7. LC-MS (ESI) m/z: 327 [M+H]⁺; ¹H-NMR (CDCl₃, 400 MHz): δ (ppm) 1.41 (s, 9H), 1.76-1.80 (m, 4H), 2.47-2.62 (m, 6H), 3.14 (s, 1H), 4.60 (s, 1H), 5.71 (s, 1H), 7.08-7.14 (m, 2H), 7.38 (s, 1H).

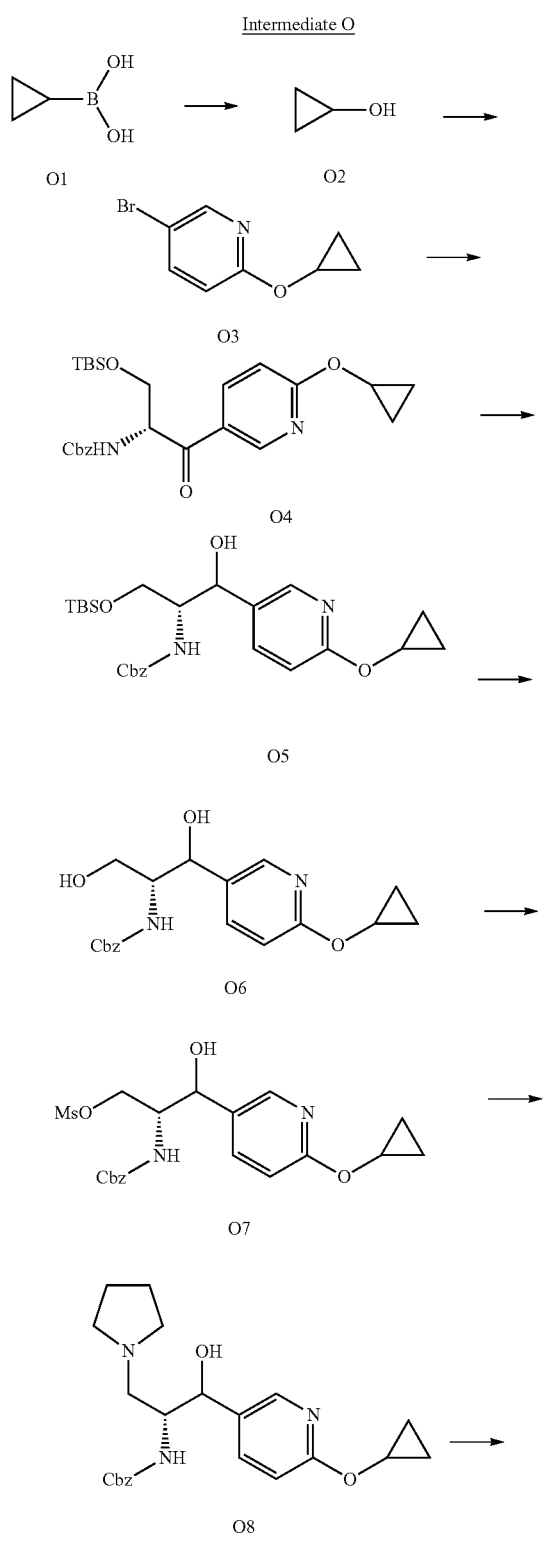

A solution of aqueous $H_2O_2$ (30%, 400 mL, 4.00 mol) was added dropwise with continuous stirring at 0° C. To a suspension of cyclopropyl boronic acid Compound O1 (62.0 g, 0.721 mol) in 10% aqueous NaOH (500 mL). The resulting mixture was stirred for 1 h at 0° C. The reaction mixture was quenched with saturated aqueous $Na_2S_2O_3$ and extracted with $Et_2O$. The combined organics were dried over anhydrous sodium sulfate, filtered, and concentrated in vacuo at 0° C. The mixture was dissolved in $Et_2O$ (400 mL), 4 Å molecular sieves were added and it was left overnight at room temperature to yield Compound O2. ¹H-NMR (CDCl₃, 400 MHz) major characteristic peaks: δ (ppm) 0.49-0.57 (m, 4H), 3.48-3.50 (m, 1H).

Compounds 5-bromo-2-fluoropyridine (25.0 g, 0.12 mol) and cyclopropanol (O2, 10.4 g, 0.18 mol) were dissolved in NMP (100 mL) and treated with potassium tert-butoxide (180 mL, 1M solution in THF, 0.18 mol) at 0° C. The solution became dark and cloudy, and warmed. After 30 min, the reaction mixture was partitioned between ethyl acetate and petroleum ether (500 mL, 1/1 v/v) and water (500 mL). The organic layer was separated, washed with water and 5% aq. LiCl, dried over anhydrous sodium sulfate, filtered and concentrated. The residue was purified with silica gel column chromatography (ethyl acetate in petroleum ether, 10% v/v) to furnish Compound O3. ¹H-NMR (CDCl₃, 400 MHz) major characteristic peaks: δ (ppm) 0.74-0.81 (m, 4H), 4.13-4.18 (m, 1H), 6.88 (d, J=8.8 Hz, 1H), 7.66 (dd, J=8.8, 2.4 Hz, 1H), 8.26 (d, J=2.4 Hz, 1H).

Intermediate O4, O5, O6, O7, O8, and O, were synthesized, by employing the procedures described for Intermediate J3, J4, J5, J6, J7, and J using O3, O4, O5, O6, O7, and O8 in lieu of J2, J3, J4, J5, J6, and J7.

Intermediate O4. LC-MS (m/z): 471 [M+1]⁺; ¹H-NMR (CDCl₃, 400 MHz) major characteristic peaks: δ (ppm) 0.00 (s, 3H), 0.16 (s, 3H), 0.86 (s, 9H), 0.93-0.98 (m, 4H), 4.01-4.03 (m, 1H), 4.11-4.13 (m, 1H), 4.43-4.45 (m, 1H), 5.25 (s, 2H), 5.40-5.42 (m, 1H), 6.03 (d, J=8.0 Hz, 1H), 6.94 (d, J=8.0 Hz, 1H), 7.38-7.49 (m, 5H), 8.25-8.28 (m, 1H), 8.97-8.98 (m, 1H).

Intermediate O5. LC-MS (m/z): 473 [M+1]⁺; ¹H-NMR (CDCl₃, 400 MHz) major characteristic peaks: δ (ppm) 0.04-0.07 (m, 6H), 0.74-0.80 (m, 4H), 0.91 (s, 9H), 3.78-3.87 (m, 2H), 4.15-4.17 (m, 1H), 5.03-5.08 (m, 3H), 5.45-5.46 (m, 1H), 6.73-6.75 (m, 1H), 7.26-7.35 (m, 5H), 7.59-7.61 (m, 1H), 8.18-8.19 (m, 1H).

Intermediate O6. LC-MS (m/z): 359 [M+1]⁺; ¹H-NMR (CDCl₃, 400 MHz) major characteristic peaks: δ (ppm) 0.67-0.71 (m, 4H), 3.68-3.79 (m, 4H), 4.01-4.05 (m, 1H), 4.93-4.98 (m, 2H), 5.53-5.57 (m, 1H), 6.65-6.67 (m, 1H), 7.19-7.26 (m, 5H), 7.52-7.55 (m, 1H), 8.08-8.11 (m, 1H).

Intermediate O7. LC-MS (m/z): 437 [M+1]⁺; ¹H-NMR (DMSO-d₆, 400 MHz) major characteristic peaks: δ (ppm) 0.63-0.76 (m, 4H), 3.15 (s, 3H), 4.17-4.18 (m, 1H), 4.34-4.36 (m, 1H), 4.78-4.79 (m, 1H), 4.95 (dd, J=30.8, 12.8 Hz, 2H), 5.72 (d, J=4.8 Hz, 1H), 6.78 (d, J=8.4 Hz, 1H), 7.24-7.36 (m, 5H), 7.65 (dd, J=8.4, 2.4 Hz, 1H), 8.11 (d, J=2.4 Hz, 1H).

Intermediate O8. LC-MS (m/z): 412 [M+1]⁺; ¹H-NMR (MeOD, 400 MHz) major characteristic peaks: δ (ppm) 0.70-0.82 (m, 4H), 1.81-1.83 (m, 4H), 2.60-2.68 (m, 4H), 2.75-2.77 (m, 1H), 3.95-3.98 (m, 1H), 4.04-4.08 (m, 1H), 4.87-4.88 (m, 1H), 4.96-5.04 (m, 2H), 6.87 (d, J=8.4 Hz, 1H), 7.25-7.34 (m, 5H), 7.65 (dd, J=8.4, 2.4 Hz, 1H), 8.11 (d, J=2.4 Hz, 1H).

Intermediate O. LC-MS (m/z): 278 [M+1]⁺; ¹H-NMR (MeOD, 400 MHz) major characteristic peaks: δ (ppm) 0.70-0.82 (m, 4H), 1.75-1.78 (m, 4H), 2.26 (dd, J=11.6, 4.4 Hz, 1H), 2.44-2.62 (m, 5H), 3.07-3.12 (m, 1H), 4.08-4.11 (m, 1H), 4.51 (d, J=5.6 Hz, 1H), 6.95 (d, J=8.8 Hz, 1H), 7.75 (dd, J=8.8, 2.4 Hz, 1H), 8.11 (d, J=2.4 Hz, 1H).

Intermediate P

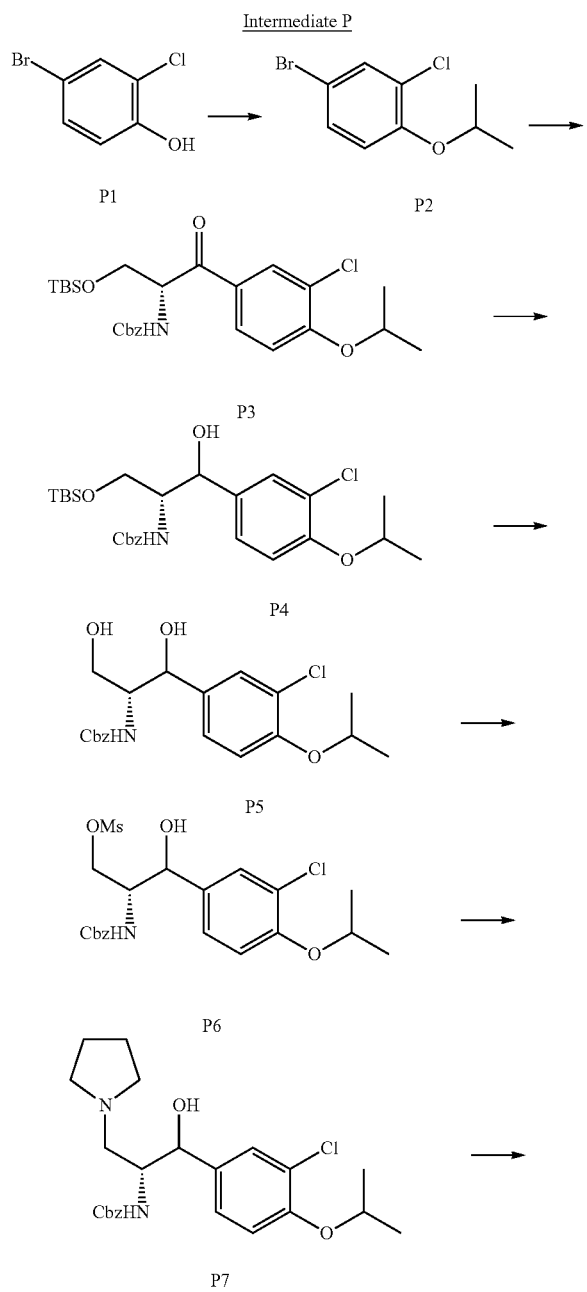

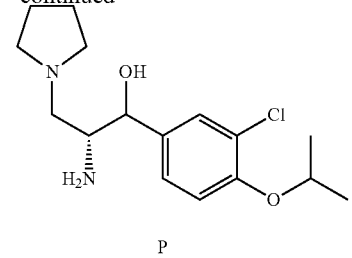

P

Compound P1 (31.1 g, 150 mmol), K₂CO₃ (31.1 g, 225 mmol) and iodopropane (18 mL, 180 mmol) were stirred at 25° C. in DMF (300 mL). After 18 hours, the mixture was diluted with ethyl acetate (600 mL), washed with H₂O (300 mL×4), and dried over anhydrous sodium sulfate. After evaporation, the crude compound was purified with flash column chromatography on silica gel (petroleum ether, 100% v/v) to yield Compound P2. ¹H-NMR (CDCl₃, 400 MHz) major characteristic peaks: δ (ppm) 1.36 (d, J=7.0 Hz, 6H), 4.49-4.52 (m, 1H), 6.81 (d, J=8.8 Hz, 1H), 7.27 (dd, J=8.8, 2.4 Hz, 1H), 7.49 (d, J=2.4 Hz, 1H).

Intermediates P3, P4, P5, P6, and P7, were synthesized, by employing the procedures described for Intermediates J3, J4, J5, J6, and J7 using Intermediates P2, P3, P4, P5, and P6 in lieu of Intermediates J2, J3, J4, J5, and J6.

Intermediate P3. LC-MS (m/z): 506 [M+1]⁺; ¹H-NMR (CDCl₃, 400 MHz) major characteristic peaks: δ (ppm) −0.11 (s, 3H), 0.01 (s, 3H), 0.87 (s, 9H), 1.54 (s, 3H), 1.55 (s, 3H), 3.98-4.01 (m, 2H), 4.78-4.85 (m, 1H), 5.23 (s, 2H), 5.39-5.42 (m, 1H), 5.60 (d, J=7.2 Hz, 1H), 7.38-7.49 (m, 5H), 7.76 (dd, J=8.8, 2.0 Hz, 1H), 8.13 (d, J=2.0 Hz, 1H).

Intermediate P4. LC-MS (m/z): 490 [M−17]⁺.

Intermediate P5. LC-MS (m/z): 338 [M−17]⁺; ¹H-NMR (CDCl₃, 400 MHz) major characteristic peaks: δ (ppm) 1.36-1.38 (m, 6H), 2.46-2.56 (m, 1H), 3.17-3.22 (m, 1H), 3.62-3.82 (m, 3H), 4.51-5.11 (m, 3H), 5.46-5.63 (m, 1H), 6.87-6.90 (m, 1H), 7.15-7.17 (m, 1H), 7.30-7.39 (m, 5H).

Intermediate P6, which was used for next step without purification. LC-MS (m/z): 454 [M−17]⁺.

Intermediate P7. LC-MS (m/z): 447 [M+1]⁺; ¹H-NMR (CDCl₃, 400 MHz) major characteristic peaks: δ (ppm) 1.35-1.39 (m, 6H), 1.94-2.00 (m, 4H), 2.82-3.32 (m, 5H), 3.49-3.58 (m, 1H), 4.07-4.10 (m, 1H), 4.48-4.59 (m, 1H), 4.99 (s, 2H), 5.08 (m, 1H), 6.84-6.89 (m, 1H), 7.23-7.33 (m, 5 h), 7.35-7.45 (m, 1H).

Intermediate P was synthesized, by employing the procedure described for Intermediate E using Intermediate P7 in lieu of Intermediate E7. LC-MS (m/z): 313 [M+1]⁺; ¹H-NMR (CDCl₃, 400 MHz) major characteristic peaks: δ (ppm) 1.37 (s, 3H), 1.38 (s, 3H), 1.77-1.83 (m, 4H), 2.48-2.99 (m, 6H), 3.09-3.14 (m, 1H), 4.35-4.57 (m, 2H), 6.91-6.94 (m, 1H), 7.14-7.21 (m, 1H), 7.28-7.35 (m, 1H).

Intermediate Q

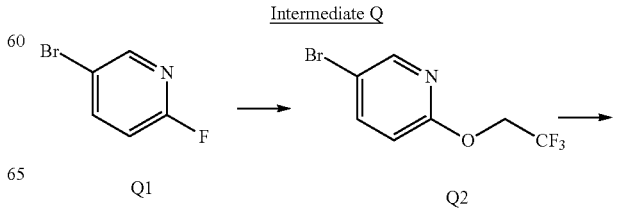

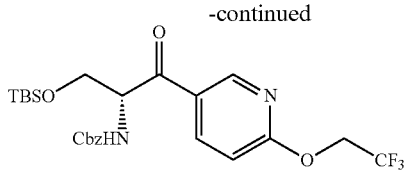

Q3

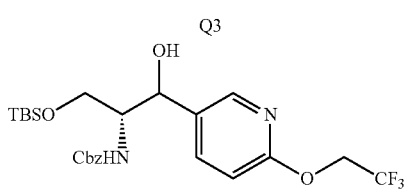

Q4

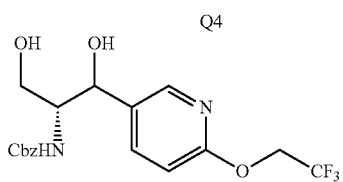

Q5

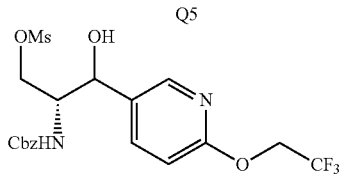

Q6

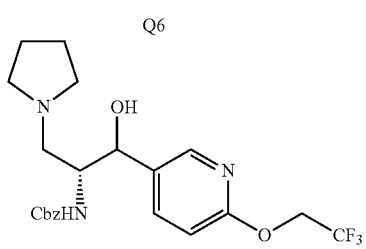

Q7

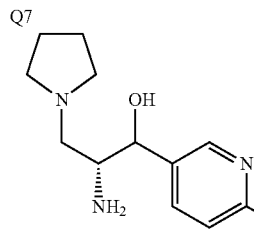

Q

Intermediates Q2, Q3, Q4, Q5, Q6, Q7, and Q, were synthesized, by employing the procedures described for Intermediates J2, J3, J4, J5, J6, J7, and J using Intermediates Q1, Q2, Q3, Q4, Q5, Q6, and Q7 in lieu of Intermediates J1, J2, J3, J4, J5, J6, and J7.

Intermediate Q2. LC-MS (m/z): 257 [M+1]$^+$, 259 [M+3]$^+$; $^1$H-NMR (CDCl$_3$, 400 MHz) major characteristic peaks: δ (ppm) 4.73 (q, J=8.4 Hz, 2H), 6.79 (d, J=8.8 Hz, 1H), 7.73 (dd, J=2.4, 8.8 Hz, 1H), 8.19 (d, J=2.4 Hz, 1H).

Intermediate Q3. LC-MS (m/z): 413 [M+1]$^+$; $^1$H-NMR (CDCl$_3$, 400 MHz) major characteristic peaks: δ (ppm) −0.12 (s, 3H), −0.10 (s, 3H), 0.74 (s, 9H), 3.86-3.90 (m, 1H), 3.98-4.02 (m, 1H), 4.80 (q, J=8.4 Hz, 2H), 5.13 (s, 2H), 5.29 (t, J=3.6 Hz, 1H), 5.89 (m, 1H), 6.95 (d, J=8.4 Hz, 1H), 7.36-7.38 (m, 5H), 8.16 (dd, J=2.0, 8.4 Hz, 1H), 8.64 (d, J=2.0 Hz, 1H).

Intermediate Q4. LC-MS (m/z): 515 [M+1]$^+$; $^1$H-NMR (CDCl$_3$, 400 MHz) major characteristic peaks: δ (ppm) 0.08 (s, 3H), 0.09 (s, 3H), 0.93 (s, 9H), 3.71-3.88 (m, 4H), 4.75 (m, 2H), 5.05-5.10 (m, 2H), 5.44 (d, J=8.4 Hz, 1H), 6.81 (d, J=8.8 Hz, 1H), 7.32-7.34 (m, 5H), 7.65 (dd, J=2.4, 8.4 Hz, 1H), 8.12 (s, 1H).

Intermediate Q5. LC-MS (m/z): 401 [M+1]$^+$; $^1$H-NMR (CDCl$_3$, 400 MHz) major characteristic peaks: δ (ppm) 2.78 (m, 1H), 3.56-3.67 (m, 1H), 3.82 (m, 3H), 4.72-4.74 (m, 2H), 5.01-5.07 (m, 3H), 5.56 (d, J=8.4 Hz, 0.7H), 5.62 (d, J=8.0 Hz, 0.3H), 6.79 (d, J=8.4 Hz, 0.7H), 6.85 (d, J=8.4 Hz, 0.3H), 7.32-7.34 (m, 5H), 7.65 (d, J=8.4 Hz, 1H), 8.11 (s, 1H).

Intermediate Q6. LC-MS (m/z): 479 [M+1]$^+$; $^1$H-NMR (CDCl$_3$, 400 MHz) major characteristic peaks: δ (ppm) 3.02 (s, 3H), 4.25-4.42 (m, 3H), 4.71-4.77 (m, 2H), 5.03 (m, 3H), 5.37 (d, J=8.4 Hz, 1H), 6.81 (d, J=8.4 Hz, 1H), 7.32-7.35 (m, 5H), 7.64 (dd, J=2.4, 8.4 Hz, 1H), 8.13 (d, J=2.4 Hz, 1H).

Intermediate Q7. LC-MS (m/z): 454 [M+1]$^+$; $^1$H-NMR (CDCl$_3$, 400 MHz) major characteristic peaks: δ (ppm) 1.80 (m, 4H), 2.67 (m, 4H), 2.86-2.88 (m, 1H), 3.40 (m, 1H), 4.00 (m, 1H), 4.74-4.76 (m, 3H), 5.03-5.07 (m, 3H), 6.82 (d, J=8.4 Hz, 1H), 7.33-7.36 (m, 5H), 7.60 (dd, J=2.4, 8.4 Hz, 1H), 8.10 (s, 1H).

Intermediate Q. LC-MS (m/z): 320 [M+1]$^+$; $^1$H-NMR (CDCl$_3$, 400 MHz) major characteristic peaks: δ (ppm) 1.80 (m, 4H), 2.48-2.53 (m, 4H), 2.61-2.66 (m, 2H), 3.15 (m, 1H), 4.66-4.70 (m, 3H), 4.76 (d, J=8.8 Hz, 2H), 6.87 (d, J=8.0 Hz, 1H), 7.66 (dd, J=2.4, 8.4 Hz, 1H), 8.11 (d, J=2.4 Hz, 1H).

Intermediate R

R1    R2

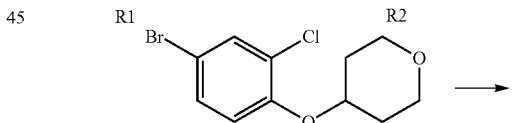

R3

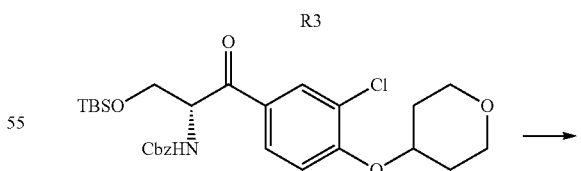

R4

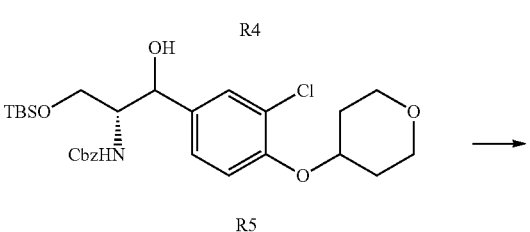

R5

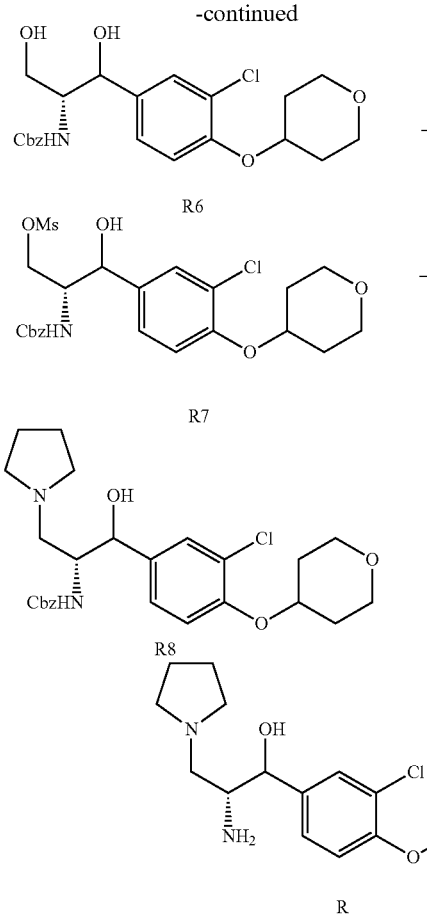

Intermediates R3, R4, R5, R6, R7, and R8, were synthesized, by employing the procedures described for Intermediates J2, J3, J4, J5, J6, and J7 using Intermediates R2, R3, R4, R5, R6, and R7 in lieu of Intermediates J1, J2, J3, J4, J5, and J6.

Intermediate R3. LC-MS (ESI) m/z: 291 [M+H]$^+$; $^1$H-NMR (CDCl$_3$, 400 MHz): δ (ppm) 1.79-1.87 (m, 2H), 1.97-2.04 (m, 2H), 3.56-3.62 (m, 2H), 3.97-4.02 (m, 2H), 4.48-4.53 (m, 1H), 6.82 (d, J=8.8 Hz, 1H), 7.28-7.31 (dd, J=8.8, 2.4 Hz, 1H), 7.51 (d, J=2.8 Hz, 1H).

Intermediate R4. LC-MS (ESI) m/z: 548 [M+H]$^+$; $^1$H-NMR (CDCl$_3$, 400 MHz): δ (ppm) −0.12 (s, 3H), −0.10 (s, 3H), 0.75 (s, 9H), 1.84-1.92 (m, 2H), 2.02-2.09 (m, 2H), 3.62-3.68 (m, 2H), 3.86-3.89 (m, 1H), 3.94-4.04 (m, 3H), 4.69-4.72 (m, 1H), 5.13 (s, 2H), 5.28-5.32 (m, 1H), 5.90 (d, J=8.0 Hz, 1H), 6.97 (d, J=8.8 Hz, 1H), 7.31-7.38 (m, 5H), 7.84 (dd, J=8.8, 2.0 Hz, 1H), 8.03 (d, J=2.0 Hz, 1H).

Intermediate R5. LC-MS (ESI) m/z: 532 [M-OH]$^+$; $^1$H-NMR (CDCl$_3$, 400 MHz): δ (ppm) −0.08-0.04 (m, 6H), 0.89-0.91 (m, 9H), 1.80-1.89 (m, 2H), 1.97-2.03 (m, 2H), 3.56-3.62 (m, 2H), 3.66-3.75 (m, 1H), 3.79-3.86 (m, 2H), 3.98-4.04 (m, 2H), 4.49-4.54 (m, 1H), 4.98-5.12 (m, 3H), 5.41-5.54 (m, 1H), 6.89-6.95 (m, 1H), 7.16-7.19 (m, 1H), 7.31-7.42 (m, 6H).

Intermediate R6. LC-MS (ESI) m/z: 418 [M-OH]$^+$; $^1$H-NMR (CDCl$_3$, 400 MHz): δ (ppm) 1.80 (m, 2H), 1.97-2.04 (m, 2H), 3.55-3.64 (m, 2H), 3.79-3.84 (m, 3H), 3.98-4.03 (m, 2H), 4.49-4.53 (m, 1H), 4.96-5.11 (m, 3H), 5.46-5.66 (m, 1H), 6.88-6.94 (m, 1H), 7.16-7.22 (m, 1H), 7.31-7.44 (m, 6H).

Intermediate R7. LC-MS (ESI) m/z: 496 [M-OH]$^+$; 1.80-1.88 (m, 2H), 1.98-2.03 (m, 2H), 3.00 (s, 3H), 3.56-3.62 (m, 2H), 3.97-4.00 (m, 2H), 4.07-4.40 (m, 4H), 4.92-5.04 (m, 3H), 5.23-5.32 (m, 1H), 6.89-6.91 (m, 1H), 7.15-7.19 (m, 1H), 7.29-7.41 (m, 6H).

Intermediate R8. LC-MS (ESI) m/z: 489 [M+H]$^+$; $^1$H-NMR (CDCl$_3$, 400 MHz): δ (ppm) 1.79-1.89 (m, 6H), 1.97-2.03 (m, 2H), 2.65-2.85 (m, 6H), 3.56-3.62 (m, 2H), 3.98-4.04 (m, 3H), 4.45-4.54 (m, 1H), 5.01-5.11 (m, 4H), 6.89-6.92 (m, 1H), 7.11-7.20 (m, 1H), 7.29-7.42 (m, 6H).

Intermediate R was synthesized, by employing the procedure described for Intermediate E using Intermediate R8 in lieu of Intermediate E7. LC-MS (ESI) m/z: 355 [M+H]$^+$.

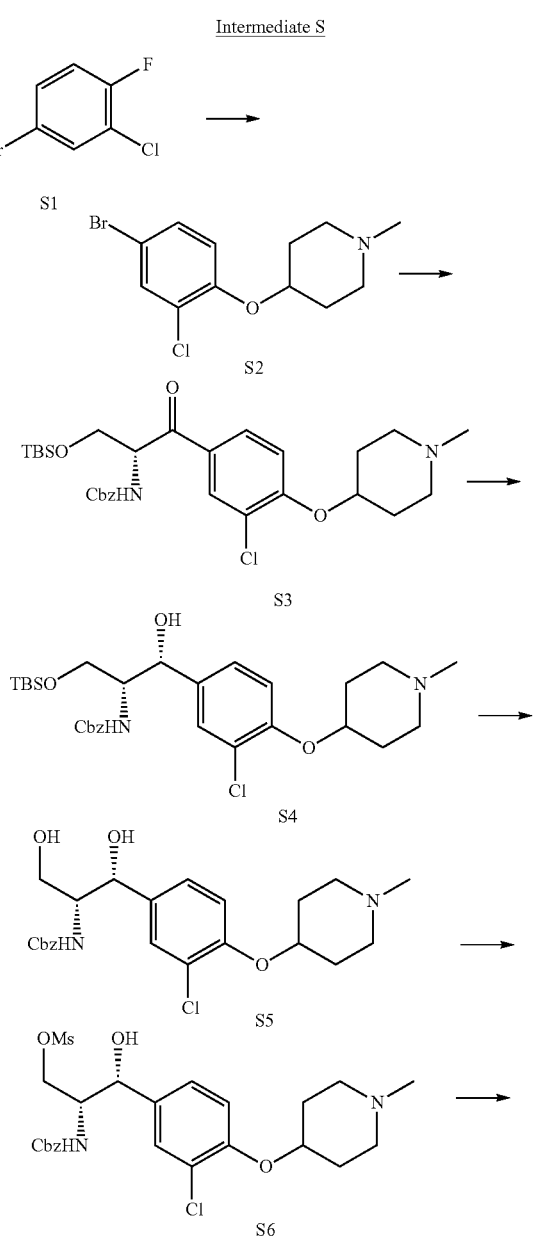

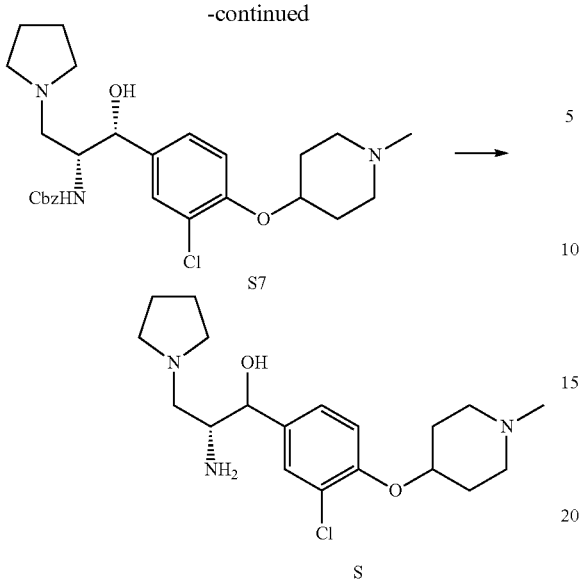

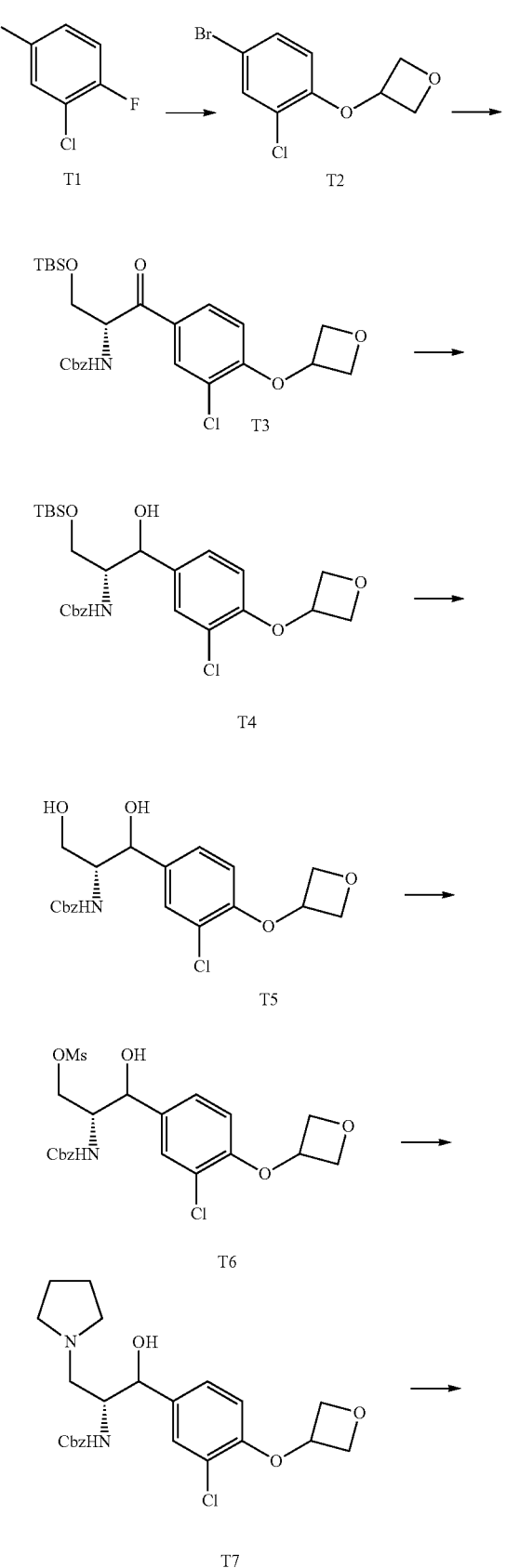

Intermediates S2, S3, S4, S5, S6, and S7, were synthesized, by employing the procedures described for Intermediates J2, J3, J4, J5, J6, and J7 using Intermediates S1, S2, S3, S4, S5, and S6 in lieu of Intermediates J1, J2, J3, J4, J5, and J6.

Intermediate S2. LC-MS (ESI) m/z: 304 [M+H]$^+$; $^1$H-NMR (CDCl$_3$, 400 MHz): δ (ppm) 1.85-2.04 (m, 4H), 2.29 (s, 3H), 2.25-2.34 (m, 2H), 2.64-2.68 (m, 2H), 4.33-4.35 (m, 1H), 6.81 (d, J=8.8 Hz, 1H), 7.28 (dd, J=8.8, 2.4 Hz, 1H), 7.50 (d, J=4.8 Hz, 1H).

Intermediate S3. LC-MS (ESI) m/z: 561 [M+H]$^+$; $^1$H-NMR (CDCl$_3$, 400 MHz): δ (ppm) −0.13 (s, 3H), −0.10 (s, 3H), 0.74 (s, 9H), 1.88-2.04 (m, 4H), 2.32 (s, 3H), 2.32-2.38 (m, 2H), 2.67-2.71 (m, 2H), 3.87-3.95 (m, 1H), 4.09-4.15 (m, 1H), 4.37-4.39 (m, 1H), 5.13 (s, 2H), 5.88 (d, J=8.0 Hz, 1H), 6.96 (d, J=8.0 Hz, 1H), 7.35-7.37 (m, 5H), 7.82-7.84 (m, 1H), 8.01 (s, 1H).

Intermediate S4. LC-MS (ESI) m/z: 563 [M+H]$^+$.

Intermediate S5. LC-MS (ESI) m/z: 449 [M+H]$^+$; $^1$H-NMR (CDCl$_3$, 400 MHz): δ (ppm) 1.81-1.94 (m, 4H), 2.25 (s, 3H), 2.27-2.29 (m, 2H), 2.55-2.63 (m, 2H), 3.58-3.83 (m, 3H), 4.33 (m, 1H), 4.93 (s, 1H), 5.00-5.09 (m, 2H), 5.55-5.78 (m, 1H), 6.84-6.90 (m, 1H), 7.15-7.45 (m, 7H).

Intermediate S6. LC-MS (ESI) m/z: 527 [M+H]$^+$; $^1$H-NMR (CDCl$_3$, 400 MHz): δ (ppm) 1.91-2.02 (m, 4H), 2.32 (s, 3H), 2.35-2.37 (m, 2H), 2.68-2.72 (m, 2H), 3.01 (s, 3H), 4.07-4.09 (m, 1H), 4.19-4.22 (m, 1H), 4.37-4.42 (m, 2H), 4.91 (d, J=3.6 Hz, 1H), 5.01-5.05 (m, 2H), 5.27-5.33 (m, 1H), 6.89 (d, J=8.8 Hz, 1H), 7.15-7.17 (m, 1H), 7.26-7.40 (m, 6H).

Intermediate S7. LC-MS (ESI) m/z: 502 [M+H]$^+$.

Intermediate S was synthesized, by employing the procedure described for Intermediate E using Intermediate S7 in lieu of Intermediate E7. LC-MS (ESI) m/z: 368 [M+H]$^+$; $^1$H-NMR (DMSO-d$_6$, 400 MHz): δ (ppm) 1.60-1.70 (m, 6H), 1.90 (m, 2H), 2.13-2.22 (m, 6H), 2.25-2.50 (m, 5H), 2.57 (m, 2H), 2.83-2.92 (m, 1H), 4.12 (s, 1H), 4.36 (d, J=4.4 Hz, 1H), 4.42 (m, 1H), 7.12 (d, J=8.4 Hz, 1H), 7.18 (d, J=8.8 Hz, 1H), 7.34 (s, 1H).

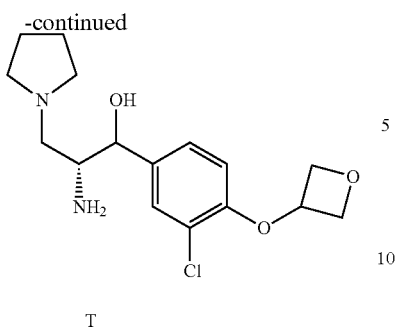

T

Intermediates T2, T3, T4, T5, T6, and T7, were synthesized, by employing the procedures described for Intermediates J2, J3, J4, J5, J6, and J7 using Intermediates T1, T2, T3, T4, T5, and T6 in lieu of Intermediates J1, J2, J3, J4, J5, and J6.

Intermediate T2. LC-MS (ESI) m/z: 263 [M+H]$^+$; $^1$H-NMR (CDCl$_3$, 400 MHz): δ (ppm) 4.79-4.82 (m, 2H), 4.97 (t, J=6.8 Hz, 2H), 5.19 (q, J=11.6, 5.6 Hz, 1H), 6.35 (d, J=8.8 Hz, 1H), 7.25-7.29 (m, 1H), 7.52-7.53 (d, J=2.4 Hz, 1H).

Intermediate T3. LC-MS (ESI) m/z: 520 [M+H]$^+$; $^1$H-NMR (CDCl$_3$, 400 MHz): δ (ppm) −0.13 (s, 3H), −0.11 (s, 3H), 0.89 (s, 9H), 1.58-1.62 (m, 2H), 2.47-2.52 (m, 2H), 2.80-2.82 (m, 1H), 2.92-3.01 (m, 1H), 4.19-4.24 (m, 2H), 4.95 (d, J=2.4 Hz, 1H), 5.15 (s, 1H), 6.54 (s, 1H), 6.79-6.87 (m, 4H), 7.24-7.25 (m, 1H), 7.35-7.38 (m, 2H), 7.50 (d, J=2 Hz, 1H).

Intermediate T4. LC-MS (ESI) m/z: 504 [M-OH]$^+$.

Intermediate T5. LC-MS (ESI) m/z: 390 [M-OH]$^+$; $^1$H-NMR (CDCl$_3$, 400 MHz): δ (ppm) 3.70-3.81 (m, 2H), 4.75-4.98 (m, 7H), 5.12-5.18 (m, 1H), 5.56 (d, J=8.4 Hz, 1H), 6.37 (d, J=8.4 Hz, 1H), 7.09-7.12 (m, 1H), 7.29-7.37 (m, 5H), 7.40-7.43 (m, 1H).

Intermediate T6. LC-MS (ESI) m/z: 468 [M-OH]$^+$; $^1$H-NMR (CDCl$_3$, 400 MHz): δ (ppm) 2.98 (s, 3H), 3.57-3.67 (m, 2H), 4.79-5.04 (m, 7H), 5.16-5.18 (m, 1H), 5.37-5.38 (m, 1H), 6.42 (d, J=8.4 Hz, 1H), 7.12-7.15 (m, 1H), 7.30-7.44 (m, 6H).

Intermediate T7. LC-MS (ESI) m/z: 461 [M+H]$^+$.

Intermediate S was synthesized, by employing the procedure described for Intermediate E using Intermediate S7 in lieu of Intermediate E7. LC-MS (ESI) m/z: 327 [M+H]$^+$; $^1$H-NMR (CD$_3$OD, 400 MHz): δ (ppm) 2.05-2.28 (m, 6H), 2.45-2.65 (m, 5H), 3.09-3.20 (m, 1H), 3.95-4.01 (m, 1H), 4.69-4.71 (m, 1H), 4.95-4.97 (m, 2H), 5.12-5.13 (m, 1H), 6.38-6.43 (d, J=8.4 Hz, 1H), 7.12-7.26 (m, 2H).

Intermediate U

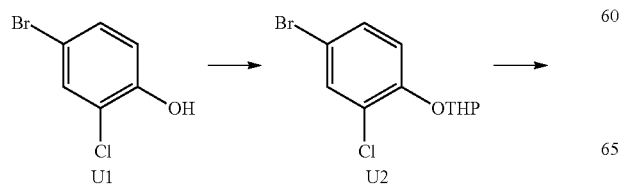

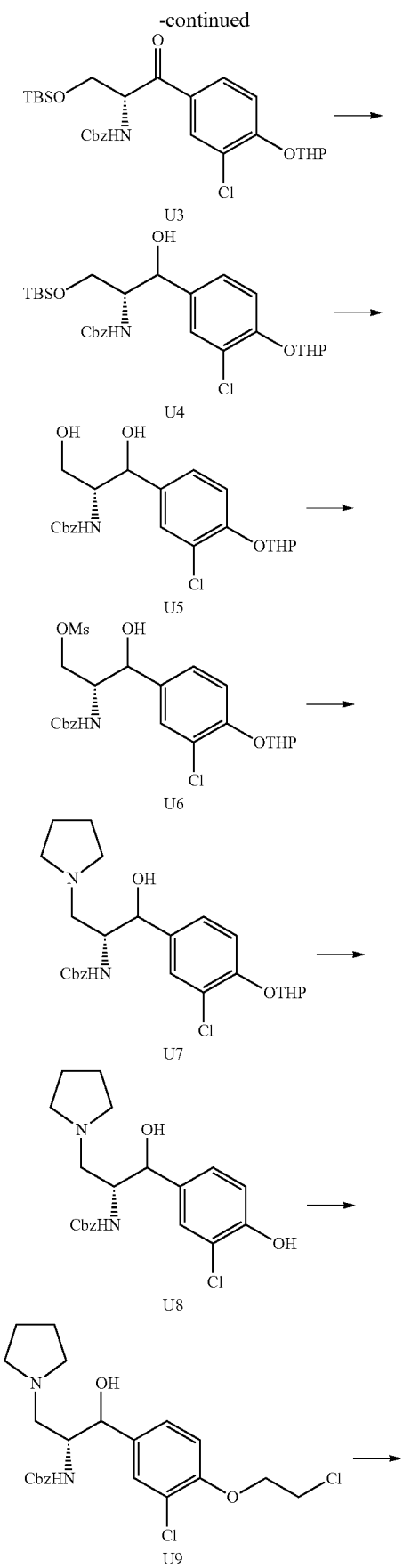

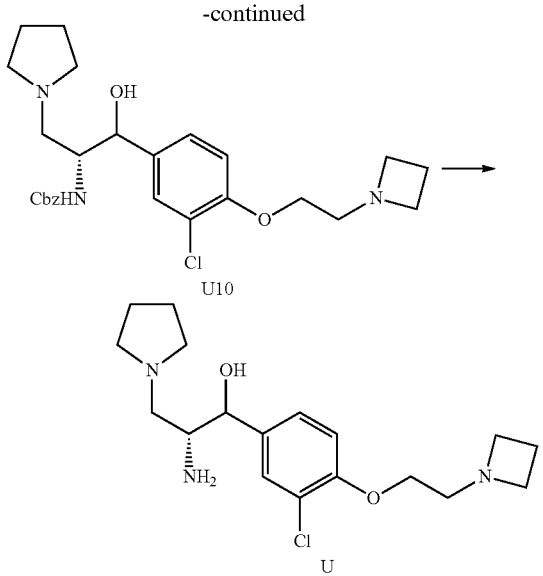

To a solution of Compound U1 (20 g, 96.2 mmol) in dichloromethane (100 mL) was added 3,4-dihydro-2H-pyran (16.2 g, 192.4 mmol) and a solution of HCl in dioxane (4.0 M, 1 mL) at 0° C. The mixture was stirred at 25° C. overnight. Saturated sodium bicarbonate solution (20 mL) and dichloromethane (200 mL) were added and the layers were separated. The aqueous layer was extracted with dichloromethane (50 mL×3). The combined organic layers were washed with water (20 mL×3) and brine (10 mL×2), dried over anhydrous sodium sulfate, filtered, and concentrated to give a crude compound. The crude product was purified with flash column chromatography on silica gel (ethyl acetate in petroleum ether, 10% v/v) to afford Compound U2. LC-MS (ESI) m/z: No; $^1$H-NMR (CDCl$_3$, 400 MHz): δ (ppm) 1.71-1.88 (m, 3H), 2.05-2.13 (m, 3H), 3.59-3.64 (m, 1H), 3.83-3.90 (m, 1H), 5.47 (t, J=2.8 Hz, 1H), 7.07 (d, J=9.2 Hz, 1H), 7.30 (dd, J=8.8, 2.4 Hz, 1H), 7.51 (d, J=2.4 Hz, 1H).

Intermediates U3, U4, U5, U6, and U7 were synthesized, by employing the procedures described correspondingly for Intermediates A5, A6, A7, A8, and A9 using Intermediates U2, U3, U4, U5, and U6 in lieu of 6-bromo-2,3-dihydrobenzo[b][1,4]dioxine, Intermediates A5, A6, A7, and A8.

Intermediates U3. LC-MS (ESI) m/z: 446 [M−101]$^+$; $^1$H-NMR (CDCl$_3$, 400 MHz): δ (ppm) −0.12 (s, 3H), −0.10 (s, 3H), 0.75 (s, 9H), 1.62-1.65 (m, 2H), 1.71-1.75 (m, 2H), 1.87-1.90 (m, 1H), 1.98-2.03 (m, 1H), 3.62-3.65 (m, 1H), 3.79-3.84 (m, 1H), 3.87-3.91 (m, 1H), 3.95-3.98 (m, 1H), 5.13 (s, 2H), 5.28-5.33 (m, 1H), 5.62-5.64 (m, 1H), 5.92-5.93 (m, 1H), 7.23-7.25 (m, 1H), 7.31-7.37 (m, 5H), 7.82 (dd, J=8.4, 2.0 Hz, 1H), 8.01 (d, J=2.0 Hz, 1H).

Intermediates U4. LC-MS (ESI) m/z: 448 [M−101]$^+$; $^1$H-NMR (CDCl$_3$, 400 MHz): δ (ppm) −0.21 (s, 3H), −0.19 (s, 3H), 0.67 (s, 9H), 1.47-1.49 (m, 2H), 1.63-1.68 (m, 2H), 1.79-1.92 (m, 1H), 2.00-2.04 (m, 1H), 3.47-3.57 (m, 2H), 3.71-3.98 (m, 3H), 4.74-4.76 (m, 1H), 5.05 (s, 2H), 5.21-5.25 (m, 1H), 5.55-5.57 (m, 1H), 5.83-5.85 (m, 1H), 7.15-7.17 (m, 1H), 7.30-7.38 (m, 5H), 7.75 (dd, J=8.4, 2.0 Hz, 1H), 7.94 (d, J=2.0 Hz, 1H).

Intermediates U5. LC-MS (ESI) m/z: 334 [M−101]$^+$; $^1$H-NMR (DMSO-d$_6$, 400 MHz): δ (ppm) 1.56-1.66 (m, 3H), 1.81-1.82 (m, 2H), 1.90-1.91 (m, 1H), 3.29-3.31 (m, 1H), 3.55-3.77 (m, 4H), 4.47-4.75 (m, 2H), 4.85-5.00 (m, 2H), 5.38-5.45 (m, 1H), 5.55-5.56 (m, 1H), 6.75 (d, J=8.8 Hz, 1H), 7.17-7.38 (m, 7H).

Intermediates U6. LC-MS (ESI) m/z: 412 [M−101]$^+$; $^1$H-NMR (DMSO-d$_6$, 400 MHz): δ (ppm) 1.57-1.66 (m, 3H), 1.81-1.83 (m, 2H), 1.91-1.93 (m, 1H), 3.15 (s, 3H), 3.53-3.56 (m, 1H), 3.72-3.77 (m, 1H), 4.00-4.09 (m, 2H), 4.33-4.36 (m, 1H), 4.75 (s, 1H), 4.88-5.02 (m, 2H), 5.57 (s, 1H), 5.71 (d, J=4.8 Hz, 1H), 7.16-7.34 (m, 7H), 7.41 (d, J=7.6 Hz, 1H).

Intermediates U7. LC-MS (ESI) m/z: 489 [M+H]$^+$; $^1$H-NMR (DMSO-d$_6$, 400 MHz): δ (ppm) 1.43-1.45 (m, 3H), 1.51-1.53 (m, 2H), 1.64-1.66 (m, 4H), 1.76-1.81 (m, 1H), 1.98-2.01 (m, 2H), 2.42-2.46 (m, 4H), 3.80-3.82 (m, 2H), 4.52-4.66 (m, 2H), 4.89-5.02 (m, 2H), 6.91 (d, J=8.4 Hz, 1H), 7.03 (d, J=8.4 Hz, 1H), 7.20-7.28 (m, 1H), 7.34-7.37 (m, 5H), 10.15 (s, 1H).

To a solution of Compound U7 (1.7 g, 3.48 mmol) in methanol (40 mL) was added p-TsOH (600 mg, 3.48 mmol). The mixture was stirred at 30° C. overnight. After removal of the solvent, the residue was extracted with ethyl acetate (50 mL×3), washed with water (10 mL) and brine (10 mL), dried over anhydrous sodium sulfate, filtered, and concentrated to furnish a crude compound. The crude product was purified with flash column chromatography on silica gel (methanol in dichloromethane, 5% v/v) to afford Compound U8. LC-MS (ESI) m/z: 405 [M+H]$^+$; $^1$H-NMR (DMSO-d$_6$, 400 MHz): δ (ppm) 1.65-1.68 (m, 4H), 2.66-2.67 (m, 4H), 3.65-3.67 (m, 1H), 3.77-3.78 (m, 1H), 4.09-4.12 (m, 1H), 4.64-4.66 (m, 1H), 4.86-5.01 (m, 2H), 6.87-6.89 (m, 1H), 7.14-7.32 (m, 8H), 9.98 (brs, 1H).

To a solution of Compound U8 (1.16 g, 2.87 mmol) in DMF (30 mL) was added K$_2$CO$_3$ (1.2 g, 8.61 mmol) and 2-chloroethyl 4-methylbenzenesulfonate (1.01 g, 4.31 mmol). The mixture was stirred at 60° C. for two hours. After the reaction was monitored with TLC, the mixture was quenched with water (10 mL) and diluted with ethyl acetate (200 mL). The organic phase was washed with water (5 mL×3) and brine (10 mL), dried over anhydrous sodium sulfate, filtered, and concentrated. The crude product was purified with flash column chromatography on silica gel (methanol in dichloromethane, 9% v/v) to furnish Compound U9. LC-MS (ESI) m/z: 467 [M+H]$^+$; $^1$H-NMR (DMSO-d$_6$, 400 MHz): δ (ppm) 1.57-1.66 (m, 3H), 1.81-1.83 (m, 2H), 1.91-1.94 (m, 1H), 3.15 (s, 3H), 3.53-3.56 (m, 1H), 3.72-3.77 (m, 1H), 4.01-4.09 (m, 2H), 4.33-4.36 (m, 1H), 4.74-4.75 (m, 1H), 4.88-5.01 (m, 2H), 5.57-5.58 (m, 1H), 5.71-5.72 (m, 1H), 7.16-7.24 (m, 4H), 7.28-7.34 (m, 3H), 7.40-7.42 (m, 1H).

To a solution of Compound U9 (1.07 g, 2.30 mmol) in THF (30 mL) was added azetidine (1.31 g, 23 mmol) under nitrogen. The mixture was stirred at 50° C. overnight. After the reaction was monitored with LC-MS, the mixture was quenched with water (10 mL) and extracted with ethyl acetate (50 mL×3), washed with water (10 mL) and brine (10 mL), dried over anhydrous sodium sulfate, filtered, and concentrated to give a crude compound. The crude product was purified with flash column chromatography on silica gel (methanol in dichloromethane, 10% v/v) to give Compound U10. LC-MS (ESI) m/z: 488 [M+H]$^+$; $^1$H-NMR (CDCl$_3$, 400 MHz): δ (ppm) 1.77-1.80 (m, 4H), 2.10-2.16 (m, 2H), 2.45-2.60 (m, 2H), 2.64-2.81 (m, 4H), 2.86-2.89 (m, 2H), 3.38 (t, J=7.2 Hz, 4H), 4.01-4.06 (m, 3H), 4.99 (d, J=2.0 Hz, 1H), 5.05 (s, 2H), 6.85 (d, J=8.8 Hz, 1H), 7.13 (dd, J=8.4, 1.6 Hz, 1H), 7.30-7.40 (m, 6H).

Intermediate U was synthesized, by employing the procedure described for Intermediate E using Intermediate U10 in lieu of Intermediate E7. LC-MS (ESI) m/z: 354 [M+H]⁺; ¹H-NMR (CDCl₃, 400 MHz): δ (ppm) 1.77-1.80 (m, 4H), 2.08-2.15 (m, 2H), 2.46-2.51 (m, 1H), 2.57-2.61 (m, 4H), 2.64-2.69 (m, 1H), 2.87 (t, J=4.8 Hz, 2H), 3.10-3.14 (m, 1H), 3.38 (t, J=7.2 Hz, 4H), 4.02 (t, J=6.0 Hz, 2H), 4.59 (d, J=4.0 Hz, 1H), 6.87 (d, J=8.4 Hz, 1H), 7.16 (dd, J=8.4, 2.0 Hz, 1H), 7.38 (d, J=2.0 Hz, 1H).

Intermediate V

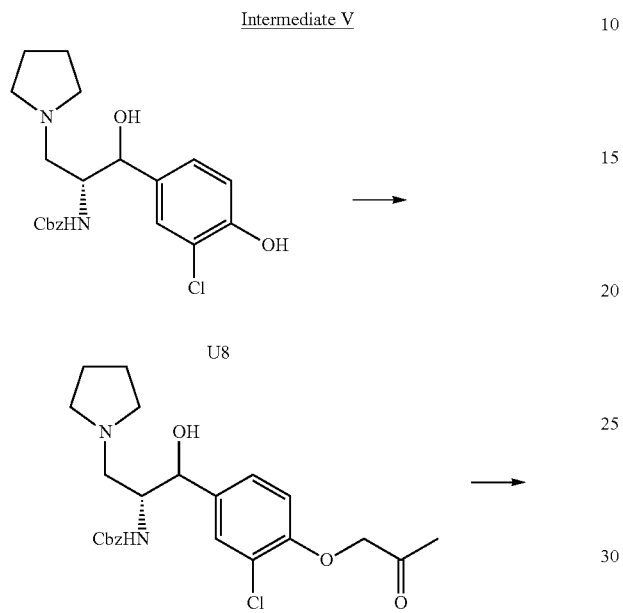

To a solution of Compound U8 (700 mg, 1.73 mol) in acetone (10 mL) was added K₂CO₃ (717 mg, 5.2 mmol) and 1-chloropropan-2-one (320 mg, 3.46 mmol). The mixture was stirred at 30° C. for two hours. The mixture was quenched with water (10 mL) and the solvent was evaporated in vacuo. The residue was extracted with dichloromethane (50 mL×3), washed with water (10 mL) and brine (10 mL), dried over anhydrous sodium sulfate, filtered, and concentrated to give a crude compound. The crude product was purified with reverse phase chromatography (methanol in pure water, from 0% to 55% v/v) to afford Compound V1. LC-MS (ESI) m/z: 461 [M+H]⁺; ¹H-NMR (CDCl₃, 400 MHz): δ (ppm) 1.79-1.81 (m, 4H), 2.37 (s, 3H), 2.65-2.72 (m, 5H), 2.86-2.90 (m, 2H), 3.97-4.00 (m, 1H), 4.55 (s, 2H), 5.04-5.06 (m, 3H), 6.75 (d, J=8.4 Hz, 1H), 7.14 (dd, J=8.4, 2.0 Hz, 1H), 7.30-7.36 (m, 5H), 7.45 (d, J=2.0 Hz, 1H).

Compound V1 (500 mg, 1.08 mmol) was dissolved in anhydrous THF (10 mL) and the mixture was cooled down to −30° C. under nitrogen atmosphere. Methylmagnesium bromide (3 M solution in ether, 1.81 mL, 5.43 mmol) was added dropwise while keeping the temperature at −30° C. The reaction was stirred at 30° C. for 2 h. The mixture was quenched with saturated NH₄Cl solution (5 mL) and extracted with ethyl acetate (100 mL×3). The combined organic phases was washed with water (10 mL) and brine (10 mL), dried over anhydrous sodium sulfate, filtered, and concentrated to give a crude compound. The crude product was purified with flash column chromatography on silica gel (methanol in dichloromethane, from 0% to 5% v/v) to afford Compound V2. LC-MS (ESI) m/z: 477 [M+H]⁺; ¹H-NMR (CDCl₃, 400 MHz): δ (ppm) 1.38 (s, 6H), 1.80-1.84 (m, 4H), 2.68-2.80 (m, 6H), 2.96-3.00 (m, 1H), 3.65-3.70 (m, 1H), 3.81-3.83 (m, 2H), 4.00-4.02 (m, 1H), 5.02 (s, 2H), 5.23 (d, J=7.2 Hz, 1H), 6.85 (d, J=8.4 Hz, 1H), 7.15 (d, J=8.4 Hz, 1H), 7.31-7.42 (m, 6H).

Intermediate V was synthesized, by employing the procedure described for Intermediate E using Intermediate V2 in lieu of Intermediate E7. LC-MS (ESI) m/z: 343 [M+H]⁺.

Intermediate W

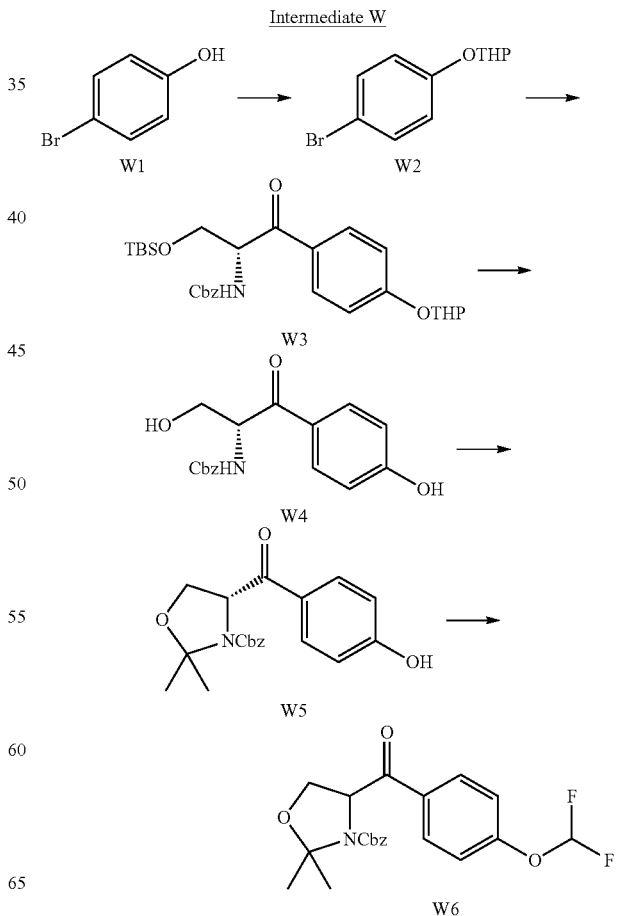

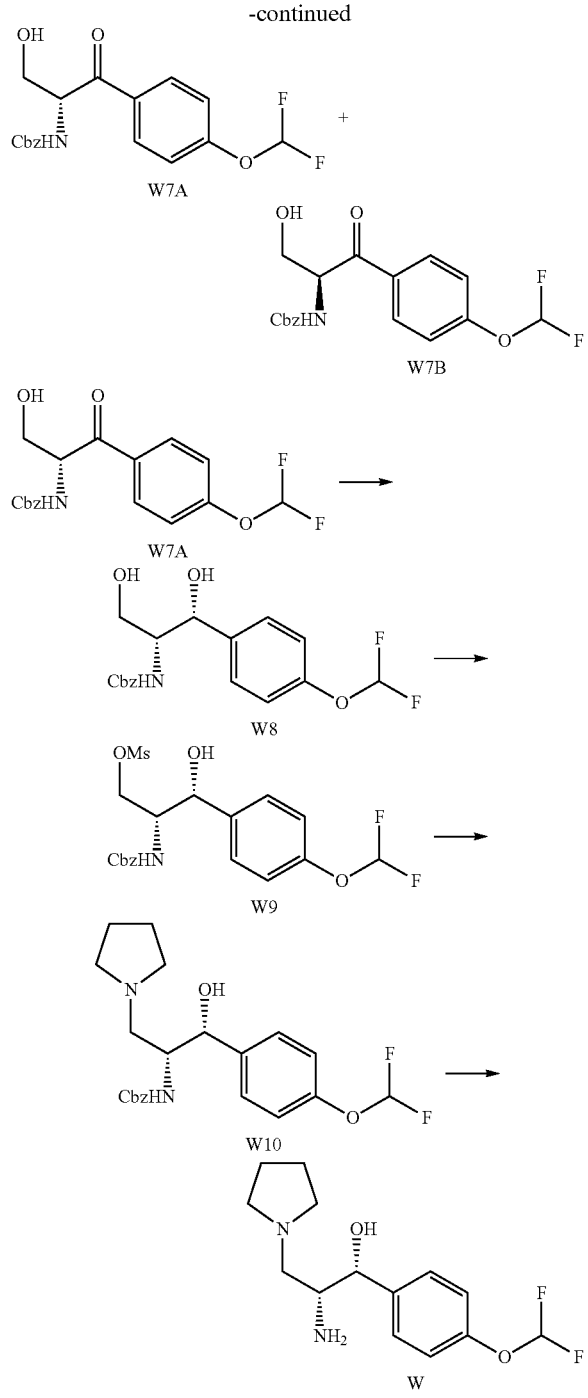

1.83-1.87 (m, 2H), 1.95-2.02 (m, 1H), 3.61-3.63 (m, 1H), 3.83-3.86 (m, 1H), 5.36-5.38 (m, 1H), 6.92-6.94 (m, 2H), 7.35-7.37 (m, 2H).

Compound W3 was synthesized, by employing the procedure described for Compound A5 using Compound W2 in lieu of 6-bromo-2,3-dihydrobenzo[b][1,4]dioxine. LC-MS (ESI) m/z: 514 [M+H]$^+$; $^1$H-NMR (CDCl$_3$, 400 MHz): δ (ppm) −0.15 (s, 3H), −0.13 (s, 3H), 0.74 (s, 9H), 1.66-1.73 (m, 2H), 1.86-1.90 (m, 2H), 2.05-2.10 (m, 1H), 3.60-3.63 (m, 1H), 3.81-3.83 (m, 1H), 3.89-3.95 (m, 2H), 5.12 (s, 2H), 5.32-5.34 (m, 1H), 5.51-5.53 (m, 1H), 5.95-5.97 (m, 1H), 7.08-7.10 (m, 2H), 7.30-7.37 (m, 5H), 7.90-7.92 (m, 2H).

To a solution of Compound W3 (4.6 g, 8.97 mmol) in methanol (120 mL) was added TsOH (1.54 g, 8.97 mmol). The reaction mixture was stirred at room temperature overnight. The resulting mixture was concentrated. The residue was purified column chromatography on silica gel (ethyl acetate in petroleum ether, 50% v/v) to give Compound W4. LC-MS (ESI) m/z: 316 [M+H]$^+$; $^1$H-NMR (DMSO-d$_6$, 400 MHz): δ (ppm) 3.62-3.63 (m, 1H), 3.73-3.74 (m, 1H), 4.86-4.87 (m, 1H), 5.02 (s, 2H), 5.09-5.11 (m, 1H), 6.87 (d, J=8.8 Hz, 2H), 7.30-7.36 (m, 5H), 7.47 (d, J=8.0 Hz, 1H), 7.89 (d, J=8.8 Hz, 2H), 10.44 (s, 1H).

To a mixture of Compound W4 (2.35 g, 7.46 mmol) dissolved in acetone (30 mL) and 2, 2-dimethoxy propane (30 mL) was added boron trifluoride etherate (1 mL). The mixture was stirred at room temperature overnight and triethyl amine (1 mL) was added. The solvent was removed to dryness. The crude product was purified with column chromatography on silica gel (ethyl acetate in petroleum ether, 50% v/v) to furnished Compound W5. LC-MS (ESI) m/z: 356 [M+H]$^+$; $^1$H-NMR (CDCl$_3$, 400 MHz): δ (ppm) 1.60 (d, J=11.6 Hz, 3H), 1.76 (d, J=11.6 Hz, 3H), 3.97-4.01 (m, 1H), 4.31-4.35 (m, 1H), 5.03 (q, J=12.4 Hz, 1H), 5.21 (q, J=12.4 Hz, 1H), 5.36-5.44 (m, 1H), 6.69-6.71 (m, 1H), 6.83-6.85 (m, 1H), 7.11-7.12 (m, 1H), 7.18-7.20 (m, 1H), 7.36-7.39 (m, 3H), 7.63-7.66 (m, 1H), 7.75-7.77 (m, 1H).

To a solution of Compound W5 (2.50 g, 7.0 mmol) in DMF (50 mL) and water (7.0 mL) was added sodium chloro(difluoro)acetate (2.66 g, 17.5 mmol) and cesium carbonate (4.56 g, 14.0 mmol). The mixture was stirred for 15 minutes at room temperature and heated to 100° C. under nitrogen for 2 hours. The mixture was partitioned between water (100 mL) and ethyl acetate (100 mL). The organic phase was separated, washed with brine (50 mL), dried over anhydrous sodium sulfate, filtered, and concentrated in vacuo to give a crude compound. The crude product was purified with column chromatography on silica gel (ethyl acetate in petroleum ether, 25% v/v) to give Compound W6. LC-MS (ESI) m/z: 428 [M+Na]$^+$; $^1$H-NMR (CDCl$_3$, 400 MHz): δ (ppm) 1.56-1.79 (m, 6H), 3.96-3.99 (m, 1H), 4.31-4.35 (m, 1H), 4.99-5.19 (m, 2H), 5.36-5.39 (m, 1H), 6.60 (t, J=72.8 Hz, 1H), 7.11-7.20 (m, 5H), 7.36-7.37 (m, 2H), 7.84-7.98 (m, 2H).

To a solution of Compound W6 (10.4 g, 25.7 mmol) in MeCN (150 mL) was added TsOH (8.84 g, 51.4 mmol). The reaction mixture was stirred at room temperature for 2 h. The resulting mixture was diluted with ethyl acetate (200 mL), washed with saturated aqueous sodium bicarbonate solution (300 mL), dried over anhydrous sodium sulfate, filtered, and concentrated to furnish a mixture of Compound W7A and Compound W7B. The mixture was separated with chiral-HPLC (solvent: MeOH (0.5% NH$_4$OH), column: (R,R)-Whelk-O1, 4.6*250 mm, 5 μm) to give Compound W7A (Rt: 5.45 min.) and Compound W7B. HPLC Rt: 8.1 min. For Compound W7A: LC-MS (ESI) m/z: 366 [M+H]$^+$; $^1$H-NMR (CDCl$_3$, 400 MHz): δ (ppm) 2.80 (brs, 1H), To a stirred solution of Compound W1 (30.0 g, 173 mmol) and p-toluenesulfonic acid (297 mg, 1.73 mmol) in dry dichloromethane (240 mL) was added freshly distilled dihydropyran (60 mL, 657 mmol). The mixture was stirred at room temperature for 1 h. To the reaction mixture was added a 2 M NaOH solution and stirred for another 30 min. The mixture was extracted with ether (200 mL×2). The combined extracts were dried over anhydrous sodium sulfate, filtered, and concentrated. The crude product was purified with flash column chromatography on silica gel (ethyl acetate in petroleum ether, 2% v/v) to give Compound W2. $^1$H-NMR (CDCl$_3$, 400 MHz): δ (ppm) 1.64-1.68 (m, 3H), 3.87-3.90 (m, 1H), 3.99-4.02 (m, 1H), 5.13 (s, 2H), 5.33-5.36 (m, 1H), 6.12 (d, J=6.8 Hz, 1H), 6.61 (t, J=72.8 Hz, 1H), 7.19 (d, J=8.4 Hz, 2H), 7.32-7.35 (m, 5H), 8.03 (d, J=8.4 Hz, 2H). For Compound W7B: LC-MS (ESI) m/z: 366 [M+H]$^+$; $^1$H-NMR (CDCl$_3$, 400 MHz): δ (ppm) 2.80 (brs, 1H), 3.87-3.90 (m, 1H), 3.99-4.02 (m, 1H), 5.13 (s, 2H), 5.33-5.36 (m, 1H), 6.12 (d, J=6.8 Hz, 1H), 6.61 (t, J=72.8 Hz, 1H), 7.19 (d, J=8.4 Hz, 2H), 7.32-7.35 (m, 5H), 8.03 (d, J=8.4 Hz, 2H).

Intermediates W8, W9, W10, and W were synthesized, by employing the procedures described correspondingly for Intermediates A7, A8, A9, and A using Intermediates W7A, W8, W9, and W10 in lieu of Intermediates A6, A7, A8, and A9.

Intermediate W8. LC-MS (ESI) m/z: 350 [M-OH]$^+$; $^1$H-NMR (CDCl$_3$, 400 MHz): δ (ppm) 2.54 (s, 1H), 3.31 (s, 1H), 3.77-3.85 (m, 3H), 5.00-5.03 (m, 3H), 5.46-5.48 (m, 1H), 6.48 (t, J=73.6 Hz, 1H), 7.05-7.07 (m, 2H), 7.29-7.35 (m, 7H).

Intermediate W9, which was directly used for the next step without further purification. LC-MS (ESI) m/z: 468 [M+Na]$^+$.

Intermediate W10. LC-MS (ESI) m/z: 421 [M+H]$^+$; $^1$H-NMR (CDCl$_3$, 400 MHz): δ (ppm) 2.10-2.17 (m, 4H), 2.82-2.92 (m, 2H), 3.38-3.49 (m, 2H), 3.81 (brs, 2H), 4.18-4.20 (m, 1H), 4.91-5.07 (m, 3H), 5.98 (d, J=8.8 Hz, 1H), 6.47 (t, J=74.0 Hz, 1H), 7.03-7.05 (m, 2H), 7.19-7.21 (m, 2H), 7.31-7.33 (m, 5H).

Intermediate W, which was directly used for the next step without further purification. LC-MS (ESI) m/z: 287 [M+H]$^+$.

Intermediate X

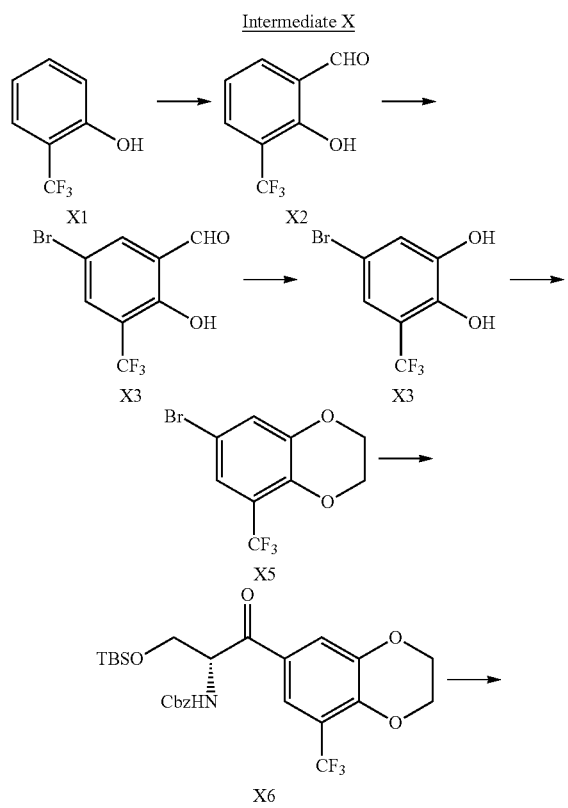

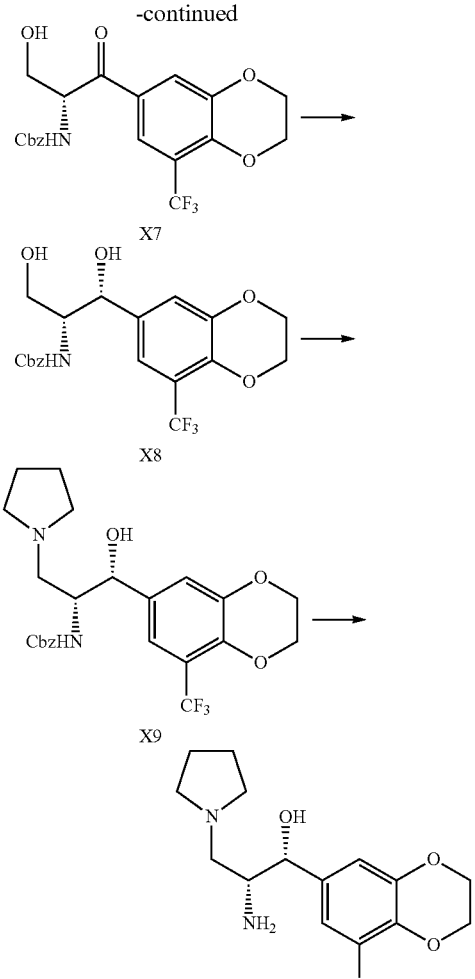

To a solution of Compound X1 (5 g, 31 mmol) in 2,2,2-trifluoroacetic acid (50 mL) was added hexamethylenetriamine (4.7 g, 33.6 mmol). The reaction solution was heated at reflux overnight. After cooling, the mixture was treated with 50% H$_2$SO$_4$ (20 mL) at room temperature for 4 h and extracted with ether (50 mL×3). The combined ether phases were washed with aqueous HCl solution (5 M, 50 mL), water (50 mL) and brine (50 mL), dried over anhydrous sodium sulfate, concentrated, and purified with flash column chromatography on silica gel (ethyl acetate in petroleum ether, 10% v/v) to afford Compound X2. LC-MS (ESI) m/z: 189 [M-]$^+$; $^1$H-NMR (CDCl$_3$, 400 MHz): δ (ppm) 7.12 (t, J=8 Hz, 1H), 7.78 (d, J=7.6 Hz, 1H), 7.84 (d, J=7.6 Hz, 1H), 9.96 (s, 1H), 11.74 (s, 1H).

Intermediates X3, X4, and X5 were synthesized, by employing the procedures described correspondingly for Intermediates C2, C3, and C4 using Intermediates X2, X3, and X4 in lieu of Intermediates C1, C2, and C3.

Intermediate X3. LC-MS (ESI) m/z: 267 [M–H]$^+$; $^1$H-NMR (CDCl$_3$, 400 MHz): δ (ppm) 7.88-7.92 (m, 1H), 7.92 (s, 1H), 9.90 (s, 1H), 11.63 (s, 1H).

Intermediate X4. LC-MS (ESI) m/z: 255 [M–H]$^+$.

Intermediate X5. LC-MS (ESI) m/z: No; $^1$H-NMR (CDCl$_3$, 400 MHz): δ (ppm) 4.30-4.34 (m, 4H), 7.18-7.19 (m, 1H), 7.24-7.25 (m, 1H).

Intermediates X6, X7, and X8 were synthesized, by employing the procedures described correspondingly for Intermediates A5, A6, and A7 using Intermediates X5, X6, and X7 in lieu of 6-bromo-2,3-dihydrobenzo[b][1,4]dioxine, Intermediates A5, A6, and A7.

Intermediate X6. LC-MS (ESI) m/z: 540 [M+H]⁺; $^1$H-NMR (CDCl$_3$, 400 MHz): δ (ppm) −0.12 (s, 3H), −0.10 (s, 3H), 0.74 (s, 9H), 3.86-3.89 (m, 1H), 3.95-3.97 (m, 1H), 4.34-4.36 (m, 2H), 5.13 (s, 4H), 5.31 (s, 1H), 5.88-5.90 (m, 1H), 7.34-7.38 (m, 5H), 7.67-7.68 (m, 1H), 7.79 (s, 1H).

Intermediate X7. LC-MS (ESI) (m/z): 426 [M+H]⁺; $^1$H-NMR (CDCl$_3$, 400 MHz): δ (ppm) 2.61-2.63 (m, 1H), 3.89-3.91 (m, 1H), 3.99-4.01 (m, 1H), 4.33-4.45 (m, 4H), 5.14 (s, 2H), 5.30-5.32 (m, 1H), 6.09 (d, J=6.8 Hz, 1H), 7.32-7.37 (m, 5H), 7.12 (s, 1H), 7.83 (s, 1H).

Intermediate X8. LC-MS (ESI) (m/z): 410 [M−OH]⁺; $^1$H-NMR (CDCl$_3$, 400 MHz): δ (ppm) 2.32 (s, 1H), 3.20 (s, 1H), 3.80-3.85 (m, 3H), 4.29-4.34 (m, 4H), 4.95-4.97 (m, 1H), 5.03-5.04 (m, 2H), 5.48 (d, J=7.2 Hz, 1H), 7.07 (s, 1H), 7.16 (s, 1H), 7.30-7.36 (m, 5H).

To a solution of Intermediate X8 (1.5 g, 3.5 mmol) in THF (50 mL) was added triethylamine (1.1 g, 10.5 mmol). The mixture was cooled to −20° C. and MsCl (0.44 g, 3.9 mmol) was added slowly. The mixture was stirred at −20° C. for about half an hour and pyrrolidine (2.1 g, 30 mmol) was added to the mixture. The resulting mixture was stirred at −60° C. for 16 h and cooled to 25° C. The mixture was diluted with ethyl acetate (200 mL), washed with water (50 mL×2) and brine (50 mL), dried over anhydrous sodium sulfate, concentrated, and purified with flash column chromatography on silica gel (methanol in dichloromethane, from 5% to 10% v/v) to give Intermediate X9. LC-MS (ESI) m/z: 481 [M+H]⁺; $^1$H-NMR (CDCl$_3$, 400 MHz): δ (ppm) 1.76-1.80 (m, 4H), 2.46-2.81 (m, 6H), 3.99 (s, 1H), 4.28-4.35 (m, 5H), 4.97-5.05 (m, 4H), 7.02 (s, 1H), 7.13 (s, 1H), 7.27-7.35 (m, 5H).

Intermediate X was synthesized, by employing the procedure described for Intermediate A using Intermediate X9 in lieu of Intermediate A9. LC-MS (ESI) m/z: 347 [M+H]⁺; $^1$H-NMR (CDCl$_3$, 400 MHz): δ (ppm) 1.78-1.81 (m, 4H), 2.51-2.72 (m, 6H), 3.13-3.14 (m, 1H), 4.31-4.36 (m, 4H), 4.60-4.61 (m, 1H), 7.05 (s, 1H), 7.12 (s, 1H).

Intermediate Y

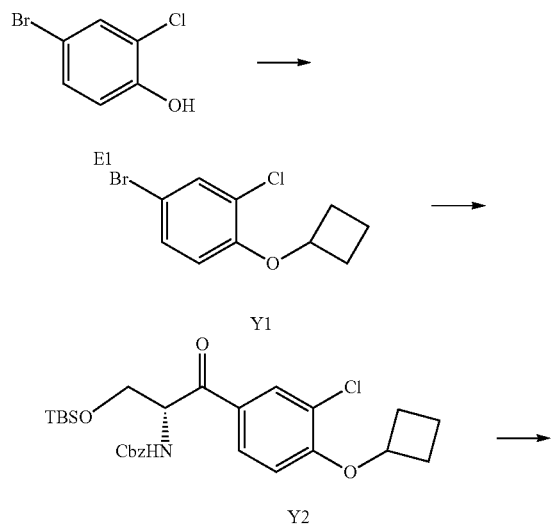

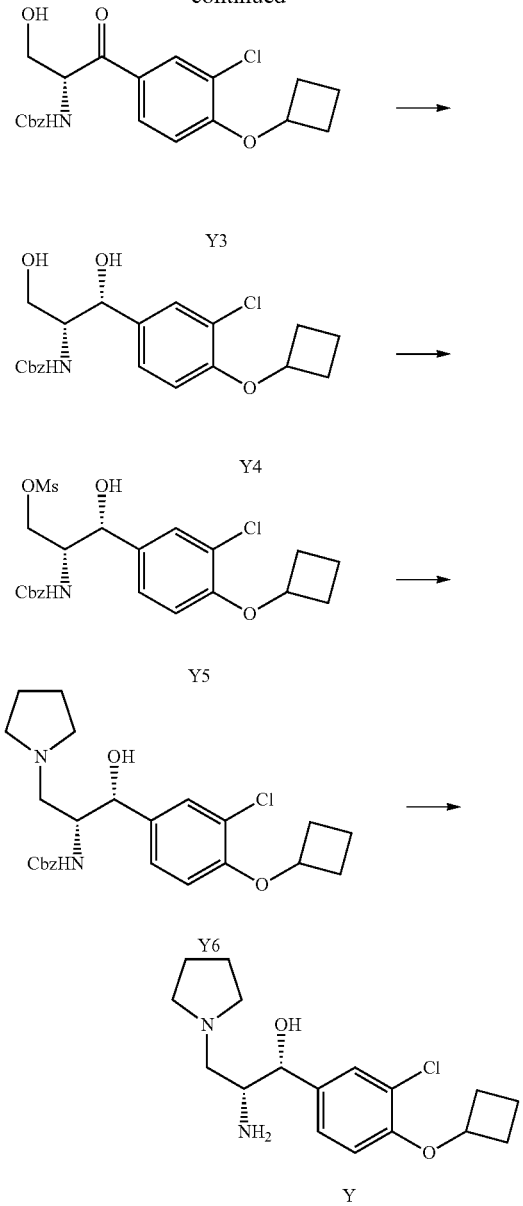

Compound Y1 was synthesized, by employing the procedure described for Intermediate E2 using bromocyclobutane in lieu of bromocyclopropane. LC-MS (ESI) m/z: No. $^1$H-NMR (CDCl$_3$, 400 MHz): δ (ppm) 1.65-1.73 (m, 1H), 1.84-1.92 (m, 1H), 2.17-2.28 (m, 2H), 2.41-2.49 (m, 2H), 4.60-4.65 (m, 1H), 6.64 (d, J=8.8 Hz, 1H), 7.26 (dd, J$_1$=8.8 Hz, J$_2$=2.4 Hz, 1H), 7.48 (d, J=2.4 Hz, 1H).

Intermediates Y2, Y3, Y4, Y5, and Y6 were synthesized, by employing the procedures described correspondingly for Intermediates A5, A6, A7, A8, and A9 using Intermediates Y1, Y2, Y3, Y4, and Y5 in lieu of 6-bromo-2,3-dihydrobenzo[b][1,4]dioxine, Intermediates A5, A6, A7, and A8.

Intermediate Y2. LC-MS (ESI) m/z: 518 [M+H]⁺; $^1$H-NMR (CDCl$_3$, 400 MHz): δ (ppm) 0.00 (s, 3H), 0.01 (s, 3H), 0.87 (s, 9H), 1.86-1.91 (m, 1H), 2.05-2.07 (m, 1H), 2.37-2.44 (m, 2H), 2.61-2.68 (m, 2H), 3.99-4.01 (m, 1H), 4.07-4.10 (m, 1H), 4.88-4.92 (m, 1H), 5.25 (s, 2H), 5.42-5.43 (m, 1H), 6.02-6.04 (m, 1H), 6.92-6.94 (m, 1H), 7.45-7.50 (m, 5H), 7.93-7.96 (m, 1H), 8.13-8.14 (m, 1H).

Intermediate Y3. LC-MS (ESI) m/z: 404 [M+H]$^+$; $^1$H-NMR (DMSO-d$_6$, 400 MHz): δ (ppm) 1.66-1.68 (m, 1H), 1.81-1.84 (m, 1H), 2.08-2.13 (m, 2H), 3.62-6.64 (m, 1H), 3.72-3.73 (m, 1H), 4.88-4.93 (m, 2H), 5.02 (s, 2H), 5.09-5.11 (m, 1H), 7.09-7.12 (m, 1H), 7.30-7.35 (m, 5H), 7.62-7.63 (m, 1H), 7.93-7.95 (m, 1H), 8.01-8.02 (m, 1H).

Intermediate Y4. LC-MS (ESI) m/z: 388 [M-OH]$^+$; $^1$H-NMR (DMS-d$_6$, 400 MHz): δ (ppm) 1.62-1.66 (m, 1H), 1.77-1.80 (m, 1H), 1.99-2.08 (m, 2H), 2.40-2.50 (m, 2H), 3.27-3.32 (m, 1H), 3.46-3.51 (m, 1H), 3.61-3.64 (m, 1H), 4.68-4.74 (m, 2H), 4.86-4.99 (m, 2H), 5.36 (brs, 1H), 6.76-6.89 (m, 2H), 7.14-7.35 (m, 6H).

Intermediate Y5, which was directly used for the next step without further purification. LC-MS (ESI) m/z: 466 [M-OH]$^+$.

Intermediate Y6. LC-MS (ESI) m/z: 459 [M+H]$^+$; $^1$H-NMR (CDCl$_3$, 400 MHz): δ (ppm) 1.67-1.89 (m, 6H), 2.21-2.27 (m, 2H), 2.44-2.49 (m, 2H), 2.62-2.72 (m, 5H), 4.00 (brs, 1H), 4.63-4.67 (m, 1H), 4.99-5.06 (m, 3H), 6.71-6.73 (m, 1H), 7.08-7.10 (m, 1H), 7.26-7.37 (m, 6H).

Intermediate Y was synthesized, by employing the procedure described for Intermediate E using Intermediate Y6 in lieu of Intermediate E7, which was directly used for the next step without further purification. LC-MS (ESI) m/z: 325 [M+H]$^+$; $^1$H-NMR (CDCl$_3$, 400 MHz): δ (ppm) 0.62-0.79 (m, 1H), 1.67-1.71 (m, 4H), 1.86-1.89 (m, 1H), 2.22-2.30 (m, 2H), 2.46-2.51 (m, 3H), 2.55-2368 (m, 5H), 3.11-3.12 (m, 1H), 4.58-4.58 (m, 1H), 4.65-4.69 (m, 2H), 6.75-6.77 (m, 1H), 7.12-7.14 (m, 1H), 7.34-7.37 (m, 3H).

Intermediate Z

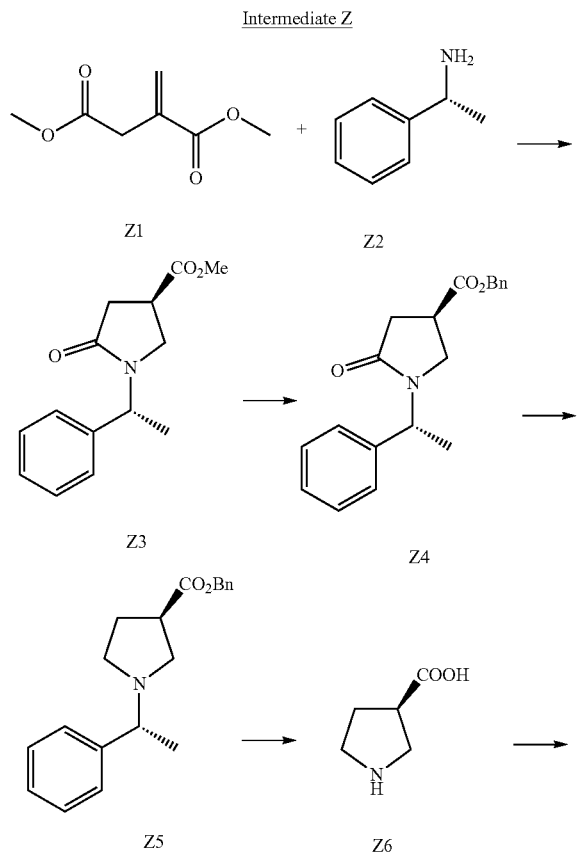

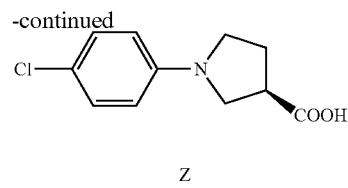

Z

A mixture of dimethyl 2-methylenesuccinate (Z1, 150 g, 10 mol) and (R)-1-phenylethanamine (Z2, 150 g, 15 mol) in methanol (500 mL) was stirred at reflux for 3 days. The reaction mixture was treated with water (500 mL) and extracted with ethyl acetate (500 mL×3). The extracts were washed with water (500 mL×3), dried over anhydrous sodium sulfate, and concentrated. The crude product was purified with flash column chromatography on silica gel (ethyl acetate in petroleum ether, from 10% to 25% v/v) to afford Compound Z3. LC-MS (ESI) m/z: 248 [M+H]$^+$; $^1$H-NMR (CDCl$_3$, 400 MHz): δ (ppm) 1.53 (d, J=6.4 Hz, 3H), 2.67-2.79 (m, 2H), 3.09-3.22 (m, 2H), 3.53-3.57 (m, 1H), 3.72 (s, 3H), 5.50 (m, 1H), 7.28-7.37 (m, 5H).

A mixture of Compound Z3 (30 g, 12.1 mmol), 4-methylbenzenesulfonic acid (4 g, 2.42 mmol), and phenylmethanol (26 g, 24.2 mmol) in toluene (150 mL) was stirred at reflux for 2 days. The reaction mixture was treated with ethyl acetate (500 mL), washed with sodium bicarbonate (500 mL×3) and water (500 mL×3), dried over anhydrous sodium sulfate, and concentrated. The crude product was purified with flash column chromatography on silica gel (ethyl acetate in petroleum ether, from 10% to 33% v/v) to furnish Compound Z4. LC-MS (ESI) m/z: 324 [M+H]$^+$; $^1$H-NMR (CDCl$_3$, 400 MHz): δ (ppm) 1.44 (d, J=6.4 Hz, 3H), 1.62-1.69 (m, 2H), 3.09-3.11 (m, 2H), 3.45-3.47 (m, 1H), 5.07 (s, 2H), 5.41-5.43 (m, 1H), 7.14-7.28 (m, 10H).

To a solution of Compound Z4 (36 g, 11.1 mmol) in tetrahydrofuran (500 mL) was added borane tetrahydrofuran complex (200 mL, 200 mmol) dropwise at 0° C. The mixture was stirred at reflux for 0.5 h. The mixture was quenched with methanol (50 mL) and water (50 mL) and stirred at reflux for 1 h and at room temperature for 18 h. The reaction mixture was evaporated in vacuo. Ethyl acetate (500 mL) was added. The organic layer was washed with water (500 mL×3), dried over anhydrous sodium sulfate, and concentrated. The crude product was purified with flash column chromatography on silica gel (ethyl acetate in petroleum ether, from 1% to 10% v/v) to give Compound Z5. LC-MS (ESI) m/z: 310 [M+H]$^+$; $^1$H-NMR (CDCl$_3$, 400 MHz): δ (ppm) 1.28 (d, J=6.4 Hz, 3H), 1.95-2.02 (m, 2H), 2.37-2.57 (m, 3H), 2.86-2.99 (m, 2H), 3.14-3.15 (m, 1H), 5.19 (s, 2H), 7.14-7.28 (m, 10H).

To a solution of Compound Z5 (20 g, 64.7 mmol) in methanol (400 mL) was added 10% palladium on carbon (0.4 g). The mixture was stirred under 1 atm of H$_2$ atmosphere at 23° C. for 2 days. After the reaction was complete, the mixture was filtered and concentrated in vacuo to give Intermediate Z6, which was directly used for the next step. LC-MS (ESI) m/z: 116 [M+H]$^+$; $^1$H-NMR (CD$_3$OD, 400 MHz): δ (ppm) 2.07-2.16 (m, 2H), 2.90-2.98 (m, 1H), 3.14-3.23 (m, 1H), 3.24-3.28 (m, 2H), 3.39-3.44 (m, 1H).

A mixture of 1-chloro-4-iodobenzene (3 g, 13 mmol), Intermediate Z6 (1 g, 8.7 mmol), CuI (190 mg, 1 mmol), and K$_2$CO$_3$ (2.4 g, 17.4 mmol) in DMSO (50 mL) was stirred at 100° C. for 18 h. The reaction mixture was treated with water (50 mL) and extracted with ethyl acetate (150 mL×3). The extractions were washed with water (100 mL×2), dried over anhydrous sodium sulfate, concentrated, and purified with flash column chromatography on silica gel (ethyl acetate in petroleum ether, from 10% to 33% v/v) to furnish Compound Z. LC-MS (ESI) m/z: 226 [M+H]$^+$.

Example 1

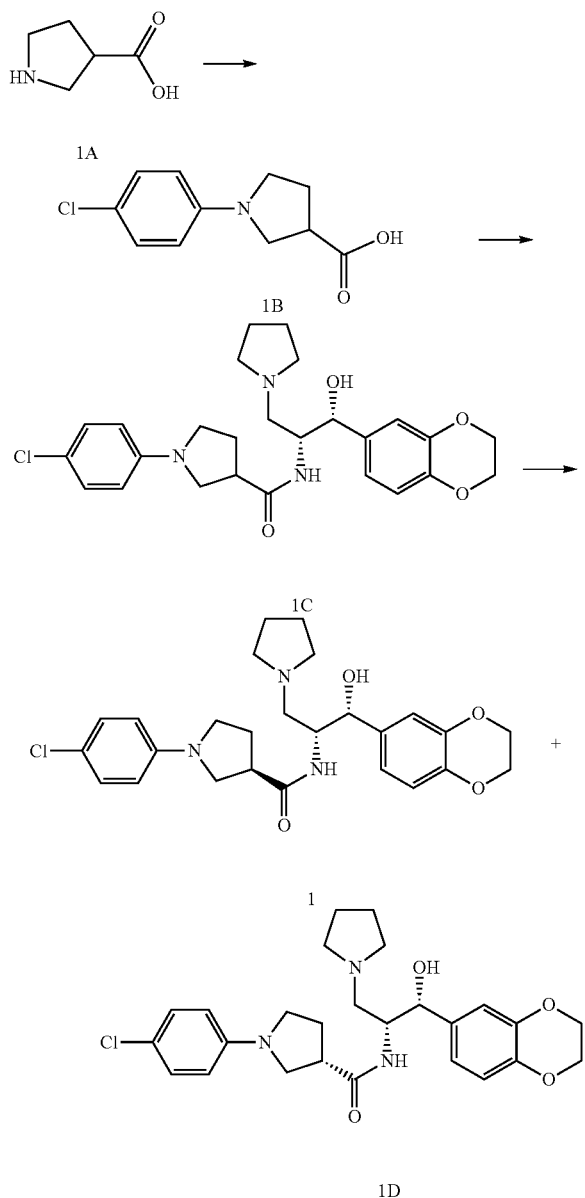

To a solution of Compound 1A (0.5 g, 4.3 mmol) in DMF (20 mL) was added 1-chloro-4-iodobenzene (1.0 g, 4.3 mmol), CuI (100 mg, 0.5 mmol) and K$_2$CO$_3$ (1.2 g, 8.6 mmol). The mixture was stirred for 8 h at 100° C. under N$_2$. The mixture was diluted with aq NH$_4$Cl (40 mL), extracted with ethyl acetate (50 mL×2), washed with brine (100 mL×2), and evaporated. The crude product was purified by silica gel column chromatography (methanol in dichloromethane, 10% v/v) to give Compound 1B. LC-MS (m/z): 224 [M−1]$^−$.

To a solution of Compound 1B (0.1 g, 0.44 mmol) in dichloromethane (10 mL) was added Intermediate A (124 mg, 0.44 mmol), EDCI (127 mg, 0.66 mmol), HOBt (89 mg, 0.66 mmol). The mixture was stirred at room temperature overnight, quenched with water (20 mL), extracted with dichloromethane (20 mL×2), washed with brine (50 mL×2), and evaporated to remove solvents. The crude product was purified by prep-HPLC to give Compound 1C. Compound 1C was further subjected to chiral resolution using prep-chiral-HPLC, which gave two isomers Compound 1 and Compound 1D. For Compound 1: LC-MS (m/z): 486 [M+1]$^+$; $^1$H-NMR (DMSO-d$_6$, 400 MHz) major characteristic peaks: δ (ppm) 1.93 (m, 6H), 2.61 (m, 1H), 3.13 (m, 7H), 3.52 (m, 2H), 4.24 (m, 5H), 4.71 (s, 1H), 5.84 (s, 1H), 6.46 (d, J=8.8 Hz, 2H), 6.83 (m, 3H), 7.20 (d, J=8.8 Hz, 2H), 7.96 (d, J=9.6 Hz, 1H), 9.38 (m, 1H). For Compound 1D: LC-MS (m/z): 486 [M+1]$^+$; $^1$H-NMR (DMSO-d$_6$, 400 MHz) major characteristic peaks: δ (ppm) 1.83 (m, 6H), 3.19 (m, 8H), 3.52 (s, 2H), 4.20 (m, 5H), 4.71 (s, 1H), 5.84 (s, 1H), 6.46 (d, J=8.8 Hz, 2H), 6.78 (m, 3H), 7.15 (d, J=12 Hz, 2H), 7.92 (d, J=9.6 Hz, 1H), 9.42 (m, 1H).

Alternatively, Compound 1 can be prepared by employing the following procedures.

To a solution of (R)-pyrrolidine-3-carboxylic acid (0.5 g, 4.3 mmol) in DMSO (20 mL) was added 1-chloro-4-iodobenzene (1.0 g, 4.3 mmol), CuI (100 mg, 0.5 mmol) and K$_2$CO$_3$ (1.2 g, 8.6 mmol). The mixture was stirred for 8 hour at 100° C. under N$_2$. The mixture was diluted with aq. NH$_4$Cl (40 mL), extracted with ethyl acetate (50 mL×2), washed with brine (100 mL×2), and evaporated to remove the solvents. The crude product was purified with column chromatography (on silica gel, methanol in dichloromethane, 10% v/v as the eluents) to furnish (R)-1-(4-chlorophenyl) pyrrolidine-3-carboxylic acid. LC-MS (m/z): 224 [M−1]$^+$.

To a solution of (R)-1-(4-chlorophenyl) pyrrolidine-3-carboxylic acid (0.1 g, 0.44 mmol) in dichloromethane (10 mL) was added Intermediate A (124 mg, 0.44 mmol), EDCI.HCl (127 mg, 0.66 mmol), and HOBt (89 mg, 0.66 mmol). The mixture was stirred at room temperature overnight, quenched with water (20 mL), extracted with dichloromethane (20 mL×2), washed with brine (50 mL×2), and evaporated to dryness. The crude product was purified with prep-HPLC to give Compound 1. LC-MS (m/z): 486 [M+1]$^+$; $^1$H-NMR (DMSO-d$_6$, 400 MHz) major characteristic peaks: δ (ppm) 1.87-1.99 (m, 6H), 2.60 (m, 1H), 3.13 (m, 7H), 3.52 (m, 2H), 4.19 (m, 5H), 4.71 (s, 1H), 5.85 (s, 1H), 6.46 (d, J=8.8 Hz, 2H), 6.78 (s, 2H), 6.88 (s, 1H), 7.20 (d, J=12 Hz, 2H), 7.98 (d, J=12 Hz, 1H), 9.31 (m, 1H).

Example 2

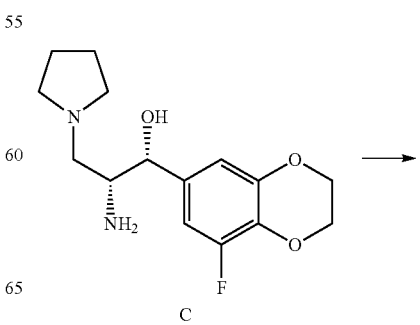

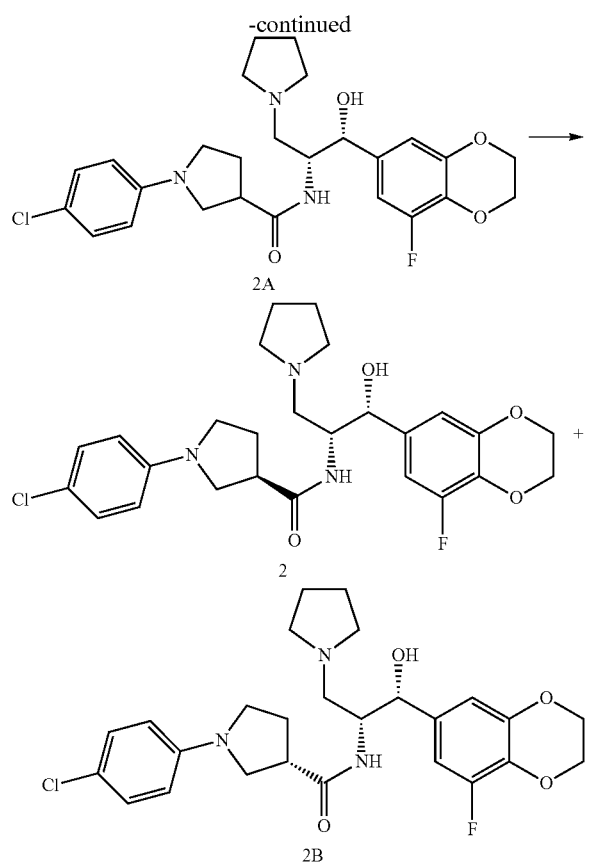

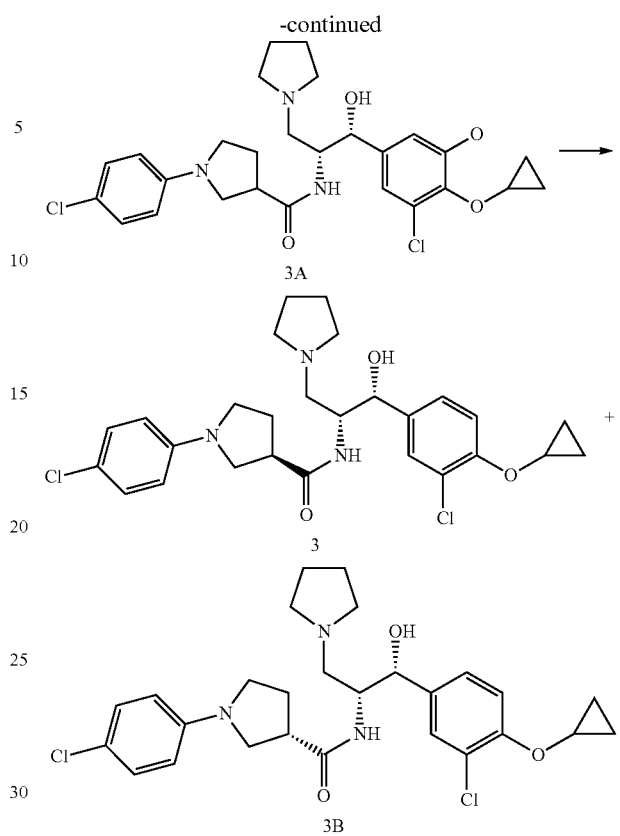

Compounds 2 and 2B were synthesized, by employing the procedure described for Compound 1 using Intermediate C in lieu of Intermediate A.

Compound 2. LC-MS (m/z): 504 [M+1]$^+$; $^1$H-NMR (CDCl$_3$, 400 MHz) major characteristic peaks: δ (ppm) 1.75 (s, 4H), 2.12-2.20 (m, 2H), 2.57-2.71 (m, 4H), 2.80-2.98 (m, 3H), 3.18-3.43 (m, 4H), 4.11-4.16 (m, 1H), 4.23-4.27 (m, 4H), 4.92 (s, 1H), 6.15 (d, J=8 Hz, 1H), 6.46 (d, J=8 Hz, 2H), 6.62-6.70 (m, 2H), 7.16 (d, J=12 Hz, 2H). Chiral-HPLC conditions, solvent: MeOH (0.5% DEA), column AD-H 250*4.6 mm 5 μm, Rt: 5.02 min.

Compound 2B. LC-MS (m/z): 504 [M+1]$^+$; $^1$H-NMR (CDCl$_3$, 400 MHz) major characteristic peaks: δ (ppm) 1.78 (s, 4H), 2.04-2.18 (m, 2H), 2.61-2.68 (m, 4H), 2.82-2.99 (m, 3H), 3.19-3.25 (m, 1H), 3.32-3.42 (m, 3H), 4.13-4.18 (m, 1H), 4.25-4.28 (m, 4H), 4.90 (s, 1H), 6.16 (d, J=8 Hz, 1H), 6.45 (d, J=8 Hz, 2H), 6.65 (t, J=16 Hz, 2H), 7.15 (d, J=8 Hz, 2H); Chiral-HPLC conditions, solvent: MeOH (0.5% DEA), column AD-H 250*4.6 mm 5 μm, Rt: 8.38 min.

Example 3

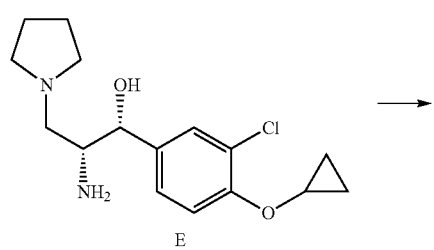

Compounds 3 and 3B were synthesized, by employing the procedure described for Compound 1 using Intermediate E in lieu of Intermediate A.

Compound 3. LC-MS (m/z): 518.0 [M+1]$^+$; $^1$H-NMR (MeOD, 400 MHz) major characteristic peaks: δ (ppm) 0.62-0.77 (m, 4H), 1.85 (s, 4H), 2.03-2.20 (m, 3H), 2.67-2.83 (m, 7H), 2.98-3.25 (m, 3H), 3.75-3.76 (m, 1H), 4.30 (m, 1H), 4.59 (s, 2H), 6.47 (d, J=6.8 Hz, 2H), 7.10-7.13 (m, 2H), 7.20-7.43 (m, 2H), 7.44 (s, 1H). Chiral-HPLC conditions, solvent: MeOH (0.1% DEA), column: AD-H 250*4.6 mm 5 μm, Rt: 3.51 min.

Compound 3B. LC-MS (m/z): 518.0 [M+1]$^+$; $^1$H-NMR (MeOD, 400 MHz) major characteristic peaks: δ (ppm) 0.65-0.80 (m, 2H), 1.85 (s, 4H), 1.86-1.98 (m, 1H), 2.13-2.20 (m, 1H), 2.57-2.75 (m, 5H), 3.09-3.37 (m, 5H), 3.83-3.86 (m, 1H), 4.26 (m, 1H), 6.49 (d, J=2.4 Hz, 2H), 7.10-7.12 (m, 2H), 7.23-7.32 (m, 2H), 7.41 (s, 1H). Chiral-HPLC conditions, solvent: MeOH (0.1% DEA), column: AD-H 250*4.6 mm 5 μm, Rt: 5.94 min.

Example 4

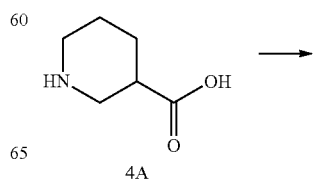

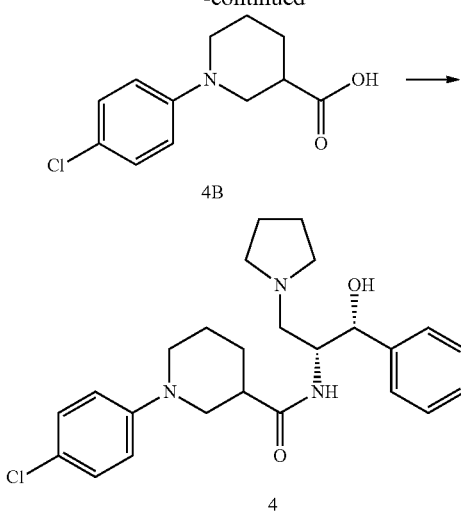

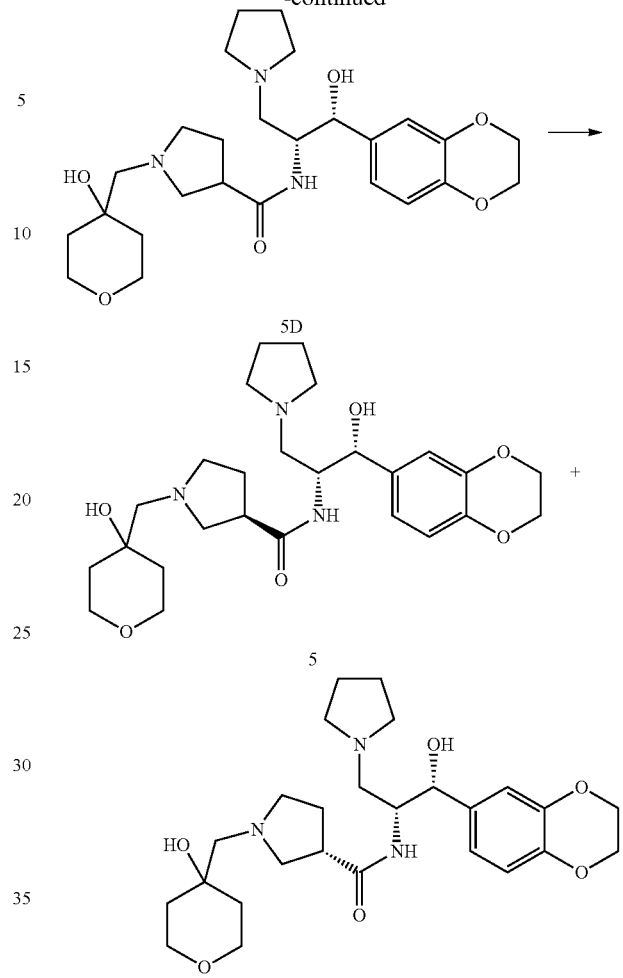

Compounds 4B and 4 were synthesized, by employing the procedures described correspondingly for Compounds 1B and 1 using Compounds 4A and 4B in lieu of Compounds 1A and 1B.

Compound 4B. LC-MS (m/z): 238 [M−1]$^+$.

Compound 4. LC-MS (m/z): 500 [M+H]$^+$; $^1$H-NMR (DMSO-d$_6$, 400 MHz) major characteristic peaks: δ (ppm) 1.20 (m, 1H), 1.47 (m, 1H), 1.64 (m, 2H), 1.85 (m, 4H), 2.45 (m, 1H), 2.61 (m, 2H), 3.10 (m, 4H), 3.39 (m, 4H), 4.17 (m, 5H), 4.66 (s, 1H), 6.82 (m, 5H), 7.21 (d, J=8.8 Hz, 2H), 7.78 (d, J=9.6 Hz, 1H), 9.35 (s, 1H).

Example 5

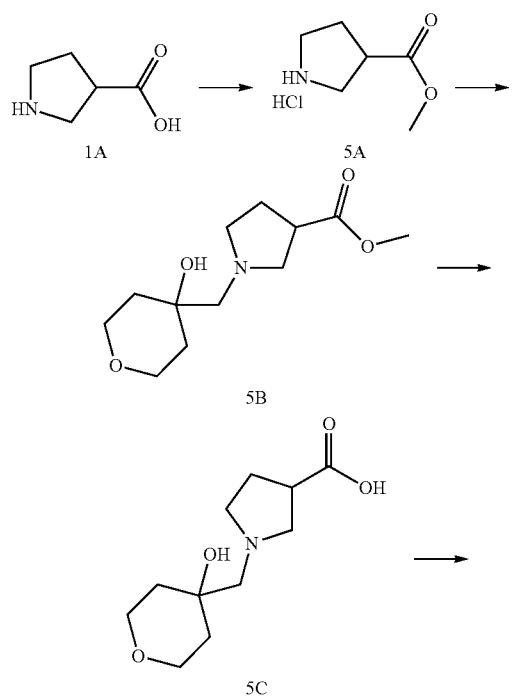

Thionyl dichloride (3.7 mL, 52.1 mmol) was added dropwise to a solution of Compound 1A (5 g, 43.4 mmol) in MeOH (80 mL) at 0° C. The reaction mixture was stirred at room temperature for 18 h. The reaction mixture was concentrated in vacuo to furnish Compound 5A. LC-MS (m/z): 130 [M+1]$^+$; $^1$H-NMR (CDCl$_3$, 400 MHz) major characteristic peaks: δ (ppm) 2.14 (m, 1H), 2.27 (m, 1H), 3.25 (m, 3H), 3.45 (m, 2H), 3.65 (s, 3H).

To a solution of Compound 5A (0.7 g, 4.2 mmol) and 1,6-dioxaspiro[2.5]octane (0.97 g, 8.48 mmol) in ethanol (30 mL) was added triethylamine (0.856 g, 8.48 mmol). The reaction mixture was stirred at 30° C. under N$_2$ overnight. The reaction mixture was concentrated and the residue was purified with silica gel chromatography (ethyl acetate in petroleum ether, from 1% to 5% v/v) to furnish Compound 5B. LC-MS (m/z): 244 [M+1]$^+$; $^1$H-NMR (CDCl$_3$, 400 MHz) major characteristic peaks: (ppm) 1.40 (d, 2H), 1.53 (m, 2H), 2.02 (m, 2H), 2.43 (dd, 2H), 2.71 (m, 2H), 2.92 (m, 3H), 3.62 (s, 3H), 3.72 (m, 4H).

A solution of 1N lithium hydroxide (5 mL, 5 mmol) was added dropwise to a solution of Compound 5B (0.6 g, 2.47 mmol) in MeOH (10 mL). The reaction mixture was stirred at room temperature for 2 h. The reaction mixture was treated with 3N HCl (1.7 mL) to adjust pH to 7 and concentrated in vacuo to yield Compound 5C. LC-MS (m/z): 230 [M+1]$^+$.

Compounds 5 and 5E were synthesized, by employing the procedures described for Compound 1 using Compound 5C in lieu of Compound 1B.

Compound 5. LC-MS (m/z): 490 [M+1]$^+$; $^1$H-NMR (MeOD, 400 MHz) major characteristic peaks: δ (ppm) 1.36 (m, 2H), 1.55 (m, 3H), 1.70 (m, 4H), 1.90 (m, 1H), 2.40 (m, 3H), 2.49 (m, 6H), 2.71 (m, 4H), 3.65 (m, 4H), 4.07 (m, 1H), 4.10 (s, 4H), 4.70 (d, J=2.8 Hz, 1H), 6.68 (m, 2H), 6.75 (s, 1H). Chiral-HPLC conditions, solvent:EtOH (0.5% DEA), column: OZ-H 250*4.6 mm 5 μm, Rt: 6.39 min.

Compound 5E. LC-MS (m/z): 490 [M+1]$^+$; $^1$H-NMR (MeOD, 400 MHz) major characteristic peaks: δ (ppm) 1.38 (m, 2H), 1.53 (m, 3H), 1.70 (m, 4H), 1.90 (m, 1H), 2.40 (m, 2H), 2.53 (m, 7H), 2.74 (m, 4H), 3.62 (m, 4H), 4.07 (m, 1H), 4.10 (s, 4H), 4.70 (d, J=2.8 Hz, 1H), 6.68 (m, 2H), 6.75 (s, 1H). Chiral-HPLC conditions, solvent:EtOH (0.5% DEA), column: OZ-H 250*4.6 mm 5 μm, Rt: 10.07 min.

Example 6

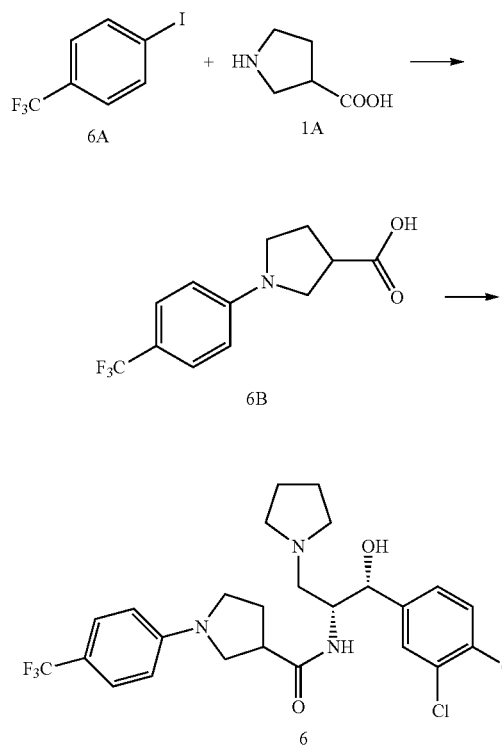

Compounds 6B and 6 were synthesized, by employing the procedures described for Compounds 1B and 1 using Compounds 6A, 6B, and Intermediate E in lieu of 1-chloro-4-iodobenzene, Compound 1B, and Intermediate A.

Compound 6B. LC-MS (ESI) m/z: 258 [M−H]$^+$.

Compound 6. LC-MS (m/z): 552.2 [M+1]$^+$. $^1$H-NMR (CDCl$_3$, 400 MHz) major characteristic peaks: δ (ppm) 0.73-0.74 (m, 4H), 1.79 (s, 1H), 2.02-(m, 4H), 2.83-2.91 (m, 5H), 3.01-3.20 (m, 4H), 3.31 (s, 1H), 3.66-3.77 (m, 4H), 4.43 (s, 1H), 4.85 (s, 1H), 6.39-6.41 (d, J=8.8 Hz, 2H), 7.07-7.09 (m, 1H), 7.14-7.16 (m, 1H), 7.31-7.38 (d, J=8.4 Hz, 3H), 7.46-7.50 (m, 1H), 11.15 (s, 1H).

Example 7

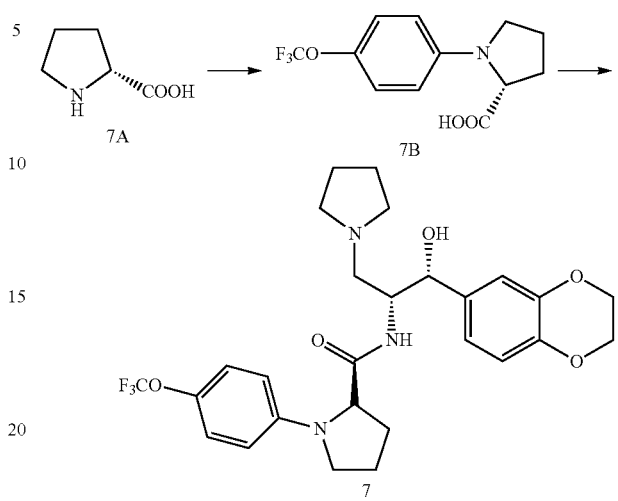

Compound 7B was synthesized, by employing the procedure described for Compound 1B using 1-(4-(trifluoromethyl)phenyl)pyrrolidine-3-carboxylic acid and Compound 7A in lieu of 1-chloro-4-iodobenzene and Compound 1A. LC-MS (m/z): 274 [M−1]$^+$; $^1$H-NMR (DMSO-d$_6$, 400 MHz) major characteristic peaks: δ (ppm) 1.978-2.088 (m, 3H), 2.255-2.285 (m, 1H), 3.401-3.438 (m, 2H), 4.156-4.182 (m, 1H), 6.491-6.515 (d, J=9.6 Hz, 2H), 7.140-7.161 (d, J=8.4 Hz, 2H).

A mixture of Compound 7B (50 mg, 0.18 mmol), Intermediate A (50 mg, 0.18 mmol), HATU (103 mg, 0.27 mmol) and DIPEA (46 mg, 0.36 mmol) in THF (5 mL) was stirred at 25° C. for 16 h. After removal of solvent the residue was purified with prep-HPLC to give Compound 7. LC-MS (m/z): 536 [M+1]$^+$; $^1$H-NMR (MeOD, 400 MHz) major characteristic peaks: δ (ppm) 1.863-2.246 (m, 8H), 3.164-3.325 (m, 4H), 3.404-3.438 (m, 1H), 3.564-3.739 (m, 4H), 4.076-4.099 (m, 1H), 4.234 (s, 4H), 4.458-4.486 (m, 1H), 4.795-4.801 (m, 1H), 6.530-6.552 (m, 2H), 6.897-6.718 (m, 2H), 6.844-6.848 (m, 1H), 7.091-7.114 (d, J=9.2 Hz, 2H).

Example 8

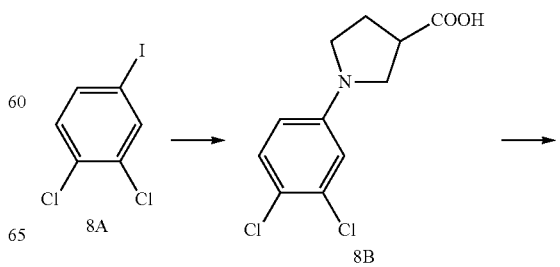

201

-continued

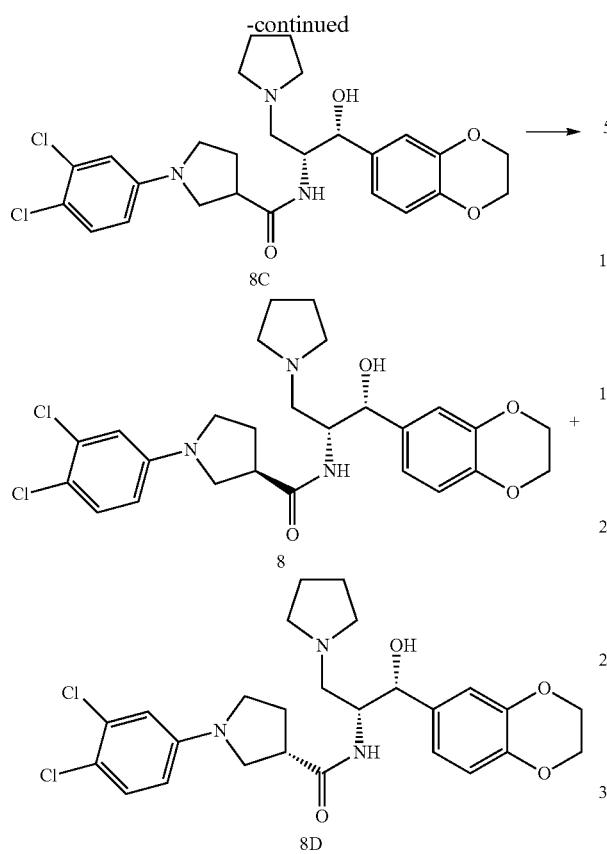

8C

8

8D

Compound 8B was synthesized, by employing the procedure described for Compound 1B using Compound 8A in lieu of 1-chloro-4-iodobenzene. LC-MS (m/z): 258 [M−1]+; 1H-NMR (DMSO-d6, 400 MHz) major characteristic peaks: δ (ppm) 2.126-2.234 (m, 2H), 3.183-3.309 (m, 3H), 3.407-3.479 (m, 2H), 6.525-6.554 (dd, J1=8.8 Hz, J2=2.8 Hz, 1H), 6.712-6.719 (d, J=2.8 Hz, 1H), 7.333-7.355 (d, J=8.8 Hz, 1H), 12.518 (s, 1H).

Compounds 8 and 8D were synthesized, by employing the procedure described for Compound 7 using Compound 8B in lieu of Compound 7B.

Compound 8. LC-MS (m/z): 520 [M+1]+; 1H-NMR (MeOD, 400 MHz) major characteristic peaks: δ (ppm) 1.769-1.818 (m, 1H), 2.010-2.229 (m, 5H), 3.151-3.279 (m, 5H), 3.349-3.412 (m, 2H), 3.473-3.600 (m, 2H), 3.658-3.696 (m, 1H), 3.789-3.830 (m, 1H), 4.249 (s, 4H), 4.477-4.518 (m, 1H), 4.847-4.858 (m, 1H), 6.459-6.488 (m, 1H), 6.635-6.642 (m, 1H), 6.816-6.968 (m, 3H), 7.244-7.266 (d, J=8.8 Hz, 1H).

Compound 8D. LC-MS (m/z): 520 [M+1]+; 1H-NMR (MeOD, 400 MHz) major characteristic peaks: δ (ppm) 2.046-2.282 (m, 5H), 2.718-2.760 (m, 1H), 3.166-3.336 (m, 4H), 3.353-3.528 (m, 4H), 3607-3.706 (m, 1H), 3.814-3.823 (m, 1H), 4.207-4.316 (m, 4H), 4.489-4.529 (m, 1H), 4.863-4.874 (m, 1H), 6.467-6.497 (m, 1H), 6.652-6.659 (m, 1H), 6.8832-6.973 (m, 3H), 7.281-7.303 (d, J=8.8 Hz, 1H).

202

Example 9

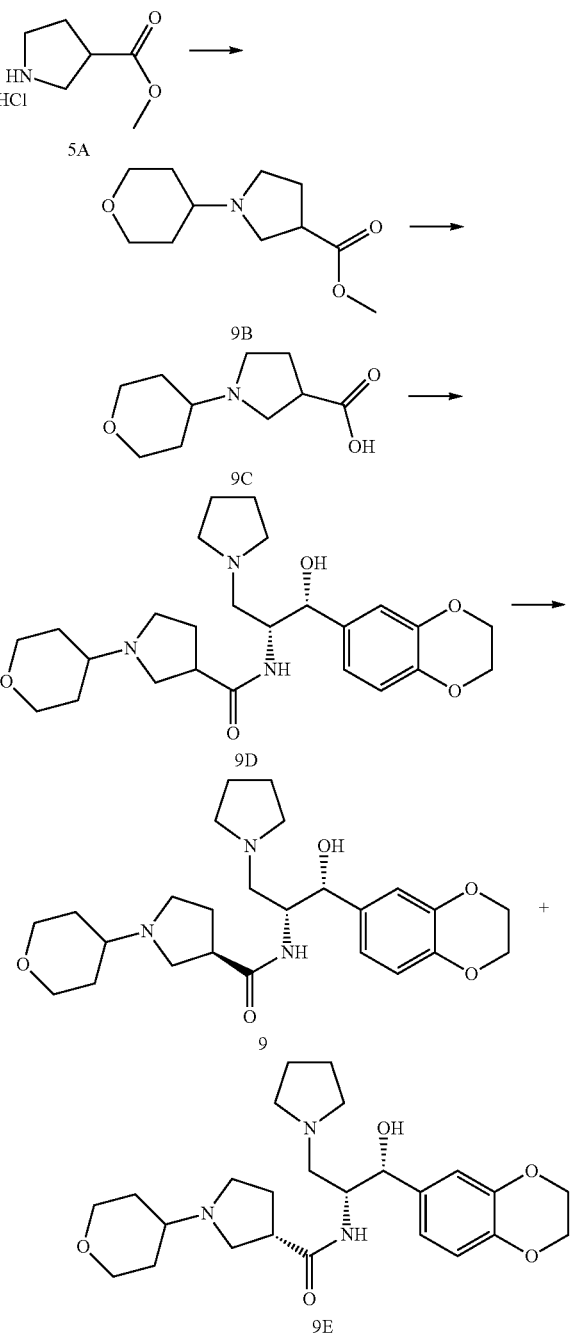

To a solution of Compound 5A (650 mg, 3.93 mmol) and dihydro-2H-pyran-4(3H)-one (471 mg, 4.71 mmol) in dichloromethane (30 mL) was added sodium triacetoxyborohyride (1.24 g, 5.09 mmol). The reaction mixture was stirred at 30° C. for 3 h. The reaction mixture was filtered and the filterate was concentrated and the residue was purified with silica gel column chromatography (methanol in dichloromethane, from 1% to 5% v/v) to yield Compound 9B. LC-MS (m/z): 214 [M+1]+; 1H-NMR (CDCl3, 400 MHz) major characteristic peaks: δ (ppm) 1.94-2.03 (m, 4H), 2.22-2.25 (m, 1H), 2.43-2.48 (m, 1H), 3.02-3.04 (m, 1H), 3.17-3.20 (m, 1H), 3.26-3.85 (m, 3H), 3.48-3.51 (m, 1H), 3.68 (s, 3H), 3.99-4.02 (m, 2H).

Compound 9C was synthesized, by employing the procedure described for Compound 5C using Compound 9B in lieu of Compound 5B. LC-MS (m/z): 200 [M+1]⁺.

Compounds 9 and 9E were synthesized, by employing the procedures described for Compound 7 using Compound 9C in lieu of Compound 7B.

Compound 9. LC-MS (m/z): 459 [M+1]⁺; ¹H-NMR (MeOD, 400 MHz) major characteristic peaks: δ (ppm) 1.45-1.51 (m, 2H), 1.71-1.83 (m, 8H), 2.17-2.19 (m, 2H), 2.42-2.61 (m, 6H), 2.65-2.69 (m, 2H), 2.76-2.79 (m, 2H), 3.34-3.35 (m, 2H), 3.84-3.89 (m, 2H), 4.08 (s, 4H), 4.08 (m, 1H), 4.70 (d, J=2.8 Hz, 1H), 6.67 (m, 2H), 6.76 (s, 1H). HPLC analysis: n-hexane (0.1% DEA):EtOH (0.1% DEA), column: AS-H 250*4.6 mm 5 μm, Rt: 9.072 min.

Compound 9E. LC-MS (m/z): 459 [M+1]⁺; ¹H-NMR (MeOD, 400 MHz) major characteristic peaks: δ (ppm) 1.47-1.54 (m, 2H), 1.73-1.85 (m, 8H), 2.00-2.04 (m, 1H), 2.29-2.34 (m, 1H), 2.52-2.69 (m, 7H), 2.73-2.79 (m, 2H), 2.87-2.90 (m, 2H), 3.34-3.44 (m, 2H), 3.92-3.95 (m, 2H), 4.20 (s, 4H), 4.20 (m, 1H), 4.78 (d, J=2.8 Hz, 1H), 6.78 (m, 2H), 6.85 (s, 1H). HPLC analysis: co-solvent n-hexane (0.1% DEA):EtOH (0.1% DEA), column: AS-H 250*4.6 mm 5 μm, Rt: 12.706 min.

Example 10

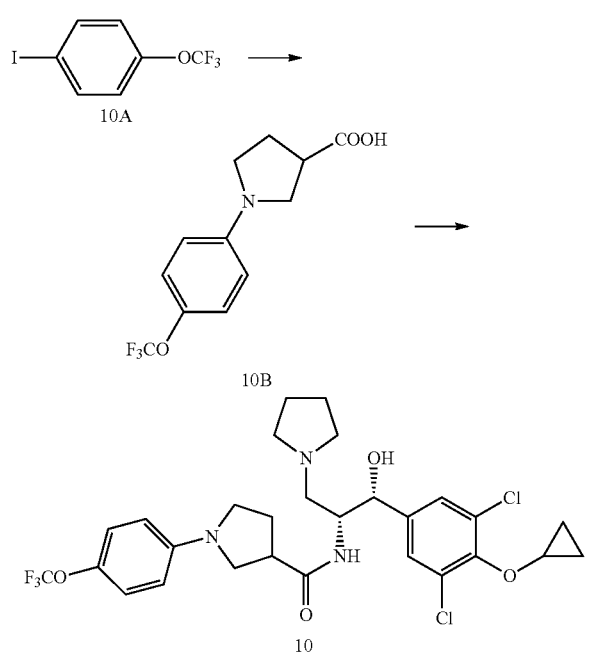

Compound 10B was synthesized, by employing the procedure described for Compound 1B using Compound 10A in lieu of 1-chloro-4-iodobenzene. LC-MS (m/z): 274 [M−1]⁺; ¹H-NMR (DMSO-d₆, 400 MHz) major characteristic peaks: δ (ppm) 2.15-2.25 (m, 2H), 3.21-3.48 (m, 5H), 6.57-6.59 (d, J=8.8 Hz, 2H), 7.15-7.17 (d, J=8.8 Hz, 2H), 12.52 (s, 1H).

Compound 10 was synthesized, by employing the procedure described for Compound 7 using Compound 10B and Intermediate E in lieu of Compound 7B and Intermediate A. LC-MS (m/z): 568 [M+1]⁺; ¹H-NMR (MeOD, 400 MHz) major characteristic peaks: δ (ppm) 0.64-0.82 (m, 4H), 2.04-2.24 (m, 6H), 2.53-2.57 (m, 1H), 3.13-3.30 (m, 6H), 3.49-3.60 (m, 5H), 4.56-4.58 (m, 1H), 4.94-4.95 (m, 1H), 6.49-6.51 (m, 2H), 7.07-7.09 (d, J=8.4 Hz, 2H), 7.30-7.32 (m, 2H), 7.54-7.55 (m, 1H).

Example 11

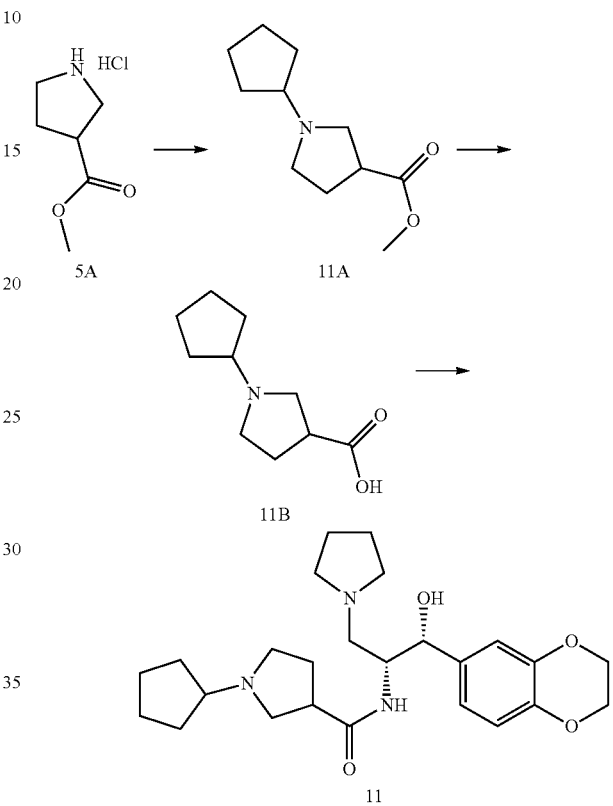

Compound 11A was synthesized, by employing the procedure described for Compound 9B using cyclopentanone in lieu of dihydro-2H-pyran-4(3H)-one. LC-MS (m/z): 198 [M+1]⁺; ¹H-NMR (CDCl₃, 400 MHz) major characteristic peaks: δ (ppm) 1.41-1.84 (m, 8H), 2.06-2.11 (m, 2H), 2.43-2.49 (m, 2H), 2.56-2.60 (m, 1H), 2.74-2.79 (m, 1H), 2.97-3.07 (m, 2H), 3.68 (s, 3H).

Compound 11B was synthesized, by employing the procedure described for Compound 5C using Compound 11A in lieu of Compound 5B. LC-MS (m/z): 184 [M+1]⁺; ¹H-NMR (DMSO-d₆, 400 MHz) major characteristic peaks: δ (ppm) 1.48-1.51 (m, 4H), 1.62-1.63 (m, 2H), 1.77-1.79 (m, 2H), 1.92-1.98 (m, 2H), 2.63-2.91 (m, 6H).

A solution of Compound 11B (110 mg, 0.6 mmol) in SOCl₂ (1 mL) was stirred at 30° C. for 18 h. The mixture was concentrated and DCM (5 mL) was added, followed by the addition of Intermediate A (167 mg, 0.6 mmol) and Et₃N (0.3 mL, 1.8 mmol). It was stirred at 30° C. for 18 h. The solvent was evaporated and the residue was purified with prep-HPLC to furnish Compound 11. LC-MS (m/z): 444 [M+1]⁺. ¹H-NMR (CDCl₃, 400 MHz) major characteristic peaks: δ (ppm) 1.58-2.06 (m, 14H), 2.90-3.87 (m, 12H), 4.19-4.22 (m, 4H), 4.45-4.50 (m, 1H), 4.75-4.86 (m, 1H), 6.81 (s, 2H), 6.88-6.92 (m, 1H), 11.46 (s, 1H), 11.65 (s, 1H).

Example 12

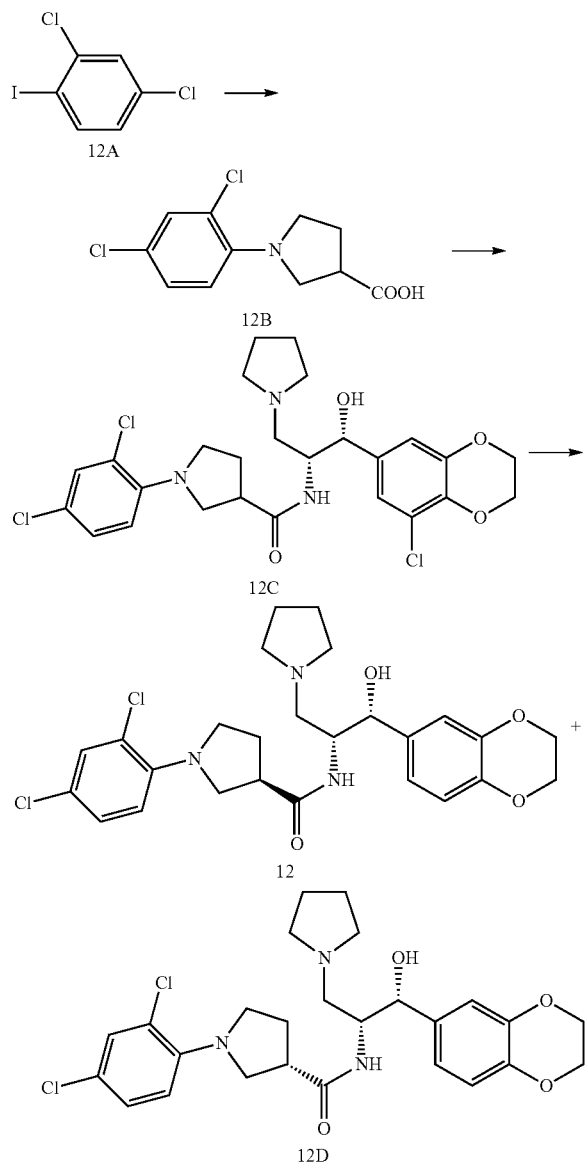

Compound 12B was synthesized, by employing the procedure described for Compound 1B using Compound 12A in lieu of 1-chloro-4-iodobenzene. LC-MS m/z: 258 [M−1]+; 1H-NMR (DMSO-d6, 400 MHz) major characteristic peaks: δ (ppm) 2.22-2.28 (m, 2H), 3.15-3.22 (m, 1H), 3.34-3.43 (m, 2H), 3.54-3.66 (m, 2H), 6.96-6.99 (m, 1H), 7.18-7.20 (m, 1H), 7.32-7.33 (m, 1H).

Compounds 12 and 12D were synthesized, by employing the procedures described for Compound 7 using Compound 12B in lieu of Compound 7B.

Compound 12. LC-MS (m/z): 520 [M+1]+; 1H-NMR (MeOD, 400 MHz) major characteristic peaks: δ (ppm) 1.67-1.78 (m, 1H), 2.00-2.05 (m, 2H), 2.16-2.18 (m, 3H), 3.08-3.16 (m, 4H), 3.20-3.25 (m, 1H), 3.34-3.36 (m, 4H), 3.54 (m, 1H), 3.65 (m, 1H), 4.22 (s, 4H), 4.45-4.50 (m, 1H), 4.84 (m, 1H), 6.77-6.70 (m, 1H), 6.85-6.87 (m, 1H), 6.94 (m, 2H), 7.17-7.20 (m, 1H), 7.33 (m, 1H). HPLC analysis: solvent: MeOH (0.1% DEA), column: AS-H (4.6*250 mm, 5 μm), R.t.: 9.45 min.

Compound 12D. LC-MS (m/z): 520 [M+1]+; 1H-NMR (MeOD, 400 MHz) major characteristic peaks: δ (ppm) 1.92-1.96 (m, 4H), 1.99-2.07 (m, 2H), 2.75-2.79 (m, 1H), 2.94-2.96 (m, 1H), 2.98-3.13 (m, 3H), 3.27-3.47 (m, 4H), 3.58-3.59 (m, 1H), 3.70 (m, 1H), 4.01 (s, 4H), 4.36-4.39 (m, 1H), 4.72 (m, 1H), 6.63 (m, 1H), 6.75 (m, 1H), 6.80-6.82 (m 2H), 7.09 (m, 1H), 7.23 (m, 1H). HPLC analysis: solvent: MeOH (0.1% DEA), column: AS-H (4.6*250 mm 5 μm, R.t.: 4.95 min.

Example 13

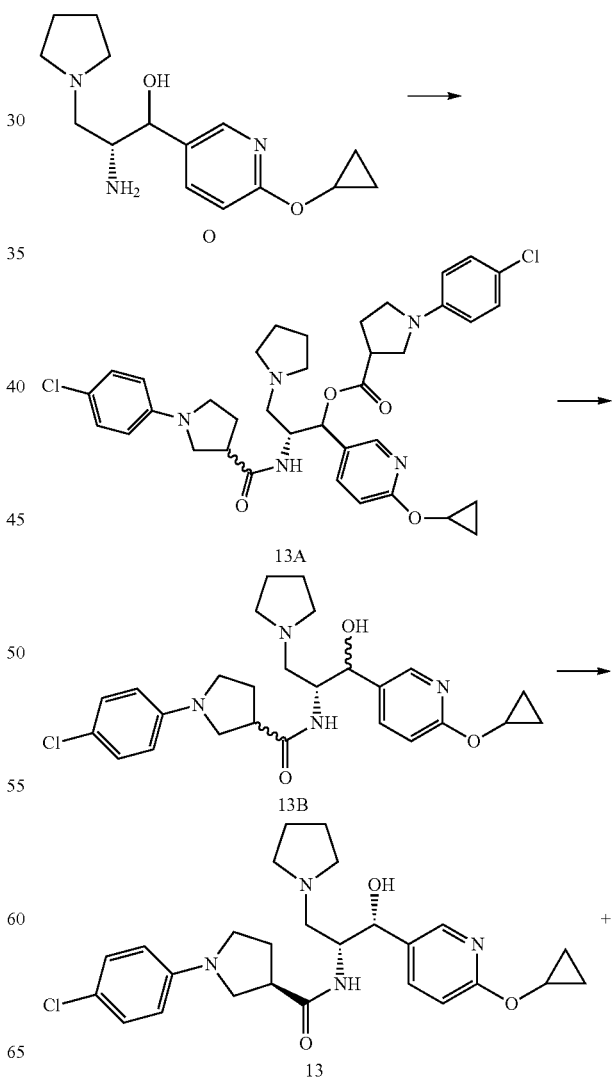

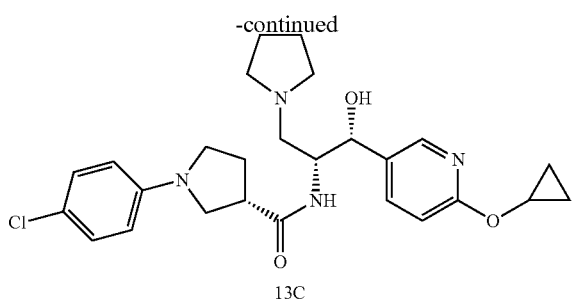

13C

To a solution of Intermediate O (175 mg, 0.63 mmol) in DMF (5 mL) was added HATU (478 mg, 1.26 mmol) DIPEA (162 mg, 1.26 mmol) and Compound 1B (283 mg, 1.26 mmol) at 0° C., and then the reaction mixture was allowed to warm to room temperature and stirred at 30° C. for 10 h. The mixture was purified with prep-HPLC to give Compound 13A. LC-MS (m/z): 692 [M+1]+.

To a solution of Compound 13A (150 mg, 0.22 mmol) in THF (5 mL) was added LiOH (1M solution, 0.44 mL, 0.44 mmol). The reaction mixture was stirred overnight at 30° C. before being neutralized with 1N hydrochloride. After the mixture was diluted with water (4 mL) and extracted with ethyl acetate (20 mL×3), the combined organic layers were dried over anhdyrous sodium sulfate, filtered, and evaporated to give a crude product mixture 13B, which was separated by chiral-prep-HPLC (co-solvent MeOH (0.1% DEA), column IC 4.6*250 mm, 5 μm) to yield Compound 13 and Compound 13C. For Compound 13: LC-MS (m/z): 485 [M+1]+; 1H-NMR (CDCl3, 400 MHz) major characteristic peaks: (ppm) 0.76-0.81 (m, 4H), 1.73-1.76 (m, 4H), 2.11-2.21 (m, 3H), 2.59-2.67 (m, 4H), 2.80 (dd, J=12.8, 4.8 Hz, 1H), 2.91-2.96 (m, 2H), 3.19-3.25 (m, 1H), 2.27-3.29 (m, 2H), 3.35-3.38 (m, 1H), 4.16-4.18 (m, 1H), 5.04 (d, J=2.8 Hz, 1H), 6.28 (d, J=8.0 Hz, 1H), 6.45-6.47 (m, 2H), 6.75 (d, J=8.4 Hz, 1H), 7.15-7.17 (m, 2H), 7.53 (dd, J=8.8, 2.4 Hz, 1H), 8.20 (d, J=2.4 Hz, 1H). Chiral-HPLC conditions: solvent: MeOH (0.1% DEA), column IC 4.6*250 mm, 5 μm), Rt: 5.52 min. For Compound 13C: LC-MS (m/z):485 [M+1]+; 1H-NMR (CDCl3, 400 MHz) major characteristic peaks: δ (ppm) 0.73-0.81 (m, 4H), 1.81-1.82 (m, 4H), 2.04-2.16 (m, 3H), 2.70-2.77 (m, 4H), 2.94-2.99 (m, 3H), 3.20-3.23 (m, 1H), 3.33-3.38 (m, 3H), 4.11-4.14 (m, 1H), 4.21-4.24 (m, 1H), 5.03 (d, J=3.2 Hz, 1H), 6.42-6.45 (m, 3H), 6.74 (d, J=8.4 Hz, 1H), 7.14-7.16 (m, 2H), 7.54 (dd, J=8.4, 2.4 Hz, 1H), 8.18 (d, J=2.4 Hz, 1H). Chiral-HPLC conditions: solvent: MeOH (0.1% DEA), column IC 4.6*250 mm, 5 μm), Rt: 6.44 min.

Example 14

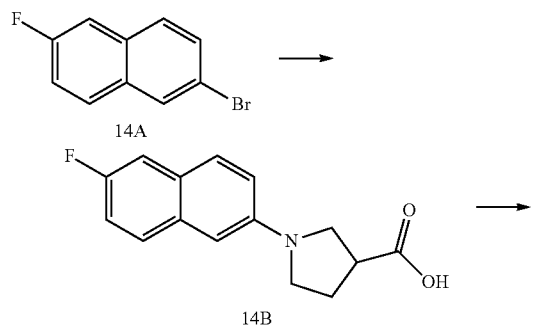

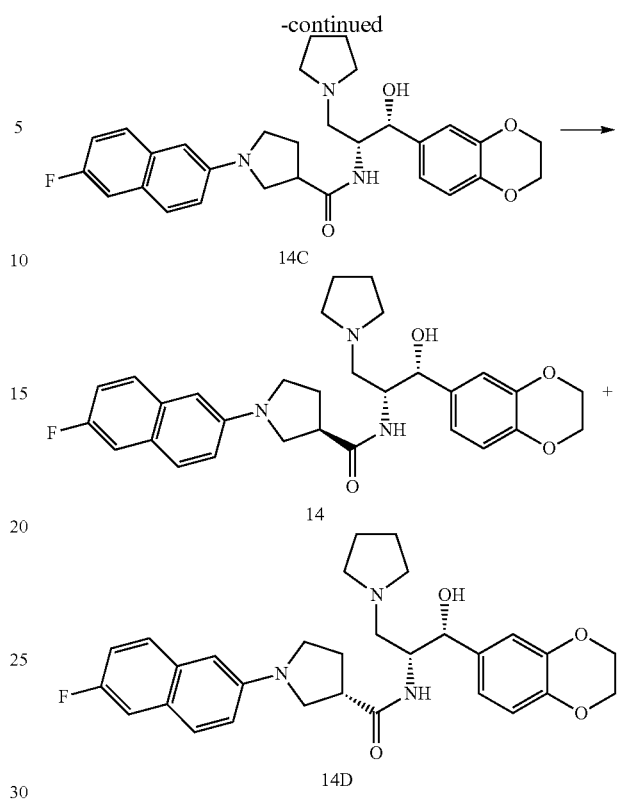

Compounds 14B, 14, and 14D were synthesized, by employing the procedures described correspondingly for Compounds 1B and 1 using Compounds 14A and 14B in lieu of 1-chloro-4-iodobenzene and Compound 1B.

Compound 14B. LC-MS (m/z): 260 [M+1]+; 1H-NMR (DMSO-d6, 400 MHz) major characteristic peaks: 2.17 (br s, 2H), 3.29-3.38 (m, 5H), 6.76 (s, 1H), 7.03 (d, J=8.0 Hz, 1H), 7.21 (t, J=7.6 Hz, 1H), 7.73 (d, J=9.2 Hz, 1H), 7.60-7.69 (m, 2H).

Compound 14. LC-MS (m/z): 520 [M+1]+; 1H-NMR (MeOD, 400 MHz) major characteristic peaks: 1.29 (br s, 4H), 1.99-2.07 (m, 1H), 2.18-2.26 (m, 1H), 2.56-2.73 (m, 6H), 3.12-3.16 (m, 1H), 3.34-4.49 (m, 4H), 4.20 (s, 4H), 4.23-4.28 (m, 1H), 4.78 (s, 1H), 6.76-6.82 (m, 3H), 6.88 (s, 1H), 7.00-7.04 (m, 1H), 7.09-7.14 (m, 1H), 7.31 (d, J=6.0 Hz, 1H), 7.60-7.64 (m, 2H). Chiral-HPLC conditions: solvent MeOH (0.5% DEA), column AS-H 250*4.6 mm 5 μm, Rt: 4.46 min.

Compound 14D. LC-MS (m/z): 520 [M+1]+; 1H-NMR (MeOD, 400 MHz) major characteristic peaks: 1.81 (br s, 4H), 1.12-2.24 (m, 2H), 2.60-3.00 (m, 6H), 3.01-3.05 (m, 1H), 3.11-3.15 (m, 1H), 3.34-3.53 (m, 3H), 4.14-4.27 (m, 5H), 4.80 (s, 1H), 6.76-6.81 (m, 3H), 6.89 (s, 1H), 7.00-7.03 (m, 1H), 7.10-7.16 (m, 1H), 7.30 (d, J=10.0 Hz, 1H), 7.61-7.66 (2H). Chiral-HPLC conditions: solvent MeOH (0.5% DEA), column AS-H 250*4.6 mm 5 μm, Rt: 6.11 min.

Example 15

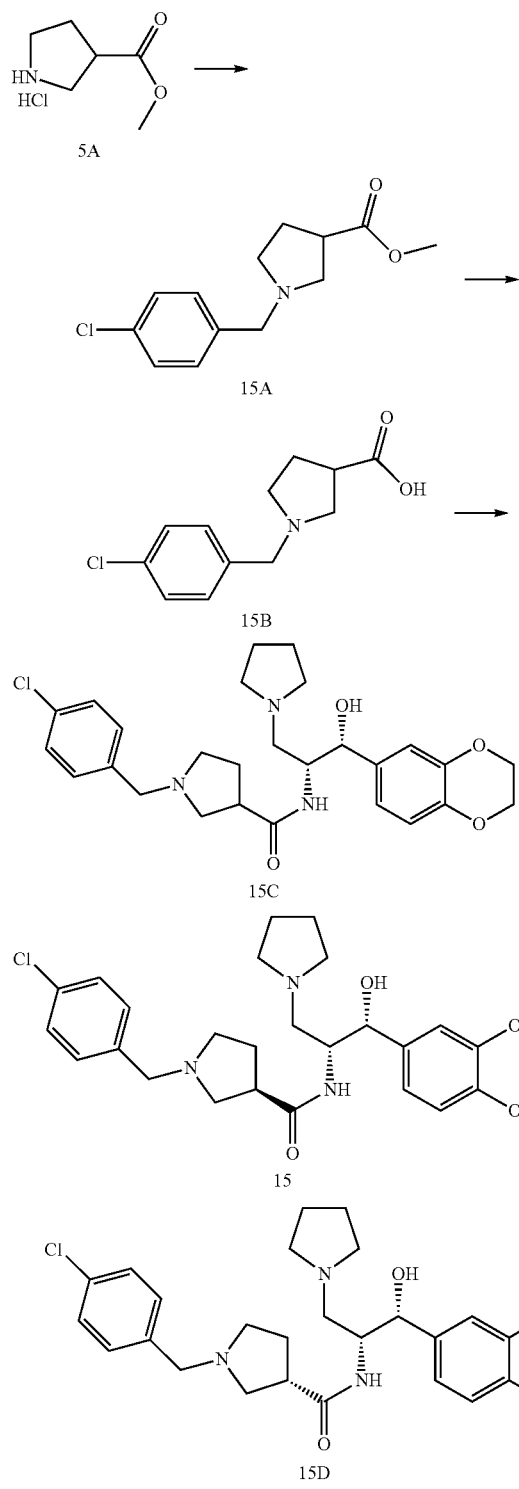

2.43-2.48 (m, 1H), 3.02-3.04 (m, 1H), 3.17-3.20 (m, 1H), 3.26-3.85 (m, 3H), 3.48-3.51 (m, 1H), 3.68 (s, 3H), 3.99-4.02 (m, 2H).

Compound 15B was synthesized, by employing the procedure described for Compound 5C using Compound 15A in lieu of Compound 5B. LC-MS (m/z): 240 [M+1]⁺.

Compounds 15 and 15D were synthesized, by employing the procedures described for Compound 7 using Compound 15B in lieu of Compound 7B.

Compound 15. LC-MS (m/z): 499 [M+1]⁺; ¹H-NMR (MeOD, 400 MHz) major characteristic peaks: δ (ppm) 1.60-1.71 (m, 2H), 1.85-1.95 (m, 8H), 2.35-2.52 (m, 8H), 2.62-2.76 (m, 3H), 3.46-3.51 (m, 2H), 4.04-4.08 (m, 5H), 4.71 (d, J=2.8 Hz, 1H), 6.61-6.66 (m, 2H), 6.74 (s, 1H), 7.21-7.26 (m, 4H). Chiral-HPLC conditions: solvent: solvent: n-hexane (0.1% DEA):EtOH (0.1% DEA) 85:15, column: AS-H 250*4.6 mm 5 µm, Rt: 7.523 min.

Compound 15D. LC-MS (m/z): 499 [M+1]⁺; ¹H-NMR (MeOD, 400 MHz) major characteristic peaks: δ (ppm) 1.60-1.73 (m, 2H), 1.91-1.99 (m, 8H), 2.40-2.59 (m, 9H), 2.65-2.76 (m, 2H), 3.41-3.61 (m, 2H), 4.074-4.08 (m, 5H), 4.70 (d, J=2.8 Hz, 1H), 6.63-6.69 (m, 2H), 6.75 (s, 1H), 7.19-7.26 (m, 4H). Chiral-HPLC conditions: solvent: n-hexane (0.1% DEA):EtOH (0.1% DEA) 85:15, column: AS-H 250*4.6 mm 5 µm, R.t.: 11.747 min.

Example 16

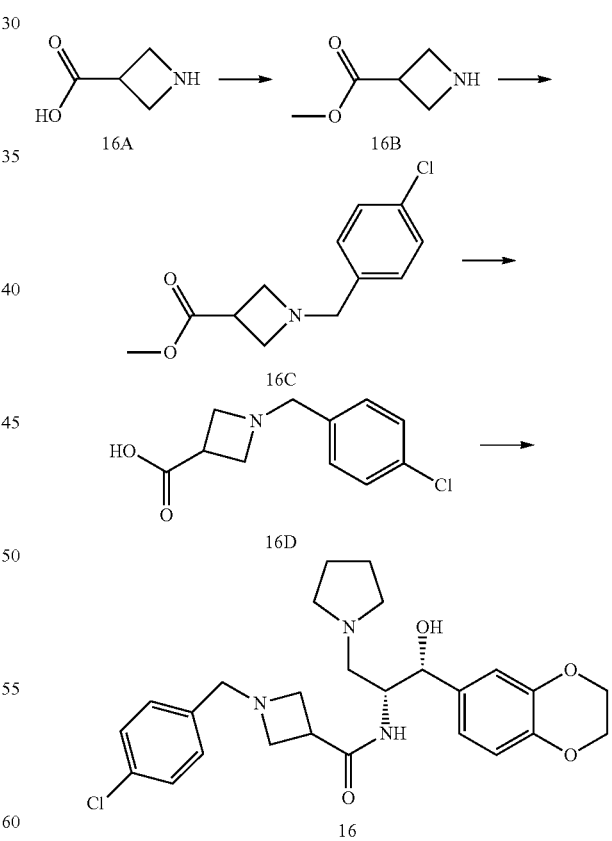

Compound 15A was synthesized, by employing the procedure described for Compound 9B using 4-chlorobenzaldehyde in lieu of tetrahydro-4H-pyran-4-one. LC-MS (m/z): 254 [M+1]⁺; ¹H-NMR (CDCl₃, 400 MHz) major characteristic peaks: δ (ppm) 1.94-2.03 (m, 4H), 2.22-2.25 (m, 1H), Compound 16B was synthesized, by employing the procedure described for Compound 5A using Compound 16A in lieu of Compound 1A. LC-MS (m/z): 115 [M+1]⁺; ¹H-NMR (CDCl₃, 400 MHz) major characteristic peaks: δ (ppm) 3.79 (s, 3H), 3.78-3.82 (m, 1H), 4.27-4.34 (m, 4H).

Compound 16C was synthesized, by employing the procedure described for Compound 9B using 4-chlorobenzaldehyde and Compound 16B in lieu of tetrahydro-4H-pyran-4-one and Compound 5A. LC-MS (m/z): 240 [M+1]+; 1H-NMR (CDCl3, 400 MHz) major characteristic peaks: δ (ppm) 3.30-3.34 (m, 3H), 3.61-3.58 (m, 4H), 3.63 (s, 3H), 7.14-7.23 (m, 4H).

Compound 16D was synthesized, by employing the procedure described for Compound 5C using Compound 16C in lieu of Compound 5B. LC-MS (m/z): 226 [M+1]+.

Compound 16 was synthesized, by employing the procedure described for Compound 7 using Compound 16D in lieu of Compound 7B. LC-MS (m/z): 486 [M+1]+; 1H-NMR (MeOD, 400 MHz) major characteristic peaks: δ (ppm) 1.80-1.81 (m, 4H), 2.52-2.57 (m, 1H), 2.63-2.70 (m, 4H), 2.87-2.90 (m, 2H), 3.11-3.18 (m, 2H), 3.34-3.35 (m, 2H), 3.48-3.52 (m, 2H), 4.00-4.16 (m, 5H), 4.73 (d, J=2.8 Hz, 1H), 6.73-6.74 (m, 2H), 6.80 (s, 1H), 7.24-7.32 (m, 4H).

Example 17

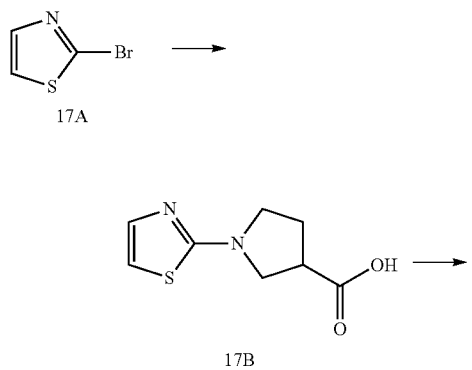

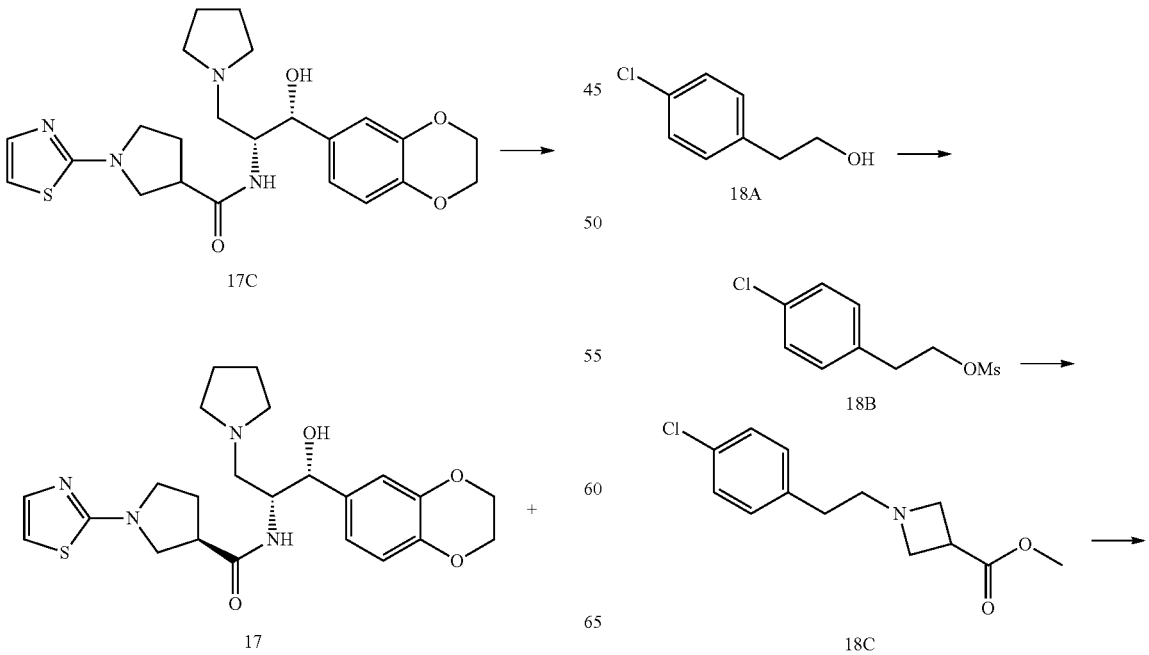

Compound 17B was synthesized, by employing the procedure described for Compound 1B using Compound 17A in lieu of 1-chloro-4-iodobenzene. LC-MS (m/z): 197 [M−1]+; 1H-NMR (DMSO-d6, 400 MHz) major characteristic peaks: δ (ppm) 2.20 (m, 2H), 3.23 (m, 1H), 3.40 (m, 2H), 3.56 (m, 2H), 6.72 (d, J=3.6 Hz, 1H), 7.14 (d, J=3.2 Hz, 1H), 12.57 (s, 1H).

Compounds 17 and 17D were synthesized, by employing the procedures described for Compound 1 using 17B in lieu of Compound 1B.

Compound 17. LC-MS (m/z): 459 [M+1]+; 1H-NMR (MeOD, 400 MHz) major characteristic peaks: δ (ppm) 2.04-2.15 (m, 6H), 3.17 (m, 3H), 3.31 (m, 3H), 3.43 (m, 1H), 3.70 (m, 6H), 4.20 (s, 4H), 4.47 (d, J=10.8 Hz, 1H), 4.80 (s, 1H), 6.79 (d, J=8.0 Hz, 1H), 6.89 (s, 2H), 6.98 (d, J=4.8 Hz, 1H), 7.36 (d, J=4.0 Hz, 1H).

Compound 17D. LC-MS (m/z): 459 [M+1]+; 1H-NMR (MeOD, 400 MHz) major characteristic peaks: δ (ppm) 1.86 (m, 1H), 2.03 (m, 4H), 2.34 (m, 1H), 3.18 (m, 2H), 3.32-3.43 (m, 5H), 3.57-3.77 (m, 6H), 4.23 (s, 4H), 4.51 (d, J=10.8 Hz, 1H), 4.83 (s, 1H), 6.79 (d, J=8.4 Hz, 1H), 6.89 (s, 2H), 6.98 (d, J=4.8 Hz, 1H), 7.34 (d, J=4.4 Hz, 1H).

Example 18

213
-continued

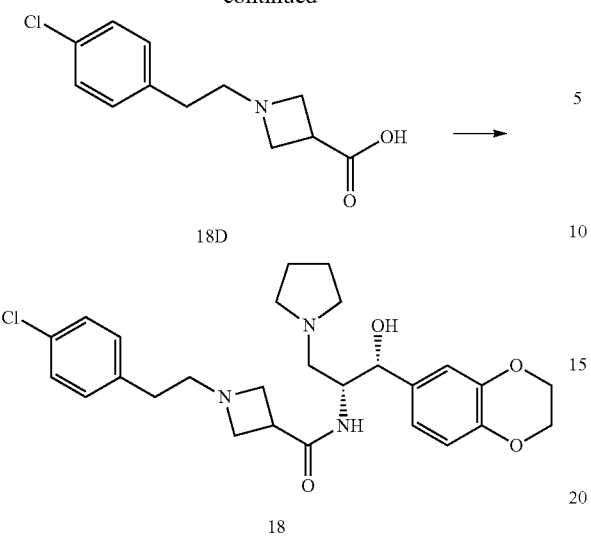

18D

18

Example 19

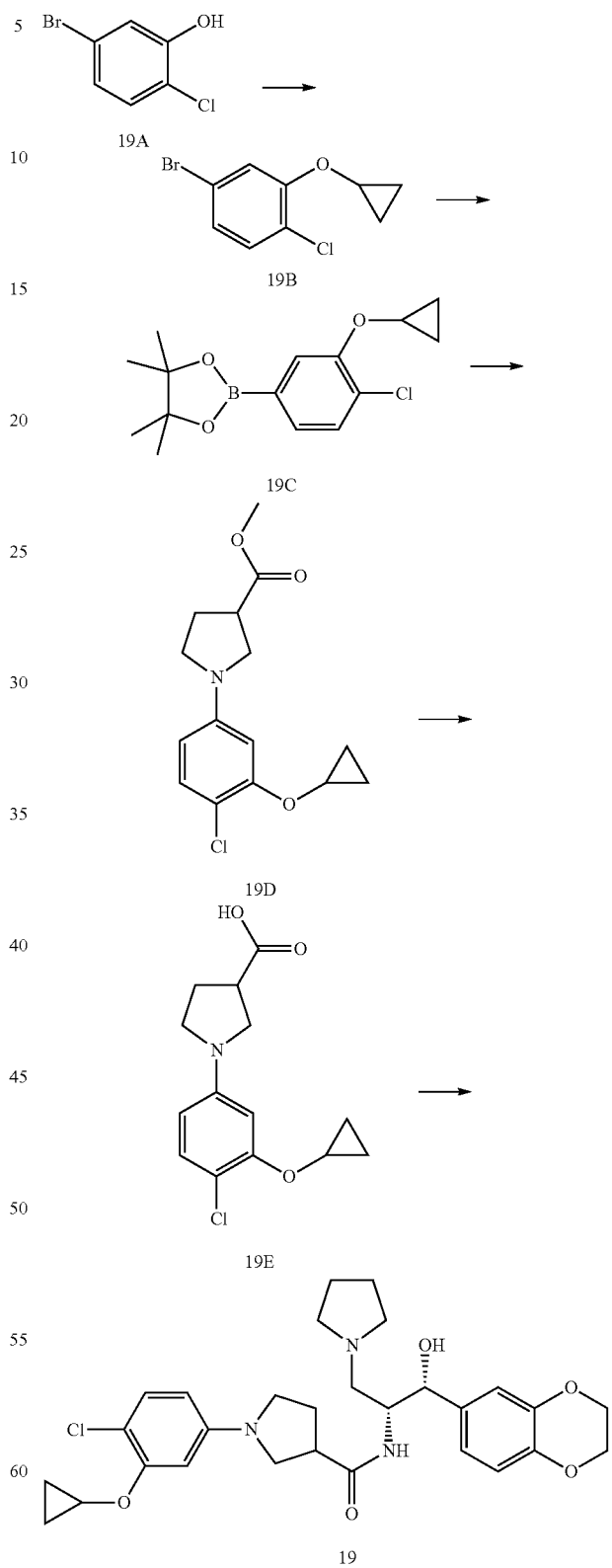

To a solution of Compound 18A (10.0 g, 64 mmol) in THF (100 mL) was added Et$_3$N (19.4 g, 192 mmol). The mixture was cooled to 0° C. and MsCl (8.1 g, 70.5 mmol) was added slowly. The mixture was stirred about half an hour at 25° C. The mixture was diluted with ethyl acetate (500 mL), washed with water (100 mL×2) and brine (100 mL), dried over sodium sulfate, and concentrated. The crude product was purified with column chromatography on silica gel (eluted with ethyl acetate in petroleum ether, from 10% to 20% v/v) to give Compound 18B. LC-MS (m/z): 235 [M+1]$^+$; $^1$H-NMR (DMSO-d$_6$, 400 MHz): major characteristic peaks δ (ppm) 2.99 (t, J=6.8 Hz, 2H), 3.11 (s, 3H), 4.41 (t, J=7.2 Hz, 2H), 7.32-7.39 (m, 4H).

A mixture of Compound 18B (2.0 g, 8.5 mmol), Et$_3$N (2.6 g, 25.6 mmol) and methyl azetidine-3-carboxylate hydrochloride (1.3 g, 8.5 mmol) in THF (20 mL) was stirred under N$_2$ at 60° C. overnight. The mixture was diluted with ethyl acetate (300 mL), washed with water (100 mL×2) and brine (100 mL), dried over sodium sulfate, and concentrated. The crude product was purified with column chromatography on silica gel (methanol in dicholromethane, from 5% to 10% v/v) to give Compound 18C. LC-MS (m/z): 254 [M+1]$^+$; $^1$H-NMR (CDCl$_3$, 400 MHz): major characteristic peaks δ (ppm) 2.62-2.66 (m, 4H), 3.25-3.26 (m, 3H), 3.48-3.51 (m, 2H), 3.70 (s, 3H), 7.09-7.12 (m, 2H), 7.23-7.25 (m, 2H).

Compound 18D was synthesized, by employing the procedure described for Compound 5C using Compound 18C in lieu of Compound 5B. LC-MS (m/z): 240 [M+1]$^+$; $^1$H-NMR (DMSO-d$_6$, 400 MHz) major characteristic peaks: δ (ppm) 2.72-2.75 (m, 2H), 2.99-3.03 (m, 2H), 3.20-3.24 (m, 1H), 3.58-3.63 (m, 2H), 3.76-3.78 (m, 2H), 7.29-7.31 (m, 2H), 7.35-7.37 (m, 2H).

Compound 18 was synthesized, by employing the procedure described for Compound 1 using Compound 18D in lieu of Compound 1B. LC-MS (m/z): 500 [M+1]$^+$; $^1$H-NMR (MeOD, 400 MHz) major characteristic peaks: δ (ppm) 2.01-2.13 (m, 4H), 2.84-2.87 (m, 2H), 3.13-3.15 (m, 2H), 3.36-3.41 (m, 3H), 3.54-3.56 (m, 2H), 3.66-3.75 (m, 3H), 4.11-4.13 (m, 1H), 4.20 (s, 5H), 4.34-4.39 (m, 1H), 4.46-4.48 (m, 1H), 4.76 (d, J=3.2 Hz, 1H), 6.78-6.90 (m, 3H), 7.27 (d, J=8.4 Hz, 2H), 7.36 (d, J=8.4 Hz, 2H).

A mixture of Compound 19A (2.0 g, 10 mmol), bromocyclopropane (2.4 g, 20 mmol), Cs$_2$CO$_3$ (9.8 g, 30 mmol) in DMSO (40 mL) was stirred at 170° C. for 2 days under high pressure. The mixture was cooled to room temperature and filtered through celite. The filtrate was diluted with ethyl acetate (100 mL), washed with brine (100 mL×2), dried over sodium sulfate, and concentrated. The crude was purified with column chromatography on silica gel (petroleum ether, 100% v/v) to render Compound 19B. LC-MS (m/z): 247 [M+1]$^+$; $^1$H-NMR (CDCl$_3$, 400 MHz) major characteristic peaks: δ (ppm) 0.78-0.82 (m, 4H), 3.71-3.73 (m, 1H), 6.95-6.95 (m, 1H), 7.13-7.18 (m, 1H), 7.34-7.36 (m, 1H).

A mixture of Compound 19B (1.0 g, 4.1 mmol), AcOK (1.2 g, 12.2 mmol), 4,4,4',4',5,5,5',5'-octamethyl-2,2'-bi(1,3,2-dioxaborolane) (1.5 g, 6.1 mmol), and Pd(dppf)Cl$_2$ (250 mg, 0.36 mmol) in 1,4-dioxane (50 mL) under N$_2$ protection was stirred at 100° C. for 18 h. The reaction mixture was cooled to room temperature and filtered through celite. The filtrate was diluted with ethyl acetate (100 mL), washed with brine (100 mL×2), dried over sodium sulfate, and concentrated. The crude was purified with column chromatography on silica gel (ethyl acetate in petroleum ether, from 1% to 10% v/v) to yield Compound 19C. LC-MS (m/z): 295 [M+1]$^+$; $^1$H-NMR (CDCl$_3$, 400 MHz) major characteristic peaks: δ (ppm) 0.78-0.82 (m, 4H), 1.27 (s, 12H), 3.82-3.85 (m, 1H), 7.27 (s, 2H), 7.57 (s, 1H).

To a solution of Compound 19C (500 mg, 1.7 mmol), methyl pyrrolidine-3-carboxylate (220 mg, 1.7 mmol), 4A molecular sieves (200 mg) and Cu(OAc)$_2$ (305 mg, 1.7 mmol) in DCM (10 mL) was added triethylamine (0.5 mL, 3.4 mmol). The reaction mixture was stirred at 30° C. equipped with a drying tube for 2 days. The reaction mixture was filtered, the filtrate was concentrated, and the residue was purified with column chromatography on silica gel (ethyl acetate in petroleum ether, from 1% to 5% v/v) to afford Compound 19D. LC-MS (m/z): 296 [M+1]$^+$; $^1$H-NMR (CDCl$_3$, 400 MHz) major characteristic peaks: δ (ppm) 0.73-0.76 (m, 4H), 2.28-2.30 (m, 2H), 3.24-3.35 (m, 3H), 3.49-3.52 (m, 2H), 3.78 (s, 3H), 3.82-3.85 (m, 1H), 6.82-6.85 (m, 2H), 7.18 (s, 1H).

Compound 19E was synthesized, by employing the procedure described for Compound 5C using Compound 19D in lieu of Compound 5B. LC-MS (m/z): 262 [M+1]$^+$.

Compound 19 was synthesized, by employing the procedure described for Compound 1 using Compound 19E in lieu of Compound 1B. LC-MS (m/z): 542 [M+1]$^+$; $^1$H-NMR (CDCl$_3$, 400 MHz) major characteristic peaks: δ (ppm) 0.76-0.80 (m, 4H), 1.68-1.70 (m, 4H), 2.08-2.10 (m, 3H), 2.56-2.89 (m, 7H), 3.19-3.34 (m, 4H), 3.70 (m, 1H), 4.15 (m, 5H), 4.65-4.89 (m, 1H), 5.99-6.10 (m, 2H), 6.40-6.41 (m, 1H), 6.73-6.75 (m, 3H), 7.06-7.07 (m, 1H).

Example 20

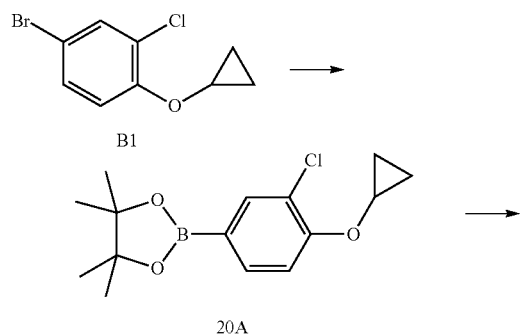

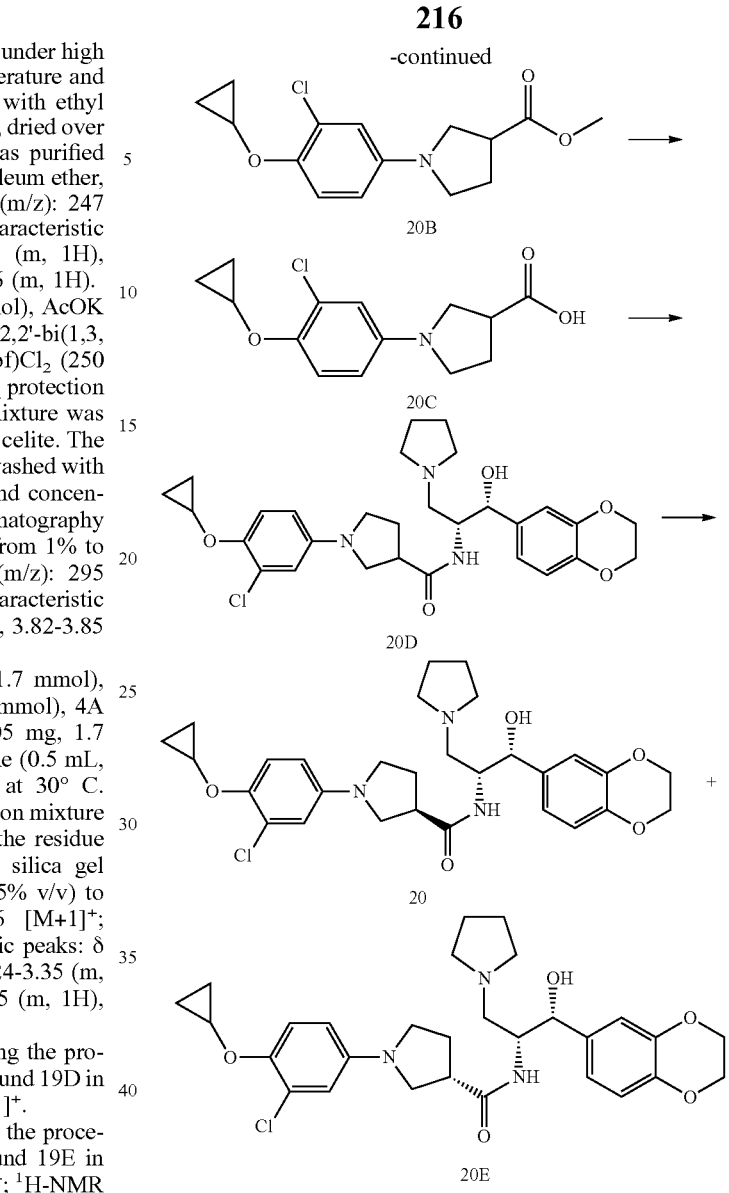

Compound 20A was synthesized, by employing the procedure described for Compound 19C using 4-bromo-2-chloro-1-cyclopropoxybenzene in lieu of Compound 19B. LC-MS (m/z): 295 [M+1]$^+$; $^1$H-NMR (CDCl$_3$, 400 MHz) major characteristic peaks: δ (ppm) 0.84-0.88 (m, 4H), 1.33 (s, 12H), 3.80-3.84 (m, 1H), 7.27 (d, J=8.4 Hz, 1H), 7.67 (dd, J=8, 1.6 Hz, 1H), 7.78 (d, J=8.6 Hz, 1H).

Compound 20B was synthesized, by employing the procedure described for Compound 19D using Compound 20A in lieu of Compound 19C. LC-MS (m/z): 296 [M+1]$^+$; $^1$H-NMR (CDCl$_3$, 400 MHz) major characteristic peaks: δ (ppm) 0.70-0.85 (m, 4H), 2.26-2.32 (m, 2H), 3.19-3.37 (m, 3H), 3.47-3.49 (m, 2H), 3.73 (s, 3H), 3.47-3.77 (m, 1H), 6.43 (dd, J=9.2, 3.2 Hz, 1H), 6.59 (d, J=3.2 Hz, 1H), 7.16 (d, J=8.4 Hz, 1H).

Compound 20C was synthesized, by employing the procedure described for Compound 5C using Compound 20B in lieu of Compound 5B. LC-MS (m/z): 262 [M+1]$^+$.

Compound 20 and 20E were synthesized, by employing the procedure described for Compound 1 using Compound 20C in lieu of Compound 1B.

Compound 20. LC-MS (m/z): 542 [M+1]$^+$; $^1$H-NMR (MeOD, 400 MHz) major characteristic peaks: δ (ppm)

0.62-0.64 (m, 4H), 1.68-1.72 (m, 4H), 1.92-2.11 (m, 2H), 2.49-2.83 (m, 7H), 2.95-3.03 (m, 1H), 3.07-3.13 (m, 1H), 3.16-3.19 (m, 1H), 3.25-3.29 (m, 1H), 3.67-3.72 (m, 1H), 4.07-4.20 (m, 5H), 4.69 (d, J=3.2 Hz, 1H), 6.38 (dd, $J_1$=9.2 Hz, $J_2$=3.2 Hz, 1H), 6.49 (d, J=2.8 Hz, 1H), 6.65-6.70 (m, 2H), 6.78 (d, J=2 Hz, 1H), 7.09 (d, J=8.8 Hz, 1H). Chiral-HPLC conditions: solvent: MeOH (0.1% DEA), column: OJ-H 250*4.6 mm 5 μm, Rt: 3.7 min.

Compound 20E. LC-MS (m/z): 542 [M+1]$^+$; $^1$H-NMR (MeOD, 400 MHz) major characteristic peaks: δ (ppm) 0.60-0.62 (m, 4H), 1.71 (m, 4H), 1.79-2.09 (m, 3H), 2.47-2.65 (m, 6H), 2.97-3.01 (m, 1H), 3.07-3.17 (m, 2H), 3.23-3.25 (m, 1H), 3.65-3.69 (m, 1H), 4.09-4.16 (m, 5H), 4.67 (d, J=3.2 Hz, 1H), 6.37 (dd, $J_1$=9.2 Hz, $J_2$=2.8 Hz, 1H), 6.45 (d, J=2.8 Hz, 1H), 6.64-6.70 (m, 2H), 6.76 (d, J=2 Hz, 1H), 7.07 (d, J=8.8 Hz, 1H). Chiral-HPLC conditions: solvent: MeOH (0.1% DEA), column: OJ-H 250*4.6 mm 5 μm, Rt: 5.9 min.

Example 21

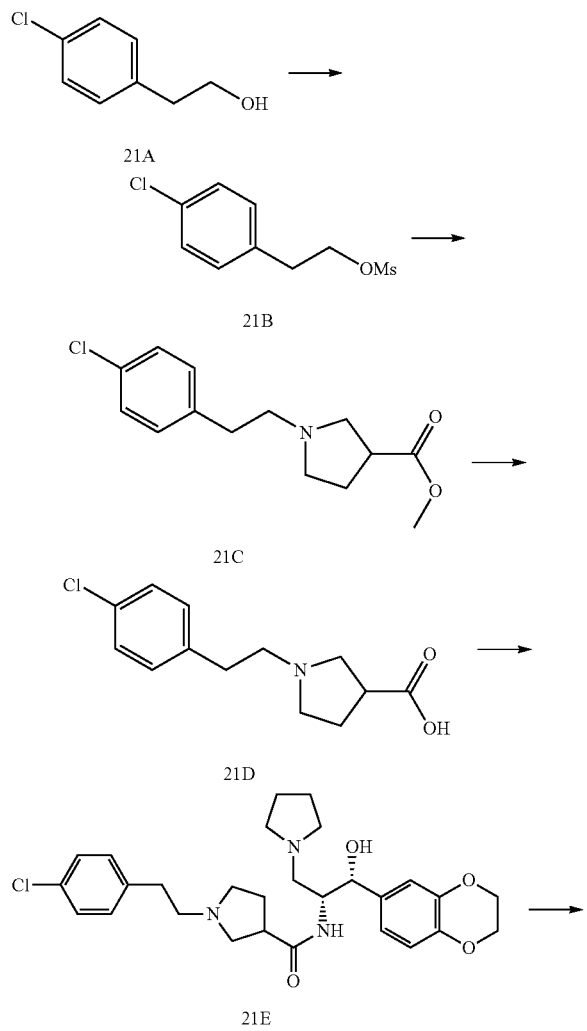

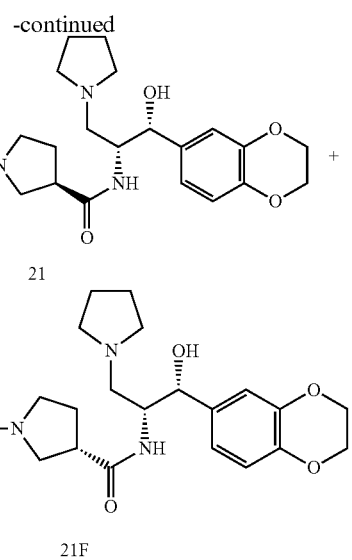

Compound 21B was synthesized, by employing the procedure described for Compound 18B using Compound 21A in lieu of Compound 18A. LC-MS (m/z): 235 [M+1]$^+$; $^1$H-NMR (DMSO-$d_6$, 400 MHz) major characteristic peaks: δ (ppm) 2.99 (t, J=6.8 Hz, 2H), 3.11 (s, 3H), 4.41 (t, J=7.2 Hz, 2H), 7.32-7.39 (m, 4H).

Compound 21C was synthesized, by employing the procedure described for Compound 18C using Compound 21B in lieu of Compound 18B. LC-MS (m/z): 268 [M+1]$^+$; $^1$H-NMR (CDCl$_3$, 400 MHz) major characteristic peaks: δ (ppm) 2.10-2.13 (m, 2H), 2.56-2.78 (m, 7H), 2.90-2.94 (m, 1H), 3.03-3.06 (m, 1H), 3.70 (s, 3H), 7.12-7.14 (m, 2H), 7.23-7.25 (m, 2H).

Compound 21D was synthesized, by employing the procedure described for Compound 5C using Compound 21C in lieu of Compound 5B. LC-MS (m/z): 254 [M+1]$^+$; 1H-NMR (DMSO-$d_6$, 400 MHz): δ (ppm) 1.95-2.00 (m, 2H), 2.67-2.69 (m, 1H), 2.77-2.85 (m, 6H), 2.90-2.97 (m, 2H), 7.26-7.27 (m, 2H), 7.33-7.35 (m, 2H).

Compound 21 and 21F were synthesized, by employing the procedure described for Compound 1 using Compound 21D in lieu of Compound 1B.

Compound 21. LC-MS (m/z): 514 [M+1]$^+$; $^1$H-NMR (MeOD, 400 MHz) major characteristic peaks: δ (ppm) 1.79 (m, 4H), 1.88 (m, 2H), 2.33 (m, 1H), 2.56-2.77 (m, 14H), 4.17 (s, 5H), 4.78 (d, J=2.8 Hz, 1H), 6.78 (m, 2H), 6.85 (s, 1H), 7.21 (m, 2H), 7.27 (m, 2H). Chiral-HPLC conditions, solvent:EtOH (0.1% DEA), column: OZ-H 250*4.6 mm 5 μm, Rt: 11.44 min.

Compound 21F. LC-MS (m/z): 514 [M+1]$^+$; $^1$H-NMR (MeOD, 400 MHz) major characteristic peaks: δ (ppm) 1.78 (m, 5H), 2.03 (m, 1H), 2.55-2.87 (m, 15H), 4.18 (s, 5H), 4.75 (d, J=3.6 Hz, 1H), 6.77 (m, 2H), 6.85 (s, 1H), 7.19 (m, 2H), 7.25 (m, 2H). Chiral-HPLC conditions, solvent:EtOH (0.1% DEA), column: OZ-H 250*4.6 mm 5 μm, Rt: 11.64 min.

Example 22

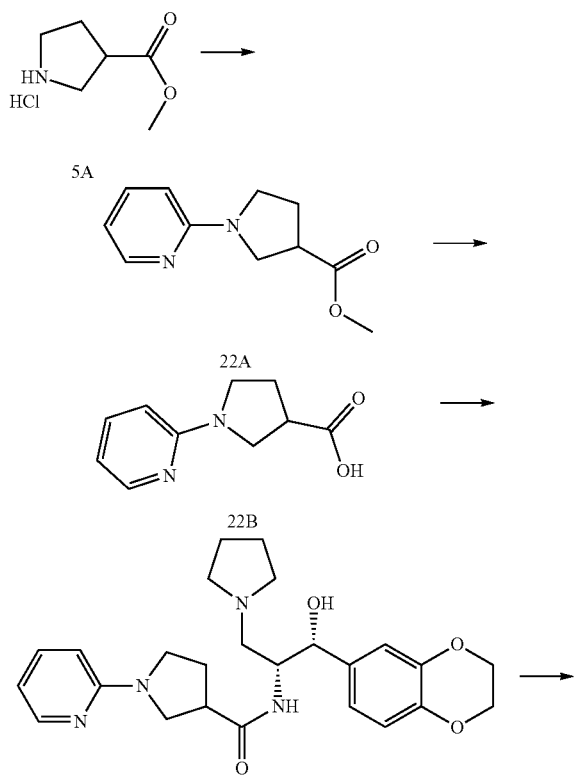

sulfate, and concentrated. The crude was purified with column chromatography on silica gel (ethyl acetate in petroleum ether, from 1% to 10% v/v) to afford Compound 22A. LC-MS (m/z): 207 [M+1]+; 1H-NMR (CDCl3, 400 MHz) major characteristic peaks: δ (ppm) 2.19-2.25 (m, 2H), 3.12-3.16 (m, 1H), 3.39-3.43 (m, 1H), 3.52-3.54 (m, 1H), 3.59-3.70 (m, 5H), 6.28 (d, J=8.8 Hz, 1H), 6.46-6.49 (m, 1H), 7.34-7.39 (m, 1H), 8.07-8.08 (d, J=4.8 Hz, 1H).

Compound 22B was synthesized, by employing the procedure described for Compound 5C using Compound 22A in lieu of Compound 5B. LC-MS (m/z): 193 [M+1]+.

Compound 22 and 22D were synthesized, by employing the procedure described for Compound 7 using Compound 22B in lieu of Compound 7B.

Compound 22. LC-MS (m/z): 453 [M+1]+; 1H-NMR (MeOD, 400 MHz) major characteristic peaks: δ (ppm) 1.72-1.73 (m, 4H), 2.06-2.07 (m, 2H), 2.54-2.70 (m, 6H), 3.07-3.10 (m, 2H), 3.30-3.32 (m, 1H), 3.48-3.50 (m, 2H), 4.08-4.15 (m, 5H), 4.68 (d, J=2.8 Hz 1H), 6.36-6.38 (m, 1H), 6.47-6.48 (m, 1H), 6.64-6.77 (m, 2H), 6.77 (s, 1H), 7.41-7.43 (m, 1H), 7.89-8.00 (m, 1H). Chiral-HPLC conditions: solvent: IPA (0.1% DEA), column: OJ-H 250*4.6 mm 5 μm, Rt: 3.64 min.

Compound 22D. LC-MS (m/z): 453 [M+1]+; 1H-NMR (MeOD, 400 MHz) major characteristic peaks: δ (ppm) 1.72-1.73 (m, 4H), 1.83-1.86 (m, 1H), 2.07-2.08 (m, 1H), 2.56-2.71 (m, 6H), 3.00-3.04 (m, 1H), 3.25-3.46 (m, 4H), 4.11-4.18 (m, 5H), 4.68 (d, J=2.8 Hz 1H), 6.35-6.37 (m, 1H), 6.44-6.47 (m, 1H), 6.65-6.72 (m, 2H), 6.78 (s, 1H), 7.38-7.42 (m, 1H), 7.86-7.88 (m, 1H). Chiral-HPLC conditions: solvent: IPA (0.1% DEA), column: OJ-H 250*4.6 mm 5 μm, Rt: 6.18 min.

Example 23

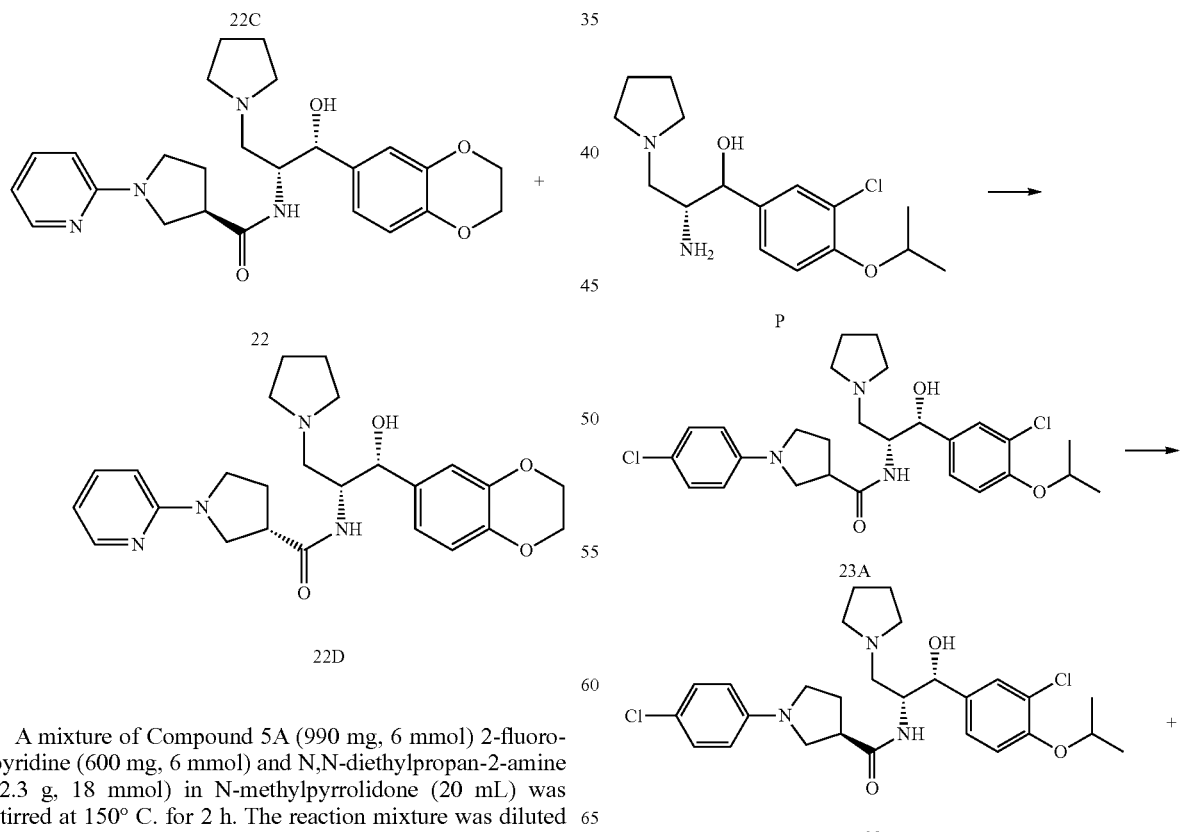

A mixture of Compound 5A (990 mg, 6 mmol) 2-fluoropyridine (600 mg, 6 mmol) and N,N-diethylpropan-2-amine (2.3 g, 18 mmol) in N-methylpyrrolidone (20 mL) was stirred at 150° C. for 2 h. The reaction mixture was diluted with water, and extracted with ethyl acetate (150 mL×3). The extraction was washed with water, dried with sodium

221
-continued

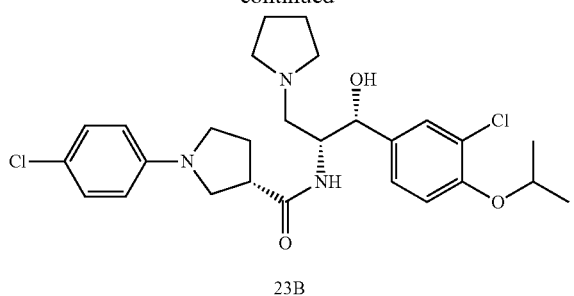

23B

222
-continued

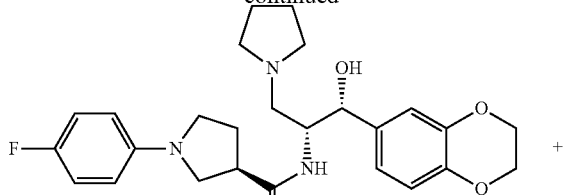

24

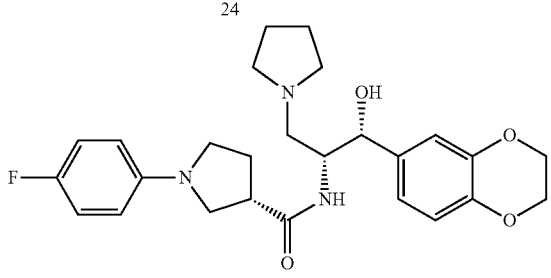

24C

Compound 23 and 23B were synthesized, by employing the procedure described for Compound 1 using Intermediate P in lieu of Compound 1B.

Compound 23. LC-MS (m/z): 520 [M+1]$^+$; $^1$H-NMR (CDCl$_3$, 400 MHz) major characteristic peaks: δ (ppm) 1.32-1.35 (m, 6H), 2.10 (m, 6H), 2.89-2.99 (m, 4H), 3.17-3.30 (m, 4H), 3.64-3.75 (m, 3H), 4.44-4.48 (m, 2H), 4.91 (s, 1H), 6.41 (d, J=8.8 Hz, 2H), 6.82 (d, J=8.4 Hz, 1H), 7.08 (d, J=8.4 Hz, 1H), 7.13 (d, J=8.8 Hz, 2 h), 7.38 (s, 1H), 7.52 (s, 1H), 11.33 (s, 1H); Chiral-HPLC conditions: solvent: MeOH (0.5% DEA), column: OJ-H 250*4.6 mm 5 μm, Rt: 3.36 min.

Compound 23B. LC-MS (m/z): 520 [M+1]$^+$; $^1$H-NMR (CDCl$_3$, 400 MHz) major characteristic peaks: δ (ppm) 1.36-1.37 (m, 6H), 1.79 (m, 4H), 1.98-2.06 (m, 1H), 2.10-2.13 (m, 1H), 2.64-2.70 (m, 4H), 2.85-2.87 (m, 2H), 2.91-2.96 (m, 1H), 3.18-3.24 (m, 1H), 3.31-3.42 (m, 3H), 4.18-4.23 (m, 1H), 4.47-4.53 (m, 1H), 4.98 (d, J=2.4 Hz, 1H), 6.20 (d, J=7.6 Hz, 1H), 6.45 (d, J=9.2 Hz, 2H), 6.83 (d, J=8.4 Hz, 1H), 7.06 (dd, J=8.4, 2.0 Hz, 1H), 7.15 (d, J=8.8 Hz, 1H), 7.36 (d, J=2.0 Hz, 1H); Chiral-HPLC conditions: solvent: MeOH (0.5% DEA), column: OJ-H 250*4.6 mm 5 μm, Rt: 5.14 min.

Example 24

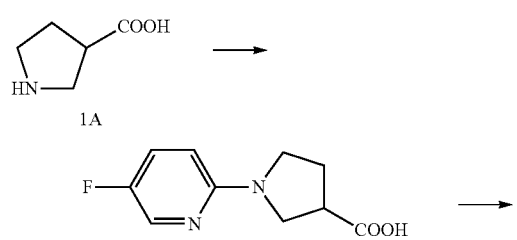

Compound 24A was synthesized, by employing the procedure described for Compound 1B using 1-fluoro-4-iodobenzene in lieu of 1-chloro-4-iodobenzene. LC-MS m/z: 208 [M−1]$^+$; $^1$H-NMR (DMSO-d$_6$, 400 MHz) major characteristic peaks: δ (ppm) 2.12-2.22 (m, 2H), 3.18-3.48 (m, 5H), 6.51-6.55 (m, 2H), 6.99-7.03 (m, 2H), 12.45 (s, 1H)

Compound 24 and 24C were synthesized, by employing the procedures described for Compound 7 using Compound 24A in lieu of Compound 7B.

Compound 24. LC-MS (m/z): 470 [M+1]$^+$; $^1$H-NMR (MeOD, 400 MHz) major characteristic peaks: δ (ppm) 1.84 (m, 4H), 2.05-2.17 (m, 2H), 2.76-2.84 (m, 5H), 2.87-2.97 (m, 2H), 3.17-3.36 (m, 4H), 4.15 (m, 4H), 4.26-4.29 (m, 1H), 4.77-4.78 (d, J=3.2 Hz, 1H), 6.47-6.51 (m, 2H), 6.73-6.77 (m, 2H), 6.86-6.92 (m, 3H). Chiral-HPLC conditions, solvent: EtOH (0.1% DEA), column: OJ-H (250*4.6 mm 5 μm), Rt: 2.62 min.

Compound 24C. LC-MS (m/z): 470 [M+1]$^+$; $^1$H-NMR (MeOD, 400 MHz) major characteristic peaks: δ (ppm) 1.73 (m, 1H), 2.03 (m, 4H), 2.10-2.18 (m, 1H), 3.09-3.11 (m, 4H), 3.16-3.39 (m, 7H), 4.20 (s, 4H), 4.40-4.25 (m, 1H), 4.79-4.80 (d, J=2.4 Hz, 1H), 6.48-6.51 (m, 2H), 6.76-6.91 (m, 5H). Chiral-HPLC conditions, solvent:EtOH (0.1% DEA), column: OJ-H (250*4.6 mm 5 μm), Rt: 3.9 min.

Example 25

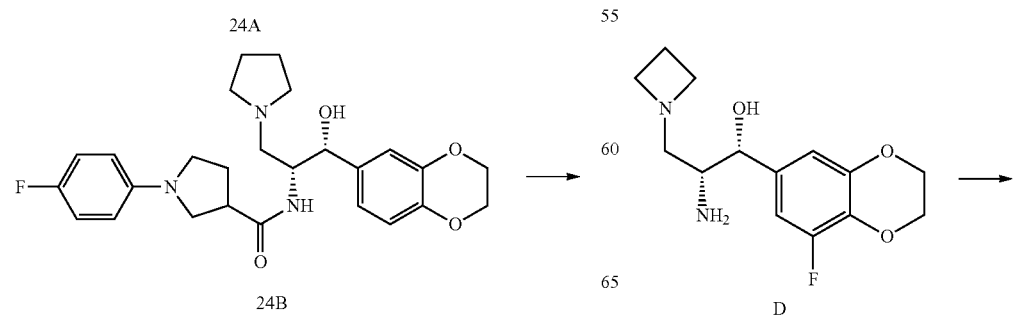

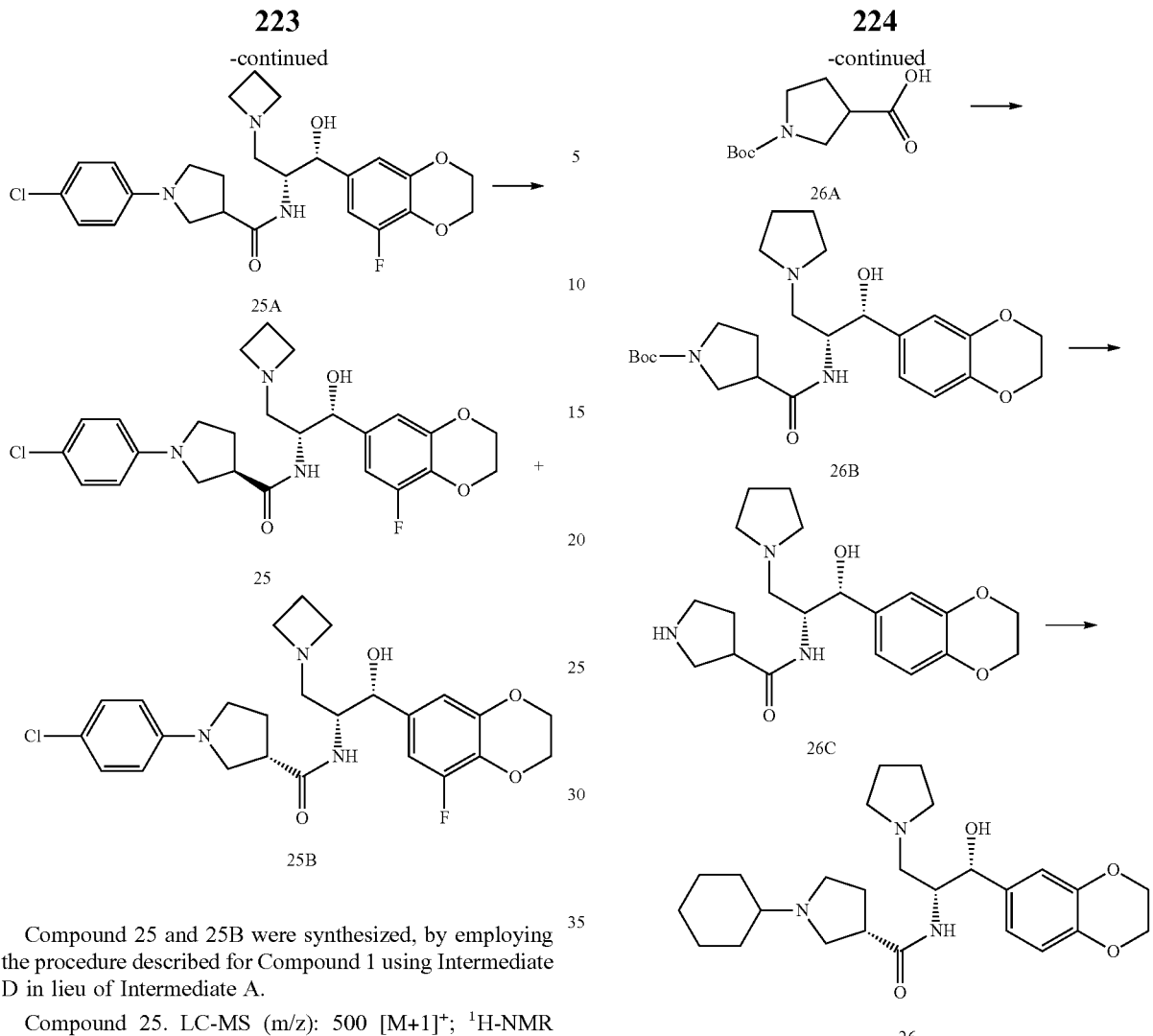

Compound 25 and 25B were synthesized, by employing the procedure described for Compound 1 using Intermediate D in lieu of Intermediate A.

Compound 25. LC-MS (m/z): 500 [M+1]$^+$; $^1$H-NMR (CDCl$_3$, 400 MHz) major characteristic peaks: δ (ppm) 2.07-2.20 (m, 4H), 2.62-2.67 (m, 1H), 2.71-2.75 (m, 1H), 2.84-2.88 (m, 1H), 3.05-3.13 (m, 1H), 3.20-3.29 (m, 2H), 3.31-3.43 (m, 4H), 4.00-4.04 (m, 1H), 4.20-4.26 (m, 4H), 4.71 (s, 1H), 6.49 (d, J=8 Hz, 2H), 6.71 (t, J=12 Hz, 2H), 7.12 (d, J=8 Hz, 2H). Chiral-HPLC conditions, solvent: MeOH (0.5% DEA), column AS-H 250*4.6 mm 5 μm, Rt: 7.05 min.

Compound 25B. LC-MS (m/z): 500 [M+1]$^+$; $^1$H-NMR (CDCl$_3$, 400 MHz) major characteristic peaks: δ (ppm) 1.71-1.91 (m, 4H), 2.01-2.19 (m, 2H), 2.38-2.46 (m, 1H), 2.56-2.63 (m, 1H), 3.06-3.24 (m, 3H), 3.35-3.56 (m, 4H), 4.20-4.27 (m, 5H), 4.79 (s, 1H), 6.50 (d, J=8 Hz, 2H), 6.77 (d, J=8 Hz, 2H), 7.12 (d, J=8 Hz, 2H); Chiral-HPLC conditions, solvent: MeOH (0.5% DEA), column AS-H 250*4.6 mm 5 μm, Rt: 5.52 min.

Example 26

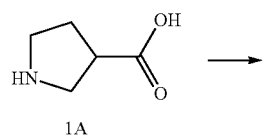

1A

To a solution of Compound 1A (575 mg, 5 mmol) in acetone (5 mL) and water (10 mL) was added Na$_2$CO$_3$ (636 mg, 6 mmol), Boc$_2$O (1.1 g, 5 mmol) at 0° C. The mixture was stirred at 25° C. for 3 h. After evaporation to remove the volitles, the aqueous layer was extracted with DCM (20 mL×2), acidified with 1M HCl, extracted with DCM (20 mL×3). The combined organic layers were dried over anhydrous sodium sulfate, and concentrated to furnish Compound 26A. LC-MS (m/z): 214 [M−1]$^+$; $^1$H-NMR (CDCl$_3$, 400 MHz) major characteristic peaks: δ (ppm) 1.39 (s, 9H), 1.96-1.98 (m, 2H), 3.00-3.02 (m, 1H), 3.25-3.28 (m, 4H), 12.48 (s, 1H).

To a solution of Compound 26A (430 mg, 2 mmol), Intermediate A (556 mg, 2 mmol), EDCI.HCl (576 mg, 3 mmol) and HOBt (405 mg, 3 mmol) in DMF (10 mL) was added DIPEA (774 mg, 6 mmol). The mixture was stirred at 25° C. for 16 h. The mixture was added ethyl acetate (50 mL), washed with water (50 mL×3) and brine (50 mL×1), and dried over anhydrous sodium sulfate. The crude compound was purified with flash column chromatograpny on silica gel (MeOH in DCM, 7% v/v) to afford Compound 26B. LC-MS (m/z): 476 [M+1]$^+$; $^1$H-NMR (CDCl$_3$, 400 MHz) major characteristic peaks: δ (ppm) 1.44 (m, 9H), 1.80 (s, 4H), 2.01 (m, 2H), 2.69 (m, 6H), 3.30 (m, 5H), 4.19 (s, 1H), 4.24 (m, 4H), 4.94 (s, 1H), 6.01 (m, 1H), 6.78 (m, 3H).

To a solution of Compound 26B (400 mg, 0.84 mmol) in DCM (5 mL) was added TFA (0.8 mL) stirred at 25° C. for 3 h, basified by NEt$_3$, and concentrated to obtain Compound 26C. LC-MS (m/z): 376 [M+1]$^+$.

To a solution of Compound 26C (380 mg, 1 mmol) and cyclohexanone (200 mg, 2 mmol) in DCM (5 mL) and MeOH (1 mL) was added NaBH(OAc)$_3$ (640 mg, 3 mmol). The mixture was stirred at 25° C. for 1 h, added NH$_4$OH (2 mL) and water (5 mL), extracted with DCM (20 mL×3). To the mixture was added ethyl acetate (100 mL), washed with water (20 mL×3), brine (20 mL×1), and dried over anhydrous sodium sulfate. The crude product was purified with prep-HPLC to give Compound 26. LC-MS (m/z): 458 [M+1]$^+$; $^1$H-NMR (CDCl$_3$, 400 MHz) major characteristic peaks: δ (ppm) 1.15 (m, 6H), 1.33 (m, 2H), 1.95 (m, 9H), 3.11 (m, 12H), 4.12 (s, 4H), 4.67 (m, 1H), 6.70 (m, 3H), 7.74 (m, 1H), 10.19 (m, 2H).

Example 27

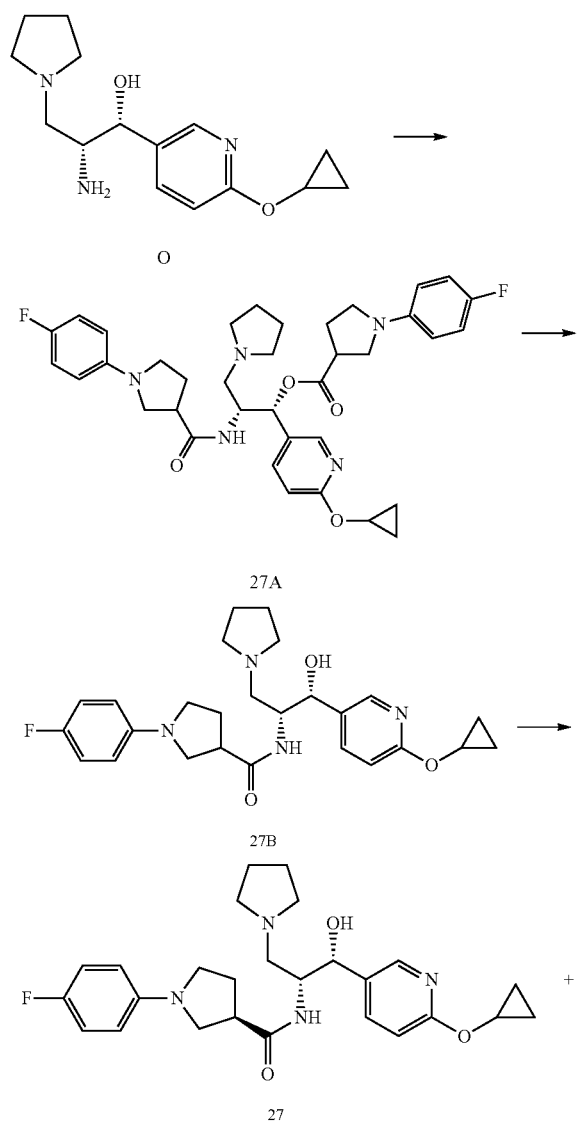

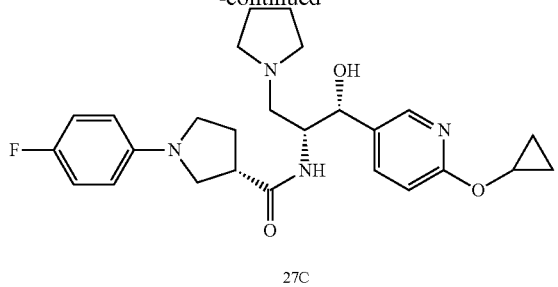

To a solution of Intermediate O (200 mg, 0.72 mmol) in CH$_2$Cl$_2$ (20 mL) was added Compound 24A (300 mg, 1.44 mmol), EDCI.HCl (275 mg, 1.44 mmol) and HOBt (194 mg, 1.44 mmol) at 30° C. The reaction mixture was stirred for 5 h at the same temperature. It was washed with sat aq NaHCO$_3$ (10 mL), dried over anhydrous sodium sulfate, and filtered. The filtrate was evaporated and the resulting residue was purified with prep-TLC (MeOH in CH$_2$Cl$_2$, 10% v/v) to yield Compound 27A. LC-MS (m/z): 660 [M+1]$^+$.

To a solution of Compound 27A (150 mg, 0.23 mmol) in THF (5 mL) was added LiOH (1M solution, 0.46 mL, 0.46 mmol). The reaction mixture was stirred overnight at 30° C., and then neutralized with 1N hydrochloride, diluted with water (4 mL), and extracted with ethyl acetate (20 mL×3). The combined organic layers were dried over anhydrous sodium sulfate and filtered. The filtrate was evaporated to dryness and the crude product was separated with chiral-prep-HPLC (solvent MeOH (0.1% DEA), column IC 4.6*150 mm, 5 μm) to furnish Compound 27 and Compound 27C. For Compound 27, LC-MS (m/z):469 [M+1]$^+$; $^1$H-NMR (CDCl$_3$, 400 MHz) major characteristic peaks: δ (ppm) 0.76-0.81 (m, 4H), 1.72-1.75 (m, 4H), 2.01-2.10 (m, 1H), 2.17-2.22 (m, 1H), 2.59-2.67 (m, 4H), 2.80 (dd, J=13.2, 4.4 Hz, 1H), 2.93 (dd, J=13.2, 4.4 Hz, 1H), 2.95-2.96 (m, 1H), 3.18-3.20 (m, 1H), 2.25-3.28 (m, 2H), 3.35-3.38 (m, 1H), 4.15-4.20 (m, 2H), 5.04 (d, J=2.8 Hz, 1H), 6.40 (d, J=8.0 Hz, 1H), 6.47-6.51 (m, 2H), 6.75 (d, J=8.8 Hz, 1H), 6.92-6.96 (m, 2H), 7.53 (dd, J=8.4, 2.4 Hz, 1H), 8.20 (d, J=2.4 Hz, 1H). For Compound 27C: LC-MS (m/z):469 [M+1]$^+$; $^1$H-NMR (CDCl$_3$, 400 MHz) major characteristic peaks: δ (ppm) 0.73-0.81 (m, 4H), 1.78-2.00 (m, 4H), 2.01-2.19 (m, 2H), 2.64-2.69 (m, 4H), 2.79-2.92 (m, 2H), 2.93-2.98 (m, 1H), 3.18-3.24 (m, 1H), 3.31-3.38 (m, 3H), 4.13-4.21 (m, 2H), 5.03 (d, J=3.2 Hz, 1H), 6.37 (d, J=7.6 Hz, 1H), 6.46-6.49 (m, 2H), 6.71 (d, J=8.8 Hz, 1H), 6.91-6.96 (m, 2H), 7.52 (dd, J=8.8, 2.4 Hz, 1H), 8.17 (d, J=2.4 Hz, 1H).

Example 28

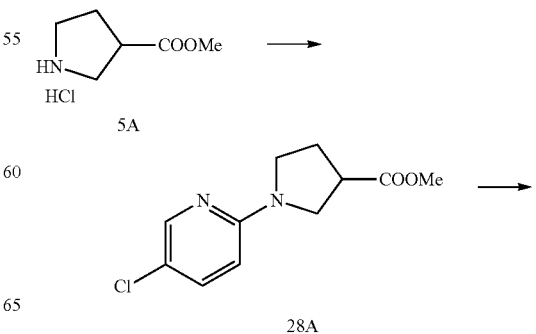

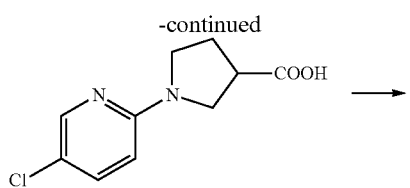

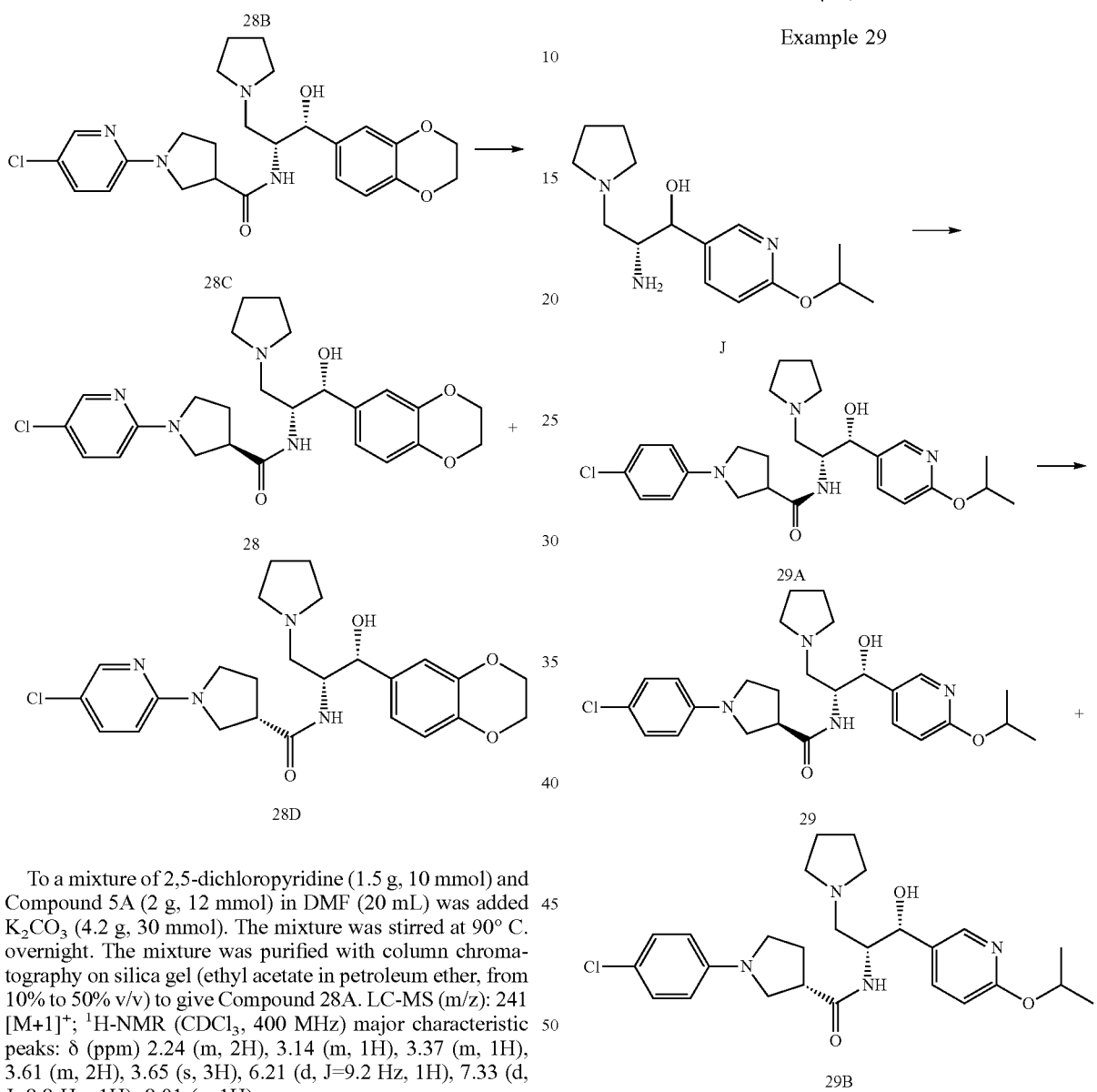

To a mixture of 2,5-dichloropyridine (1.5 g, 10 mmol) and Compound 5A (2 g, 12 mmol) in DMF (20 mL) was added $K_2CO_3$ (4.2 g, 30 mmol). The mixture was stirred at 90° C. overnight. The mixture was purified with column chromatography on silica gel (ethyl acetate in petroleum ether, from 10% to 50% v/v) to give Compound 28A. LC-MS (m/z): 241 [M+1]$^+$; $^1$H-NMR (CDCl$_3$, 400 MHz) major characteristic peaks: δ (ppm) 2.24 (m, 2H), 3.14 (m, 1H), 3.37 (m, 1H), 3.61 (m, 2H), 3.65 (s, 3H), 6.21 (d, J=9.2 Hz, 1H), 7.33 (d, J=8.8 Hz, 1H), 8.01 (s, 1H).

Compound 28B was synthesized, by employing the procedure described for Compound 5C using Compound 28A in lieu of Compound 5B, which was used for the next step without further purification. LC-MS (m/z): 227 [M+1]$^+$.

Compounds 28 and 28D were synthesized, by employing the procedure described for Compound 1 using Compound 28B in lieu of Compound 1B.

Compound 28. LC-MS (m/z): 487 [M+1]$^+$; $^1$H-NMR (CDCl$_3$, 400 MHz) major characteristic peaks: δ (ppm) 1.78 (m, 4H), 2.18 (m, 2H), 2.66 (m, 4H), 2.84 (m, 2H), 2.96 (m, 1H), 3.58 (m, 4H), 4.24 (m, 5H), 4.95 (s, 1H), 6.10 (m, 1H), 6.29 (s, 1H), 6.85 (m, 3H), 7.39 (m, 1H), 8.07 (s, 1H); Chiral-HPLC conditions, solvent:EtOH (0.5% DEA), column: OZ-H 250*4.6 mm 5 μm, Rt.: 3.13 min.

Compound 28D. LC-MS (m/z): 487 [M+1]$^+$; $^1$H-NMR (CDCl$_3$, 400 MHz) major characteristic peaks: δ (ppm) 1.83 (m, 4H), 2.08 (m, 2H), 2.78 (m, 4H), 2.91 (m, 2H), 2.98 (m, 1H), 3.58 (m, 4H), 4.24 (m, 5H), 4.95 (s, 1H), 6.10 (m, 1H), 6.29 (s, 1H), 6.85 (m, 3H), 7.39 (m, 1H), 8.07 (s, 1H). Chiral-HPLC conditions, solvent:EtOH (0.5% DEA), column: OZ-H 250*4.6 mm 5 μm, Rt.: 4.48 min.

Example 29

Compounds 29 and 29B were synthesized, by employing the procedure described for Compound 1 using Intermediate J in lieu of Intermediate A.

Compound 29. LC-MS (m/z): 487 [M+1]$^+$; $^1$H-NMR (MeOD, 400 MHz) major characteristic peaks: δ (ppm) 1.30 (d, J=5.6 Hz, 6H), 1.81-1.83 (m, 4H), 2.11-2.18 (m, 2H), 2.60-2.66 (m, 4H), 2.68-2.72 (m, 2H), 2.83-2.94 (m, 1H), 3.07-3.14 (m, 1H), 3.19-3.25 (m, 1H), 3.33-3.37 (m, 2H), 4.26-4.30 (m, 1H), 4.90 (d, J=2.8 Hz, 1H), 5.12-5.18 (m, 1H), 6.48 (d, J=9.2 Hz, 2H), 6.66 (d, J=8.4 Hz, 1H), 7.11 (d, J=8.8 Hz, 2H), 7.64 (dd, J=8.8, 2.4 Hz, 1H), 8.10 (d, J=2.4 Hz, 1H). Chiral-HPLC conditions, solvent: MeOH (0.5% DEA), column: AD-H 250*4.6 mm 5 μm, Rt: 3.18 min.

Compound 29B. LC-MS (m/z): 487 [M+1]⁺; ¹H-NMR (MeOD, 400 MHz) major characteristic peaks: δ (ppm) 1.31 (d, J=6.0 Hz, 6H), 1.81-1.83 (m, 4H), 1.87-1.93 (m, 1H), 2.11-2.19 (m, 1H), 2.60-2.68 (m, 4H), 2.72-2.81 (m, 2H), 3.08-3.15 (m, 1H), 3.21-3.26 (m, 2H), 3.33-3.40 (m, 2H), 4.26-4.30 (m, 1H), 4.90 (d, J=2.8 Hz, 1H), 5.14-5.20 (m, 1H), 6.48 (d, J=9.2 Hz, 2H), 6.68 (d, J=8.4 Hz, 1H), 7.11 (d, J=9.2 Hz, 2H), 7.66 (dd, J=8.8, 2.4 Hz, 1H), 8.10 (d, J=2.0 Hz, 1H). Chiral-HPLC conditions, solvent: MeOH (0.5% DEA), column: AD-H 250*4.6 mm 5 μm, Rt: 6.16 min.

Example 30

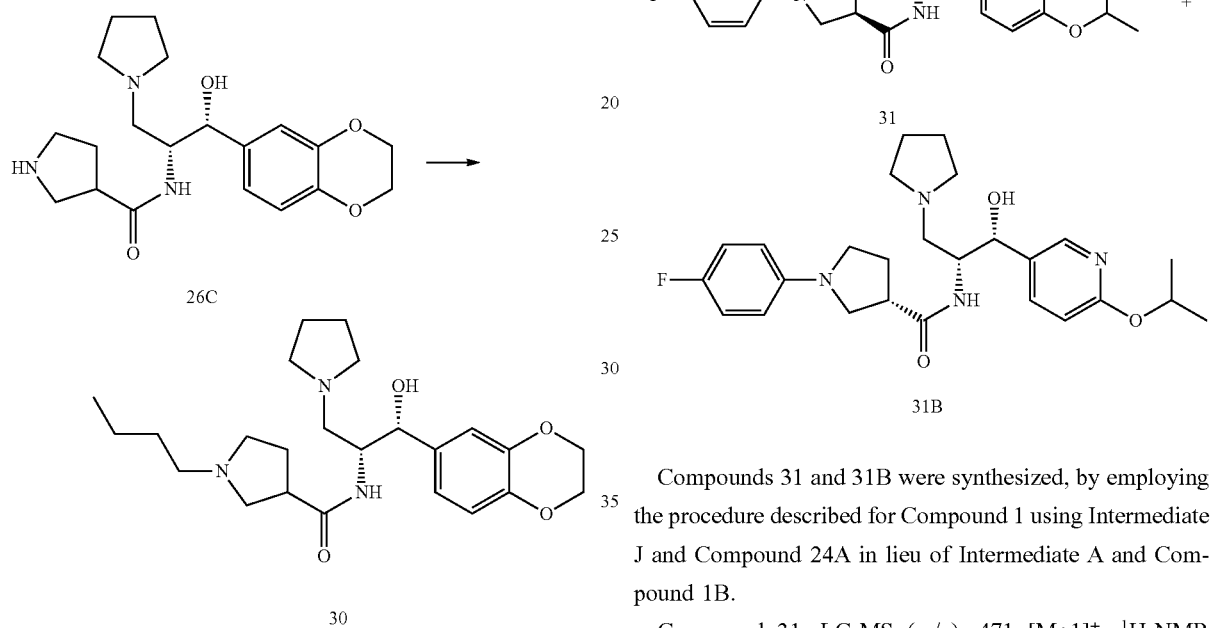

Compound 30 was synthesized, by employing the procedure described for Compound 9B using butyraldehyde and Compound 26C in lieu of tetrahydro-4H-pyran-4-one and Compound 5A. LC-MS (m/z): 432 [M+1]⁺; ¹H-NMR (MeOD, 400 MHz) major characteristic peaks: δ (ppm) 0.89-0.955 (m, 3H), 1.32-1.38 (m, 2H), 1.57-1.63 (m, 2H), 1.87-2.35 (m, 6H), 3.03-3.14 (m, 6H), 3.24-3.82 (m, 7H), 4.15 (d, J=8.1 Hz, 4H), 4.36-4.46 (m, 1H), 4.73 (d, J=2.8 Hz, 1H), 6.74-6.87 (m, 3H).

Example 31

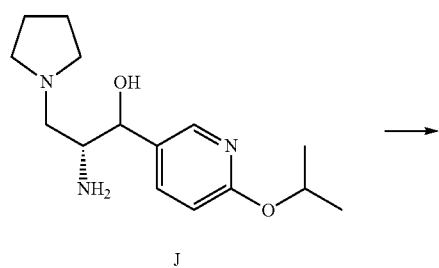

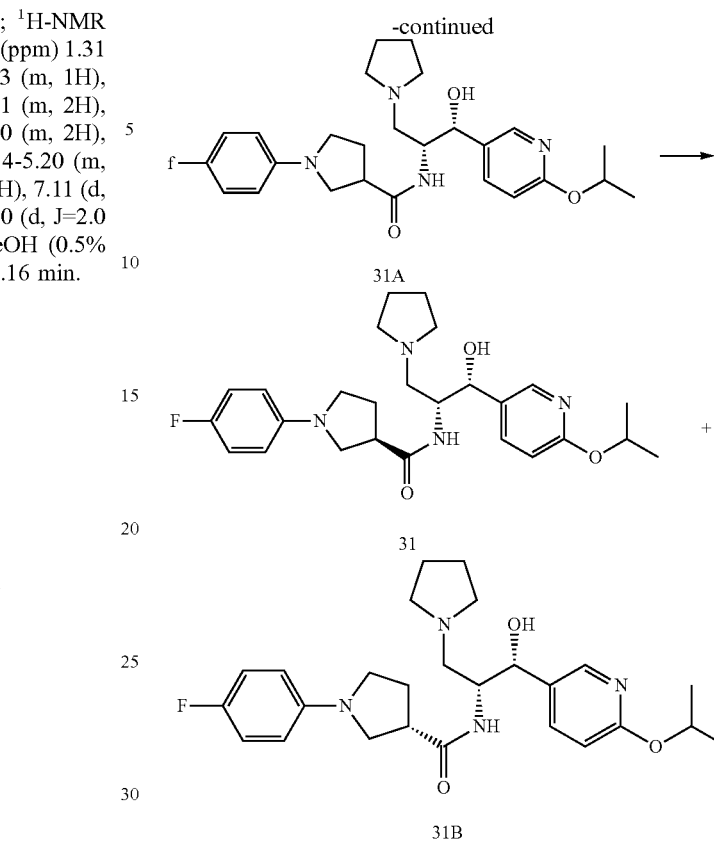

Compounds 31 and 31B were synthesized, by employing the procedure described for Compound 1 using Intermediate J and Compound 24A in lieu of Intermediate A and Compound 1B.

Compound 31. LC-MS (m/z): 471 [M+1]⁺; ¹H-NMR (MeOD, 400 MHz) major characteristic peaks δ (ppm) 1.30 (d, J=6.4 Hz, 6H), 1.81-1.83 (m, 4H), 2.11-2.17 (m, 2H), 2.62-2.70 (m, 4H), 2.75-2.85 (m, 2H), 2.90-2.94 (m, 1H), 3.07-3.14 (m, 1H), 3.20-3.29 (m, 2H), 3.34-3.36 (m, 1H), 4.27-4.31 (m, 1H), 4.91 (d, J=2.8 Hz, 1H), 5.13-5.20 (m, 1H), 6.49-6.52 (m, 2H), 6.67 (d, J=8.4 Hz, 1H), 6.89-6.93 (m, 2H), 7.65 (dd, J=8.4, 2.4 Hz, 1H), 8.11 (d, J=2.4 Hz, 1H). Chiral-HPLC conditions, solvent: MeOH (0.1% DEA), column: IC 250*4.6 mm 5 μm, Rt: 2.44 min.

Compound 31B. LC-MS (m/z): 471 [M+1]⁺; ¹H-NMR (MeOD, 400 MHz) major characteristic peaks δ (ppm) 1.32 (d, J=6.0 Hz, 6H), 1.82-1.84 (m, 4H), 1.86-1.91 (m, 1H), 2.12-2.20 (m, 2H), 2.63-2.71 (m, 4H), 2.77-2.83 (m, 2H), 3.08-3.15 (m, 1H), 3.21-3.25 (m, 2H), 3.35-3.37 (m, 1H), 4.27-4.31 (m, 1H), 4.90 (d, J=2.8 Hz, 1H), 5.15-5.21 (m, 1H), 6.48-6.52 (m, 2H), 6.68 (d, J=8.8 Hz, 1H), 6.88-6.92 (m, 2H), 7.66 (dd, J=8.4, 2.4 Hz, 1H), 8.10 (d, J=2.4 Hz, 1H). Chiral-HPLC conditions, solvent: MeOH (0.1% DEA), column: OJ-H 250*4.6 mm 5 μm, Rt: 6.51 min.

Example 32

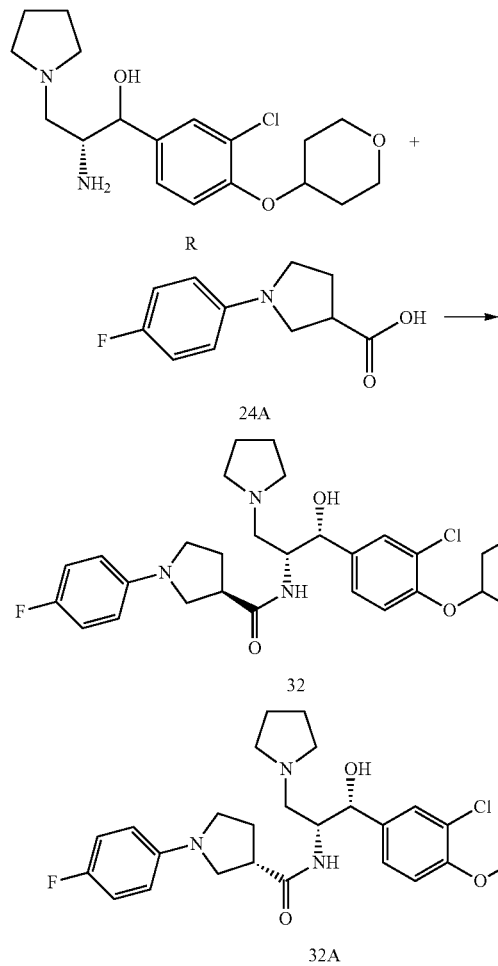

Example 33

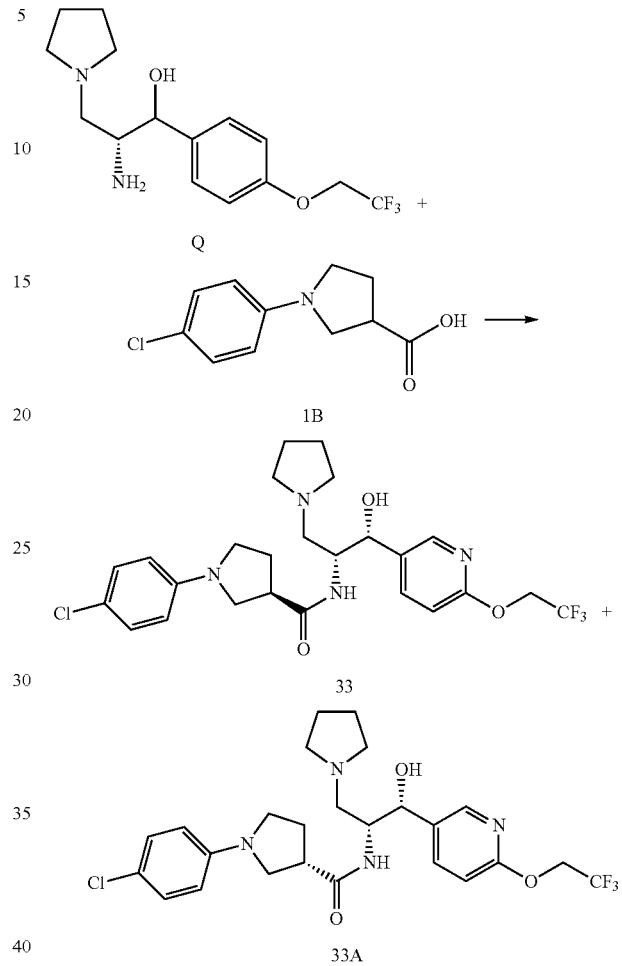

Compounds 32 and 32A were synthesized, by employing the procedure described for Compound 1 using Intermediate R and Compound 24A in lieu of Intermediate A and Compound 1B.

Compound 32. LC-MS (m/z): 545 [M+1]$^+$; $^1$H-NMR (CDCl$_3$, 400 MHz) major characteristic peaks: δ (ppm) 1.72 (m, 4H), 1.79-1.87 (m, 2H), 1.97-2.19 (m, 4H), 2.60-2.67 (m, 4H), 2.79-2.84 (m, 1H), 2.90-2.97 (m, 2H), 3.15-3.24 (m, 3H), 3.34-3.39 (m, 1H), 3.55-3.60 (m, 2H), 3.97-4.03 (m, 2H), 4.17-4.22 (m, 1H), 4.45-4.51 (m, 1H), 5.00 (d, J=2.4 Hz, 1H), 6.35 (d, J=7.6 Hz, 1H), 6.48 (dd, J=8.8, 4.4 Hz, 2H), 6.86 (d, J=8.4 Hz, 1H), 6.92-6.97 (m, 2H), 7.08 (dd, J=8.4, 2.0 Hz, 1H), 7.41 (d, J=2.0 Hz, 1H). Chiral-HPLC conditions, solvent: MeOH (0.5% DEA), column: OJ-H 250*4.6 mm 5 μm, Rt: 3.17 min.

Compound 32A. LC-MS (m/z): 545 [M+1]$^+$; $^1$H-NMR (CDCl$_3$, 400 MHz) major characteristic peaks: δ (ppm) 1.70 (m, 4H), 1.87-1.97 (m, 6H), 2.21 (m, 1H), 2.88 (m, 2H), 3.22 (m, 2H), 3.41-3.47 (m, 4H), 3.69 (m, 4H), 3.87 (m, 2H), 4.41-4.49 (m, 2H), 4.82 (s, 1H), 6.82 (m, 1H), 6.98 (m, 3H), 7.15 (m, 3H), 7.33 (m, 1H), 7.80 (s, 1H), 10.31 (s, 1H). Chiral-HPLC conditions, solvent: MeOH (0.5% DEA), column: OJ-H 250*4.6 mm 5 μm, Rt: 5.29 min.

Compounds 33 and 33A were synthesized, by employing the procedure described for Compound 1 using Intermediate Q in lieu of Intermediate A.

Compound 33. LC-MS (m/z): 527 [M+1]$^+$; $^1$H-NMR (MeOD, 400 MHz) major characteristic peaks: δ (ppm) 1.82-1.85 (m, 4H), 2.11-2.15 (m, 2H), 2.66-2.71 (m, 5H), 2.79-2.86 (m, 2H), 2.92-2.95 (m, 1H), 3.07-3.15 (m, 1H), 3.20-3.26 (m, 1H), 3.35-3.37 (m, 1H), 4.29-4.33 (m, 1H), 4.80 (q, J=8.8 Hz, 2H), 4.95 (d, J=2.8 Hz, 1H), 6.48 (d, J=8.8 Hz, 2H), 6.83 (d, J=8.8 Hz, 1H), 7.13 (d, J=9.2 Hz, 2H), 7.75 (dd, J=8.8, 2.4 Hz, 1H), 8.17 (d, J=2.4 Hz, 1H). Chiral-HPLC conditions, solvent: MeOH (0.1% DEA), column: OZ-H 250*4.6 mm 5 μm, Rt: 3.25 min.

Compound 33A. LC-MS (m/z): 527 [M+1]$^+$; $^1$H-NMR (MeOD, 400 MHz) major characteristic peaks: δ (ppm) 1.82-1.90 (m, 5H), 2.11-2.15 (m, 1H), 2.63-2.70 (m, 4H), 2.77-2.81 (m, 2H), 3.07-3.15 (m, 1H), 3.21-3.25 (m, 1H), 3.35-3.38 (m, 2H), 4.28-4.32 (m, 1H), 4.80-4.84 (m, 2H), 4.94 (d, J=3.2 Hz, 1H), 6.48 (d, J=8.8 Hz, 2H), 6.85 (d, J=8.8 Hz, 1H), 7.11 (d, J=8.8 Hz, 2H), 7.76 (dd, J=8.8, 2.4 Hz, 1H), 8.16 (d, J=2.0 Hz, 1H). Chiral-HPLC conditions, solvent: MeOH (0.1% DEA), column: OJ-H 250*4.6 mm 5 μm, Rt: 10.05 min.

Example 34

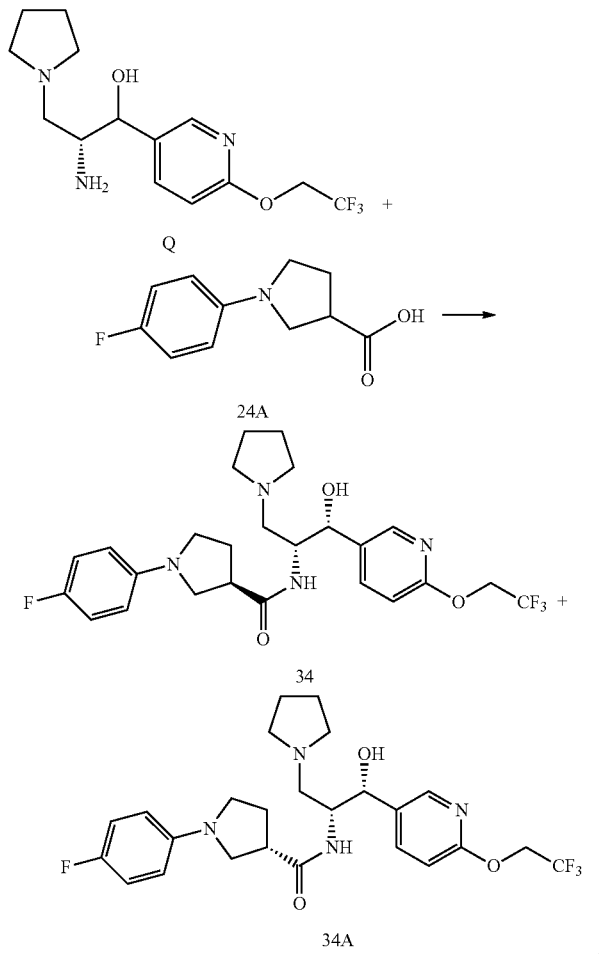

Compounds 34 and 34A were synthesized, by employing the procedure described for Compound 1 using Intermediate Q and Compound 24A in lieu of Intermediate A and Compound 1B.

Compound 34. LC-MS (m/z): 511 [M+1]$^+$; $^1$H-NMR (MeOD, 400 MHz) major characteristic peaks: δ (ppm) 1.81-1.84 (m, 4H), 2.10-2.15 (m, 2H), 2.63-2.67 (m, 4H), 2.75-2.83 (m, 2H), 2.90-2.94 (m, 1H), 3.06-3.14 (m, 1H), 3.19-3.21 (m, 1H), 3.23-3.29 (m, 2H), 4.27-4.31 (m, 1H), 4.79 (q, J=8.8 Hz, 2H), 4.95 (d, J=2.8 Hz, 1H), 6.48-6.51 (m, 2H), 6.83 (d, J=8.4 Hz, 1H), 6.89-6.93 (m, 2H), 7.74 (dd, J=8.4, 2.4 Hz, 1H), 8.16 (d, J=2.4 Hz, 1H). Chiral-HPLC conditions, solvent: MeOH (0.5% DEA), column: OJ-H 250*4.6 mm 5 μm, Rt: 2.96 min.

Compound 34A. LC-MS (m/z): 511 [M+1]$^+$; $^1$H-NMR (MeOD, 400 MHz) major characteristic peaks: δ (ppm) 1.80-1.83 (m, 4H), 1.84-1.89 (m, 1H), 2.09-2.14 (m, 1H), 2.62-2.66 (m, 4H), 2.74-2.79 (m, 2H), 3.06-3.14 (m, 1H), 3.20-3.24 (m, 2H), 3.33-3.38 (m, 2H), 4.27-4.31 (m, 1H), 4.81-4.86 (m, 2H), 4.94 (d, J=2.8 Hz, 1H), 6.48-6.51 (m, 2H), 6.85 (d, J=8.4 Hz, 1H), 6.87-6.92 (m, 2H), 7.75 (dd, J=8.4, 2.4 Hz, 1H), 8.16 (d, J=2.0 Hz, 1H). Chiral-HPLC conditions, solvent: MeOH (0.5% DEA), column: OJ-H 250*4.6 mm 5 μm, Rt: 5.73 min.

Example 35

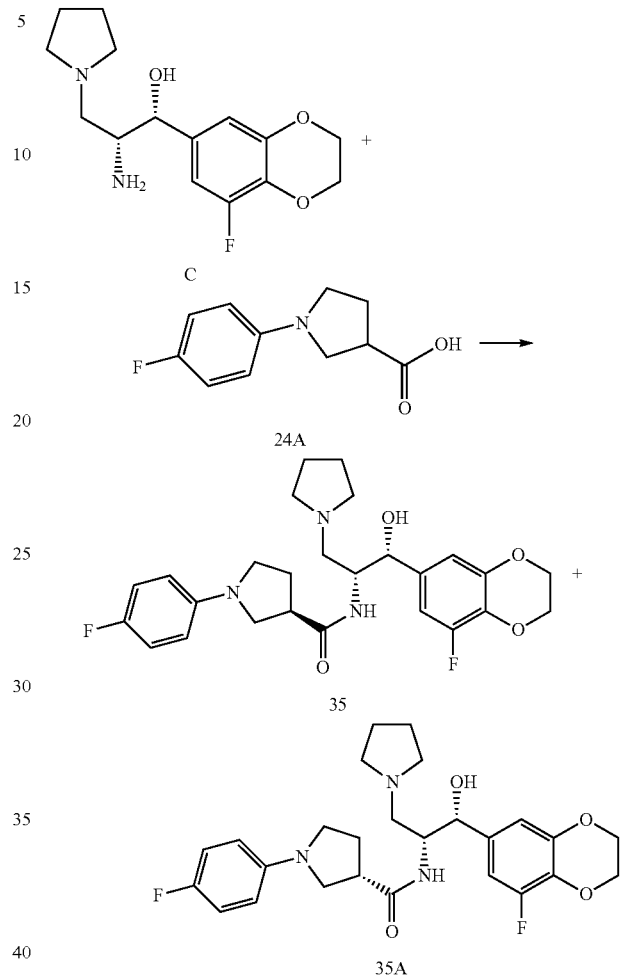

Compounds 35 and 35A were synthesized, by employing the procedure described for Compound 7 using Intermediate C and Compound 24A in lieu of Intermediate A and Compound 7B.

Compound 35. LC-MS (m/z): 488 [M+1]$^+$; $^1$H-NMR (CDCl$_3$, 400 MHz) major characteristic peaks: δ (ppm) 1.92-1.96 (m, 1H), 2.07 (m, 4H), 2.17-2.20 (m, 1H), 3.07-3.54 (m, 12H), 4.25-4.29 (m, 5H), 4.84-4.87 (m, 1H), 6.46-6.49 (m, 2H), 6.63-6.70 (m, 3H), 6.91-6.96 (m, 2H). Chiral-HPLC conditions, solvent: MeOH (0.1% DEA), column: OJ-H (250*4.6 mm 5 μm), R.t.: 2.42 min.

Compound 35A. LC-MS (m/z): 488 [M+1]$^+$; $^1$H-NMR (CDCl$_3$, 400 MHz) major characteristic peaks: δ (ppm) 1.60 (m, 1H), 2.09 (m, 5H), 3.09-3.62 (m, 12H) 4.23 (s, 4H), 4.33 (m, 1H), 4.83-4.85 (m, 1H), 6.43-6.47 (m, 2H), 6.62-6.67 (m, 2H), 6.87-6.94 (m, 3H). Chiral-HPLC conditions, solvent: MeOH (0.1% DEA), column: OJ-H (250*4.6 mm 5 μm), R.t.: 4.42 min.

Example 36

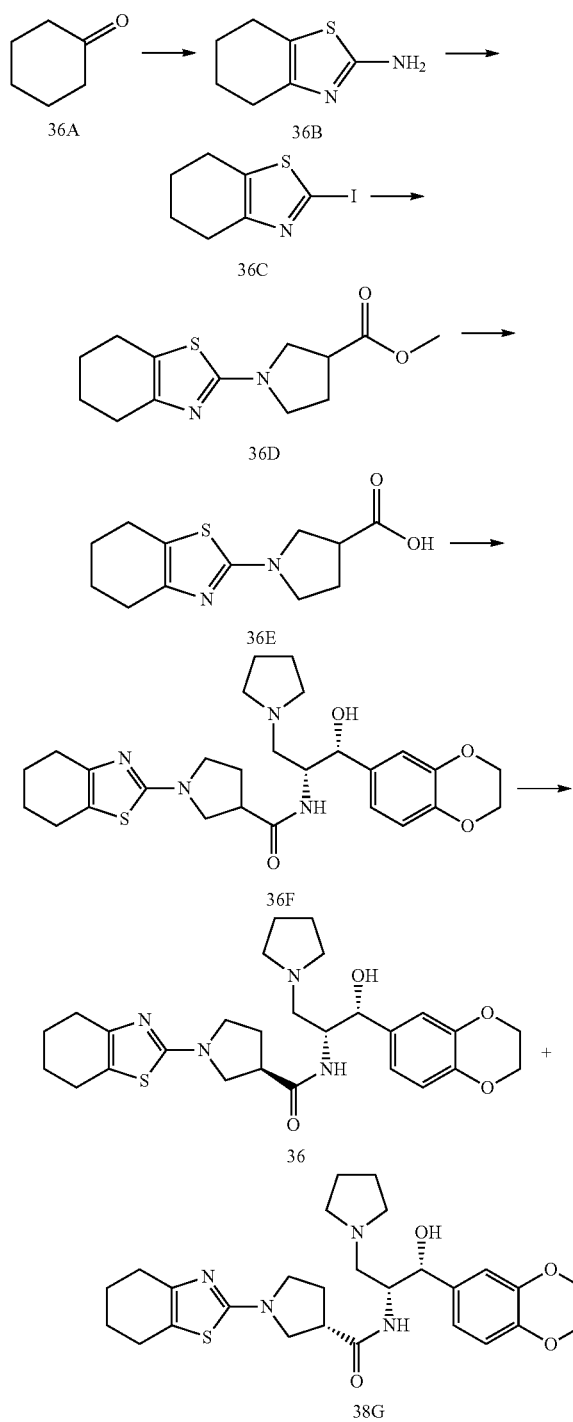

A mixture of Compound 36A (3 g, 30.6 mmol), thiourea (4.62 g, 61.1 mmol), $I_2$ (7.76 g, 30.6 mmol) was stirred at 120° C. overnight. The reaction mixture was cooled down, hot water (50 mL) was added and the mixture was stirred for 0.5 h, then extracted with ethyl acetate (50 mL×3). The aqueous layer was basified by $Na_2CO_3$, extracted with DCM (50 mL×3), dried over anhydrous sodium sulfate, and concentrated to afford Compound 36B. LC-MS (m/z): 155 [M+1]$^+$; $^1$H NMR (CDCl$_3$, 400 MHz) major characteristic peaks: δ (ppm) 1.79 (m, 4H), 2.53 (m, 4H), 4.88 (br, 2H).

To a solution of Compound 36B (460 mg, 3 mmol) and p-TsOH (1.55 g, 9 mmol) in MeCN (20 mL) was added a solution of KI (1.3 g, 7.8 mmol) and $NaNO_2$ (414 mg, 6 mmol) in water (3 mL) at 0° C. and the resultant mixture was stirred at room temperature overnight. To the mixture was added saturated aqueous $Na_2SO_3$ solution (20 mL) and saturated aqueous $NaHCO_3$ solution (20 mL), then the mixture was extracted with ethyl acetate (30 mL×3), dried over anhydrous sodium sulfate, and purified with flash column chromatograhpy (ethyl acetate in petroleum ether, 0-20% v/v) to render Compound 36C. LC-MS (m/z): 266 [M+1]$^+$; $^1$H NMR (CDCl$_3$, 400 MHz) major characteristic peaks: δ (ppm) 1.83 (m, 4H), 2.75 (m, 2H), 2.80 (m, 2H).

Compound 36D was synthesized, by employing the procedure described for Compound 1B using Compound 36C in lieu of 1-chloro-4-iodobenzene. LC-MS (m/z): 267 [M+1]$^+$; $^1$H NMR (CDCl$_3$, 400 MHz) major characteristic peaks: δ (ppm) 1.80 (m, 4H), 2.29 (m, 2H), 2.59 (s, 4H), 3.21 (m, 1H), 3.47 (m, 1H), 3.56 (m, 1H), 3.68 (m, 2H), 3.70 (s, 3H).

Compound 36E was synthesized, by employing the procedure described for Compound 5C using Compound 36D in lieu of Compound 5B. LC-MS (m/z): 253 [M+1]$^+$.

Compounds 36 and 36G were synthesized, by employing the procedure described for Compound 1 using Compound 36E in lieu of Compound 1B.

Compound 36. LC-MS (m/z): 513 [M+1]$^+$; $^1$H NMR (CDCl$_3$, 400 MHz) major characteristic peaks: δ (ppm) 1.78 (m, 8H), 2.16 (m, 3H), 2.58 (m, 6H), 2.83 (m, 2H), 2.93 (m, 1H), 3.48 (m, 5H), 4.17 (m, 1H), 4.25 (s, 4H), 4.93 (d, J=3.2 Hz, 1H), 6.05 (d, J=7.6 Hz, 1H), 6.74 (m, 1H), 6.83 (m, 2H). Chiral-HPLC conditions, solvent:EtOH (0.5% DEA), column: OJ-H 250*4.6 mm 5 μm, Rt: 4.38 min.

Compound 36G. LC-MS (m/z): 513 [M+1]$^+$; $^1$H NMR (CDCl$_3$, 400 MHz) major characteristic peaks: δ (ppm) 1.78 (m, 8H), 2.11 (m, 3H), 2.57 (m, 6H), 2.81 (m, 2H), 2.92 (m, 1H), 3.41 (m, 5H), 4.20 (m, 1H), 4.24 (s, 4H), 4.93 (d, J=2.8 Hz, 1H), 5.96 (d, J=7.2 Hz, 1H), 6.75 (m, 1H), 6.83 (m, 2H). Chiral-HPLC conditions, solvent:EtOH (0.5% DEA), column: OJ-H 250*4.6 mm 5 μm, Rt: 6.72 min.

Example 37

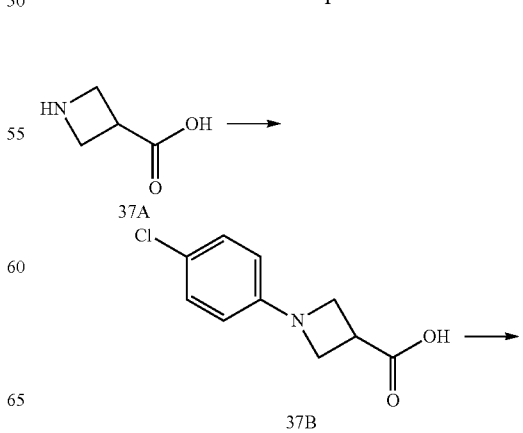

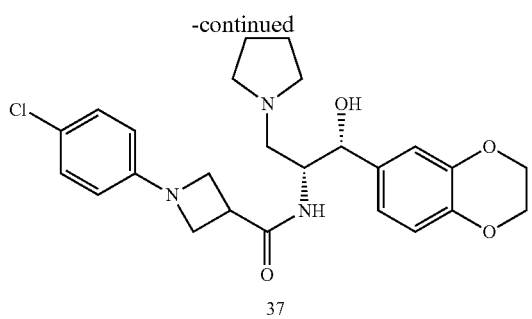

Compound 37B was synthesized, by employing the procedure described for Compound 1B using Compound 37A in lieu of Compound 1A. LC-MS (m/z): 210 [M−1]⁻.

Compound 37 was synthesized, by employing the procedure described for Compound 1 using Compound 37B in lieu of Compound 1B. LC-MS (m/z): 472 [M+H]⁺; $^1$H-NMR (CD$_3$OD, 400 MHz) major characteristic peaks: δ (ppm) 2.01 (m, 4H), 3.16 (m, 2H), 3.32 (m, 4H), 3.40 (m, 3H), 3.69 (m, 2H), 4.17 (m, 4H), 4.46 (m, 1H), 4.80 (s, 1H), 5.43 (m, 2H), 6.79 (m, 3H), 7.15 (m, 2H).

Example 38

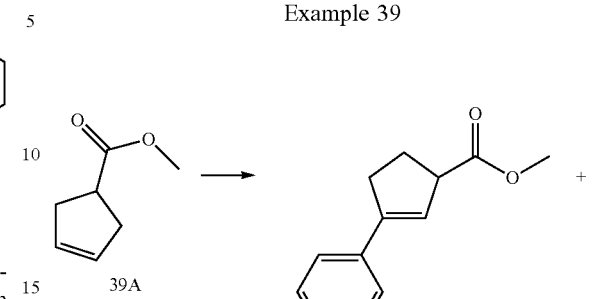

A mixture of cyclopentane-1,3-dicarboxylic acid (124 mg, 0.78 mmol), EDCI (227 mg, 1.18 mmol), HOBt (161 mg, 1.18 mmol), Compound 38A (100 mg, 0.78 mmol) in DCM (20 mL) was stirred at room temperature overnight. After addition of water, the mixture was extracted with DCM (50 mL×2), washed with brine (50 mL), dried over Na$_2$SO$_4$, and concentrated to render a crude Compound 38B. LC-MS (m/z): 268 [M+1]⁺.

Compound 38 was synthesized, by employing the procedure described for Compound 1 using Compound 38B in lieu of Compound 1B. LC-MS (m/z): 528 [M+1]⁺; $^1$H NMR (CDCl$_3$, 400 MHz) major characteristic peaks: δ (ppm) 2.14 (m, 8H), 2.92 (m, 5H), 3.13 (s, 1H), 3.74 (m, 3H), 4.11 (s, 4H), 4.59 (m, 1H), 4.86 (m, 1H), 6.77 (s, 2H), 6.86 (s, 1H), 7.23 (s, 2H), 7.51 (m, 2H), 7.63 (d, J=8.0 Hz, 0.5H), 7.96 (d, J=8.0 Hz, 0.5H), 9.25 (s, 0.5H), 9.58 (s, 0.5H), 11.61 (s, 0.5H), 11.78 (s, 0.5H).

Example 39

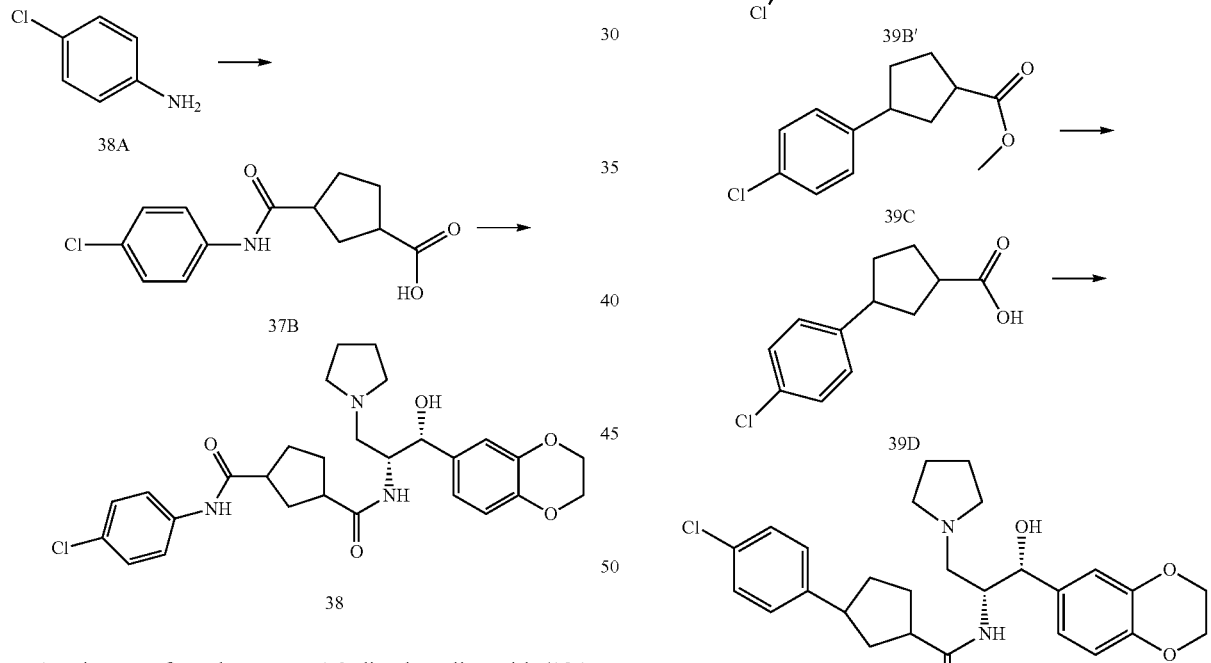

To a solution of Compound 39A (1.26 g, 10 mmol) and 4-chloroiodobenzene (3.57 g, 15 mmol) in Et$_3$N (30 mL) was added Pd(OAc)$_2$ (38 mg, 3%) under N$_2$ atmosphere. The mixture was heated at 90° C. for 24 h in the dark. The mixture was cooled to room temperature, filtered, concentrated under reduced pressure, and purified by column chromatography on silica gel (dichloromethane in petroleum, 50% v/v) to yield a mixture of Compounds 39B and 39B'. LC-MS (m/z): 237 [M+1]⁺.

To a solution of Compounds 39B and 39B' (200 mg, 0.85 mmol) in MeOH (20 mL) was added Pt/C (10 mg, 5%) under H$_2$ atmosphere. The mixture was stirred at 25° C. overnight. It was filtered and concentrated in vacuo. Diluted with water, the mixture was extracted with ethyl acetate (20 mL×3). The combined organic layers were dried over anhydrous Na$_2$SO$_4$ and concentrated in vacuo to give a crude product Compound 39C. LC-MS (m/z): 239 [M+1]$^+$.

Compound 39D was synthesized, by employing the procedure described for Compound 5C using Compound 39C in lieu of Compound 5B (crude), which was used for next step without purification. LC-MS (m/z): 225 [M+1]$^+$.

Compound 39 was synthesized, by employing the procedure described for Compound 1 using Compound 39D in lieu of Compound 1B. LC-MS (m/z): 485 [M+1]$^+$; $^1$H NMR (CDCl$_3$, 400 MHz) major characteristic peaks: δ (ppm) 1.54-1.73 (m, 4H), 1.90-1.97 (m, 6H), 2.65-2.71 (m, 1H), 2.86-2.98 (m, 3H), 3.18 (s, 1H), 3.54 (s, 1H), 3.74 (s, 2H), 4.19 (s, 4H), 4.39 (s, 1H), 4.88 (s, 1H), 6.75-6.85 (m, 3H), 7.08-7.16 (m, 2H), 7.22 (d, J=8 Hz, 2H), 7.34 (s, 1H), 11.68 (s, 1H).

Example 40

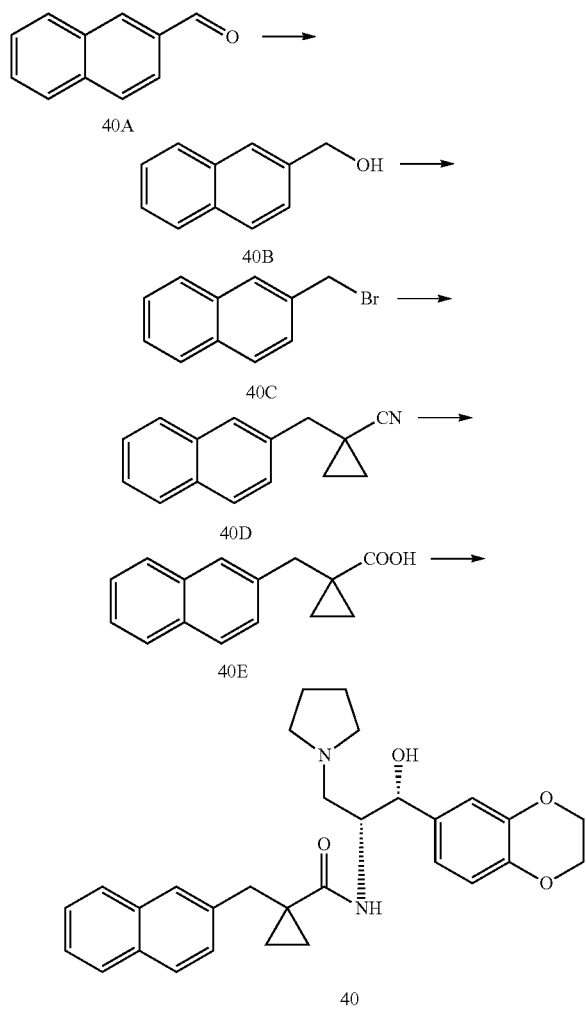

To a solution of Compound 40A (14.10 g, 90.38 mmol) in EtOH (100 mL) was added NaBH$_4$ (3.43 g, 90.83 mmol). The mixture was stirred at room temperature for 2 h. The mixture was diluted with ethyl acetate (300 mL), washed with water and brine, dried with anhydrous Na$_2$SO$_4$, and evaporated to render Compound 40B. LCMS (m/z): 159 [M+1]$^+$; $^1$H-NMR (CDCl$_3$, 400 MHz) major characteristic peaks: δ (ppm) 4.89 (s, 2H), 7.46-7.49 (m. 3H), 7.81-7.86 (m, 4H).

A mixture of Compound 40B (6.00 g, 37.97 mmol) in conc. HBr (200 mL) was stirred at 90° C. overnight. The mixture was diluted with ethyl acetate (200 mL), washed with water and brine, and purified with silica gel column chromatography (ethyl acetate in petroleum ether, 5% v/v) to afford Compound 40C. LCMS (m/z): 221 [M+1]$^+$, $^1$H-NMR (CDCl$_3$, 400 MHz) major characteristic peaks: δ (ppm) 4.67 (s, 2H), 7.48-7.52 (m. 3H), 7.80-7.85 (m, 4H).

To a solution of Compound 40C (550 mg, 2.50 mmol) and cyclopropanecarbonitrile (502 mg, 7.50 mmol) in dry THF (5 mL) was added LDA in THF (3.75 mL, 7.50 mmol, 2 M) dropwised at −10° C. Then it was stirred at 0° C. for 5 h. It was quenched with water, diluted with ethyl acetate (150 mL), washed with water and brine, and purified with silica gel column chromatography (ethyl acetate in petroleum ether, 10% v/v) to yield Compound 40D. LCMS (m/z): 208 [M+1]$^+$, $^1$H-NMR (CDCl$_3$, 400 MHz) major characteristic peaks: δ (ppm) 0.99-1.02 (m, 2H), 1.30-1.33 (m, 2H), 2.99 (s, 2H), 7.40 (d, J=10.2 Hz, 1H), 7.46-7.50 (m, 2H), 7.72 (s, 1H), 7.82-7.84 (m, 3H).

A mixture of Compound 40D (400 mg, 1.93 mmol) and NaOH (4.00 g, 100 mmol) in EtOH/H$_2$O (⅕ mL) was added stirred at 100° C. overnight. Then it was adjusted to pH=1 with conc.HCl, diluted with ethyl acetate (200 mL), washed with water and brine, dried with anhydrous Na$_2$SO$_4$, and evaporated to give Compound 40E. LCMS (m/z): 225 [M−1]$^−$, $^1$H-NMR (CDCl$_3$, 400 MHz) major characteristic peaks: δ (ppm) 0.91-0.94 (m, 2H), 1.37-1.40 (m, 2H), 3.15 (s, 2H), 7.37-7.47 (m, 3H), 7.66 (s, 1H), 7.74-7.80 (m, 3H).

Compound 40 was synthesized, by employing the procedure described for Compound 1 using Compound 40E in lieu of Compound 1B. LCMS (m/z): 487 [M+1]$^+$, $^1$H NMR (CDCl$_3$, 400 MHz) major characteristic peaks: δ (ppm) 0.82-0.91 (m, 2H), 1.17-1.25 (m, 2H), 1.57-1.78 (m, 4H), 2.99 (br s, 1H), 2.51 (br s, 1H), 2.99-3.21 (m, 4H), 3.47 (br s, 1H), 4.06 (br s, 2H), 4.21 (s, 5H), 4.77 (s, 1H), 6.52 (d, J=10.3 Hz, 1H), 6.66 (d, J=8.0 Hz, 1H), 6.74 (s, 1H), 6.80 (d, J=7.6 Hz, 1H), 7.40-7.50 (m, 3H), 7.75-7.80 (m, 4H).

Example 41

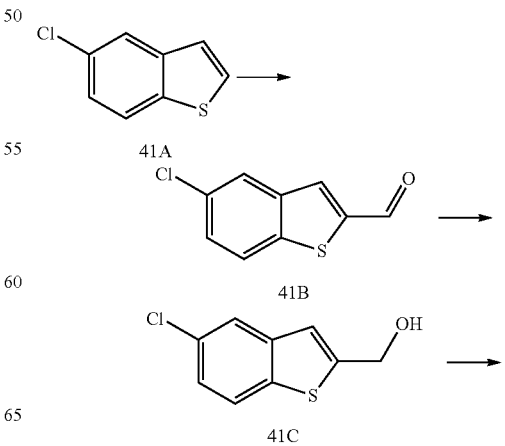

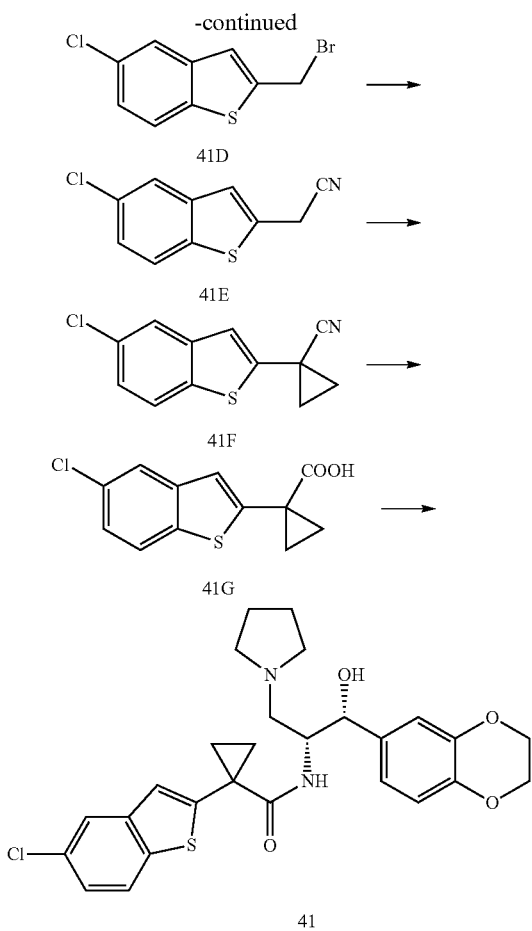

To a solution of Compound 41A (500 mg, 2.97 mmol) in THF (30 mL) was added n-BuLi (1.42 ml, 3.56 mmol) at −78° C. under the protection of nitrogen. Then it was stirred at −78° C. for 1 h, DMF (434 mg, 5.94 mmol) was added to the mixture and stirred for another one hour at −78° C. The reaction was quenched with sat. NH$_4$Cl. After separation, the organic phase was washed with brine, and dried over anhydrous Na$_2$SO$_4$, and purified by silica gel column chromatography (ethyl acetate in petroleum 20% v/v) to render Compound 41B. $^1$H-NMR (CDCl$_3$, 400 MHz) major characteristic peaks: δ (ppm) 7.47 (dd, J=2.0, 8.8 Hz, 1H), 7.83 (d, J=8.8 Hz, 1H), 7.93 (d, J=2.0 Hz, 1H), 7.97 (s, 1H), 10.11 (s, 1H).

To a solution of Compound 41B (500 mg, 2.54 mmol) in EtOH (10 mL) was added NaBH$_4$ (97 mg, 2.54 mmol) at 0° C. under N$_2$ and stirred at 25° C. for 1 h. The reaction was quenched with water (10 ml). The mixture was extracted with ethyl acetate (50 mL×3). The combined organic phase was washed with brine, and dried over anhydrous Na$_2$SO$_4$, and concentrated to afford Compound 41C. $^1$H-NMR (CDCl$_3$, 400 MHz) major characteristic peaks: δ (ppm) 2.00 (br s, 1H), 4.93 (s, 2H), 7.15 (s, 1H), 7.27 (dd, J=2.4, 8.8 Hz, 1H), 7.71 (m, 2H).

To a solution of Compound 41C (5.83 g, 0.29.7 mmol) in ether (100 mL) was added a solution of PBr$_3$ (6.71 mL) in 50 mL of ether at 0° C. The mixture was stirred at 0° C. for 2 h. The reaction was poured into ice-water (300 mL) and the mixture was extracted with ether (100 mL×3). The combined organic layers were washed with water and brine, and dried over anhydrous Na$_2$SO$_4$. The crude product Compound 41D was used for the next step of reaction without further purification. Compound 41D. $^1$H-NMR (DMSO-d$_6$, 400 MHz) major characteristic peaks: δ (ppm) 5.10 (s, 2H), 7.41 (dd, J=2.0, 8.8 Hz, 1H), 7.53 (s, 1H), 7.94 (s, 1H), 8.00 (d, J=8.8 Hz, 1H).

To a stirred solution of Compound 41D (5.12 g, 19.6 mmol) in CHCl$_3$ (60 mL) was added a mixture of NaCN (1.45 g, 29.5 mmol), KOH (275 mg, 4.91 mmol), n-Bu$_4$NHSO$_4$ (1.68 g, 4.91 mmol) and water (60 mL). After one hour at 25° C., the mixture was heated to reflux for 30 min. The mixture was cooled and partitioned between DCM and water. The aqueous phase was extracted with DCM (100 mL×3). The combined organic phase was washed with water and brine, and dried over anhydrous Na$_2$SO$_4$, and purified by column chromatography on silica gel (ethyl acetate in petroleum, 20% v/v) to give Compound 41E. $^1$H-NMR (DMSO-d$_6$, 400 MHz) major characteristic peaks: δ (ppm) 4.46 (s, 2H), 7.41 (m, 2H), 7.96 (s, 1H), 8.01 (d, J=8.8 Hz, 1H).

To a solution of Compound 41E (1.5 g, 7.25 mmol) in dry DMF (30 mL) was added NaH (60%, 870 mg, 21.74 mmol) at 0° C. under nitrogen protection. After stirring for 90 min at 30° C., 1,2-dibromoethane (1.88 g, 21.74 mmol) was added dropwise at 0° C., and the mixture was warmed to 25° C. and stood overnight. The reaction was quenched with 1 M HCl. It was extracted with ethyl acetate (100 mL×3). The extracts were washed with water and brine, and dried over anhydrous Na$_2$SO$_4$. The crude product was purified by column chromatography on silica gel (ethyl acetate in petroleum, 20% v/v) to yield Compound 41F. $^1$H-NMR (DMSO-d$_6$, 400 MHz) major characteristic peaks: δ (ppm) 1.65 (m, 2H), 1.95 (m, 2H), 7.40 (dd, J=2.0, 8.8 Hz, 1H), 7.43 (s, 1H), 7.89 (s, 1H), 8.00 (d, J=8.4 Hz, 1H).

To a solution of Compound 41F (570 mg, 2.75 mmol) in water (30 mL) was added NaOH (3 g, 75 mmol). The mixture was stirred at reflux overnight. After reaction, cooled and adjusted pH to 3 with conc. HCl, filtered and washed with water, then dried to furnish Compound 41G. $^1$H-NMR (DMSO-d$_6$, 400 MHz) major characteristic peaks: δ (ppm) 1.42 (m, 2H), 1.65 (m, 2H), 7.26 (s, 1H), 7.33 (dd, J=1.6, 8.4 Hz, 1H), 7.81 (s, 1H), 7.91 (d, J=8.4 Hz, 1H) 12.80 (br s, 1H).

Compound 41 was synthesized, by employing the procedure described for Compound 1 using Compound 41G in lieu of Compound 1B. LCMS: 513 [M+1]$^+$; $^1$H-NMR (DMSO-d$_6$, 400 MHz) major characteristic peaks: δ (ppm) 1.16 (m, 2H), 1.38 (m, 2H), 1.65 (m, 4H), 2.21 (m, 1H), 2.61 (m, 3H), 2.66 (m, 1H), 3.89 (m, 1H), 4.23 (m, 5H), 4.70 (s, 1H), 5.53 (s, 1H), 6.47 (d, J=8.4 Hz, 1H), 6.60 (d, J=8.4 Hz, 1H), 6.63 (s, 1H), 6.73 (d, J=8.0 Hz, 1H), 7.34 (s, 1H), 7.40 (d, J=8.4 Hz, 1H), 7.90 (s, 1H), 8.00 (d, J=8.4 Hz, 1H).

Example 42

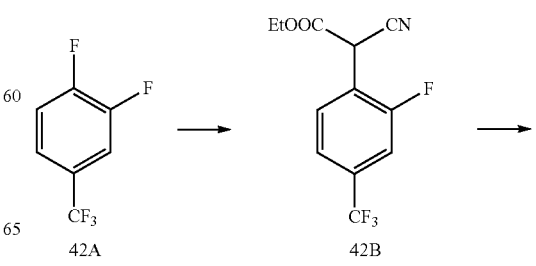

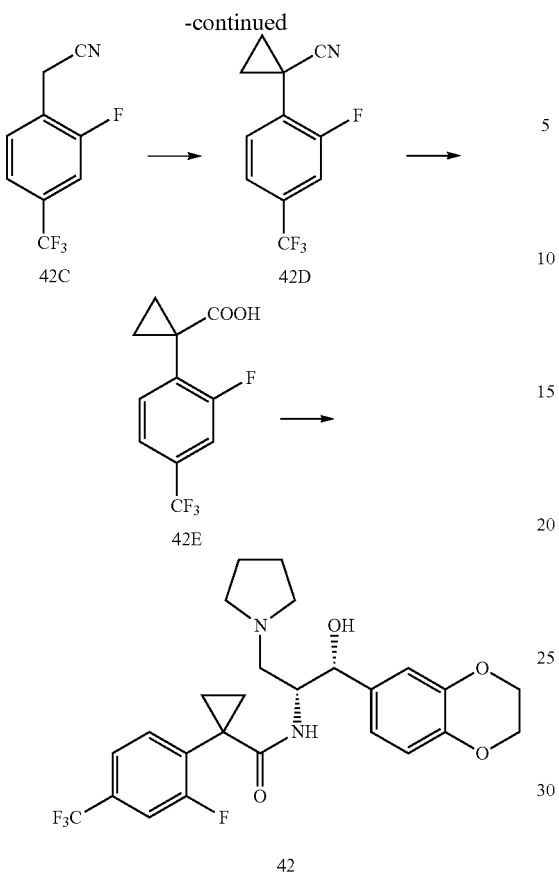

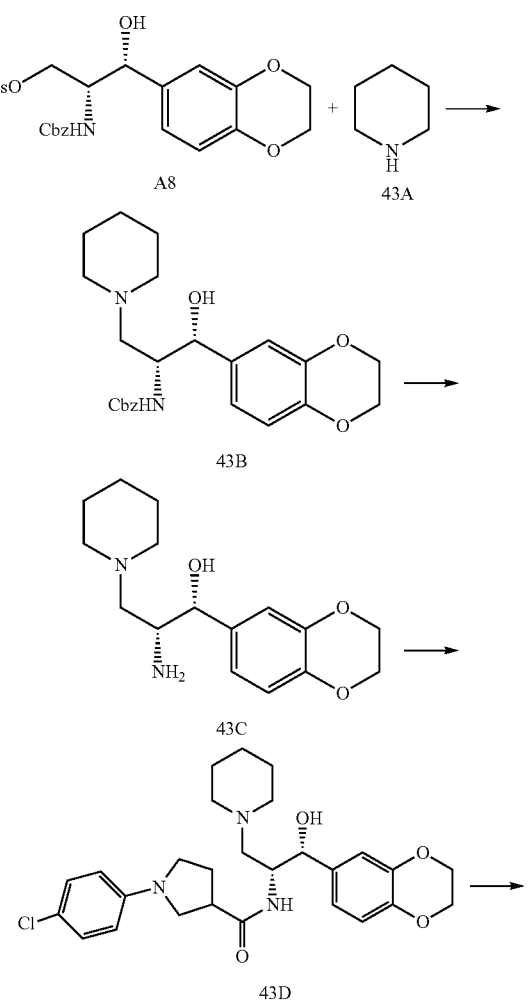

was dissolved in ethyl acetate (50 mL) and washed with water (15 mL), dried over anhydrous Na$_2$SO$_4$, and concentrated to yield a crude Compound 42D. LC-MS (m/z): 230 [M+1]$^+$ A suspension of Compound 42D (1 g, 4 mmol) in aq. NaOH solution (3 M, 20 mL) was heated to reflux for 18 h, and then cooled to room temperature. The resulting solution was adjusted to pH=3 with aq. HCl solution (1 M) and extracted with ethyl acetate (50 mL×3), dried over anhydrous Na$_2$SO$_4$, and concentrated to give Compound 42E. LC-MS (m/z): 249 [M+1]$^+$; $^1$H-NMR (CDCl$_3$, 400 MHz) major characteristic peaks: δ (ppm) 1.282 (q, J=4.0 MHz, 2H), 1.780 (q, J=4.0 MHz, 2H), 7.310 (d, J=9.6 MHz, 1H), 7.380~7.415 (m, 3H).

Compound 42 was synthesized, by employing the procedure described for Compound 1 using Compound 42E in lieu of Compound 1B. LC-MS (m/z): 509 [M+1]$^+$; $^1$H-NMR (CDCl$_3$, 400 MHz) major characteristic peaks: δ (ppm) 0.97~1.078 (m, 2H), 1.601 (m, 2H), 1.856 (m, 4H), 2.813 (m, 4H), 2.954 (m, 2H), 4.113 (m, 1H), 4.252 (s, 4H), 4.916 (s, 1H), 5.712 (d, J=6.8 MHz, 1H), 6.535 (m, 1H), 6.600 (d, J=2 MHz, 1H), 6.730 (d, J=8.4 MHz, 1H), 7.380 (m, 1H), 7.451 (m, 2H).

Example 43

A suspension of Compound 42A (2.5 g, 13.7 mmol), ethyl cyanacetate (1.35 mL, 12.5 mmol), benzyltriethylammonium chloride (285 mg, 1.25 mmol) and K$_2$CO$_3$ (5.18 g, 37.5 mmol) in DMSO (60 mL) was stirred at 90° C. under N$_2$ overnight. The mixture was diluted with ethyl acetate (100 mL), and then further cooled to 5° C. Aqueous HCl solution (6 M) was added to the mixture, leading to precipitation of a white solid. The resulting suspension was stirred for 30 min until the precipitate dissolved. The organic layer was separated and washed with water (150 mL×3) and brine (200 mL), dried over anhydrous Na$_2$SO$_4$, and concentrated to give a crude Compound 42B. LC-MS (m/z): 276 [M+1]$^+$.

To a solution of Compound 42B (2.75 g, 10 mmol) in DMSO (50 mL) was added NaCl (820 mg, 14 mmol) and the mixture was heated to 110° C. for 15 h. The mixture was then cooled to 25° C. and diluted with dichloromethane (100 mL), followed by water (50 mL). The organic and aqueous phases were separated. The aqueous phase was extracted with dichloromethane (100 mL) and the combined organic phase were washed with water (200 mL) and brine (100 mL), dried over anhydrous Na$_2$SO$_4$, and concentrated to give a crude Compound 42C. LC-MS (m/z): 204 [M+1]$^+$. $^1$H-NMR (CDCl$_3$, 400 MHz) major characteristic peaks: δ (ppm) 3.837 (s, 2H), 7.384 (d, J=9.6 MHz, 1H), 7.384 (d, J=8.0 MHz, 1H), 7.625 (t, J=8.0 MHz, 1H).

To a solution of Compound 42C (1 g, 5 mmol) in THF (20 mL) at 0° C. was added NaH (60%, 0.6 g, 15 mmol) and the mixture was stirred at 0° C. for 5 min, followed by the addition of 1,2-dibromoethane (2.8 g, 15 mmol) in THF (2 mL). The mixture was stirred at 0° C. for 2 h and continued for 16 h at room temperature. It was quenched with addition of water (1 mL) and then concentrated. The resulting slurry

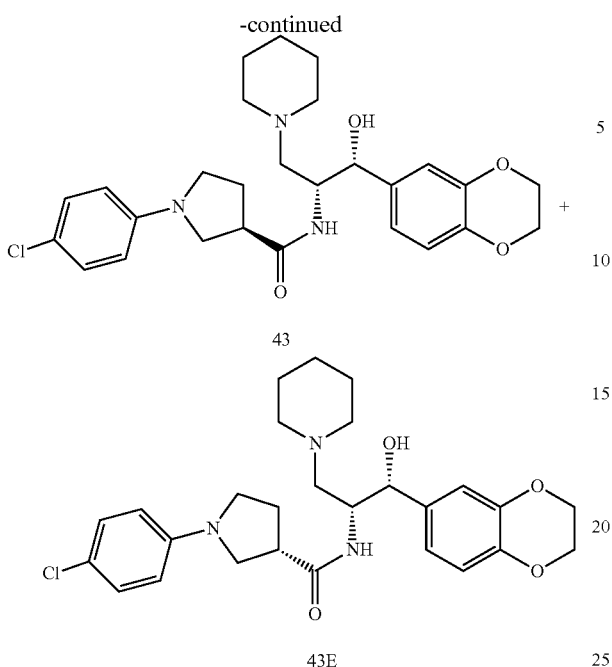

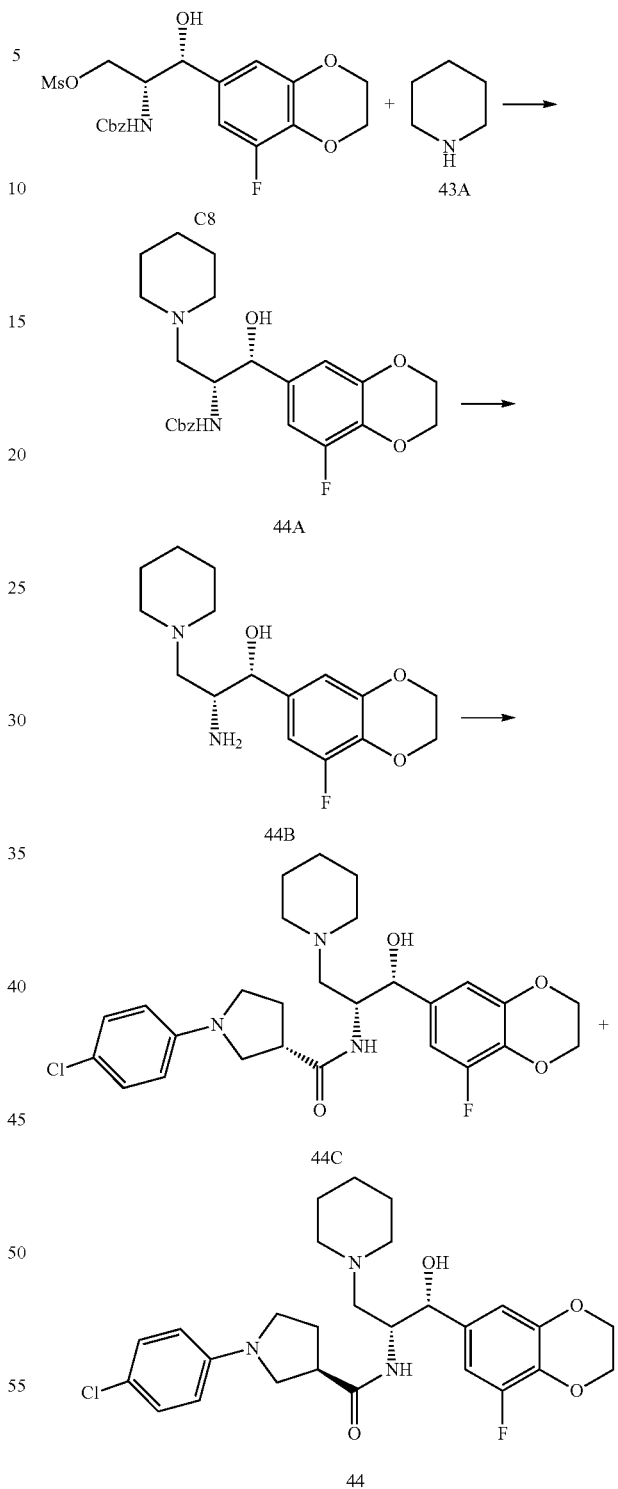

Example 44

Compound 43B was synthesized, by employing the procedure described for Intermediate A9 using Compound 43A in lieu of pyrrolidine. LC-MS (ESI) m/z: 427 [M+H]$^+$; $^1$H-NMR (CDCl$_3$, 400 MHz) δ (ppm) 1.42-1.47 (m, 2H), 1.60-1.63 (m, 4H), 2.45-2.60 (m, 4H), 4.09-4.13 (m, 1H), 4.25 (s, 4H), 4.88-4.89 (m, 1H), 5.05-5.06 (m, 2H), 6.76-6.82 (m, 1H), 6.82-6.84 (m, 2H), 7.29-7.37 (m, 5H).

Compound 43C was synthesized, by employing the procedure described for Intermediate E using Compound 43B in lieu of Intermediate E7. LC-MS (ESI) m/z: 293 [M+H]$^+$; $^1$H-NMR (CDCl$_3$, 400 MHz) δ (ppm) 1.43 (s, 2H), 1.56-1.60 (m, 4H), 2.37-2.45 (m, 6H), 3.20 (s, 1H), 4.26 (s, 4H), 4.54 (d, J=3.2 Hz, 1H), 6.80-6.85 (m, 3H).

Compound 43 and 43E were synthesized, by employing the procedures described for Compound 1 using Compound 43C in lieu of Intermediate A.

Compound 43. LC-MS (ESI) m/z: 500 [M+H]$^+$; $^1$H-NMR (MeOD, 400 MHz) δ (ppm) 1.46-1.47 (m, 2H), 1.58-1.61 (m, 4H), 2.08-2.19 (m, 2H), 2.49-2.52 (m, 4H), 2.98-3.02 (m, 1H), 3.06-3.10 (m, 1H), 3.18-3.24 (m, 1H), 3.36-3.41 (m, 1H), 4.17-4.21 (m, 4H), 4.26-4.30 (m, 1H), 4.80 (d, J=2.8 Hz, 1H), 6.49 (d, J=9.2 Hz, 2H), 6.78 (d, J=1.2 Hz, 2H), 6.87 (s, 1H), 7.13 (d, J=8.8 Hz, 2H). Chiral-HPLC condition, solvent: MeOH (0.1% DEA), column: OJ-H (250*4.6 mm 5 um), Rt: 2.87 min.

Compound 43E. LC-MS (ESI) m/z: 500 [M+H]$^+$; $^1$H-NMR (MeOD, 400 MHz) δ (ppm) 1.49-1.94 (m, 7H), 2.12-2.17 (m, 1H), 2.90-3.22 (m, 5H), 3.35-3.50 (m, 5H), 3.80-3.83 (m, 1H), 4.22 (s, 4H), 4.49-4.53 (m, 1H), 4.81 (d, J=3.2 Hz, 1H), 6.50 (d, J=8.8 Hz, 2H), 6.81-6.84 (m, 2H), 6.94 (s, 1H), 7.12 (d, J=8.8 Hz, 2H). Chiral-HPLC condition, solvent: MeOH (0.1% DEA), column: OJ-H (250*4.6 mm 5 um), Rt: 4.9 min.

Compounds 44A and 44B were synthesized, by employing the procedures described for Intermediate A9 and A using Intermediate C8, Compound 43A, and 44A in lieu of Intermediate A8, pyrrolidine, and Intermediate A9.

Compound 44A. LC-MS (ESI) m/z: 445 [M+H]$^+$.

Compound 44B, which was directly used for the next step without further purification. LC-MS (ESI) m/z: 311 [M+H]$^+$.

Compounds 44C and 44 were synthesized, by employing the procedures described for Compound 1 using Compound 43B in lieu of Intermediate A.

Compound 44C. LC-MS (ESI) m/z: 518 [M+H]+; $^1$H-NMR (CDCl$_3$, 400 MHz): δ (ppm) 1.43 (s, 1H), 1.88 (s, 5H), 2.03 (s, 1H), 2.12 (s, 2H), 2.98-3.07 (m, 3H), 3.18-3.30 (m, 3H), 3.40-3.50 (m, 2H), 3.69 (s, 1H), 4.23 (s, 5H), 4.50 (s, 1H), 4.79 (s, 1H), 6.44 (d, J=8 Hz, 2H), 6.66-6.71 (m, 2H), 7.14 (d, J=8 Hz, 2H), 7.78 (s, 1H), 10.78 (s, 1H).

Compound 44. LC-MS (ESI) m/z: 518 [M+H]+; $^1$H-NMR (CDCl$_3$, 400 MHz) δ (ppm) 1.40 (s, 1H), 1.85 (s, 4H), 1.98 (s, 2H), 2.14 (s, 1H), 2.61 (s, 1H), 3.06 (s, 2H), 3.23-3.37 (m, 4H), 3.50 (s, 2H), 3.68 (s, 1H), 4.22-4.26 (s, 4H), 4.52 (s, 1H), 4.79 (s, 1H), 6.47 (d, J=8 Hz, 2H), 6.65-6.71 (m, 2H), 7.14 (d, J=8 Hz, 2H), 7.78 (s, 1H), 10.69 (s, 1H).

Example 45

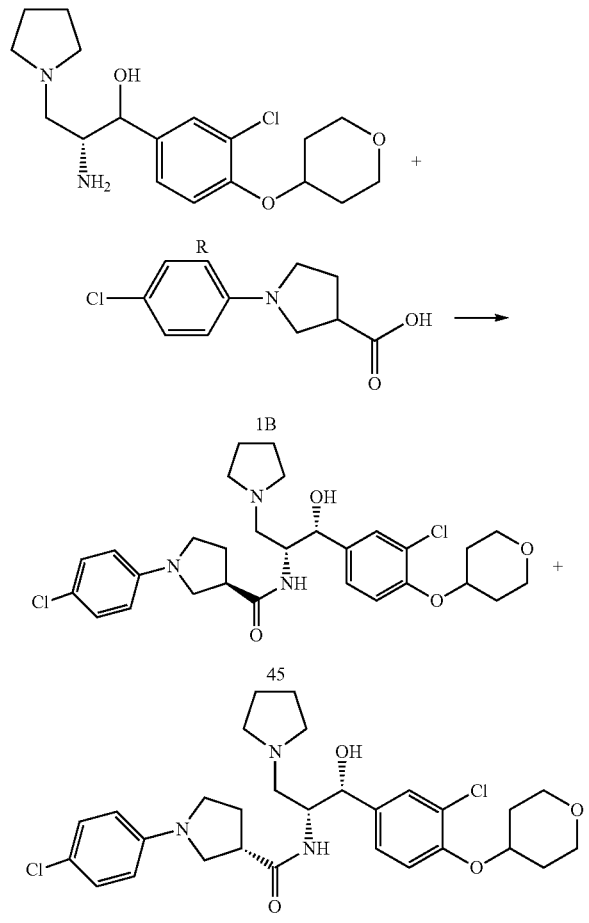

Compounds 45 and 45A were synthesized, by employing the procedures described for Compound 1 using Intermediate R in lieu of Intermediate A.

Compound 45. LC-MS (ESI) m/z: 562 [M+H]+; $^1$H-NMR (CDCl$_3$, 400 MHz) δ (ppm) 1.78-1.87 (m, 6H), 1.96-2.01 (m, 2H), 2.07-2.20 (m, 2H), 2.67-2.70 (m, 4H), 2.83-2.87 (m, 1H), 2.93-2.97 (m, 2H), 3.16-3.38 (m, 4H), 3.55-3.61 (m, 2H), 3.97-4.02 (m, 2H), 4.19-4.23 (m, 1H), 4.46-4.51 (m, 1H), 5.00 (d, J=2.4 Hz, 1H), 6.30 (d, J=8.0 Hz, 1H), 6.45 (d, J=8.8 Hz, 2H), 6.85 (d, J=8.8 Hz, 1H), 7.07 (dd, J=8.0, 2.0 Hz, 1H), 7.16 (d, J=9.2 Hz, 2H), 7.41 (d, J=2.0 Hz, 1H); Chiral-HPLC condition, solvent: MeOH (0.1% DEA), column: OZ-H (250*4.6 mm 5 um), Rt: 4.04 min.

Compound 45A. LC-MS (ESI) m/z: 562 [M+H]+; $^1$H-NMR (CDCl$_3$, 400 MHz) δ (ppm) 1.77 (m, 3H), 1.88-1.96 (m, 2H), 2.02-2.10 (m, 4H), 2.92-2.03 (m, 3H), 3.22-3.24 (m, 3H), 3.36-3.38 (m, 2H), 3.56-4.10 (m, 8H), 4.47-4.52 (m, 2H), 4.93 (s, 1H), 6.52 (d, J=8.8 Hz, 2H), 6.87 (d, J=8.4 Hz, 1H), 7.12-7.17 (m, 3H), 7.40 (s, 1H), 7.55 (d, J=7.6 Hz, 1H), 11.08 (s, 1H); Chiral-HPLC condition, solvent: MeOH (0.1% DEA), column: AD-H (250*4.6 mm 5 um), Rt: 5.65 min.

Example 46

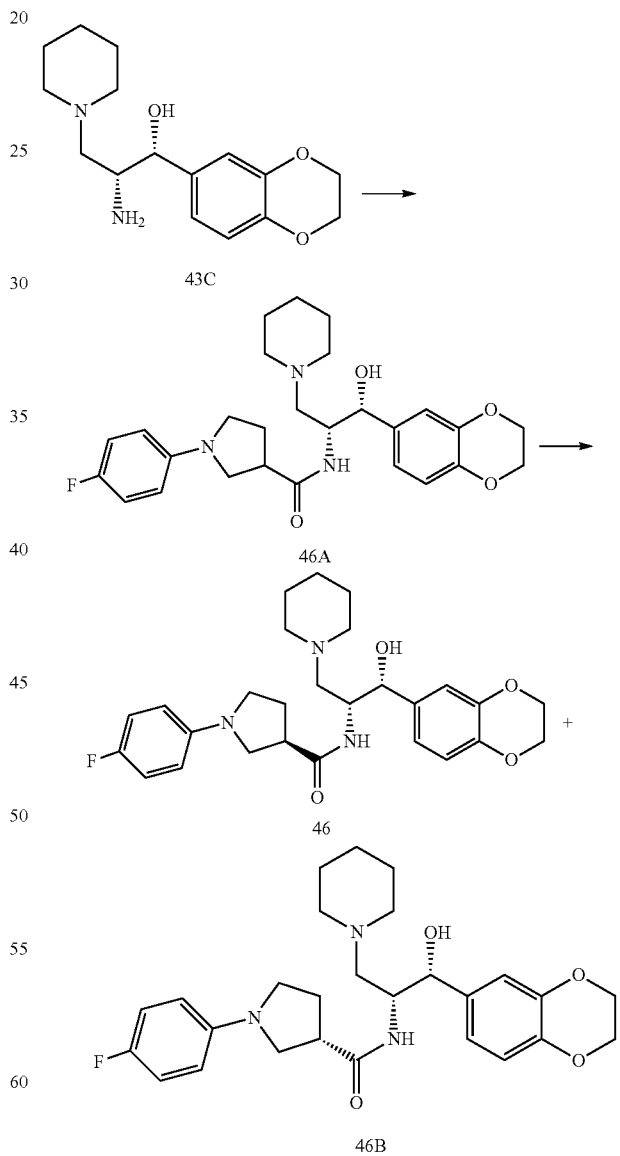

Compounds 46 and 46B were synthesized, by employing the procedures described for Compound 1 using Compounds 43C and 24A in lieu of Intermediate A and Compound 1B.

Compound 46. LC-MS (ESI) m/z: 484 [M+H]$^+$; $^1$H-NMR (MeOD, 400 MHz) δ (ppm) 1.48-1.52 (m, 2H), 1.59-1.62 (m, 4H), 2.05-2.17 (m, 2H), 2.47-2.62 (m, 6H), 3.00-3.02 (m, 1H), 3.09-3.24 (m, 1H), 3.31-3.38 (m, 2H), 4.18-4.21 (m, 4H), 4.22-4.23 (m, 1H), 4.80 (d, J=3.2 Hz, 1H), 6.51-6.54 (m, 2H), 6.77-6.78 (m, 2H), 6.90-6.95 (m, 3H). Chiral-HPLC condition, solvent: MeOH (0.1% DEA), column OJ-H (250*4.6 mm 5 um), Rt: 2.71 min.

Compound 46B. LC-MS (ESI) m/z: 484 [M+H]$^+$; $^1$H-NMR (MeOD, 400 MHz) δ (ppm) 1.37-1.38 (m, 2H), 1.50-1.53 (m, 4H), 1.83-1.89 (m, 1H), 2.01-2.09 (m, 1H), 2.46-2.52 (m, 6H), 3.08-3.25 (m, 5H), 4.08-4.09 (m, 4H), 4.18-4.21 (m, 1H), 4.67 (d, J=3.6 Hz, 1H), 6.38-6.41 (m, 2H), 6.67-6.68 (m, 2H), 6.75-6.82 (m, 3H). Chiral-HPLC condition, solvent: MeOH (0.1% DEA), column OJ-H (250*4.6 mm 5 um), Rt: 4.44 min.

Example 47

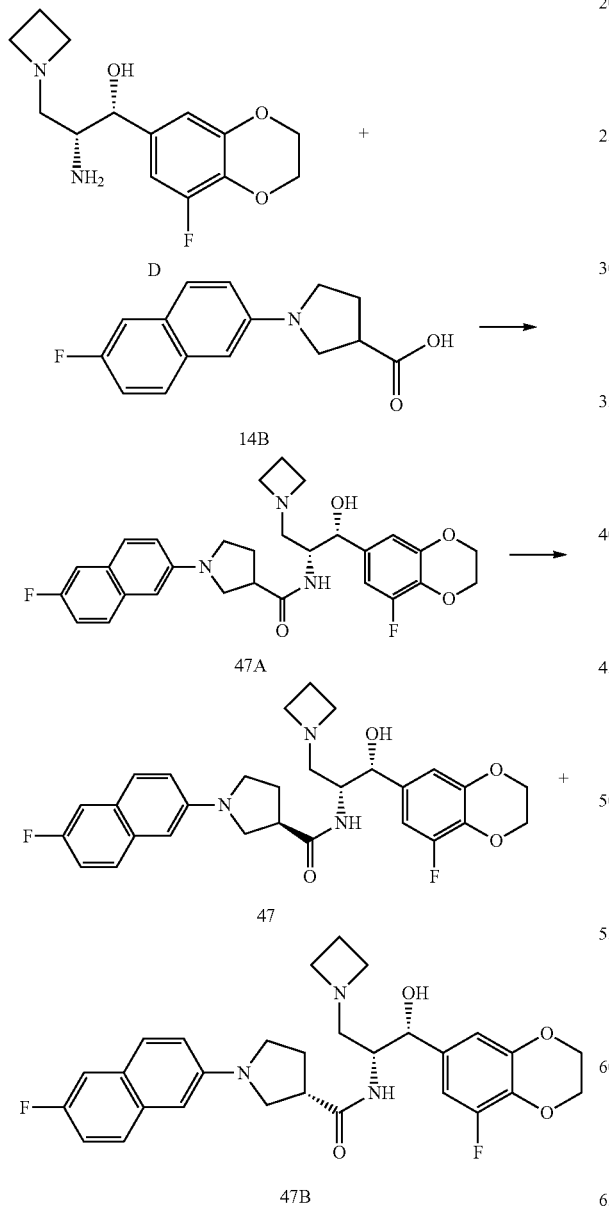

Compounds 47 and 47B were synthesized, by employing the procedures described for Compound 1 using Intermediate D and Compound 14B in lieu of Intermediate A and Compound 1B.

Compound 47. LC-MS (ESI) m/z: 506 [M+H]$^+$; $^1$H-NMR (MeOD, 400 MHz) δ (ppm) 2.03-2.21 (m, 4H), 2.59-2.69 (m, 2H), 2.72-2.88 (m, 1H), 3.01-3.11 (m, 1H), 3.23-3.32 (m, 5H), 3.37-3.45 (m, 2H), 3.97-4.09 (m, 5H), 4.67 (s, 1H), 6.61 (s, 1H), 6.68-6.72 (m, 2H), 6.97 (d, J=8.4 Hz, 1H), 7.04-7.09 (m, 1H), 7.24 (d, J=8.8 Hz, 1H), 7.58 (d, J=8.8 Hz, 2H).

Compound 47B. LC-MS (ESI) m/z: 506 [M+H]$^+$; $^1$H-NMR (MeOD, 400 MHz) δ (ppm) 1.84-2.15 (m, 4H), 2.53-2.67 (m, 2H), 3.04-3.07 (m, 1H), 3.24-3.35 (m, 6H), 3.40-3.43 (m, 2H), 3.93-3.97 (m, 1H), 4.17 (s, 1H), 6.62 (s, 1H), 6.61-6.70 (m, 3H), 6.97 (d, J=9.2 Hz, 1H), 7.02-7.07 (m, 1H), 7.23 (d, J=9.2 Hz, 1H), 7.52-7.57 (m, 2H).

Example 48

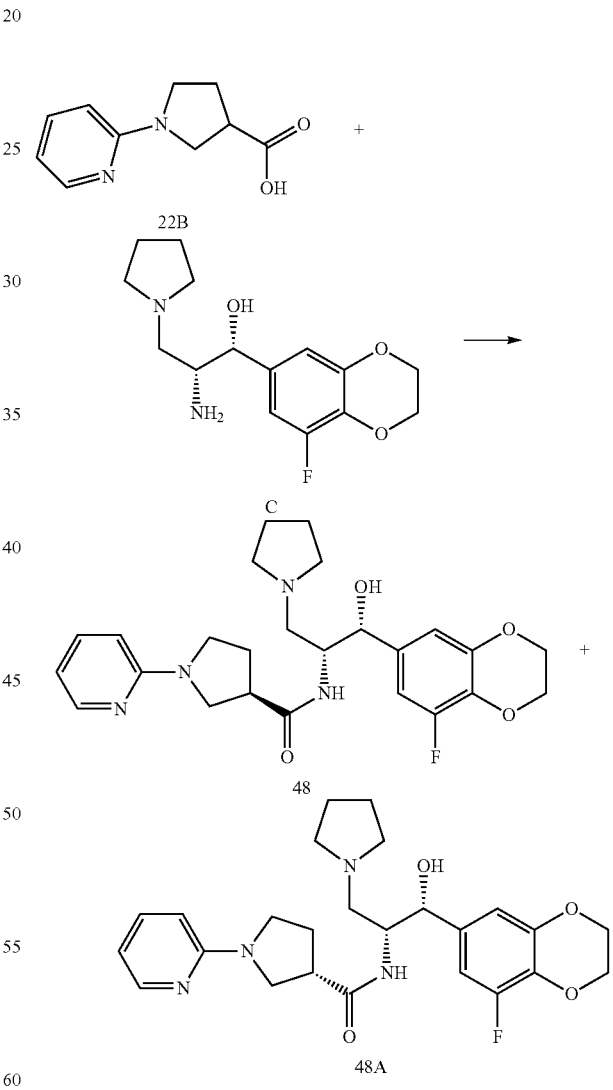

Compounds 48 and 48A were synthesized, by employing the procedures described for Compound 7 using Intermediate C and Compound 22B in lieu of Intermediate A and Compound 7B.

Compound 48. LC-MS (ESI) m/z: 471 [M+H]$^+$; $^1$H-NMR (MeOD, 400 MHz) δ (ppm) 1.70-1.76 (m, 4H), 2.10-2.20

(m, 2H), 2.52-2.68 (m, 6H), 3.02-3.04 (m, 2H), 3.28-3.31 (m, 1H), 3.47-3.48 (m, 2H), 4.13-4.16 (m, 5H), 4.47 (d, J=2.4 Hz, 1H), 6.35-6.37 (m, 1H), 6.46-6.49 (m, 1H), 6.59-6.64 (m, 2H), 7.41-7.43 (m, 1H), 7.88-7.89 (m, 1H). Chiral-HPLC condition, solvent: IPA (0.1% DEA), column: OD-H 250*4.6 mm 5 um, Rt: 7.33 min.

Compound 48A. LC-MS (ESI) m/z: 471 [M+H]+; 1H-NMR (MeOD, 400 MHz) δ (ppm) 1.68-1.72 (m, 4H), 1.78-1.87 (m, 1H), 2.02-2.12 (m, 1H), 2.47-2.65 (m, 6H), 3.01-3.03 (m, 1H), 3.25-3.47 (m, 4H), 4.12-4.15 (m, 5H), 4.67 (d, J=3.2 Hz, 1H), 6.34-6.36 (m, 1H), 6.45-6.47 (m, 1H), 6.59-6.64 (m, 2H), 7.39-7.40 (m, 1H), 7.86-7.87 (m, 1H). Chiral-HPLC condition, solvent: IPA (0.1% DEA), column: OD-H 250*4.6 mm 5 um, Rt: 8.33 min.

Example 49

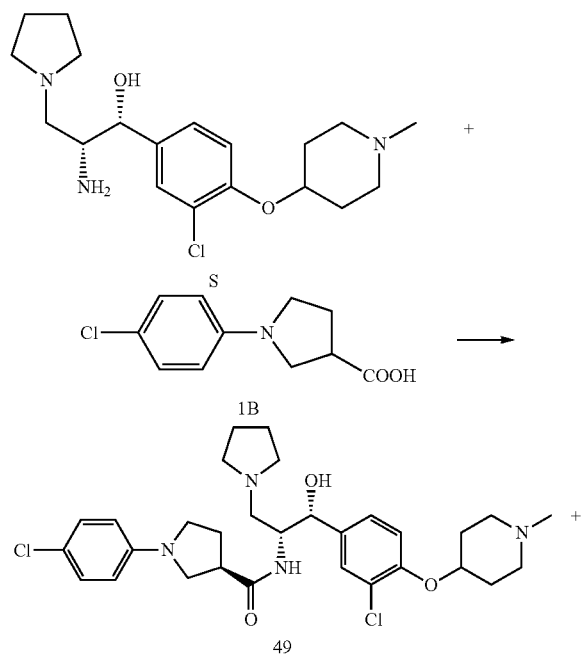

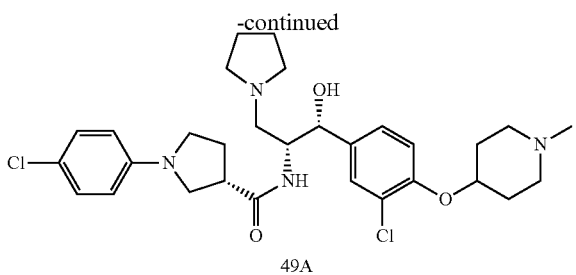

Compounds 49 and 49A were synthesized, by employing the procedures described for Compound 1 using Intermediate S in lieu of Intermediate A.

Compound 49. LC-MS (ESI) m/z: 575 [M+H]+; 1H-NMR (MEOD, 400 MHz) δ (ppm) 2.04-2.22 (m, 10H), 2.51-2.55 (m, 1H), 2.85 (s, 2H), 2.88 (s, 1H), 3.10-3.30 (m, 7H), 3.32-3.76 (m, 7H), 4.56-4.59 (m, 1H), 4.71 (m, 1H), 6.48-6.52 (m, 2H), 7.05-7.07 (d, J=8.4 Hz, 1H), 7.14-7.18 (m, 2H), 7.30-7.33 (m, 1H), 7.57-7.59 (m, 1H); Chiral-HPLC condition, solvent: MeOH (0.5% DEA), column: AD-H (250*4.6 mm 5 um), Rt: 2.39 min.

Compound 49A. LC-MS (ESI) m/z: 575 [M+H]+; 1H-NMR (MEOD, 400 MHz) δ (ppm) 1.64-1.65 (m, 1H), 2.02-2.19 (m, 9H), 2.89 (s, 1H), 2.91 (s, 2H), 3.12-3.30 (m, 6H), 3.30-3.74 (m, 8H), 4.53-4.56 (m, 1H), 4.80 (m, 1H), 4.91 (d, J=2.0 Hz, 1H), 6.47-6.49 (d, J=8.8 Hz, 2H), 7.10-7.15 (m, 2H), 7.32-7.35 (m, 1H), 7.53-7.55 (m, 1H); Chiral-HPLC condition, solvent: MeOH (0.5% DEA), column: AD-H (250*4.6 mm 5 um), Rt: 3.82 min.

Example 50

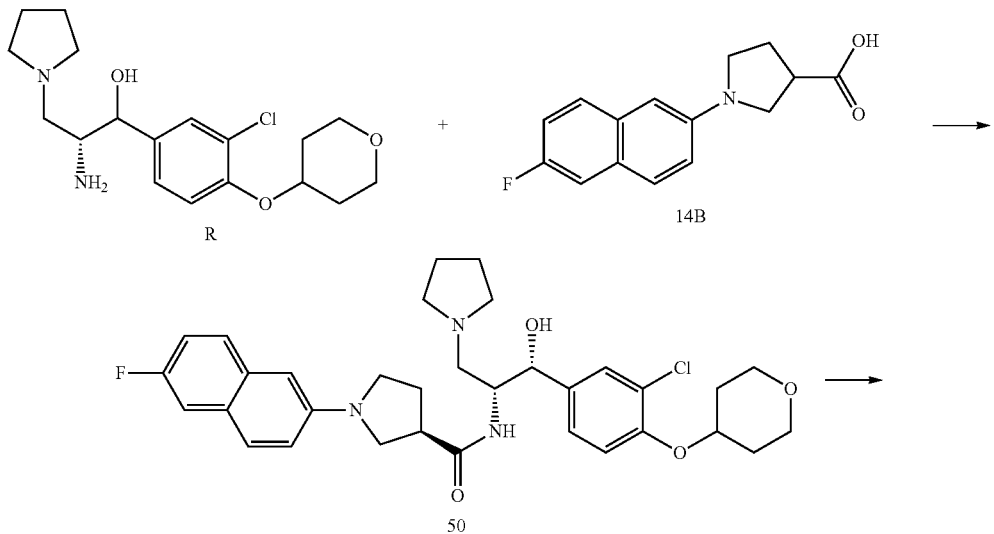

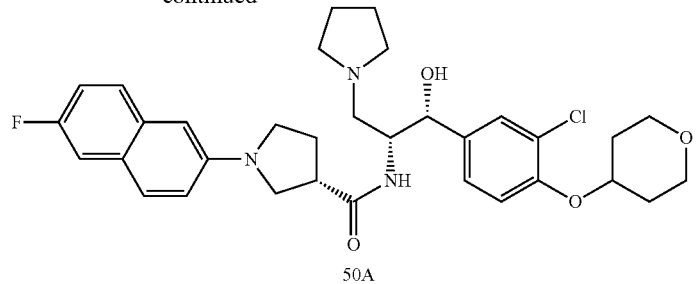

50A

Compounds 50 and 50A were synthesized, by employing the procedures described for Compound 1 using Intermediate R and Compound 14B in lieu of Intermediate A and Compound 1B.

Compound 50. LC-MS (ESI) m/z: 596 [M+H]$^+$; $^1$H-NMR (CDCl$_3$, 400 MHz) δ (ppm) 1.72 (m, 4H), 1.77-1.85 (m, 2H), 1.92-1.99 (m, 2H), 2.11-2.25 (m, 2H), 2.63-2.71 (m, 4H), 2.83-2.87 (m, 1H), 2.94-3.01 (m, 2H), 3.30-3.42 (m, 3H), 3.48-3.57 (m, 3H), 3.95-4.01 (m, 2H), 4.21-4.26 (m, 1H), 4.41-4.46 (m, 1H), 5.01 (d, J=2.4 Hz, 1H), 6.35 (d, J=8.0 Hz, 1H), 6.77 (d, J=2.4 Hz, 1H), 6.84 (d, J=8.4 Hz, 1H), 7.00 (dd, J=8.8, 2.0 Hz, 1H), 7.09 (dd, J=8.8, 2.4 Hz, 1H), 7.14-7.19 (m, 1H), 7.31 (dd, J=10.0, 2.4 Hz, 1H), 7.44 (d, J=2.0 Hz, 1H), 7.62-7.66 (m, 2H); Chiral-HPLC condition, solvent: n-hexane (0.1% DEA): EtOH (0.1% DEA)=70:30, column (OZ-H 250*4.6 mm 5 um), Rt: 7.22 min.

Compound 50A. LC-MS (ESI) m/z: 596 [M+H]$^+$; $^1$H-NMR (CDCl$_3$, 400 MHz) δ (ppm) 1.80 (m, 6H), 1.93-2.00 (m, 2H), 2.05-2.11 (m, 1H), 2.17-2.23 (m, 1H), 2.65-2.75 (m, 4H), 2.86-2.92 (m, 2H), 2.99-2.03 (m, 1H), 3.31-3.37 (m, 1H), 3.43-3.59 (m, 5H), 3.96-4.02 (m, 2H), 4.21-4.25 (m, 1H), 4.39-4.44 (m, 1H), 4.99 (d, J=2.8 Hz, 1H), 6.35 (d, J=8.0 Hz, 1H), 6.76-6.79 (m, 2H), 7.00 (dd, J=9.2, 2.4 Hz, 1H), 7.07 (dd, J=8.4. 2.0 Hz, 1H), 7.13-7.18 (m, 1H), 7.31 (dd, J=10.0, 2.4 Hz, 1H), 7.38 (d, J=2.0 Hz, 1H), 7.59-7.65 (m, 2H); Chiral-HPLC condition, solvent: n-hexane (0.1% DEA):EtOH (0.1% DEA)=70:30, column (OZ-H 250*4.6 mm 5 um), Rt: 8.27 min.

Example 51

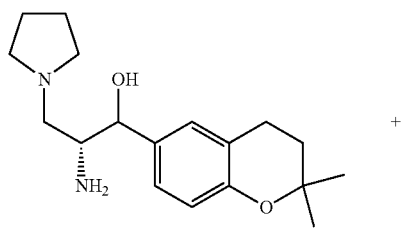

M

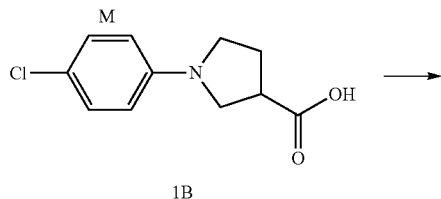

1B

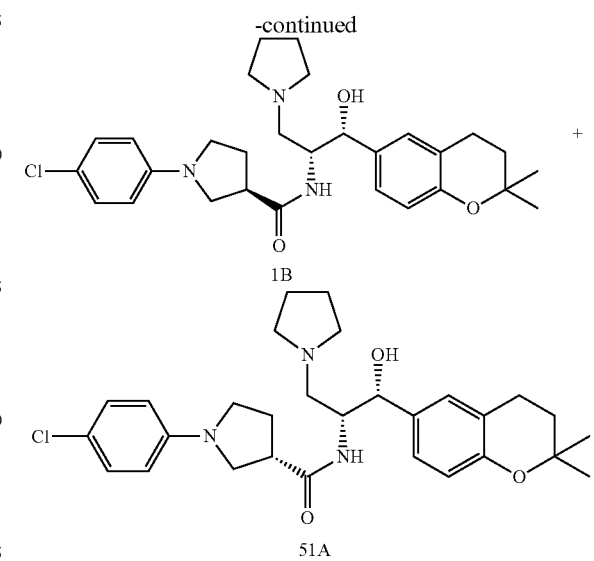

1B

51A

Compounds 51 and 51A were synthesized, by employing the procedures described for Compound 1 using Intermediate M in lieu of Intermediate A.

Compound 51. LC-MS (ESI) m/z: 512 [M+H]$^+$; $^1$H-NMR (DMSO-d$_6$, 400 MHz) δ (ppm) 1.16 (s, 3H), 1.28 (s, 3H), 1.76-1.81 (m, 6H), 2.11-2.19 (m, 2H), 2.59-2.88 (m, 6H), 2.95-2.99 (m, 1H), 2.97-2.99 (m, 1H), 3.06-3.13 (m, 1H), 3.20-3.34 (m, 4H), 4.26-4.31 (m, 1H), 4.81 (s, 1H), 6.47 (dJ=9.2 Hz, 2H), 6.68 (dJ=8.8 Hz, 1H), 7.14-7.13 (m, 4H). Chiral-HPLC condition, solvent MeOH (0.1% DEA), column OJ-H (250*4.6 mm 5 um), Rt: 2.78 min.

Compound 51A. LC-MS (ESI) m/z: 512 [M+H]$^+$; $^1$H-NMR (DMSO-d$_6$, 400 MHz) δ (ppm) 1.21 (s, 6H), 1.69-1.72 (m, 6H), 1.82-1.87 (m, 1H), 2.03-2.10 (m, 1H), 2.49-2.69 (m, 6H), 3.00-3.06 (m, 1H), 3.13-3.17 (m, 2H), 3.22-3.28 (m, 4H), 4.17-4.22 (m, 1H), 4.70 (s, 1H), 6.40 (d, J=8.8 Hz, 2H), 6.57 (d, J=8.8 Hz, 1H), 6.95-7.03 (m, 4H). Chiral-HPLC condition, solvent MeOH (0.1% DEA), column OJ-H (250*4.6 mm 5 um), Rt: 3.49 min.

Example 52

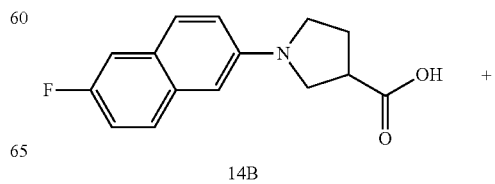

14B

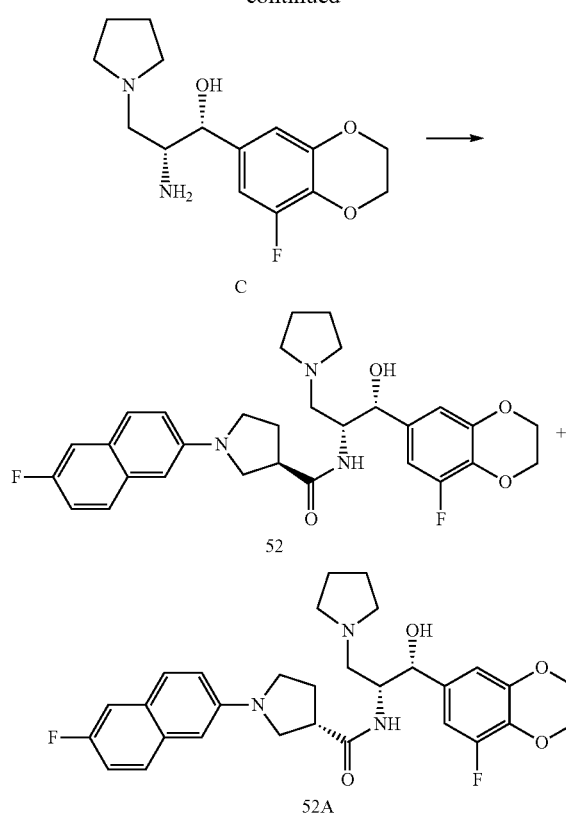

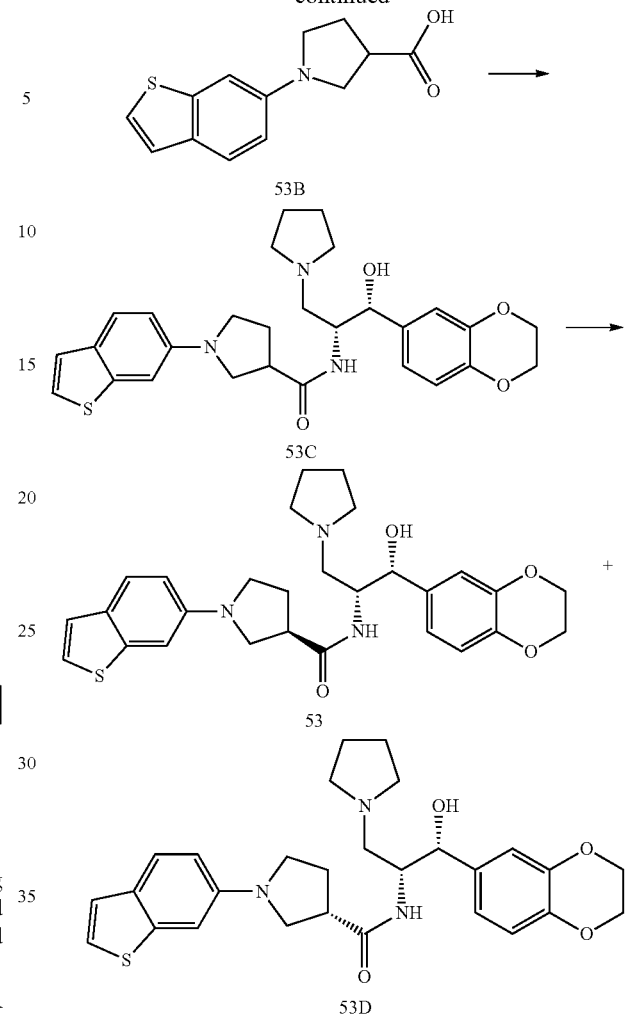

Compounds 52 and 52A were synthesized, by employing the procedures described for Compound 1 using Compound 14B and Intermediate C in lieu of Compound 1B and Intermediate A.

Compound 52. LC-MS (ESI) m/z: 538 [M+H]$^+$; $^1$H-NMR (MeOD, 400 MHz) δ (ppm) 1.72 (s, 4H), 2.01-2.17 (m, 2H), 2.50-2.64 (m, 5H), 2.83-2.86 (m, 1H), 3.01-3.09 (m, 1H), 3.34-3.42 (m, 4H), 4.05-4.17 (m, 5H), 4.71 (s, 1H), 6.60-6.70 (m, 3H), 6.95 (dJ=8.4 Hz, 1H), 7.02-7.06 (m, 1H), 7.20-7.23 (m, 1H), 7.54-7.58 (m, 2H); Chiral-HPLC condition, solvent: MeOH (0.1% DEA), column AD-H (4.6*250 mm 5 um), Rt: 6.63 min.

Compound 52A. LC-MS (ESI) m/z: 538 [M+H]$^+$; $^1$H-NMR (MeOD, 400 MHz) δ (ppm) 1.71 (s, 4H), 1.85-1.90 (m, 1H), 1.92-2.15 (m, 1H), 2.48-2.65 (m, 6H), 3.00-3.08 (m, 1H), 3.29-3.39 (m, 4H), 4.14 (s, 5H), 4.67 (s, 1H), 6.59-6.67 (m, 3H), 6.93 (d, J=8.4 Hz, 1H), 6.99-7.04 (m, 1H), 7.18 (d, J=8.0 Hz, 1H), 7.19-7.53 (m, 2H); Chiral-HPLC condition, solvent: MeOH (0.1% DEA), column AD-H (4.6*250 mm 5 um), Rt: 13.47 min.

Example 53

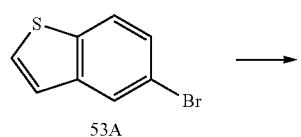

Compounds 53B, 53, and 53D were synthesized, by employing the procedures described for Compound 1B and Compound 1 using Compound 53A and 53B in lieu of 1-chloro-4-iodobenzene and Compound 1B.

Compound 53B. LC-MS (ESI) m/z: 248 [M+H]$^+$; $^1$H-NMR (DMSO-d$_6$, 400 MHz) δ (ppm) 2.05-2.15 (m, 2H), 2.87-2.95 (m, 1H), 2.23-2.29 (m, 2H), 2.38-2.41 (m, 2H), 6.67-6.69 (m, 1H), 6.97 (d, J=2 Hz, 1H), 7.19-7.24 (m, 2H) 7.60-7.63 (m, 1H).

Compound 53. LC-MS (ESI) m/z: 508 [M+H]$^+$; $^1$H-NMR (MeOD, 400 MHz) δ (ppm) 1.70 (s, 4H), 1.85-1.90 (m, 1H), 2.06-2.09 (m, 1H), 2.25-2.66 (m, 6H), 2.98-3.02 (m, 1H), 3.20-3.21 (m, 4H), 4.09 (s, 4H), 4.15-4.18 (m, 1H), 4.67 (d, J=3.2 Hz, 1H), 6.58-6.61 (m, 1H), 6.66-6.69 (m, 2H), 6.77 (d, J=1.6 Hz, 2H), 6.85 (d, J=1.2 Hz, 2H), 6.99-7.02 (m, 2H), 7.48-7.50 (m, 1H). Chiral-HPLC condition, solvent: MeOH (0.5% DEA), column AS-H (250*4.6 mm 5 um), Rt: 5.58 min.

Compound 53D. LC-MS (ESI) m/z: 508 [M+H]$^+$; $^1$H-NMR (MeOD, 400 MHz) δ (ppm) 1.91-2.12 (m, 6H), 2.59-2.63 (m, 1H), 3.04-3.14 (m, 3H), 3.32-3.38 (m, 4H), 3.46-3.59 (m, 2H), 3.67-3.74 (m, 1H), 4.07-4.17 (m, 4H), 4.38-4.42 (m, 1H), 4.76 (d, J=2.4 Hz, 1H), 6.63-6.65 (m, 1H), 6.75-6.78 (m, 2H), 6.87-6.89 (m, 2H), 7.05-7.06 (m, 2H), 7.53-7.55 (m, 1H). Chiral-HPLC condition, solvent: MeOH (0.5% DEA), column AS-H (250*4.6 mm 5 um), Rt: 6.85 min.

Example 54

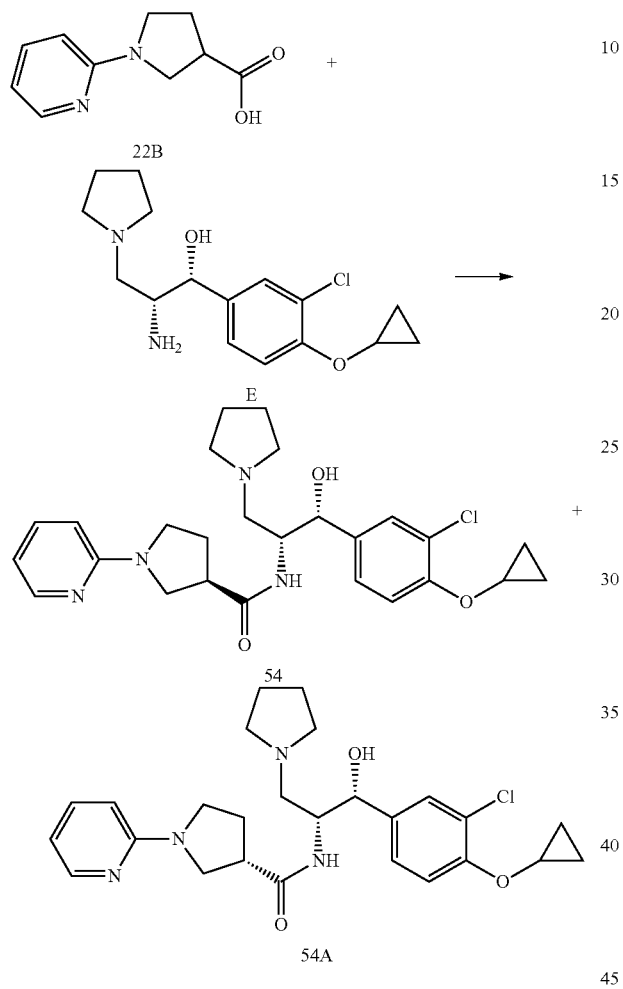

Example 55

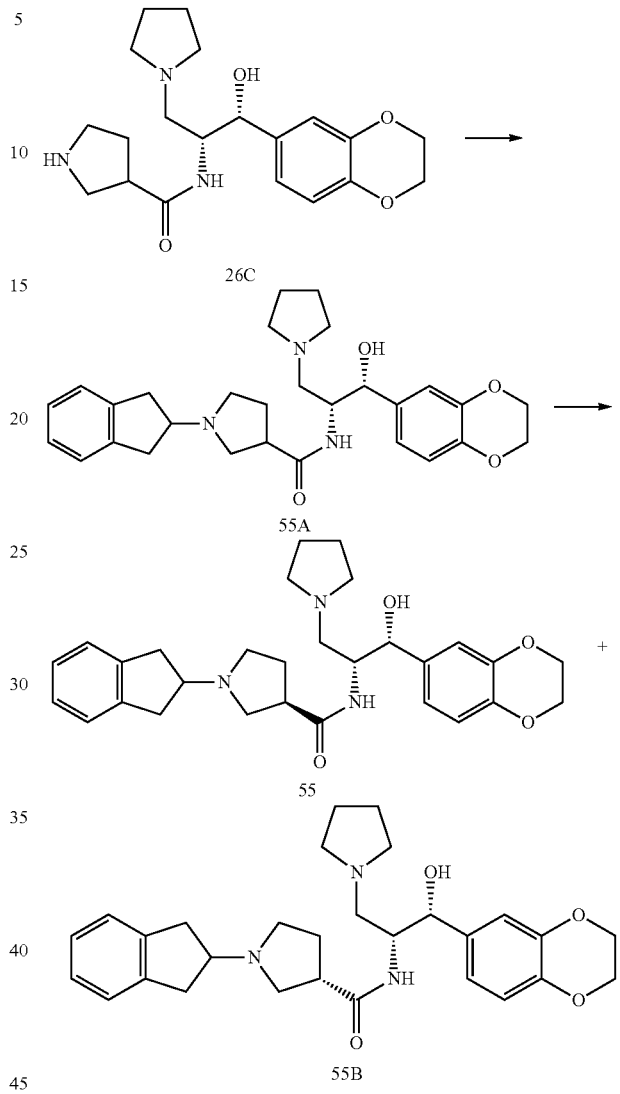

Compounds 54 and 54A were synthesized, by employing the procedures described for Compound 7 using Compound 22B and Intermediate E in lieu of Compound 7B and Intermediate A.

Compound 54. LC-MS (ESI) m/z: 485 [M+H]+; 1H-NMR (MeOD, 400 MHz) δ (ppm) 0.56-0.60 (m, 4H), 1.92-2.08 (m, 4H), 2.10-2.37 (m, 2H), 2.90-3.00 (m, 1H), 3.01-3.20 (m, 3H), 3.32-3.74 (m, 9H), 4.45 (d, J=2.8 Hz 1H), 6.78-6.81 (m, 1H), 6.84-6.87 (m, 1H), 7.21-7.22 (m, 2H), 7.39 (s, 1H), 7.79-7.80 (m, 1H), 7.88-7.92 (m, 1H). Chiral-HPLC condition, solvent: IPA (0.5% DEA), column: OZ-H 250*4.6 mm 5 um, Rt: 3.88 min.

Compound 54A. LC-MS (ESI) m/z: 485 [M+H]+; 1H-NMR (MeOD, 400 MHz) δ (ppm) 0.60-0.72 (m, 4H), 1.64-1.80 (m, 5H), 2.00-2.10 (m, 1H), 2.51-2.73 (m, 6H), 3.01-3.08 (m, 1H), 3.25-3.32 (m, 2H), 3.36-3.47 (m, 2H), 3.73-3.76 (m, 1H), 4.18-4.19 (m, 1H), 4.76 (d, J=2.8 Hz 1H), 6.34-6.36 (m, 1H), 6.44-6.47 (m, 1H), 7.15-7.16 (m, 1H), 7.21-7.22 (m, 1H), 7.30 (s, 1H), 7.37-7.39 (m, 1H), 7.86-7.87 (m, 1H). Chiral-HPLC condition, solvent: IPA (0.5% DEA), column: OZ-H 250*4.6 mm 5 um, Rt: 5.25 min.

Compounds 55 and 55B were synthesized, by employing the procedures described for Compound 9B using Compound 26C and 1H-inden-2(3H)-one in lieu of Compound 5A and tetrahydro-4H-pyran-4-one.

Compounds 55. LC-MS (ESI) m/z: 492 [M+H]+; 1H-NMR (CDCl3, 400 MHz) δ (ppm) 2.02 (m, 4H), 2.28 (m, 2H), 3.21 (m, 10H), 3.76 (m, 6H), 4.18 (m, 4H), 4.48 (m, 1H), 4.81 (m, 1H), 6.79 (m, 3H), 7.20 (m, 4H), 7.90-11.44 (m, 2H); Chiral-HPLC condition, solvent:EtOH (0.5% DEA), column IC (150*4.6 mm 5 um), Rt: 4.97 min.

Compounds 55B. LC-MS (ESI) m/z: 492 [M+H]+; 1H-NMR (CDCl3, 400 MHz) δ (ppm) 1.58 (m, 1H), 1.95 (m, 5H), 3.17 (m, 11H), 3.70 (m, 5H), 4.09 (m, 4H), 4.41 (m, 1H), 4.73 (m, 1H), 6.71 (m, 3H), 7.11 (m, 4H), 7.73-11.59 (m, 2H). Chiral-HPLC condition, solvent:EtOH (0.5% DEA), column IC (150*4.6 mm 5 um), Rt: 5.8 min.

Example 56

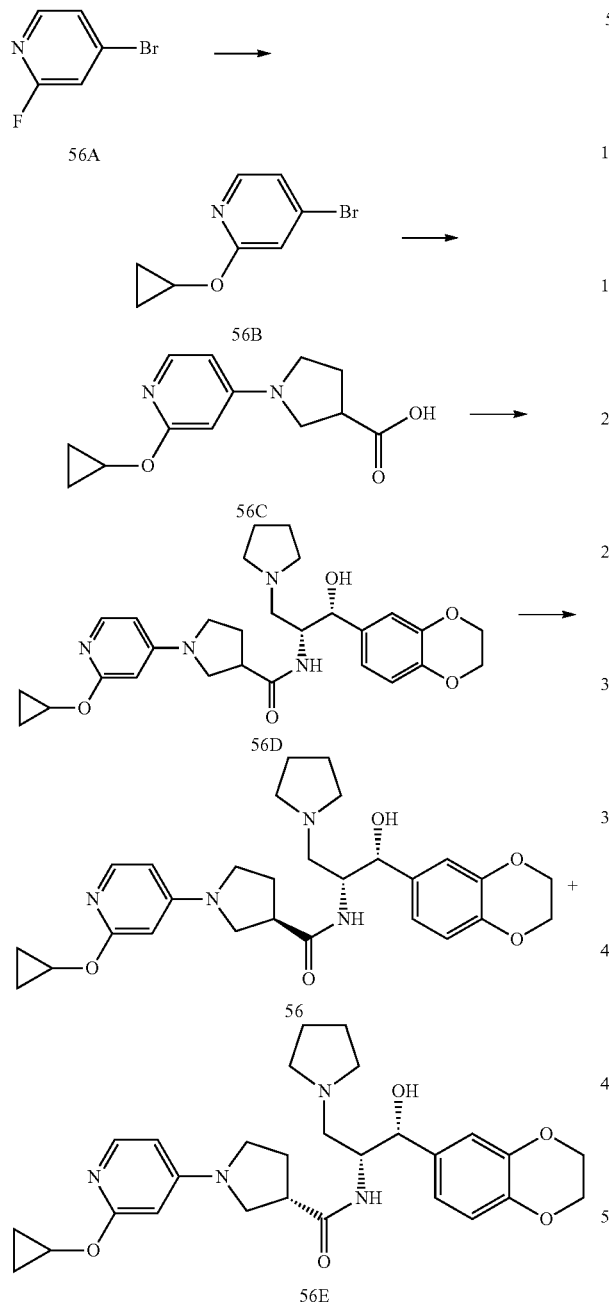

To a mixture of cyclopropanol (1.5 g, 25.8 mmol) and Compound 56A (3.0 g, 17.2 mmol) in N-methyl-2-pyrrolidone (20 mL) was added potassium tert-butoxide (2.9 g, 25.8 mmol) in tetrahydrofuran (25 mL) dropwise and the resultant mixture was stirred at room temperature for 0.5 h under nitrogen protection. Then it was diluted with ethyl acetate (50 mL) and petroleum ether (50 mL), washed with water (30 mL) and brine (30 mL), dried over anhydrous sodium sulfate, evaporated and purified with flash column chromatography on silica gel (petroleum ether, 100% v/v) to furnish Compound 56B. LC-MS: (m/z) 216 [M+2]⁺; $^1$H-NMR (DMSO-d$_6$, 400 MHz) δ (ppm) 0.66-0.69 (m, 2H), 0.75-0.78 (m, 2H), 4.19-4.22 (m, 1H), 7.16 (m, 1H), 7.26-7.28 (m, 1H), 8.11-8.12 (d, J=5.2 Hz, 1H).

Compounds 56C, 56, and 56E were synthesized, by employing the procedures described for Compound 1B and 1 using Compound 56B and 56C in lieu of 1-chloro-4-iodobenzene and Compound 1B.

Compound 56C. LC-MS (ESI) m/z: 249 [M+H]⁺; $^1$H-NMR (DMSO-d$_6$, 400 MHz) δ (ppm) 0.84-0.91 (m, 4H), 2.19-2.30 (m, 2H), 3.53-3.73 (m, 5H), 4.31 (s, 1H), 6.27-6.78 (m, 2H), 7.80-8.15 (m, 1H), 12.72-12.95 (m, 1H).

Compound 56. LC-MS (ESI) m/z: 509 [M+H]⁺; $^1$H-NMR (CDCl$_3$, 400 MHz) δ (ppm) 0.73-0.77 (m, 4H), 1.78-1.79 (m, 4H), 2.16-2.20 (m, 2H), 2.64-2.69 (m, 4H), 2.87-2.92 (m, 2H), 3.20-3.29 (m, 2H), 3.37-3.41 (m, 2H), 4.12-4.14 (m, 2H), 4.23-4.26 (m, 4H), 4.97-4.98 (m, 1H), 5.79 (s, 1H), 6.09-6.11 (m, 2H), 6.77-6.86 (m, 3H), 7.87-7.89 (m, 1H). Chiral-HPLC condition, solvent: n-hexane (0.1% DEA): EtOH (0.1% DEA)=30:70 column AD-H (4.6*250 mm 5 um), Rt: 7.54 min.

Compound 56E. LC-MS (ESI) m/z: 509 [M+H]⁺; $^1$H-NMR (CDCl$_3$, 400 MHz) δ (ppm) 0.71-0.75 (m, 4H), 1.79-1.80 (m, 4H), 2.00-2.14 (m, 2H), 2.67-2.75 (m, 4H), 2.87-2.95 (m, 2H), 3.24-3.47 (m, 4H), 4.06-4.12 (m, 2H), 4.20-4.23 (m, 4H), 4.94-4.94 (m, 1H), 5.77-5.79 (m, 1H), 6.08-6.22 (m, 2H), 6.76-6.84 (m, 3H), 7.85-7.87 (m, 1H). Chiral-HPLC condition, solvent: n-hexane (0.1% DEA): EtOH (0.1% DEA)=30:70 column AD-H (4.6*250 mm 5 um), Rt: 26.19 min.

Example 57

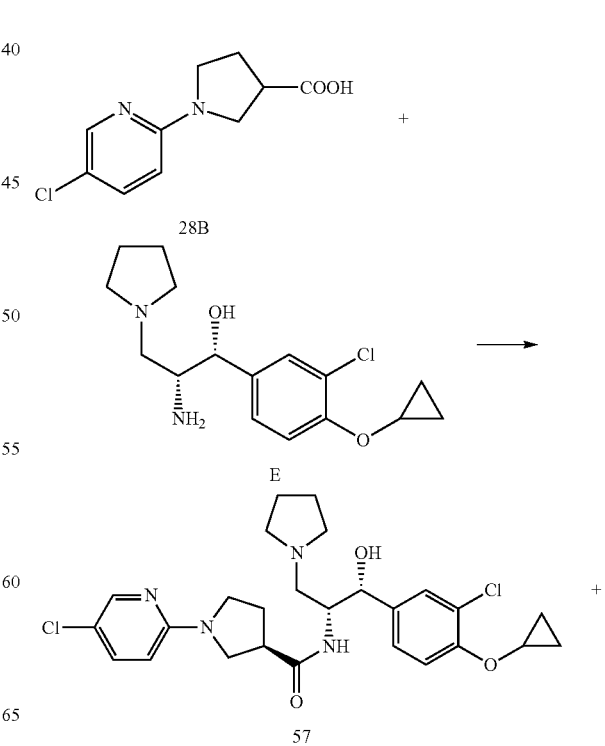

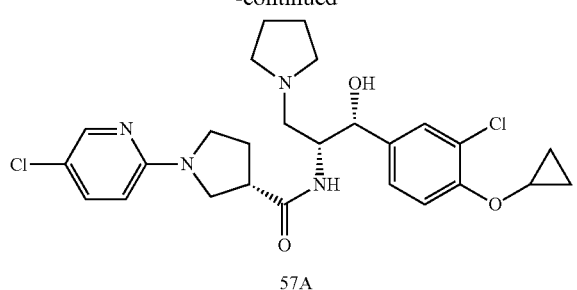

57A

Compounds 57 and 57A were synthesized, by employing the procedures described for Compound 1 using Compound 28B and Intermediate E in lieu of Compound 1B and Intermediate A.

Compound 57. LC-MS (ESI) m/z: 519 [M+H]$^+$; $^1$H-NMR (CDCl$_3$, 400 MHz) δ (ppm) 0.81-0.85 (m, 4H), 1.72-1.74 (m, 5H), 2.21-2.23 (m, 2H), 2.61-2.65 (m, 4H), 2.72-2.73 (m, 2H), 2.93-2.96 (m, 1H), 3.40-3.52 (m, 4H), 3.72-3.73 (m, 1H), 4.10-4.13 (m, 1H), 4.75 (d, J=4.8 Hz, 1H), 6.15-6.18 (m, 1H), 6.26 (d, J=8.8 Hz, 1H), 7.21-7.23 (m, 3H), 7.26 (s, 1H), 7.43-7.44 (m, 1H), 7.94 (s, 1H); Chiral-HPLC condition, solvent: MeOH (0.5% DEA), column OJ-H (4.6*250 mm 5 um), Rt: 4.24 min.

Compound 57A. LC-MS (ESI) m/z: 519 [M+H]$^+$; $^1$H-NMR (CDCl$_3$, 400 MHz) δ (ppm) 0.83-0.85 (m, 4H), 1.77-1.79 (m, 5H), 2.16-2.18 (m, 2H), 2.56-2.59 (m, 4H), 2.68-2.71 (m, 2H), 2.93-2.94 (m, 1H), 3.40-3.57 (m, 4H), 3.76-3.77 (m, 1H), 4.11-4.13 (m, 1H), 4.73 (d, J=4.8 Hz, 1H), 6.11-6.15 (m, 1H), 6.30 (d, J=8.8 Hz, 1H), 7.24-7.24 (m, 3H), 7.26 (s, 1H), 7.36-7.37 (m, 1H), 8.02 (s, 1H); Chiral-HPLC condition, solvent: MeOH (0.1% DEA), column AS-H (4.6*250 mm 5 um), Rt: 4.90 min.

Example 58

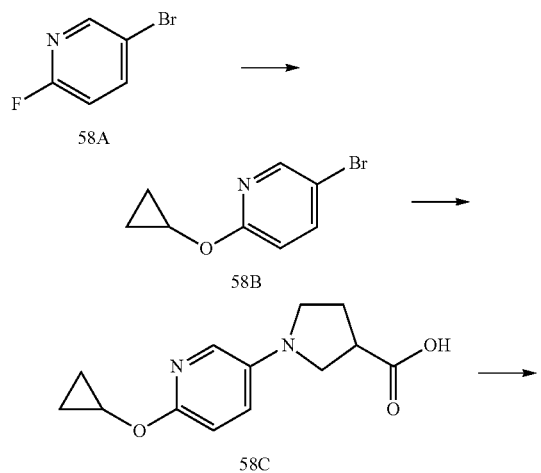

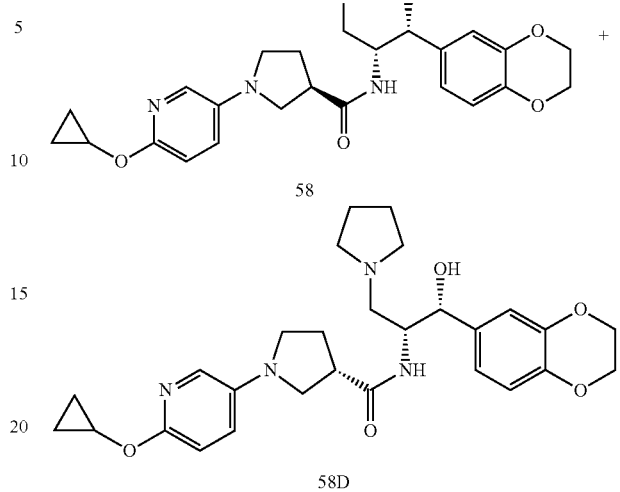

Compound 58B was synthesized, by employing the procedure described for Compound 56B using Compound 58A in lieu of Compound 56A. LC-MS: (m/z) 216 [M+2]$^+$.

Compound 58C, 58, and 58D were synthesized, by employing the procedures described for Compound 1B and 1 using Compound 58B and 58C in lieu of 1-chloro-4-iodobenzene and Compound 1B.

Compound 58C. LC-MS (ESI) m/z: 249 [M+H]$^+$; $^1$H-NMR (DMSO-d$_6$, 400 MHz) (ppm) 0.62-0.72 (m, 4H), 2.14-2.19 (m, 2H), 3.16-3.27 (m, 3H), 3.36-3.42 (m, 2H), 4.07 (s, 1H), 6.51-6.90 (m, 2H), 7.12-7.14 (m, 1H).

Compound 58. LC-MS (ESI) m/z: 509 [M+H]$^+$; $^1$H-NMR (CDCl$_3$, 400 MHz) δ (ppm) 0.72-0.76 (m, 4H), 1.73-1.75 (m, 4H), 2.13-2.18 (m, 2H), 2.60-2.67 (m, 4H), 2.84-2.86 (m, 2H), 2.92-2.96 (m, 1H), 3.16-3.18 (m, 1H), 3.24-3.25 (m, 2H), 3.34-3.37 (m, 1H), 4.04-4.07 (m, 1H), 4.15-4.18 (m, 1H), 4.22-4.24 (m, 4H), 4.95-4.96 (m, 1H), 6.25-6.27 (m, 1H), 6.69-6.74 (m, 2H), 6.80-6.85 (m, 2H), 6.92-6.95 (m, 1H), 7.571-7.578 (m, 1H). Chiral-HPLC condition, solvent: MeOH (0.5% DEA) column OJ-H (4.6*250 mm 5 um), Rt: 3.58 min.

Compound 58D. LC-MS (ESI) m/z: 509 [M+H]$^+$; $^1$H-NMR (CDCl$_3$, 400 MHz) δ (ppm) 0.84-0.88 (m, 4H), 1.91-2.21 (m, 6H), 2.83-2.97 (m, 2H), 3.01-3.27 (m, 4H), 3.33-3.46 (m, 2H), 3.57-3.67 (m, 3H), 4.03-4.05 (m, 1H), 4.16-4.22 (m, 4H), 4.46-4.54 (m, 1H), 4.78-4.82 (m, 1H), 6.73-6.86 (m, 3H), 7.10-7.17 (m, 1H), 7.29-7.32 (m, 1H), 7.59-7.70 (m, 2H), 11.07-11.19 (m, 1H). Chiral-HPLC condition, solvent: MeOH (0.5% DEA) column OJ-H (4.6*250 mm 5 um), Rt: 4.25 min.

Example 59
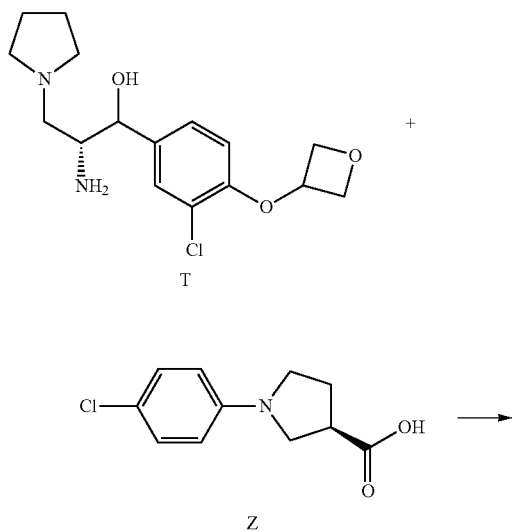
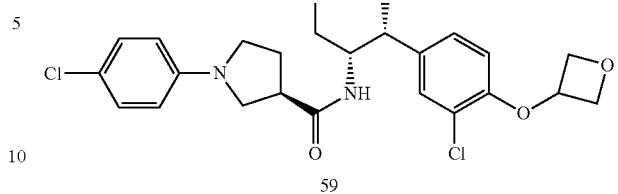
Compound 59 was synthesized, by employing the procedure described for Compound 1 using Intermediate T and Intermediate Z in lieu of Intermediate A and Compound 1B. LC-MS (ESI) m/z: 534 [M+H]$^+$; $^1$H-NMR (MeOD, 400 MHz) δ (ppm) 2.02-2.06 (m, 6H), 2.15-2.19 (m, 1H), 2.92-2.99 (m, 1H), 3.10-3.26 (m, 5H), 3.31-3.35 (m, 1H), 3.68-3.71 (m, 3H), 4.46-4.50 (m, 2H), 4.62-4.69 (m, 2H), 4.92-4.99 (m, 2H), 5.11-5.12 (m, 1H), 6.38-6.41 (d, J=9.2 Hz, 1H), 6.57-6.60 (d, J=8.4 Hz, 1H), 7.11-7.14 (m, 2H), 7.26-7.45 (m, 1H), 7.44-7.45 (d, J=2.0 Hz, 1H), 8.07-8.09 (d, J=9.6 Hz, 1H).
Example 60
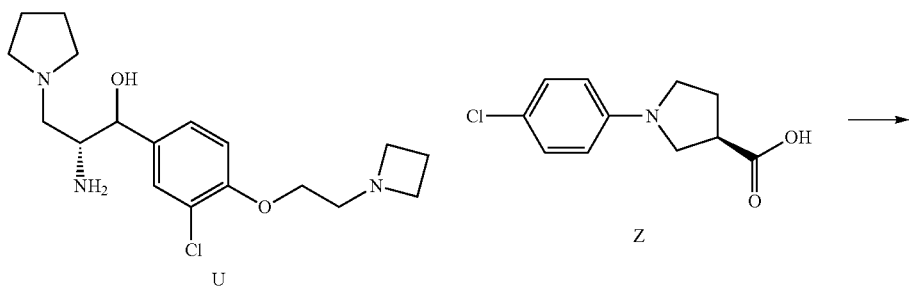
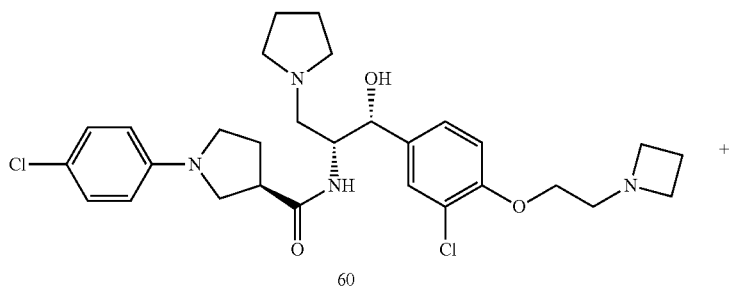
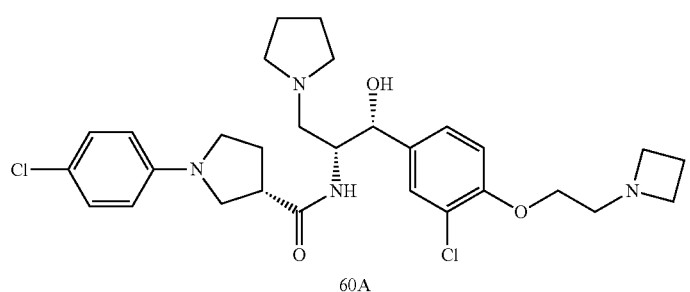

Compounds 60 and 60A were synthesized, by employing the procedures described for Compound 1 using intermediates U and Z in lieu of intermediate A and Compound 1B.

Compound 60. LC-MS (ESI) m/z: 561 [M+H]$^+$. $^1$H-NMR (MeOD, 400 MHz) δ (ppm) 1.77-1.78 (m, 4H), 2.05-2.12 (m, 4H), 2.58-2.62 (m, 4H), 2.71-2.84 (m, 4H), 3.01-3.07 (m, 1H), 3.14-3.19 (m, 1H), 3.25-3.31 (m, 3H), 3.39 (t, J=7.2 Hz, 4H), 3.94 (t, J=5.6 Hz, 2H), 4.20-4.25 (m, 1H), 4.82 (d, J=2.4 Hz, 1H), 6.44 (d, J=8.8 Hz, 2H), 6.86 (d, J=8.8 Hz, 1H), 7.08 (d, J=9.2 Hz, 2H), 7.15 (dd, J=8.4, 2.0 Hz, 1H), 7.41 (d, J=1.6 Hz, 1H). Chiral-HPLC condition, solvent: n-hexane (0.1% DEA):EtOH (0.1% DEA)=30:70, column IA (4.6*250 mm 5 um), Rt: 6.41 min.

Compound 60A. LC-MS (ESI) m/z: 561 [M+H]$^+$. $^1$H-NMR (MeOD, 400 MHz) δ (ppm) 1.75-1.77 (m, 4H), 1.81-1.86 (m, 1H), 2.07-2.12 (m, 3H), 2.55-2.61 (m, 4H), 2.68-2.70 (m, 2H), 2.84 (t, J=4.8 Hz, 2H), 3.02-3.09 (m, 1H), 3.16-3.20 (m, 2H), 3.27-3.30 (m, 3H), 3.39 (t, J=6.8 Hz, 4H), 3.99 (t, J=5.2 Hz, 2H), 4.20-4.21 (m, 1H), 4.81 (d, J=2.0 Hz, 1H), 6.43 (d, J=8.4 Hz, 2H), 6.91 (d, J=8.4 Hz, 1H), 7.06 (d, J=8.4 Hz, 2H), 7.17 (d, J=7.8 Hz, 1H), 7.38 (s, 1H). Chiral-HPLC condition, solvent: n-hexane (0.1% DEA):EtOH (0.1% DEA)=30:70, column O IA (4.6*250 mm 5 um), Rt: 10.69 min.

Example 61

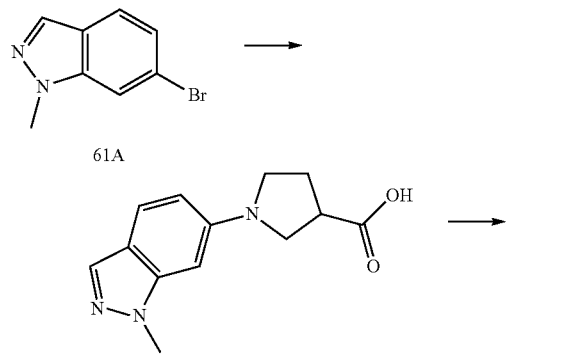

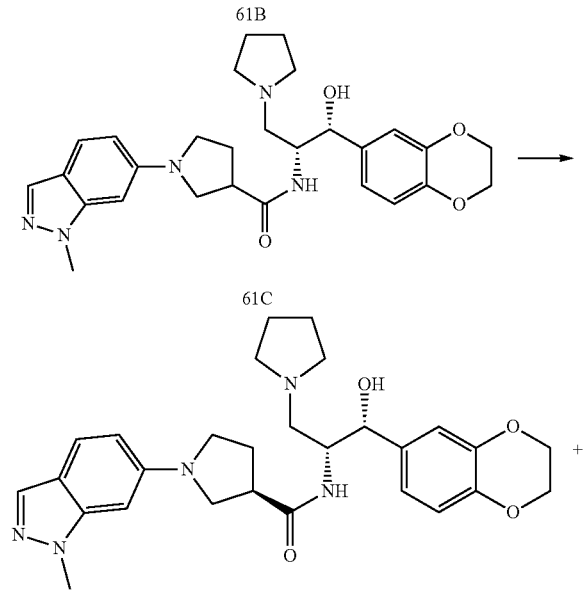

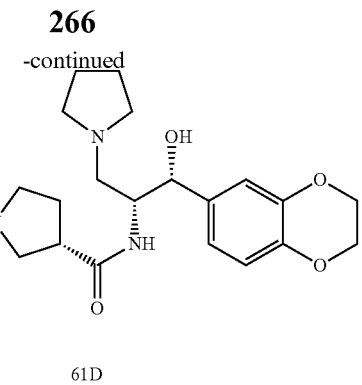

Compounds 61B, 61 and 61D were synthesized, by employing the procedures described for Compound 1B and 1 using Compound 61A and 61B in lieu of Compound 1A and 1B.

Compound 61B. LC-MS (ESI) m/z: 246 [M+H]$^+$; $^1$H-NMR (DMSO-d$_6$, 400 MHz) δ (ppm) 2.17-2.25 (m, 2H), 3.20-3.24 (m, 1H), 3.32-3.41 (m, 2H), 3.47-3.56 (m, 2H), 3.89 (s, 3H), 6.43 (s, 1H), 6.58 (dd, J$_1$=9.6 Hz, J$_2$=2.0 Hz, 1H), 7.50 (d, J=9.6 Hz, 1H), 7.76 (d, J=2.0 Hz, 1H).

Compound 61. LC-MS (ESI) m/z: 506 [M+H]$^+$; $^1$H-NMR (MeOD, 400 MHz) δ (ppm) 1.85-1.86 (m, 4H), 1.94-2.01 (m, 1H), 2.20-2.25 (m, 1H), 2.68-2.83 (m, 6H), 3.14-3.31 (m, 1H), 3.37-3.41 (m, 1H), 3.48-3.50 (m, 2H), 3.91 (s, 1H), 4.22 (s, 1H), 4.28-4.31 (m, 1H), 4.79 (d, J=3.2 Hz, 1H), 6.32 (s, 1H), 6.62 (dd, J$_1$=8.8 Hz, J$_2$=2.0 Hz, 1H), 6.76-6.83 (m, 2H), 6.89 (d, J=2.0 Hz, 1H), 7.51 (d, J=8.8 Hz, 1H), 7.75 (d, J=0.8 Hz, 1H).

Compound 61D. LC-MS (ESI) m/z: 506 [M+H]$^+$; $^1$H-NMR (MeOD, 400 MHz) δ (ppm) 1.93-1.98 (m, 4H), 2.20-2.23 (m, 2H), 2.88-2.92 (m, 1H), 2.90-3.19 (m, 8H), 3.31-3.34 (m, 1H), 3.45-3.50 (m, 2H), 3.95 (s, 3H), 4.09-4.15 (m, 4H), 4.38-4.42 (m, 1H), 4.82 (d, J=2.8 Hz, 1H), 6.28 (s, 1H), 6.62 (dd, J$_1$=8.8 Hz, J$_2$=2.0 Hz, 1H), 6.81-6.90 (m, 3H), 7.53 (d, J=8.8 Hz, 1H), 7.76 (d, J=0.8 Hz, 1H).

Example 62

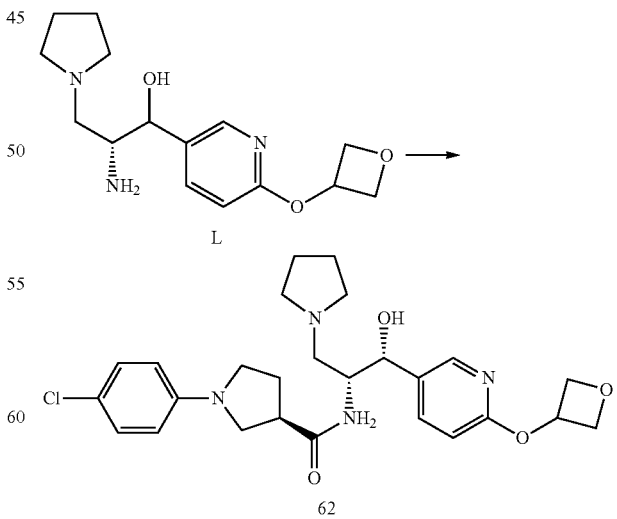

Compound 62 was synthesized, by employing the procedure described for Compound 1 using Intermediate L and Z in lieu of Intermediate A and Compound 1B. LC-MS (ESI) m/z: 502 [M+H]⁺; ¹H-NMR (MeOD, 400 MHz) δ (ppm) 2.01-2.10 (m, 6H), 2.82-2.84 (m, 1H), 3.10-3.18 (m, 5H), 3.21-3.27 (m, 1H), 3.45-3.46 (m, 1H), 3.53-3.70 (m, 4H), 3.87-3.96 (m, 1H), 4.58-4.64 (m, 1H), 4.72-4.74 (m, 2H), 4.97-4.98 (m, 1H), 5.29-5.34 (m, 1H), 6.38-6.43 (m, 2H), 7.04-7.08 (m, 2H), 7.17-7.26 (m, 1H), 8.29-8.34 (m, 1H), 8.49 (s, 1H).

Example 63

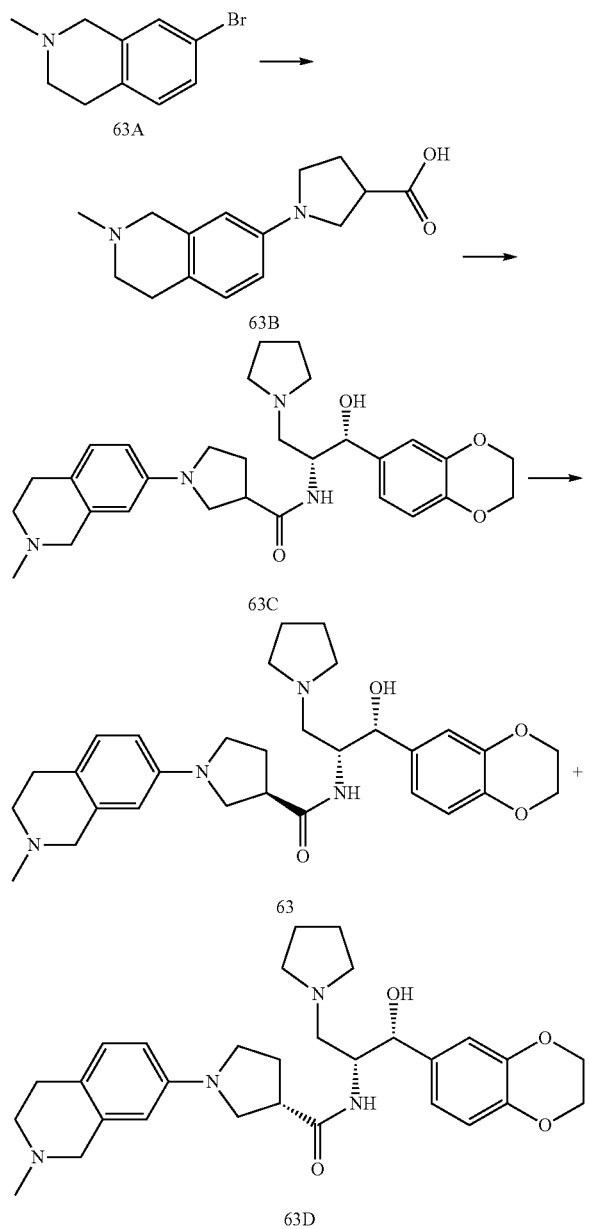

Compounds 63B, 63, and 63D were synthesized, by employing the procedures described for Compounds 1B and 1 using Compounds 63A and 63B in lieu of 1-chloro-4-iodobenzene and Compound 1B.

Compound 63B. LC-MS (ESI) m/z: 261 [M+H]⁺; ¹H-NMR (CDCl₃, 400 MHz) δ (ppm) 2.05-2.15 (m, 3H), 2.53 (s, 3H), 2.62 (s, 2H), 2.81-2.97 (m, 4H), 3.35-3.37 (m, 2H), 3.75-3.81 (m, 2H), 6.17 (s, 1H), 6.37-6.39 (m, 1H), 7.85-6.89 (m, 1H).

Compound 63. LC-MS (ESI) m/z: 521 [M+H]⁺; ¹H-NMR (MeOD, 400 MHz) δ (ppm) 2.03-2.20 (m, 6H), 2.68-2.72 (m, 1H), 3.05 (s, 4H), 3.14-3.25 (m, 5H), 3.32-3.33 (m, 3H), 3.36-3.37 (m, 1H), 3.56-3.62 (m, 1H), 3.67-3.81 (m, 3H), 4.19-4.30 (m, 5H), 4.47-4.52 (m, 2H), 4.84 (d, J=2.8 Hz, 1H), 6.28-6.29 (m, 1H), 6.55-6.58 (m, 1H), 6.82-6.92 (m, 3H), 7.09-7.11 (m, 1H). Chiral-HPLC condition, solvent: MeOH (0.5% DEA), column AD-H (250*4.6 mm 5 um), Rt: 2.56 min.

Compound 63D. LC-MS (ESI) m/z: 521 [M+H]⁺; ¹H-NMR (MeOD, 400 MHz) δ (ppm) 1.74-1.79 (m, 1H), 2.02-2.18 (m, 5H), 2.98-3.02 (s, 4H), 3.14-3.20 (m, 6H), 3.35-3.44 (m, 4H), 3.54-3.75 (m, 4H), 4.22-4.26 (m, 5H), 4.43-4.51 (m, 2H), 4.81 (d, J=2.4 Hz, 1H), 6.30 (s, 1H), 6.54-6.56 (m, 1H), 6.78-6.94 (m, 3H), 7.05-7.08 (m, 1H). Chiral-HPLC condition, solvent: MeOH (0.5% DEA), column AD-H (250*4.6 mm 5 um), Rt: 6.78 min.

Example 64

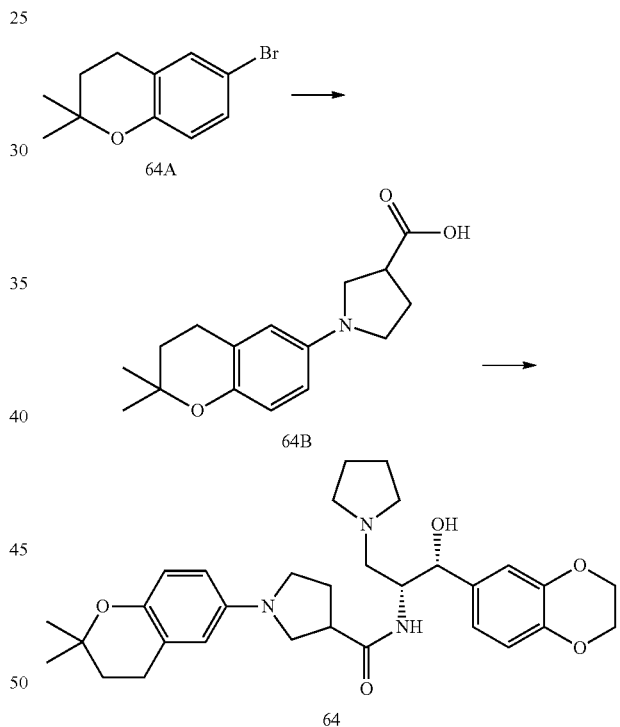

Compounds 64B and 64 were synthesized, by employing the procedures described for Compounds 1B and 1 using Compounds 64A and 64B in lieu of 1-chloro-4-iodobenzene and Compound 1B.

Compound 64B. LC-MS (ESI) m/z: 276 [M+H]⁺; ¹H-NMR (DMSO-d₆, 400 MHz) δ (ppm) 1.21 (s, 6H), 1.90 (t, J=6.8 Hz, 2H), 1.94-2.08 (m, 2H), 2.66 (t, J=6.8 Hz, 2H), 3.07-3.27 (m, 5H), 6.18-6.27 (m, 2H), 6.49 (d, J=8.8 Hz, 1H).

Compound 64. LC-MS (ESI) m/z: 536 [M+H]⁺; ¹H-NMR (MeOD, 400 MHz) δ (ppm) 1.32-1.35 (m, 6H), 1.83 (s, 2H), 2.16-2.41 (m, 6H), 2.83 (m, 2H), 3.21 (s, 3H), 3.40-3.46 (m, 2H), 3.58-3.69 (m, 5H), 3.80-3.91 (m, 1H), 3.88-4.10 (m, 4H), 4.19-4.55 (m, 1H), 4.83 (s, 1H), 6.76-7.30 (m, 6H).

Example 65

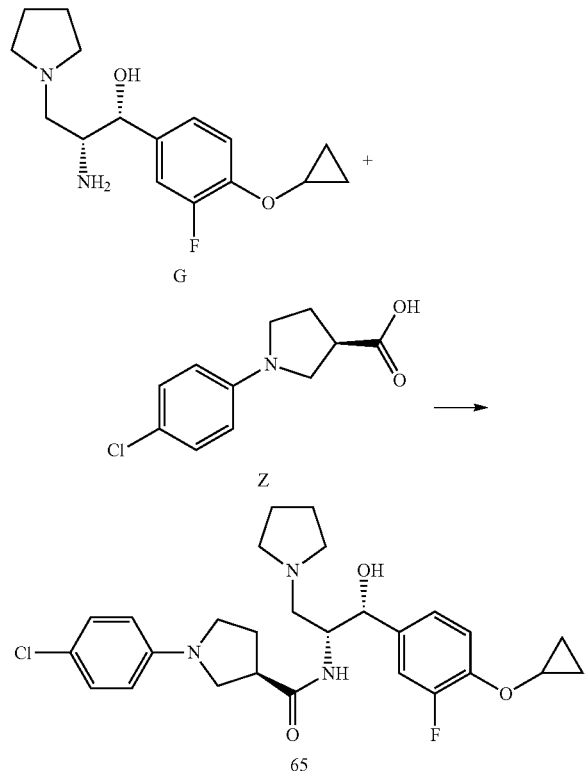

Compound 65 was synthesized, by employing the procedure described for Compound 1 using Intermediate G and Z in lieu of Intermediate A and Compound 1B. LC-MS (ESI) m/z: 502 [M+H]$^+$; $^1$H-NMR (CDCl$_3$, 400 MHz) δ (ppm) 0.75-0.81 (m, 4H), 1.99-2.25 (m, 6H), 2.89-3.31 (m, 7H), 3.62 (m, 1H), 3.69-3.77 (m, 3H), 4.45 (s, 1H), 4.95 (s, 1H), 6.44 (d, J=8.8 Hz, 2H), 6.98 (d, J=8.0 Hz, 1H), 7.09-7.23 (m, 4H), 7.56 (s, 1H), 11.55 (s, 1H).

Example 66

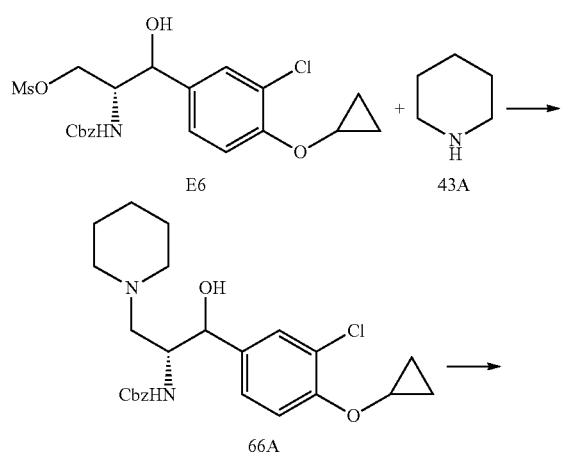

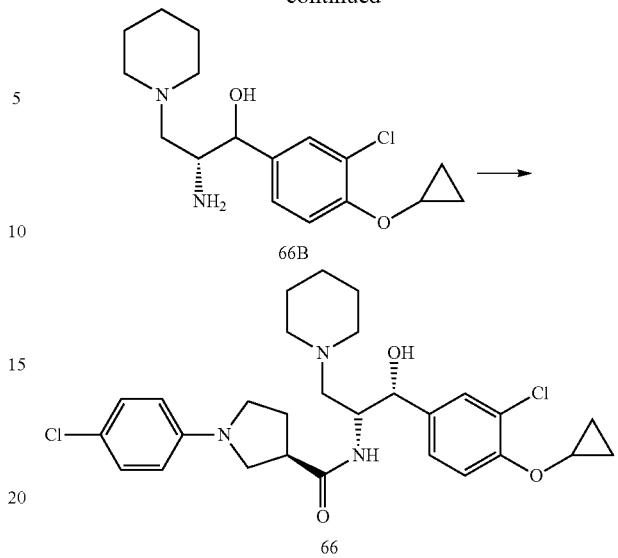

Compound 66A was synthesized, by employing the procedure described for Intermediate A9 using Intermediate E6 and Compound 43A in lieu of Intermediate A8 and pyrrolidine. LC-MS (ESI) m/z: 459 [M+H]$^+$.

Compound 66B was synthesized, by employing the procedure described for Intermediate E using Compound 66A in lieu of Intermediate E7, which was directly used for the next step without further purification. LC-MS (ESI) m/z: 325 [M+H]$^+$.

Compound 66 was synthesized, by employing the procedure described for Compound 1 using Compound 66B and Intermediate Z in lieu of Intermediate A and Compound 1B. LC-MS (ESI) m/z: 532.1 [M+H]$^+$; $^1$H-NMR (MeOD, 400 MHz) δ (ppm) 0.55-0.83 (m, 4H), 1.53-1.59 (m, 1H), 1.71-1.74 (m, 1H), 1.84-1.85 (m, 1H), 1.87-1.98 (m, 4H), 2.05-2.21 (m, 2H), 2.54 (m, 1H), 2.94-3.32 (m, 6H), 3.46-3.54 (m, 3H), 3.72-3.88 (m, 2H), 4.58-4.63 (m, 1H), 6.44 (d, J=8.8 Hz, 2H), 7.12 (d, J=9.2 Hz, 2H), 7.33 (s, 2H), 7.53 (s, 1H).

Example 67

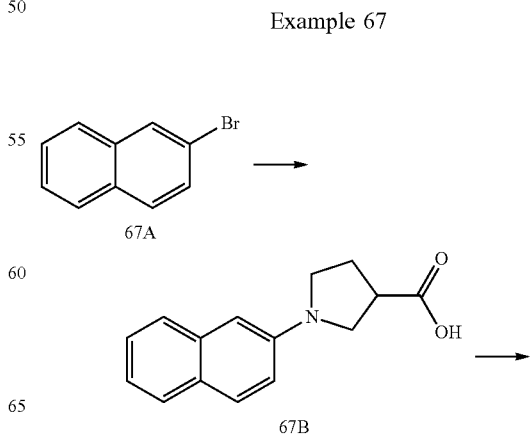

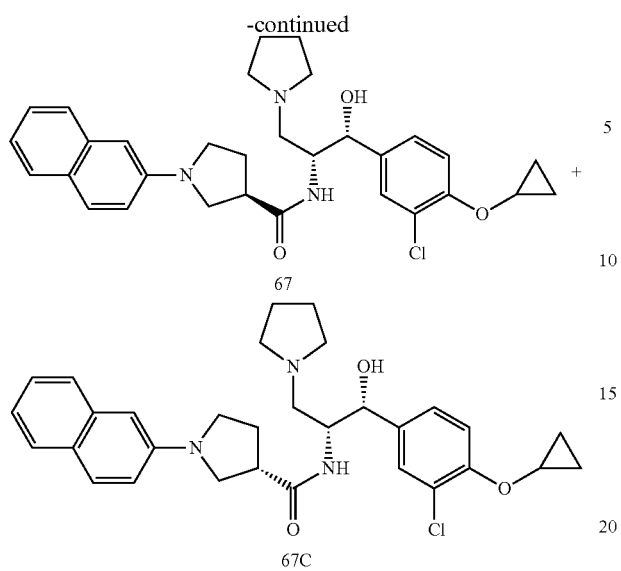

Compounds 67B, 67, and 67C were synthesized, by employing the procedures described for Compounds 1B and 1 using Compounds 67A, 67B, and Intermediate E in lieu of 1-chloro-4-iodobenzene, Compound 1B, and Intermediate A.

Compound 67B. LC-MS (ESI) m/z: 242 [M+H]+; 1H-NMR (CDCl3, 400 MHz) δ (ppm) 2.17-2.20 (m, 2H), 2.98-3.02 (m, 1H), 3.25-3.30 (m, 1H), 3.39-3.52 (m, 3H), 6.65 (s, 1H), 6.90-6.92 (m, 1H), 6.96-7.00 (m, 1H), 7.15-7.19 (m, 1H), 7.47-7.55 (m, 3H).

Compound 67. LC-MS (ESI) m/z: 534 [M+H]+; 1H-NMR (MeOD, 400 MHz) δ (ppm) 0.44-0.55 (m, 4H), 1.78-1.82 (m, 4H), 2.00-2.03 (m, 2H), 2.11-2.13 (m, 2H), 2.63-2.71 (m, 4H), 2.77-2.81 (m, 3H), 3.01-3.05 (m, 1H), 3.24-3.36 (m, 3H), 3.49-3.51 (m, 1H), 4.24-4.25 (m, 1H), 4.80 (d, J=2.0 Hz, 1H), 6.62 (s, 1H), 6.85-6.88 (m, 1H), 7.00-7.04 (m, 1H), 7.08-7.14 (m, 2H), 7.19-7.23 (m, 1H), 7.37 (s, 1H), 7.53-7.57 (m, 3H). Chiral HPLC condition, solvent: n-hexane (0.1% DEA):EtOH (0.1% DEA)=30:70, column IA-H 250*4.6 mm 5 um), Rt: 4.88 min.

Compound 67C. LC-MS (ESI) m/z: 534 [M+H]+; 1H-NMR (MeOD, 400 MHz) δ (ppm) 0.60-0.67 (m, 4H), 1.70-1.72 (m, 4H), 1.87-2.19 (m, 2H), 2.47-2.62 (m, 4H), 2.64-2.67 (m, 2H), 3.01-3.08 (m, 1H), 3.27-3.40 (m, 4H), 3.65-3.70 (m, 1H), 4.14-4.21 (m, 1H), 4.76 (d, J=2.8 Hz, 1H), 6.63 (s, 1H), 6.88-6.90 (m, 1H), 7.00-7.04 (m, 1H), 7.14-7.20 (m, 3H), 7.30 (s, 1H), 7.47-7.56 (m, 3H). Chiral HPLC condition, solvent: n-hexane (0.1% DEA):EtOH (0.1% DEA)=40:60, column OZ-H 250*4.6 mm 5 um), Rt: 11.57 min.

Example 68

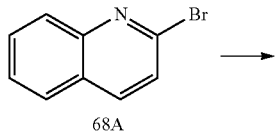

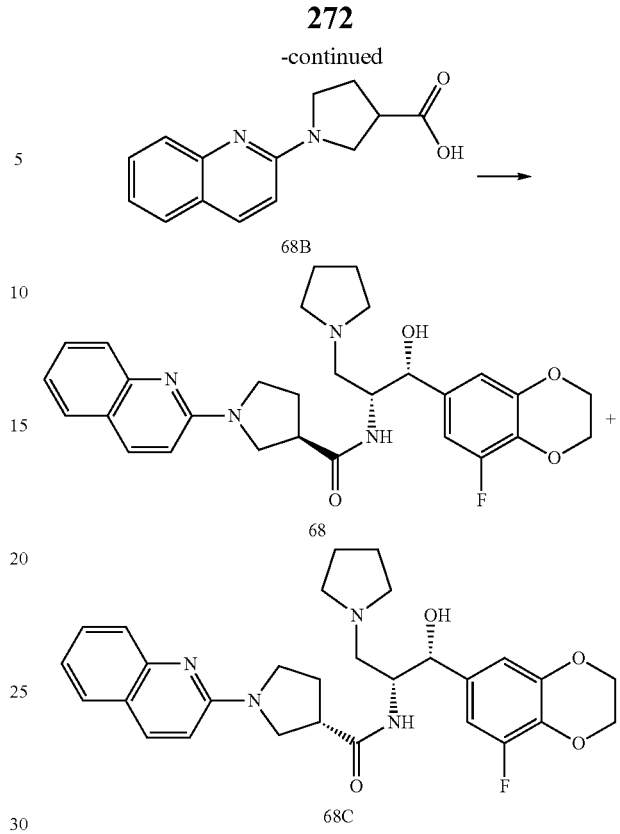

Compounds 68B, 68, and 68C were synthesized, by employing the procedures described for Compounds 1B and 7 using Compounds 68A, 68B, and Intermediate C in lieu of 1-chloro-4-iodobenzene, Compound 1B, and Intermediate A.

Compound 68B. LC-MS (ESI) m/z: 242 [M+H]+; 1H-NMR (MeOD, 400 MHz) δ (ppm) 2.24-2.27 (m, 2H), 3.09-3.12 (m, 1H), 3.54-3.80 (m, 4H), 6.85-6.87 (d, J=9.6 Hz, 1H), 7.21-7.27 (t, 1H), 7.52-7.56 (t, 1H), 7.62 (d, J=9.6 Hz, 1H), 7.68 (d, J=9.6 Hz, 1H), 7.99 (d, J=9.6 Hz, 1H).

Compound 68. LC-MS (ESI) m/z: 521 [M+H]+; 1H-NMR (MeOD, 400 MHz) δ (ppm) 1.76-1.79 (m, 4H), 2.07-2.15 (m, 2H), 2.57-2.79 (m, 6H), 3.06-3.21 (m, 2H), 3.43-3.49 (m, 1H), 3.65-3.72 (m, 2H), 4.09-4.18 (m, 5H), 4.68 (d, J=2.8 Hz, 1H), 6.61-6.73 (m, 3H), 7.09-7.11 (m, 1H), 7.41-7.42 (m, 1H), 7.53-7.59 (m, 2H), 7.86 (d, J=9.2 Hz, 1H). Chiral-HPLC condition, solvent: MeOH (0.1% DEA), column AS-H 250*4.6 mm 5 um, Rt: 4.37 min.

Compound 68C. LC-MS (ESI) m/z: 521 [M+H]+; 1H-NMR (MeOD, 400 MHz) δ (ppm) 1.79-1.81 (m, 4H), 1.97-2.05 (m, 1H), 2.11-2.23 (m, 1H), 2.55-2.80 (m, 7H), 3.15-3.19 (m, 1H), 3.56-3.78 (m, 5H), 4.23-4.27 (m, 5H), 4.78 (d, J=2.8 Hz, 1H), 6.71-6.84 (m, 3H), 7.16-7.20 (m, 1H), 7.48-7.52 (m, 1H), 7.61-7.67 (m, 2H), 7.93 (d, J=9.2 Hz, 1H). Chiral-HPLC condition, solvent: MeOH (0.1% DEA), column AS-H 250*4.6 mm 5 um, Rt: 4.55 min.

Example 69

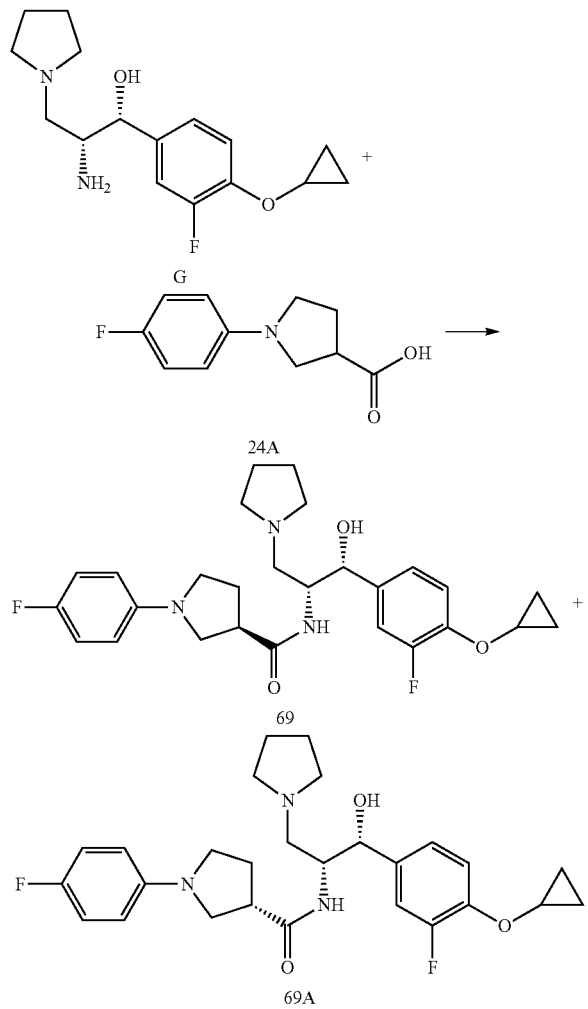

Compounds 69 and 69A were synthesized, by employing the procedures described for Compound 7 using Compound 24A and Intermediate G in lieu of Compound 7B, and Intermediate A.

Compound 69. LC-MS (ESI) m/z: 486 [M+H]⁺; ¹H-NMR (CDCl₃, 400 MHz) δ (ppm) 0.78-0.82 (m, 4H), 1.82-1.87 (m, 3H), 2.02-2.19 (m, 4H), 2.85-3.36 (m, 1H), 3.75-3.78 (m, 1H), 4.26-4.28 (m, 1H), 5.06 (d, J=2.8 Hz, 1H), 6.45-6.48 (m, 2H), 6.51-6.52 (m, 1H), 6.92-6.99 (m, 3H), 7.10-7.13 (dd, J=12.4, 2.0 Hz, 1H), 7.19 (t, J=8.4 Hz, 1H); Chiral-HPLC condition, solvent: MeOH (0.5% DEA), column OJ-H 250*4.6 mm 5 um, Rt: 2.62 min.

Compound 69A. LC-MS (ESI) m/z: 486 [M+H]⁺; ¹H-NMR (MEOD, 400 MHz) δ (ppm) 0.69-0.83 (m, 4H), 1.64-1.69 (m, 1H), 2.02-2.15 (m, 5H), 3.14-3.24 (m, 5H), 3.36-3.87 (m, 7H), 4.52-4.55 (m, 1H), 4.89 (d, J=2.8 Hz, 1H), 6.60 (m, 2H), 6.92-6.95 (m, 2H), 7.16-7.23 (m, 2H), 7.33 (t, J=8.8 Hz, 1H); Chiral-HPLC condition, solvent: MeOH (0.5% DEA), column OJ-H 250*4.6 mm 5 um, Rt: 4.62 min.

Example 70

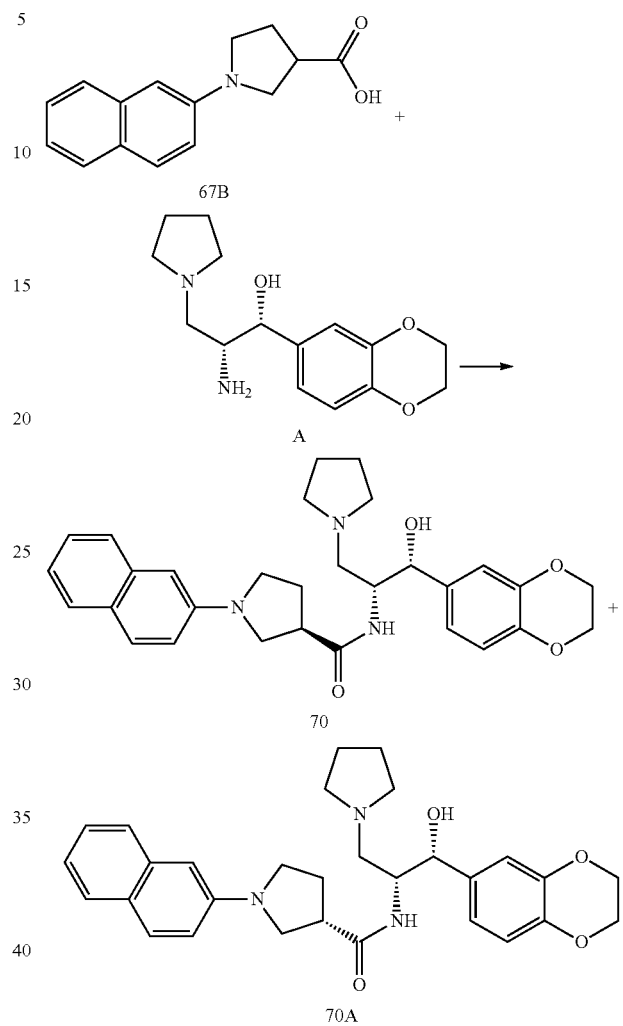

Compounds 70 and 70A were synthesized, by employing the procedures described for Compound 7 using Compound 67B in lieu of Compound 7B.

Compound 70. LC-MS (ESI) m/z: 502 [M+H]⁺; ¹H-NMR (MeOD, 400 MHz) δ (ppm) 1.69-1.78 (m, 4H), 1.99-2.22 (m, 2H), 2.61-2.70 (m, 4H), 2.75-2.77 (m, 2H), 2.91-2.93 (m, 1H), 3.02-3.03 (m, 1H), 3.25-3.28 (m, 1H), 3.38-3.44 (m, 2H), 4.03-4.10 (m, 4H), 4.20-4.21 (m, 1H), 4.72 (d, J=2.8 Hz, 1H), 6.64 (s, 1H), 6.69-6.73 (m, 2H), 6.81 (s, 1H), 6.89-6.92 (m, 1H), 7.01-7.04 (m, 1H), 7.19-7.23 (m, 1H), 7.51-7.59 (m, 3H). Chiral-HPLC condition, solvent: MeOH (0.1% DEA), column IC-H 250*4.6 mm 5 um, Rt: 4.9 min Compound 70A. LC-MS (ESI) m/z: 502 [M+H]⁺; ¹H-NMR (MeOD, 400 MHz) δ (ppm) 1.69-1.76 (m, 4H), 1.88-2.18 (m, 2H), 2.61-2.71 (m, 4H), 2.74-2.76 (m, 2H), 3.03-3.07 (m, 1H), 3.25-3.32 (m, 2H), 3.39-3.41 (m, 2H), 4.09-4.11 (m, 4H), 4.19-4.20 (m, 1H), 4.69 (d, J=3.6 Hz, 1H), 6.63 (s, 1H), 6.66-6.73 (m, 2H), 6.79 (s, 1H), 6.87-6.90 (m, 1H), 6.99-7.03 (m, 1H), 7.16-7.21 (m, 1H), 7.47-7.56 (m, 3H). Chiral-HPLC condition, solvent: MeOH (0.1% DEA), column IC-H 250*4.6 mm 5 um, Rt: 7.09 min.

Example 71

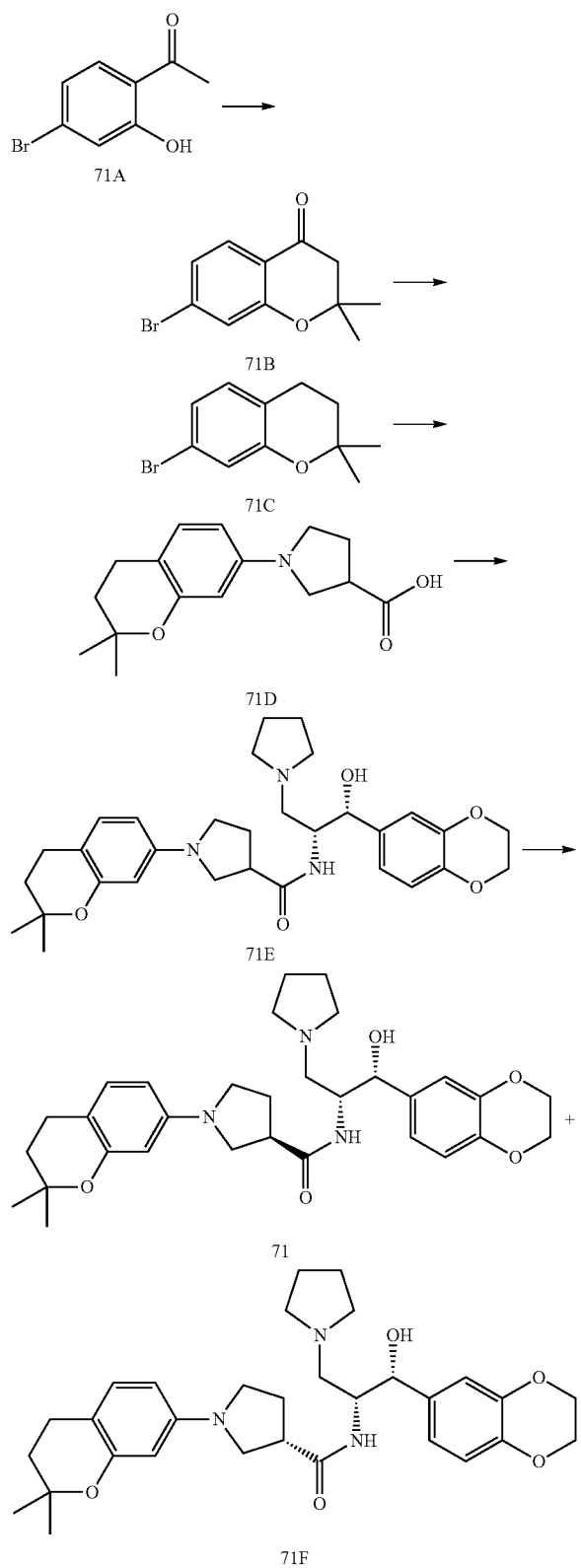

A solution of Compound 71A (4.50 g, 20.93 mmol), acetone (12.14 g, 0.209 mol), and pyrrolidine (1.51 g, 20.93 mmol) in toluene (50 mL) was stirred at 80° C. for 16 h. It was purified with flash column chromatography on silica gel (ethyl acetate in petroleum ether, from 0% to 8% v/v) to furnish Compound 71B. $^1$H-NMR (CDCl$_3$, 400 MHz) δ (ppm) 1.46 (s, 6H), 2.71 (s, 2H), 7.10-7.14 (m, 2H), 27.72 (d, J=8.4 Hz, 1H).

A mixture of Compound 71B (3.80 g, 5.90 mmol) and TES (5 mL) in TFA (5 mL) was stirred at 30° C. for 16 h. It was purified with flash column chromatography on silica gel (ethyl acetate in petroleum ether, from 0% to 5% v/v) to furnish Compound 71C. $^1$H-NMR (CDCl$_3$, 400 MHz) δ (ppm) 1.32 (s, 6H), 1.79 (t, J=6.8 Hz, 2H), 2.71 (t, J=6.8 Hz, 2H), 6.91-6.95 (m, 3H).

Compounds 71D, 71, and 71F were synthesized, by employing the procedures described for Compounds 1B and 1 using Compounds 71C and 71D in lieu of 1-chloro-4-iodobenzene and Compound 1B.

Compound 71D. LC-MS (ESI) m/z: 276 [M+H]$^+$; $^1$H-NMR (CDCl$_3$, 400 MHz) δ (ppm) 1.32 (s, 6H), 1.77 (t, J=6.8 Hz, 2H), 2.26-2.30 (m, 2H), 2.68 (t, J=6.8 Hz, 2H), 3.20-3.39 (m, 3H), 3.50-3.53 (m, 2H), 6.04 (s, 1H), 6.15 (d, J=8.4 Hz, 1H), 6.91 (d, J=8.4 Hz, 1H).

Compound 71. LC-MS (ESI) m/z: 536 [M+H]$^+$; $^1$H-NMR (CDCl$_3$, 400 MHz) δ (ppm) 1.32 (s, 6H), 1.78 (t, J=6.0 Hz, 2H), 2.09 (s, 4H), 2.23-2.30 (m, 2H), 2.73 (s, 2H), 2.87-2.97 (m, 2H), 3.11-3.23 (m, 3H), 3.31 (s, 1H), 3.49 (s, 2H), 3.66-3.79 (m, 4H), 4.11-4.23 (m, 4H), 4.48 (s, 1H), 4.86 (s, 1H), 6.51-6.59 (m, 2H), 6.72-6.80 (m, 2H), 6.91 (s, 1H), 7.01-7.04 (m, 1H), 7.71 (d, J=8.8 Hz, 1H), 11.03 (s, 1H); Chiral-HPLC condition, solvent EtOH (0.1% DEA), column OZ-H (250*4.6 mm 5 um), RT: 4.94 min.

Compound 71F. LC-MS (ESI) m/z: 536 [M+H]$^+$; $^1$H-NMR (CDCl$_3$, 400 MHz) δ (ppm) 1.32 (s, 6H), 1.78 (t, J=6.0 Hz, 2H), 1.98-2.08 (m, 5H), 2.25-2.33 (m, 1H), 2.73 (s, 2H), 2.91-2.99 (m, 3H), 3.16 (s, 1H), 3.28 (s, 1H), 3.42-3.50 (m, 2H), 3.64-3.84 (m, 5H), 4.21 (s, 4H), 4.50 (s, 1H), 4.86 (s, 1H), 6.64-6.70 (m, 2H), 6.81 (s, 2H), 6.90 (s, 1H), 7.04 (d, J=8.8 Hz, 1H), 7.80 (s, 1H), 10.89 (s, 1H); Chiral-HPLC condition, solvent EtOH (0.1% DEA), column OZ-H (250*4.6 mm 5 um), RT: 6.11 min.

Example 72

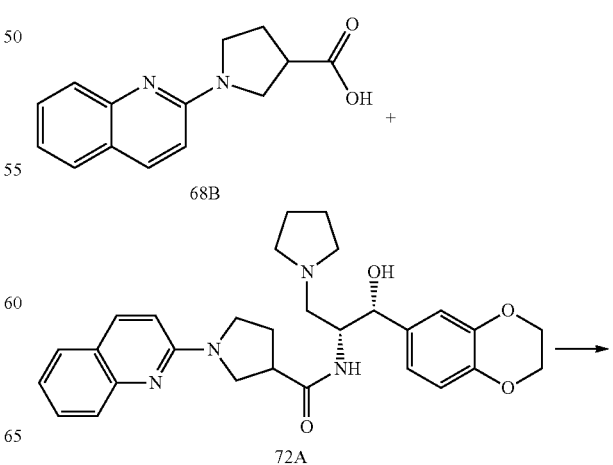

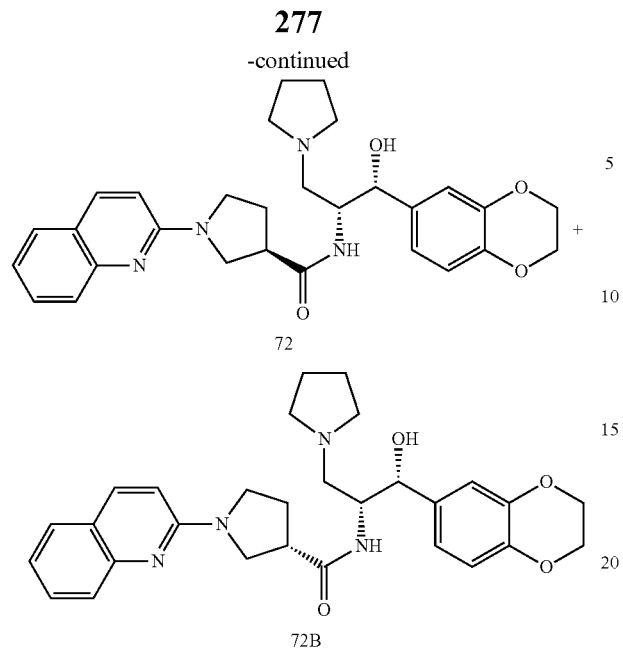

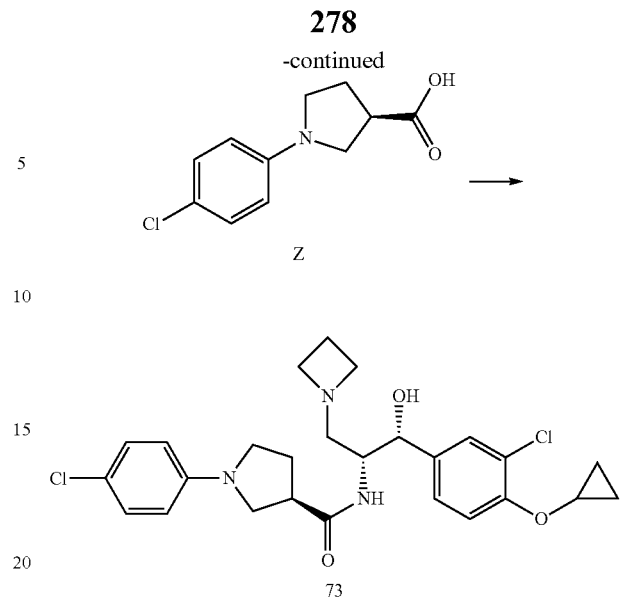

Compounds 72 and 72B were synthesized, by employing the procedures described for Compound 1 using Compound 68B in lieu of Compound 1B.

Compound 72. LC-MS (ESI) m/z: 503 [M+H]$^+$; $^1$H-NMR (MeOD, 400 MHz) δ (ppm) 1.94 (m, 2H), 2.05 (m, 2H), 2.20 (m, 1H), 2.30 (m, 1H), 3.08 (m, 2H), 3.22 (m, 2H), 3.31-3.34 (m, 1H), 3.49-3.51 (m, 1H), 3.64 (m, 3H), 3.77-3.84 (m, 3H), 4.00-4.02 (m, 2H), 4.08-4.12 (m, 1H), 4.38-4.41 (m, 1H), 4.71 (m, 1H), 6.68-6.71 (m, 1H), 6.79-6.82 (m, 1H), 6.97-7.09 (m, 1H), 7.45 (t, J=7.6 Hz, 1H), 7.72 (t, J=7.6 Hz, 1H), 7.82 (d, J=7.6 Hz, 2H), 8.29-8.35 (m, 1H); Chiral-HPLC condition, solvent: n-hexane (0.1% DEA):EtOH (0.1% DEA)=10:90, column (S,S)-Whelk-O1 (250*4.6 mm 5 um), Rt: 7.19 min.

Compound 72B. LC-MS (ESI) m/z: 503 [M+H]$^+$; $^1$H-NMR (MeOD, 400 MHz) δ (ppm) 1.76-1.81 (m, 1H), 1.92-1.94 (m, 2H), 2.04 (m, 2H), 2.24-2.26 (m, 1H), 3.05-3.10 (m, 2H), 3.27-3.33 (m, 2H), 3.44-3.54 (m, 2H), 3.62-3.74 (m, 4H), 3.88 (m, 1H), 4.12 (s, 4H), 4.42 (m, 1H), 4.72 (d, J=3.2 Hz, 1H), 6.69 (d, J=8.0 Hz, 1H), 6.77-6.79 (m, 1H), 6.87 (s, 1H), 7.03 (m, 1H), 7.42 (t, J=7.8 Hz, 1H), 7.69 (t, J=7.8 Hz, 1H), 7.78 (d, J=7.2 Hz, 2H), 8.23-8.25 (m, 1H); Chiral-HPLC condition, solvent: n-hexane (0.1% DEA): EtOH (0.1% DEA)=10:90, column (S,S)-Whelk-O1 (250*4.6 mm 5 um), Rt: 8.56 min.

Example 73

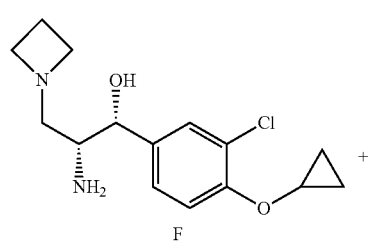

Compound 73 was synthesized, by employing the procedure described for Compound 1 using Intermediates F and Z in lieu of Intermediate A and Compound 1B. LC-MS (ESI) m/z: 504 [M+H]$^+$; $^1$H-NMR (MeOD, 400 MHz) δ (ppm) 0.57-0.81 (m, 4H), 2.05-2.08 (m, 1H), 2.18-2.43 (m, 1H), 2.42-2.62 (m, 3H), 3.08-3.32 (m, 4H), 3.45-3.50 (m, 1H), 3.65-3.60 (m, 1H), 3.69-3.72 (m, 1H), 4.16-4.37 (m, 5H), 4.89 (d, J=2.4 Hz, 1H), 6.42 (d, J=8.8 Hz, 2H), 7.11 (d, J=8.8 Hz, 2H), 7.25 (s, 2H), 7.50 (d, J=0.8 Hz, 1H).

Example 74

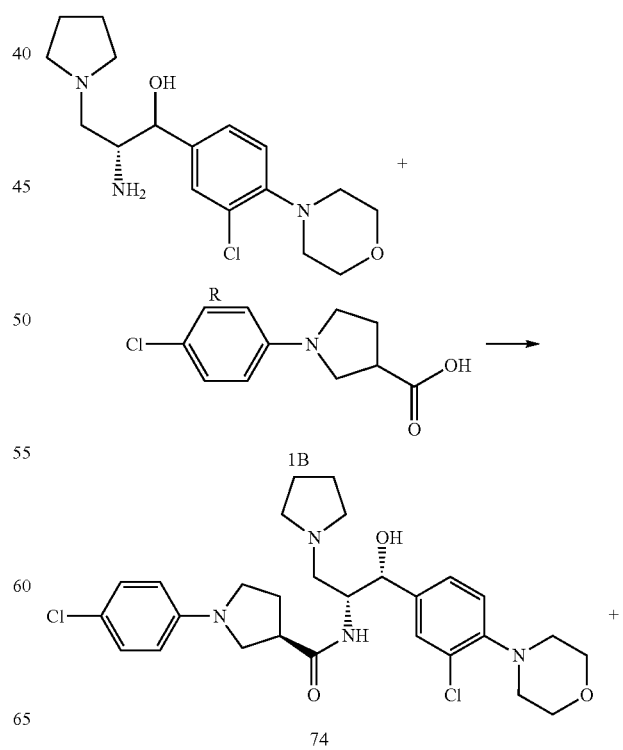

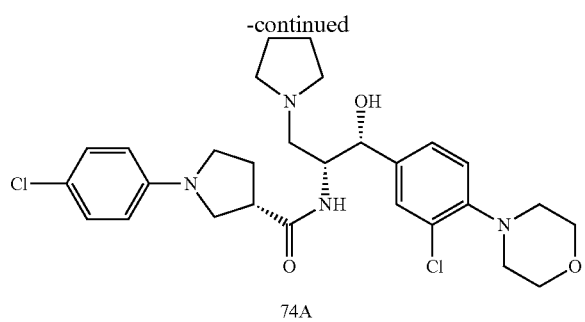

74A

Compounds 74 and 74A were synthesized, by employing the procedures described for Compound 1 using Intermediate R in lieu of Intermediate A.

Compound 74. LC-MS (ESI) m/z: 547 [M+H]$^+$; $^1$H-NMR (MeOD, 400 MHz) δ (ppm) 1.83 (s, 4H), 2.04-2.20 (m, 2H), 2.60-2.70 (m, 4H), 2.76-2.83 (m, 3H), 2.85-2.89 (m, 4H), 2.92-2.98 (m, 1H), 3.06-3.11 (m, 2H), 3.31-3.38 (m, 1H), 3.82 (t, J=10.4 Hz, 4H), 4.27-4.31 (m, 1H), 4.88-4.91 (m, 1H), 6.50 (dJ=9.2 Hz, 2H), 7.02 (dJ=8.4 Hz, 1H), 7.12-7.14 (m, 2H), 7.23-7.25 (m, 1H), 7.46 (s, 1H); Chiral-HPLC condition, solvent MeOH (0.5% DEA), column AD-H 250*4.6 mm 5 um, RT: 3.48 min.

Compound 74A. LC-MS (ESI) m/z: 547 [M+H]$^+$; $^1$H-NMR (MeOD, 400 MHz) δ (ppm) 1.76-1.84 (m, 5H), 2.08-2.15 (m, 1H), 2.55-2.72 (m, 6H), 2.94-2.97 (m, 4H), 3.03-3.09 (m, 1H), 3.16-3.19 (m, 2H), 3.26-3.31 (m, 2H), 3.78-3.80 (m, 4H), 4.21-4.25 (m, 1H), 4.83 (s, 1H), 6.43 (dJ=8.8 Hz, 2H), 7.01-7.07 (m, 3H), 7.19-7.21 (m, 1H), 7.40 (s, 1H); Chiral-HPLC condition, solvent MeOH (0.5% DEA), column AD-H 250*4.6 mm 5 um, RT: 5.45 min.

Example 75

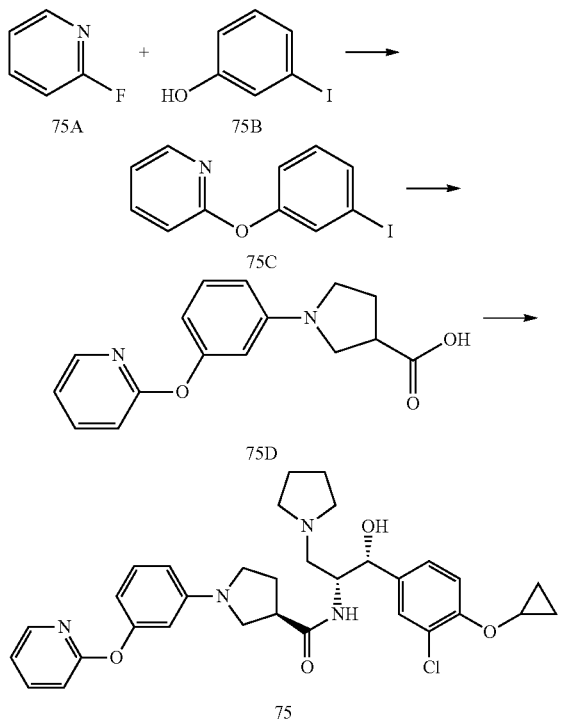

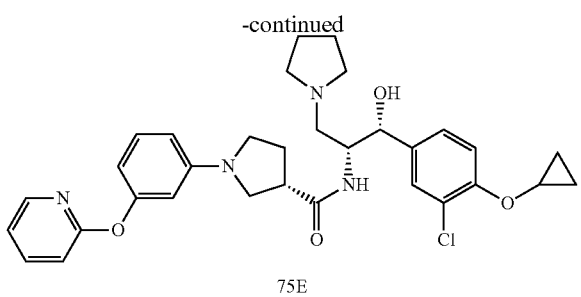

75E

To a mixture of Compound 75B (1.5 g, 6.82 mmol) and potassium tert-butoxide (1.53 g, 13.64 mmol) in DMSO (20 mL) was added Compound 75A (662 mg, 6.82 mmol). The reaction mixture was heated at 100° C. for 6 hours. It was quenched with a saturated aqueous solution of ammonium chloride (100 mL) and extracted with ethyl acetate (80 mL×3). The organic phase was washed with a saturated aqueous solution of ammonium chloride (100 mL×5), dried over anhydrous sodium sulfate, filtered, and concentrated. The crude product was purified with silica gel column chromatography eluting with petroleum ether/ethyl acetate (20:1) to furnish Compound 75C. LC-MS (ESI) m/z: 298 [M+H]$^+$.

Compounds 75D, 75, and 75E were synthesized, by employing the procedures described for Compounds 1B and 1 using Compounds 75C, 75D, and Intermediate E in lieu of Compounds 1A, 1B, and Intermediate A.

Compound 75D. LC-MS m/z: 283 [M-]$^+$; $^1$H-NMR (CDCl$_3$, 400 MHz) δ (ppm) 8.23 (dd, J=4.9, 1.5 Hz, 1H), 7.66 (ddd, J=8.4, 7.2, 2.0 Hz, 1H), 7.22 (t, J=8.1 Hz, 1H), 6.98 (ddd, J=7.1, 5.0, 0.7 Hz, 1H), 6.86 (d, J=8.3 Hz, 1H), 6.47-6.37 (m, 2H), 6.33 (t, J=2.2 Hz, 1H), 3.55 (d, J=7.3 Hz, 2H), 3.48-3.26 (m, 2H), 3.20 (p, J=7.4 Hz, 1H), 2.36-2.21 (m, 2H), 2.07 (s, 1H).

Compound 75. LC-MS (ESI) m/z: 577 [M+H]$^+$; $^1$H-NMR (MeOD, 400 MHz) δ (ppm) 8.16 (dd, J=5.1, 1.4 Hz, 1H), 7.84-7.76 (m, 1H), 7.40 (d, J=1.9 Hz, 1H), 7.3-7.17 (m, 3H), 7.11 (dd, J=6.8, 5.5 Hz, 1H), 6.87 (d, J=8.4 Hz, 1H), 6.43 (dd, J=8.2, 2.1 Hz, 1H), 6.37-6.32 (m, 1H), 6.30 (t, J=2.2 Hz, 1H), 4.87 (s, 1H), 4.29 (s, 1H), 3.77 (dd, J=7.5, 4.4 Hz, 2H), 3.41-3.34 (m, 2H), 3.27-3.20 (m, 1H), 3.10 (m, 2H), 2.9-2.63 (m, 8H), 2.17-2.09 (m, 2H), 1.85 (s, 4H), 0.77-0.61 (m, 4H). Chiral-HPLC condition, solvent: n-hexane (0.1% DEA):EtOH (0.1% DEA)=60:40, column IC 4.6*250 mm 5 um, Rt: 8.512 min.

Compound 75E. LC-MS (ESI) m/z: 577 [M+H]$^+$; $^1$H-NMR (MeOD, 400 MHz) δ (ppm) 8.18-8.12 (m, 1H), 7.84-7.73 (m, 1H), 7.40 (d, J=1.9 Hz, 1H), 7.35-7.16 (m, 3H), 7.10 (dd, J=6.8, 5.5 Hz, 1H), 6.85 (d, J=8.4 Hz, 1H), 6.42 (d, J=8.6 Hz, 1H), 6.33 (d, J=8.0 Hz, 1H), 6.27 (d, J=2.2 Hz, 1H), 4.86 (d, J=2.8 Hz, 1H), 4.28 (s, 1H), 3.89-3.78 (m, 1H), 3.39-3.36 (m, 1H), 3.24 (m, 2H), 3.15-3.04 (m, 2H), 2.85-2.53 (m, 6H), 2.22-2.11 (m, 1H), 1.83 (s, 3H), 0.84-0.59 (m, 4H). Chiral-HPLC condition, solvent: n-hexane (0.1% DEA):EtOH (0.1% DEA)=60:40, column IC 4.6*250 mm 5 um, Rt: 21.180 min.

Example 76

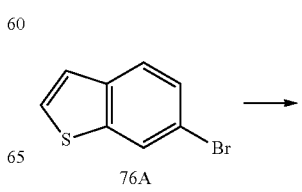

76A

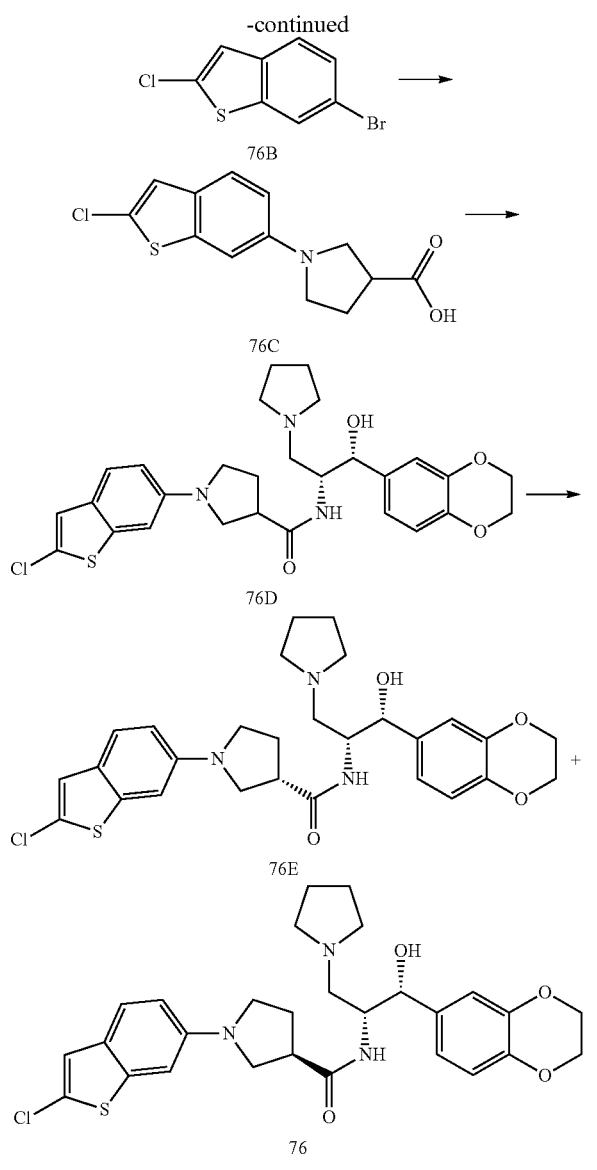

2.14-2.19 (m, 2H), 3.16-3.27 (m, 3H), 3.36-3.42 (m, 2H), 4.07 (s, 1H), 6.51-6.90 (m, 2H), 7.12-7.14 (m, 1H).

Compound 76E. LC-MS (ESI) m/z: 542 [M+H]$^+$; $^1$H-NMR (MeOD, 400 MHz) δ (ppm) 1.97-2.29 (m, 6H), 2.65-2.69 (m, 1H), 3.11-3.30 (m, 4H), 3.32-3.64 (m, 4H), 3.71-3.85 (m, 2H), 4.14-4.27 (m, 4H), 4.48-4.56 (m, 1H), 4.86 (m, 1H), 6.68-6.70 (m, 1H), 6.83-6.85 (m, 2H), 6.89-6.91 (m, 1H), 6.97-6.98 (m, 1H), 7.07-7.08 (m, 1H), 7.51-7.53 (m, 1H), 8.02-8.05 (m, 1H). Chiral-HPLC condition, solvent: MeOH (0.1% DEA) column OJ-H (4.6*250 mm 5 um), Rt: 6.20 min.

Compound 76. LC-MS (ESI) m/z: 542 [M+H]$^+$; $^1$H-NMR (MeOD, 400 MHz) δ (ppm) 1.75-1.83 (m, 1H), 2.01-2.09 (m, 2H), 2.16-2.22 (m, 3H), 3.11-3.30 (m, 4H), 3.37-3.62 (m, 4H), 3.69-3.81 (m, 2H), 4.19-4.25 (m, 4H), 4.45-4.53 (m, 1H), 4.82-4.83 (m, 1H), 6.65-6.72 (m, 1H), 6.79-6.81 (m, 1H), 6.81-6.88 (m, 2H), 6.94-6.97 (m, 1H), 7.04 (m, 1H), 7.48-7.50 (m, 1H), 8.01-8.05 (m, 1H). Chiral-HPLC condition, solvent: MeOH (0.1% DEA) column OJ-H (4.6*250 mm 5 um), Rt: 4.02 min.

Example 77

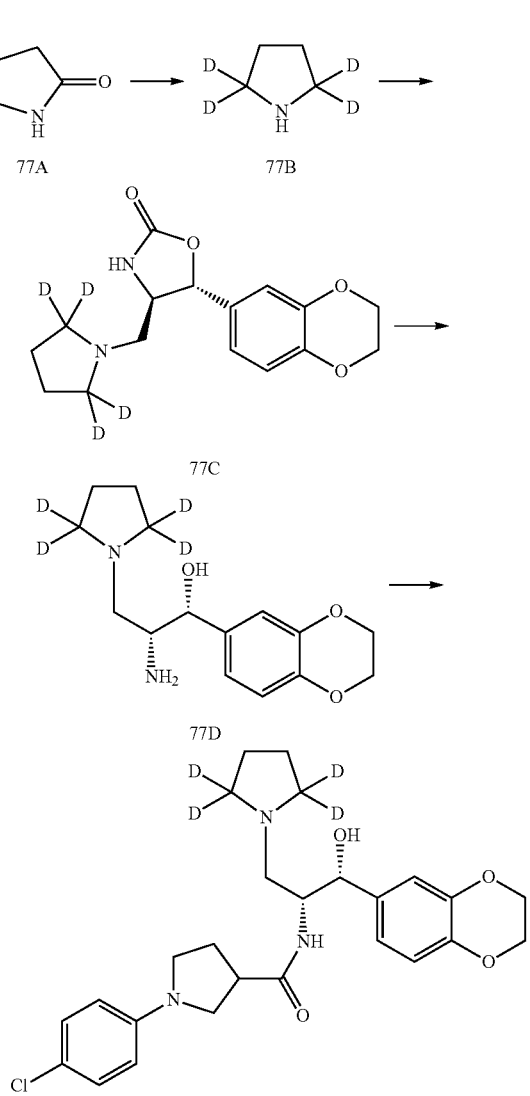

To a mixture of LDA (7.8 mL, 15.5 mmol) in tetrahydrofuran (10 mL) was added Compound 76A (3.0 g, 14.1 mmol) in tetrahydrofuran (5 mL) dropwise at −78° C. and the mixture was stirred under nitrogen protection for 1 h. The solution was added to a mixture of carbon tetrachloride (5.5 mL, 56.6 mmol) in tetrahydrofuran (15 mL) at −78° C. and the reaction mixture was stirred under nitrogen protection for 1.5 h. It was quenched with ammonium chloride solution (50 mL), warmed to room temperature, extracted with DCM (100 mL×2), washed with water (30 mL) and brine (30 mL), dried over anhydrous sodium sulfate, evaporated and purified with flash column chromatography on silica gel (petroleum ether, 100% v/v) to furnish Compound 76B. $^1$H-NMR (DMSO-d$_6$, 400 MHz) δ (ppm) 7.55-7.58 (m, 2H), 7.72-7.74 (d, J=8.0 Hz, 1H), 8.27 (m, 1H).

Compounds 76C, 76E, and 76 were synthesized, by employing the procedures described for Compounds 1B and 1 using Compounds 76B, and 76C in lieu of Compounds 1A and 1B.

Compound 76C. LC-MS (ESI) m/z: 282 [M+H]$^+$; $^1$H-NMR (DMSO-d$_6$, 400 MHz) δ (ppm) 0.62-0.72 (m, 4H), To a solution of succinimide 77A (0.99 g, 10 mmol) in THF (50 mL) was added lithium aluminum deuteride. The reaction mixture was stirred at 0° C. for 1 h and room temperature for 2 h, and heated to reflux for overnight. The reaction mixture was quenched with deuterium oxide, filtered, and washed with THF (50 mL×2). The filtrate (77B) was directly used for the next step.

To a solution of Compound 77B in THF (150 mL) was added Compound A8 (880 mg, 2 mmol). The reaction was stirred at 55° C. for 15 hours. The solvent was evaporated under reduced pressure and the residue was extracted with acetate ethyl (50 mL×3). The extracts were washed with brine (50 mL) and dried over sodium sulfate. Evaporation of the solvent under reduced pressure afforded the crude product. The crude product was purified with silica gel column chromatography (ethyl acetate in petroleum ether, from 20% to 60% v/v) to furnish Compound 77C. LC-MS (ESI) m/z: 309 [M+H]$^+$.

To a solution of Compound 77C (150 mg, 0.487 mmol) in methanol-d$_4$ (5.0 mL) was added Lithium hydroxide monohydrate (210 mg, 5.0 mmol). The reaction was stirred at reflux for 24 h. The solvent was evaporated under reduced pressure and the residue was extracted with THF (50 mL×3). The extracts were dried over sodium sulfate. Evaporation of the solvent under reduced pressure afforded a crude product. The crude product Compound 77D was directly used for the next step. LC-MS (ESI) m/z: 283 [M+H]$^+$.

Compound 77 was synthesized, by employing the procedure described for Compound 7 using Compound 77D in lieu of Intermediate A. LC-MS (ESI) m/z: 486 [M+H]$^+$; $^1$H-NMR (CDCl$_3$, 400 MHz) δ (ppm) 7.16 (d, J=8.8 Hz, 2H), 6.85-6.75 (m, 3H), 6.45 (d, J=8.8 Hz, 2H), 6.21 (m, 1H), 4.98-4.95 (m, 5H), 3.4-3.2 (m, 4H), 2.98-2.89 (m, 3H), 2.17-2.14 (m, 2H), 1.80 (d, J=10.4 Hz, 4H).

Example 78

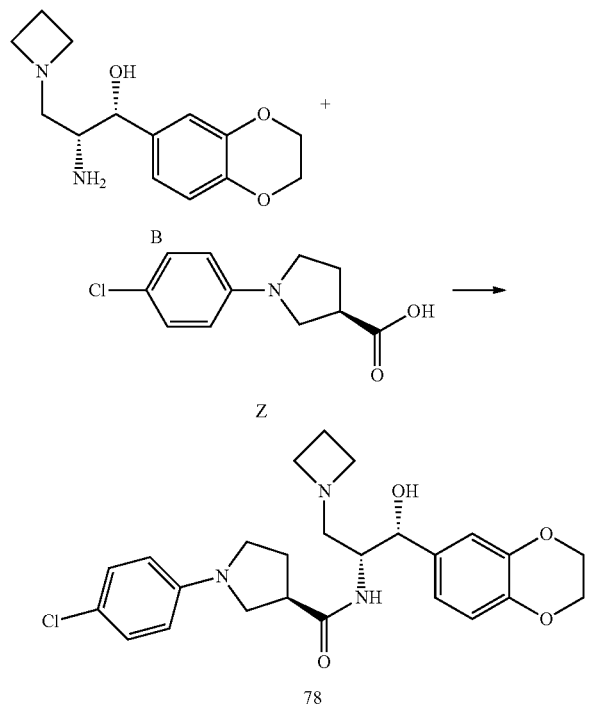

Compound 78 was synthesized, by employing the procedure described for Compound 1 using Intermediates B and Z in lieu of Intermediate A and Compound 1B. LC-MS (ESI) m/z: 472 [M+H]$^+$; $^1$H-NMR (MeOD, 400 MHz) δ (ppm) 2.07-2.24 (m, 2H), 2.39-2.44 (m, 1H), 2.57-2.71 (m, 2H), 3.12-3.24 (m, 1H), 3.31-3.32 (m, 1H), 3.33-3.35 (m, 2H), 3.45-3.48 (m, 1H), 3.54-3.58 (m, 1H), 4.19-4.28 (m, 9H), 4.81 (d, J=2.8 Hz, 1H), 6.48-6.50 (m, 2H), 6.80-6.86 (m, 2H), 6.92 (s, 1H), 7.13-7.16 (m, 2H).

Example 79

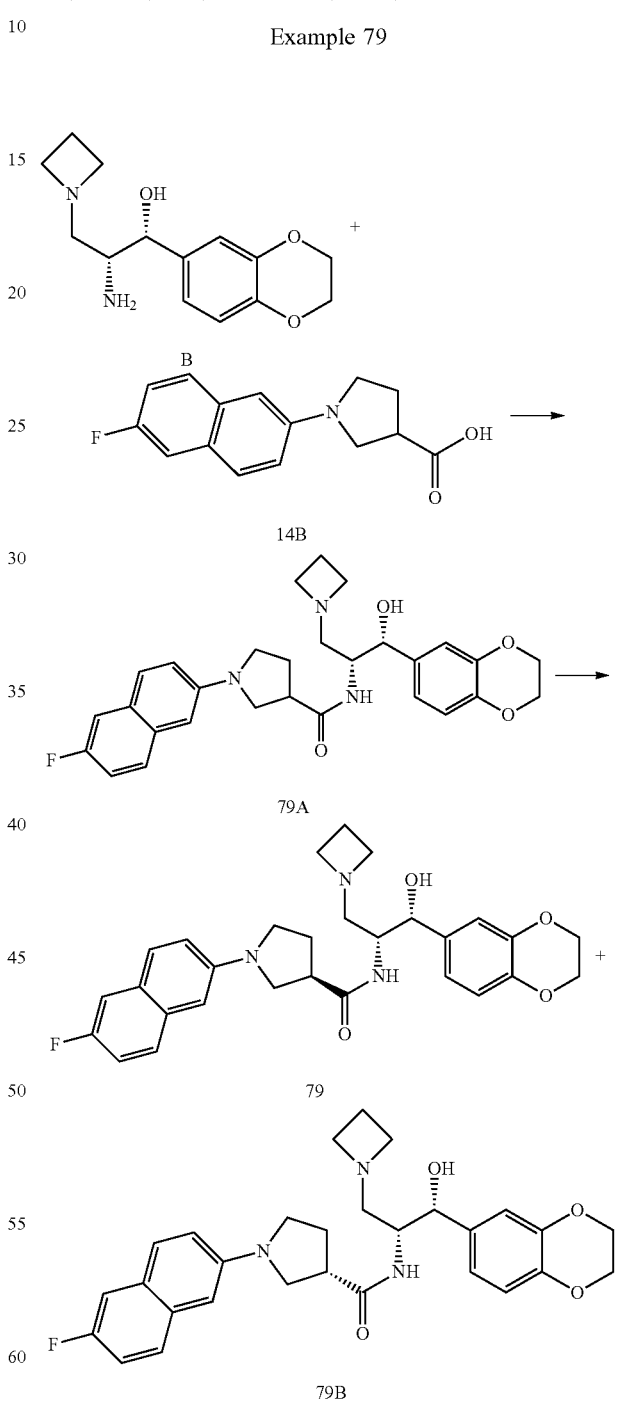

Compounds 79 and 79B were synthesized, by employing the procedures described for Compound 1 using Intermediate B and Compound 14B in lieu of Intermediate A and Compound 1B.

Compound 79. LC-MS (ESI) m/z: 506 [M+H]⁺; ¹H-NMR (MeOD, 400 MHz) δ (ppm) 2.08-2.11 (m, 2H), 2.54-2.60 (m, 3H), 2.89-2.98 (m, 2H), 3.16-3.22 (m, 6H), 3.30-3.37 (m, 2H), 3.96-4.07 (m, 5H), 4.63 (d, J=2.8 Hz, 1H), 6.64-6.78 (m, 4H), 6.90-6.92 (m, 1H), 7.01-7.05 (m, 1H), 7.18-7.21 (m, 1H), 7.51-7.53 (m, 2H). Chiral-HPLC, solvent: MeOH (0.1% DEA), column OJ-H (250*4.6 mm 5 um), Rt: 3.57 min.

Compound 79B. LC-MS (ESI) m/z: 506 [M+H]⁺; ¹H-NMR (MeOD, 400 MHz) δ (ppm) 1.79-1.84 (m, 1H), 2.19-2.23 (m, 1H), 2.37-2.44 (s, 1H), 2.57-2.62 (m, 1H), 3.17-3.19 (m, 1H), 3.33-3.57 (m, 6H), 4.11-4.32 (m, 9H), 4.80 (d, J=3.2 Hz, 1H), 6.79-6.94 (m, 3H), 7.08-7.17 (m, 2H), 7.32-7.35 (m, 1H), 7.66-7.68 (m, 1H). Chiral-HPLC condition, solvent: MeOH (0.1% DEA), column OJ-H (250*4.6 mm 5 um), Rt: 7.04 min.

Example 80

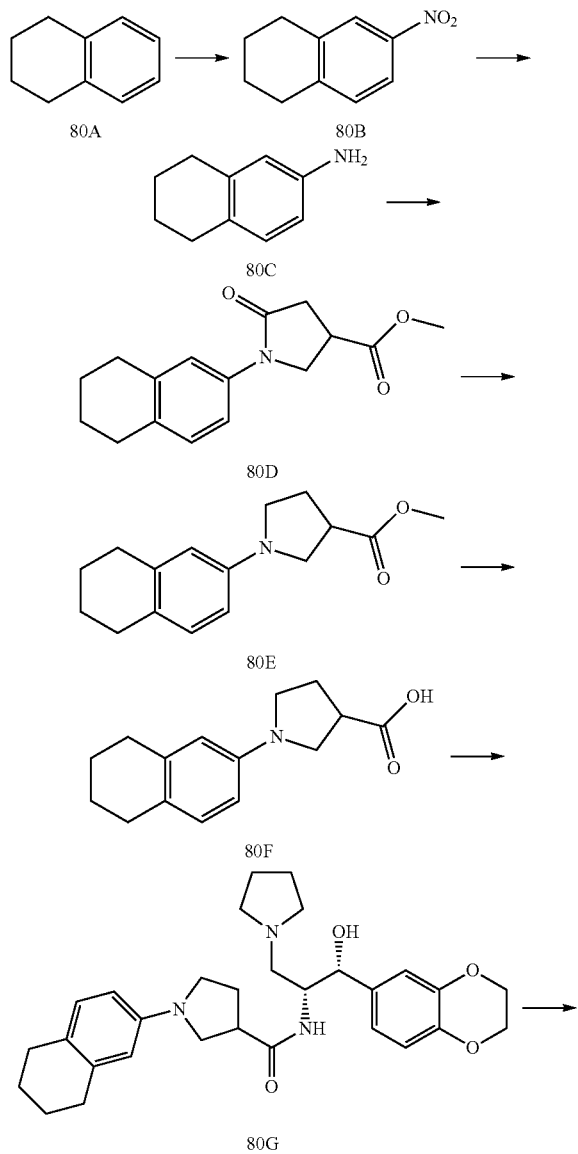

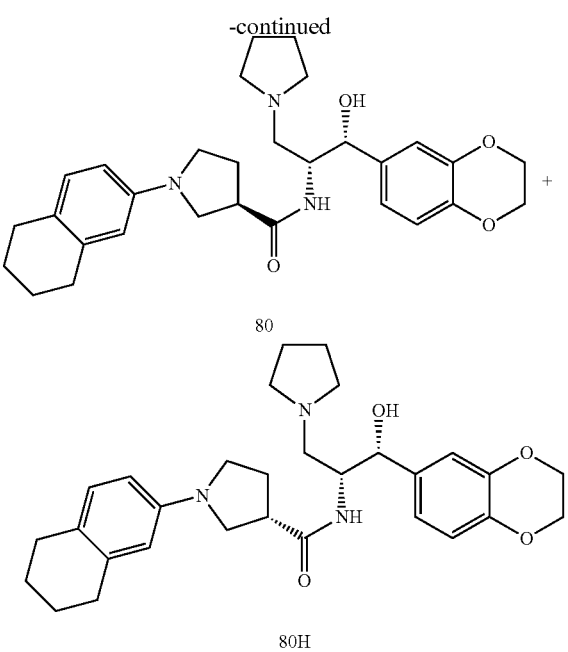

To a solution of Compound 80A (1.32 g, 10 mmol) in Ac₂O (10 mL) was added dropwise a solution of HNO₃ (3.15 g, 50 mmol) in Ac₂O (1 mL) at 0° C. The mixture was stirred at 25° C. for 2 h, poured onto ice, extracted with ethyl acetate (50 mL×2), washed with saturated aqueous sodium bicarbonate solution (50 mL×2) and water (50 mL×1), dried over anhydrous sodium sulfate, concentrated, and purified with flash column chromatography on silica gel (ethyl acetate in petroleum ether, 0-18% v/v) to furnish Compound 80B. ¹H-NMR (CDCl₃, 400 MHz) δ (ppm) 1.84 (m, 4H), 2.85 (m, 4H), 7.18 (d, J=8.0 Hz, 1H), 7.91 (m, 2H).

A mixture of Compound 80B (10 g, 56.5 mmol), Pd/C (10%, 0.7 g) in MeOH (100 mL) was stirred at 25° C. under H₂ overnight. The mixture was filtered to remove the catalyst. The filtrate was concentrated and the resulting residue was purified with flash column chromatography on silica gel (ethyl acetate in petroleum ether, 15% v/v) to furnish Compound 80C. LC-MS (ESI) m/z: 148 [M+H]⁺; ¹H-NMR (CDCl₃, 400 MHz) δ (ppm) 1.66 (m, 4H), 2.58 (m, 4H), 3.38 (br, 2H), 6.35 (d, J=2.4 Hz, 1H), 6.39 (m, 1H), 6.78 (d, J=8.0 Hz, 1H).

A mixture of Compound 80C (1 g, 6.8 mmol), dimethyl 2-methylenesuccinate (1 g, 6.3 mmol) was stirred at 180° C. overnight. The mixture was purified with flash column chromatography on silica gel (ethyl acetate in petroleum ether, 60% v/v) to furnish Compound 80D. LC-MS (ESI) m/z: 274 [M+H]⁺; ¹H-NMR (CDCl₃, 400 MHz) δ (ppm) 1.76 (m, 4H), 2.73 (m, 4H), 2.83 (m, 2H), 3.31 (m, 1H), 3.77 (s, 3H), 3.97 (m, 1H), 4.06 (m, 1H), 7.05 (d, J=8.4 Hz, 1H), 7.24 (m, 2H).

To a solution of Compound 80D (770 mg, 2.8 mmol) in THF (50 mL) was added BH₃ (1 Min THF, 5.1 mL, 5.1 mmol). The mixture was stirred at 60° C. for 3 h and quenched with MeOH (5 mL) and water (50 mL). The mixture was concentrated to remove THF, extracted with DCM (50 mL×3), dried over anhydrous sodium sulfate, and purified with flash column chromatography on silica gel (ethyl acetate in petroleum ether, 0-20% v/v) to furnish Compound 80E. LC-MS (ESI) m/z: 260 [M+H]⁺; ¹H-NMR (CDCl₃, 400 MHz) δ (ppm) 1.76 (m, 4H), 2.27 (m, 2H), 2.73

(m, 4H), 3.18 (m, 1H), 3.36 (m, 2H), 3.51 (m, 2H), 3.72 (s, 3H), 6.29 (d, J=2.4 Hz, 1H), 6.38 (m, sH), 6.92 (d, J=8.0 Hz, 1H).

To a solution of Compound 80E (470 mg, 1.8 mmol) in THF (10 mL) and water (2 mL) was added LiOH water (87 mg, 3.6 mmol). The mixture was stirred at 25° C. overnight, acidified by 1 M HCl, extracted with DCM (20 mL×3), dried over anhydrous sodium sulfate and concentrated to furnish Compound 80F. LC-MS (ESI) m/z: 246 [M+H]+.

Compounds 80 and 80H were synthesized, by employing the procedures described for Compound 1 using Compound 80F in lieu of Compound 1B.

Compound 80. LC-MS (ESI) m/z: 506 [M+H]+; 1H-NMR (MeOD, 400 MHz) δ (ppm) 1.79 (s, 5H), 2.02-2.32 (m, 5H), 2.74 (m, 4H), 3.20 (m, 3H), 3.45-3.80 (m, 8H), 4.21 (s, 4H), 4.50 (m, 1H), 4.82 (d, J=3.2 Hz, 1H), 6.79-7.07 (m, 6H). Chiral-HPLC condition, solvent: MeOH (0.1% DEA), column AS-H 250*4.6 mm 5 um, Rt: 4.12 min.

Compound 80H. LC-MS (ESI) m/z: 506 [M+H]+; 1H-NMR (MeOD, 400 MHz) δ (ppm) 1.70 (m, 4H), 1.92-2.27 (m, 6H), 2.65 (m, 4H), 2.78 (m, 1H), 3.06 (m, 1H), 3.23-3.66 (m, 8H), 3.78-3.96 (m, 4H), 4.38 (m, 1H), 4.72 (d, J=3.2 Hz, 1H), 6.64-7.03 (m, 6H). Chiral-HPLC condition, solvent: MeOH (0.1% DEA), column AS-H 250*4.6 mm 5 um, Rt: 4.85 min.

Example 81

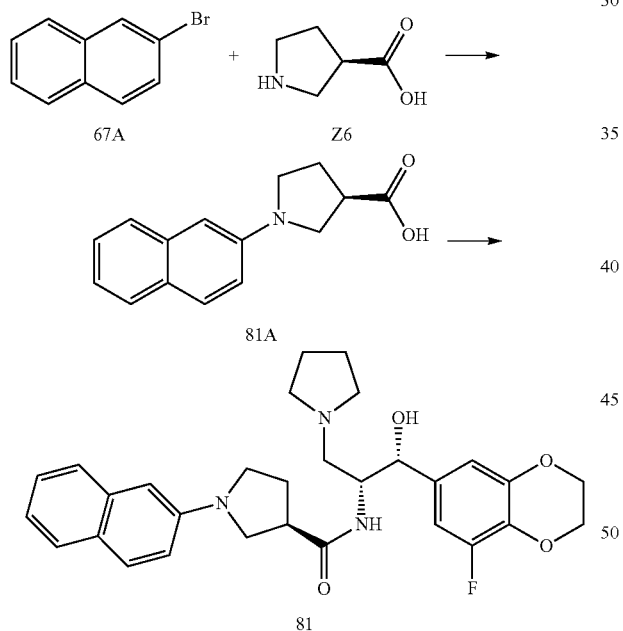

Compound 81A was synthesized, by employing the procedure described for Compound 1B using Compound 67A and Intermediate Z6 in lieu of 1-chloro-4-iodobenzene and Compound 1A. LC-MS (ESI) m/z: 242 [M+H]+;

Compound 81 was synthesized, by employing the procedure described for Compound 7 using Compound 81A and Intermediate C in lieu of Compound 7B and Intermediate A. LC-MS (ESI) m/z: 520 [M+H]+; 1H-NMR (MeOD, 400 MHz) δ (ppm) 1.72-1.78 (m, 4H), 1.97-2.13 (m, 2H), 2.57-2.65 (m, 4H), 2.72-2.74 (m, 2H), 2.85-2.87 (m, 1H), 3.02-3.06 (m, 1H), 3.27-3.28 (m, 1H), 3.37-3.42 (m, 2H), 4.04-4.19 (m, 5H), 4.71 (d, J=2.4 Hz, 1H), 6.62-6.64 (m, 2H), 6.67-6.70 (m, 1H), 6.88-6.91 (m, 1H), 7.02-7.04 (m, 1H), 7.19-7.21 (m, 1H), 7.53-7.58 (m, 3H). Chiral-HPLC condition, solvent: MeOH (0.1% DEA), column OJ-H 250*4.6 mm 5 um), Rt: 5.44 min.

Example 82

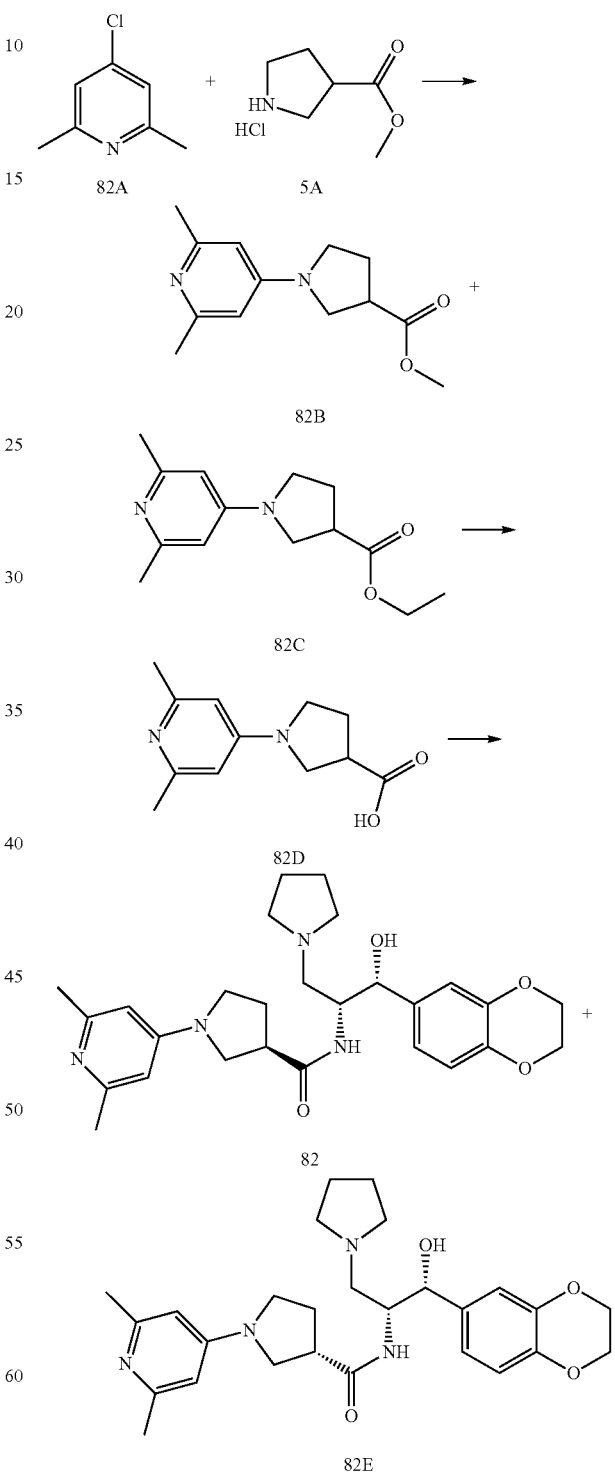

A mixture of 4-chloro-2,6-dimethylpyridine (82A, 400 mg, 2.42 mmol), Compound 5A (400 mg, 2.83 mmol), and triethylamine (708 mg, 7.01 mmol) in ethanol (6 mL) was stirred at 150° C. for 5 h. The reaction mixture was treated with water, and extracted with ethyl acetate (150 mL×3). The extraction was washed with water, dried over sodium sulfate, concentrated, and purified with flash column chromatography on silica gel (ethyl acetate in petroleum ether, from 10% to 50% v/v) to furnish a mixture of Compound 82B and 82C. LC-MS (ESI) m/z: 235 [M+H]+.

Compound 82D was synthesized, by employing the procedure described for Compound 5C using a mixture of Compound 82B and 82C in lieu of Compound 5B. LC-MS (ESI) m/z: 221 [M+H]+.

Compounds 82 and 82E were synthesized, by employing the procedures described for Compound 7 using Compound 82D in lieu of Compound 7B, Compound 82. LC-MS (ESI) m/z: 481 [M+H]+; 1H-NMR (MeOD, 400 MHz) δ (ppm) 1.91-1.93 (m, 2H), 2.03-2.08 (m, 2H), 2.10-2.19 (m, 1H), 2.36 (s, 3H), 2.44 (s, 3H), 2.81-2.85 (m, 1H), 3.08-3.12 (m, 3H), 3.31-3.37 (m, 2H), 3.44-3.53 (m, 3H), 3.54-5.69 (m, 2H), 4.02-4.13 (m, 4H), 4.39-4.41 (m, 1H), 4.71 (d, J=2.8 Hz, 1H), 6.25-6.26 (m, 1H), 6.42-6.43 (m, 1H), 6.71-6.73 (m, 1H), 6.78-6.79 (m, 1H), 6.82-6.84 (m, 1H). Chiral-HPLC condition, solvent: MeOD (0.1% DEA), column AD-H 250*4.6 mm 5 um, Rt: 2.81 min.

Compound 82E. LC-MS (ESI) m/z: 481 [M+H]+; 1H-NMR (MeOD, 400 MHz) δ (ppm) 1.61-1.75 (m, 1H), 1.85-1.93 (m, 2H), 2.00-2.08 (m, 2H), 2.10-2.15 (m, 1H), 2.36 (s, 3H), 2.37 (s, 3H), 3.04-3.12 (m, 3H), 3.31-3.67 (m, 8H), 4.11 (s, 4H), 4.38-4.39 (m, 1H), 4.70 (d, J=2.8 Hz, 1H), 6.37 (brs, 2H), 6.67-6.69 (m, 1H), 6.75-6.77 (m, 1H), 6.83-6.84 (m, 1H). Chiral-HPLC condition, solvent: MeOD (0.1% DEA), column AD-H 250*4.6 mm 5 um, Rt: 5.03 min.

Example 83

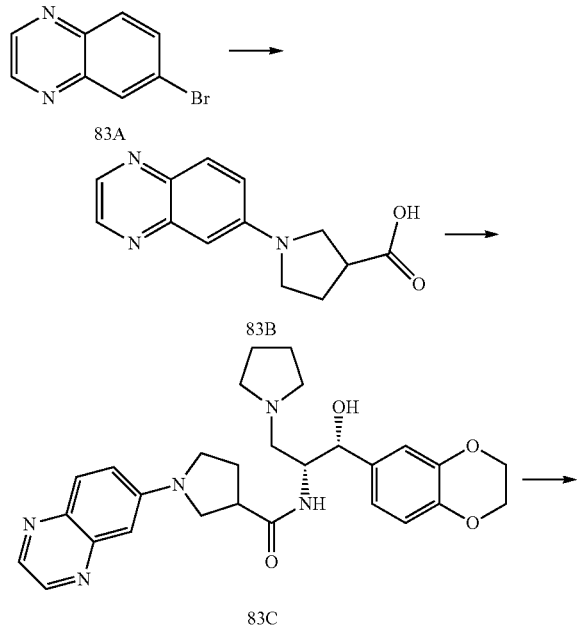

Compounds 83B, 83, and 83D were synthesized, by employing the procedures described for Compounds 1B and 1 using Compounds 83A and 83B in lieu of 1-chloro-4-iodobenzene and Compound 1B.

Compound 83B. LC-MS (ESI) m/z: 244 [M+H]+; 1H-NMR (MeOD, 400 MHz) δ (ppm) 2.19-2.28 (m, 2H), 3.20-3.24 (m, 1H), 3.43-3.49 (m, 2H), 3.60-3.65 (m, 2H), 6.80 (d, J=2.0 Hz, 1H), 7.35 (dd, J=2.4, 9.2 Hz, 1H), 7.85 (d, J=9.2 Hz, 1H), 8.50 (d, J=1.6 Hz, 1H), 8.67 (d, J=2.0 Hz, 1H).

Compound 83. LC-MS (ESI) m/z: 504 [M+H]+; 1H-NMR (MeOD, 400 MHz) δ (ppm) 1.98-2.05 (m, 2H), 2.14-2.19 (m, 3H), 2.28-2.33 (m, 1H), 2.94-3.01 (m, 1H), 3.16-3.24 (m, 3H), 3.43-3.47 (m, 2H), 3.55-3.67 (m, 4H), 3.75-3.79 (m, 1H), 4.06-4.12 (m, 3H), 4.25-4.29 (m, 1H), 4.45-4.50 (m, 1H), 4.81 (d, J=2.4 Hz, 1H), 6.79-6.88 (m, 3H), 6.93 (d, J=2.0 Hz, 1H), 7.35-7.38 (m, 1H), 7.90 (d, J=9.6 Hz, 1H), 8.51 (d, J=2.0 Hz, 1H), 8.63 (d, J=2.4 Hz, 1H); Chiral-HPLC condition, solvent: n-hexane (0.1% DEA):EtOH (0.1% DEA)=65:35, column OJ-H (4.6*250 mm 5 um), Rt: 7.84 min.

Compound 83D. LC-MS (ESI) m/z: 504 [M+H]+; 1H-NMR (MeOD, 400 MHz) δ (ppm) 1.76-1.84 (m, 1H), 1.97-2.02 (m, 2H), 2.11-2.15 (m, 2H), 2.20-2.26 (m, 1H), 3.13-3.23 (m, 3H), 3.31-3.37 (m, 1H), 3.39-3.48 (m, 2H), 3.51-3.57 (m, 2H), 3.61-3.65 (m, 2H), 3.73-3.78 (m, 1H), 4.19 (s, 4H), 4.44-4.49 (m, 1H), 4.79 (d, J=2.8 Hz, 1H), 6.77 (d, J=8.0 Hz, 2H), 6.84 (dd, J=1.6, 8.4 Hz, 1H), 7.38-7.41 (m, 1H), 7.87 (d, J=9.2 Hz, 1H), 8.50 (d, J=2.4 Hz, 1H), 8.57 (d, J=2.4 Hz, 1H); Chiral-HPLC condition, solvent: n-hexane (0.1% DEA):EtOH (0.1% DEA)=65:35, column OJ-H (4.6*250 mm 5 um), Rt: 11.32 min.

Example 84

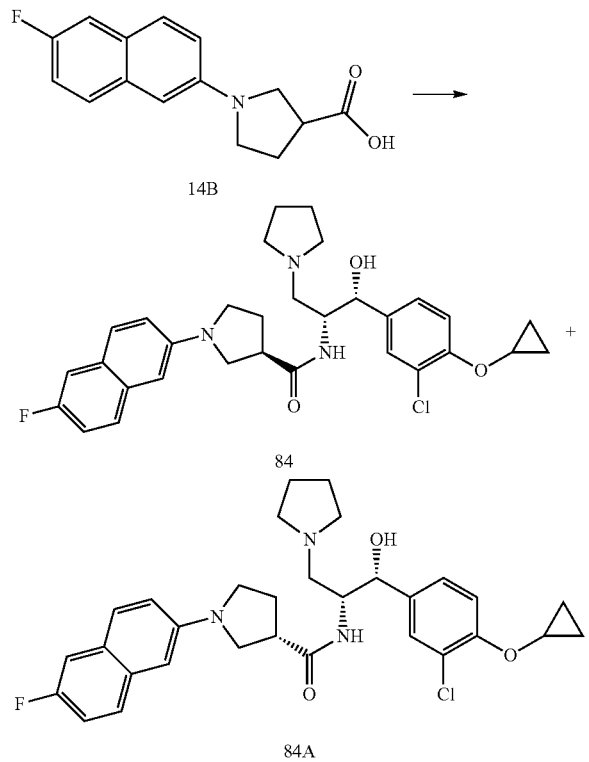

Example 85

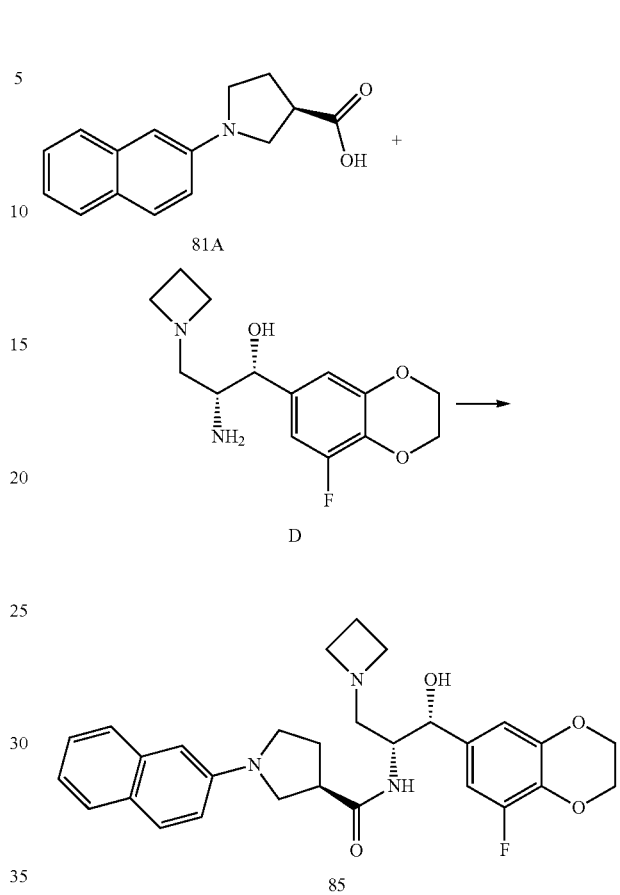

Compounds 84 and 84A were synthesized, by employing the procedures described for Compound 1 using Compound 14B and Intermediate E in lieu of Compound 1B and Intermediate A.

Compound 84. LC-MS (ESI) m/z: 552 [M+H]$^+$; $^1$H-NMR (MeOD, 400 MHz) δ (ppm) 0.46-0.57 (m, 4H), 1.72 (s, 4H), 1.98-2.17 (m, 2H), 2.49-2.60 (m, 4H), 2.68-2.69 (m, 2H), 2.75-2.79 (m, 1H), 2.98-3.06 (m, 1H), 3.20-3.24 (m, 1H), 3.25-3.36 (m, 2H), 3.52-3.58 (m, 1H), 4.20-4.24 (m, 1H), 4.80 (s, 1H), 6.66 (s, 1H), 6.90-6.94 (m, 1H), 7.01-7.06 (m, 1H), 7.11 (s, 2H), 7.20 (dJ=8.8 Hz, 1H), 7.37 (s, 1H), 7.55 (d, J=8.8 Hz, 1H), 7.60-7.64 (m, 1H); Chiral-HPLC condition, solvent: MeOH (0.5% DEA), column RegisCell (4.6*250 mm 5 um), RT: 4.78 min.

Compound 84A. LC-MS (ESI) m/z: 552 [M+H]$^+$; $^1$H-NMR (MeOD, 400 MHz) δ (ppm) 0.57-0.67 (m, 4H), 1.70 (s, 4H), 1.71-1.86 (m, 1H), 2.05-2.15 (m, 1H), 2.48-2.65 (m, 6H), 2.99-3.07 (m, 1H), 3.22-3.28 (m, 2H), 3.34-3.37 (m, 2H), 3.66-3.71 (m, 1H), 4.13-4.18 (m, 1H), 4.74 (d, J=4.8 Hz, 1H), 6.66 (s, 1H), 6.90-6.92 (m, 1H), 6.97-7.02 (m, 1H), 7.10-7.19 (m, 3H), 7.28 (s, 1H), 7.48-7.52 (m, 2H); Chiral-HPLC condition, solvent: MeOH (0.5% DEA), column OJ-H (4.6*250 mm 5 um), RT: 5.99 min.

Compound 85 was synthesized, by employing the procedure described for Compound 7 using Compound 81A and Intermediate D in lieu of Compound 7B and Intermediate A. LC-MS (ESI) m/z: 506 [M+H]$^+$; $^1$H-NMR (MeOD, 400 MHz) δ (ppm) 2.01-2.13 (m, 4H), 2.78-2.83 (m, 3H), 3.03-3.05 (m, 1H), 3.25-3.28 (m, 1H), 3.40-3.46 (m, 6H), 4.02-4.10 (m, 5H), 4.65 (d, J=2.4 Hz, 1H), 6.61-6.63 (m, 2H), 6.67-6.71 (m, 1H), 6.87-6.90 (m, 1H), 7.02-7.04 (m, 1H), 7.19-7.23 (m, 1H), 7.53-7.58 (m, 3H). Chiral-HPLC condition, solvent: MeOH (0.1% DEA), column AS-H 250*4.6 mm 5 um, Rt: 3.54 min.

Example 86

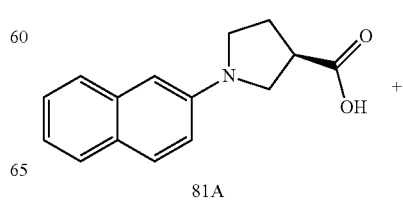

-continued

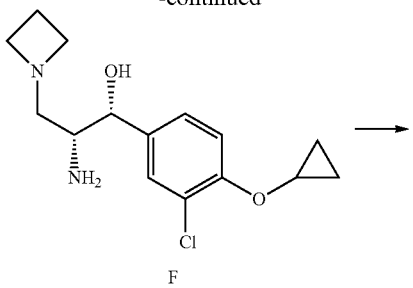

F

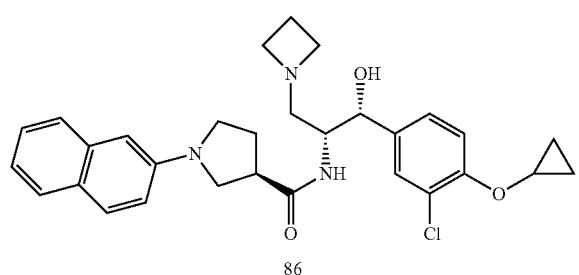

86

Compound 86 was synthesized, by employing the procedure described for Compound 7 using Compound 81A and Intermediate F in lieu of Compound 7B and Intermediate A. LC-MS (ESI) m/z: 520 [M+H]+; ¹H-NMR (MeOD, 400 MHz) δ (ppm) 0.46-0.56 (m, 4H), 2.01-2.14 (m, 4H), 2.60-2.71 (m, 2H), 2.81-2.83 (m, 1H), 3.00-3.04 (m, 1H), 3.26-3.37 (m, 7H), 3.51-3.53 (m, 1H), 4.01-4.02 (m, 1H), 4.72 (d, J=2.4 Hz, 1H), 6.62 (s, 1H), 6.86-6.89 (m, 1H), 7.00-7.04 (m, 1H), 7.10 (m, 2H), 7.20-7.21 (m, 1H), 7.35 (s, 1H), 7.53-7.57 (m, 3H). Chiral-HPLC condition, solvent: MeOH (0.1% DEA), column OZ-H 250*4.6 mm 5 um, Rt: 5.25 min.

Example 87

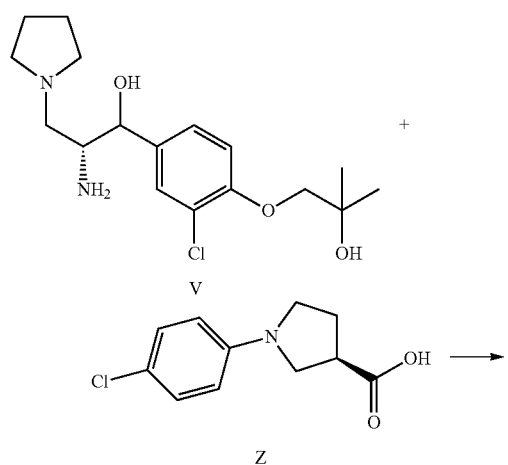

-continued

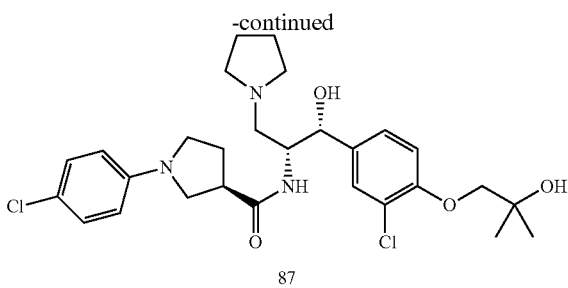

87

Compound 87 was synthesized, by employing the procedure described for Compound 1 using Intermediates Z and V in lieu of Compound 7B and Intermediate A. LC-MS (ESI) m/z: 550 [M+H]+; ¹H-NMR (MeOD, 400 MHz) δ (ppm) 1.31 (s, 3H), 1.34 (s, 3H), 2.01-2.09 (m, 3H), 2.16-2.21 (m, 3H), 2.60-2.65 (m, 1H), 3.07-3.15 (m, 1H), 3.17-3.22 (m, 3H), 3.25-3.27 (m, 2H), 3.46-3.50 (m, 1H), 3.56-3.62 (m, 1H), 3.66-3.68 (m, 1H), 3.76-3.77 (m, 3H), 4.49-4.52 (m, 1H), 4.88 (d, J=2.4 Hz, 1H), 6.46 (d, J=8.8 Hz, 1H), 6.96 (d, J=8.0 Hz, 1H), 7.12 (d, J=8.8 Hz, 2H), 7.26 (dd, J=2.4, 8.4 Hz, 1H), 7.51 (d, J=2.4 Hz, 1H).

Example 88

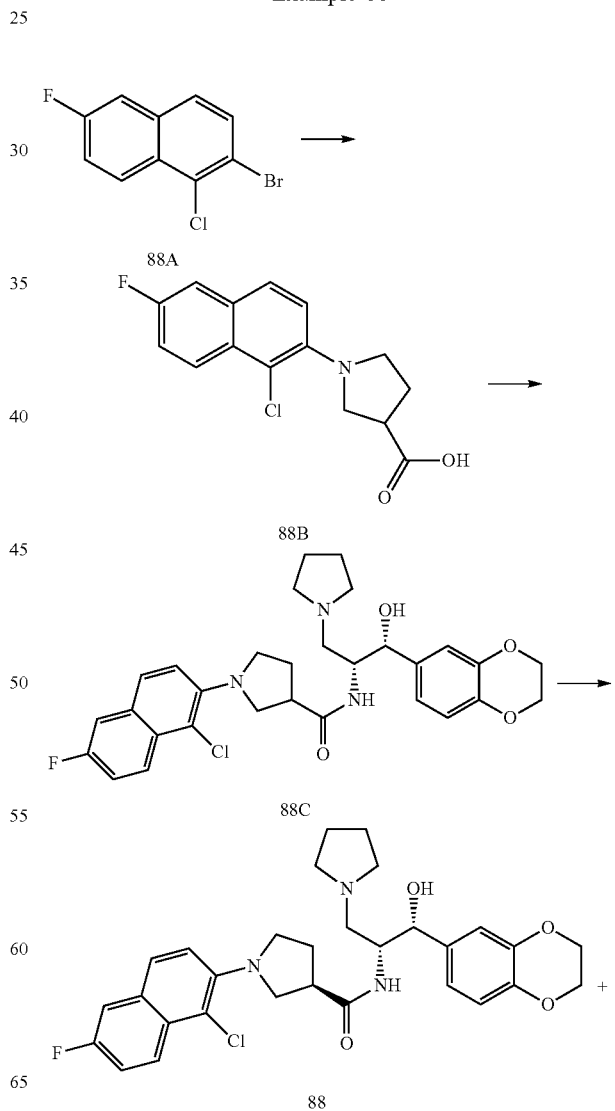

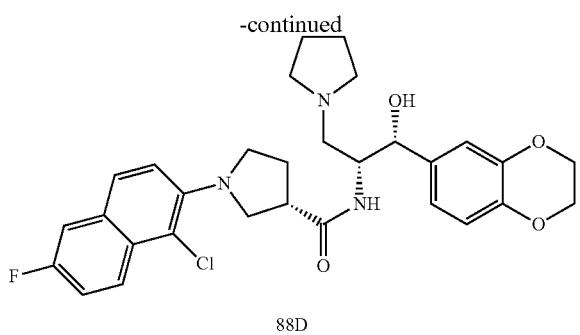

88D

Compounds 88B, 88, and 88D were synthesized, by employing the procedures described for Compounds 1B and 1 using Compounds 88A and 88B in lieu of 1-chloro-4-iodobenzene and Compound 1B.

Compound 88B. LC-MS (ESI) m/z: 294 [M+H]$^+$; $^1$H-NMR (DMSO-d$_6$, 400 MHz) δ (ppm) 2.08-2.22 (m, 2H), 3.10-3.17 (m, 1H), 3.50-3.62 (m, 1H), 3.64-3.73 (m, 2H), 7.42-7.50 (m, 2H), 7.67-7.79 (m, 1H), 7.79 (d, J=8.0 Hz, 1H), 8.12-8.15 (m, 1H).

Compound 88. LC-MS (ESI) m/z: 554 [M+H]$^+$; $^1$H-NMR (CD$_3$OD, 400 MHz) δ (ppm) 1.80 (s, 4H), 2.11-2.17 (m, 2H), 2.58-2.80 (m, 6H), 3.03-3.11 (m, 1H), 3.25-3.29 (m, 1H), 3.41-3.47 (m, 1H), 3.51-3.58 (m, 2H), 4.06-4.10 (m, 4H), 4.25-4.29 (m, 1H), 4.81 (s, 1H), 6.72-6.87 (m, 3H), 7.33-7.40 (m, 2H), 7.49 (d, J=9.6 Hz, 1H), 7.72 (d, J=8.8 Hz, 1H), 8.22-8.26 (m, 1H). Chiral-HPLC condition, solvent: MeOH (0.1% DEA), column: OJ-H (250*4.6 mm 5 um), Rt: 4.45 min.

Compound 88D. LC-MS (ESI) m/z: 554 [M+H]$^+$; $^1$H-NMR (CD$_3$OD, 400 MHz) δ (ppm) 1.80 (s, 4H), 1.94-2.03 (m, 1H), 2.17-2.25 (m, 1H), 2.58-2.80 (m, 6H), 3.03-3.11 (m, 1H), 3.42-3.65 (m, 4H), 4.17 (s, 4H), 4.24-4.29 (m, 1H), 4.79 (s, 1H), 6.70-6.85 (m, 3H), 7.33-7.40 (m, 2H), 7.48 (d, J=9.6 Hz, 1H), 7.71 (d, J=8.8 Hz, 1H), 8.20-8.24 (m, 1H). Chiral-HPLC condition, solvent: MeOH (0.1% DEA), column: OJ-H (250*4.6 mm 5 um), Rt: 6.82 min.

Example 89

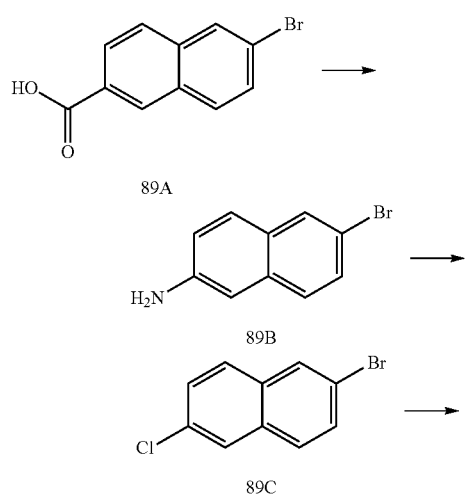

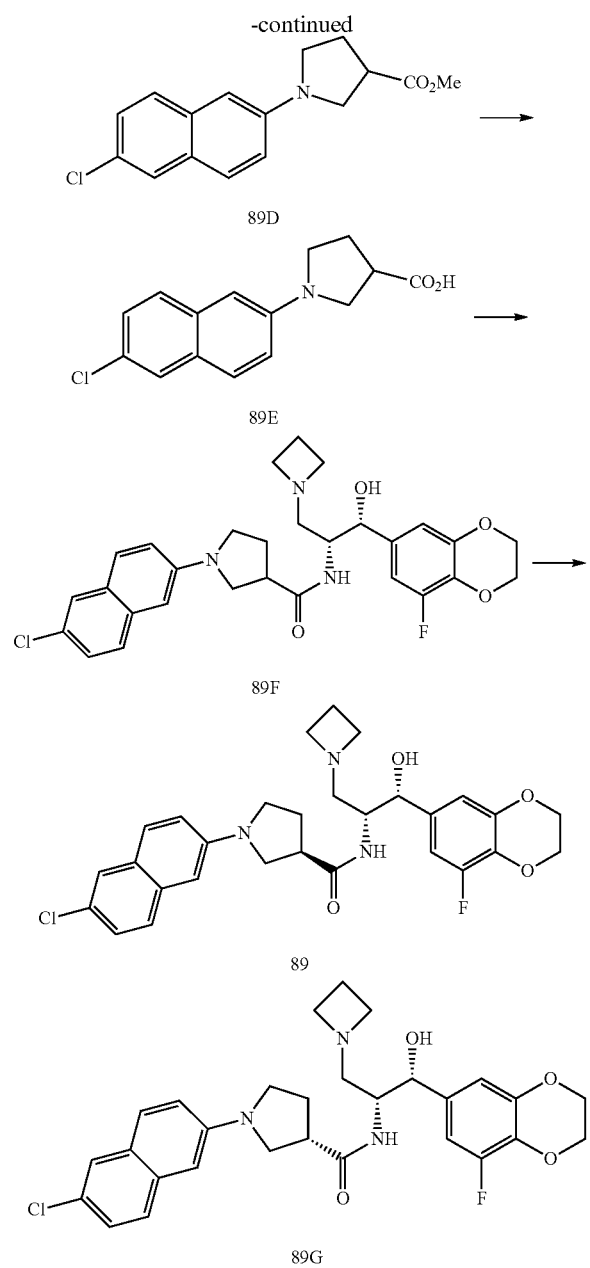

To a solution of Compound 89A (3.77 g, 15 mmol) and TEA (2.27 g, 22.5 mmol) in DMF (100 mL) was added DPPA (5.47 g, 22.5 mmol). The mixture was stirred at 25° C. for 3 h. Water (30 mL) was added, and the mixture was heated at 100° C. for 2 h. DMF was removed by distillation under vacuum. The residue was dissolved in ethyl acetate (300 mL) and saturated sodium bicarbonate (200 mL), and filtrated through celite. The organic phase was separated, washed with water (200 mL) and brine (200 mL), dried over anhydrous sodium sulfate, and evaporated to furnish Compound 89B. LC-MS (ESI) m/z: 222 [M+H]$^+$; $^1$H-NMR (DMSO-d$_6$, 400 MHz) δ (ppm) 5.55 (s, 2H), 6.83 (s, 1H), 6.99 (d, J=8.8 Hz, 1H), 7.36 (dd, J=8.8, 1.6 Hz, 1H), 7.47 (d, J=8.4 Hz, 1H), 7.59 (d, J=8.8 Hz, 1H), 7.87 (s, 1H).

To a solution of Compound 89B (2.04 g, 9.19 mmol) in 6 N HCl (20 mL) was added a solution of NaNO$_2$ (698 mg, 10.1 mmol) in water (10 mL) at 0° C. The mixture was stirred at room temperature for 1 h. Then a solution of CuCl (4.55 g, 46 mmol) in 6 N HCl (10 mL) was added. The mixture was stirred at room temperature for 4 h, diluted with water (200 mL), and extracted with ethyl acetate (150 mL×3). The organic layer was washed with water (150 mL×3) and brine (150 mL×1), dried over sodium sulfate, concentrated, and purified with flash column chromatography on silica gel (petroleum ether, 100% v/v) to yield Compound 89C. $^1$H-NMR (DMSO-$d_6$, 400 MHz) δ (ppm) 7.60 (d, J=8.8 Hz, 1H), 7.71 (d, J=8.8 Hz, 1H), 7.90 (d, J=8.8 Hz, 1H), 7.97 (d, J=8.8 Hz, 1H), 8.11 (s, 1H), 8.28 (s, 1H).

A mixture of Compound 89C (605 mg, 2.5 mmol), methyl pyrrolidine-3-carboxylate (355 mg, 2.75 mmol), Pd(OAc)$_2$ (56 mg, 0.25 mmol), XantPhos (145 mg, 0.25 mmol), and CsCO$_3$ (1.22 g, 3.75 mmol) in dioxane (30 mL) was refluxed for 18 h. After evaporation, the crude compound was suspended in water (50 mL), extracted with ethyl acetate (100 mL), and dried over anhydrous sodium sulfate. After evaporation of solvent, the crude product was purified with flash column chromatography on silica gel (ethyl acetate in petroleum ether, 8% v/v) to give Compound 89D. LC-MS (ESI) m/z: 290 [M+H]$^+$; $^1$H-NMR (CDCl$_3$, 400 MHz) δ (ppm) 2.31-2.37 (m, 2H), 3.22-3.30 (m, 1H), 3.42-3.56 (m, 2H), 3.62-3.69 (m, 2H), 3.74 (s, 3H), 6.72 (d, J=2.0 Hz, 1H), 6.98 (dd, J=8.8, 2.4 Hz, 1H), 7.28 (dd, J=8.8, 2.0 Hz, 1H), 7.54-7.65 (m, 3H).

Compound 89E was synthesized, by employing the procedure described for Compound 5C using Compound 89D in lieu of Compound 5B. LC-MS (ESI) m/z: 276 [M+H]$^+$.

Compounds 89 and 89G were synthesized, by employing the procedures described for Compound 1 using Intermediate D and Compound 89E in lieu of Intermediate A and Compound 1B.

Compound 89. LC-MS (ESI) m/z: 540 [M+H]$^+$; $^1$H-NMR (CDCl$_3$, 400 MHz) δ (ppm) 2.10-2.21 (m, 4H), 2.82-2.86 (m, 2H), 2.95-3.01 (m, 2H), 3.25-3.52 (m, 8H), 4.02 (s, 1H), 4.22 (s, 4H), 4.92 (s, 1H), 6.21 (d, J=7.6 Hz, 1H), 6.63 (s, 1H), 6.74 (m, 2H), 6.97 (dd, J=9.2, 2.0 Hz, 1H), 7.29 (dd, J=8.8, 2.0 Hz, 1H), 7.58-7.65 (m, 3H); Chiral-HPLC condition, solvent: MeOH (0.1% DEA), column: OJ-H (250*4.6 mm 5 um), Rt: 3.44 min.

Compound 89G. LC-MS (ESI) m/z: 540 [M+H]$^+$; $^1$H-NMR (CD$_3$OD, 400 MHz) δ (ppm) 1.75-1.83 (m, 1H), 2.16-2.24 (m, 11H, 2.38-2.45 (m, 1H), 2.56-2.63 (m, 1H), 3.14-3.20 (m, 1H), 3.35-3.57 (m, 6H), 4.16-4.35 (m, 9H), 4.79 (d, J=2.4 Hz, 1H), 6.75-6.81 (m, 3H), 7.04 (d, J=8.8 Hz, 1H), 7.25 (dd, J=8.8, 2.4 Hz, 1H), 7.57-7.65 (m, 3H), 8.01 (d, J=9.6 Hz, 1H); Chiral-HPLC condition, solvent: MeOH (0.1% DEA), column: OJ-H (250*4.6 mm 5 um), Rt: 6.20 min.

Example 90

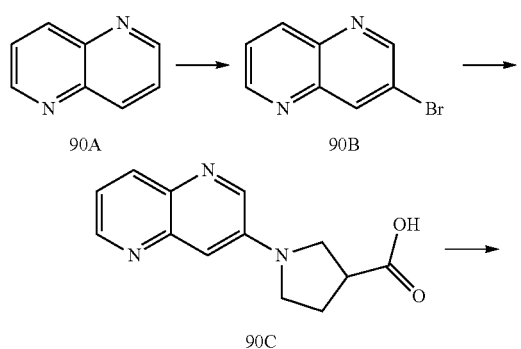

-continued

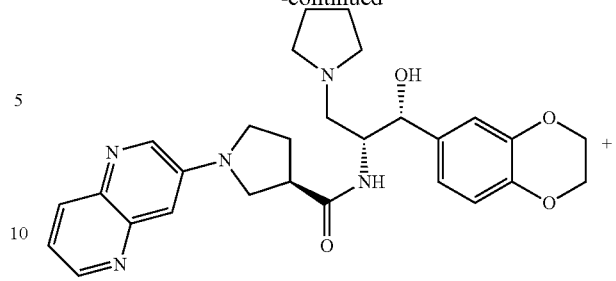

90

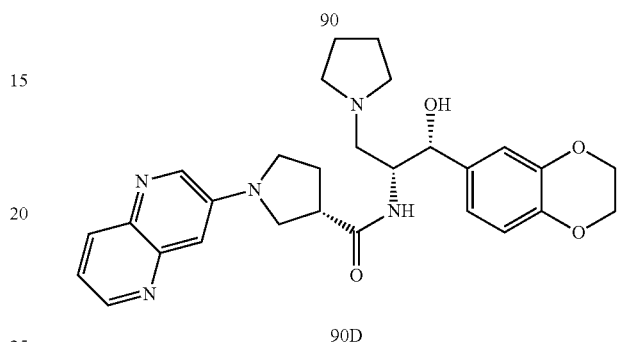

90D

To a solution of Compound 90A (1.0 g, 7.69 mol) in acetic acid (8 mL) was added NaOAc (1.26 g, 15.38 mmol) and a solution of bromine (0.43 mL, 8.46 mmol) in acetic acid (2 mL) at 85° C. The mixture was stirred at 85° C. for four hours, cooled to room temperature, and filtered. The filtrate was concentrated under vacuum and the residue was purified with flash column chromatography on silica gel (petroleum in ethyl acetate, 30% v/v) to render Compound 90B. LC-MS (ESI) m/z: 209 [M+H]$^+$; $^1$H-NMR (CDCl$_3$, 400 MHz) δ (ppm) 7.70 (dd, J=4.0, 8.8 Hz, 1H), 8.43 (d, J=8.4 Hz, 1H), 8.63 (d, J=2.4 Hz, 1H), 7.45 (t, J=2.4 Hz, 1H).

Compounds 90C, 90, and 90D were synthesized, by employing the procedures described for Compounds 1B and 1 using Compounds 90B and 90C in lieu of 1-chloro-4-iodobenzene and Compound 1B.

Compound 90C. LC-MS (ESI) m/z: 244 [M+H]$^+$.

Compound 90. LC-MS (ESI) m/z: 504 [M+H]$^+$; $^1$H-NMR (MeOD, 400 MHz) δ (ppm) 2.00-2.02 (m, 2H), 2.13-2.21 (m, 3H), 2.29-2.37 (m, 1H), 3.11-3.22 (m, 3H), 3.39-3.43 (m, 1H), 3.50-3.55 (m, 2H), 3.61-3.67 (m, 3H), 4.00-4.05 (m, 2H), 4.14-4.19 (m, 2H), 4.44-4.47 (m, 1H), 4.77 (d, J=2.8 Hz, 1H), 6.75 (d, J=8.4 Hz, 1H), 6.86-6.88 (m, 2H), 7.00 (d, J=2.0 Hz, 1H), 7.67-7.70 (m, 1H), 8.15 (d, J=10.0 Hz, 1H), 8.78-8.80 (m, 3H); Chiral-HPLC condition, solvent: MeOH (0.1% DEA), column RegisCell (4.6*250 mm 5 um), Rt: 4.53 min.

Compound 90D. LC-MS (ESI) m/z: 504 [M+H]$^+$; $^1$H-NMR (MeOD, 400 MHz) δ (ppm) 1.80-1.82 (m, 2H), 2.00-2.10 (m, 4H), 2.25-2.27 (m, 1H), 3.14-3.40 (m, 5H), 3.57-3.73 (m, 4H), 4.18 (s, 4H), 4.46-4.48 (m, 1H), 4.80 (m, 1H), 6.77-7.00 (m, 4H), 7.65 (m, 1H), 8.77 (m, 3H); Chiral-HPLC condition, solvent: MeOH (0.1% DEA), column RegisCell (4.6*250 mm 5 um), Rt: 5.63 min.

Example 91

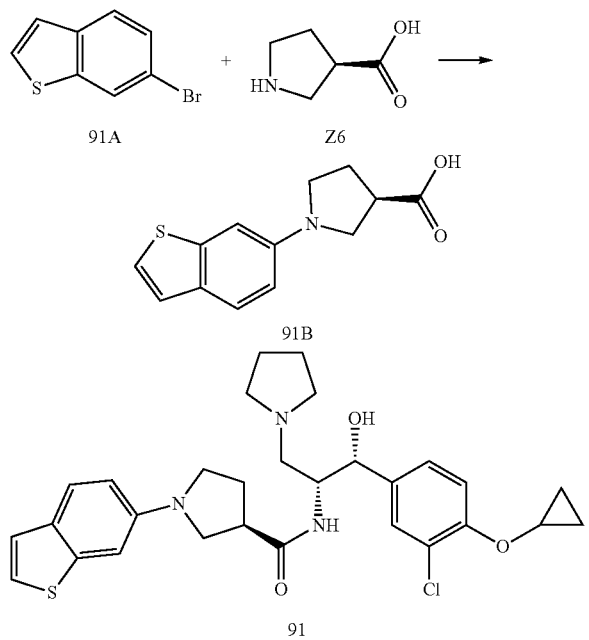

Compounds 91B and 91 were synthesized, by employing the procedures described for Compounds 1B and 1 using Compound 91A, Intermediate Z6, Compound 91B, and Intermediate E in lieu of 1-chloro-4-iodobenzene, Compounds 1A, 1B, and Intermediate A.

Compound 91B. LC-MS (ESI) m/z: 248 [M+H]$^+$; $^1$H-NMR (MeOD, 400 MHz) δ (ppm) 2.27-2.31 (m, 2H), 3.13-3.17 (m, 1H), 3.32-3.56 (m, 4H), 6.72-6.75 (m, 1H), 6.99 (s, 1H), 7.09-7.14 (m, 2H), 7.59-7.61 (m, 1H).

Compound 91. LC-MS (ESI) m/z: 540 [M+H]$^+$; $^1$H-NMR (MeOD, 400 MHz) δ (ppm) 0.50-0.68 (m, 4H), 2.05-2.28 (m, 6H), 2.62-2.66 (m, 1H), 3.13-3.25 (m, 4H), 3.39-3.63 (m, 6H), 3.79-3.87 (m, 1H), 4.55-4.60 (m, 1H), 4.93 (d, J=2.8 Hz, 1H), 6.69-6.71 (m, 1H), 6.96 (s, 1H), 7.17 (s, 2H), 7.25-7.27 (m, 2H), 7.53 (s, 1H), 7.63-7.65 (m, 1H).

Example 92

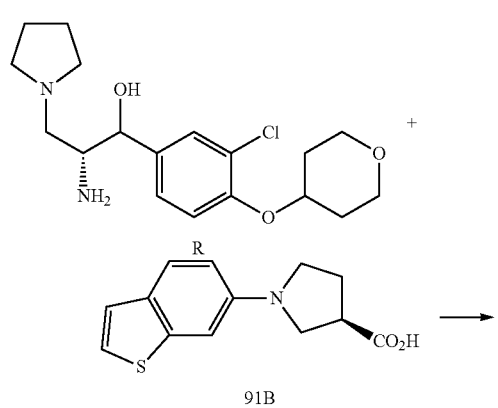

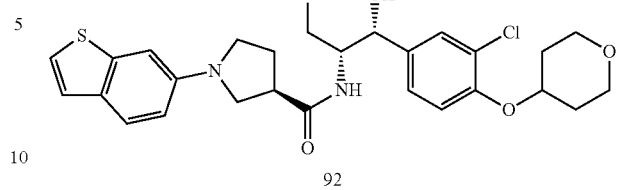

Compound 92 was synthesized, by employing the procedure described for Compound 1 using Compound 91B and Intermediate R in lieu of Compound 1B and Intermediate A. LC-MS (ESI) m/z: 584 [M+H]$^+$; $^1$H-NMR (MeOD, 400 MHz) δ (ppm) 1.57-1.72 (m, 2H), 1.84-1.89 (m, 2H), 2.03-2.29 (m, 7H), 2.65-2.69 (m, 1H), 3.12-3.29 (m, 3H), 3.36-3.52 (m, 5H), 3.61-3.89 (m, 5H), 4.40-4.47 (m, 1H), 4.55-4.59 (m, 1H), 4.91 (s, 1H), 6.76 (d, J=8.8 Hz, 1H), 6.98 (d, J=8.4 Hz, 1H), 7.03 (s, 1H), 7.19 (s, 2H), 7.27 (dd, J=8.4, 2.0 Hz, 1H), 7.56 (d, J=2.0 Hz, 1H), 7.65 (d, J=8.8 Hz, 1H).

Example 93

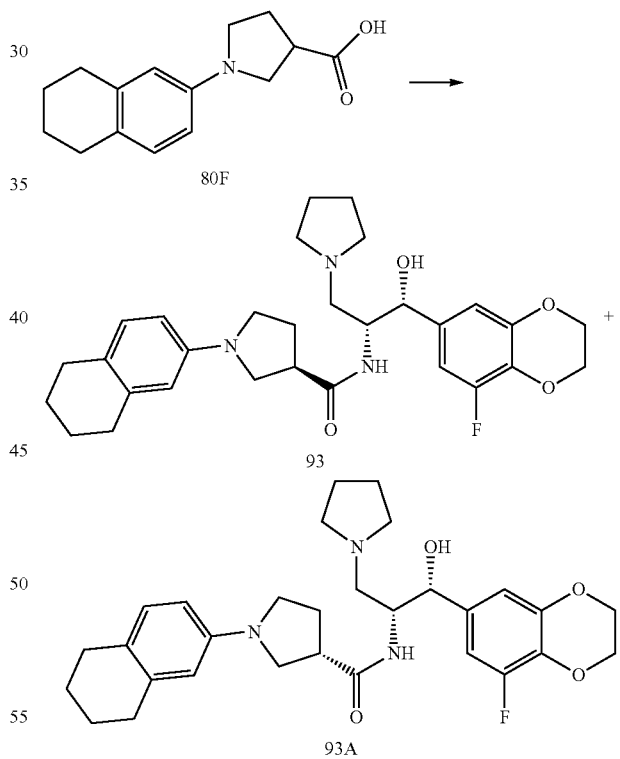

Compounds 93 and 93A were synthesized, by employing the procedures described for Compound 1 using Compound 80F and Intermediate C in lieu of Compound 1B and Intermediate A.

Compound 93. LC-MS (ESI) m/z: 524 [M+H]$^+$; $^1$H-NMR (MeOD, 400 MHz) δ (ppm) 1.79 (m, 4H), 2.05-2.22 (m, 6H), 2.62-2.76 (m, 5H), 3.11-3.29 (m, 5H), 3.37-3.49 (m, 2H), 3.56-3.62 (m, 1H), 3.68-3.81 (m, 2H), 4.18 (m, 4H), 4.49 (m, 1H), 4.83 (d, J=2.4 Hz, 1H), 6.35 (d, J=2.0 Hz, 1H), 6.44 (m, 1H), 6.75 (s, 1H), 6.82 (m, 1H), 6.90 (d, J=8.0 Hz, 1H), Chiral-HPLC condition, solvent: MeOH (0.5% DEA), column AD-H (250*4.6 mm 5 um), Rt: 3.74 min.

Compound 93A. LC-MS (ESI) m/z: 524 [M+H]⁺; ¹H-NMR (MeOD, 400 MHz) δ (ppm) 1.79 (m, 5H), 2.02-2.32 (m, 5H), 2.73 (m, 4H), 3.18 (m, 2H), 3.42-3.77 (m, 8H), 4.25 (s, 4H), 4.50 (m, 1H), 4.81 (d, J=2.4 Hz, 1H), 6.79-7.07 (m, 5H). Chiral-HPLC condition, solvent: MeOH (0.5% DEA), column AD-H (250*4.6 mm 5 um), Rt: 6.18 min.

Example 94

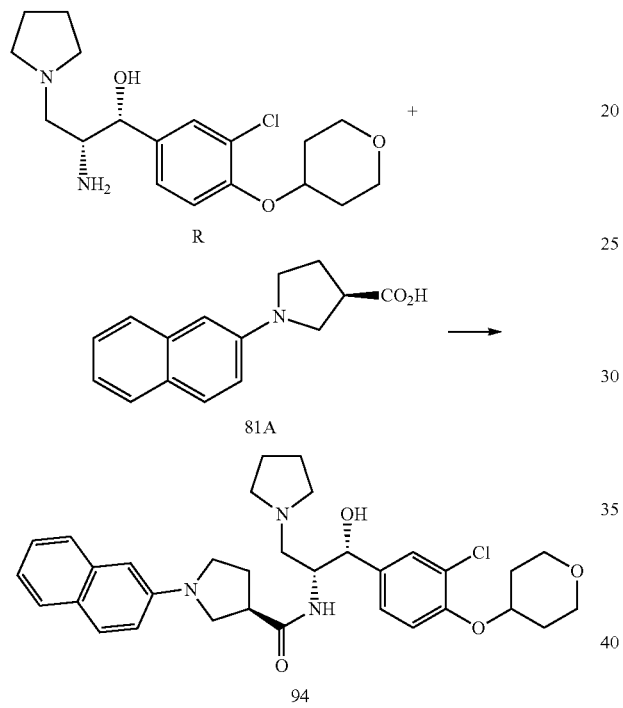

Compound 94 was synthesized, by employing the procedure described for Compound 1 using Compound 81A and Intermediate R in lieu of Compound 1B and Intermediate A. LC-MS (ESI) m/z: 578 [M+H]⁺; ¹H-NMR (CD₃OD, 400 MHz) δ (ppm) 1.55-1.68 (m, 2H), 1.79-1.85 (m, 2H), 2.04-2.31 (m, 6H), 2.73-2.77 (m, 1H), 3.19-3.26 (m, 2H), 3.36-3.54 (m, 6H), 3.62-3.88 (m, 6H), 4.37-4.41 (m, 1H), 4.56-4.60 (m, 1H), 4.93 (s, 1H), 6.99 (dd, J=14.4, 4.4 Hz, 2H), 7.15-7.17 (m, 1H), 7.28-7.34 (m, 2H), 7.57 (d, J=2.0 Hz, 1H), 7.66-7.73 (m, 3H).

Example 95

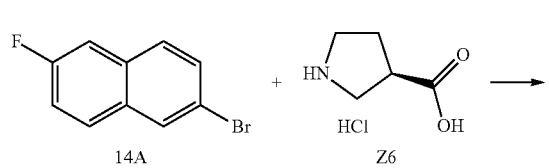

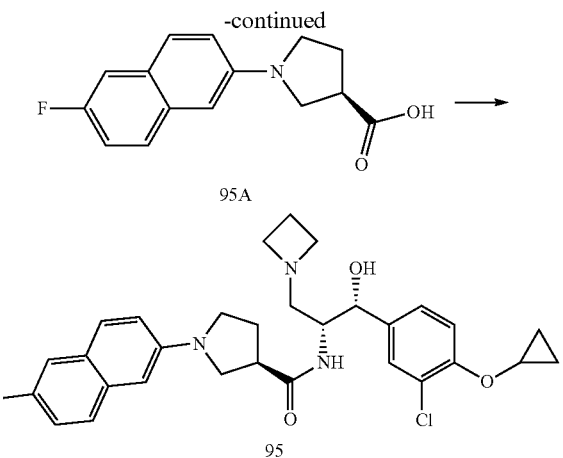

Compounds 95A and 95 were synthesized, by employing the procedures described for Compounds 1B and 1 using Compound 14A, Intermediate Z6, Compound 95A, and Intermediate F in lieu of 1-chloro-4-iodobenzene, Compounds 1A, 1B, and Intermediate A.

Compound 95A. LC-MS (ESI) m/z: 260 [M+H]⁺; ¹H-NMR (DMSO-d₆, 400 MHz) δ (ppm) 2.14-2.30 (m, 2H), 3.20-3.27 (m, 1H), 3.33-3.44 (m, 2H), 3.49-3.58 (m, 2H), 6.84 (s, 1H), 7.09 (d, J=8.8 Hz, 1H), 7.21-7.27 (m, 1H), 7.48 (d, J=8.8 Hz, 1H), 7.67-7.73 (m, 2H), 12.50 (s, 1H).

Compound 95. LC-MS (ESI) m/z: 538 [M+H]⁺; ¹H-NMR (CD₃OD, 400 MHz) δ (ppm) 0.48-0.69 (m, 4H), 2.07-2.15 (m, 1H), 2.23-2.30 (m, 1H), 2.40-2.49 (m, 1H), 2.56-2.66 (m, 2H), 3.10-3.18 (m, 1H), 3.31-3.38 (m, 2H), 3.42-3.62 (m, 4H), 4.16-4.42 (m, 5H), 4.92 (s, 1H), 6.73 (s, 1H), 6.98-7.01 (m, 1H), 7.13-7.19 (m, 1H), 7.25 (s, 2H), 7.32 (d, J=10.0 Hz, 1H), 7.56 (s, 1H), 7.65 (d, J=9.2 Hz, 1H), 7.73-7.77 (m, 1H), 8.03 (d, J=10.0 Hz, 1H).

Example 96

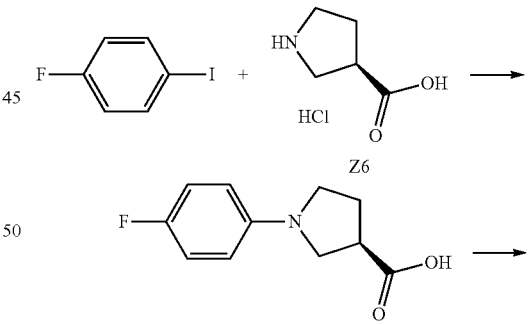

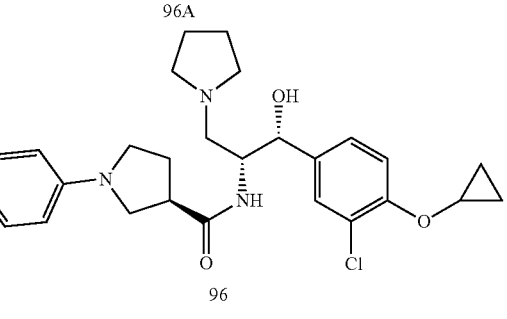

Compounds 96A and 96 were synthesized, by employing the procedures described for Compounds 1B and 1 using 1-fluoro-4-iodobenzene, Intermediate Z6, Compound 96A, and Intermediate E in lieu of 1-chloro-4-iodobenzene, Compounds 1A, 1B, and Intermediate A.

Compound 96A. LC-MS (ESI) m/z: 208 [M–H]+; 1H-NMR (CD3OD, 400 MHz): δ (ppm) 2.25-2.32 (m, 2H), 3.20-3.36 (m, 3H), 3.47-3.49 (m, 2H), 6.54-6.57 (m, 2H), 6.90-6.94 (m, 2H).

Compound 96. LC-MS (ESI) m/z: 502 [M+H]+; 1H-NMR (CD3OD, 400 MHz) δ (ppm) 0.69-0.79 (m, 4H), 2.08-2.15 (m, 6H), 2.51-2.52 (m, 1H), 3.12-3.24 (m, 6H), 3.48-3.82 (m, 5H), 4.53-4.56 (m, 1H), 4.93-4.94 (m, 1H), 6.56 (m, 2H), 6.94 (m, 2H), 7.30 (m, 2H), 7.53 (m, 1H). Chiral-HPLC condition, solvent: MeOH (0.1% DEA), column: OZ-H 250*4.6 mm 5 um), Rt: 4.31 min.

Example 97

Compound 97. LC-MS (ESI) m/z: 526 [M+H]+; 1H-NMR (CD3OD, 400 MHz) δ (ppm) 2.04-2.26 (m, 6H), 2.67-2.71 (m, 1H), 3.17-3.19 (m, 3H), 3.35-3.44 (m, 4H), 3.48-3.61 (m, 3H), 4.17-4.30 (m, 4H), 4.51-4.53 (m, 1H), 4.84 (d, J=2.8 Hz, 1H), 6.73-6.86 (m, 3H), 7.00 (d, J=1.6 Hz, 1H), 7.17-7.18 (m, 2H), 7.64-7.66 (m, 1H). Chiral-HPLC condition, solvent: n-hexane (0.1% DEA):EtOH (0.1% DEA)=10:90, column: (S,S)-Whelk-01 250*4.6 mm 5 um), Rt: 8.26 min.

Compound 97C. LC-MS (ESI) m/z: 526 [M+H]+; 1H-NMR (CD3OD, 400 MHz) δ (ppm) 1.73-1.86 (m, 6H), 2.08-2.12 (m, 1H), 2.57-2.63 (m, 5H), 3.01-3.07 (m, 1H), 3.22-3.34 (m, 4H), 4.15 (s, 5H), 4.68 (d, J=2.8 Hz, 1H), 6.60-6.61 (m, 3H), 6.86 (d, J=2.0 Hz, 1H), 7.01-7.03 (m, 2H), 7.48-7.50 (m, 1H). Chiral-HPLC condition, solvent: n-hexane (0.1% DEA):EtOH (0.1% DEA)=10:90, column: (S,S)-Whelk-01 250*4.6 mm 5 um), Rt: 12.87 min.

Example 98

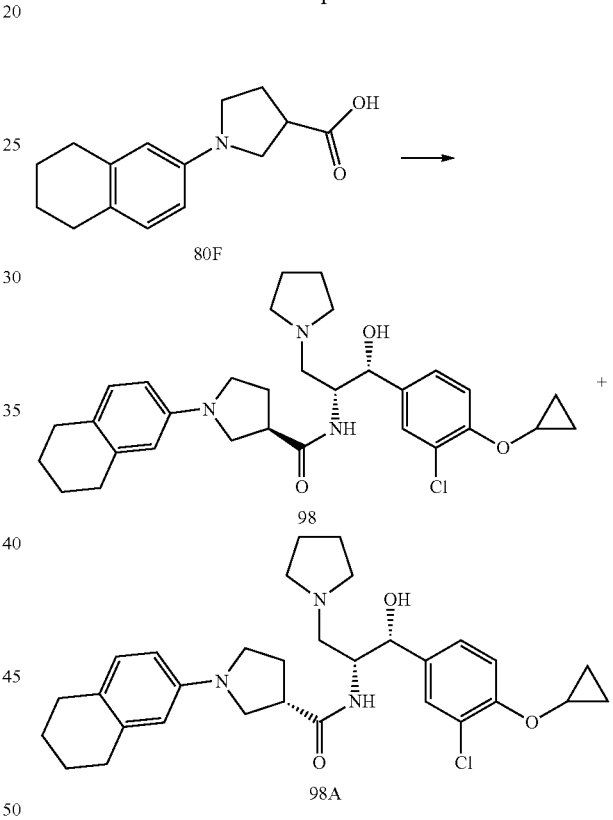

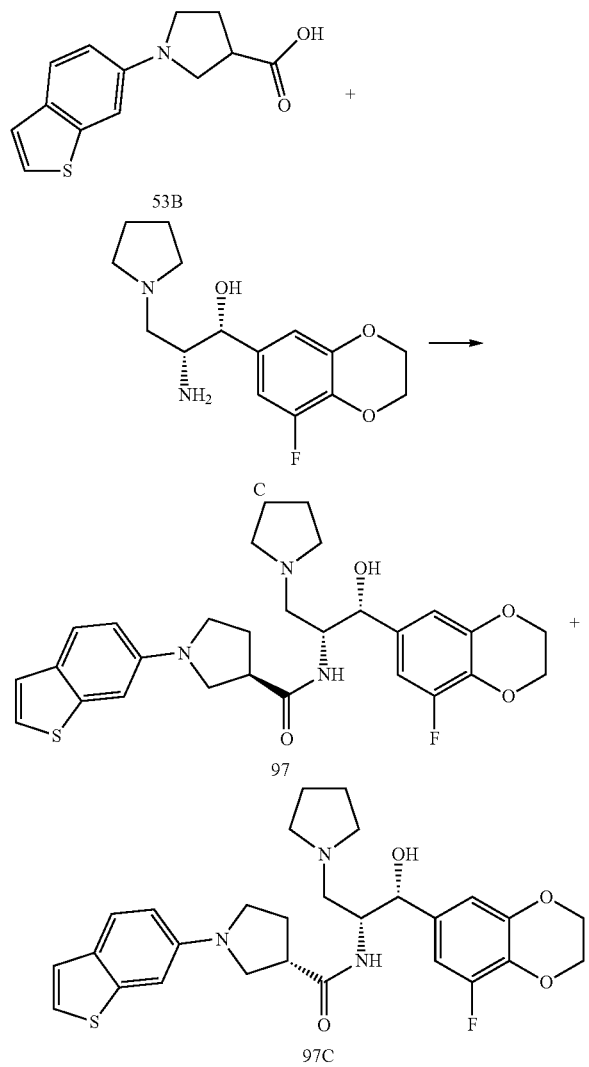

Compounds 97 and 97C were synthesized, by employing the procedures described for Compound 1 using Compound 53B and Intermediate C in lieu of Compound 1B and Intermediate A.

Compounds 98 and 98A were synthesized, by employing the procedures described for Compound 1 using Compound 80F and Intermediate E in lieu of 1-chloro-4-iodobenzene, Compound 1B, and Intermediate A.

Compound 98. LC-MS (ESI) m/z: 538 [M+H]+; 1H-NMR (CD3OD, 400 MHz) δ (ppm) 0.61-0.75 (m, 4H), 2.81 (m, 4H), 2.06-2.34 (m, 6H), 2.65-2.79 (m, 5H), 3.19-3.28 (m, 4H), 3.45-3.81 (m, 8H), 4.53-4.57 (m, 1H), 6.65 (m, 2H), 7.01 (d, J=8.0 Hz, 1H), 7.29 (m, 2H), 7.49 (s, 1H). Chiral-HPLC condition, solvent: n-hexane (0.1% DEA):EtOH (0.1% DEA)=90:10, column: IC (250*4.6 mm 5 um), Rt: 11.74 min.

Compound 98A. LC-MS (ESI) m/z: 538 [M+H]+; 1H-NMR (CD3OD, 400 MHz) δ (ppm) 0.70-0.83 (m, 4H), 1.66-1.79 (m, 5H), 2.03-2.29 (m, 5H), 2.72-2.76 (m, 4H), 3.19-3.28 (m, 5H), 3.43-3.84 (m, 8H), 4.52-4.56 (m, 1H), 6.75-6.81 (m, 2H), 7.03 (d, J=8.4 Hz, 1H), 7.34 (m, 2H), 7.49 (d, J=1.2 Hz, 1H). Chiral-HPLC condition, solvent: n-hexane (0.1% DEA):EtOH (0.1% DEA)=90:10, column: IC (250*4.6 mm 5 um), Rt: 14.51 min.

Example 99

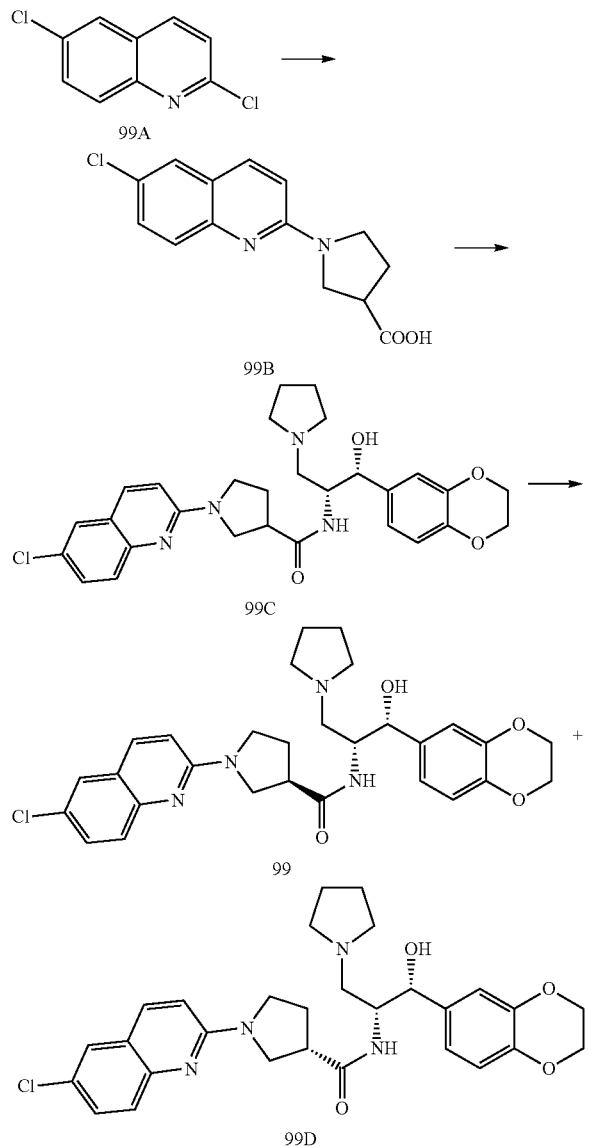

Compounds 99B, 99, and 99D were synthesized, by employing the procedures described for Compounds 1B and 1 using Compounds 99A and 99B in lieu of 1-chloro-4-iodobenzene and Compound 1B.

Compound 99B. LC-MS m/z: 275 [M-]$^+$; $^1$H-NMR (DMSO-d$_6$, 400 MHz) δ (ppm) 1.96-2.14 (m, 2H), 2.67-2.71 (m, 1H), 3.43-3.54 (m, 4H), 3.65-3.69 (m, 1H), 6.85-6.88 (m, 1H), 7.41-7.44 (m, 1H), 7.48-7.50 (m, 1H), 7.73 (m, 1H), 7.91-7.93 (m, 1H).

Compound 99. LC-MS (ESI) m/z: 537 [M+H]$^+$; $^1$H-NMR (CD$_3$OD, 400 MHz) δ (ppm) 1.96-2.23 (m, 4H), 2.31-2.44 (m, 2H), 3.11-3.23 (m, 2H), 3.32-3.40 (m, 2H), 3.42-3.45 (m, 1H), 3.56-3.62 (t, J=12.0 Hz, 1H), 3.65-3.77 (m, 3H), 3.83-3.96 (m, 2H), 4.00-4.22 (m, 4H), 4.48-4.50 (m, 1H), 4.80 (s, 1H), 6.77-6.82 (m, 1H), 6.91-6.92 (m, 2H), 7.11-7.20 (m, 1H), 7.81-7.83 (m, 1H), 7.90-7.93 (m, 1H), 8.00-8.03 (m, 1H), 8.36-8.39 (m, 1H); Chiral-HPLC condition, solvent: n-hexane (0.1% DEA):EtOH (0.1% DEA)=10:90, column: OZ-H (250*4.6 mm 5 um)), Rt: 4.64 min.

Compound 99D. LC-MS (ESI) m/z: 537 [M+H]$^+$; $^1$H-NMR (CD$_3$OD, 400 MHz) δ (ppm) 1.87-1.88 (m, 1H), 2.03-2.15 (m, 4H), 2.34-2.36 (m, 1H), 3.19-3.30 (m, 2H), 3.32-3.45 (m, 2H), 3.57-3.61 (m, 3H), 3.63-3.85 (m, 4H), 3.98-4.01 (m, 1H), 4.23 (s, 4H), 4.50-4.53 (m, 1H), 4.82-4.83 (m, 1H), 6.80-6.82 (m, 1H), 6.87-6.90 (m, 1H), 6.97 (m, 1H), 7.20-7.22 (m, 1H), 7.77-7.80 (m, 1H), 7.88-7.90 (m, 1H), 7.96-7.97 (m, 1H), 8.29-8.32 (m, 1H); Chiral-HPLC condition, solvent: n-hexane (0.1% DEA):EtOH (0.1% DEA)=10:90, column: OZ-H (250*4.6 mm 5 um)), Rt: 6.26 min.

Example 100

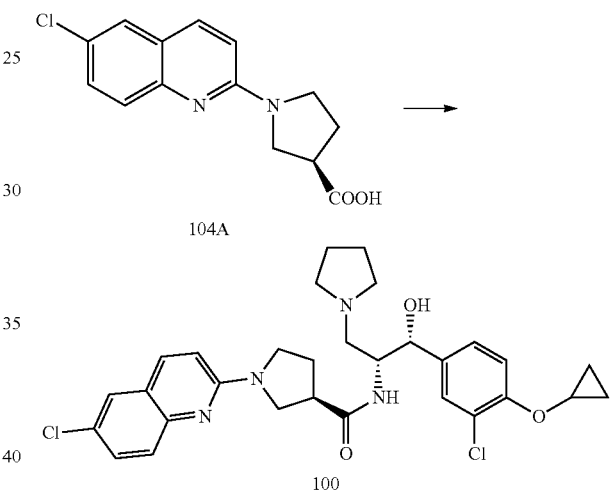

Compound 100 was synthesized, by employing the procedure described for Compound 1 using Compound 104A and Intermediate E in lieu of Compound 1B and Intermediate A.

Compound 100. LC-MS (ESI) m/z: 569 [M+H]$^+$; $^1$H-NMR (CD$_3$OD, 400 MHz) δ (ppm) 0.58-0.76 (m, 4H), 2.04-2.40 (m, 6H), 3.19-3.26 (m, 4H), 3.47-3.50 (m, 1H), 3.60-3.70 (m, 2H), 3.72-3.85 (m, 3H), 3.85-3.89 (m, 2H), 4.55-4.59 (m, 1H), 4.89 (m, 1H), 6.98-7.11 (m, 1H), 7.27-7.33 (m, 2H), 7.52 (s, 1H), 7.80-7.83 (m, 1H), 7.88-7.90 (m, 1H), 8.01-8.02 (m, 1H), 8.35-8.38 (m, 1H); Chiral-HPLC, solvent: MeOH (0.5% DEA) column: AS-H (4.6*250 mm 5 um), Rt: 4.48 min.

Example 101

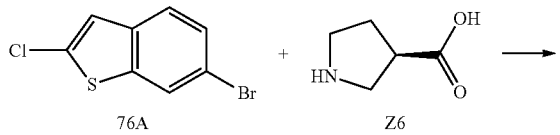

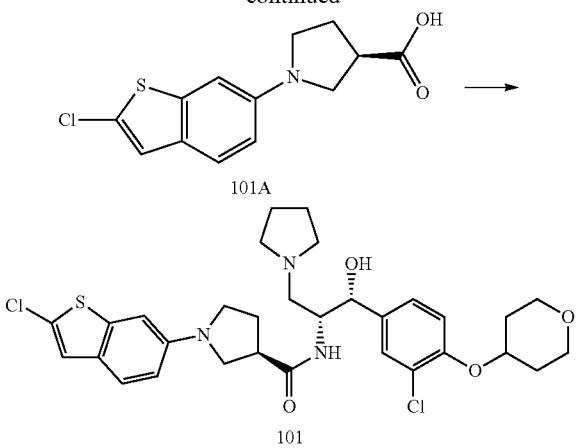

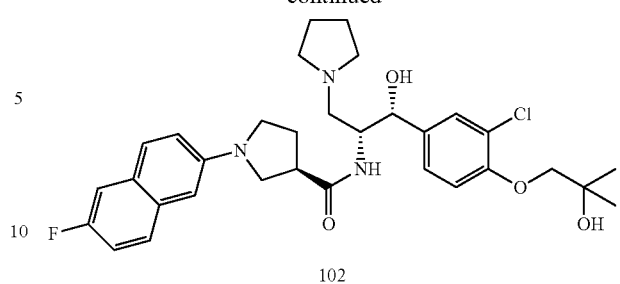

Compounds 101A and 101 were synthesized, by employing the procedures described for Compounds 1B and 1 using Compound 76A, Intermediate Z6, Compound 101A, and Intermediate R in lieu of 1-chloro-4-iodobenzene, Compounds 1A, 1B, and Intermediate A.

Compound 101A. LC-MS (ESI) m/z: 282 [M+H]$^+$; $^1$H-NMR (DMSO-d$_6$, 400 MHz) δ (ppm) 1.94-1.99 (m, 1H), 2.10-2.15 (m, 1H), 2.64-2.67 (m, 1H), 3.16-3.29 (m, 3H), 3.41-3.44 (m, 1H), 6.62-6.65 (dd, J=9.2, 2.4 Hz, 1H), 6.87 (d, J=1.6 Hz, 1H), 7.22 (s, 1H), 7.49-7.51 (d, J=8.8 Hz, 1H).

Compound 101. LC-MS (ESI) m/z: 618 [M+H]$^+$; $^1$H-NMR (CD$_3$OD, 400 MHz) δ (ppm) 1.58-1.76 (m, 2H), 1.87-1.95 (m, 2H), 2.05-2.21 (m, 6H), 2.49 (m, 1H), 2.99 (m, 1H), 3.21-3.32 (m, 4H), 3.32-3.47 (m, 4H), 3.71-3.93 (m, 5H), 4.42-4.54 (m, 3H), 6.62-6.65 (dd, J=9.2, 2.4 Hz, 1H), 6.77 (d, J=2.4 Hz, 1H), 7.07 (s, 1H), 7.09 (s, 1H), 7.34 (dd, J=8.4, 2.4 Hz, 1H), 7.45 (d, J=2.0 Hz, 1H), 7.50 (d, J=8.8 Hz, 1H).

Example 102

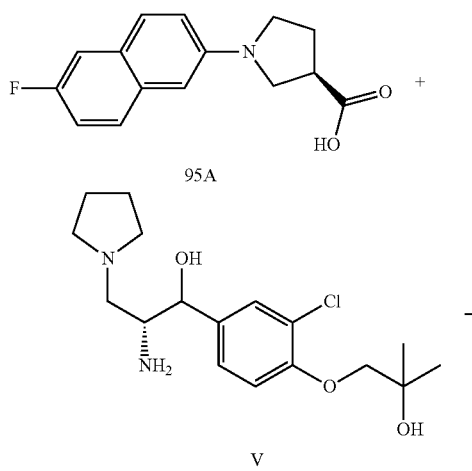

Compound 102 was synthesized, by employing the procedure described for Compound 1 using Compound 95A and Intermediate V in lieu of Compound 1B and Intermediate A. LC-MS (ESI) m/z: 584 [M+H]$^+$; $^1$H-NMR (CD$_3$OD, 400 MHz) δ (ppm) 1.22 (s, 3H), 1.25 (s, 3H), 2.00-2.03 (m, 2H), 2.12-2.25 (m, 4H), 2.76-2.80 (m, 1H), 3.14-3.24 (m, 3H), 3.32-3.49 (m, 4H), 3.57-3.79 (m, 5H), 4.50-4.53 (m, 1H), 4.88 (s, 1H), 6.78 (d, J=1.6 Hz, 1H), 6.95 (d, J=8.8 Hz, 1H), 7.01 (d, J=9.2 Hz, 1H), 7.10-7.15 (m, 1H), 7.25-7.31 (m, 2H), 7.53 (d, J=2.0 Hz, 1H), 7.64-7.69 (m, 1H).

Example 103

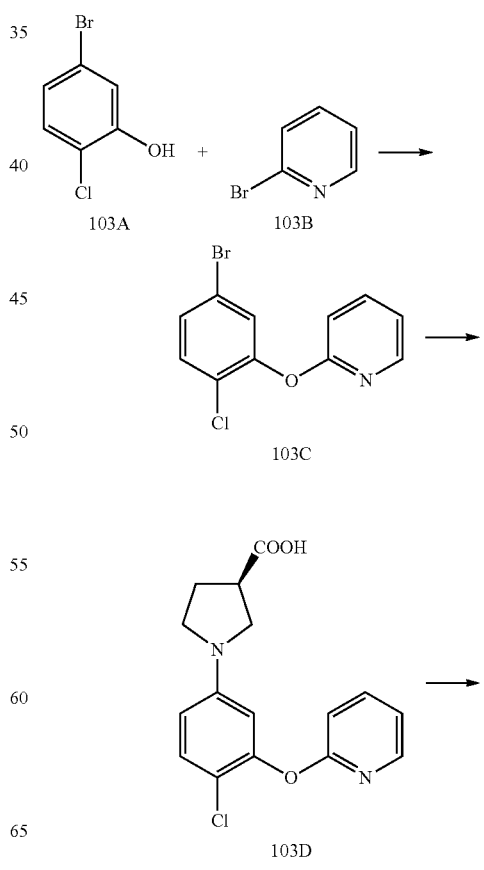

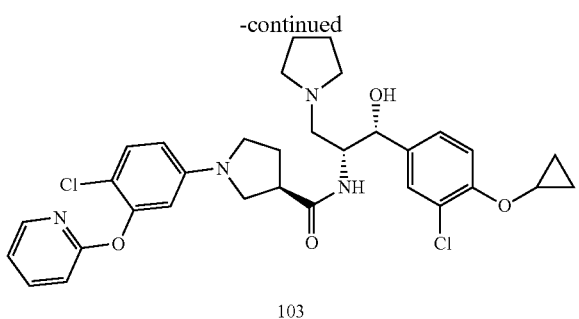

103

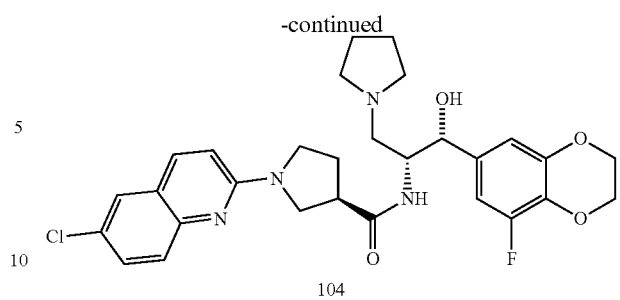

104

A mixture of Compound 103A (4.5 g, 21.8 mmol), Compound 103B (3.43 g, 21.8 mmol), and $K_2CO_3$ (7.5 g, 54.4 mmol) in DMF (18 mL) was stirred at 150° C. for 18 h. The reaction mixture was treated with water and extracted with ethyl acetate (150 mL×3). The extracts were washed with water (50 mL), dried over sodium sulfate, concentrated, and purified with flash column chromatography on silica gel (ethyl acetate in petroleum ether, from 5% to 20% v/v) to furnish Compound 103C. LC-MS (ESI) m/z: 283.0 [M+H]$^+$; $^1$H-NMR (CDCl$_3$, 400 MHz) δ (ppm) 6.90-6.97 (m, 2H), 7.08-7.10 (m, 1H), 7.18-7.30 (m, 2H), 7.64-7.68 (m, 1H), 8.07-8.08 (m, 1H).

Compounds 103D and 103 were synthesized, by employing the procedures described for Compounds 1B and 1 using Compound 103C, Intermediate Z6, Compound 103D, and Intermediate E in lieu of 1-chloro-4-iodobenzene, Compound 1A, 1B, and Intermediate A.

Compound 103D. LC-MS (ESI) m/z: 319.1 [M+H]$^+$.

Compound 103. LC-MS (ESI) m/z: 611.2 [M+H]$^+$; $^1$H-NMR (CD$_3$OD, 400 MHz) δ (ppm) 0.57-0.76 (m, 4H), 2.04-2.20 (m, 6H), 2.56-2.60 (m, 1H), 3.11-3.30 (m, 6H), 3.50-3.51 (m, 1H), 3.58-3.73 (m, 4H), 4.50-4.55 (m, 1H), 6.36-6.41 (m, 2H), 6.89 (d, J=8.4 Hz, 1H), 7.09-7.12 (m, 1H), 7.25-7.28 (m, 3H), 7.48 (s, 1H), 7.82-7.83 (m, 1H), 8.08-8.11 (m, 2H).

Example 104

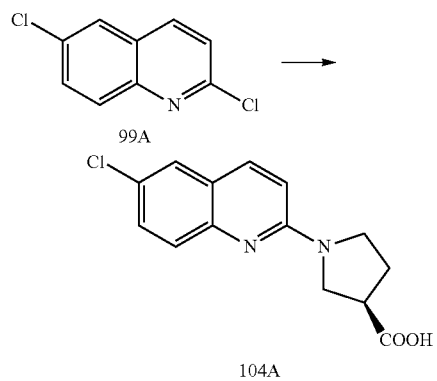

Compounds 104A and 104 were synthesized, by employing the procedures described for Compounds 1B and 1 using Compound 99A, Intermediate Z6, Compound 104A, and Intermediate C in lieu of 1-chloro-4-iodobenzene, Compounds 1A, 1B, and Intermediate A.

Compound 104A. LC-MS m/z: 275 [M-]$^+$; $^1$H-NMR (DMSO-d$_6$, 400 MHz) δ (ppm) 1.97-2.13 (m, 2H), 2.68-2.71 (m, 1H), 3.42-3.54 (m, 4H), 3.65-3.67 (m, 1H), 6.85-6.88 (m, 1H), 7.42-7.44 (m, 1H), 7.48-7.50 (m, 1H), 7.73 (m, 1H), 7.91-7.93 (m, 1H).

Compound 104. LC-MS (ESI) m/z: 555 [M+H]$^+$; $^1$H-NMR (CD$_3$OD, 400 MHz) δ (ppm) 2.02-2.17 (m, 4H), 2.32-2.39 (m, 2H), 3.14-3.30 (m, 2H), 3.31-3.36 (m, 2H), 3.43-3.47 (m, 1H), 3.58-3.64 (m, 1H), 3.70-3.76 (m, 3H), 3.88-3.97 (m, 2H), 4.13-4.30 (m, 4H), 4.48-4.50 (m, 1H), 4.51 (s, 1H), 6.75 (s, 1H), 6.83-6.85 (m, 1H), 7.09-7.18 (m, 1H), 7.80-7.83 (m, 1H), 7.90-7.92 (m, 1H), 8.00 (s, 1H), 8.37-8.39 (m, 1H). Chiral-HPLC condition, solvent: MeOH (0.5% DEA) column: AS-H (4.6*250 mm 5 um), Rt: 6.15 min.

Example 105

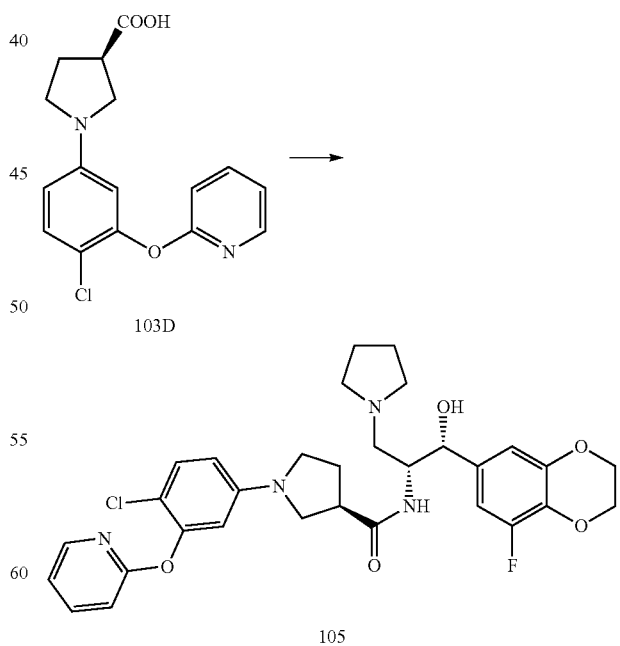

105

Compound 105 was synthesized, by employing the procedure described for Compound 1 using Compound 103D and Intermediate C in lieu of Compound 1B and Intermediate A. LC-MS (ESI) m/z: 597.2 [M+H]+; 1H-NMR (CD3OD, 400 MHz) δ (ppm) 2.03-2.20 (m, 6H), 2.60-2.67 (m, 1H), 3.14-3.32 (m, 4H), 3.34-3.48 (m, 3H), 3.57-3.81 (m, 3H), 4.11-4.20 (m, 4H), 4.45-4.52 (m, 1H), 4.81 (d, J=2.0 Hz, 1H), 6.40-6.47 (m, 2H), 6.75-6.79 (m, 2H), 6.90 (d, J=8.4 Hz, 1H), 7.10-7.13 (m, 1H), 7.27 (d, J=8.8 Hz, 1H), 7.82-7.84 (m, 1H), 8.11-8.13 (m, 2H).

Example 106

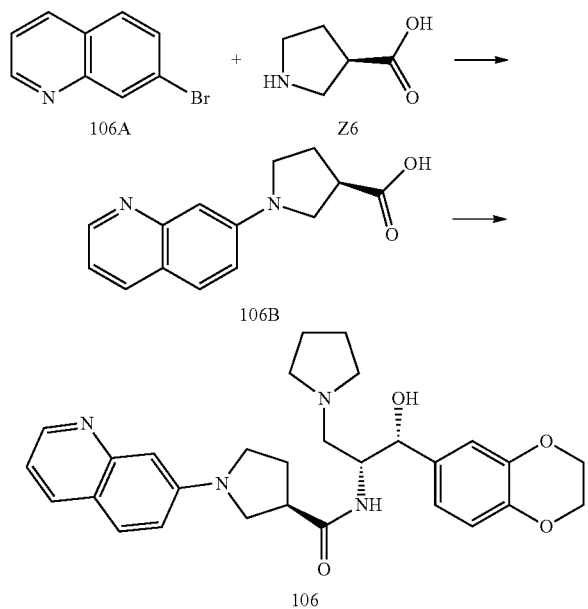

Compounds 106B and 106 were synthesized, by employing the procedures described for Compounds 1B and 1 using Compound 106A, Intermediate Z6, and Compound 106B in lieu of 1-chloro-4-iodobenzene, Compounds 1A, and 1B.

Compound 106B. LC-MS (ESI) m/z: 243 [M+H]+; 1H-NMR (DMSO-d6, 400 MHz) δ (ppm) 2.06-2.12 (m, 1H), 2.18-2.23 (m, 1H), 2.83-2.87 (m, 1H), 3.29-3.59 (m, 4H), 6.75 (d, J=2.0 Hz, 1H), 7.04-7.09 (m, 2H), 7.71 (d, J=8.8 Hz, 1H), 8.04 (d, J=7.2 Hz, 1H), 8.61-8.63 (m, 1H).

Compound 106. LC-MS (ESI) m/z: 503 [M+H]+; 1H-NMR (CD3OD, 400 MHz) δ (ppm) 2.06-2.37 (m, 6H), 3.07-3.29 (m, 4H), 3.43-3.79 (m, 7H), 3.98-4.15 (m, 4H), 4.49-4.53 (m, 1H), 4.83 (d, J=2.8 Hz, 1H), 6.76 (d, J=1.2 Hz, 1H), 6.83 (d, J=8.0 Hz, 1H), 6.90-6.94 (m, 2H), 7.33 (d, J=9.2 Hz, 1H), 7.49 (t, J=7.2 Hz, 1H), 8.06 (d, J=9.2 Hz, 1H), 8.69 (d, J=5.6 Hz, 1H), 8.74 (d, J=8.0 Hz, 1H).

Example 107

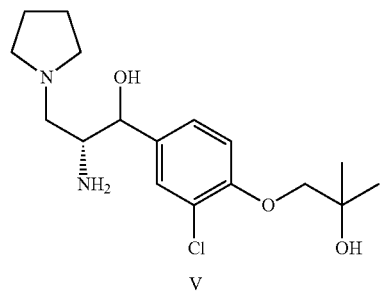

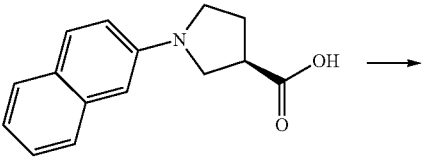

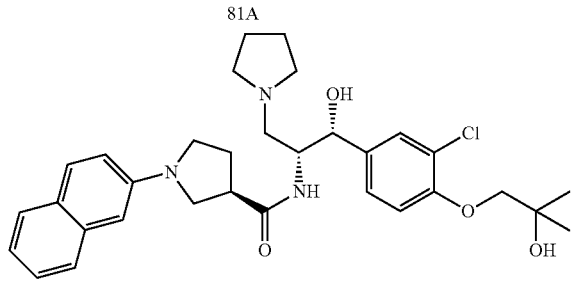

Compound 107 was synthesized, by employing the procedure described for Compound 1 using Compound 81A and Intermediate V in lieu of Compound 1B and Intermediate A. LC-MS (ESI) m/z: 566 [M+H]+; 1H-NMR (CD3OD, 400 MHz) δ (ppm) 1.22 (s, 3H), 1.25 (s, 3H), 2.00-2.05 (m, 2H), 2.10-2.26 (m, 4H), 2.79-2.83 (m, 1H), 3.14-3.25 (m, 3H), 3.32-3.38 (m, 1H), 3.41-3.51 (m, 3H), 3.57-3.62 (m, 1H), 3.66-3.71 (m, 3H), 3.75-3.79 (m, 1H), 4.50-4.55 (m, 1H), 4.87 (s, 1H), 6.94-6.97 (m, 2H), 7.10-7.14 (m, 1H), 7.25-7.31 (m, 2H), 7.52 (d, J=1.6 Hz, 1H), 7.62-7.68 (m, 3H).

Example 108

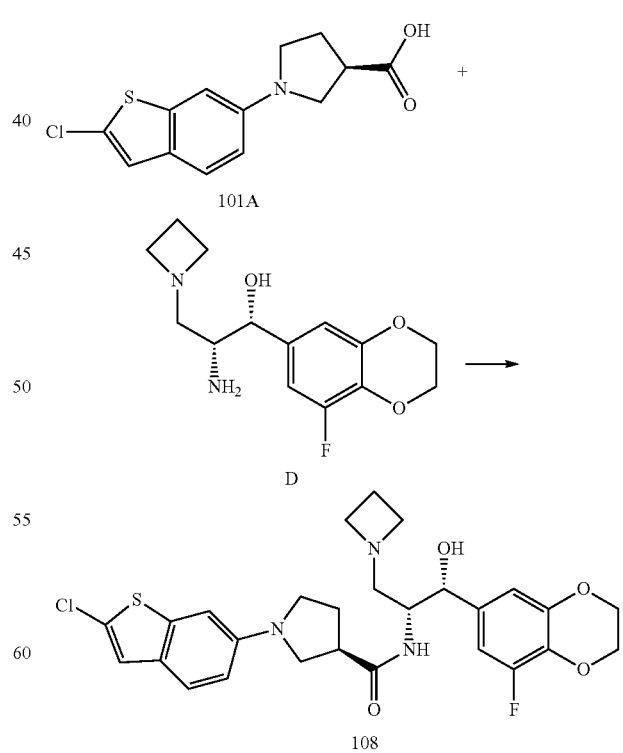

Compound 108 was synthesized, by employing the procedure described for Compound 1 using Compound 101A and Intermediate D in lieu of Compound 1B and Intermediate A. LC-MS (ESI) m/z: 546 [M+H]⁺; ¹H-NMR (CD₃OD, 400 MHz) δ (ppm) 2.10-2.13 (m, 1H), 2.23-2.26 (m, 1H), 2.39-2.47 (m, 1H), 2.60-2.68 (m, 2H), 3.13-3.17 (m, 1H), 3.37-3.50 (m, 3H), 3.55-3.59 (m, 1H), 4.16-4.36 (m, 10H), 4.82 (d, J=2.0 Hz, 1H), 6.68 (d, J=8.2 Hz, 1H), 6.75 (s, 1H), 6.82-6.86 (m, 2H), 7.06 (s, 1H), 7.51 (d, J=8.8 Hz, 1H), 8.00 (d, J=9.6 Hz, 1H).

Example 109

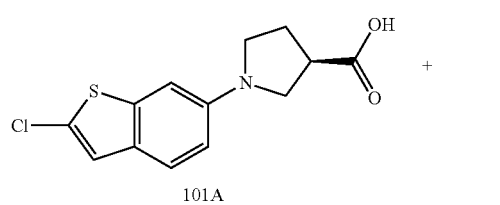

101A

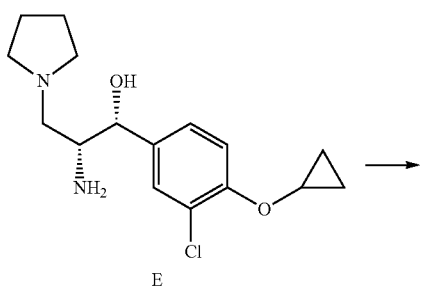

E

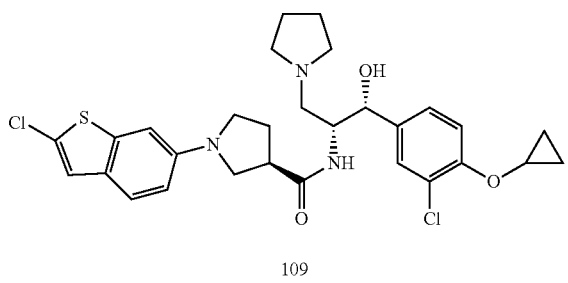

109

Compound 109 was synthesized, by employing the procedure described for Compound 1 using Compound 101A and Intermediate E in lieu of Compound 1B and Intermediate A. LC-MS (ESI) m/z: 546 [M+H]⁺; ¹H-NMR (CD₃OD, 400 MHz) δ (ppm) 0.54-0.55 (m, 1H), 0.68-0.72 (m, 3H), 2.03-2.25 (m, 6H), 2.52-2.56 (m, 1H), 3.11-3.28 (m, 5H), 3.37-3.38 (m, 1H), 3.48-3.52 (m, 1H), 3.60-3.72 (m, 3H), 3.81-3.86 (m, 1H), 4.56-4.61 (m, 1H), 4.94 (d, J=2.4 Hz, 1H), 6.63-6.66 (dd, J=8.8, 1.6 Hz, 1H), 6.79 (s, 1H), 7.06 (s, 1H), 7.26 (s, 2H), 7.50 (d, J=8.4 Hz, 1H), 7.55 (s, 1H), 8.09 (d, J=9.6 Hz, 1H).

Example 110

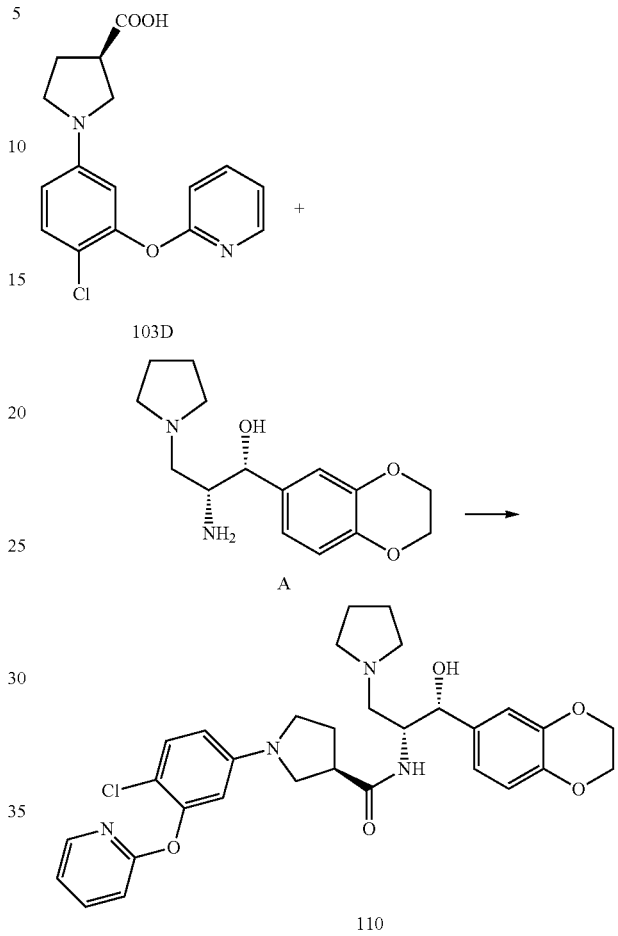

Compound 110 was synthesized, by employing the procedure described for Compound 1 using Compound 103D in lieu of Compound 1B. LC-MS (ESI) m/z: 579.2 [M+H]⁺; ¹H-NMR (CD₃OD, 400 MHz) δ (ppm) 2.03-2.21 (m, 6H), 2.64-2.69 (m, 1H), 3.12-3.26 (m, 4H), 3.31-3.37 (m, 2H), 3.45-3.49 (m, 1H), 3.57-3.82 (m, 3H), 4.05-4.08 (m, 2H), 4.10-4.20 (m, 2H), 4.45-4.53 (m, 1H), 4.82 (d, J=2.4 Hz, 1H), 6.40 (d, J=2.8 Hz, 1H), 6.44-6.48 (m, 1H), 6.74 (d, J=8.4 Hz, 1H), 6.82-6.85 (m, 1H), 6.90 (d, J=8.4 Hz, 1H), 6.93 (d, J=2.0 Hz, 1H), 7.12-7.14 (m, 1H), 7.28 (d, J=8.8 Hz, 1H), 7.83-7.85 (m, 1H), 8.03-8.14 (m, 2H).

Example 111

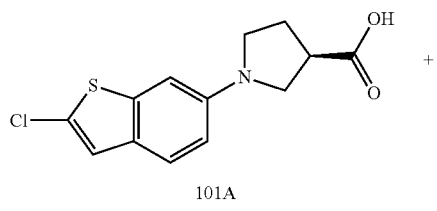

101A

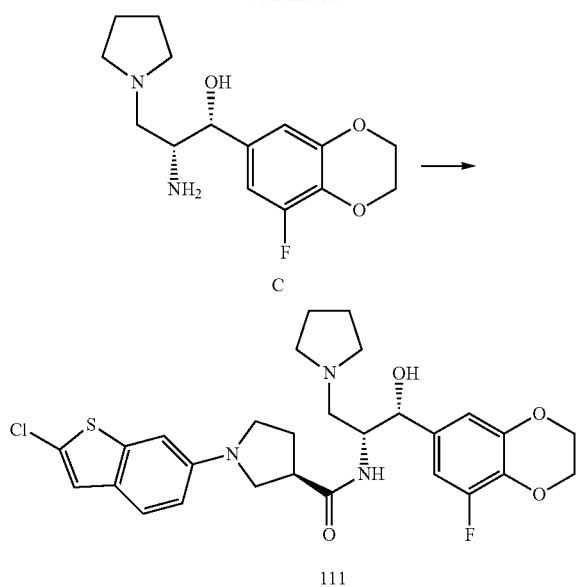

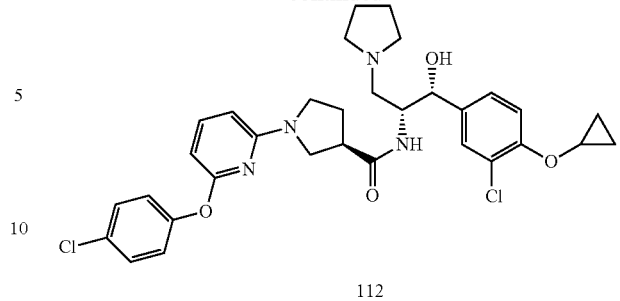

Compound 111 was synthesized, by employing the procedure described for Compound 1 using Compound 101A and Intermediate C in lieu of Compound 1B and Intermediate A. LC-MS (ESI) m/z: 560 [M+H]$^+$; $^1$H-NMR (CD$_3$OD, 400 MHz) δ (ppm) 2.02-2.28 (m, 6H), 2.63-2.67 (m, 1H), 3.14-3.27 (m, 3H), 3.39-3.81 (m, 6H), 4.16-7.27 (m, 4H), 4.49-4.52 (m, 1H), 4.85 (d, J=2.0 Hz, 1H), 6.69 (dd, J=8.8, 2.4 Hz, 1H), 6.77 (s, 1H), 6.82-6.87 (m, 2H), 7.52 (d, J=8.8 Hz, 1H), 8.07 (d, J=9.6 Hz, 1H).

Example 112

Compound 112C was synthesized, by employing the procedure described for Compound 103C using Compound 112A and 112B at 120° C. in lieu of Compound 103A and 103B at 150° C. LC-MS (ESI) m/z: 240 [M+H]$^+$.

Compounds 112D and 112 were synthesized, by employing the procedures described for Compounds 1B and 1 using Compound 112C, Intermediate Z6, Compound 112D, and Intermediate E in lieu of 1-chloro-4-iodobenzene, Compounds 1A, 1B, and Intermediate A.

Compound 112D. LC-MS (ESI) m/z: 319 [M+H]$^+$; $^1$H-NMR (CD$_3$OD, 400 MHz) δ (ppm) 1.91-2.08 (m, 1H), 2.18-2.21 (m, 2H), 3.08-3.12 (m, 1H), 3.51-3.57 (m, 3H), 6.00-6.02 (m, 1H), 6.13-6.15 (m, 1H), 7.08-7.11 (m, 2H), 7.34-7.36 (m, 2H), 7.46-7.49 (m, 1H).

Compound 112. LC-MS (ESI) m/z: 611 [M+H]$^+$; $^1$H-NMR (CD$_3$OD, 400 MHz) δ (ppm) 0.65-0.77 (m, 4H), 2.04-2.17 (m, 6H), 2.82-2.86 (m, 1H), 3.08-3.26 (m, 4H), 3.46-3.51 (m, 3H), 3.57-3.75 (m, 4H), 4.50-4.53 (m, 1H), 4.88 (d, J=2.4 Hz, 1H), 6.04-6.12 (m, 2H), 7.12-7.14 (m, 1H), 7.24-7.26 (m, 2H), 7.37-7.39 (m, 2H), 7.45 (s, 1H), 7.52-7.54 (m, 1H).

Example 113

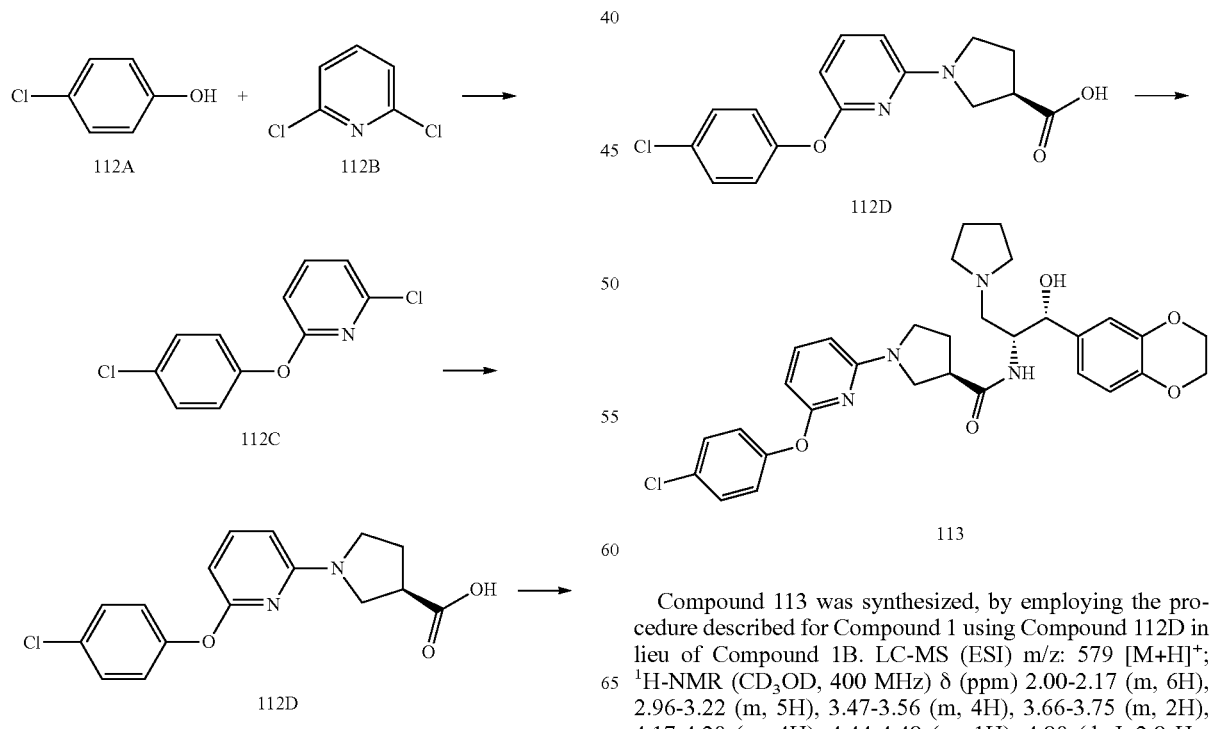

Compound 113 was synthesized, by employing the procedure described for Compound 1 using Compound 112D in lieu of Compound 1B. LC-MS (ESI) m/z: 579 [M+H]$^+$; $^1$H-NMR (CD$_3$OD, 400 MHz) δ (ppm) 2.00-2.17 (m, 6H), 2.96-3.22 (m, 5H), 3.47-3.56 (m, 4H), 3.66-3.75 (m, 2H), 4.17-4.20 (m, 4H), 4.44-4.48 (m, 1H), 4.80 (d, J=2.8 Hz, 1H), 6.03-6.05 (m, 1H), 6.16-6.18 (m, 1H), 6.73-6.91 (m, 3H), 7.13-7.15 (m, 2H), 7.38-7.40 (m, 2H), 7.54-7.58 (m, 1H).

Example 114

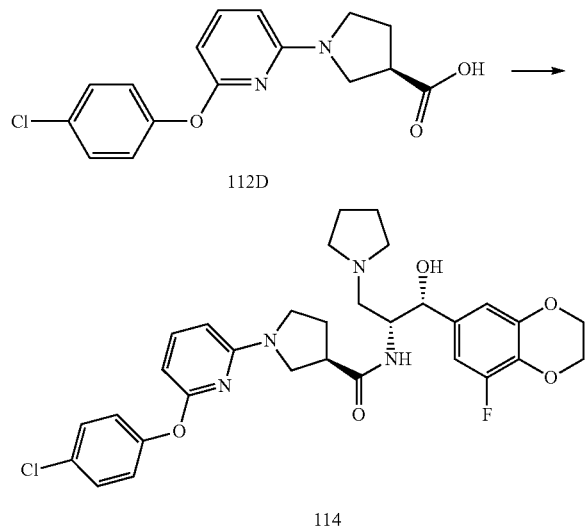

Compound 114 was synthesized, by employing the procedure described for Compound 1 using Compound 112D and Intermediate C in lieu of Compound 1B and Intermediate A. LC-MS (ESI) m/z: 597 [M+H]$^+$; $^1$H-NMR (CD$_3$OD, 400 MHz) δ (ppm) 2.02-2.18 (m, 6H), 2.87-3.23 (m, 5H), 3.45-3.76 (m, 6H), 4.22-4.26 (m, 4H), 4.44-4.49 (m, 1H), 4.80 (d, J=2.4 Hz, 1H), 6.03-6.05 (m, 1H), 6.13-6.15 (m, 1H), 6.75-6.79 (m, 2H), 7.11-7.13 (m, 2H), 7.36-7.39 (m, 2H), 7.50-7.56 (m, 1H).

Example 115

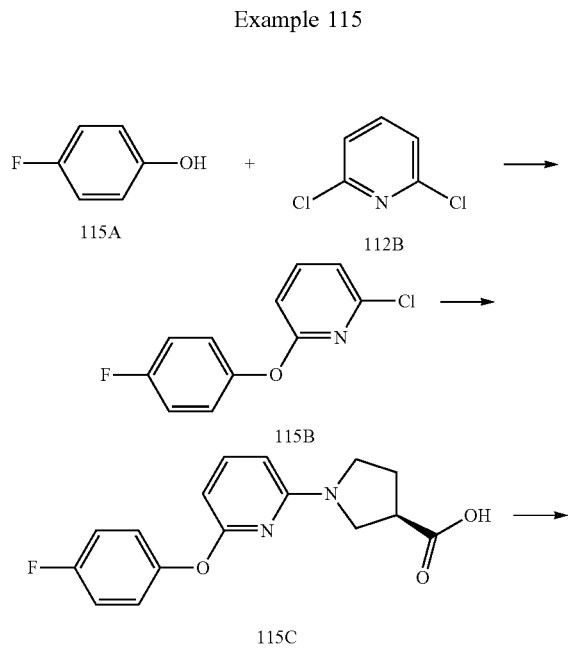

-continued

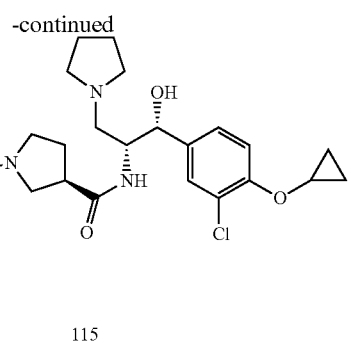

Compound 115B was synthesized, by employing the procedure described for Compound 103C using Compound 115A at 120° C. in lieu of Compound 103A at 150° C. LC-MS (ESI) m/z: 224 [M+H]$^+$; $^1$H-NMR (CD$_3$OD, 400 MHz): δ (ppm) 6.76-6.78 (m, 1H), 7.01-7.05 (m, 5H), 7.65-7.67 (m, 1H).

Compounds 115C and 115 were synthesized, by employing the procedures described for Compounds 1B and 1 using Compound 115B, Intermediate Z6, Compound 115C, and Intermediate E in lieu of 1-chloro-4-iodobenzene, Compounds 1A, 1B, and Intermediate A.

Compound 115C. LC-MS (ESI) m/z: 303 [M+H]$^+$; $^1$H-NMR (CD$_3$OD, 400 MHz): δ (ppm) 1.85-2.16 (m, 3H), 2.90-2.97 (m, 1H), 3.42-3.52 (m, 3H), 5.89-5.91 (m, 1H), 6.06-6.08 (m, 1H), 7.02-7.06 (m, 4H), 7.38-7.40 (m, 1H).

Compound 115. LC-MS (ESI) m/z: 595 [M+H]$^+$; $^1$H-NMR (CD$_3$OD, 400 MHz): δ (ppm) 0.62-0.78 (m, 4H), 2.00-2.20 (m, 6H), 2.80-2.84 (m, 1H), 3.06-3.28 (m, 4H), 3.43-3.50 (m, 3H), 3.68-3.78 (m, 4H), 4.49-4.55 (m, 1H), 4.88 (d, J=2.8 Hz, 1H), 5.98-5.60 (m, 2H), 6.08-6.10 (m, 1H), 7.13-7.15 (m, 4H), 7.26-7.27 (m, 2H), 7.45-7.52 (m, 2H).

Example 116

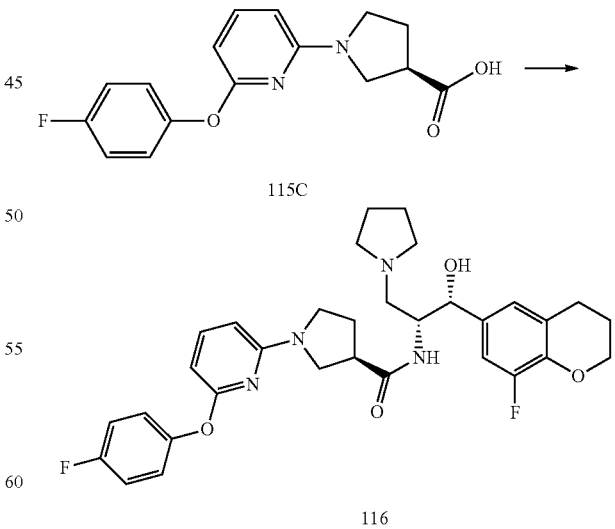

Compound 116 was synthesized, by employing the procedure described for Compound 1 using Compound 115C and Intermediate C in lieu of Compound 1B and Intermediate A. LC-MS (ESI) m/z: 581 [M+H]$^+$; $^1$H-NMR (CD₃OD, 400 MHz): δ (ppm) 2.02-2.19 (m, 6H), 2.94-2.98 (m, 1H), 3.13-3.23 (m, 3H), 3.36-3.76 (m, 7H), 4.22-4.26 (m, 4H), 4.47-4.51 (m, 1H), 4.80 (d, J=2.4 Hz, 1H), 5.95-5.97 (m, 1H), 6.19-6.21 (m, 1H), 6.75-6.81 (m, 2H), 7.15-7.18 (m, 4H), 7.56-7.60 (m, 1H).

Example 117

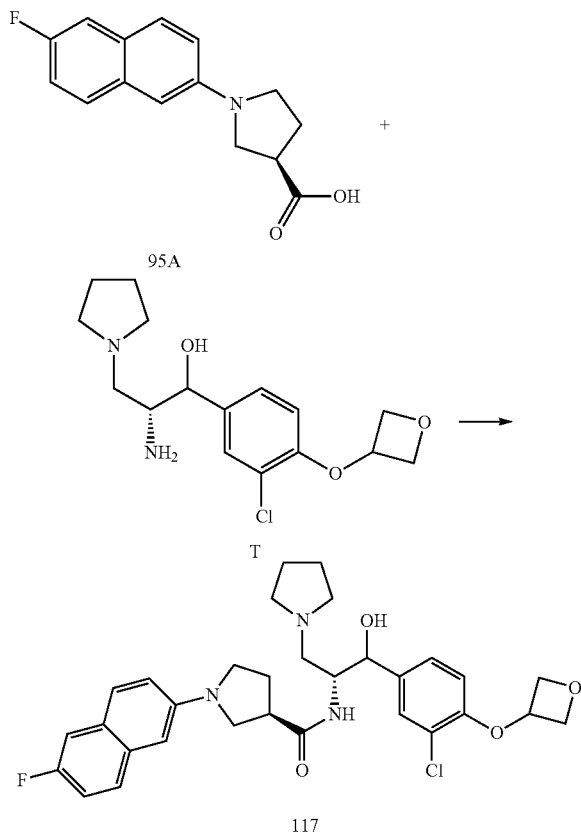

Compound 117 was synthesized, by employing the procedure described for Compound 1 using Compound 95A and Intermediate T in lieu of Compound 1B and Intermediate A. LC-MS (ESI) m/z: 568 [M+H]⁺; ¹H-NMR (CD₃OD, 400 MHz): δ (ppm) 2.04-2.28 (m, 6H), 2.60-2.62 (m, 1H), 3.11-3.25 (m, 3H), 3.34-3.82 (m, 7H), 4.48-4.71 (m, 4H), 4.82-4.86 (m, 1H), 4.94-4.99 (m, 2H), 6.50 (d, J=8.0 Hz, 1H), 7.03 (d, J=8.8 Hz, 1H), 7.16-7.38 (m, 4H), 7.63-7.82 (m, 3H).

Example 118

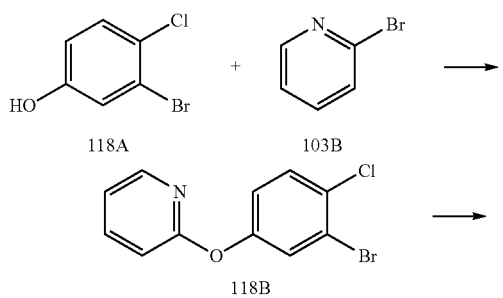

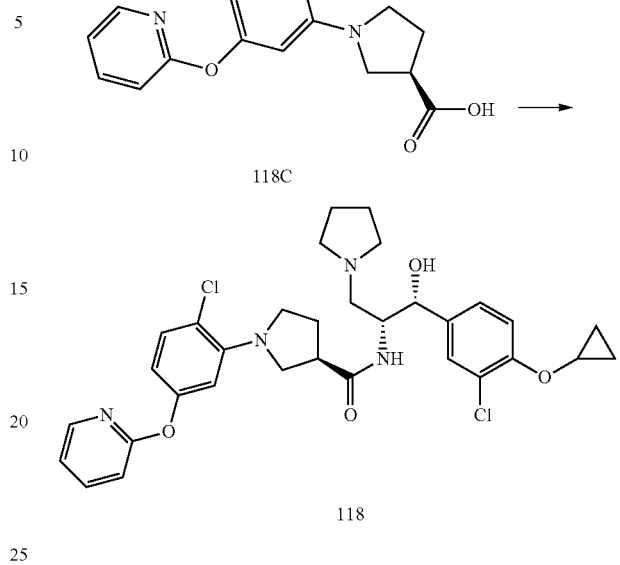

Compound 118B was synthesized, by employing the procedure described for Compound 103C using Compound 118A in lieu of Compound 103A. LC-MS (ESI) m/z: 284 [M+H]⁺; ¹H-NMR (CDCl₃, 400 MHz): δ (ppm) 6.88 (d, J=8.4 Hz, 1H), 6.96-7.01 (m, 2H), 7.36-7.40 (m, 2H), 7.63-7.67 (m, 1H), 8.11 (d, J=4.8 Hz, 1H).

Compounds 118C and 118 were synthesized, by employing the procedures described for Compounds 1B and 1 using Compound 118B, Intermediate Z6, Compound 118C, and Intermediate E in lieu of 1-chloro-4-iodobenzene, Compounds 1A, 1B, and Intermediate A.

Compound 118C. LC-MS (ESI) m/z: 319 [M+H]⁺; ¹H-NMR (CDCl₃, 400 MHz): δ (ppm) 1.94-2.09 (m, 2H), 2.71-2.79 (m, 1H), 3.25-3.32 (m, 2H), 3.42-3.47 (m, 1H), 3.57-3.61 (m, 1H), 6.46-6.49 (m, 1H), 6.56 (d, J=2.4 Hz, 1H), 6.99-7.01 (m, 1H), 7.11-7.14 (m, 1H), 7.26 (d, J=8.4 Hz, 1H) 7.82-7.86 (m, 1H), 8.15-8.16 (m, 1H).

Compound 118. LC-MS (ESI) m/z: 611 [M+H]⁺; ¹H-NMR (DMSO-d₆, 400 MHz): δ (ppm) 0.58-0.61 (m, 2H), 0.72-0.76 (m, 2H), 1.83-2.03 (m, 7H), 2.81-2.85 (m, 1H), 3.01-3.30 (m, 5H), 3.35-3.46 (m, 3H), 3.49-3.56 (m, 2H), 3.77-3.82 (m, 1H), 4.32-4.38 (m, 1H), 4.76 (d, J=2.0 Hz, 1H), 6.56-6.62 (m, 2H), 7.01 (d, J=8.4 Hz, 1H), 7.12-7.15 (m, 1H), 7.22-7.36 (m, 4H), 7.84-7.88 (m, 1H), 7.96-7.98 (m, 1H), 8.15-8.17 (m, 1H), 9.29 (m, 1H).

Example 119

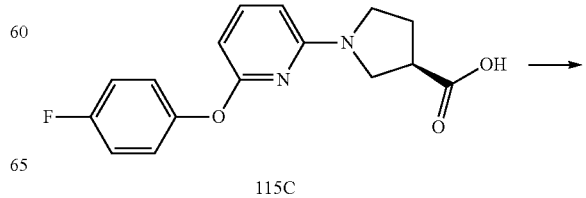

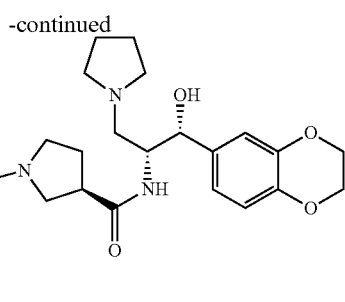

119

Compound 119 was synthesized, by employing the procedure described for Compound 1 using Compound 115C in lieu of Compound 1B. LC-MS (ESI) m/z: 563 [M+H]$^+$; $^1$H-NMR (CD$_3$OD, 400 MHz): δ (ppm) 2.01-2.20 (m, 6H), 2.96-3.00 (m, 1H), 3.11-3.21 (m, 3H), 3.33-3.76 (m, 7H), 4.18-4.25 (m, 4H), 4.45-4.48 (m, 1H), 4.81 (d, J=2.4 Hz, 1H), 5.97-5.99 (m, 1H), 6.17-6.20 (m, 1H), 6.74-6.91 (m, 3H), 7.15-7.17 (m, 4H), 7.55-7.59 (m, 1H).

Example 120

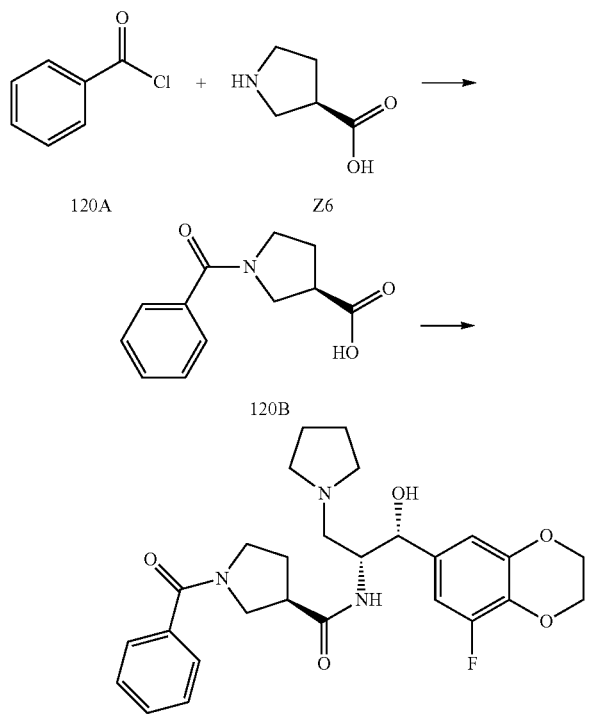

To a mixture of Intermediate Z6 (1.00 g, 8.70 mmol) and sodium bicarbonate (1.46 g, 17.39 mmol) in dioxane (10 mL) and water (1 mL) was added benzoyl chloride 120A (1.22 g, 8.70 mmol) at room temperature. The mixture was stirred at room temperature for 1 h, and adjusted to pH 1 with aqueous HCl solution (6 N, 1 mL). The mixture was diluted with ice water (50 mL) to form a solid, filtered, and dried to afford Compound 120B. LC-MS (ESI) m/z: 220 [M+H]$^+$; $^1$H-NMR (DMSO-d$_6$, 400 MHz): δ (ppm) 1.94-2.20 (m, 2H), 3.03-3.16 (m, 1H), 3.44-3.70 (m, 4H), 7.43-7.52 (m, 5H), 12.59 (s, 1H).

Compound 120 was synthesized, by employing the procedure described for Compound 1 using Compound 120B and Intermediate C in lieu of Compound 1B and Intermediate A. LC-MS (ESI) m/z: 498 [M+H]$^+$; $^1$H-NMR (CD$_3$OD, 400 MHz): δ (ppm) 1.81 (s, 4H), 2.00-2.17 (m, 2H), 2.60-2.77 (m, 6H), 2.96-3.10 (m, 1H), 3.34-3.77 (m, 4H), 4.04-4.33 (m, 5H), 4.69-4.78 (m, 1H), 6.58-6.74 (m, 2H), 7.44-7.52 (m, 5H).

Example 121

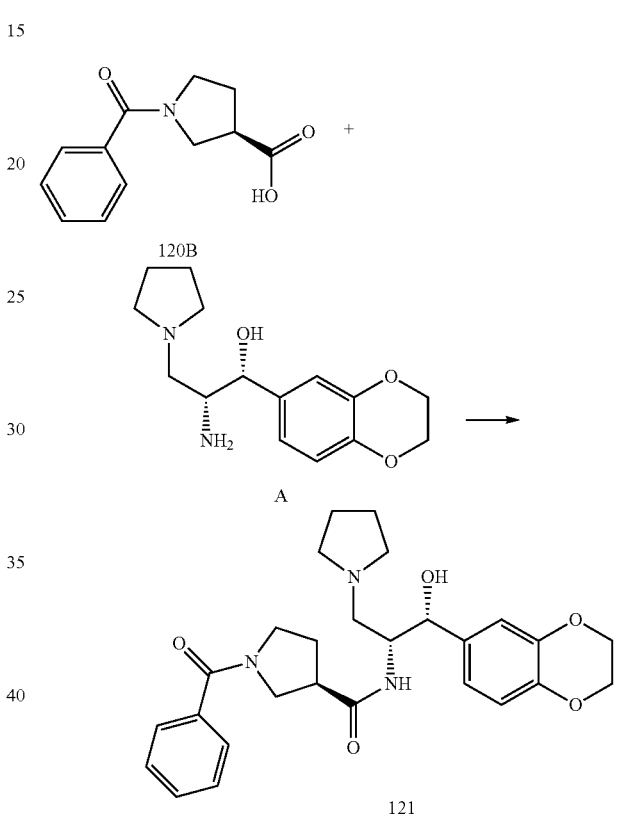

Compound 121 was synthesized, by employing the procedure described for Compound 1 using Compound 120B in lieu of Compound 1B. LC-MS (ESI) m/z: 480 [M+H]$^+$; $^1$H-NMR (CD$_3$OD, 400 MHz): δ (ppm) 1.84 (s, 4H), 2.00-2.17 (m, 2H), 2.63-2.82 (m, 6H), 2.96-3.13 (m, 1H), 3.34-3.79 (m, 4H), 4.00-4.32 (m, 5H), 4.69-4.79 (m, 1H), 6.56-6.90 (m, 3H), 7.43-7.52 (m, 5H).

Example 122

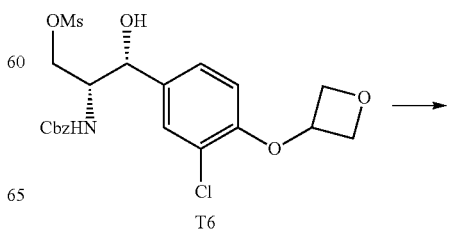

T6

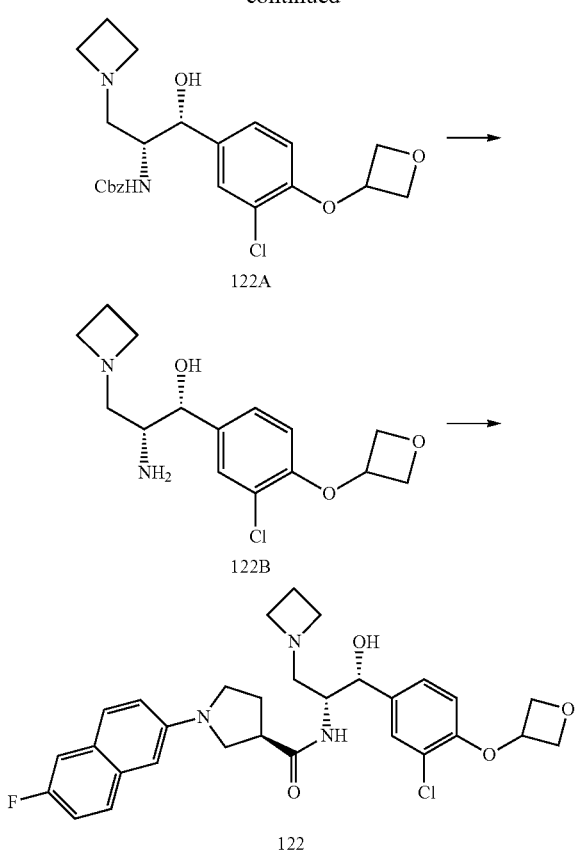

122A

122B

122

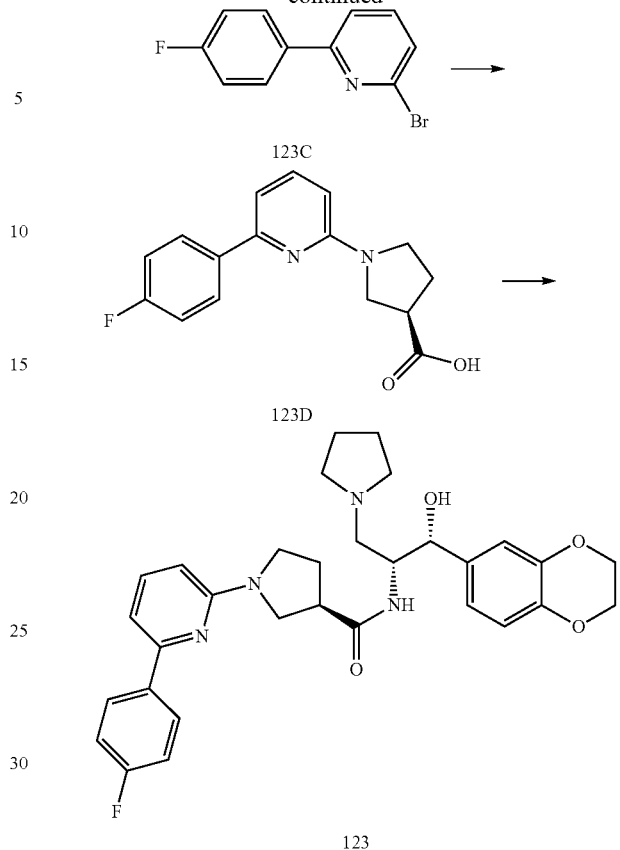

123C

123D

123

Compound 122A was synthesized, by employing the procedure described for Intermediate A9 using azetidine and Intermediate T6 in lieu of pyrrolidine and Intermediate A8. LC-MS (ESI) m/z: 447 [M+H]⁺.

Compound 122B was synthesized, by employing the procedure described for Intermediate E using Intermediate Compound 122A in lieu of Intermediate E7. LC-MS (ESI) m/z: 313 [M+H]⁺; $^1$H NMR (CD$_3$OD, 400 MHz): δ (ppm) 2.21-2.59 (m, 2H), 2.45-2.65 (m, 2H), 3.11-3.20 (m, 3H), 3.96-4.03 (m, 2H), 4.69-4.71 (m, 2H), 4.97 (m, 2H), 5.12-5.13 (m, 2H), 6.41-6.43 (m, 1H), 7.14-7.29 (m, 2H).

Compound 122 was synthesized, by employing the procedure described for Compound 1 using Compounds 122B and 95A in lieu of Intermediate A and Compound 1B. LC-MS (ESI) m/z: 554 [M+H]⁺; $^1$H-NMR (CD$_3$OD, 400 MHz): δ (ppm) 2.13-2.14 (m, 1H), 2.29-2.63 (m, 4H), 3.15-3.21 (m, 1H), 3.41-3.60 (m, 6H), 4.18-4.84 (m, 9H), 4.95-4.98 (m, 1H), 6.50 (d, J=8.8 Hz, 1H), 7.02-7.06 (m, 1H), 7.20-7.83 (m, 7H).

Example 123

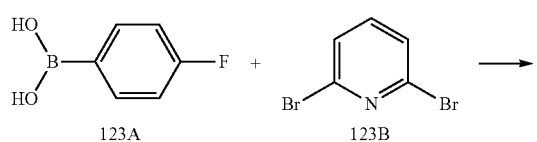

123A  123B

A mixture of 4-fluorophenylboronic acid (123A, 3 g, 21.4 mmol), 2,6-dibromopyridine (123B, 3 g, 21.4 mmol), Pd(PPh$_3$)$_4$ (247 mg, 2.14 mmol), and Na$_2$CO$_3$ (6.8 g, 64.2 mmol) in toluene (96 mL), ethanol (48 mL) and water (96 mL) was stirred at 50° C. for 18 hours. The reaction mixture was treated with water (50 mL) and extracted with ethyl acetate (150 mL×3). The extraction was washed with water (50 mL), dried over anhydrous sodium sulfate, concentrated, and purified with flash column chromatography on silica gel (ethyl acetate in petroleum ether, from 1% to 5% v/v) to furnish Compound 123C. LC-MS (ESI) m/z: 252 [M+H]⁺;

Compounds 123D and 123 were synthesized, by employing the procedures described for Compound 1B and 1 using Compound 123C, Intermediate Z6, and Compound 123D in lieu of 1-chloro-4-iodobenzene, Compound 1A, and 1B.

Compound 123D. LC-MS (ESI) m/z: 287 [M+H]⁺; $^1$H-NMR (CDCl$_3$, 400 MHz): δ (ppm) 2.31-2.38 (m, 2H), 3.23-3.29 (m, 1H), 3.56-3.61 (m, 1H), 3.68-3.75 (m, 1H), 3.82-3.89 (m, 2H), 6.32 (d, 1H), 7.00 (d, 1H), 7.08-7.12 (m, 2H), 7.50-7.53 (m, 1H), 7.99-8.03 (m, 2H).

Compound 123. LC-MS (ESI) m/z: 547 [M+H]⁺; $^1$H-NMR (CD$_3$OD, 400 MHz): δ (ppm) 1.82-1.84 (m, 4H), 2.16-2.21 (m, 2H), 2.63-2.78 (m, 6H), 3.11-3.28 (m, 2H), 3.45-3.48 (m, 1H), 3.66-3.76 (m, 2H), 4.16-4.27 (m, 5H), 4.80 (d, J=3.2 Hz, 1H), 6.40 (d, J=8 Hz, 1H), 6.77-7.88 (m, 3H), 7.06 (d, J=7.2 Hz, 1H), 7.14-7.18 (m, 2H), 7.54-7.58 (m, 1H), 8.06-8.10 (m, 2H).

Example 124

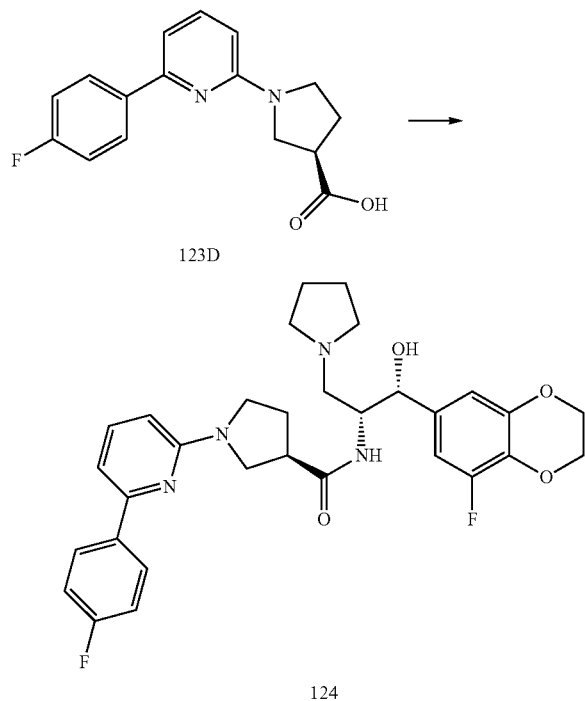

Compound 124 was synthesized, by employing the procedure described for Compound 1 using Compound 123D and Intermediate C in lieu of Compound 1B and Intermediate A. LC-MS (ESI) m/z: 565 [M+H]$^+$; $^1$H-NMR (CD$_3$OD, 400 MHz): δ (ppm) 1.82-1.84 (m, 4H), 2.16-2.20 (m, 2H), 2.63-2.79 (m, 6H), 3.13-3.22 (m, 2H), 3.46-3.48 (m, 1H), 3.66-3.76 (m, 2H), 4.20-4.26 (m, 5H), 4.80 (d, J=2.4 Hz, 1H), 6.39 (d, J=8 Hz, 1H), 6.71-6.79 (m, 2H), 7.05 (d, J=7.2 Hz, 1H), 7.13-7.18 (m, 2H), 7.54-7.58 (m, 1H), 8.06-8.10 (m, 2H).

Example 125

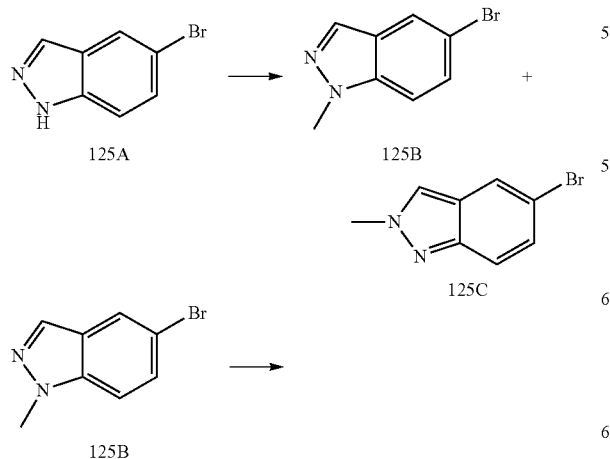

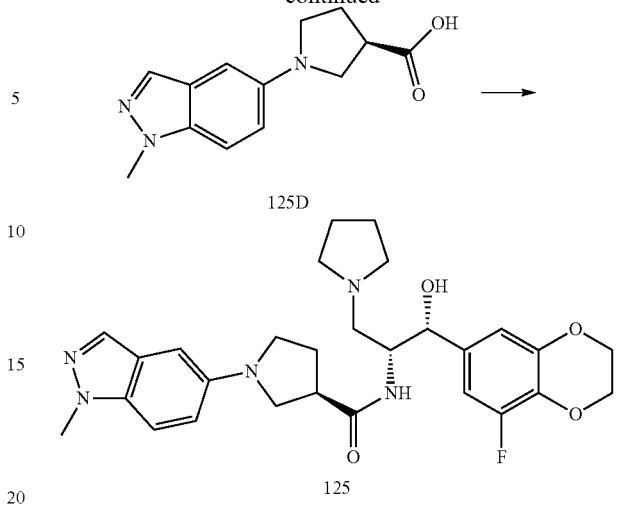

To a solution of Compound 125A (4.92 g, 25.0 mmol) in THF (300 mL) was added NaH (1.10 g, 27.5 mmol) at 0° C. The reaction solution was stirred at this temperature for 1 h before methyl iodide (5.32 g, 37.5 mmol) was added at 0° C. The reaction was allowed to warm to room temperature slowly, stirred for 2 h, and quenched with water and concentrated in vacuo. The residue was diluted with water and extracted with dichloromethane (80 mL×2). The organic layers were combined, dried over anhydrous sodium sulfate, and concentrated. The crude product was purified with flash column chromatography on silica gel (ethyl acetate in petroleum ether, 10% v/v) to give Compound 125B and Compound 125C. For Compound 125B: LC-MS (ESI) m/z: 211 [M+H]$^+$; $^1$H-NMR (CDCl$_3$, 400 MHz): δ (ppm) 4.06 (s, 3H), 7.26-7.28 (m, 1H), 7.44-7.48 (m, 1H), 7.86-7.87 (m, 1H), 7.91 (s, 1H). For Compound 125C: LC-MS (ESI) m/z: 211 [M+H]$^+$; $^1$H-NMR (CDCl$_3$, 400 MHz) δ (ppm) 4.20 (s, 3H), 7.31-7.34 (m, 1H), 7.56-7.58 (m, 1H), 7.79-7.80 (m, 1H), 7.84 (s, 1H).

Compounds 125D and 125 were synthesized, by employing the procedures described for Compounds 1B and 1 using Compound 125B, Intermediate Z6, Compound 125D, and Intermediate C in lieu of 1-chloro-4-iodobenzene, Compound 1A, 1B and Intermediate A.

Compound 125D. LC-MS (ESI) m/z: 246 [M+H]$^+$.

Compound 125. LC-MS (m/z) 524 [M+H]$^+$; $^1$H-NMR (CDCl$_3$, 400 MHz): δ (ppm) 2.10 (s, 4H), 2.44 (s, 2H), 3.01-3.02 (m, 2H), 3.17-3.21 (m, 1H), 3.41-3.46 (m, 2H), 3.75-3.83 (m, 7H), 4.02-4.03 (m, 3H), 4.17 (s, 3H), 4.53-4.54 (m, 1H), 4.84 (s, 1H), 6.69 (s, 2H), 7.46-7.59 (m, 2H), 7.83 (s, 1H), 8.03 (s, 1H), 10.58 (brs, 1H).

Example 126

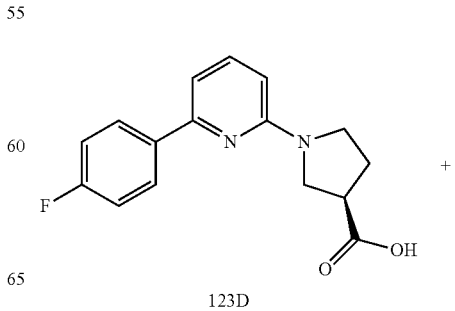

327

-continued

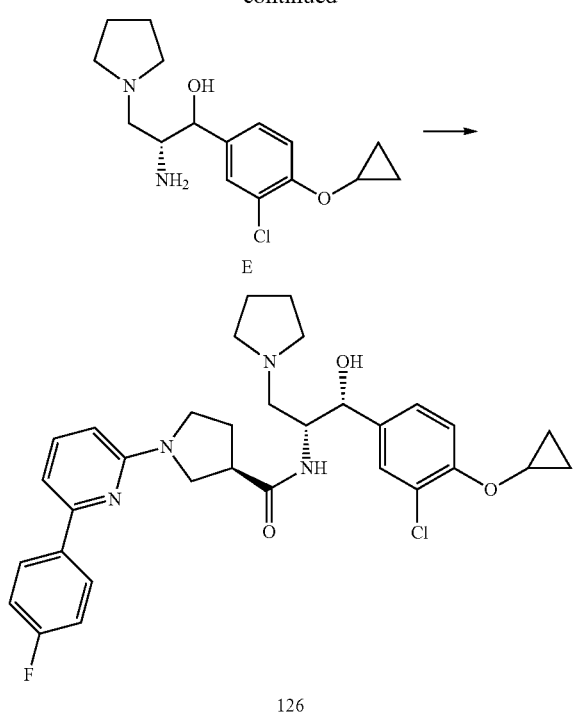

126

Compound 126 was synthesized, by employing the procedure described for Compound 1 using Compound 123D and Intermediate E in lieu of Compound 1B and Intermediate A. LC-MS (ESI) m/z: 579 [M+H]⁺; ¹H-NMR (CD₃OD, 400 MHz): δ (ppm) 0.54-0.58 (m, 4H), 1.74-1.76 (m, 4H), 2.04-2.09 (m, 2H), 2.57-2.74 (m, 6H), 3.00-3.12 (m, 2H), 3.34-3.36 (m, 1H), 3.53-3.61 (m, 3H), 4.19-4.20 (m, 1H), 4.77 (d, J=2.4 Hz, 1H), 6.26 (d, J=8 Hz, 1H), 6.94 (d, J=7.2 Hz, 1H), 7.03-7.07 (m, 2H), 7.14 (s, 2H), 7.31 (s, 1H), 7.42-7.45 (m, 1H), 7.95-7.99 (m, 2H); Chiral-HPLC condition, solvent: MeOH (0.1% DEA), column: OJ-H 250×4.6 mm, 5 μm), Rt: 5.65 min.

Example 127

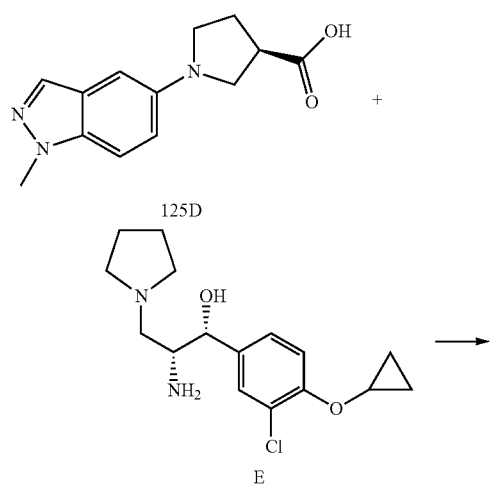

328

-continued

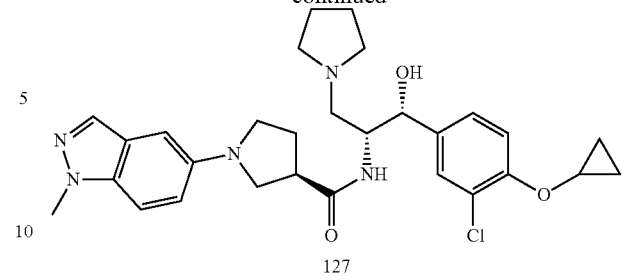

Compound 127 was synthesized, by employing the procedure described for Compound 1 using Compound 125D and Intermediate E in lieu of Compound 1B and Intermediate A. LC-MS (ESI) m/z: 538 [M+H]⁺; ¹H-NMR (CDCl₃, 400 MHz): δ (ppm) 0.73-0.77 (m, 4H), 2.06-2.11 (m, 7H), 3.09-3.37 (m, 10H), 3.66-3.67 (m, 1H), 4.01 (s, 3H), 4.42-4.45 (m, 1H), 5.18-5.19 (m, 1H), 6.69-6.70 (m, 1H), 6.86-6.89 (m, 1H), 7.05-7.08 (m, 1H), 7.17-7.18 (m, 2H), 7.26-7.28 (m, 1H), 7.43 (s, 1H), 7.82 (s, 1H).

Example 128

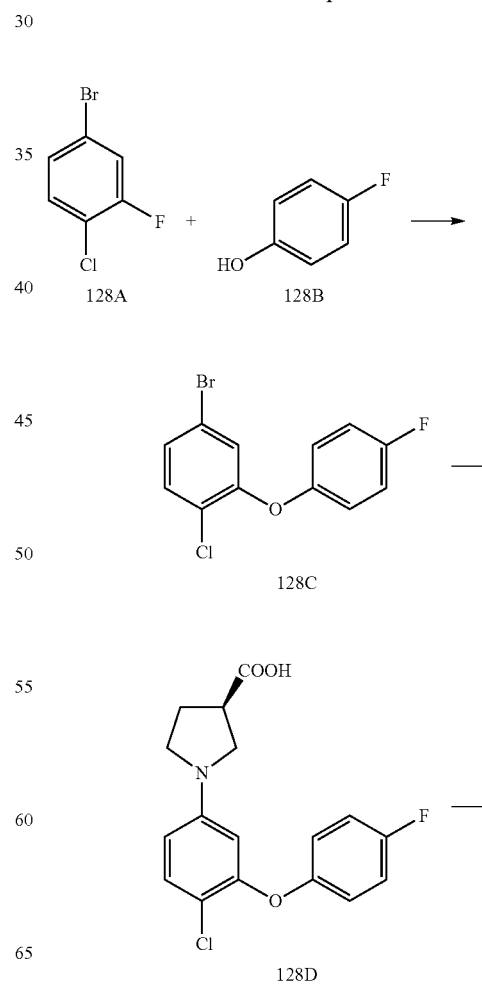

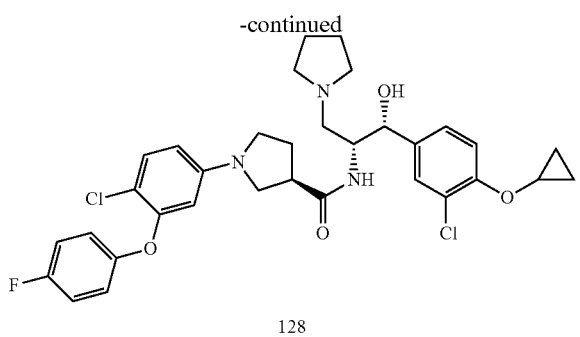

128

Compound 128C was synthesized, by employing the procedure described for Compound 103C using Compound 128A and 128B in lieu of Compound 103A and 103B. LC-MS (ESI) m/z: 301.0 [M+H]+.

Compounds 128D and 128 were synthesized, by employing the procedures described for Compounds 1B and 1 using Compound 128C, Intermediate Z6, Compound 128D, and Intermediate E in lieu of 1-chloro-4-iodobenzene, Compound 1A, 1B and Intermediate A.

Compound 128D. LC-MS (ESI) m/z: 334.0 [M–H]+.

Compound 128. LC-MS (ESI) m/z: 628.2 [M+H]+; $^1$H-NMR (CD$_3$OD, 400 MHz): δ (ppm) 0.57-0.77 (m, 4H), 2.02-2.19 (m, 6H), 2.56-2.59 (m, 1H), 3.11-3.30 (m, 6H), 3.48-3.51 (m, 1H), 3.58-3.73 (m, 4H), 4.50-4.55 (m, 1H), 4.89 (d, J=2.4 Hz, 1H), 6.18 (d, J=2.8 Hz, 1H), 6.31 (dd, J=8.8, 3.2 Hz, 1H), 6.88-6.91 (m, 2H), 7.03-7.07 (m, 2H), 7.23-7.26 (m, 3H), 7.47 (s, 1H), 8.10 (d, J=2.8 Hz, 1H).

Example 129

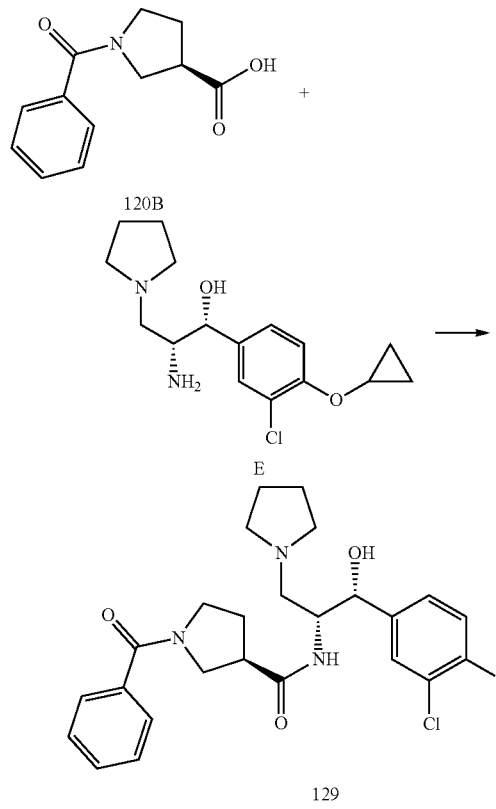

129

Compound 129 was synthesized, by employing the procedure described for Compound 1 using Compound 120B and Intermediate E in lieu of Compound 1B and Intermediate A. LC-MS (ESI) m/z: 512 [M+H]+; $^1$H-NMR (CD$_3$OD, 400 MHz): δ (ppm) 0.67-0.81 (m, 4H), 1.81 (s, 4H), 2.01-2.17 (m, 2H), 2.59-2.75 (m, 6H), 2.98-3.11 (m, 1H), 3.38-3.58 (m, 3H), 3.62-3.85 (m, 2H), 4.16-4.28 (m, 1H), 4.80 (d, J=30.4 Hz, 1H), 7.11-7.35 (m, 3H), 7.37-7.51 (m, 5H).

Example 130

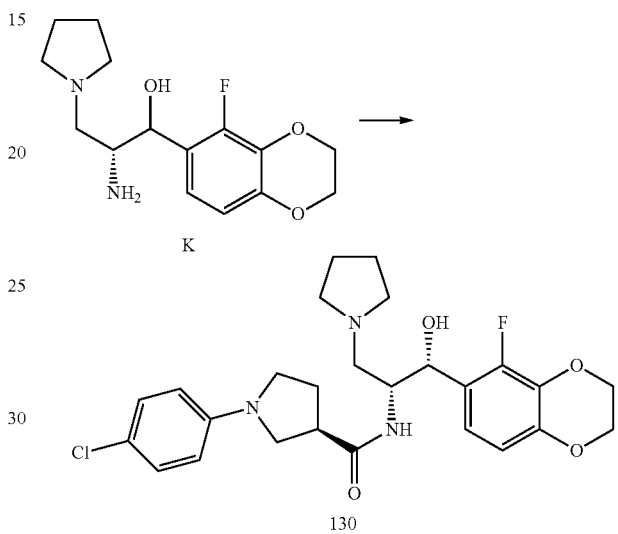

130

Compound 130 was synthesized, by employing the procedure described for Compound 1 using Intermediate Z and K in lieu of Compound 1B and Intermediate A. LC-MS (ESI) m/z: 504 [M+H]+; $^1$H-NMR (CD$_3$OD, 400 MHz): δ (ppm) 1.97-2.17 (m, 6H), 2.57-2.61 (m, 1H), 2.93-3.00 (m, 1H), 3.17-3.25 (m, 5H), 3.34-3.40 (m, 1H), 3.65-3.76 (m, 3H), 4.14-4.26 (m, 4H), 4.46-4.75 (m, 1H), 4.76 (d, J=9.2 Hz, 1H), 6.42 (d, J=9.2 Hz, 2H), 6.63 (d, J=10.4 Hz, 1H), 6.88 (t, J=8.8 Hz, 1H), 7.10 (d, J=8.8 Hz, 2H), 8.16 (d, J=9.6 Hz, 1H).

Example 131

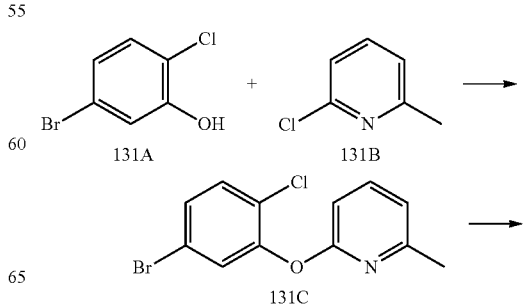

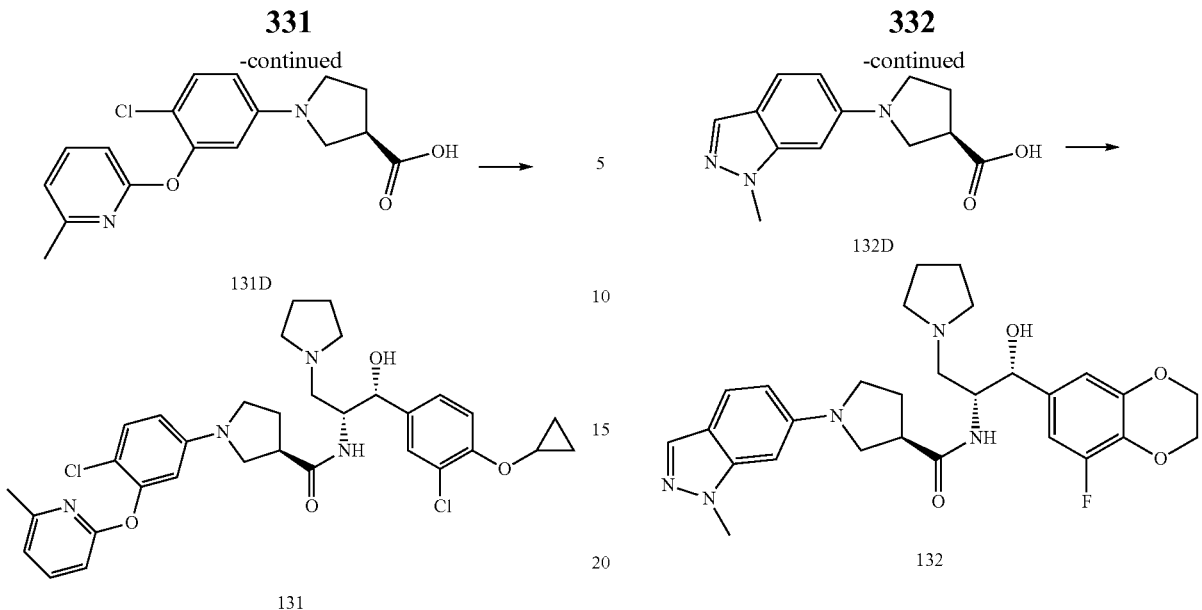

Compound 131C was synthesized, by employing the procedure described for Compound 103C using Compound 131A and 131B in NMP in lieu of Compound 103A and 103B in DMF. LC-MS (ESI) m/z: 298 [M+H]$^+$; $^1$H-NMR (CDCl$_3$, 400 MHz): δ (ppm) 2.42 (s, 3H), 6.67 (d, J=8.4 Hz, 1H), 6.90 (d, J=7.2 Hz, 1H), 7.29 (d, J=9.2 Hz, 1H), 7.33 (d, J=7.2 Hz, 2H), 7.60 (t, J=8.0 Hz, 1H).

Compounds 131D and 131 were synthesized, by employing the procedures described for Compounds 1B and 1 using Compound 131C, Intermediate Z6, Compound 131D, and Intermediate E in lieu of 1-chloro-4-iodobenzene, Compounds 1A, 1B and Intermediate A.

Compound 131D. LC-MS (ESI) m/z: 333 [M+H]$^+$.

Compound 131. LC-MS (ESI) m/z: 625 [M+H]$^+$; $^1$H-NMR (DMSO-d$_6$, 400 MHz): δ (ppm) 0.68-0.70 (m, 2H), 0.82-0.83 (m, 2H), 1.65 (d, J=7.2 Hz, 6H), 1.90-1.93 (m, 2H), 2.02-2.05 (m, 2H), 3.14-3.24 (m, 2H), 3.5.-3.59 (m, 4H), 3.93-3.97 (m, 1H), 4.57-4.60 (m, 1H), 4.92 (d, J=2.4 Hz, 1H), 5.02-5.09 (m, 1H), 7.36 (dd, J=8.8, 2.0 Hz, 1H), 7.42 (d, J=8.8 Hz, 1H), 7.45 (d, J=1.6 Hz, 1H), 7.81 (d, J=8.4 Hz, 2H), 7.85 (d, J=8.4 Hz, 2H), 7.93 (dd, J=8.8, 1.6 Hz, 1H), 8.16 (d, J=9.2 Hz, 2H), 9.54 (s, 1H), 9.84 (s, 1H).

Example 132

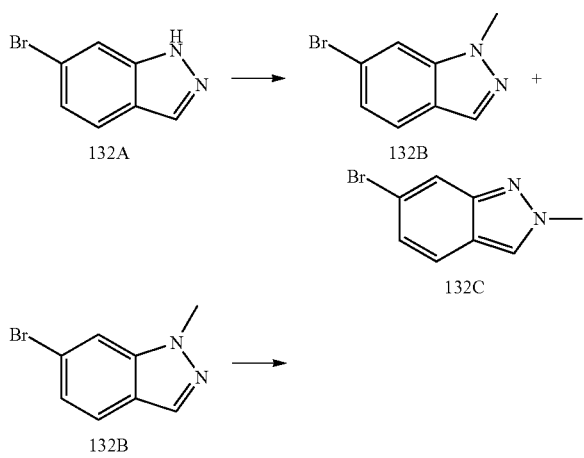

To Compound 132A (10 g, 50.8 mmol) in THF (50 mL) was added sodium hydride (60% in mineral, 2.2 g, 55.8 mmol) with ice bath cooling. The mixture was stirred at room temperature for 30 min. Methyl iodide (4.74 mL, 76.1 mmol) was added at room temperature. The reaction mixture was stirred at room temperature for 1 h, quenched with saturated aqueous ammonium chloride solution (30 mL), and extracted with ethyl acetate (100 mL×3). The combined organic layers were washed with brine (200 mL), dried over anhydrous sodium sulfate, and concentrated. Purification with flash column chromatography on silica gel (ethyl acetate in petroleum ether, 10% to 30% v/v) gave Compound 132B and Compound 132C. For Compound 132B: LC-MS (ESI) m/z: 211 [M+H]$^+$; $^1$H-NMR (DMSO-d$_6$, 400 MHz): δ (ppm) 4.04 (s, 3H), 7.26 (dd, J=8.8, 2.0 Hz, 1H), 7.72 (d, J=8.4 Hz, 1H), 7.99 (s, 1H), 8.08 (d, J=0.8 Hz, 1H). For Compound 132C: LC-MS (ESI) m/z: 211 [M+H]$^+$; $^1$H-NMR (DMSO-d$_6$, 400 MHz): δ (ppm) 4.17 (s, 3H), 7.13 (dd, J=8.8, 2.0 Hz, 1H), 7.69 (d, J=8.8 Hz, 1H), 7.85 (s, 1H), 8.41 (s, 1H).

Compounds 132D and 132 were synthesized, by employing the procedures described for Compounds 1B and 1 using Compound 132B, Intermediate Z6, Compound 132D, and Intermediate C in lieu of 1-chloro-4-iodobenzene, Compounds 1A, 1B and Intermediate A.

Compound 132D. LC-MS (ESI) m/z: 246 [M+H]$^+$; $^1$H-NMR (DMSO-d$_6$, 400 MHz): δ (ppm) 2.18-2.29 (m, 2H), 3.35-3.60 (m, 5H), 3.90 (s, 3H), 6.43 (s, 1H), 6.58 (d, J=8.8 Hz, 1H), 7.50 (d, J=8.4 Hz, 1H), 7.79 (s, 1H), 12.53 (s, 1H).

Compound 132. LC-MS (ESI) m/z: 524 [M+H]$^+$; $^1$H-NMR (DMSO-d$_6$, 400 MHz): δ (ppm) 1.84-2.16 (m, 6H), 2.63-2.67 (m, 1H), 3.08-3.43 (m, 8H), 3.55-3.59 (m, 2H), 3.92 (m, 3H), 4.14-4.38 (m, 5H), 4.72 (d, J=2.0 Hz, 1H), 6.28 (s, 1H), 6.51 (dd, J=8.8, 1.6 Hz, 1H), 6.73 (s, 1H), 6.85 (dd, J=11.6, 1.6 Hz, 1H), 7.53 (d, J=8.8 Hz, 1H), 7.79 (s, 1H), 8.02 (d, J=10.0 Hz, 1H), 9.24 (brs, 1H).

Example 133

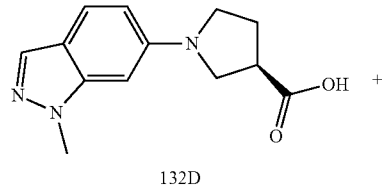

132D

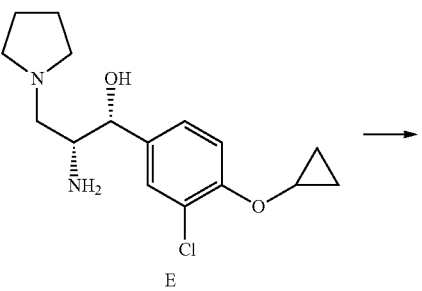

E

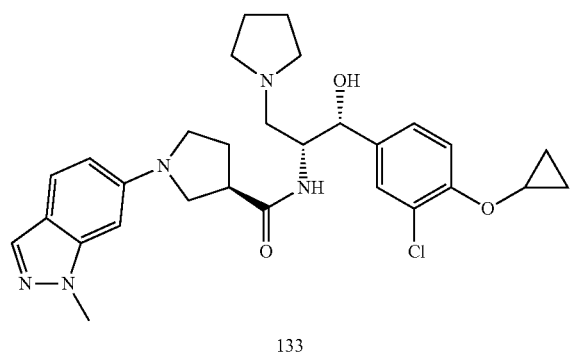

133

Compound 133 was synthesized, by employing the procedure described for Compound 1 using Compound 132D and Intermediate E in lieu of Compound 1B and Intermediate A. LC-MS (ESI) m/z: 538 [M+H]$^+$; $^1$H-NMR (CD$_3$OD, 400 MHz): δ (ppm) 0.55-0.73 (m, 4H), 2.03-2.28 (m, 6H), 2.62-2.66 (m, 1H), 3.17-3.31 (m, 3H), 3.40-3.69 (m, 7H), 3.78-3.84 (m, 1H), 4.08 (s, 3H), 4.56-4.58 (m, 1H), 4.96 (d, J=2.8 Hz, 1H), 6.72 (d, J=9.2 Hz, 1H), 7.27 (s, 2H), 7.36 (s, 1H), 7.58 (s, 1H), 7.64 (d, J=8.8 Hz, 1H), 8.10 (s, 1H).

Example 134

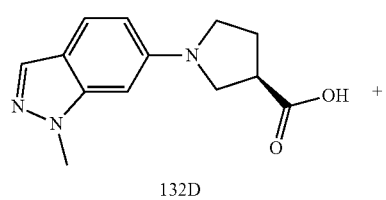

132D

-continued

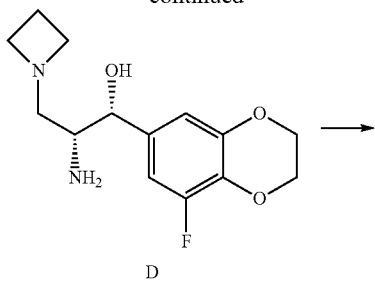

D

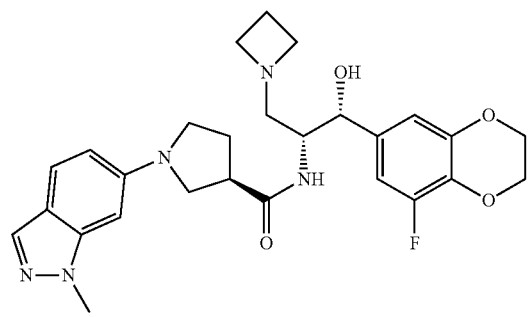

134

Compound 134 was synthesized, by employing the procedure described for Compound 1 using Compound 132D and Intermediate D in lieu of Compound 1B and Intermediate A. LC-MS (ESI) m/z: 510 [M+H]$^+$; $^1$H-NMR (CD$_3$OD, 400 MHz): δ (ppm) 2.15-2.19 (m, 1H), 2.29-2.34 (m, 1H), 2.42-2.48 (m, 1H), 2.58-2.65 (m, 1H), 2.75-2.79 (m, 1H), 3.19-3.23 (m, 1H), 3.43-3.62 (m, 5H), 3.98-4.34 (m, 12H), 4.84 (d, J=2.4 Hz, 1H), 6.71 (s, 1H), 6.84 (d, J=9.2 Hz, 1H), 6.91 (dd, J=11.6, 1.6 Hz, 1H), 7.35 (s, 1H), 7.71 (d, J=8.8 Hz, 1H), 8.28 (s, 1H).

Example 135

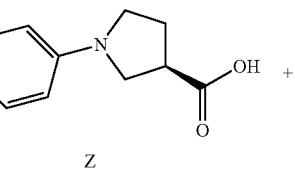

Z

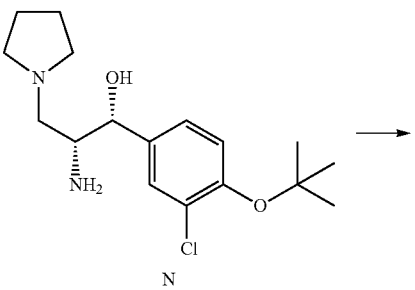

N

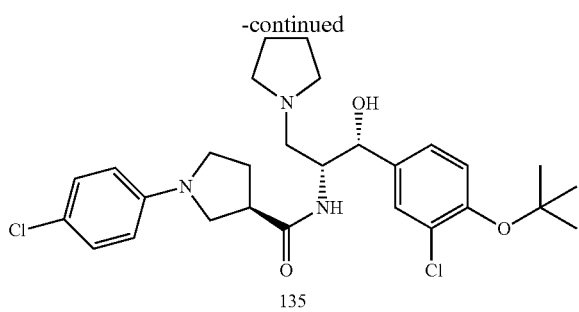

135

Compound 135 was synthesized, by employing the procedure described for Compound 1 using Intermediates Z and N in lieu of 1B and Intermediate A. LC-MS (ESI) m/z: 534 [M+H]+; 1H-NMR (CD3OD, 400 MHz): δ (ppm) 1.28 (s, 9H), 1.88-2.10 (m, 6H), 2.51 (t, J=8.8 Hz, 1H), 2.98-3.17 (m, 6H), 3.39-3.42 (m, 1H), 3.49-3.59 (m, 2H), 3.66-3.72 (m, 1H), 4.40-4.47 (m, 1H), 4.78 (s, 1H), 6.37 (d, J=9.2 Hz, 2H), 7.01 (d, J=9.2 Hz, 3H), 7.13 (d, J=8.8 Hz, 1H), 7.45 (s, 1H), 8.00 (d, J=9.6 Hz, 1H).

Example 136

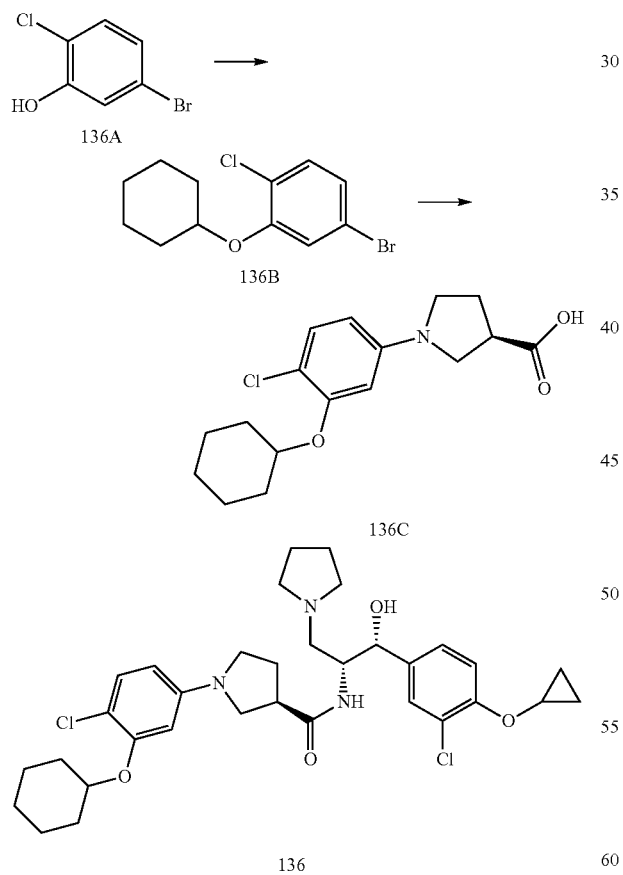

To a solution of Compound 136A (2.0 g, 9.71 mmol) and bromocyclohexane (4.75 g, 29.1 mmol) in NMP (30 mL) was added cesium carbonate (6.33 mg, 19.4 mmol). The mixture was stirred under nitrogen at 150° C. overnight. After cooling to room temperature the mixture was poured into water (150 mL) and extracted with ethyl acetate (100 mL×2). The combined organic phases were washed with water (10 mL×3) and brine (10 mL), dried over anhydrous sodium sulfate, filtered, and concentrated to afford a crude compound. The crude product was purified with flash column chromatography on silica gel (ethyl acetate in petroleum ether, 5% v/v) to furnish Compound 136B. LC-MS (ESI) m/z: 289 [M+H]+; 1H-NMR (CDCl3, 400 MHz): δ (ppm) 1.37-1.42 (m, 3H), 1.53-1.56 (m, 1H), 1.63-1.68 (m, 2H), 1.82-1.85 (m, 2H), 1.93-1.96 (m, 2H), 4.27-4.33 (m, 1H), 7.01 (dd, J=8.4, 2.4 Hz, 1H), 7.07 (d, J=2.4 Hz, 1H), 7.21 (d, J=8.4 Hz, 1H).

Compounds 136C and 136 were synthesized, by employing the procedures described for Compounds 1B and 1 using Compound 136B, Intermediate Z6, Compound 136C, and Intermediate E in lieu of 1-chloro-4-iodobenzene, Compounds 1A, 1B and Intermediate A.

Compound 136C. LC-MS (ESI) m/z: 324 [M+H]+; 1H-NMR (DMSO-d6, 400 MHz): δ (ppm) 1.33-1.38 (m, 3H), 1.47-1.52 (m, 3H), 1.70-1.73 (m, 2H), 1.83-1.87 (m, 2H), 2.10-2.15 (m, 2H), 3.03-3.06 (m, 1H), 3.18-3.25 (m, 2H), 3.36-3.38 (m, 2H), 4.40-4.44 (m, 1H), 6.09 (dd, J=8.8, 2.4 Hz, 1H), 6.21 (d, J=2.8 Hz, 1H), 7.10 (d, J=9.2 Hz, 1H).

Compound 136. LC-MS (ESI) m/z: 616 [M+H]+; 1H-NMR (DMSO-d6, 400 MHz): δ (ppm) 0.53-0.56 (m, 1H), 0.59-0.74 (m, 3H), 1.34-1.36 (m, 3H), 1.52-1.58 (m, 3H), 1.76-2.13 (m, 10H), 2.56-2.60 (m, 1H), 3.04-3.23 (m, 6H), 3.42-3.74 (m, 5H), 4.31-4.35 (m, 1H), 4.45-4.48 (m, 1H), 4.85 (d, J=2.0 Hz, 1H), 6.01-6.04 (m, 1H), 6.11 (s, 1H), 7.04 (d, J=8.4 Hz, 1H), 7.20 (s, 2H), 7.44 (s, 1H).

Example 137

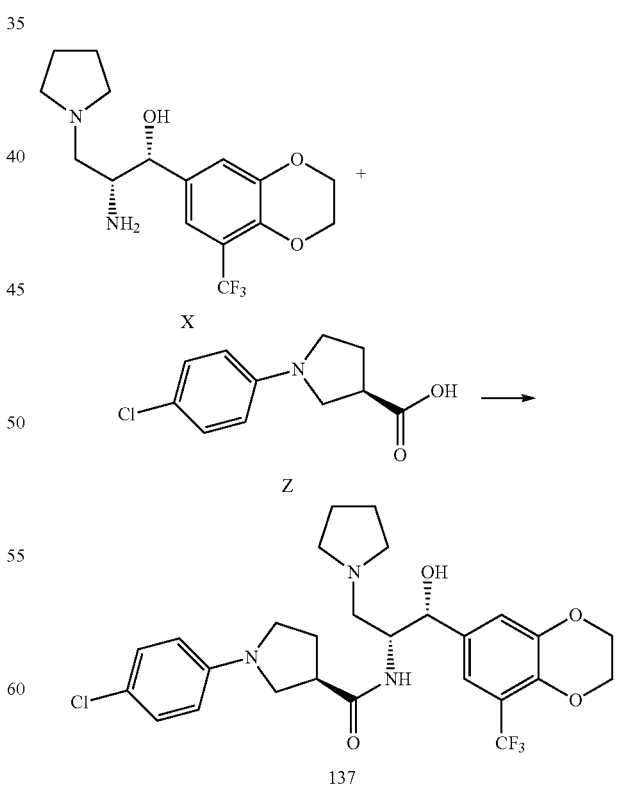

Compound 137 was synthesized, by employing the procedure described for Compound 1 using Intermediates Z and Compound X in lieu of Compound 1B and Intermediate A. LC-MS (ESI) m/z: 554 [M+H]⁺; ¹H-NMR (CD₃OD, 400 MHz): δ (ppm) 2.02-2.18 (m, 6H), 2.56-2.61 (m, 1H), 3.08-3.25 (m, 4H), 3.35-3.79 (m, 6H), 4.17-4.28 (m, 4H), 4.50-4.55 (m, 1H), 4.89 (d, J=2 Hz, 1H), 6.46-6.48 (m, 2H), 7.12-7.17 (m, 3H), 7.29 (s, 1H), 8.14 (d, J=9.6 Hz, 1H).

Example 138

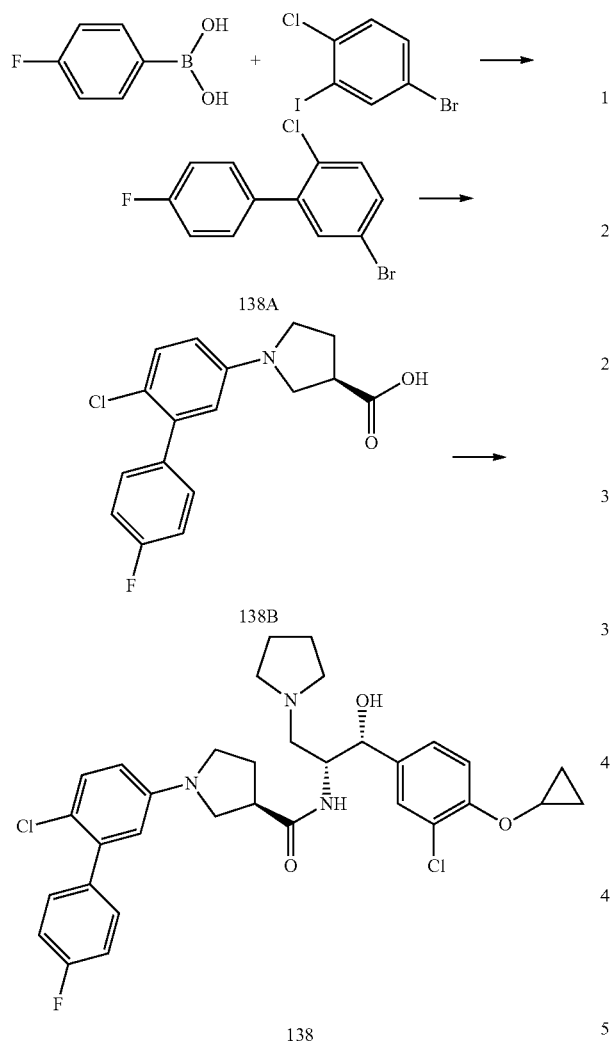

A mixture of 4-bromo-1-chloro-2-iodobenzene (1.83 g, 5.79 mmol), (4-fluorophenyl)boronic acid (810 mg, 5.79 mmol), Pd(PPh₃)₄ (943 mg, 0.82 mmol), and Na₂CO₃ (3.25 g, 30 mmol) in toluene (85 mL) and H₂O (19 mL) was stirred under nitrogen at 100° C. for 16 h. The reaction mixture was cooled to room temperature, and filtered through celite. The filtrate was treated with water (50 mL), and extracted with ethyl acetate (150 mL×2). The aqueous layer was acidified to pH 3 with aqueous HCl solution (1 N) and extracted with ethyl acetate (100 mL×2). The combined organic layers were washed with water (50 mL×2) and brine (150 mL), dried over anhydrous sodium sulfate, and concentrated to give Compound 138A. [M+H]⁺; ¹H-NMR (CDCl₃, 400 MHz): δ (ppm) 7.10-7.15 (m, 2H), 7.33 (d, J=8.4 Hz, 1H), 7.37-7.42 (m, 3H), 7.46 (d, J=2.4 Hz, 1H).

Compounds 138B and 138 were synthesized, by employing the procedures described for Compounds 1B and 1 using Compound 138A, Intermediate Z6, Compound 138B, and Intermediate E in lieu of 1-chloro-4-iodobenzene, Intermediate 1A, 1B and Intermediate A.

Compound 138C. LC-MS (ESI) m/z: 320.1 [M+H]⁺.

Compound 138. LC-MS (ESI) m/z: 612.3 [M+H]⁺; ¹H-NMR (CD₃OD, 400 MHz): δ (ppm) 0.57-0.73 (m, 4H), 2.02-2.23 (m, 6H), 2.62 (dd, J=9.6, 7.2 Hz, 1H), 3.13-3.27 (m, 4H), 3.34-3.37 (m, 2H), 3.48-3.52 (m, 1H), 3.59-3.66 (m, 4H), 4.52-4.55 (m, 1H), 4.90 (d, J=2.0 Hz, 1H), 6.45-6.49 (m, 2H), 7.13-7.18 (m, 2H), 7.24-7.28 (m, 3H), 7.42-7.49 (m, 2H), 7.49 (d, J=1.6 Hz, 1H), 8.11 (d, J=9.6 Hz, 1H).

Example 139

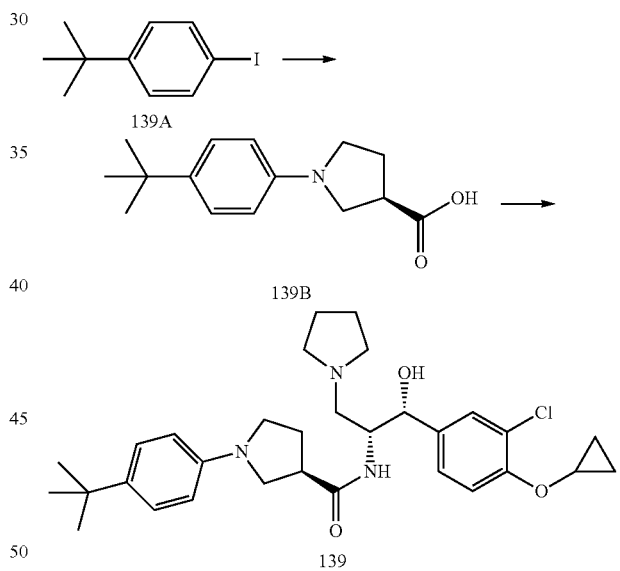

Compound 139B and 139 were synthesized, by employing the procedures described for Compounds 1B and 1 using Compound 139A, Intermediate Z6, Compound 139B, and Intermediate E in lieu of 1-chloro-4-iodobenzene, Intermediates 1A, 1B and Intermediate A.

Compound 139B. LC-MS (ESI) m/z: 248 [M+H]⁺; ¹H-NMR (CD₃OD, 400 MHz): δ (ppm) 1.28 (s, 9H), 2.25-2.27 (m, 2H), 3.22-3.26 (m, 1H), 3.31-3.35 (m, 2H), 3.36-3.54 (m, 2H), 6.53 (d, J=8.8 Hz, 2H), 7.21 (d, J=8.8 Hz, 2H).

Compound 139. LC-MS (ESI) m/z: 540 [M+H]⁺; ¹H-NMR (CD₃OD, 400 MHz): δ (ppm) 0.62-0.79 (m, 4H), 1.29 (s, 9H), 2.01-2.13 (m, 3H), 2.14-2.28 (m, 3H), 2.54-2.58 (m, 1H), 3.09-3.28 (m, 3H), 3.48-3.82 (m, 8H), 4.53-4.57 (m, 1H), 4.86 (m, 1H), 6.60 (d, J=8.4 Hz, 2H), 7.27-7.35 (m, 4H), 7.52 (s, 1H).

Example 140

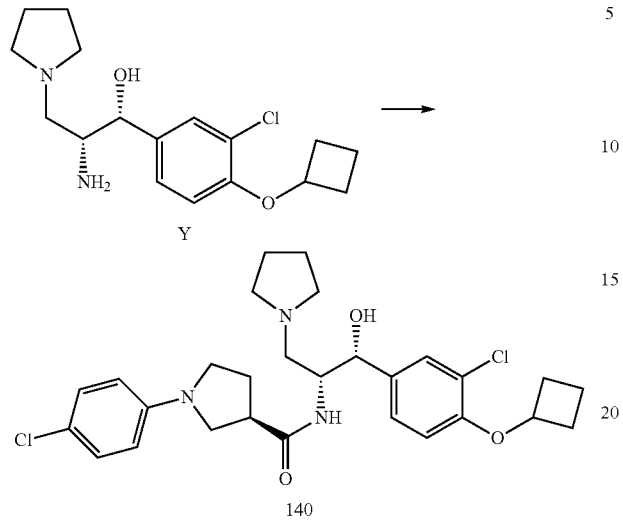

Compound 140 was synthesized, by employing the procedure described for Compound 1 using Intermediates Z and Y in lieu of Compound 1B and Intermediate A. LC-MS (ESI) m/z: 532 [M+H]$^+$; $^1$H-NMR (DMSO-d$_6$, 400 MHz): δ (ppm) 1.55-1.70 (m, 1H), 1.72-1.78 (m, 1H), 1.96-2.06 (m, 7H), 2.39-2.40 (m, 2H), 2.48-2.50 (m, 1H), 3.10-3.18 (m, 4H), 3.24-3.26 (m, 2H), 3.39-3.44 (m, 1H), 3.54-3.56 (m, 2H), 4.31-4.36 (m, 1H), 4.58-4.65 (m, 1H), 4.79-4.80 (m, 1H), 5.99 (brs, 1H), 6.41-6.43 (m, 2H), 6.83-6.85 (m, 1H), 7.16-7.19 (m, 3H), 7.44-7.45 (m, 1H), 8.01-8.03 (m, 1H).

Example 141

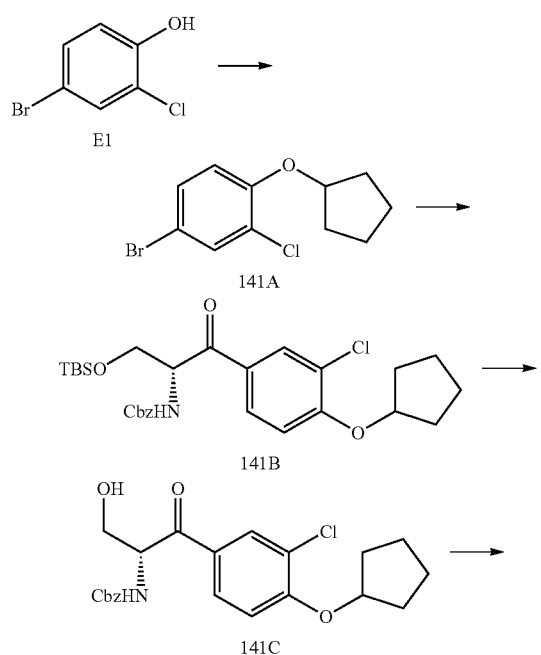

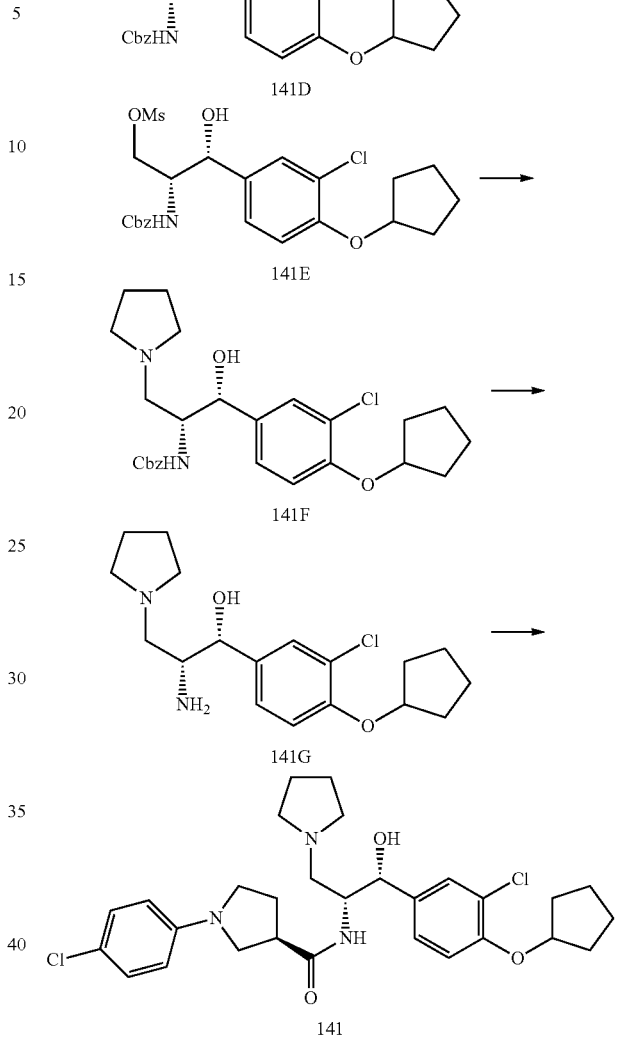

Compound 141A was synthesized, by employing the procedure described for Intermediate E2 using bromocyclopentane in lieu of bromocyclopropane. LC-MS (ESI) m/z: No; $^1$H-NMR (CDCl$_3$, 400 MHz): δ (ppm) 1.57-1.91 (m, 8H), 4.74-4.78 (m, 1H), 6.78 (d, J=12.8 Hz, 1H), 7.28 (dd, J=11.2, 2.4 Hz, 1H), 7.47 (d, J=2.4 Hz, 1H).

Compounds 141B, 141C, 141D, 141E, and 141F were synthesized, by employing the procedures described correspondingly for Intermediates A5, A6, A7, A8, and A9 using Compounds 141A, 141B, 141C, 141D, and 141E in lieu of 6-bromo-2,3-dihydrobenzo[b][1,4]dioxine, Intermediates A5, A6, A7, and A8.

Compound 141B. LC-MS (ESI) m/z: 532 [M+H]$^+$; $^1$H-NMR (CDCl$_3$, 400 MHz): δ (ppm) −0.12 (d, 6H), 0.74 (s, 9H), 1.59-1.69 (m, 2H), 1.82-2.01 (m, 6H), 3.85-3.97 (m, 2H), 4.88-4.92 (m, 1H), 5.13 (s, 2H), 5.27-5.31 (m, 1H), 5.90 (d, J=8.0 Hz, 1H), 6.95 (d, J=8.4 Hz, 1H), 7.29-7.37 (m, 5H), 7.82-7.85 (dd, J=8.8, 2.0 Hz, 1H), 7.99 (d, J=1.6 Hz, 1H).

Compound 141C. LC-MS (ESI) m/z: 418 [M+H]$^+$; $^1$H-NMR (CDCl$_3$, 400 MHz): δ (ppm) 1.65-1.76 (m, 2H), 1.80-1.90 (m, 4H), 1.96-2.06 (m, 2H), 3.80 (dd, J=12.0, 5.6

Hz, 1H), 3.93 (dd, J=11.2, 4.8 Hz, 1H), 5.00-5.03 (m, 1H), 5.11 (s, 2H), 5.23 (t, J=5.2 Hz, 1H), 7.15 (d, J=8.8 Hz, 1H), 7.27-7.36 (m, 5H), 7.97 (dd, J=8.4, 2.0 Hz, 1H), 8.04 (d, J=2.0 Hz, 1H).

Compound 141D. LC-MS (ESI) m/z: 402 [M-OH]$^+$; $^1$H-NMR (CD$_3$OD, 400 MHz): δ (ppm) 1.66-1.96 (m, 8H), 3.48-3.55 (m, 1H), 3.67-3.82 (m, 2H), 4.60 (d, J=7.2 Hz, 2H), 5.00 (dd, J=30.8, 12.8 Hz, 2H), 6.82 (d, J=4.0 Hz, 2H), 7.17-7.34 (m, 5H), 7.41 (d, J=1.6 Hz, 1H).

Compound 141E, which was directly used for the next step without further purification. LC-MS (ESI) m/z: 480 [M-OH]$^+$.

Compound 141F. LC-MS (ESI) m/z: 473 [M+H]$^+$; $^1$H-NMR (CD$_3$OD, 400 MHz): δ (ppm) 2.40-2.68 (m, 12H), 3.15-3.46 (m, 6H), 4.57-4.61 (m, 1H), 5.52 (s, 1H), 5.66-5.71 (m, 2H), 5.78 (t, J=12.8 Hz, 1H), 7.62-7.90 (m, 2H), 7.97-8.03 (m, 2H), 8.07-8.15 (m, 4H).

Compound 141G was synthesized, by employing the procedure described for Intermediate E using Compound 141F in lieu of Intermediate E7, which was directly used for the next step without further purification. LC-MS (ESI) m/z: 339 [M+H]$^+$; $^1$H-NMR (CD$_3$OD, 400 MHz): δ (ppm) 1.62-2.00 (m, 12H), 2.44-2.75 (m, 6H), 3.02-3.26 (m, 1H), 4.29-4.54 (m, 1H), 4.87-4.90 (m, 1H), 7.03-7.06 (m, 1H), 7.19-7.26 (m, 1H), 7.31-7.37 (m, 1H).

Compound 141 was synthesized, by employing the procedure described for Compound 1 using Intermediate Z and Compound 141G in lieu of Compound 1B and Intermediate A. LC-MS (ESI) m/z: 546 [M+H]$^+$; $^1$H-NMR (CD$_3$OD, 400 MHz): δ (ppm) 1.58-2.24 (m, 15H), 2.54-2.58 (m, 1H), 3.08-3.29 (m, 6H), 3.48-3.69 (m, 3H), 3.78-3.84 (m, 1H), 4.51-4.60 (m, 1H), 4.77-4.79 (m, 1H), 6.46 (d, 2H), 6.95 (d, 1H), 7.10-7.15 (m, 2H), 7.22-7.25 (m, 1H), 7.51 (d, J=2.0 Hz, 1H), 8.08 (d, J=10.0 Hz, 1H).

Example 142

Compounds 142B and 142 were synthesized, by employing the procedures described for Compounds 1B and 1 using Compound 142A, Intermediate Z6, Compound 142B, and Intermediate C in lieu of 1-chloro-4-iodobenzene, Compound 1A, 1B and Intermediate A.

Compound 142B. LC-MS (ESI) m/z: 248 [M+H]$^+$; $^1$H-NMR (CD$_3$OD, 400 MHz): δ (ppm) 1.28 (s, 9H), 2.25-2.27 (m, 2H), 3.22-3.26 (m, 1H), 3.31-3.35 (m, 2H), 3.36-3.54 (m, 2H), 6.53 (d, J=8.8 Hz, 2H), 7.21 (d, J=8.8 Hz, 2H).

Compound 142. LC-MS (ESI) m/z: 526 [M+H]$^+$; $^1$H-NMR (CD$_3$OD, 400 MHz): δ (ppm) 1.24 (s, 9H), 1.92-2.01 (m, 4H), 2.02-2.12 (m, 1H), 2.13-2.19 (m, 1H), 2.65-2.70 (m, 1H), 3.06-3.26 (m, 7H), 3.29-3.36 (m, 3H), 4.16-4.21 (m, 4H), 4.35-4.41 (m, 1H), 4.77 (d, J=2.8 Hz, 1H), 6.47 (d, J=8.4 Hz, 2H), 6.70 (s, 1H), 6.74-6.78 (m, 1H), 7.18 (d, J=8.4 Hz, 2H).

Example 143

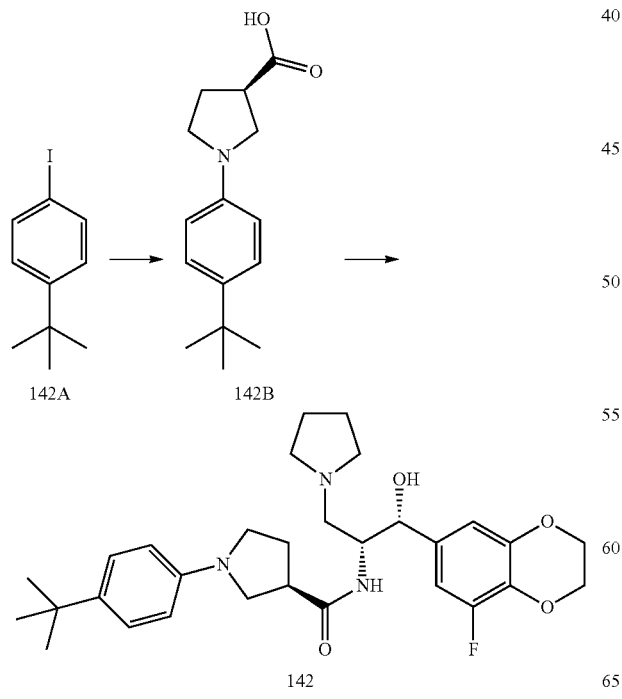

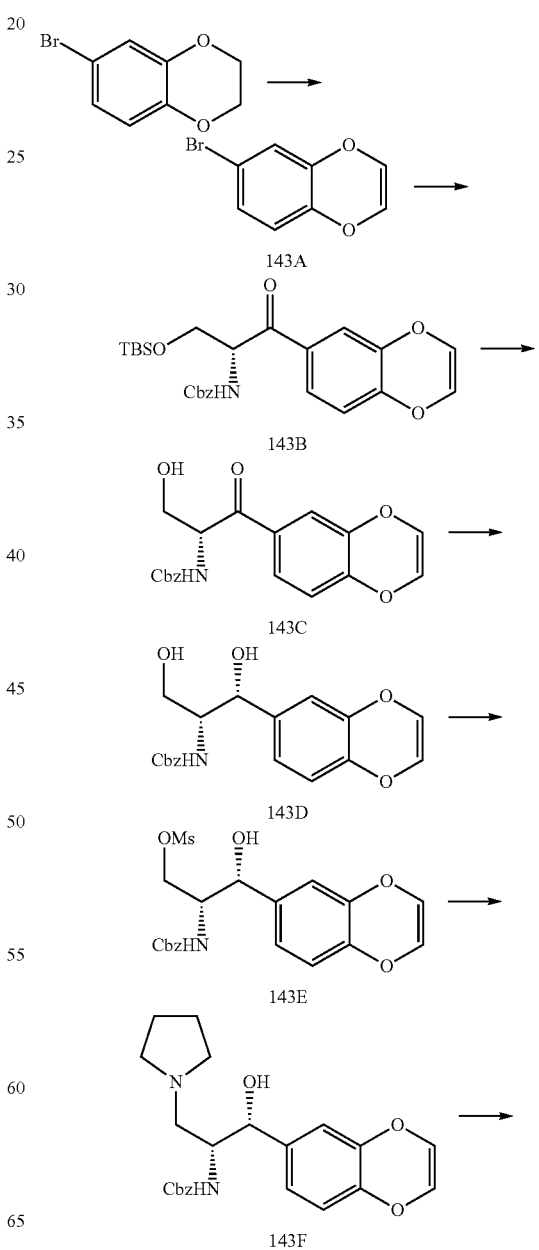

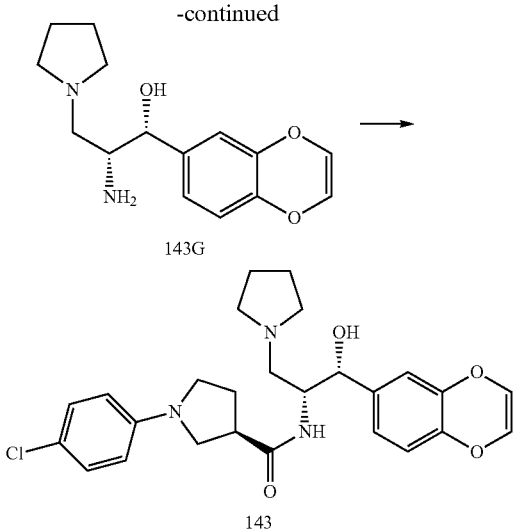

A mixture of 6-bromo-2,3-dihydrobenzo[b][1,4]dioxine (1.07 g, 5 mmol), NBS (2.1 g, 12 mmol), and AIBN (20 mg) in CCl$_4$ (60 mL) was refluxed under nitrogen for 18 h. The mixture was cooled down to room temperature and filtered. The filtrate was washed with water (50 mL×2) and dried over anhydrous magnesium sulfate. After removal of the solvent, the residue was dissolved in acetone (50 mL) and refluxed under nitrogen for 3 h with NaI (3.75 g, 25 mmol). The mixture was cooled down to room temperature and evaporated. The residue was diluted with water (100 mL) and extracted with dichloromethane (50 mL×3). The organic layer was washed with aqueous Na$_2$S$_2$O$_3$ solution (100 mL×2) and brine (100 mL), dried over anhydrous sodium sulfate, concentrated, and purified with flash column chromatography on silica gel (petroleum ether, 100% v/v) to yield Compound 143A. $^1$H-NMR (CDCl$_3$, 400 MHz): δ (ppm) 5.86 (s, 2H), 6.49 (d, J=8.8 Hz, 1H), 6.76 (d, J=2.8 Hz, 1H), 6.92 (dd, J=8.8, 2.8 Hz, 1H).

Compounds 143B, 143C, 143D, 143E, and 143F were synthesized, by employing the procedures described correspondingly for Intermediates A5, A6, A7, A8, and A9 using Compounds 143A, 143B, 143C, 143D, and 143E in lieu of 6-bromo-2,3-dihydrobenzo[b][1,4]dioxine, Intermediates A5, A6, A7, and A8.

Compound 143B. LC-MS (ESI) m/z: 470 [M+H]$^+$; $^1$H-NMR (CDCl$_3$, 400 MHz): δ (ppm) 0.00 (d, J=2.4 Hz, 6H), 0.85 (s, 9H), 3.97 (d, J=9.2 Hz, 2H), 5.15 (d, J=2.8 Hz, 2H), 5.22-5.25 (m, 1H), 6.12 (s, 2H), 6.78 (d, J=8.0 Hz, 1H), 7.29 (d, J=2.0 Hz, 1H), 7.39-7.40 (m, 5H), 7.60-7.63 (m, 1H).

Compound 143C. LC-MS (ESI) m/z: 356 [M+H]$^+$; $^1$H-NMR (CDCl$_3$, 400 MHz): δ (ppm) 2.59-2.62 (m, 1H), 3.83-3.89 (m, 1H), 3.97-4.02 (m, 1H), 5.14 (s, 2H), 5.22-5.23 (m, 1H), 5.89-5.91 (m, 2H), 6.05-6.06 (m, 1H), 6.67-6.69 (m, 1H), 7.25-7.25 (m, 1H), 7.33-7.37 (m, 5H), 7.50-7.52 (m, 1H).

Compound 143D. LC-MS (ESI) m/z: 380 [M+Na]$^+$; $^1$H-NMR (CDCl$_3$, 400 MHz): δ (ppm) 2.38 (s, 1H), 3.08 (s, 1H), 3.80-3.84 (m, 3H), 4.86 (s, 1H), 5.05 (s, 2H), 5.43-5.44 (m, 1H), 5.86 (s, 2H), 6.55-6.57 (m, 1H), 6.64 (s, 1H), 6.78-6.80 (m, 1H), 7.30-7.39 (m, 5H).

Compound 143E. LC-MS (ESI) m/z: 418 [M-OH]$^+$.

Compound 143F. LC-MS (ESI) m/z: 411 [M+H]$^+$; $^1$H-NMR (CDCl$_3$, 400 MHz): δ (ppm) 1.77-1.80 (m, 4H), 2.67-2.68 (m, 4H), 2.76-2.80 (m, 1H), 2.86-2.91 (m, 1H), 3.98 (brs, 1H), 4.89-4.90 (m, 1H), 5.01-5.03 (m, 1H), 5.06 (s, 2H), 5.86 (s, 2H), 6.56 (d, J=8.0 Hz, 1H), 6.61 (s, 1H), 6.74-6.76 (m, 1H), 7.29-7.39 (m, 5H).

Compound 143G was synthesized, by employing the procedure described for Intermediate E using Compound 143F in lieu of Intermediate E7. LC-MS (ESI) m/z: 277 [M+H]$^+$.

Compound 143G. LC-MS (ESI) m/z: 277 [M+H]$^+$.

Compound 143 was synthesized, by employing the procedure described for Compound 1 using Intermediate Z and Compound 143G in lieu of Compound 1B and Intermediate A. LC-MS (ESI) m/z: 484 [M+H]$^+$; $^1$H-NMR (CD$_3$OD, 400 MHz): δ (ppm) 2.01-2.29 (m, 6H), 2.72-2.76 (m, 1H), 3.11-3.29 (m, 4H), 3.35-3.41 (m, 2H), 3.46-3.50 (m, 1H), 3.56-3.62 (m, 1H), 3.65-3.70 (m, 1H), 3.78-3.83 (m, 1H), 4.47-4.50 (m, 1H), 4.82 (d, J=2.4 Hz, 1H), 6.03 (s, 2H), 6.59-6.61 (m, 3H), 6.79 (d, J=1.6 Hz, 1H), 6.87-6.90 (m, 1H), 7.16-7.18 (m, 2H).

Example 144

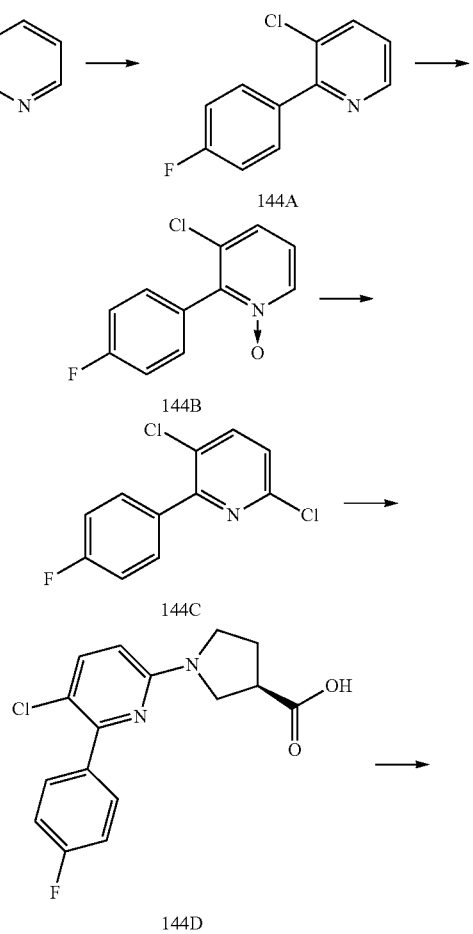

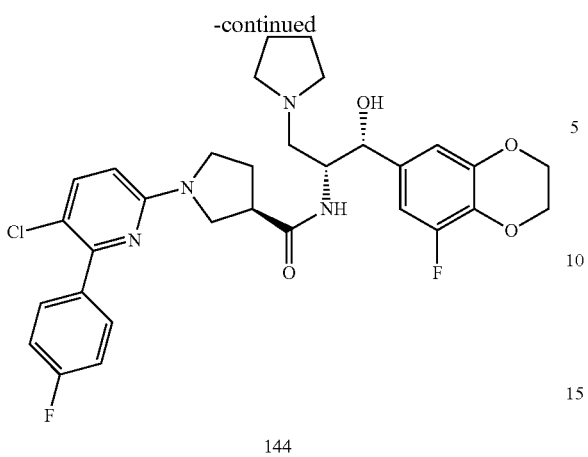

144

A mixture of 2-bromo-3-chloropyridine (5 g, 26 mmol), 4-fluorophenylboronic acid (3.64 g, 26 mmol), Pd(PPh)$_2$Cl$_2$ (1.8 g, 2.6 mmol), and K$_2$CO$_3$ (5.0 g, 39 mmol) in dioxane (100 mL) and water (10 mL) was stirred at 80° C. for 2 h. The mixture was diluted with ethyl acetate (200 mL), washed with water (100 mL×2) and brine (100 mL), dried over anhydrous sodium sulfate, concentrated, and purified with flash column chromatography on silica gel (ethyl acetate in petroleum ether, 10% v/v) to afford Compound 144A. LC-MS (ESI) m/z: 208 [M+H]$^+$; $^1$H-NMR (CDCl$_3$, 400 MHz): δ (ppm) 7.14-7.14 (m, 2H), 7.24 (dd, J$_j$=4.4 Hz, J$_2$=8.0 Hz, 1H), 7.71-7.76 (m, 2H), 7.80 (dd, J$_1$=1.6 Hz, J$_2$=8.4 Hz, 1H), 8.59 (dd, J$_1$=1.2 Hz, J$_2$=4.4 Hz, 1H).

To a mixture of Compound 144A (4.1 g, 19.75 mmol) in dichloromethane (80 mL) was added MCPBA (4.1 g, 23.7 mmol) in portions at room temperature. The mixture was stirred at room temperature for 1 h, diluted with dichloromethane (200 mL), washed with water (200 mL×2) and brine (100 mL), dried over anhydrous sodium sulfate, concentrated, and purified with flash column chromatography on silica gel (ethyl acetate in petroleum ether, 50% v/v) to afford Compound 144B. LC-MS (ESI) m/z: 224 [M+H]$^+$; $^1$H-NMR (CDCl$_3$, 400 MHz): δ (ppm) 7.12-7.16 (m, 3H), 7.33-7.41 (m, 3H), 8.21 (dd, J$_1$=1.2 Hz, J$_2$=7.2 Hz, 1H).

A mixture of Compound 144B (3.3 g, 14.76 mmol) in POCl$_3$ (32 mL) was stirred at 135° C. for 1 h. POCl$_3$ was removed with evaporation under vacuo. The residue was dissolved in dichloromethane (200 mL), washed with water (100 mL×3) and brine (100 mL), dried over anhydrous sodium sulfate, concentrated, and purified with flash column chromatography on silica gel (ethyl acetate in petroleum ether, 20% v/v) to afford Compound 144C. LC-MS (ESI) m/z: 242 [M+H]$^+$; $^1$H-NMR (CDCl$_3$, 400 MHz): δ (ppm) 7.13-7.18 (m, 2H), 7.25 (d, J=8.4 Hz, 1H), 7.74-7.77 (m, 3H).

Compounds 144D and 144 were synthesized, by employing the procedures described for Compounds 1B and 1 using Compound 144C, Intermediate Z6, Compound 144D, and Intermediate C in lieu of 1-chloro-4-iodobenzene, Compound 1A, 1B and Intermediate A.

Compound 144D. LC-MS (ESI) m/z: 321 [M+H]$^+$; $^1$H-NMR (DMSO-d$_6$, 400 MHz): δ (ppm) 2.12-2.24 (m, 2H), 3.15-3.21 (m, 1H), 3.40-3.48 (m, 2H), 3.55-3.67 (m, 2H), 6.51 (d, J=8.4 Hz, 1H), 7.26-7.31 (m, 2H), 7.64 (d, J=8.8 Hz, 1H), 7.73-7.76 (m, 2H), 12.51 (brs, 1H).

Compound 144. LC-MS (ESI) m/z: 599 [M+H]$^+$; $^1$H-NMR (DMSO-d$_6$, 400 MHz): δ (ppm) 1.82-1.91 (m, 2H), 1.97-2.07 (m, 4H), 2.87-2.92 (m, 1H), 3.08-3.17 (m, 3H), 3.22-3.59 (m, 7H), 4.16-4.17 (m, 4H), 4.27-4.34 (m, 1H), 4.68-4.69 (m, 1H), 5.97 (brs, 1H), 6.39 (d, J=8.8 Hz, 1H), 6.71 (s, 1H), 6.77 (d, J=12.8 Hz, 1H), 7.27-7.32 (m, 2H), 7.68-7.75 (m, 3H), 8.02 (d, J=9.6 Hz, 1H), 9.29 (brs, 1H).

Example 145

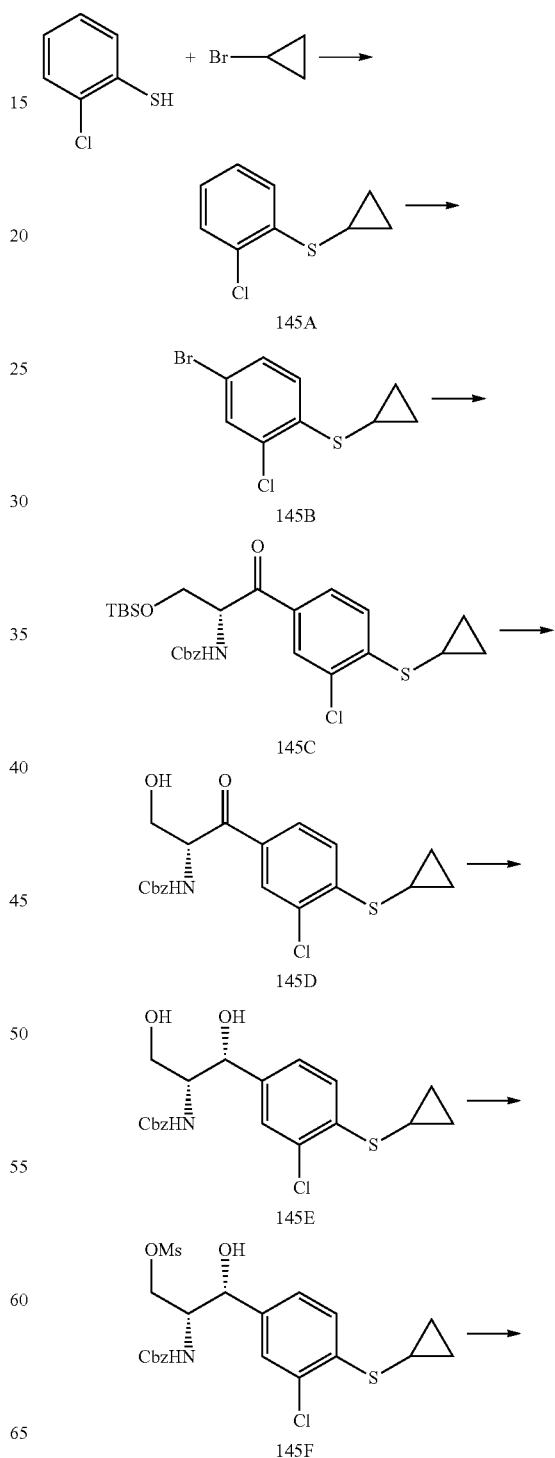

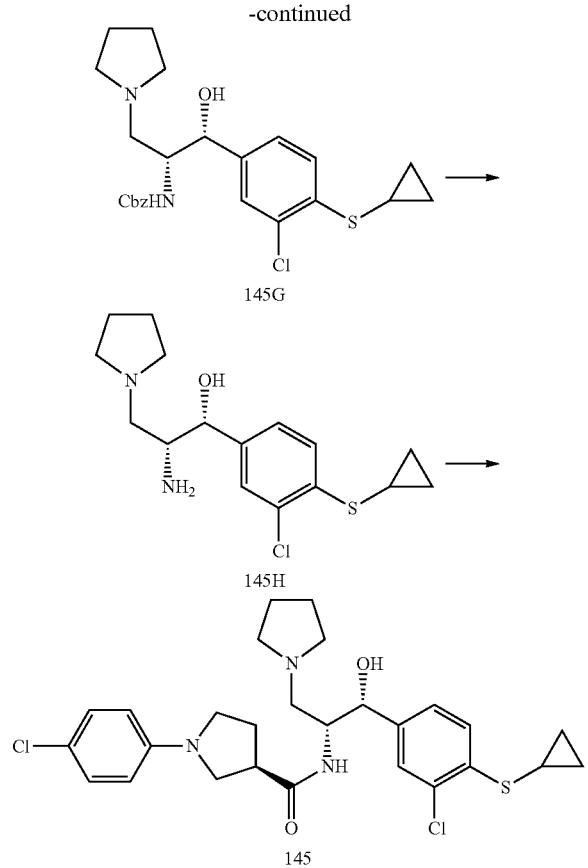

spondingly for Intermediates A5, A6, A7, A8, and A9 using Compounds 145B, 145C, 145D, 145E, and 145F in lieu of 6-bromo-2,3-dihydrobenzo[b][1,4]dioxine, Intermediates A5, A6, A7, and A8.

Compound 145C. LC-MS (ESI) m/z: 520 [M+H]$^+$; $^1$H-NMR (CDCl$_3$, 400 MHz): δ (ppm) −0.12 (s, 3H), −0.10 (s, 3H), 0.84 (s, 9H), 0.85-0.86 (m, 2H), 1.20-1.26 (m, 2H), 2.14-2.16 (m, 1H), 3.89-3.96 (m, 2H), 5.13 (s, 2H), 5.30-5.31 (m, 1H), 7.32-7.40 (m, 4H), 7.49 (d, J=8.4 Hz, 1H), 7.64 (d, J=8.4 Hz, 1H), 7.81-7.84 (m, 1H), 7.89 (d, J=2.0 Hz, 1H).

Compound 145D. LC-MS (ESI) m/z: 406 [M+H]$^+$; $^1$H-NMR (CDCl$_3$, 400 MHz): δ (ppm) 0.74-0.78 (m, 2H), 1.19-1.28 (m, 2H), 2.11-2.16 (m, 1H), 2.74 (s, 1H), 3.87-4.03 (m, 2H), 5.14 (s, 2H), 5.30-5.34 (m, 1H), 6.12 (d, J=6.8 Hz, 1H), 7.34-7.37 (m, 5H), 7.66 (d, J=8.0 Hz, 1H), 7.87 (d, J=8.4 Hz, 1H), 7.93 (s, 1H).

Compound 145E. LC-MS (ESI) m/z: 408 [M+H]$^+$; $^1$H-NMR (CDCl$_3$, 400 MHz): δ (ppm) 0.69-0.73 (m, 2H), 1.10-1.15 (m, 2H), 2.08-2.12 (m, 1H), 2.89 (s, 1H), 3.60 (s, 1H), 3.77-3.85 (m, 3H), 4.97-5.01 (m, 3H), 5.53 (d, J=8.0 Hz, 1H), 7.20-7.24 (m, 2H), 7.26-7.36 (m, 5H), 7.48 (d, J=8.4 Hz, 1H).

Compound 145F, which was directly used for the next step without further purification. LC-MS (ESI) m/z: 468 [M-OH]$^+$.

Compound 145G. LC-MS (ESI) m/z: 461 [M+H]$^+$.

Compound 145H was synthesized, by employing the procedure described for Intermediate E using Compound 145G in lieu of Intermediate E7, which was directly used for the next step without further purification. LC-MS (ESI) m/z: 327 [M+H]$^+$; $^1$H-NMR (CDCl$_3$, 400 MHz): δ (ppm) 0.69-0.73 (m, 2H), 1.12-1.15 (m, 2H), 1.84-1.88 (m, 2H), 2.11-2.16 (m, 1H), 2.24-2.26 (m, 2H), 3.15-3.27 (m, 2H), 3.45-3.58 (m, 4H), 4.38-4.49 (m, 1H), 4.71 (s, 1H), 7.25-7.36 (m, 2H), 7.48 (m, 1H).

Compound 145 was synthesized, by employing the procedure described for Compound 1 using Intermediate Z and Compound 145H in lieu of Compound 1B and Intermediate A. LC-MS (m/z) 534 [M+H]$^+$; $^1$H-NMR (CD$_3$OD, 400 MHz): δ (ppm) 0.55-0.57 (m, 2H), 1.08-1.18 (m, 2H), 2.02-2.22 (m, 7H), 2.45-2.50 (m, 1H), 3.07-3.11 (m, 1H), 3.18-3.24 (m, 5H), 3.49-3.53 (m, 1H), 3.60-3.69 (m, 2H), 3.80-3.87 (m, 1H), 4.57-4.62 (m, 1H), 4.95 (d, J=2.4 Hz, 1H), 6.44 (d, J=8.8 Hz, 2H), 7.13 (d, J=8.8 Hz, 2H), 7.31 (dd, J=8.0, 1.6 Hz, 1H), 7.53-7.56 (m, 2H), 8.12 (d, J=10.0 Hz, 1H).

To a solution of 2-chlorobenzenethiol (7.2 g, 50 mmol) in DMSO (20 mL) was added potassium tert-butoxide (6.7 g, 60 mmol) in portions under nitrogen at 5° C. The reaction mixture was stirred at 25° C. for 15 min. To the above solution was added bromocyclopropane (12 g, 100 mmol) in DMSO (10 mL) dropwise. The reaction mixture was stirred under nitrogen at 80° C. After the reaction mixture was cooled to ambient temperature, the dark solution was diluted with water (400 mL) and extracted with ethyl acetate (60 mL×3). The combined organic phases were washed with brine (50 mL×2), dried over anhydrous sodium sulfate, filtered, and concentrated to afford the crude product. The crude product was purified with flash column chromatography on silica gel (petroleum ether) to furnish Compound 145A. LC-MS (m/z) 185 [M+H]$^+$; $^1$H-NMR (CDCl$_3$, 400 MHz): δ (ppm) 0.71-0.75 (m, 2H), 1.11-1.16 (m, 2H), 2.10-2.16 (m, 1H), 7.05-7.10 (m, 1H), 7.23-7.27 (m, 1H), 7.31 (dd, J=8.0, 1.2 Hz, 1H), 7.55 (dd, J=8.0, 1.2 Hz, 1H).

To a solution of Compound 145A (36 g, 195.6 mmol) in dry dichloromethane (600 mL) was added Br$_2$ (37.6 g, 235 mmol) at 5° C. dropwise. The reaction mixture was stirred at 25° C. for 22 hours. It was washed with water (200 mL), saturated sodium thiosulfate (200 mL) and brine (200 mL), dried over anhydrous sodium sulfate, filtered, and concentrated to afford a crude product. The crude product was purified with flash column chromatography on silica gel (petroleum ether) to furnish Compound 145B. LC-MS (m/z) 263 [M+H]$^+$; $^1$H-NMR (CDCl$_3$, 400 MHz): δ (ppm) 0.71-0.75 (m, 2H), 1.12-1.16 (m, 2H), 2.08-2.12 (m, 1H), 7.37 (d, J=2.0 Hz, 1H), 7.40 (s, 1H), 7.47 (d, J=2.0 Hz, 1H).

Compounds 145C, 145D, 145E, 145F, and 145G were synthesized, by employing the procedures described corre- Example 146

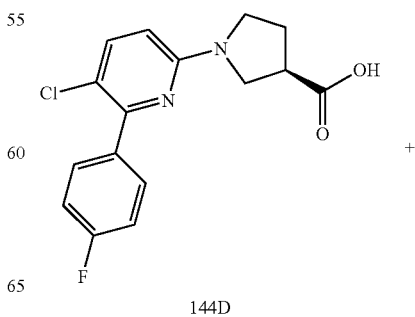

144D

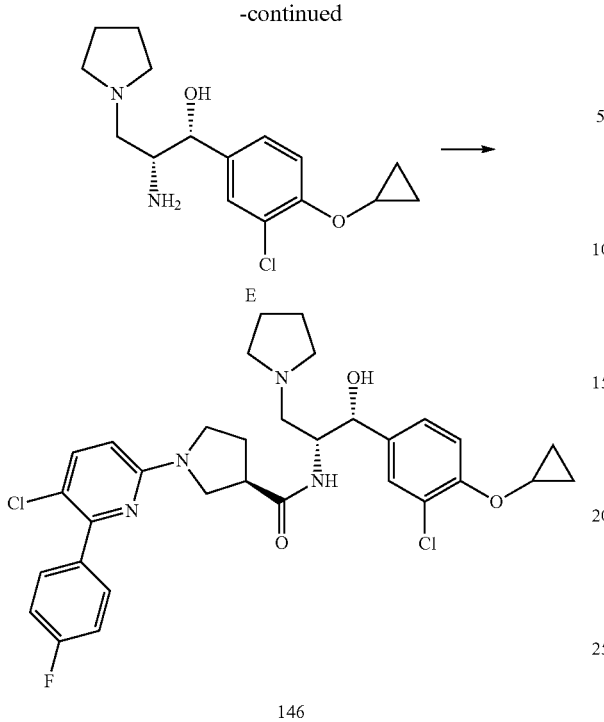

Compound 146 was synthesized, by employing the procedure described for Compound 1 using Compound 144D and Intermediate E in lieu of Compound 1B and Intermediate A. LC-MS (ESI) m/z: 613 [M+H]$^+$; $^1$H-NMR (DMSO-d$_6$, 400 MHz): δ (ppm) 0.57-0.59 (m, 2H), 0.70-0.72 (m, 2H), 1.82-1.91 (m, 2H), 1.98-2.07 (m, 4H), 2.85-2.92 (m, 1H), 3.08-3.17 (m, 3H), 3.22-3.36 (m, 2H), 3.41-3.56 (m, 5H), 3.70-3.76 (m, 1H), 4.33-4.37 (m, 1H), 4.77-4.78 (m, 1H), 5.98 (brs, 1H), 6.38 (d, J=8.8 Hz, 1H), 7.23-7.32 (m, 4H), 7.39 (s, 1H), 7.65 (d, J=8.4 Hz, 1H), 7.73-7.76 (m, 2H), 8.04 (d, J=9.6 Hz, 1H), 9.36 (brs, 1H).

Example 147

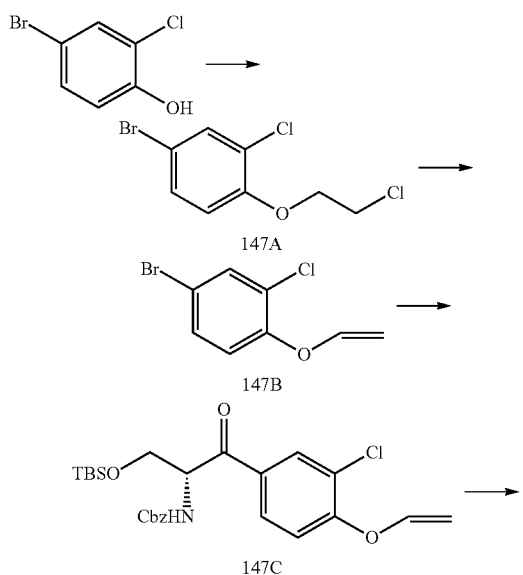

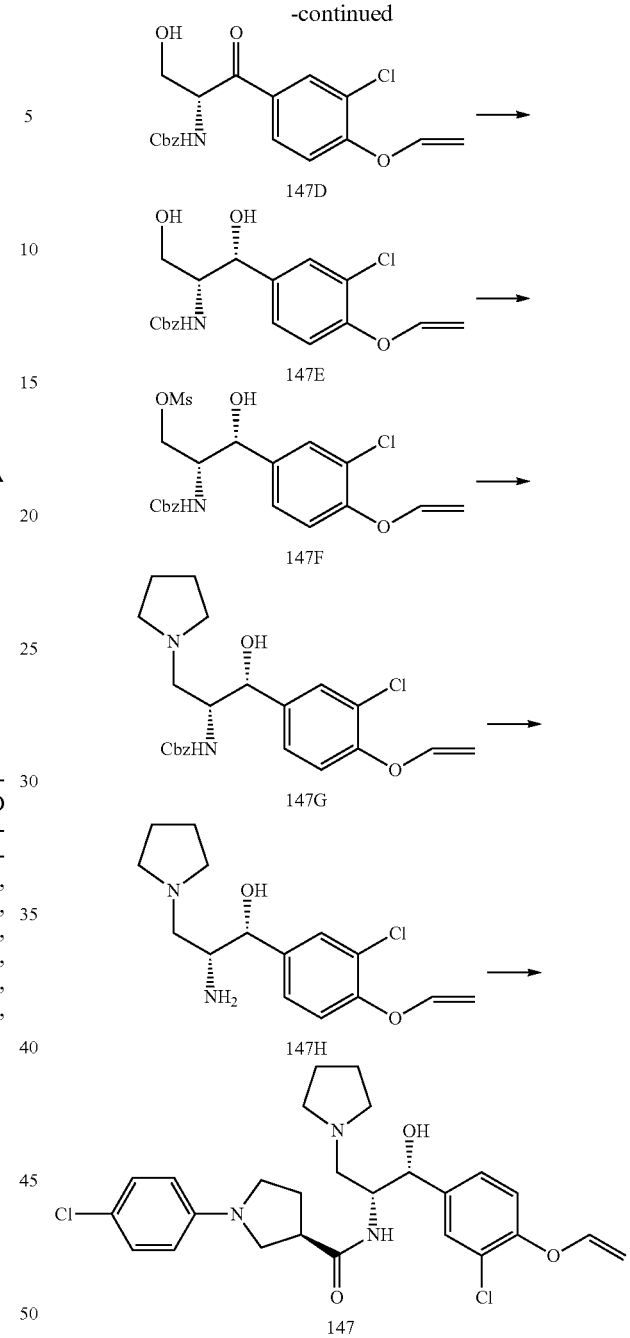

To a solution of 4-bromo-2-chlorophenol (5.04 g, 24.3 mmol) in DMF (30 mL) and was added K$_2$CO$_3$ (10.10 g, 72.9 mmol) and 2-chloroethyl-p-toluenesulfonate (4.86 mL, 26.7 mmol). The resulting mixture was heated to 60° C. for 3 hours and cooled to room temperature. The reaction mixture was diluted with ethyl acetate (150 mL) and washed with water (150 mL×3). The organic phases were dried over anhydrous sodium sulfate and concentrated to furnish Compound 147A. LC-MS (ESI) m/z: 269 [M+H]$^+$.

To a solution of Compound 147A (6.46 g, 24.1 mmol) in DMF (30 mL) was added sodium hydride (1.94 g of 60% dispersion in mineral oil, 48.6 mmol). The resulting mixture was stirred at room temperature for 16 hours. The reaction was diluted with ethyl acetate (150 mL) and washed with water (150 mL×3). The organic phases were dried over anhydrous sodium sulfate and concentrated to afford Compound 147B. LC-MS (ESI) m/z: No.

Compounds 147C, 147D, 147E, 147F, and 147G were synthesized, by employing the procedures described correspondingly for Intermediates A5, A6, A7, A8, and A9 using Compounds 147B, 147C, 147D, 147E, and 147F in lieu of 6-bromo-2,3-dihydrobenzo[b][1,4]dioxine, Intermediates A5, A6, A7, and A8.

Compound 147C. LC-MS (ESI) m/z: 490 [M+H]$^+$.

Compound 147D. LC-MS (ESI) m/z: 376 [M+H]$^+$.

Compound 147E. LC-MS (ESI) m/z: 360 [M-OH]$^+$; $^1$H-NMR (CDCl$_3$, 400 MHz): δ (ppm) 1.62 (s, 1H), 2.37-2.38 (m, 1H), 3.27 (s, 1H), 3.83-3.84 (m, 3H), 4.50 (dd, J=2.0 Hz, 6.0 Hz, 1H), 4.76 (dd, J=1.6 Hz, 13.2 Hz, 1H), 5.02 (s, 2H), 5.46 (s, 1H), 6.54-6.59 (m, 1H), 6.98 (d, J=8.8 Hz, 1H), 7.19-7.22 (m, 1H), 7.27-7.35 (m, 5H), 7.44 (s, 1H).

Compound 147F, which was directly used for the next step without further purification. LC-MS (ESI) m/z: 438 [M-OH]$^+$.

Compound 147G. LC-MS (ESI) m/z: 431 [M+H]$^+$.

Compound 147H was synthesized, by employing the procedure described for Intermediate E using Compound 147G in lieu of Intermediate E7, which was directly used for the next step without further purification. LC-MS (ESI) m/z: 297 [M+H]$^+$.

Compound 147 was synthesized, by employing the procedure described for Compound 1 using Intermediate Z and Compound 147H in lieu of Compound 1B and Intermediate A. LC-MS (ESI) m/z: 504 [M+H]$^+$; $^1$H-NMR (CD$_3$OD, 400 MHz): δ (ppm) 2.03-2.21 (m, 6H), 2.56-2.60 (m, 1H), 3.11-3.29 (m, 6H), 3.48-3.51 (m, 1H), 3.60-3.67 (m, 3H), 4.47 (dd, J=6.0 Hz, 2.0 Hz, 1H), 4.50-4.53 (m, 1H), 4.66 (dd, J=14.0 Hz, 2.0 Hz, 1H), 4.93-4.94 (m, 1H), 6.44 (d, J=9.2 Hz, 2H), 6.57-6.62 (m, 1H), 7.04 (d, J=8.4 Hz, 1H), 7.10-7.14 (m, 2H), 7.32 (dd, J=8.4 Hz, 2.0 Hz, 1H), 7.59 (d, J=1.6 Hz, 1H), 8.13 (d, 1H).

Example 148

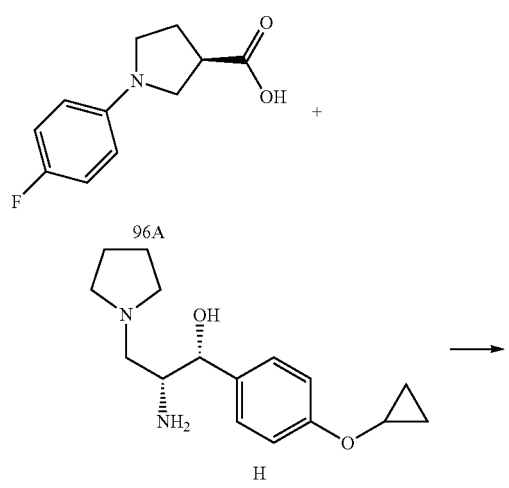

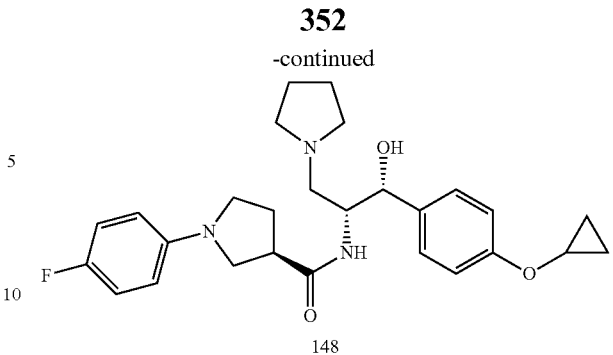

Compound 148 was synthesized, by employing the procedure described for Compound 1 using Intermediate 96A and Intermediate H in lieu of Compound 1B and Intermediate A. LC-MS (ESI) m/z: 468 [M+H]$^+$; $^1$H-NMR (CD$_3$OD, 400 MHz): δ (ppm) 0.57-0.67 (m, 2H), 0.71-0.76 (m, 2H), 1.36-1.39 (m, 1H), 2.02-2.10 (m, 3H), 2.11-2.24 (m, 3H), 2.62-2.66 (m, 1H), 3.10-3.30 (m, 6H), 3.46-3.84 (m, 6H), 4.52-4, 56 (m, 1H), 6.50-6.53 (m, 2H), 6.95 (d, J=8.8 Hz, 2H), 7.02 (d, J=8.8 Hz, 1H), 7.35 (d, J=8.4 Hz, 2H).

Example 149

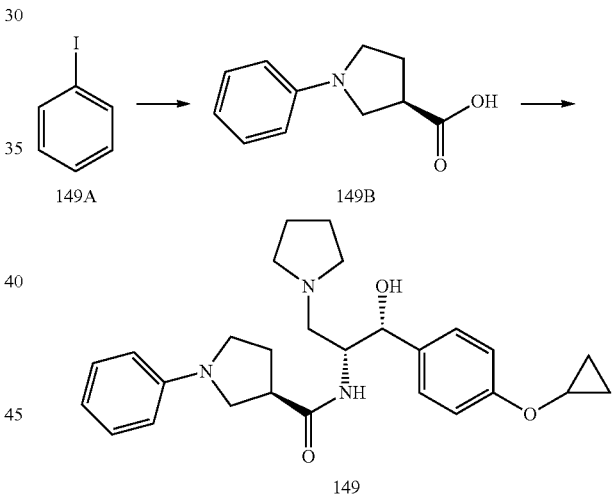

Compounds 149B and 149 were synthesized, by employing the procedures described for Compounds 1B and 1 using Compound 149A, Intermediate Z6, Compound 149B, and Intermediate H in lieu of 1-chloro-4-iodobenzene, Compound 1A, 1B and Intermediate A.

Compound 149B. LC-MS (ESI) m/z: 192 [M+H]$^+$; $^1$H-NMR (CD$_3$OD, 400 MHz): δ (ppm) 2.01-2.07 (m, 2H), 2.88-3.17 (m, 3H), 3.23-3.30 (m, 2H), 6.33-6.41 (m, 3H), 6.91-6.95 (m, 2H).

Compound 149. LC-MS (ESI) m/z: 450 [M+H]$^+$; $^1$H-NMR (CD$_3$OD, 400 MHz): δ (ppm) 0.49-0.60 (m, 2H), 0.66-0.74 (m, 2H), 1.98-2.09 (m, 2H), 2.18-2.41 (m, 4H), 2.84-2.88 (m, 1H), 3.17-3.32 (m, 3H), 3.46-3.62 (m, 6H), 3.67-3.72 (m, 1H), 3.76-3.84 (m, 1H), 4.51-4.55 (m, 1H), 4.98 (d, J=2.4 Hz, 1H), 6.99-7.04 (m, 4H), 7.14 (t, J=7.6 Hz, 1H), 7.33-7.51 (m, 5H).

Example 150

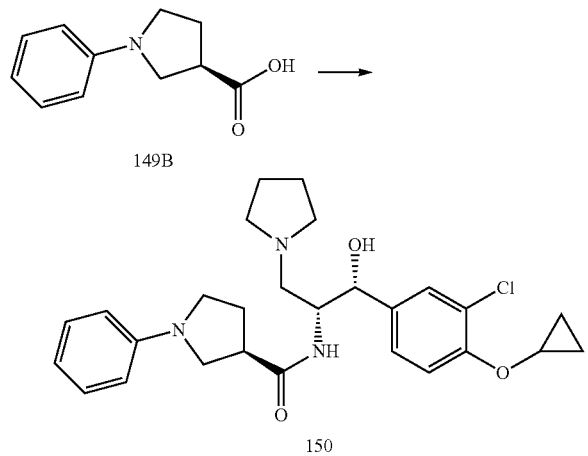

Compound 150 was synthesized, by employing the procedure described for Compound 1 using Intermediate 149B and Intermediate E in lieu of Compound 1B and Intermediate A. LC-MS (ESI) m/z: 484 [M+H]$^+$; $^1$H-NMR (CD$_3$OD, 400 MHz): δ (ppm) 0.58-0.64 (m, 2H), 0.65-0.78 (m, 2H), 2.01-2.17 (m, 2H), 2.20-2.40 (m, 4H), 2.80-2.87 (m, 1H), 3.19-3.32 (m, 3H), 3.50-3.54 (m, 1H), 3.55-3.65 (m, 4H), 3.68-3.72 (m, 2H), 4.52-4.56 (m, 1H), 4.93 (d, J=2.4 Hz, 1H), 7.06 (d, J=8.0 Hz, 2H), 7.18 (t, J=7.6 Hz, 1H), 7.29-7.37 (m, 2H), 7.42 (t, J=8.4 Hz, 2H), 7.48-7.51 (m, 1H).

Example 151

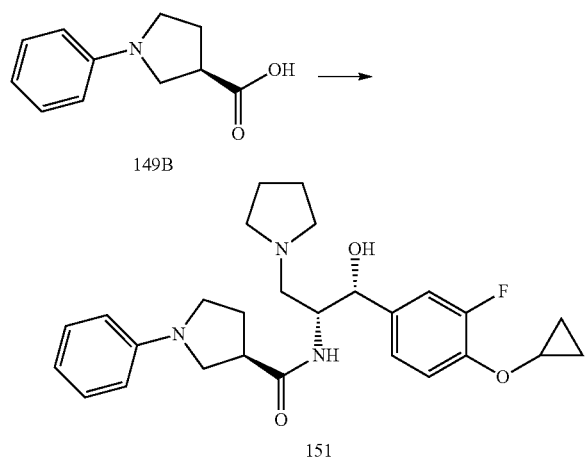

Compound 151 was synthesized, by employing the procedure described for Compound 1 using Intermediate 149B and Intermediate G in lieu of Compound 1B and Intermediate A. LC-MS (ESI) m/z: 468 [M+H]$^+$; $^1$H-NMR (CD$_3$OD, 400 MHz): δ (ppm) 0.61-0.78 (m, 4H), 1.98-2.15 (m, 3H), 2.20-2.27 (m, 3H), 2.61-2.65 (m, 1H), 3.09-3.33 (m, 6H), 3.48-3.61 (m, 2H), 3.63-3.70 (m, 1H), 3.74-3.84 (m, 2H), 4.52-4.56 (m, 1H), 4.91 (d, J=2.4 Hz, 1H), 6.49-6.55 (m, 2H), 6.63-6.70 (m, 1H), 7.13-7.36 (m, 5H).

Example 152

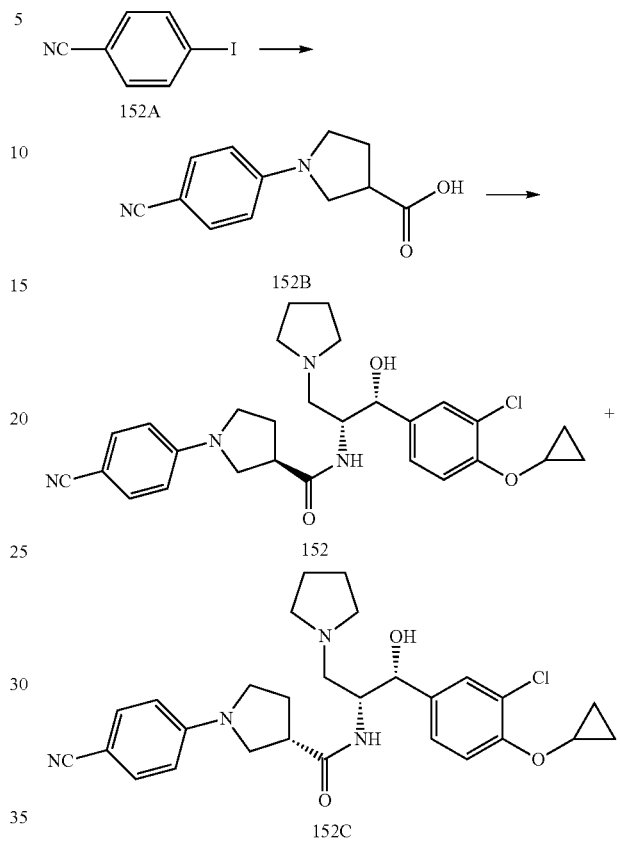

Compounds 152B, 152 and 152C were synthesized, by employing the procedures described for Compounds 1B and 1 using Compound 152A, Compound 152B, and Intermediate E in lieu of 1-chloro-4-iodobenzene, Compound 1B and Intermediate A.

Compound 152B. LC-MS (ESI) m/z: 217 [M+H]$^+$.

Compound 152. LC-MS (ESI) m/z: 509 [M+H]$^+$; $^1$H-NMR (CD$_3$OD, 400 MHz): δ (ppm) 0.61-0.75 (m, 4H), 1.64-1.73 (m, 4H), 1.82-1.87 (m, 3H), 2.09-2.19 (m, 1H), 2.46-2.52 (m, 5H), 2.70-2.74 (m, 1H), 3.20-3.24 (m, 1H), 3.52-3.54 (m, 1H), 3.74-3.77 (m, 1H), 3.97-3.99 (m, 1H), 4.14-4.15 (m, 1H), 4.77 (d, J=2.4 Hz, 1H), 6.35 (d, J=8.4 Hz, 2H), 7.15-7.25 (m, 2H), 7.32 (d, J=8.4 Hz, 2H), 7.38 (s, 1H). Chiral-HPLC condition, solvent: MeOH (0.1% NH$_4$OH), column: RegisCell (4.6*250 mm, 5 μm), Rt: 3.76 min.

Compound 152C. LC-MS (ESI) m/z: 509 [M+H]$^+$; $^1$H-NMR (CD$_3$OD, 400 MHz): δ (ppm) 0.58-0.72 (m, 4H), 1.72-1.77 (m, 4H), 2.06-2.12 (m, 2H), 2.55-2.62 (m, 4H), 2.70-2.72 (m, 2H), 2.80-2.82 (m, 1H), 3.03-3.07 (m, 1H), 3.24-3.26 (m, 1H), 3.32-3.37 (m, 1H), 3.67-3.69 (m, 1H), 3.67-3.69 (m, 1H), 4.20-4.21 (m, 1H), 4.84 (d, J=2.4 Hz, 1H), 6.48 (d, J=8.4 Hz, 2H), 7.13-7.20 (m, 2H), 7.36 (s, 1H), 7.39 (d, J=8.4 Hz, 2H). Chiral-HPLC condition, solvent: MeOH (0.1% NH$_4$OH), column: RegisCell (4.6*250 mm, 5 μm), Rt: 4.98 min.

Example 153

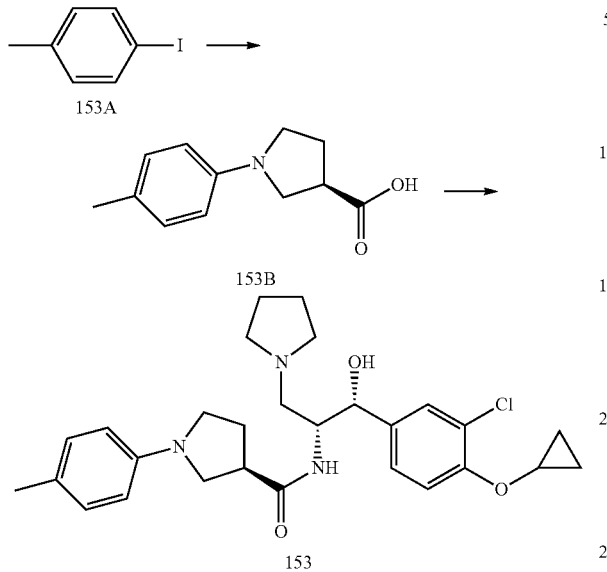

Compounds 153B and 153 were synthesized, by employing the procedures described for Compounds 1B and 1 using Compound 153A, Intermediate Z6, Compound 153B, and Intermediate E in lieu of 1-chloro-4-iodobenzene, Compounds 1A, 1B and Intermediate A.

Compound 153B. LC-MS (ESI) m/z: 206 [M+H]⁺.

Compound 153. LC-MS (ESI) m/z: 498 [M+H]⁺; ¹H-NMR (CD₃OD, 400 MHz): δ (ppm) 0.53-0.68 (m, 4H), 1.73-1.76 (m, 4H), 1.95-2.09 (m, 2H), 2.11 (s, 3H), 2.57-2.74 (m, 7H), 2.93-2.97 (m, 1H), 3.06-3.22 (m, 3H), 3.62-3.66 (m, 1H), 4.17-4.21 (m, 1H), 4.77 (d, J=2.2 Hz, 1H), 6.35 (d, J=8.4 Hz, 2H), 6.87 (d, J=8.4 Hz, 2H), 7.10-7.17 (m, 2H), 7.31 (s, 1H). Chiral-HPLC condition, solvent: n-hexane (0.1% NH₄OH):EtOH (0.1% NH₄OH), column: IA-H (4.6*250 mm, 5 μm), Rt: 7.25 min.

Example 154

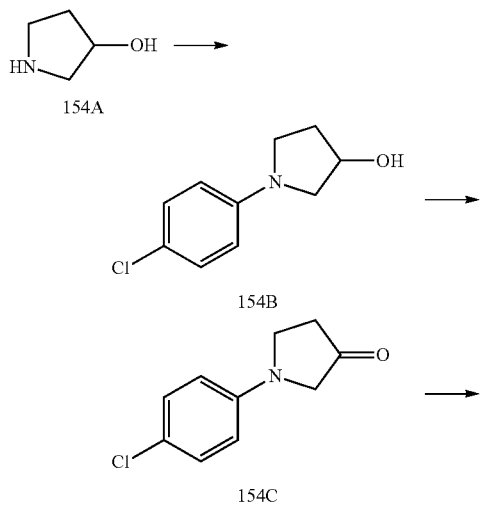

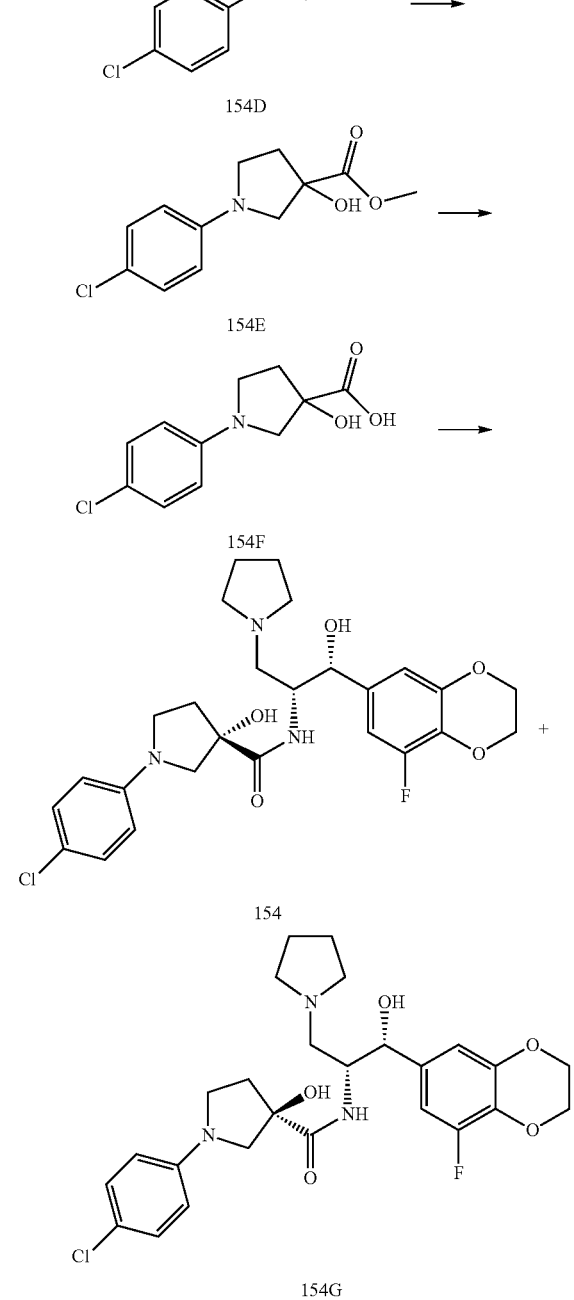

Compound 154B was synthesized, by employing the procedure described for Compound 1B using Compound 154A in lieu of Compound 1A. LC-MS (ESI) m/z: 198 [M+H]⁺; ¹H-NMR (CDCl₃, 400 MHz): δ (ppm) 1.69-1.7 (m, 1H), 2.04-2.08 (m, 1H), 2.13-2.22 (m, 1H), 3.22-3.24 (m, 1H), 3.29-3.33 (m, 1H), 3.44-3.50 (m, 2H), 4.59-4.61 (m, 1H), 6.46 (d, J=8.8 Hz, 2H), 7.16 (d, J=8.8 Hz, 2H).

To a solution of oxalyl dichloride (5.7 g, 44.9 mmol) in dichloromethane (30 mL) was added dropwise DMSO (7.2 g, 73.4 mmol) under nitrogen at −78° C. The mixture was stirred at −78° C. for 30 min and Compound 154B (4.3 g, 21.8 mmol) was added dropwise. The reaction mixture was stirred at −78° C. for 2 h and triethylamine (16 mL) was slowly added to the mixture at −78° C. The mixture was allowed to warm to room temperature and stirred for 2 h. The reaction mixture was quenched with water (50 mL) and diluted with dichloromethane (100 mL). The organic layer was washed with water (50 mL) and brine (50 mL), dried over anhydrous sodium sulfate, concentrated, and purified with flash column chromatography on silica gel (ethyl acetate in petroleum ether, 10% v/v) to give Compound 154C. LC-MS (ESI) m/z: 196 [M+H]$^+$; $^1$H-NMR (CDCl$_3$, 400 MHz): δ (ppm) 2.74 (m, 2H), 3.65-3.68 (m, 4H), 6.58 (d, J=8.8 Hz, 2H), 7.24 (d, J=8.8 Hz, 2H).

To a solution of Compound 154C (415 mg, 2.12 mmol) in methanol (20 mL) was added NaCN (251 mg, 4.5 mmol) and acetic acid (255 mg, 4.5 mmol). The reaction mixture was stirred at room temperature overnight. The mixture was diluted with water (30 mL) and stirred for 30 min and extracted with ethyl acetate (50 mL×2). The organic layer was washed with water (50 mL) and brine (50 mL), dried over anhydrous sodium sulfate, filtered, and concentrated to give Compound 154D. The crude product was directly used for the next step without further purification. LC-MS (ESI) m/z: 223 [M+H]$^+$.

A solution of Compound 154D (1 g, 9.5 mmol) in methanol (20 mL) was stirred at room temperature for 4 h under HCl (gas) atmosphere. The mixture was diluted with water (20 mL) and extracted with ethyl acetate (50 mL×2). The organic layer was washed with water (20 mL) and brine (20 mL), dried over anhydrous sodium sulfate, filtered, and concentrated to give a crude compound. The crude product was purified with reverse flash column chromatography on silica gel using eluent (methanol in water, from 0% to 55% v/v) to furnish Compound 154E. LC-MS (ESI) m/z: 256 [M+H]$^+$; $^1$H-NMR (CD$_3$OD, 400 MHz): δ (ppm) 1.98-2.03 (m, 1H), 2.23-2.31 (m, 1H), 3.34 (d, J=11.2 Hz, 1H), 3.49-3.63 (m, 2H), 3.84 (d, J=12.4 Hz, 1H), 4.8 (s, 3H), 7.13-7.17 (m, 4H).

Compound 154F was synthesized, by employing the procedure described for Compound 5C using Compound 154E in lieu of Compound 5B. LC-MS (ESI) m/z: 242 [M+H]$^+$.

Compounds 154 and 154G were synthesized, by employing the procedures described for Compound 7 using Compound 154F and Intermediate C in lieu of Compound 7B and Intermediate A.

Compound 154. LC-MS (ESI) m/z: 520 [M+H]$^+$; $^1$H-NMR (CD$_3$OD, 400 MHz): δ (ppm) 1.93-2.18 (m, 6H), 3.16-3.28 (m, 3H), 3.36-3.51 (m, 3H), 3.66-3.76 (m, 4H), 4.28 (s, 4H), 4.38-4.41 (m, 1H), 4.80-4.81 (m, 1H), 6.49 (d, J=8.8 Hz, 2H), 6.77-6.79 (m, 2H), 7.12 (d, J=8.8 Hz, 2H). Chiral-HPLC, solvent: n-hexane (0.1% NH$_4$OH):EtOH (0.1% NH$_4$OH)=50:50, column: IA (4.6*250 mm, 5 μm), Rt: 8.01 min.

Compound 154G. LC-MS (ESI) m/z: 520 [M+H]$^+$; $^1$H-NMR (CD$_3$OD, 400 MHz): δ (ppm) 2.03-2.18 (m, 5H), 2.49-2.57 (m, 1H), 3.02-3.05 (m, 1H), 3.13-3.21 (m, 3H), 3.42-3.53 (m, 3H), 3.67-3.74 (m, 3H), 4.3 (s, 4H), 4.41-4.43 (m, 1H), 4.83-4.84 (m, 1H), 6.48 (d, J=8.8 Hz, 2H), 6.76-6.81 (m, 2H), 7.15 (d, J=8.8 hz, 2H). Chiral-HPLC condition, solvent: n-hexane (0.1% NH$_4$OH):EtOH (0.1% NH$_4$OH)=50:50, column: IA (4.6*250 mm, 5 μm), Rt: 10.90 min.

Example 155

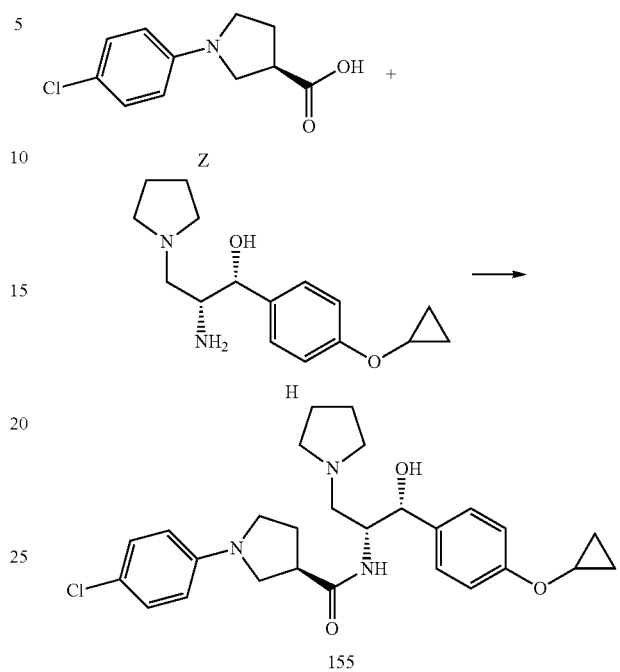

Compound 155 was synthesized, by employing the procedure described for Compound 7 using Intermediates Z and H in lieu of Compound 7B and Intermediate A. LC-MS (ESI) m/z: 484 [M+H]$^+$; $^1$H-NMR (CD$_3$OD, 400 MHz): δ (ppm) 0.53-0.78 (m, 4H), 1.95-2.24 (m, 6H), 2.64 (dd, J=9.3, 6.7 Hz, 1H), 3.07-3.30 (m, 6H), 3.47-3.69 (m, 4H), 3.76-3.86 (m, 1H), 4.52 (dt, J=10.4, 2.9 Hz, 1H), 4.92 (d, J=2.7 Hz, 1H), 6.48 (d, J=8.9 Hz, 2H), 7.00 (d, J=8.7 Hz, 2H), 7.15 (d, J=8.9 Hz, 2H), 7.34 (d, J=8.6 Hz, 2H).

Example 156

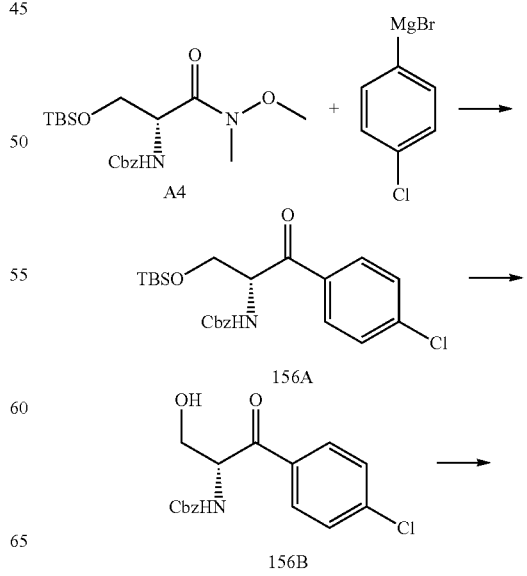

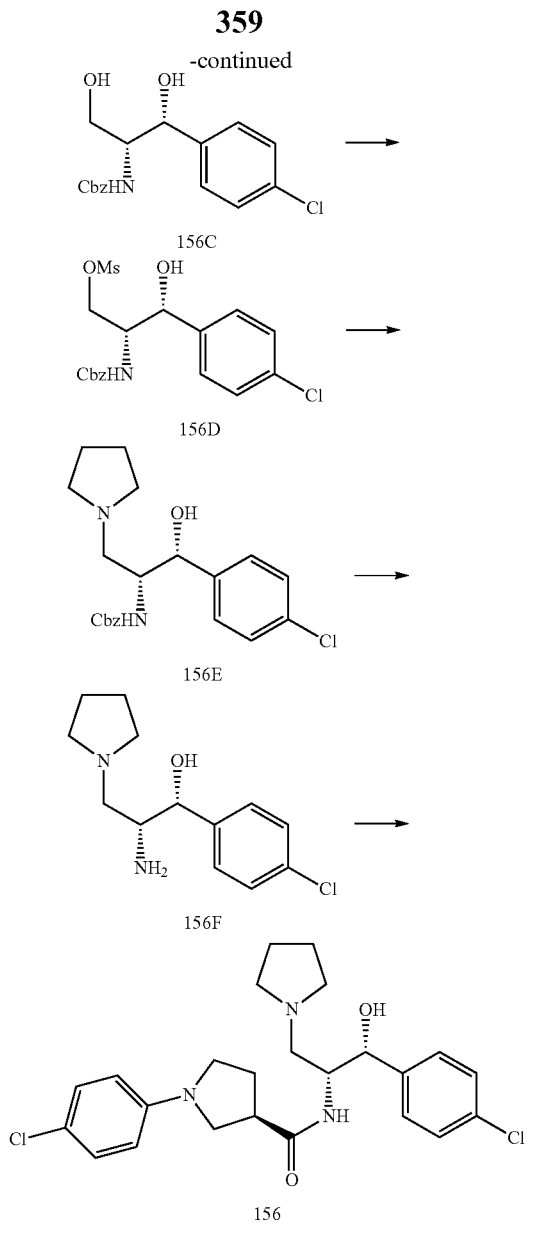

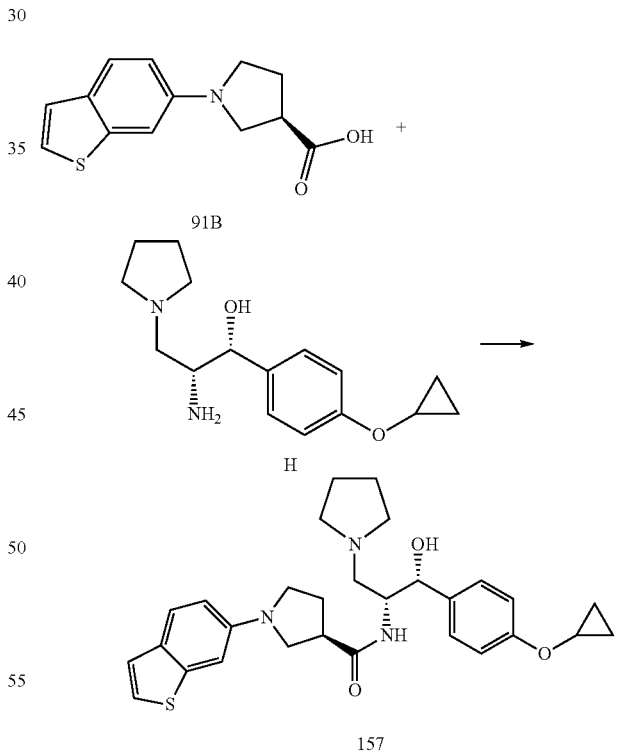

Compound 156B. LC-MS (ESI) m/z: 334 [M+H]$^+$; $^1$H-NMR (CDCl$_3$, 400 MHz): δ (ppm) 2.54 (t, J=6.0 Hz, 1H), 3.88-4.05 (m, 2H), 5.15 (s, 2H), 5.32-5.34 (m, 1H), 6.04-6.05 (m, 1H), 7.34-7.36 (m, 5H), 7.47-7.49 (m, 2H), 7.93-7.95 (m, 2H).

Compound 156C. LC-MS (ESI) m/z: 336 [M+H]$^+$; $^1$H-NMR (CDCl$_3$, 400 MHz): δ (ppm) 2.29 (s, 1H), 3.15 (s, 1H), 3.85-3.86 (m, 3H), 5.02-5.04 (m, 3H), 5.42 (s, 1H), 7.29-7.35 (m, 9H).

Compound 156D. LC-MS (ESI) m/z: 414 [M+H]$^+$.

Compound 156E. LC-MS (ESI) m/z: 389 [M+H]$^+$; $^1$H-NMR (CDCl$_3$, 400 MHz): δ (ppm) 1.77-1.79 (m, 4H), 2.64-2.66 (m, 4H), 2.81-2.87 (m, 2H), 4.01 (s, 1H), 4.98-5.05 (m, 4H), 7.23-7.24 (m, 2H), 7.29-7.37 (m, 7H).

Compound 156F was synthesized, by employing the procedure described for Intermediate E using Compound 156E in lieu of Intermediate E7. LC-MS (ESI) m/z: 255 [M+H]$^+$.

Compound 156 was synthesized, by employing the procedure described for Compound 7 using Intermediate Z and Compound 156F in lieu of Compound 7B and Intermediate A. LC-MS (ESI) m/z: 462 [M+H]$^+$; $^1$H-NMR (DMSO-d$_6$, 400 MHz): δ (ppm) 1.87-2.04 (m, 6H), 2.41-2.45 (m, 1H), 3.08-3.53 (m, 10H), 4.38-4.42 (m, 1H), 4.85-4.85 (m, 1H), 6.01 (s, 1H), 6.40 (d, J=9.2 Hz, 2H), 7.18 (d, J=8.4 Hz, 2H), 7.38 (s, 4H), 7.98 (d, J=9.6 Hz, 1H), 9.32 (s, 1H).

Example 157

To a solution of Intermediate A4 (8.0 g, 20 mmol) in dry THF (200 mL) was added (4-chlorophenyl)magnesium bromide (1 Min 2-methyltetrahydrofuran, 100 mL, 100 mmol) under nitrogen at 0° C. and stirred at room temperature overnight. The mixture was quenched with saturated aqueous ammonium chloride solution (100 mL) and extracted with ethyl acetate (200 mL×3). The organic layer was washed with brine (200 mL), dried over anhydrous sodium sulfate, concentrated, and purified with flash column chromatography on silica gel (ethyl acetate in petroleum ether, 10% v/v) to furnish Compound 156A. LC-MS (ESI) m/z: 448 [M+H]$^+$; $^1$H-NMR (CDCl$_3$, 400 MHz): δ (ppm) 0.12 (s, 3H), 0.16 (s, 3H), 0.74 (s, 9H), 3.88-3.98 (m, 2H), 5.13 (s, 2H), 5.30-5.34 (m, 1H), 5.90-5.91 (m, 1H), 7.32-7.37 (m, 5H), 7.45-7.47 (m, 2H), 7.87-7.89 (m, 2H).

Compounds 156B, 156C, 156D, and 156E were synthesized, by employing the procedures described correspondingly for Intermediates A6, A7, A8, and A9 using Compounds 156A, 156B, 156C, and 156D in lieu of Intermediates A5, A6, A7, and A8.

Compound 157 was synthesized, by employing the procedure described for Compound 7 using Compound 91B and Intermediate H in lieu of Compound 7B and Intermediate A. LC-MS (ESI) m/z: 506 [M+H]$^+$; $^1$H-NMR (CD$_3$OD, 400 MHz): δ (ppm) 0.49-0.69 (m, 4H), 1.95-2.31 (m, 6H), 2.78-2.82 (m, 1H), 3.14-3.28 (m, 3H), 3.34-3.62 (m, 6H), 3.66-3.74 (m, 1H), 3.81-3.87 (m, 1H), 4.53-4.57 (m, 1H), 4.92-4.95 (m, 1H), 6.80 (d, J=8.8 Hz, 1H), 6.98-7.04 (m, 2H), 7.11 (s, 1H), 7.24 (dd, J=14.4, 5.2 Hz, 2H), 7.35 (d, J=8.8 Hz, 2H), 7.70 (d, J=8.4 Hz, 1H).

Example 158

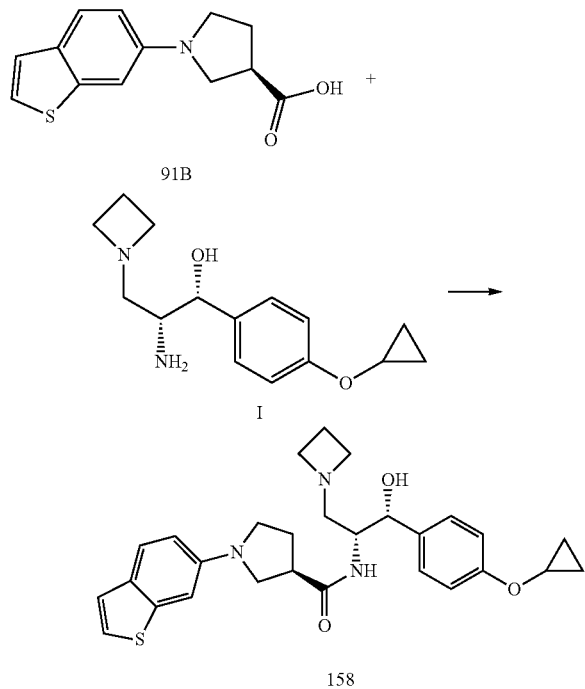

Compound 158 was synthesized, by employing the procedure described for Compound 7 using Compound 91B and Intermediate I in lieu of Compound 7B and Intermediate A. LC-MS (ESI) m/z: 492 [M+H]$^+$; $^1$H-NMR (CD$_3$OD, 400 MHz): δ (ppm) 0.50-0.69 (m, 4H), 2.13-2.21 (m, 1H), 2.26-2.35 (m, 1H), 2.56-2.68 (m, 1H), 2.78-2.82 (m, 1H), 2.80-2.87 (m, 1H), 3.14-3.21 (m, 1H), 3.37-3.50 (m, 4H), 3.53-3.61 (m, 2H), 4.16-4.37 (m, 5H), 4.86-4.91 (m, 1H), 6.80 (d, J=8.8 Hz, 1H), 6.98-7.04 (m, 2H), 7.11 (s, 1H), 7.24 (dd, J=15.6, 5.6 Hz, 2H), 7.35 (d, J=8.4 Hz, 2H), 7.70 (d, J=8.8 Hz, 1H).

Example 159

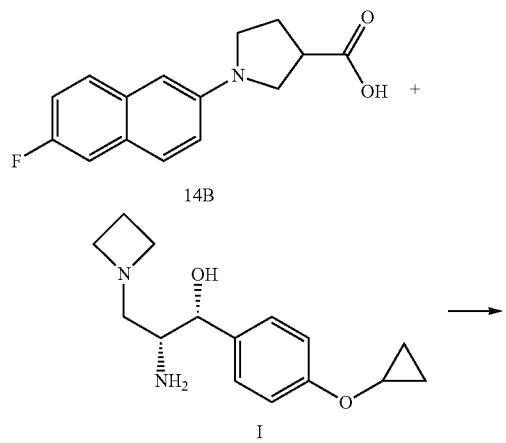

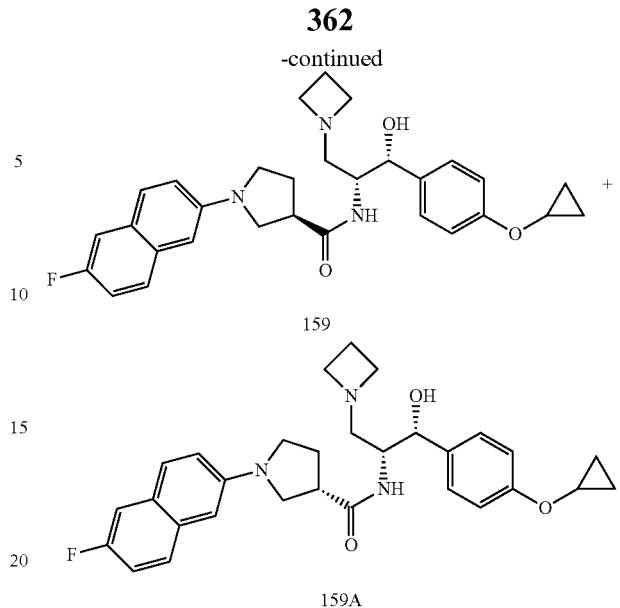

Compound 159 and 159A were synthesized, by employing the procedures described for Compound 7 using Compound 14B and Intermediate I in lieu of Compound 7B and Intermediate A.

Compound 159. LC-MS (ESI) m/z: 504 [M+H]$^+$; $^1$H-NMR (CD$_3$OD, 400 MHz): δ (ppm) 0.46-0.55 (m, 4H), 1.97-2.13 (m, 4H), 2.15-2.26 (m, 2H), 2.92-3.03 (m, 2H), 3.17-3.22 (m, 2H), 3.22-3.34 (m, 5H), 3.46-3.49 (m, 1H), 3.99-4.01 (m, 1H), 4.70 (d, J=3.2 Hz, 1H), 6.63-6.64 (m, 1H), 6.86-6.92 (m, 3H), 7.01-7.06 (m, 1H), 7.16-7.22 (m, 3H), 7.53-7.57 (m, 2H). Chiral-HPLC condition, solvent: MeOH (0.5% NH$_4$OH), column: AD-H (4.6*250 mm, 5 μm), Rt: 3.24 min.

Compound 159A. LC-MS (ESI) m/z: 504 [M+H]$^+$; $^1$H-NMR (CD$_3$OD, 400 MHz): δ (ppm) 0.53-0.69 (m, 4H), 1.65-1.70 (m, 1H), 2.01-2.06 (m, 1H), 2.35-2.46 (m, 2H), 3.03-3.07 (m, 1H), 3.19-3.21 (m, 1H), 3.22-3.23 (m, 1H), 3.36-3.47 (m, 4H), 3.61-3.64 (m, 1H), 4.08-4.14 (m, 4H), 4.21-4.24 (m, 1H), 4.76 (d, J=3.2 Hz, 1H), 6.67-6.68 (m, 1H), 6.90-6.95 (m, 3H), 7.00-7.05 (m, 1H), 7.19-7.24 (m, 3H), 7.50-7.55 (m, 2H). Chiral-HPLC condition, solvent: MeOH (0.5% NH$_4$OH), column: AD-H (4.6*250 mm, 5 μm), Rt: 8.01 min.

Example 160

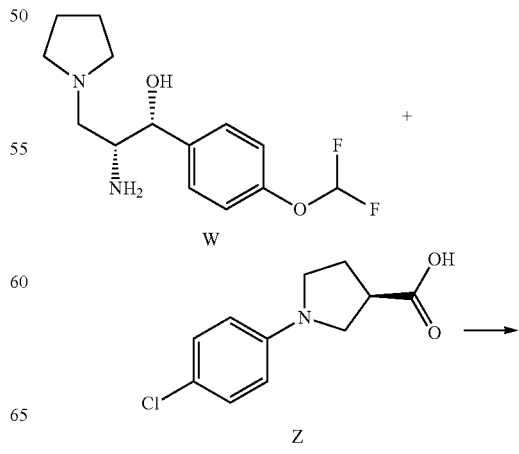

363

-continued

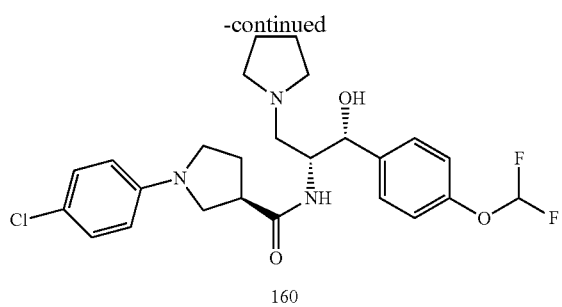

160

Compound 160 was synthesized, by employing the procedure described for Compound 7 using Intermediates Z and W in lieu of Compound 7B and Intermediate A. LC-MS (ESI) m/z: 494 [M+H]$^+$; $^1$H-NMR (acetone-d$_6$, 400 MHz): δ (ppm) 2.09-2.26 (m, 5H), 2.96-2.97 (m, 1H), 3.30-3.52 (m, 6H), 3.80-3.83 (m, 4H), 4.18-4.25 (m, 2H), 4.75-4.82 (m, 1H), 5.17 (d, J=2.8 Hz, 1H), 6.69-6.70 (m, 1H), 6.93 (t, J=74.4 Hz, 1H), 7.16 (d, J=8.4 Hz, 2H), 7.25 (d, J=8.8 Hz, 2H), 7.46 (d, J=8.8 Hz, 1H), 7.53 (d, J=8.8 Hz, 2H).

Example 161

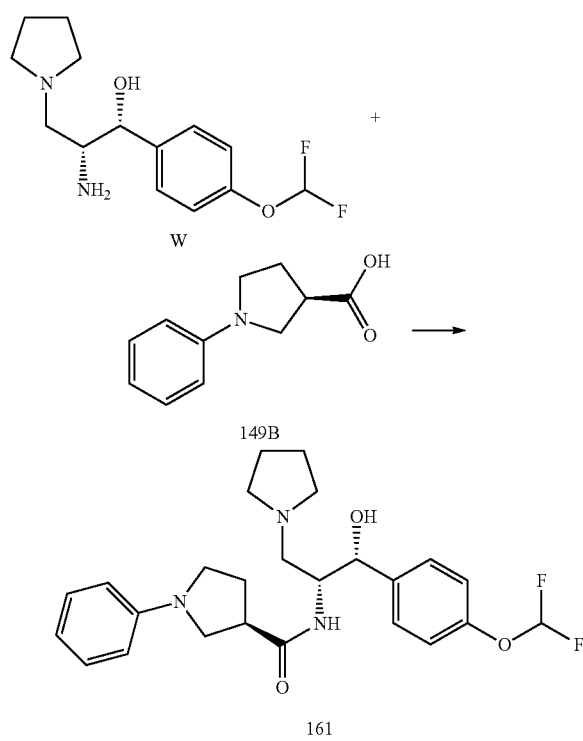

161

Compound 161 was synthesized, by employing the procedure described for Compound 7 using Compound 149B and Intermediate W in lieu of Compound 7B and Intermediate A. LC-MS (ESI) m/z: 460 [M+H]$^+$; $^1$H-NMR (CDCl$_3$, 400 MHz): δ (ppm) 1.74-1.76 (m, 4H), 2.04-2.16 (m, 3H), 2.60-2.69 (m, 4H), 2.81-2.89 (m, 1H), 2.91-2.99 (m, 2H), 3.21-3.27 (m, 3H), 3.34-3.36 (m, 1H), 4.23-4.24 (m, 1H), 5.07 (d, J=2.4 Hz, 1H), 6.46 (t, J=74.0 Hz, 1H), 6.54 (d, J=8.0 Hz, 2H), 6.73 (t, J=7.6 Hz, 1H), 7.07 (d, J=8.8 Hz, 2H), 7.22-7.24 (m, 2H), 7.32 (d, J=8.4 Hz, 2H).

364

Example 162

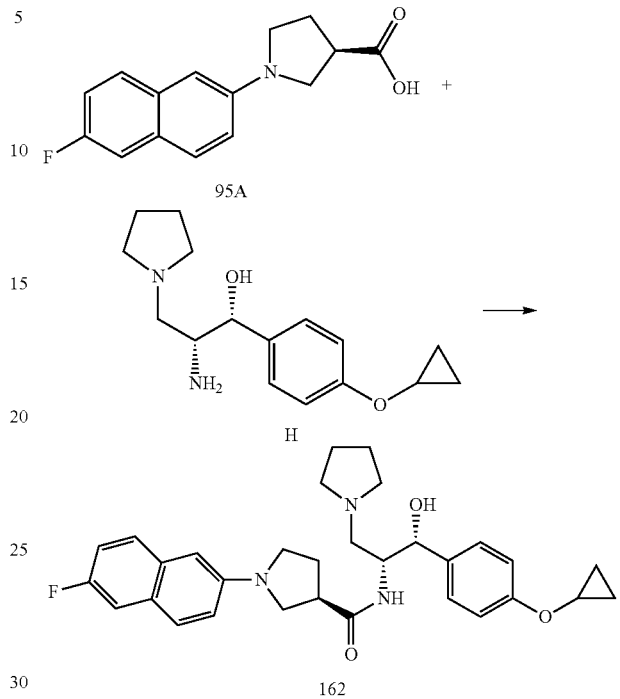

162

Compound 162 was synthesized, by employing the procedure described for Compound 7 using Compound 95A and Intermediate H in lieu of Compound 7B and Intermediate A. LC-MS (ESI) m/z: 518 [M+H]$^+$; $^1$H-NMR (CD$_3$OD, 400 MHz): δ (ppm) 0.49-0.64 (m, 4H), 2.03-2.31 (m, 6H), 2.73-2.77 (m, 1H), 3.26-3.31 (m, 3H), 3.32-3.56 (m, 6H), 3.66-3.70 (m, 1H), 3.83-3.86 (m, 1H), 4.54-4.57 (m, 1H), 4.94 (d, J=2.0 Hz, 1H), 6.73 (s, 1H), 6.99-7.04 (m, 3H), 7.14-7.19 (m, 1H), 7.32-7.38 (m, 3H), 7.66-7.73 (m, 2H), 7.97-7.99 (m, 1H).

BIOLOGICAL EXAMPLES

The following describes ways in which the compounds described herein were tested to measure in vitro activity in enzymatic and cell-based assays. A person of ordinary skill in the art would know that variations in the assay conditions could be used to determine the activity of the compounds.

Assay 1: GCS Enzymatic Assay

This assay was modified based on the study by Larsen et al. (*J. Lipid Res.* 2011, 53, 282). Madin-Darby canine kidney (MDCK) cell lysate was prepared using M-PER Mammalian Protein Extraction Reagent (Thermal Scientific) in the presence of a protease inhibitor cocktail (Roche). Protein concentration was determined using BCA assay kit (Pierce). Sixty micrograms of MDCK cell lysate was incubated with various concentrations of a compound described herein from 0.001 μM-10 μM, respectively, or as indicated in Table 2, in 100 mM Tris buffer (pH 7.5) containing 10 mM MgCl$_2$, 1 mM dithiothreitol, 1 mM EGTA, 2 mM NAD, 100 μM UDP-glucose, 10 μM C6-NBD-Ceramide (Matreya LLC, Pleasant Gap, Pa.), 35 μM dioleoylphosphatidylcholine and 5 μM sulfatide (Sigma) in a final reaction volume of 100 μL at 37° C. for 1 hour. 0.1% DMSO was used as mock treatment or control. The reaction was terminated by adding 100 µL acetonitrile solution and subjected to LC/MS analysis.

The quantitative analysis of NBD-Ceramide and glucosylceramide was performed on a Shimadzu ultra-fast liquid chromatography (Shimadzu, Japan) coupled with API 4000 triple quadrupole mass spectrometer (Applied Biosystems, Concord, Ontario, Canada). Sample separation was conducted on a Waters Xbridge™ BEH130 C18, 100 mm×4.6 mm i.d, 3.5 µm (Milford, Mass., USA). The mobile phase consisted of water and acetonitrile supplemented with 0.1% formic acid (v/v). The flow rate was 1.0 mL/min. The initial mobile phase was 20% acetonitrile and was ramped in a linear fashion to 50% acetonitrile in 0.4 min. From 0.4 to 1.5 min, the gradient was ramped to 98% acetonitrile, and then was held at 100% until 8.0 min. Acetonitrile was reset to 20% in 1.5 min, and maintained until 10.0 min. The total run time was 10.0 min. The MS/MS detection was performed in ESI positive mode. The mass transition of NBD-Ceramide was m/z 576.36→558.40 under the collision energy of 15 V, and the mass transition of glucosylceramide was m/z 738.35→558.40 under 21V collision energy. The cell lysate was diluted with equal volume of acetonitrile. Aliquots of 50 µL diluted samples were added to 1.5 mL tubes, and 100 µL of acetonitrile containing internal standard (100 ng/mL tolbutamide) were added for protein precipitation. The mixture were vortexed and then centrifuged at 13000 rpm for 10 min. 70 µL of supernatant were mixed with 140 µL of $H_2O$ and the final solution were injected for LC/MS/MS analysis and $IC_{50}$'s and/or percent inhibitions calculated.

Assay 2: K562 Cell-based Assay

This assay was modified based on the study by Gupta et al. (*J. Lipid Res.* 2010, 51, 866). K562 cells were seeded into 12-well plates at $3\times10^5$ cells/well/mL in RPMI-1640 medium with 5% FBS and incubated at 37° C. for 24 h. One µL of a compound described herein at desired concentration (10 mM, 1 mM, 0.1 mM, 0.01 mM, 0.001 mM and 0.0001 mM in DMSO) or DMSO was added into the corresponding well and mixed. Cells were incubated at 37° C. for 4 h. Then 100 µL of RPMI-1640 medium containing 110 µM of NBD-Ceramide, 11% BSA, 5% FBS, and corresponding concentration of a compound described herein was added into each well and mixed. Cells were incubated for additional 0.5 h at 37° C., followed by washing the cells with ice-cold PBS (pH 7.4) twice with centrifugation and resuspended with 50 µL cold PBS+1% Triton X-100. The cell lysate was sonicated for 15 min before adding equal volume of methanol for LCMS analysis. A small aliquot of cell lysate was used to determine protein concentration by BCA assay kit. The HPLC equipment and methods used in Assay 1 were used in this assay as well and $IC_{50}$'s were calculated.

Assay 3: NCl/ADR-Res Cell-Based Assay

NCl/ADR-RES cells are seeded into 12-well plates ($4\times10^5$ cells/well) in RPMI-1640 medium with 10% FBS and incubated at 37° C. for 24 h. Before treatment with a compound described herein, cell culture media are removed and replaced with 1 mL per well RPMI-1640 medium containing 5% FBS and a compound as described herein at desired concentrations (10 µM, 1 µM, 0.1 µM, 0.01 µM, 0.001 µM, and 0.0001 µM), respectively, or 0.1% DMSO only. Cells are cultured for 4 hours at 37° C. followed by replacing the media with RPMI-1640 containing 1% BSA and 10 µM of C6-NBD-Ceramide in the present of a compound described herein, and incubated for additional 0.5 hour at 37° C. Cells are then washed twice with ice-cold PBS (pH 7.4), scraped with 50 µL cold PBS+1% Trition X-100. The cell lysate is sonicated for 15 min before adding equal volume of methanol for LCMS analysis. A small aliquot of cell lysate is used to determine protein concentration by BCA assay kit. The HPLC equipment and methods used in Assay 1 are used in this assay as well and $IC_{50}$'s are calculated.

Using the above assays, the following compounds were tested.

TABLE 2

| Example No. | Name | Data Range |
|---|---|---|
| 1C | 1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 2A | 1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | A |
| 3A | N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide | B |
| 1 | (R)-1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 1D | (S)-1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | B |
| 5D | N-((1R,2R)-1-(2,3-dihydrobenzo[b][1,4]dioxin-6-yl)-1-hydroxy-3-(pyrrolidin-1-yl)propan-2-yl)-1-((4-hydroxytetrahydro-2H-pyran-4-yl)methyl)pyrrolidine-3-carboxamide | F |
| 6 | N-((1R,2R)-1-(3-chloro-4-cyclopropoxyphenyl)-1-hydroxy-3-(pyrrolidin-1-yl)propan-2-yl)-1-(4-(trifluoromethyl)phenyl)pyrrolidine-3-carboxamide | F |
| 8D | (S)-1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | E |
| 8 | (R)-1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | D |
| 9D | N-((1R,2R)-1-(2,3-dihydrobenzo[b][1,4]dioxin-6-yl)-1-hydroxy-3-(pyrrolidin-1-yl)propan-2-yl)-1-(tetrahydro-2H-pyran-4-yl)pyrrolidine-3-carboxamide | F |
| 10 | N-((1R,2R)-1-(3-chloro-4-cyclopropoxyphenyl)-1-hydroxy-3-(pyrrolidin-1-yl)propan-2-yl)-1-(4-(trifluoromethoxy)phenyl)pyrrolidine-3-carboxamide | D |
| 5 | (R)-N-((1R,2R)-1-(2,3-dihydrobenzo[b][1,4]dioxin-6-yl)-1-hydroxy-3-(pyrrolidin-1-yl)propan-2-yl)-1-((4-hydroxytetrahydro-2H-pyran-4-yl)methyl)pyrrolidine-3-carboxamide | F |
| 5E | (S)-N-((1R,2R)-1-(2,3-dihydrobenzo[b][1,4]dioxin-6-yl)-1-hydroxy-3-(pyrrolidin-1-yl)propan-2-yl)-1-((4-hydroxytetrahydro-2H-pyran-4-yl)methyl)pyrrolidine-3-carboxamide | F |
| 11 | 1-cyclopentyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | NA |
| 12D | (S)-1-(2,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 12 | (R)-1-(2,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 13 | (R)-1-(4-chlorophenyl)-N-((1R,2R)-1-(6-cyclopropoxypyridin-3-yl)-1-hydroxy-3-(pyrrolidin-1-yl)propan-2-yl)pyrrolidine-3-carboxamide | B |
| 13C | (S)-1-(4-chlorophenyl)-N-((1R,2R)-1-(6-cyclopropoxypyridin-3-yl)-1-hydroxy-3-(pyrrolidin-1-yl)propan-2-yl)pyrrolidine-3-carboxamide | F |

TABLE 2-continued

| Example No. | Name | Data Range |
|---|---|---|
| 14C | N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide | A |
| 2 | (R)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | A |
| 2B | (S)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | F |
| 3 | (S)-N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide | A |
| 3B | (R)-N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide | F |
| 9 | (R)-N-((1R,2R)-1-(2,3-dihydrobenzo[b][1,4]dioxin-6-yl)-1-hydroxy-3-(pyrrolidin-1-yl)propan-2-yl)-1-(tetrahydro-2H-pyran-4-yl)pyrrolidine-3-carboxamide | NA |
| 9E | (S)-N-((1R,2R)-1-(2,3-dihydrobenzo[b][1,4]dioxin-6-yl)-1-hydroxy-3-(pyrrolidin-1-yl)propan-2-yl)-1-(tetrahydro-2H-pyran-4-yl)pyrrolidine-3-carboxamide | NA |
| 15C | 1-(4-chlorobenzyl)-N-((1R,2R)-1-(2,3-dihydrobenzo[b][1,4]dioxin-6-yl)-1-hydroxy-3-)pyrrolidin-1-yl)propan-2-yl)pyrrolidine-3-carboxamide | F |
| 14D | (R)-N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide | F |
| 14 | (S)-N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide | A |
| 36F | N-((1R,2R)-1-(2,3-dihydrobenzo[b][1,4]dioxin-6-yl)-1-3-hydroxy-(pyrrolidin-1-yl)propan-2-yl)-1-(4,5,6,7-tetrahydrobenzo[d]thiazol-2-yl)pyrrolidine-3-carboxamide | F |
| 17D | (S)-N-((1R,2R)-1-(2,3-dihydrobenzo[b][1,4]dioxin-6-yl)-1-hydroxy-3-(pyrrolidin-1-yl)propan-2-yl)-1-(thiazol-2-yl)pyrrolidine-3-carboxamide | NA |
| 19 | 1-(4-chloro-3-cyclopropoxyphenyl)-N-((1R,2R)-1-(2,3-dihydrobenzo[b][1,4]dioxin-6-yl)-1-hydroxy-3-)pyrrolidin-1-yl)propan-2-yl)pyrrolidine-3-carboxamide | E |
| 20D | 1-(3-chloro-4-cyclopropoxyphenyl)-N-((1R,2R)-1-(2,3-dihydrobenzo[b][1,4]dioxin-6-yl)-1-hydroxy-3-)pyrrolidin-1-yl)propan-2-yl)pyrrolidine-3-carboxamide | E |
| 22C | N-((1R,2R)-1-(2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | F |
| 17 | (R)-N-((1R,2R)-1-(2,3-dihydrobenzo[b][1,4]dioxin-6-yl)-1-hydroxy-3-(pyrrolidin-1-yl)propan-2-yl)-1-(thiazol-2-yl)pyrrolidine-3-carboxamide | E |
| 21E | 1-(4-chlorophenethyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 15 | (R)-1-(4-chlorobenzyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 15D | (S)-1-(4-chlorobenzyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 36 | (R)-N-((1R,2R)-1-(2,3-dihydrobenzo[b][1,4]dioxin-6-yl)-1-hydroxy-3-(pyrrolidin-1-yl)propan-2-yl)-1-(4,5,6,7-tetrahydrobenzo[d]thiazol-2-yl)pyrrolidine-3-carboxamide | F |
| 36G | (S)-N-((1R,2R)-1-(2,3-dihydrobenzo[b][1,4]dioxin-6-yl)-1-hydroxy-3-(pyrrolidin-1-yl)propan-2-yl)-1-(4,5,6,7-tetrahydrobenzo[d]thiazol-2-yl)pyrrolidine-3-carboxamide | NA |
| 20 | (R)-1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 20E | (S)-1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 23 | (R)-N-((1R,2R)-1-(3-chloro-4-isopropoxyphenyl)-1-hydroxy-3-(pyrrolidin-1-yl)propan-2-yl)-1-(4-chlorophenyl)pyrrolidine-3-carboxamide | A |
| 23B | (S)-N-((1R,2R)-1-(3-chloro-4-isopropoxyphenyl)-1-hydroxy-3-(pyrrolidin-1-yl)propan-2-yl)-1-(4-chlorophenyl)pyrrolidine-3-carboxamide | F |
| 24B | N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | A |
| 25 | (R)-N-((1R,2R)-3-(azetidin-1-yl)-1-(8-fluoro-2,3-dihydrobenzo[b][1,4]dioxin-6-yl)-1-hydroxypropan-2-yl)-1-(4-chlorophenyl)pyrrolidine-3-carboxamide | A |
| 25B | (S)-N-((1R,2R)-3-(azetidin-1-yl)-1-(8-fluoro-2,3-dihydrobenzo[b][1,4]dioxin-6-yl)-1-hydroxypropan-2-yl)-1-(4-chlorophenyl)pyrrolidine-3-carboxamide | F |
| 26 | 1-cyclohexyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | NA |
| 27 | (R)-N-((1R,2R)-1-(6-cyclopropoxypyridin-3-yl)-1-hydroxy-3-(pyrrolidin-1-yl)propan-2-yl)-1-(4-fluorophenyl)pyrrolidine-3-carboxamide | E |
| 27C | (S)-N-((1R,2R)-1-(6-cyclopropoxypyridin-3-yl)-1-hydroxy-3-(pyrrolidin-1-yl)propan-2-yl)-1-(4-fluorophenyl)pyrrolidine-3-carboxamide | F |
| 28C | 1-(5-chloropyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 22 | (R)-N-((1R,2R)-1-(2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | E |
| 22D | (S)-N-((1R,2R)-1-(2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | F |
| 29 | (R)-1-(4-chlorophenyl)-N-((1R,2R)-1-hydroxy-1-(6-isopropoxypyridin-3-yl)-3-(pyrrolidin-1-yl)propan-2-yl)pyrrolidine-3-carboxamide | F |
| 29B | (S)-1-(4-chlorophenyl)-N-((1R,2R)-1-hydroxy-1-(6-isopropoxypyridin-3-yl)-3-(pyrrolidin-1-yl)propan-2-yl)pyrrolidine-3-carboxamide | F |
| 30 | 1-butyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | NA |
| 31 | (R)-1-(4-fluorophenyl)-N-((1R,2R)-1-hydroxy-1-(6-isopropoxypyridin-3-yl)-3-(pyrrolidin-1-yl)propan-2-yl)pyrrolidine-3-carboxamide | C |
| 31B | (S)-1-(4-fluorophenyl)-N-((1S,2R)-1-hydroxy-1-(6-isopropoxypyridin-3-yl)-3-(pyrrolidin-1-yl)propan-2-yl)pyrrolidine-3-carboxamide | E |
| 32 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(4-fluorophenyl)pyrrolidine-3-carboxamide | A |
| 32A | (S)-N-((1R,2R)-1-(3-chloro-4-((tetrahydro-2H-pyran-4-yl)oxy)phenyl)-1-hydroxy-3-(pyrrolidin-1-yl)propan-2-yl)-1-(4-fluorophenyl)pyrrolidine-3-carboxamide | F |
| 21 | (R)-1-(4-chlorophenethyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 21F | (S)-1-(4-chlorophenethyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 28 | (R)-1-(5-chloropyridin-2-yl)-N((1R,2R)-1-(2,3-dihydrobenzo[b][1,4]dioxin-6-yl)-1-hydroxy-3-(pyrrolidin-1-yl)propan-2-yl)pyrrolidine-3-carboxamide | E |
| 28D | (S)-1-(5-chloropyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | NA |
| 54 | (R)-N-((1R,2R)-1-(3-chloro-4-cyclopropoxyphenyl)-1-hydroxy-3-(pyrrolidin-1-yl)propan-2-yl)-1-(pyridin-2-yl)pyrrolidine-3-carboxamide | A |
| 33 | (R)-1-(4-chlorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide | F |
| 33A | (S)-1-(4-chlorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide | NA |
| 34 | (R)-1-(4-fluorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide | E |
| 34A | (S)-1-(4-fluorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide | NA |

TABLE 2-continued

| Example No. | Name | Data Range |
|---|---|---|
| 24 | (R)-N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | A |
| 24C | (S)-N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | NA |
| 35 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | A |
| 35A | (S)-N-((1R,2R)-1-(8-fluoro-2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide | A |
| 44C | (S)-1-(4-chlorophenyl)-N-((1R,2R)-1-(8-fluoro-2,3-dihydrobenzo[b][1,4]dioxin-6-yl)-1-hydroxy-3-(piperidin-1-yl)propan-2-yl)pyrrolidine-3-carboxamide | NA |
| 44 | (R)-1-(4-chlorophenyl)-N-((1R,2R)-1-(8-fluoro-2,3-dihydrobenzo[b][1,4]dioxin-6-yl)-1-hydroxy-3-(piperidin-1-yl)propan-2-yl)pyrrolidine-3-carboxamide | F |
| 43D | 1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide | F |
| 54A | (S)-N-((1R,2R)-1-(3-chloro-4-cyclopropoxyphenyl)-1-hydroxy-3-(pyrrolidin-1-yl)propan-2-yl)-1-(pyridin-2-yl)pyrrolidine-3-carboxamide | F |
| 45 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(4-chlorophenyl)pyrrolidine-3-carboxamide | A |
| 45A | (S)-N-((1R,2R)-1-(3-chloro-4-((tetrahydro-2H-pyran-4-yl)oxy)phenyl)-1-hydroxy-3-(pyrrolidin-1-yl)propan-2-yl)-1-(4-chlorophenyl)pyrrolidine-3-carboxamide | F |
| 55A | 1-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 56D | 1-(2-cyclopropoxypyridin-4-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 46A | N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide | F |
| 47A | N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide | A |
| 48 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | A |
| 48A | (S)-N-((1R,2R)-1-(8-fluoro-2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide | F |
| 49 | (R)-N-((1R,2R)-1-(3-chloro-4-((1-methylpiperidin-4-yl)oxy)phenyl)-1-hydroxy-3-(pyrrolidin-1-yl)propan-2-yl)-1-(4-chlorophenyl)pyrrolidine-3-carboxamide | B |
| 49A | (S)-N-((1R,2R)-1-(3-chloro-4-((1-methylpiperidin-4-yl)oxy)phenyl)-1-hydroxy-3-(pyrrolidin-1-yl)propan-2-yl)-1-(4-chlorophenyl)pyrrolidine-3-carboxamide | F |
| 50 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(6-fluoronaphthalen-2-yl)pyrrolidine-3-carboxamide | A |
| 50A | (S)-N-((1R,2R)-1-(3-chloro-4-((tetrahydro-2H-pyran-4-yl)oxy)phenyl)-1-hydroxy-3-(pyrrolidin-1-yl)propan-2-yl)-1-(6-fluoronaphthalen-2-yl)pyrrolidine-3-carboxamide | E |
| 51 | (R)-1-(4-chlorophenyl)-N-((1R,2R)-1-(2,2-dimethylchroman-6-yl)-1-hydroxy-3-(pyrrolidin-1-yl)propan-2-yl)pyrrolidine-3-carboxamide | F |
| 51A | (S)-1-(4-chlorophenyl)-N-((1R,2R)-1-(2,2-dimethylchroman-6-yl)-1-hydroxy-3-(pyrrolidin-1-yl)propan-2-yl)pyrrolidine-3-carboxamide | NA |
| 43 | (R)-1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide | F |
| 43E | (S)-1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide | F |
| 56 | (R)-1-(2-cyclopropoxypyridin-4-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 56E | (S)-1-(2-cyclopropoxypyridin-4-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 52 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide | A |
| 52A | (S)-N-((1R,2R)-1-(8-fluoro-2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide | E |
| 55 | (R)-1-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 55B | (S)-1-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 46 | (R)-N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide | F |
| 46B | (S)-N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide | NA |
| 53C | 1-(benzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | B |
| 47 | (R)-N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide | A |
| 47B | (S)-N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide | B |
| 57A | (S)-N-((1R,2R)-1-(3-chloro-4-cyclopropoxyphenyl)-1-hydroxy-3-(pyrrolidin-1-yl)propan-2-yl)-1-(5-chloropyridin-2-yl)pyrrolidine-3-carboxamide | A |
| 57 | (R)-N-((1R,2R)-1-(3-chloro-4-cyclopropoxyphenyl)-1-hydroxy-3-(pyrrolidin-1-yl)propan-2-yl)-1-(5-chloropyridin-2-yl)pyrrolidine-3-carboxamide | F |
| 58 | (R)-1-(6-cyclopropoxypyridin-3-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | E |
| 58D | (S)-1-(6-cyclopropoxypyridin-3-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 59 | (R)-N-((1R,2R)-1-(3-chloro-4-(oxetan-3-yloxy)phenyl)-1-hydroxy-3-(pyrrolidin-1-yl)propan-2-yl)-1-(4-chlorophenyl)pyrrolidine-3-carboxamide | F |
| 60 | (R)-N-((1R,2R)-1-(4-(2-(azetidin-1-yl)ethoxy)-3-chlorophenyl)-1-hydroxy-3-(pyrrolidin-1-yl)propan-2-yl)-1-(4-chlorophenyl)pyrrolidine-3-carboxamide | A |
| 60A | (S)-N-((1R,2R)-1-(4-(2-(azetidin-1-yl)ethoxy)-3-chlorophenyl)-1-hydroxy-3-(pyrrolidin-1-yl)propan-2-yl)-1-(4-chlorophenyl)pyrrolidine-3-carboxamide | NA |
| 61C | N-((1R,2R)-1-(2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide | A |
| 62 | (R)-1-(4-chlorophenyl)-N-((1R,2R)-1-hydroxy-1-(6-(oxetan-3-yloxy)pyridin-3-yl)-3-(pyrrolidin-1-yl)propan-2-yl)pyrrolidine-3-carboxamide | NA |
| 63C | N-((1R,2R)-1-(2,3-dihydrobenzo[b][1,4]dioxin-6-yl)-1-hydroxy-3-(pyrrolidin-1-yl)propan-2-yl)-1-(2-methyl-1,2,3,4-tetrahydroisoquinolin-7-yl)pyrrolidine-3-carboxamide | F |
| 64 | N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-6-yl)pyrrolidine-3-carboxamide | F |
| 65 | (R)-1-(4-chlorophenyl)-N-((1R,2R)-1-(4-cyclopropoxy-3-fluorophenyl)-1-hydroxy-3-(pyrrolidin-1-yl)propan-2-yl)pyrrolidine-3-carboxamide | A |
| 66 | (R)-N-((1R,2R)-1-(3-chloro-4-cyclopropoxyphenyl)-1-hydroxy-3-(piperidin-1-yl)propan-2-yl)-1-(4-chlorophenyl)pyrrolidine-3-carboxamide | F |
| 67C | (S)-N-((1R,2R)-1-(3-chloro-4-cyclopropoxyphenyl)-1-hydroxy-3-(pyrrolidin-1-yl)propan-2-yl)-1-(naphthalen-2-yl)pyrrolidine-3-carboxamide | E |
| 68C | (S)-N-((1R,2S)-1-(8-fluoro-2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | F |

TABLE 2-continued

| Example No. | Name | Data Range |
|---|---|---|
| 61 | (R)-N-((1R,2R)-1-(2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide | NA |
| 61D | (S)-N-((1R,2R)-1-(2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide | A |
| 69 | (R)-N-((1R,2R)-1-(4-cyclopropoxy-3-fluorophenyl)-1-hydroxy-3-(pyrrolidin-1-yl)propan-2-yl)-1-(4-fluorophenyl)pyrrolidine-3-carboxamide | A |
| 69A | (S)-N-((1R,2R)-1-(4-cyclopropoxy-3-fluorophenyl)-1-hydroxy-3-(pyrrolidin-1-yl)propan-2-yl)-1-(4-fluorophenyl)pyrrolidine-3-carboxamide | F |
| 70 | (R)-N-((1R,2R)-1-(2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide | A |
| 70A | (S)-N-((1R,2R)-1-(2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide | E |
| 71E | N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-7-yl)pyrrolidine-3-carboxamide | E |
| 72A | N-((1R,2R)-1-(2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | D |
| 73 | (R)-N-((1R,2R)-3-(azetidin-1-yl)-1-(3-chloro-4-cyclopropoxyphenyl)-1-hydroxypropan-2-yl)-1-(4-chlorophenyl)pyrrolidine-3-carboxamide | A |
| 67 | (R)-N-((1R,2R)-1-(3-chloro-4-cyclopropoxyphenyl)-1-hydroxy-3-(pyrrolidin-1-yl)propan-2-yl)-1-(naphthalen-2-yl)pyrrolidine-3-carboxamide | A |
| 53 | (R)-1-(benzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | E |
| 53D | (S)-1-(benzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 74 | (R)-N-((1R,2R)-1-(3-chloro-4-morpholinophenyl)-1-hydroxy-3-(pyrrolidin-1-yl)propan-2-yl)-1-(4-chlorophenyl)pyrrolidine-3-carboxamide | D |
| 74C | (S)-N-((1R,2R)-1-(3-chloro-4-morpholinophenyl)-1-hydroxy-3-(pyrrolidin-1-yl)propan-2-yl)-1-(4-chlorophenyl)pyrrolidine-3-carboxamide | NA |
| 75 | (R)-N-((1R,2R)-1-(3-chloro-4-cyclopropoxyphenyl)-1-hydroxy-3-(pyrrolidin-1-yl)propan-2-yl)-1-(3-(pyridin-2-yloxy)phenyl)pyrrolidine-3-carboxamide | A |
| 75E | (S)-N-((1R,2R)-1-(3-chloro-4-cyclopropoxyphenyl)-1-hydroxy-3-(pyrrolidin-1-yl)propan-2-yl)-1-(3-(pyridin-2-yloxy)phenyl)pyrrolidine-3-carboxamide | D |
| 76D | 1-(2-chlorobenzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 77 | N-[2-(2H,3H-benzo[e]1,4-dioxan-6-yl)(1R,2R)-2-hydroxy-1-(pyrrolidinylmethyl)ethyl][1-(4-chlorophenyl)pyrrolidin-3-yl]carboxamide | A |
| 78 | (R)-N-((1R,2R)-3-(azetidin-1-yl)-1-(2,3-dihydrobenzo[b][1,4]dioxin-6-yl)-1-hydroxypropan-2-yl)-1-(4-chlorophenyl)pyrrolidine-3-carboxamide | A |
| 72 | (R)-N-((1R,2R)-1-(2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | A |
| 72B | (S)-N-((1R,2R)-1-(2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | F |
| 71 | (R)-N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-7-yl)pyrrolidine-3-carboxamide | B |
| 71F | (S)-N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-7-yl)pyrrolidine-3-carboxamide | F |
| 79A | N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide | A |
| 80G | N-((1R,2R)-1-(2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | A |
| 68 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide | A |
| 63 | (R)-N-((1R,2R)-1-(2,3-dihydrobenzo[b][1,4]dioxin-6-yl)-1-hydroxy-3-(pyrrolidin-1-yl)propan-2-yl)-1-(2-methyl-1,2,3,4-tetrahydroisoquinolin-7-yl)pyrrolidine-3-carboxamide | F |
| 63D | (S)-N-((1R,2R)-1-(2,3-dihydrobenzo[b][1,4]dioxin-6-yl)-1-hydroxy-3-(pyrrolidin-1-yl)propan-2-yl)-1-(2-methyl-1,2,3,4-tetrahydroisoquinolin-7-yl)pyrrolidine-3-carboxamide | NA |
| 76E | (S)-1-(2-chlorobenzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 76 | (R)-1-(2-chlorobenzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | B |
| 81 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide | A |
| 82 | (R)-N-((1R,2R)-1-(2,3-dihydrobenzo[b][1,4]dioxin-6-yl)-1-hydroxy-3-(pyrrolidin-1-yl)propan-2-yl)-1-(2,6-dimethylpyridin-4-yl)pyrrolidine-3-carboxamide | NA |
| 82E | (S)-N-((1R,2R)-1-(2,3-dihydrobenzo[b][1,4]dioxin-6-yl)-1-hydroxy-3-(pyrrolidin-1-yl)propan-2-yl)-1-(2,6-dimethylpyridin-4-yl)pyrrolidine-3-carboxamide | NA |
| 83C | N-((1R,2R)-1-(2,3-dihydrobenzo[b][1,4]dioxin-6-yl)-1-hydroxy-3-(pyrrolidin-1-yl)propan-2-yl)-1-(quinoxalin-6-yl)pyrrolidine-3-carboxamide | F |
| 84 | (R)-N-((1R,2R)-1-(3-chloro-4-cyclopropoxyphenyl)-1-hydroxy-3-(pyrrolidin-1-yl)propan-2-yl)-1-(6-fluoronaphthalen-2-yl)pyrrolidine-3-carboxamide | A |
| 84A | (S)-N-((1R,2R)-1-(3-chloro-4-cyclopropoxyphenyl)-1-hydroxy-3-(pyrrolidin-1-yl)propan-2-yl)-1-(6-fluoronaphthalen-2-yl)pyrrolidine-3-carboxamide | F |
| 79 | (R)-N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide | A |
| 79B | (S)-N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide | E |
| 80 | (R)-N-((1R,2R)-1-(2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | E |
| 80H | (S)-N-((1R,2R)-1-(2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | A |
| 85 | (R)-N-((1R,2R)-3-(azetidin-1-yl)-1-(8-fluoro-2,3-dihydrobenzo[b][1,4]dioxin-6-yl)-1-hydroxypropan-2-yl)-1-(naphthalen-2-yl)pyrrolidine-3-carboxamide | A |
| 86 | (R)-N-((1R,2R)-3-(azetidin-1-yl)-1-(3-chloro-4-cyclopropoxyphenyl)-1-hydroxypropan-2-yl)-1-(naphthalen-2-yl)pyrrolidine-3-carboxamide | A |
| 87 | (R)-N-((1R,2R)-1-(3-chloro-4-(2-hydroxy-2-methylpropoxy)phenyl)-1-hydroxy-3-(pyrrolidin-1-yl)propan-2-yl)-1-(4-chlorophenyl)pyrrolidine-3-carboxamide | A |
| 88C | 1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | D |
| 89F | N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide | A |
| 90 | (R)-N-((1R,2R)-1-(2,3-dihydrobenzo[b][1,4]dioxin-6-yl)-1-hydroxy-3-(pyrrolidin-1-yl)propan-2-yl)-1-(1,5-naphthyridin-3-yl)pyrrolidine-3-carboxamide | F |
| 90D | (S)-N-((1R,2R)-1-(2,3-dihydrobenzo[b][1,4]dioxin-6-yl)-1-hydroxy-3-(pyrrolidin-1-yl)propan-2-yl)-1-(1,5-naphthyridin-3-yl)pyrrolidine-3-carboxamide | F |
| 92 | (R)-1-(benzo[b]thiophen-6-yl)-N-((1R,2R)-1-(3-chloro-4-((tetrahydro-2H-pyran-4-yl)oxy)phenyl)-1-hydroxy-3-(pyrrolidin-1-yl)propan-2-yl)pyrrolidine-3-carboxamide | A |
| 83 | (R)-N-((1R,2R)-1-(2,3-dihydrobenzo[b][1,4]dioxin-6-yl)-1-hydroxy-3-(pyrrolidin-1-yl)propan-2-yl)-1-(quinoxalin-6-yl)pyrrolidine-3-carboxamide | F |
| 83D | (S)-N-((1R,2R)-1-(2,3-dihydrobenzo[b][1,4]dioxin-6-yl)-1-hydroxy-3-(pyrrolidin-1-yl)propan-2-yl)-1-(quinoxalin-6-yl)pyrrolidine-3-carboxamide | NA |

TABLE 2-continued

| Example No. | Name | Data Range |
|---|---|---|
| 88 | (R)-1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | D |
| 88D | (S)-1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 89 | (R)-N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide | A |
| 89G | (S)-N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide | E |
| 93 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | A |
| 93A | (S)-N-((1R,2R)-1-(8-fluoro-2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide | E |
| 91 | (R)-1-(benzo[b]thiophen-6-yl)-N-((1R,2R)-1-(3-chloro-4-cyclopropoxyphenyl)-1-hydroxy-3-(pyrrolidin-1-yl)propan-2-yl)pyrrolidine-3-carboxamide | A |
| 94 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(naphthalen-2-yl)pyrrolidine-3-carboxamide | A |
| 95 | (R)-N-((1R,2R)-3-(azetidin-1-yl)-1-(3-chloro-4-cyclopropoxyphenyl)-1-hydroxypropan-2-yl)-1-(6-fluoronaphthalen-2-yl)pyrrolidine-3-carboxamide | D |
| 96 | (R)-N-((1R,2R)-1-(3-chloro-4-cyclopropoxyphenyl)-1-hydroxy-3-(pyrrolidin-1-yl)propan-2-yl)-1-(4-fluorophenyl)pyrrolidine-3-carboxamide | A |
| 97 | (R)-1-(benzo[b]thiophen-6-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | A |
| 97C | (S)-1-(benzo[b]thiophen-6-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | E |
| 98 | (R)-N-((1R,2R)-1-(3-chloro-4-cyclopropoxyphenyl)-1-hydroxy-3-(pyrrolidin-1-yl)propan-2-yl)-1-(5,6,7,8-tetrahydronaphthalen-2-yl)pyrrolidine-3-carboxamide | D |
| 98A | (S)-N-((1R,2R)-1-(3-chloro-4-cyclopropoxyphenyl)-1-hydroxy-3-(pyrrolidin-1-yl)propan-2-yl)-1-(5,6,7,8-tetrahydronaphthalen-2-yl)pyrrolidine-3-carboxamide | F |
| 99C | 1-(6-chloroquinolin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 100 | (R)-N-((1R,2R)-1-(3-chloro-4-cyclopropoxyphenyl)-1-hydroxy-3-(pyrrolidin-1-yl)propan-2-yl)-1-(6-chloroquinolin-2-yl)pyrrolidine-3-carboxamide | A |
| 101 | (R)-N-((1R,2R)-1-(3-chloro-4-((tetrahydro-2H-pyran-4-yl)oxy)phenyl)-1-hydroxy-3-(pyrrolidin-1-yl)propan-2-yl)-1-(2-chlorobenzo[b]thiophen-6-yl)pyrrolidine-3-carboxamide | A |
| 102 | (R)-N-((1R,2R)-1-(3-chloro-4-(2-hydroxy-2-methylpropoxy)phenyl)-1-hydroxy-3-(pyrrolidin-1-yl)propan-2-yl)-1-(6-fluoronaphthalen-2-yl)pyrrolidine-3-carboxamide | A |
| 103 | (R)-1-(4-chloro-3-(pyridin-2-yloxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide | A |
| 104 | (R)-1-(6-chloroquinolin-2-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | A |
| 105 | (R)-1-(4-chloro-3-(pyridin-2-yloxy)phenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | A |
| 106 | (R)-N-((1R,2R)-1-(2,3-dihydrobenzo[b][1,4]dioxin-6-yl)-1-hydroxy-3-(pyrrolidin-1-yl)propan-2-yl)-1-(quinolin-7-yl)pyrrolidine-3-carboxamide | D |
| 107 | (R)-N-((1R,2R)-1-(3-chloro-4-(2-hydroxy-2-methylpropoxy)phenyl)-1-hydroxy-3-(pyrrolidin-1-yl)propan-2-yl)-1-(naphthalen-2-yl)pyrrolidine-3-carboxamide | A |
| 99 | (R)-1-(6-chloropyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 99D | (S)-1-(6-chloroquinolin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | F |
| 108 | (R)-N-((1R,2R)-3-(azetidin-1-yl)-1-(8-fluoro-2,3-dihydrobenzo[b][1,4]dioxin-6-yl)-1-hydroxypropan-2-yl)-1-(2-chlorobenzo[b]thiophen-6-yl)pyrrolidine-3-carboxamide | A |
| 109 | (R)-N-((1R,2R)-1-(3-chloro-4-cyclopropoxyphenyl)-1-hydroxy-3-(pyrrolidin-1-yl)propan-2-yl)-1-(2-chlorobenzo[b]thiophen-6-yl)pyrrolidine-3-carboxamide | B |
| 110 | (R)-1-(4-chloro-3-(pyridin-2-yloxy)phenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 111 | (R)-1-(2-chlorobenzo[b]thiophen-6-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | A |
| 112 | (R)-N-((1R,2R)-1-(3-chloro-4-cyclopropoxyphenyl)-1-hydroxy-3-(pyrrolidin-1-yl)propan-2-yl)-1-(6-(4-chlorophenoxy)pyridin-2-yl)pyrrolidine-3-carboxamide | A |
| 113 | (R)-1-(6-(4-chlorophenoxy)pyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | A |
| 114 | (R)-1-(6-(4-chlorophenoxy)pyridin-2-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | A |
| 115 | (R)-N-((1R,2R)-1-(3-chloro-4-cyclopropoxyphenyl)-1-hydroxy-3-(pyrrolidin-1-yl)propan-2-yl)-1-(6-(4-fluorophenoxy)pyridin-2-yl)pyrrolidine-3-carboxamide | A |
| 116 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(6-(4-fluorophenoxy)pyridin-2-yl)pyrrolidine-3-carboxamide | A |
| 117 | (R)-N-((1R,2R)-1-(3-chloro-4-(oxetan-3-yloxy)phenyl)-1-hydroxy-3-(pyrrolidin-1-yl)propan-2-yl)-1-(6-fluoronaphthalen-2-yl)pyrrolidine-3-carboxamide | A |
| 118 | (R)-N-((1R,2R)-1-(3-chloro-4-cyclopropoxyphenyl)-1-hydroxy-3-(pyrrolidin-1-yl)propan-2-yl)-1-(2-chloro-5-(pyridin-2-yloxy)phenyl)pyrrolidine-3-carboxamide | A |
| 119 | (R)-N-((1R,2R)-1-(2,3-dihydrobenzo[b][1,4]dioxin-6-yl)-1-hydroxy-3-(pyrrolidin-1-yl)propan-2-yl)-1-(6-(4-fluorophenoxy)pyridin-2-yl)pyrrolidine-3-carboxamide | A |
| 121 | (R)-1-benzoyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide | NA |
| 120 | (R)-1-benzoyl-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | F |
| 122 | (R)-N-((1R,2R)-3-(azetidin-1-yl)-1-(3-chloro-4-(oxetan-3-yloxy)phenyl)-1-hydroxypropan-2-yl)-1-(6-fluoronaphthalen-2-yl)pyrrolidine-3-carboxamide | A |
| 123 | (R)-N-((1R,2R)-1-(2,3-dihydrobenzo[b][1,4]dioxin-6-yl)-1-hydroxy-3-(pyrrolidin-1-yl)propan-2-yl)-1-(6-(4-fluorophenyl)pyridin-2-yl)pyrrolidine-3-carboxamide | A |
| 124 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(6-(4-fluorophenyl)pyridin-2-yl)pyrrolidine-3-carboxamide | A |
| 125 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(1-methyl-1H-indazol-5-yl)pyrrolidine-3-carboxamide | E |
| 127 | (R)-N-((1R,2R)-1-(3-chloro-4-cyclopropoxyphenyl)-1-hydroxy-3-(pyrrolidin-1-yl)propan-2-yl)-1-(1-methyl-1H-indazol-5-yl)pyrrolidine-3-carboxamide | E |
| 128 | (R)-1-(4-chloro-3-(4-chlorophenoxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide | A |
| 129 | (R)-1-benzoyl-N-((1R,2R)-1-(3-chloro-4-cyclopropoxyphenyl)-1-hydroxy-3-(pyrrolidin-1-yl)propan-2-yl)pyrrolidine-3-carboxamide | F |
| 126 | (R)-N-((1R,2R)-1-(3-chloro-4-cyclopropoxyphenyl)-1-hydroxy-3-(pyrrolidin-1-yl)propan-2-yl)-1-(6-(4-fluorophenyl)pyridin-2-yl)pyrrolidine-3-carboxamide | A |
| 130 | (R)-1-(4-chlorophenyl)-N-((1R,2R)-1-(5-fluoro-2,3-dihydrobenzo[b][1,4]dioxin-6-yl)-1-hydroxy-3-(pyrrolidin-1-yl)propan-2-yl)pyrrolidine-3-carboxamide | E |
| 131 | (R)-1-(4-chloro-3-((6-methylpyridin-2-yl)oxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide | A |
| 132 | (R)-N-((1R,2R)-1-(8-fluoro-2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide | A |

TABLE 2-continued

| Example No. | Name | Data Range |
|---|---|---|
| 133 | (R)-N-((1R,2R)-1-(3-chloro-4-cyclopropoxyphenyl)-1-hydroxy-3-(pyrrolidin-1-yl)propan-2-yl)-1-(1-methyl-1H-indazol-6-yl)pyrrolidine-3-carboxamide | A |
| 134 | (R)-N-((1R,2R)-3-(azetidin-1-yl)-1-(8-fluoro-2,3-dihydrobenzo[b][1,4]dioxin-6-yl)-1-hydroxypropan-2-yl)-1-(1-methyl-1H-indazol-6-yl)pyrrolidine-3-carboxamide | A |
| 135 | (R)-N-((1R,2R)-1-(4-(tert-butoxy)-3-chlorophenyl)-1-hydroxy-3-(pyrrolidin-1-yl)propan-2-yl)-1-(4-chlorophenyl)pyrrolidine-3-carboxamide | A |
| 136 | (R)-1-(4-chloro-3-(cyclohexyloxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide | A |
| 137 | (R)-1-(4-chlorophenyl)-N-((1R,2R)-1-hydroxy-3-(pyrrolidin-1-yl)-1-(8-(trifluoromethyl)-2,3-dihydrobenzo[b][1,4]dioxin-6-yl)propan-2-yl)pyrrolidine-3-carboxamide | B |
| 138 | (R)-1-(6-chloro-4'-fluoro-[1,1'-biphenyl]-3-yl)-N-((1R,2R)-1-(3-chloro-4-cyclopropoxyphenyl)-1-hydroxy-3-(pyrrolidin-1-yl)propan-2-yl)pyrrolidine-3-carboxamide | B |
| 139 | (R)-1-(4-(tert-butyl)phenyl)-N-((1R,2R)-1-(3-chloro-4-cyclopropoxyphenyl)-1-hydroxy-3-(pyrrolidin-1-yl)propan-2-yl)pyrrolidine-3-carboxamide | B |
| 140 | (R)-N-((1R,2R)-1-(3-chloro-4-cyclobutoxyphenyl)-1-hydroxy-3-(pyrrolidin-1-yl)propan-2-yl)-1-(4-chlorophenyl)pyrrolidine-3-carboxamide | A |
| 141 | (R)-N-((1R,2R)-1-(3-chloro-4-(cyclopentyloxy)phenyl)-1-hydroxy-3-(pyrrolidin-1-yl)propan-2-yl)-1-(4-chlorophenyl)pyrrolidine-3-carboxamide | B |
| 142 | (R)-1-(4-(tert-butyl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | B |
| 143 | (R)-N-((1R,2R)-1-(benzo[b][1,4]dioxin-6-yl)-1-hydroxy-3-(pyrrolidin-1-yl)propan-2-yl)-1-(4-chlorophenyl)pyrrolidine-3-carboxamide | A |
| 144 | (R)-1-(5-chloro-6-(4-fluorophenyl)pyridin-2-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide | A |
| 145 | (R)-N-((1R,2R)-1-(3-chloro-4-(cyclopropylthio)phenyl)-1-hydroxy-3-(pyrrolidin-1-yl)propan-2-yl)-1-(4-chlorophenyl)pyrrolidine-3-carboxamide | A |
| 146 | (R)-N-((1R,2R)-1-(3-chloro-4-cyclopropoxyphenyl)-1-hydroxy-3-(pyrrolidin-1-yl)propan-2-yl)-1-(5-chloro-6-(4-fluorophenyl)pyridin-2-yl)pyrrolidine-3-carboxamide | A |
| 147 | (R)-N-((1R,2R)-1-(3-chloro-4-(vinyloxy)phenyl)-1-hydroxy-3-(pyrrolidin-1-yl)propan-2-yl)-1-(4-chlorophenyl)pyrrolidine-3-carboxamide | A |
| 148 | (R)-N-((1R,2R)-1-(4-cyclopropoxyphenyl)-1-hydroxy-3-(pyrrolidin-1-yl)propan-2-yl)-1-(4-fluorophenyl)pyrrolidine-3-carboxamide | A |
| 149 | (R)-N-((1R,2R)-1-(4-cyclopropoxyphenyl)-1-hydroxy-3-(pyrrolidin-1-yl)propan-2-yl)-1-phenylpyrrolidine-3-carboxamide | A |
| 150 | (R)-N-((1R,2R)-1-(3-chloro-4-cyclopropoxyphenyl)-1-hydroxy-3-(pyrrolidin-1-yl)propan-2-yl)-1-phenylpyrrolidine-3-carboxamide | A |
| 151 | (R)-N-((1R,2R)-1-(4-cyclopropoxy-3-fluorophenyl)-1-hydroxy-3-(pyrrolidin-1-yl)propan-2-yl)-1-phenylpyrrolidine-3-carboxamide | A |
| 152 | (R)-N-((1R,2R)-1-(3-chloro-4-cyclopropoxyphenyl)-1-hydroxy-3-(pyrrolidin-1-yl)propan-2-yl)-1-(4-cyanophenyl)pyrrolidine-3-carboxamide | C |
| 152C | (R)-N-((1S,2R)-1-(3-chloro-4-cyclopropoxyphenyl)-1-hydroxy-3-(pyrrolidin-1-yl)propan-2-yl)-1-(4-cyanophenyl)pyrrolidine-3-carboxamide | B |
| 153 | (R)-N-((1R,2R)-1-(3-chloro-4-cyclopropoxyphenyl)-1-hydroxy-3-(pyrrolidin-1-yl)propan-2-yl)-1-(p-tolyl)pyrrolidine-3-carboxamide | A |
| 154 | (S)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)-3-hydroxypyrrolidine-3-carboxamide | A |
| 154C | (R)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)-3-hydroxypyrrolidine-3-carboxamide | C |
| 155 | (R)-1-(4-chlorophenyl)-N-((1R,2R)-1-(4-cyclopropoxyphenyl)-1-hydroxy-3-(pyrrolidin-1-yl)propan-2-yl)pyrrolidine-3-carboxamide | A |
| 156 | (R)-1-(4-chlorophenyl)-N-((1R,2R)-1-(4-chlorophenyl)-1-hydroxy-3-(pyrrolidin-1-yl)propan-2-yl)pyrrolidine-3-carboxamide | C |
| 157 | (R)-1-(benzo[b]thiophen-6-yl)-N-((1R,2R)-1-(4-cyclopropoxyphenyl)-1-hydroxy-3-(pyrrolidin-1-yl)propan-2-yl)pyrrolidine-3-carboxamide | A |
| 158 | (R)-N-((1R,2R)-3-(azetidin-1-yl)-1-(4-cyclopropoxyphenyl)-1-hydroxypropan-2-yl)-1-(benzo[b]thiophen-6-yl)pyrrolidine-3-carboxamide | B |
| 159 | (R)-N-((1R,2R)-3-(azetidin-1-yl)-1-(4-cyclopropoxyphenyl)-1-hydroxypropan-2-yl)-1-(6-fluoronaphthalen-2-yl)pyrrolidine-3-carboxamide | B |
| 159C | (S)-N-((1R,2R)-3-(azetidin-1-yl)-1-(4-cyclopropoxyphenyl)-1-hydroxypropan-2-yl)-1-(6-fluoronaphthalen-2-yl)pyrrolidine-3-carboxamide | C |
| 160 | (R)-1-(4-chlorophenyl)-N-((1R,2R)-1-(4-(difluoromethoxy)phenyl)-1-hydroxy-3-(pyrrolidin-1-yl)propan-2-yl)pyrrolidine-3-carboxamide | B |
| 161 | (R)-N-((1R,2R)-1-(4-(difluoromethoxy)phenyl)-1-hydroxy-3-(pyrrolidin-1-yl)propan-2-yl)-1-phenylpyrrolidine-3-carboxamide | A |
| 162 | (R)-N-((1R,2R)-1-(4-cyclopropoxyphenyl)-1-hydroxy-3-(pyrrolidin-1-yl)propan-2-yl)-1-(6-fluoronaphthalen-2-yl)pyrrolidine-3-carboxamide | A |

In Table 2, biological data is provided as follows:
For $IC_{50}$ values:
A: 1-30 nM;
B: >30-100 nM;
C: >100-1000 nM;
For % Inhibition values at 0.1 μM:
D: 75-100%;
E: 50-74% (or less than 75%);
F: 1-49% (or less than 50%); and
NA: not active—a negative value was generated for % inhibition.

Sandhoff Disease Mouse Model

The murine model of Sandhoff disease is a knock out (KO) of the HEXB gene, which codes for beta-hexosaminidase in mice, as it does in humans. This KO mouse displays a phenotype closely resembling that seen in humans, although at a more advanced age, compared to humans. At ~3 months of age, the animals develop tremor and increased limb tone, which is worse in the hind legs. These manifestations become progressively more severe until 4-5 months of age, when the animals become moribund and rapidly lose weight. The motor phenotype has been quantified by activity monitor, bar-crossing, and inverted screen tests (Jayakumar M et al *Blood* 2001, 97, 327-329; Cachon-Gonzalez et al *PNAS* 2006, 103(27), 1037-10378). Histologically, the mouse neurons appear to be distended by lysosomal storage material, and signs of neuroinflammation are present. Biochemically, levels of beta-hexosaminidase are absent, and accumulations of gangliosides GM2, GA2, as well as sialic acid, can be demonstrated (Cachon-Gonzalez et al 2006; Arthur et al *Neurochem Res* 2013, DOI 10.1007/s11064-013-0992-5).

To evaluate the potential efficacy of different compounds described herein in Sandhoff disease, homozygous male mice are mated with heterozygous females. All pups (approximately 50% KO and 50% het) in a litter are treated by daily IP or SC injection with the same test (or control) article for 14 days, beginning at 3 days old. The chosen route of administration is determined based on pharmacokinetic/pharmacodynamic properties of the compound to be tested. At the end of the dosing period, pups are deeply anesthetized using isoflurane through nose cones (4% for induction and 1.5% for maintenance), blood is collected by cardiac puncture method, then the mice are euthanized. Brains and livers are collected and snap frozen. These tissues are used for analysis of experimental endpoints (GM2 and sialic acid in brain, GA2 and sialic acid in liver). An additional tissue sample (tail tip or toe) is collected and snap frozen, then sent for genotyping.

If tested compounds are found which have a marked effect on the experimental endpoints, an additional experiment is performed looking at effects on activity, inverted screen, and bar crossing tests, as well as average survival time, compared to vehicle-treated mice.

Polycystic Kidney Disease Mouse Model

To jck mice is administered a compound of the invention ad libitum in food (standard chow) from 26-64 days of age. Control jck mice are fed a control diet from 26-64 days of age. At 63 days of age, the animals are transferred to metabolic cages for 24 hour urine collection. At 64 days of age, animals are sacrificed, weighed, and blood is collected by heart puncture for serum isolation. Kidneys are isolated, bisected, and weighed and half of each kidney is fixed in 4% paraformaldehyde in PBS overnight for paraffin embedding and hematoxylin and eosin staining Kidney weight to body weight ratio is used to determine activity of the compound. Cyst volume is measured by quantitating the percentage of cystic area in histological sections of kidneys from the treated and control animals and multiplied by the kidney/body weight ratio. Kidney function is assessed by measuring blood urea nitrogen (BUN) levels in serum samples derived from animals at sacrifice. BUN levels are elevated in untreated controls while the treated animals demonstrated a significant reduction of BUN levels.

Other objects, features and advantages of the compounds, methods and compositions described herein will become apparent from the following description. It should be understood, however, that the description and the specific examples, while indicating specific embodiments, are given by way of illustration only, since various changes and modifications within the spirit and scope of the present description will become apparent from this detailed description.

All publications including patents, patent applications and published patent applications cited herein are hereby incorporated by reference for all purposes.

I claim:
1. A compound of Formula I:

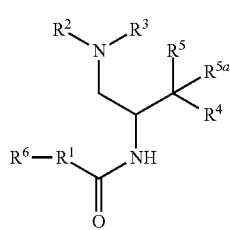

Formula I where
R$^1$ is N—(R$^6$)-azetidinyl, N—(R$^6$)-pyrrolidinyl, or N—(R$^6$)-piperidinyl, each of which is attached to the C(O) group by a carbon atom and is optionally substituted with hydroxy;
R$^2$ and R$^3$ together with the nitrogen to which they are attached form a 4-6 membered heterocycloalkyl ring with 1 or 2 nitrogen atoms, which is optionally substituted with 1 or 2 R$^8$;
R$^4$ is aryl or heteroaryl each of which is optionally substituted with 1, 2, or 3 R$^9$ groups;
R$^5$ is halo, hydroxy, —N$_3$, —NH$_2$, —NHC(O)CH$_3$, —NH(OCH$_3$), or —NHC(O)H and R$^{5a}$ is hydrogen, halo, alkyl, or deuterium; or R$^5$ and R$^{5a}$ together with the carbon to which they are attached form C(O) or C(NOH);
R$^6$ is alkyl, alkoxycarbonyl, aryl, arylalkyl, arylcarbonyl, cycloalkyl, cycloalkylalkyl, heterocycloalkyl, heterocycloalkylalkyl, heteroaryl, heteroarylalkyl, or —C(O)NR$^{6a}$R$^{6b}$; wherein each aryl and heteroaryl, whether alone or as part of another group, is optionally substituted with 1 or 2 R$^{10}$ groups; and wherein each heterocycloalkyl and cycloalkyl, whether alone or as part of another group, is optionally substituted with 1 or 2 groups independently selected from hydroxy, halo, haloalkyl, alkoxy, alkyl, alkylcarbonyl, and alkoxycarbonyl;
R$^{6a}$ is hydrogen or alkyl, and R$^{6b}$ is aryl or heteroaryl each of which is optionally substituted with 1 or 2 halo; or R$^{6a}$ and R$^{6b}$ together with the nitrogen to which they are attached form a heterocycloalkyl optionally substituted with alkyl, hydroxy, alkylcarbonyl, or alkoxycarbonyl;
each R$^8$, when present, is independently deuterium, amino, alkylamino, dialkylamino, alkyl, hydroxy, alkoxy, halo, haloalkyl, or cycloalkyl;
each R$^9$, when present, is independently cyano, nitro, amino, alkylamino, dialkylamino, halo, haloalkyl, alkyl, —NR$^{11}$C(O)NR$^{11a}$R$^{11b}$, hydroxy, alkoxy, haloalkoxy, hydroxyalkoxy, alkenyloxy, cycloalkyloxy, cycloalkylalkyloxy, cycloalkylthio, heterocycloalkyl, heterocycloalkyloxy, heterocycloalkylalkyloxy, or phenyl; where the phenyl is optionally substituted with 1 or 2 R$^{9a}$; where each heterocycloalkyl, either alone or as part of another group, is optionally substituted with 1 or 2 groups independently selected from alkyl, hydroxy, alkylcarbonyl, and alkoxycarbonyl;
each R$^{9a}$, when present, is independently selected from alkyl, hydroxy, alkoxy, halo, haloalkyl, haloalkoxy, alkoxycarbonyl, amino, alkylamino, and dialkylamino;
each R$^{10}$, when present, is independently cyano, nitro, amino, alkylamino, dialkylamino, halo, haloalkyl, alkyl, alkenyl, alkynyl, —NR$^{11}$C(O)NR$^{11a}$R$^{11b}$, alkoxycarbonyl, aminocarbonyl, alkylaminocarbonyl, dialkylaminocarbonyl, cycloalkyl, hydroxy, alkoxy, haloalkoxy, hydroxyalkoxy, alkenyloxy, cycloalkyloxy, cycloalkylalkyloxy, cycloalkylthio, aryl, arylalkyl, aryloxy, heteroaryl, heteroarylalkyl, heteroaryloxy, heterocycloalkyl, heterocycloalkyloxy, or heterocycloalkylalkyloxy; where each aryl or heteroaryl either alone or as part of another group, is independently optionally substituted with 1, 2 or 3 R$^{10a}$; and each heterocycloalkyl, either alone or as part of another group, is optionally substituted with 1 or 2 groups independently selected from alkyl, hydroxy, alkylcarbonyl, and alkoxycarbonyl groups;

each $R^{10a}$, when present, is independently selected from cyano, halo, alkyl, alkenyl, haloalkyl, hydroxyalkyl, and cycloalkyl; and $R^{11}$, $R^{11a}$, and $R^{11b}$ are independently hydrogen, alkyl, or cycloalkyl; and optionally a tautomer, a single stereoisomer or mixture of stereoisomers thereof and additionally optionally a pharmaceutically acceptable salt thereof.

2. The compound of claim 1, which is according to Formula I(a):

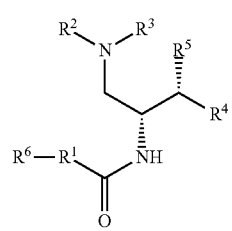

Formula I(a)

optionally as a tautomer, a single stereoisomer or mixture of stereoisomers thereof and additionally optionally as a pharmaceutically acceptable salt thereof.

3. The compound of claim 1, which is according to Formula I(d1):

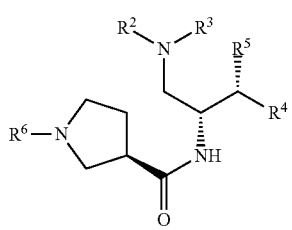

Formula I(d1)

optionally as a tautomer, a single stereoisomer or mixture of stereoisomers thereof and additionally optionally as a pharmaceutically acceptable salt thereof.

4. The compound of claim 1, wherein $R^5$ is hydroxy and $R^{5a}$ is hydrogen; optionally as a tautomer, a single stereoisomer or mixture of stereoisomers thereof and additionally optionally as a pharmaceutically acceptable salt thereof.

5. The compound of claim 1, wherein $R^6$ is aryl, optionally independently substituted with 1 or 2 $R^{10}$ groups; optionally as a tautomer, a single stereoisomer or mixture of stereoisomers thereof and additionally optionally as a pharmaceutically acceptable salt thereof.

6. The compound of claim 1, wherein $R^6$ is heterocycloalkyl or heteroaryl, each optionally substituted with 1 or 2 $R^{10}$ groups; optionally as a tautomer, a single stereoisomer or mixture of stereoisomers thereof and additionally optionally as a pharmaceutically acceptable salt thereof.

7. The compound of claim 1, wherein:
$R^4$ is aryl or heteroaryl each of which is optionally substituted with 1 or 2 $R^9$ groups;
$R^5$ is hydroxy, and $R^{5a}$ is hydrogen;
$R^6$ is alkyl, aryl, arylalkyl, arylcarbonyl, cycloalkyl, cycloalkylalkyl, heterocycloalkyl, heterocycloalkylalkyl, heteroaryl, or heteroarylalkyl; wherein each aryl and heteroaryl, whether alone or as part of another group, is optionally substituted with 1 or 2 $R^{10}$ groups; and wherein each heterocycloalkyl and cycloalkyl, whether alone or as part of another group, is optionally substituted with 1 or 2 groups independently selected from hydroxy, halo, haloalkyl, alkoxy, and alkyl;

each $R^8$, when present, is independently alkyl, hydroxy, alkoxy, halo, or haloalkyl;

each $R^9$, when present, is independently cyano, nitro, halo, haloalkyl, alkyl, hydroxy, alkoxy, haloalkoxy, hydroxyalkoxy, alkenyloxy, cycloalkyloxy, cycloalkylalkyloxy, cycloalkylthio, heterocycloalkyl, heterocycloalkyloxy, or heterocycloalkylalkyloxy; where each heterocycloalkyl, whether alone or as part of another group, is optionally substituted with 1 or 2 groups independently selected from alkyl, hydroxy, alkylcarbonyl, and alkoxycarbonyl;

each $R^{10}$, when present, is independently is cyano, halo, haloalkyl, alkyl, hydroxy, alkoxy, haloalkoxy, cycloalkyloxy, cycloalkylalkyloxy, aryl, aryloxy, heteroaryloxy, heterocycloalkyl, heterocycloalkyloxy, or heterocycloalkylalkyloxy; where each aryl or heteroaryl either alone or as part of another group, is independently optionally substituted with 1 or 2 halo or alkyl groups; and each heterocycloalkyl, either alone or as part of another group, is optionally substituted with 1 or 2 groups independently selected from alkyl and hydroxy; and optionally a tautomer, a single stereoisomer or mixture of stereoisomers thereof and additionally optionally a pharmaceutically acceptable salt thereof.

8. The compound of claim 1, which is according to Formula I(c):

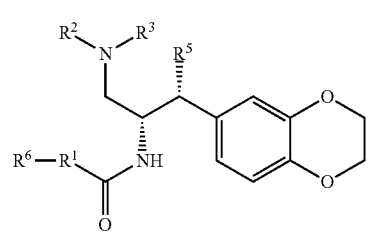

Formula I(c)

optionally as a tautomer, a single stereoisomer or mixture of stereoisomers thereof and additionally optionally as a pharmaceutically acceptable salt thereof.

9. The compound of claim 1, which is according to Formula I(d2):

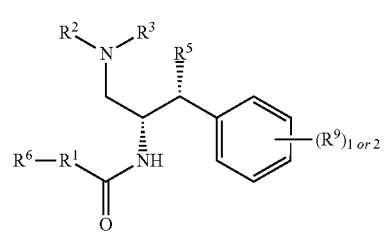

Formula I(d2)

optionally as a tautomer, a single stereoisomer or mixture of stereoisomers thereof and additionally optionally as a pharmaceutically acceptable salt thereof.

10. The compound of claim 1, wherein:
$R^1$ is N—($R^6$)-pyrrolidinyl attached to the C(O) by a carbon atom;

R² and R³ together with the nitrogen to which they are attached form azetidinyl or pyrrolidinyl;
R⁵ is hydroxy and R⁵ᵃ is hydrogen; and optionally as a tautomer, a single stereoisomer or mixture of stereoisomers thereof and additionally optionally as a pharmaceutically acceptable salt thereof.

11. The compound of claim 1, wherein R⁶ is aryl or heteroaryl, wherein the aryl is optionally independently substituted with 1 or 2 halo, alkyl, cycloalkyloxy, or heterocycloalkyloxy; and the heteroaryl is optionally independently substituted with 1 or 2 halo, alkyl, or cycloalkyloxy; and optionally as a tautomer, a single stereoisomer or mixture of stereoisomers thereof and additionally optionally as a pharmaceutically acceptable salt thereof.

12. The compound of claim 1, wherein R⁶ is heterocycloalkyl optionally independently substituted with 1 or 2 halo, hydroxy, or alkyl; and optionally as a tautomer, a single stereoisomer or mixture of stereoisomers thereof and additionally optionally as a pharmaceutically acceptable salt thereof.

13. The compound of claim 1, wherein the compound is selected from the group consisting of
(R)-1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(S)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-((4-hydroxytetrahydro-2H-pyran-4-yl)methyl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-((4-hydroxytetrahydro-2H-pyran-4-yl)methyl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-((4-hydroxytetrahydro-2H-pyran-4-yl)methyl)pyrrolidine-3-carboxamide;
(R)-1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(tetrahydro-2H-pyran-4-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(tetrahydro-2H-pyran-4-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(tetrahydro-2H-pyran-4-yl)pyrrolidine-3-carboxamide;
1-cyclopentyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(2,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(2,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;
(R)-1-(4-chlorobenzyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(4-chlorobenzyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(4-chlorobenzyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(thiazol-2-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(thiazol-2-yl)pyrrolidine-3-carboxamide;
1-(4-chloro-3-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(4-chlorophenethyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(4-chlorophenethyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(4-chlorophenethyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide;

(S)—N-((1R,2R)-1-(2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;
(R)—N-((1R,2R)-3-(azetidin-1-yl)-1-(8-fluoro-2,3-dihydrobenzo[b][1,4]dioxin-6-yl)-1-hydroxypropan-2-yl)-1-(4-chlorophenyl)pyrrolidine-3-carboxamide;
(S)—N-((1R,2R)-3-(azetidin-1-yl)-1-(8-fluoro-2,3-dihydrobenzo[b][1,4]dioxin-6-yl)-1-hydroxypropan-2-yl)-1-(4-chlorophenyl)pyrrolidine-3-carboxamide;
1-cyclohexyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(5-chloropyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(5-chloropyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(5-chloropyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-butyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;
(S)—N-((1R,2R)-1-(8-fluoro-2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(4,5,6,7-tetrahydrobenzo[d]thiazol-2-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(4,5,6,7-tetrahydrobenzo[d]thiazol-2-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(4,5,6,7-tetrahydrobenzo[d]thiazol-2-yl)pyrrolidine-3-carboxamide;
(R)-1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide;
1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide;
(S)-1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide;
(R)-1-(4-chlorophenyl)-N-((1R,2R)-1-(8-fluoro-2,3-dihydrobenzo[b][1,4]dioxin-6-yl)-1-hydroxy-3-(piperidin-1-yl)propan-2-yl)pyrrolidine-3-carboxamide;
(S)-1-(4-chlorophenyl)-N-((1R,2R)-1-(8-fluoro-2,3-dihydrobenzo[b][1,4]dioxin-6-yl)-1-hydroxy-3-(piperidin-1-yl)propan-2-yl)pyrrolidine-3-carboxamide;
(R)—N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide;
N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide;
(S)—N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide;
(R)—N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide;
N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide;
(S)—N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide;
(S)—N-((1R,2R)-1-(8-fluoro-2,3-dihydrobenzo[b][1,4]dioxin-6-yl)-1-hydroxy-3-(pyrrolidin-1-yl)propan-2-yl)-1-(pyridin-2-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;
(S)—N-((1R,2R)-1-(8-fluoro-2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;
(R)-1-(benzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(benzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(benzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(2-cyclopropoxypyridin-4-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(2-cyclopropoxypyridin-4-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(2-cyclopropoxypyridin-4-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(6-cyclopropoxypyridin-3-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(6-cyclopropoxypyridin-3-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

(R)—N-((1R,2R)-1-(2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(2-methyl-1,2,3,4-tetrahydroisoquinolin-7-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(2-methyl-1,2,3,4-tetrahydroisoquinolin-7-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(2-methyl-1,2,3,4-tetrahydroisoquinolin-7-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-6-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide;
(S)—N-((1R,2R)-1-(8-fluoro-2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-7-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-7-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(2,2-dimethylchroman-7-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(quinolin-2-yl)pyrrolidine-3-carboxamide;
(R)-1-(2-chlorobenzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(2-chlorobenzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(2-chlorobenzo[b]thiophen-6-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
N-[2-(2H,3H-benzo[e]1,4-dioxan-6-yl)(1R,2R)-2-hydroxy-1-(pyrrolidinylmethyl)ethyl][1-(4-chlorophenyl)pyrrolidin-3-yl]carboxamide;
(R)—N-((1R,2R)-3-(azetidin-1-yl)-1-(2,3-dihydrobenzo[b][1,4]dioxin-6-yl)-1-hydroxypropan-2-yl)-1-(4-chlorophenyl)pyrrolidine-3-carboxamide;
(R)—N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide;
N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide;
(S)—N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(2,6-dimethylpyridin-4-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(2,6-dimethylpyridin-4-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(quinoxalin-6-yl)pyrrolidine-3-carboxamide;
N-((1R,2R)-1-(2,3-dihydrobenzo[b][1,4]dioxin-6-yl)-1-hydroxy-3-(pyrrolidin-1-yl)propan-2-yl)-1-(quinoxalin-6-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(quinoxalin-6-yl)pyrrolidine-3-carboxamide;
(R)—N-((1R,2R)-3-(azetidin-1-yl)-1-(8-fluoro-2,3-dihydrobenzo[b][1,4]dioxin-6-yl)-1-hydroxypropan-2-yl)-1-(naphthalen-2-yl)pyrrolidine-3-carboxamide;
(R)-1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide;
N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide;
(S)—N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide;

(R)—N-((1R,2R)-1-(2,3-dihydrobenzo[b][1,4]dioxin-6-yl)-1-hydroxy-3-(pyrrolidin-1-yl)propan-2-yl)-1-(1,5-naphthyridin-3-yl)pyrrolidine-3-carboxamide;
(S)—N-((1R,2R)-1-(2,3-dihydrobenzo[b][1,4]dioxin-6-yl)-1-hydroxy-3-(pyrrolidin-1-yl)propan-2-yl)-1-(1,5-naphthyridin-3-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide;
(S)—N-((1R,2R)-1-(8-fluoro-2,3-dihydrobenzo[b][1,4]dioxin-6-yl)-1-hydroxy-3-(pyrrolidin-1-yl)propan-2-yl)-1-(5,6,7,8-tetrahydronaphthalen-2-yl)pyrrolidine-3-carboxamide;
(R)-1-(benzo[b]thiophen-6-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(S)-1-(benzo[b]thiophen-6-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(R)-1-(6-chloroquinolin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(6-chloroquinolin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(6-chloroquinolin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(6-chloroquinolin-2-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(R)-1-(4-chloro-3-(pyridin-2-yloxy)phenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(quinolin-7-yl)pyrrolidine-3-carboxamide;
(R)—N-((1R,2R)-3-(azetidin-1-yl)-1-(8-fluoro-2,3-dihydrobenzo[b][1,4]dioxin-6-yl)-1-hydroxypropan-2-yl)-1-(2-chlorobenzo[b]thiophen-6-yl)pyrrolidine-3-carboxamide;
(R)-1-(4-chloro-3-(pyridin-2-yloxy)phenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(2-chlorobenzo[b]thiophen-6-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(R)-1-(6-(4-chlorophenoxy)pyridin-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)-1-(6-(4-chlorophenoxy)pyridin-2-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(6-(4-fluorophenoxy)pyridin-2-yl)pyrrolidine-3-carboxamide;
(R)—N-((1 R,2R)-1-(2,3-dihydrobenzo[b][1,4]dioxin-6-yl)-1-hydroxy-3-(pyrrolidin-1-yl)propan-2-yl)-1-(6-(4-fluorophenoxy)pyridin-2-yl)pyrrolidine-3-carboxamide;
(R)-1-benzoyl-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(R)-1-benzoyl-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(2,3-dihydrobenzo[b][1,4]dioxin-6-yl)-1-hydroxy-3-(pyrrolidin-1-yl)propan-2-yl)-1-(6-(4-fluorophenyl)pyridin-2-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(6-(4-fluorophenyl)pyridin-2-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(1-methyl-1H-indazol-5-yl)pyrrolidine-3-carboxamide;
(R)-1-(4-chlorophenyl)-N-((1R,2R)-1-(5-fluoro-2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(1-methyl-1H-indazol-6-yl)pyrrolidine-3-carboxamide;
(R)—N-((1R,2R)-3-(azetidin-1-yl)-1-(8-fluoro-2,3-dihydrobenzo[b][1,4]dioxin-6-yl)-1-hydroxypropan-2-yl)-1-(1-methyl-1H-indazol-6-yl)pyrrolidine-3-carboxamide;
(R)-1-(4-chlorophenyl)-N-((1R,2R)-1-hydroxy-3-(pyrrolidin-1-yl)-1-(8-(trifluoromethyl)-2,3-dihydrobenzo[b][1,4]dioxin-6-yl)propan-2-yl)pyrrolidine-3-carboxamide;
(R)-1-(4-(tert-butyl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(R)-1-(5-chloro-6-(4-fluorophenyl)pyridin-2-yl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(S)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)-3-hydroxypyrrolidine-3-carboxamide; and
(R)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)-3-hydroxypyrrolidine-3-carboxamide;
and optionally as a tautomer, a single stereoisomer or mixture of stereoisomers thereof and additionally optionally as a pharmaceutically acceptable salt thereof.

14. The compound of claim 1, wherein the compound is selected from the group consisting of:
(S)—N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide;
N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide;
(R)—N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide;
N-((1R,2R)-1-(3-chloro-4-cyclopropoxyphenyl)-1-hydroxy-3-(pyrrolidin-1-yl)propan-2-yl)-1-(4-(trifluoromethyl)phenyl)pyrrolidine-3-carboxamide;
N-((1R,2R)-1-(3-chloro-4-cyclopropoxyphenyl)-1-hydroxy-3-(pyrrolidin-1-yl)propan-2-yl)-1-(4-(trifluoromethoxy)phenyl)pyrrolidine-3-carboxamide;

(R)—N-((1R,2R)-1-(3-chloro-4-isopropoxyphenyl)-1-hydroxy-3-(pyrrolidin-1-yl)propan-2-yl)-1-(4-chlorophenyl)pyrrolidine-3-carboxamide;

(S)—N-((1R,2R)-1-(3-chloro-4-isopropoxyphenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-((tetrahydro-2H-pyran-4-yl)oxy)phenyl)-1-hydroxy-3-(pyrrolidin-1-yl)propan-2-yl)-1-(4-fluorophenyl)pyrrolidine-3-carboxamide;

(S)—N-((1R,2R)-1-(3-chloro-4-((tetrahydro-2H-pyran-4-yl)oxy)phenyl)-1-hydroxy-3-(pyrrolidin-1-yl)propan-2-yl)-1-(4-fluorophenyl)pyrrolidine-3-carboxamide;

(R)—N-((1R,2R)-1-(3-chloro-4-((tetrahydro-2H-pyran-4-yl)oxy)phenyl)-1-hydroxy-3-(pyrrolidin-1-yl)propan-2-yl)-1-(4-chlorophenyl)pyrrolidine-3-carboxamide;

(S)—N-((1R,2R)-1-(3-chloro-4-((tetrahydro-2H-pyran-4-yl)oxy)phenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-((1-methylpiperidin-4-yl)oxy)phenyl)-1-hydroxy-3-(pyrrolidin-1-yl)propan-2-yl)-1-(4-chlorophenyl)pyrrolidine-3-carboxamide;

(S)—N-((1R,2R)-1-(3-chloro-4-((1-methylpiperidin-4-yl)oxy)phenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-((tetrahydro-2H-pyran-4-yl)oxy)phenyl)-1-hydroxy-3-(pyrrolidin-1-yl)propan-2-yl)-1-(6-fluoronaphthalen-2-yl)pyrrolidine-3-carboxamide;

(S)—N-((1R,2R)-1-(3-chloro-4-((tetrahydro-2H-pyran-4-yl)oxy)phenyl)-1-hydroxy-3-(pyrrolidin-1-yl)propan-2-yl)-1-(6-fluoronaphthalen-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(pyridin-2-yl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(pyridin-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(5-chloropyridin-2-yl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(5-chloropyridin-2-yl)pyrrolidine-3-carboxamide;

(R)—N-((1R,2R)-1-(3-chloro-4-(oxetan-3-yloxy)phenyl)-1-hydroxy-3-(pyrrolidin-1-yl)propan-2-yl)-1-(4-chlorophenyl)pyrrolidine-3-carboxamide;

(R)—N-((1R,2R)-1-(4-(2-(azetidin-1-yl)ethoxy)-3-chlorophenyl)-1-hydroxy-3-(pyrrolidin-1-yl)propan-2-yl)-1-(4-chlorophenyl)pyrrolidine-3-carboxamide;

(S)—N-((1R,2R)-1-(4-(2-(azetidin-1-yl)ethoxy)-3-chlorophenyl)-1-hydroxy-3-(pyrrolidin-1-yl)propan-2-yl)-1-(4-chlorophenyl)pyrrolidine-3-carboxamide;

(R)-1-(4-chlorophenyl)-N-((1R,2R)-1-(4-cyclopropoxy-3-fluorophenyl)-1-hydroxy-3-(pyrrolidin-1-yl)propan-2-yl)pyrrolidine-3-carboxamide;

(R)—N-((1R,2R)-1-(3-chloro-4-cyclopropoxyphenyl)-1-hydroxy-3-(piperidin-1-yl)propan-2-yl)-1-(4-chlorophenyl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(naphthalen-2-yl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(naphthalen-2-yl)pyrrolidine-3-carboxamide;

(R)—N-((1R,2R)-1-(4-cyclopropoxy-3-fluorophenyl)-1-hydroxy-3-(pyrrolidin-1-yl)propan-2-yl)-1-(4-fluorophenyl)pyrrolidine-3-carboxamide;

(S)—N-((1R,2R)-1-(4-cyclopropoxy-3-fluorophenyl)-1-hydroxy-3-(pyrrolidin-1-yl)propan-2-yl)-1-(4-fluorophenyl)pyrrolidine-3-carboxamide;

(R)—N-((1R,2R)-3-(azetidin-1-yl)-1-(3-chloro-4-cyclopropoxyphenyl)-1-hydroxypropan-2-yl)-1-(4-chlorophenyl)pyrrolidine-3-carboxamide;

(R)—N-((1R,2R)-1-(3-chloro-4-morpholinophenyl)-1-hydroxy-3-(pyrrolidin-1-yl)propan-2-yl)-1-(4-chlorophenyl)pyrrolidine-3-carboxamide;

(S)—N-((1R,2R)-1-(3-chloro-4-morpholinophenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(3-(pyridin-2-yloxy)phenyl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(3-(pyridin-2-yloxy)phenyl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(6-fluoronaphthalen-2-yl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(6-fluoronaphthalen-2-yl)pyrrolidine-3-carboxamide;

(R)—N-((1R,2R)-3-(azetidin-1-yl)-1-(3-chloro-4-cyclopropoxyphenyl)-1-hydroxypropan-2-yl)-1-(naphthalen-2-yl)pyrrolidine-3-carboxamide;

(R)—N-((1R,2R)-1-(3-chloro-4-(2-hydroxy-2-methylpropoxy)phenyl)-1-hydroxy-3-(pyrrolidin-1-yl)propan-2-yl)-1-(4-chlorophenyl)pyrrolidine-3-carboxamide;

(R)-1-(benzo[b]thiophen-6-yl)-N-((1R,2R)-1-(3-chloro-4-cyclopropoxyphenyl)-1-hydroxy-3-(pyrrolidin-1-yl)propan-2-yl)pyrrolidine-3-carboxamide;

(R)-1-(benzo[b]thiophen-6-yl)-N-((1R,2R)-1-(3-chloro-4-((tetrahydro-2H-pyran-4-yl)oxy)phenyl)-1-hydroxy-3-(pyrrolidin-1-yl)propan-2-yl)pyrrolidine-3-carboxamide;

(R)—N-((1R,2R)-1-(3-chloro-4-((tetrahydro-2H-pyran-4-yl)oxy)phenyl)-1-hydroxy-3-(pyrrolidin-1-yl)propan-2-yl)-1-(naphthalen-2-yl)pyrrolidine-3-carboxamide;

(R)—N-((1R,2R)-3-(azetidin-1-yl)-1-(3-chloro-4-cyclopropoxyphenyl)-1-hydroxypropan-2-yl)-1-(6-fluoronaphthalen-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(4-fluorophenyl)pyrrolidine-3-carboxamide;

(R)—N-((1 R,2R)-1-(3-chloro-4-cyclopropoxyphenyl)-1-hydroxy-3-(pyrrolidin-1-yl)propan-2-yl)-1-(5,6,7,8-tetrahydronaphthalen-2-yl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(5,6,7,8-tetrahydronaphthalen-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(6-chloroquinolin-2-yl)pyrrolidine-3-carboxamide;

(R)—N-((1R,2R)-1-(3-chloro-4-((tetrahydro-2H-pyran-4-yl)oxy)phenyl)-1-hydroxy-3-(pyrrolidin-1-yl)propan-2-yl)-1-(2-chlorobenzo[b]thiophen-6-yl)pyrrolidine-3-carboxamide;

(R)—N-((1R,2R)-1-(3-chloro-4-(2-hydroxy-2-methylpropoxy)phenyl)-1-hydroxy-3-(pyrrolidin-1-yl)propan-2-yl)-1-(6-fluoronaphthalen-2-yl)pyrrolidine-3-carboxamide;

(R)-1-(4-chloro-3-(pyridin-2-yloxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;

(R)—N-((1R,2R)-1-(3-chloro-4-(2-hydroxy-2-methylpropoxy)phenyl)-1-hydroxy-3-(pyrrolidin-1-yl)propan-2-yl)-1-(naphthalen-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(2-chlorobenzo[b]thiophen-6-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(6-(4-chlorophenoxy)pyridin-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(6-(4-fluorophenoxy)pyridin-2-yl)pyrrolidine-3-carboxamide;

(R)—N-((1R,2R)-1-(3-chloro-4-(oxetan-3-yloxy)phenyl)-1-hydroxy-3-(pyrrolidin-1-yl)propan-2-yl)-1-(6-fluoronaphthalen-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(2-chloro-5-(pyridin-2-yloxy)phenyl)pyrrolidine-3-carboxamide;

(R)—N-((1R,2R)-3-(azetidin-1-yl)-1-(3-chloro-4-(oxetan-3-yloxy)phenyl)-1-hydroxypropan-2-yl)-1-(6-fluoronaphthalen-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(6-(4-fluorophenyl)pyridin-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(1-methyl-1H-indazol-5-yl)pyrrolidine-3-carboxamide;

(R)-1-(4-chloro-3-(4-fluorophenoxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;

(R)-1-benzoyl-N-((1R,2R)-1-(3-chloro-4-cyclopropoxyphenyl)-1-hydroxy-3-(pyrrolidin-1-yl)propan-2-yl)pyrrolidine-3-carboxamide;

(R)-1-(4-chloro-3-((6-methylpyridin-2-yl)oxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(1-methyl-1H-indazol-6-yl)pyrrolidine-3-carboxamide;

(R)—N-((1R,2R)-1-(4-(tert-butoxy)-3-chlorophenyl)-1-hydroxy-3-(pyrrolidin-1-yl)propan-2-yl)-1-(4-chlorophenyl)pyrrolidine-3-carboxamide;

(R)-1-(4-chloro-3-(cyclohexyloxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;

(R)-1-(6-chloro-4'-fluoro-[1,1'-biphenyl]-3-yl)-N-((1R,2R)-1-(3-chloro-4-cyclopropoxyphenyl)-1-hydroxy-3-(pyrrolidin-1-yl)propan-2-yl)pyrrolidine-3-carboxamide;

(R)-1-(4-(tert-butyl)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;

(R)—N-((1R,2R)-1-(3-chloro-4-cyclobutoxyphenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-(cyclopentyloxy)phenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-(cyclopropylthio)phenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(5-chloro-6-(4-fluorophenyl)pyridin-2-yl)pyrrolidine-3-carboxamide;

(R)—N-((1R,2R)-1-(3-chloro-4-(vinyloxy)phenyl)-1-hydroxy-3-(pyrrolidin-1-yl)propan-2-yl)-1-(4-chlorophenyl)pyrrolidine-3-carboxamide;

(R)—N-((1R,2R)-1-(4-cyclopropoxyphenyl)-1-hydroxy-3-(pyrrolidin-1-yl)propan-2-yl)-1-(4-fluorophenyl)pyrrolidine-3-carboxamide;

(R)—N-((1R,2R)-1-(4-cyclopropoxyphenyl)-1-hydroxy-3-(pyrrolidin-1-yl)propan-2-yl)-1-phenylpyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-phenylpyrrolidine-3-carboxamide;

(R)—N-((1R,2R)-1-(4-cyclopropoxy-3-fluorophenyl)-1-hydroxy-3-(pyrrolidin-1-yl)propan-2-yl)-1-phenylpyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(4-cyanophenyl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(4-cyanophenyl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(p-tolyl)pyrrolidine-3-carboxamide;

(R)-1-(4-chlorophenyl)-N-((1R,2R)-1-(4-cyclopropoxyphenyl)-1-hydroxy-3-(pyrrolidin-1-yl)propan-2-yl)pyrrolidine-3-carboxamide;

(R)-1-(4-chlorophenyl)-N-((1R,2R)-1-(4-chlorophenyl)-1-hydroxy-3-(pyrrolidin-1-yl)propan-2-yl)pyrrolidine-3-carboxamide;

(R)-1-(benzo[b]thiophen-6-yl)-N-((1R,2R)-1-(4-cyclopropoxyphenyl)-1-hydroxy-3-(pyrrolidin-1-yl)propan-2-yl)pyrrolidine-3-carboxamide;

(R)—N-((1R,2R)-3-(azetidin-1-yl)-1-(4-cyclopropoxyphenyl)-1-hydroxypropan-2-yl)-1-(benzo[b]thiophen-6-yl)pyrrolidine-3-carboxamide;

(R)—N-((1R,2R)-3-(azetidin-1-yl)-1-(4-cyclopropoxyphenyl)-1-hydroxypropan-2-yl)-1-(6-fluoronaphthalen-2-yl)pyrrolidine-3-carboxamide;

(S)—N-((1R,2R)-3-(azetidin-1-yl)-1-(4-cyclopropoxyphenyl)-1-hydroxypropan-2-yl)-1-(6-fluoronaphthalen-2-yl)pyrrolidine-3-carboxamide;

(R)-1-(4-chlorophenyl)-N-((1R,2R)-1-(4-(difluoromethoxy)phenyl)-1-hydroxy-3-(pyrrolidin-1-yl)propan-2-yl)pyrrolidine-3-carboxamide;

(R)—N-((1R,2R)-1-(4-(difluoromethoxy)phenyl)-1-hydroxy-3-(pyrrolidin-1-yl)propan-2-yl)-1-phenylpyrrolidine-3-carboxamide; and (R)—N-((1R,2R)-1-(4-cyclopropoxyphenyl)-1-hydroxy-3-(pyrrolidin-1-yl)propan-2-yl)-1-(6-fluoronaphthalen-2-yl)pyrrolidine-3-carboxamide;

and optionally as a tautomer, a single stereoisomer or mixture of stereoisomers thereof and additionally optionally as a pharmaceutically acceptable salt thereof.

15. The compound of claim 1, wherein the compound is selected from the group consisting of:

(R)-1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

(S)-1-(4-chlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

(R)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;

1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;

(S)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide;

N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(4-chlorophenyl)pyrrolidine-3-carboxamide;

N-((1R,2R)-1-(3-chloro-4-cyclopropoxyphenyl)-1-hydroxy-3-(pyrrolidin-1-yl)propan-2-yl)-1-(4-(trifluoromethyl)phenyl)pyrrolidine-3-carboxamide;

(R)-1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

(S)-1-(3,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

N-((1R,2R)-1-(3-chloro-4-cyclopropoxyphenyl)-1-hydroxy-3-(pyrrolidin-1-yl)propan-2-yl)-1-(4-(trifluoromethoxy)phenyl)pyrrolidine-3-carboxamide;

(R)-1-(2,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

(S)-1-(2,4-dichlorophenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

(R)-1-(4-chlorophenyl)-N-((1R,2R)-1-(6-cyclopropoxypyridin-3-yl)-1-hydroxy-3-(pyrrolidin-1-yl)propan-2-yl)pyrrolidine-3-carboxamide;

(S)-1-(4-chlorophenyl)-N-((1R,2R)-1-(6-cyclopropoxypyridin-3-yl)-1-hydroxy-3-(pyrrolidin-1-yl)propan-2-yl)pyrrolidine-3-carboxamide;

(S)—N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;

N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;

(R)—N-((1R,2R)-1-(2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;

1-(4-chloro-3-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

(R)-1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

(S)-1-(3-chloro-4-cyclopropoxyphenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;

(R)—N-((1R,2R)-1-(3-chloro-4-isopropoxyphenyl)-1-hydroxy-3-(pyrrolidin-1-yl)propan-2-yl)-1-(4-chlorophenyl)pyrrolidine-3-carboxamide;

(S)—N-((1R,2R)-1-(3-chloro-4-isopropoxyphenyl)-1-hydroxy-3-(pyrrolidin-1-yl)propan-2-yl)-1-(4-chlorophenyl)pyrrolidine-3-carboxamide;

(R)—N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;

N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;

(S)—N-((1R,2R)-1-(2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;

(R)—N-((1R,2R)-3-(azetidin-1-yl)-1-(8-fluoro-2,3-dihydrobenzo[b][1,4]dioxin-6-yl)-1-hydroxypropan-2-yl)-1-(4-chlorophenyl)pyrrolidine-3-carboxamide;

(S)—N-((1R,2R)-3-(azetidin-1-yl)-1-(8-fluoro-2,3-dihydrobenzo[b][1,4]dioxin-6-yl)-1-hydroxypropan-2-yl)-1-(4-chlorophenyl)pyrrolidine-3-carboxamide;

(R)—N-((1R,2R)-1-(6-cyclopropoxypyridin-3-yl)-1-hydroxy-3-(pyrrolidin-1-yl)propan-2-yl)-1-(4-fluorophenyl)pyrrolidine-3-carboxamide;

(S)—N-((1R,2R)-1-(6-cyclopropoxypyridin-3-yl)-1-hydroxy-3-(pyrrolidin-1-yl)propan-2-yl)-1-(4-fluorophenyl)pyrrolidine-3-carboxamide;

(R)-1-(4-chlorophenyl)-N-((1R,2R)-1-hydroxy-1-(6-isopropoxypyridin-3-yl)-3-(pyrrolidin-1-yl)propan-2-yl)pyrrolidine-3-carboxamide;

(S)-1-(4-chlorophenyl)-N-((1R,2R)-1-hydroxy-1-(6-isopropoxypyridin-3-yl)-3-(pyrrolidin-1-yl)propan-2-yl)pyrrolidine-3-carboxamide;

(R)-1-(4-fluorophenyl)-N-((1R,2R)-1-hydroxy-1-(6-isopropoxypyridin-3-yl)-3-(pyrrolidin-1-yl)propan-2-yl)pyrrolidine-3-carboxamide;

(S)-1-(4-fluorophenyl)-N-((1R,2R)-1-hydroxy-1-(6-isopropoxypyridin-3-yl)-3-(pyrrolidin-1-yl)propan-2-yl)pyrrolidine-3-carboxamide;

(R)—N-((1R,2R)-1-(3-chloro-4-((tetrahydro-2H-pyran-4-yl)oxy)phenyl)-1-hydroxy-3-(pyrrolidin-1-yl)propan-2-yl)-1-(4-fluorophenyl)pyrrolidine-3-carboxamide;

(S)—N-((1R,2R)-1-(3-chloro-4-((tetrahydro-2H-pyran-4-yl)oxy)phenyl)-1-hydroxy-3-(pyrrolidin-1-yl)propan-2-yl)-1-(4-fluorophenyl)pyrrolidine-3-carboxamide;

(R)-1-(4-chlorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide;

(S)-1-(4-chlorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide;

(R)-1-(4-fluorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide;

(S)-1-(4-fluorophenyl)-N-((1R,2R)-1-hydroxy-3-(pyrrolidin-1-yl)-1-(6-(2,2,2-trifluoroethoxy)pyridin-3-yl)propan-2-yl)pyrrolidine-3-carboxamide;

(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;

(S)—N-((1R,2R)-1-(8-fluoro-2,3-dihydrobenzo[b][1,4]dioxin-6-yl)-1-hydroxy-3-(pyrrolidin-1-yl)propan-2-yl)-1-(4-fluorophenyl)pyrrolidine-3-carboxamide;

(R)-1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide;

1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide;

(S)-1-(4-chlorophenyl)-N-((1R,2R)-1-(2,3-dihydrobenzo[b][1,4]dioxin-6-yl)-1-hydroxy-3-(piperidin-1-yl)propan-2-yl)pyrrolidine-3-carboxamide;

(R)-1-(4-chlorophenyl)-N-((1R,2R)-1-(8-fluoro-2,3-dihydrobenzo[b][1,4]dioxin-6-yl)-1-hydroxy-3-(piperidin-1-yl)propan-2-yl)pyrrolidine-3-carboxamide;

(S)-1-(4-chlorophenyl)-N-((1R,2R)-1-(8-fluoro-2,3-dihydrobenzo[b][1,4]dioxin-6-yl)-1-hydroxy-3-(piperidin-1-yl)propan-2-yl)pyrrolidine-3-carboxamide;

(R)—N-((1R,2R)-1-(3-chloro-4-((tetrahydro-2H-pyran-4-yl)oxy)phenyl)-1-hydroxy-3-(pyrrolidin-1-yl)propan-2-yl)-1-(4-chlorophenyl)pyrrolidine-3-carboxamide;

(S)—N-((1R,2R)-1-(3-chloro-4-((tetrahydro-2H-pyran-4-yl)oxy)phenyl)-1-hydroxy-3-(pyrrolidin-1-yl)propan-2-yl)-1-(4-chlorophenyl)pyrrolidine-3-carboxamide;

(R)—N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide;

N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide;

(S)—N-((1R,2R)-1-(2,3-dihydrobenzo[b][1,4]dioxin-6-yl)-1-hydroxy-3-(piperidin-1-yl)propan-2-yl)-1-(4-fluorophenyl)pyrrolidine-3-carboxamide;

(R)—N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide;

N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide;

(S)—N-((1R,2R)-3-(azetidin-1-yl)-1-(8-fluoro-2,3-dihydrobenzo[b][1,4]dioxin-6-yl)-1-hydroxypropan-2-yl)-1-(6-fluoronaphthalen-2-yl)pyrrolidine-3-carboxamide;

(R)—N-((1R,2R)-1-(3-chloro-4-((1-methylpiperidin-4-yl)oxy)phenyl)-1-hydroxy-3-(pyrrolidin-1-yl)propan-2-yl)-1-(4-chlorophenyl)pyrrolidine-3-carboxamide;

(S)—N-((1R,2R)-1-(3-chloro-4-((1-methylpiperidin-4-yl)oxy)phenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-((tetrahydro-2H-pyran-4-yl)oxy)phenyl)-1-hydroxy-3-(pyrrolidin-1-yl)propan-2-yl)-1-(6-fluoronaphthalen-2-yl)pyrrolidine-3-carboxamide;

(S)—N-((1R,2R)-1-(3-chloro-4-((tetrahydro-2H-pyran-4-yl)oxy)phenyl)-1-hydroxy-3-(pyrrolidin-1-yl)propan-2-yl)-1-(6-fluoronaphthalen-2-yl)pyrrolidine-3-carboxamide;

(R)-1-(4-chlorophenyl)-N-((1R,2R)-1-(2,2-dimethylchroman-6-yl)-1-hydroxy-3-(pyrrolidin-1-yl)propan-2-yl)pyrrolidine-3-carboxamide;

(S)-1-(4-chlorophenyl)-N-((1R,2R)-1-(2,2-dimethylchroman-6-yl)-1-hydroxy-3-(pyrrolidin-1-yl)propan-2-yl)pyrrolidine-3-carboxamide;

(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;

(S)—N-((1R,2R)-1-(8-fluoro-2,3-dihydrobenzo[b][1,4]dioxin-6-yl)-1-hydroxy-3-(pyrrolidin-1-yl)propan-2-yl)-1-(6-fluoronaphthalen-2-yl)pyrrolidine-3-carboxamide;

(R)—N-((1R,2R)-1-(3-chloro-4-(oxetan-3-yloxy)phenyl)-1-hydroxy-3-(pyrrolidin-1-yl)propan-2-yl)-1-(4-chlorophenyl)pyrrolidine-3-carboxamide;

(R)—N-((1 R,2R)-1-(4-(2-(azetidin-1-yl)ethoxy)-3-chlorophenyl)-1-hydroxy-3-(pyrrolidin-1-yl)propan-2-yl)-1-(4-chlorophenyl)pyrrolidine-3-carboxamide;

(S)—N-((1R,2R)-1-(4-(2-(azetidin-1-yl)ethoxy)-3-chlorophenyl)-1-hydroxy-3-(pyrrolidin-1-yl)propan-2-yl)-1-(4-chlorophenyl)pyrrolidine-3-carboxamide;

(R)-1-(4-chlorophenyl)-N-((1R,2R)-1-hydroxy-1-(6-(oxetan-3-yloxy)pyridin-3-yl)-3-(pyrrolidin-1-yl)propan-2-yl)pyrrolidine-3-carboxamide;

(R)-1-(4-chlorophenyl)-N-((1R,2R)-1-(4-cyclopropoxy-3-fluorophenyl)-1-hydroxy-3-(pyrrolidin-1-yl)propan-2-yl)pyrrolidine-3-carboxamide;

(R)—N-((1R,2R)-1-(3-chloro-4-cyclopropoxyphenyl)-1-hydroxy-3-(piperidin-1-yl)propan-2-yl)-1-(4-chlorophenyl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(naphthalen-2-yl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(naphthalen-2-yl)pyrrolidine-3-carboxamide;

(R)—N-((1R,2R)-1-(4-cyclopropoxy-3-fluorophenyl)-1-hydroxy-3-(pyrrolidin-1-yl)propan-2-yl)-1-(4-fluorophenyl)pyrrolidine-3-carboxamide;

(S)—N-((1R,2R)-1-(4-cyclopropoxy-3-fluorophenyl)-1-hydroxy-3-(pyrrolidin-1-yl)propan-2-yl)-1-(4-fluorophenyl)pyrrolidine-3-carboxamide;

(R)—N-((1 R,2R)-1-(2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide;

(S)—N-((1R,2R)-1-(2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide;

(R)—N-((1R,2R)-3-(azetidin-1-yl)-1-(3-chloro-4-cyclopropoxyphenyl)-1-hydroxypropan-2-yl)-1-(4-chlorophenyl)pyrrolidine-3-carboxamide;

(R)—N-((1R,2R)-1-(3-chloro-4-morpholinophenyl)-1-hydroxy-3-(pyrrolidin-1-yl)propan-2-yl)-1-(4-chlorophenyl)pyrrolidine-3-carboxamide;

(S)—N-((1R,2R)-1-(3-chloro-4-morpholinophenyl)-1-hydroxy-3-(pyrrolidin-1-yl)propan-2-yl)-1-(4-chlorophenyl)pyrrolidine-3-carboxamide;

(R)—N-((1R,2R)-1-(3-chloro-4-cyclopropoxyphenyl)-1-hydroxy-3-(pyrrolidin-1-yl)propan-2-yl)-1-(3-(pyridin-2-yloxy)phenyl)pyrrolidine-3-carboxamide;

(S)—N-((1R,2R)-1-(3-chloro-4-cyclopropoxyphenyl)-1-hydroxy-3-(pyrrolidin-1-yl)propan-2-yl)-1-(3-(pyridin-2-yloxy)phenyl)pyrrolidine-3-carboxamide;

N-[2-(2H,3H-benzo[e]1,4-dioxan-6-yl)(1R,2R)-2-hydroxy-1-(pyrrolidinylmethyl)ethyl][1-(4-chlorophenyl)pyrrolidin-3-yl]carboxamide;
(R)—N-((1R,2R)-3-(azetidin-1-yl)-1-(2,3-dihydrobenzo[b][1,4]dioxin-6-yl)-1-hydroxypropan-2-yl)-1-(4-chlorophenyl)pyrrolidine-3-carboxamide;
(R)—N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide;
N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide;
(S)—N-((1R,2R)-3-(azetidin-1-yl)-1-(2,3-dihydrobenzo[b][1,4]dioxin-6-yl)-1-hydroxypropan-2-yl)-1-(6-fluoronaphthalen-2-yl)pyrrolidine-3-carboxamide;
(R)—N-((1R,2R)-1-(8-fluoro-2,3-dihydrobenzo[b][1,4]dioxin-6-yl)-1-hydroxy-3-(pyrrolidin-1-yl)propan-2-yl)-1-(naphthalen-2-yl)pyrrolidine-3-carboxamide;
(R)—N-((1R,2R)-1-(3-chloro-4-cyclopropoxyphenyl)-1-hydroxy-3-(pyrrolidin-1-yl)propan-2-yl)-1-(6-fluoronaphthalen-2-yl)pyrrolidine-3-carboxamide;
(S)—N-((1R,2R)-1-(3-chloro-4-cyclopropoxyphenyl)-1-hydroxy-3-(pyrrolidin-1-yl)propan-2-yl)-1-(6-fluoronaphthalen-2-yl)pyrrolidine-3-carboxamide;
(R)—N-((1R,2R)-3-(azetidin-1-yl)-1-(8-fluoro-2,3-dihydrobenzo[b][1,4]dioxin-6-yl)-1-hydroxypropan-2-yl)-1-(naphthalen-2-yl)pyrrolidine-3-carboxamide;
(R)—N-((1R,2R)-3-(azetidin-1-yl)-1-(3-chloro-4-cyclopropoxyphenyl)-1-hydroxypropan-2-yl)-1-(naphthalen-2-yl)pyrrolidine-3-carboxamide;
(R)—N-((1R,2R)-1-(3-chloro-4-(2-hydroxy-2-methylpropoxy)phenyl)-1-hydroxy-3-(pyrrolidin-1-yl)propan-2-yl)-1-(4-chlorophenyl)pyrrolidine-3-carboxamide;
(R)-1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(S)-1-(1-chloro-6-fluoronaphthalen-2-yl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide;
N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide;
(S)—N-((1R,2R)-3-(azetidin-1-yl)-1-(8-fluoro-2,3-dihydrobenzo[b][1,4]dioxin-6-yl)-1-hydroxypropan-2-yl)-1-(6-chloronaphthalen-2-yl)pyrrolidine-3-carboxamide;
(R)—N-((1R,2R)-1-(3-chloro-4-((tetrahydro-2H-pyran-4-yl)oxy)phenyl)-1-hydroxy-3-(pyrrolidin-1-yl)propan-2-yl)-1-(naphthalen-2-yl)pyrrolidine-3-carboxamide;
(R)—N-((1R,2R)-3-(azetidin-1-yl)-1-(3-chloro-4-cyclopropoxyphenyl)-1-hydroxypropan-2-yl)-1-(6-fluoronaphthalen-2-yl)pyrrolidine-3-carboxamide;
(R)—N-((1R,2R)-1-(3-chloro-4-cyclopropoxyphenyl)-1-hydroxy-3-(pyrrolidin-1-yl)propan-2-yl)-1-(4-fluorophenyl)pyrrolidine-3-carboxamide;
(R)—N-((1R,2R)-1-(3-chloro-4-(2-hydroxy-2-methylpropoxy)phenyl)-1-hydroxy-3-(pyrrolidin-1-yl)propan-2-yl)-1-(6-fluoronaphthalen-2-yl)pyrrolidine-3-carboxamide;
(R)-1-(4-chloro-3-(pyridin-2-yloxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;
(R)-1-(4-chloro-3-(pyridin-2-yloxy)phenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(3-chloro-4-(2-hydroxy-2-methylpropoxy)phenyl)-1-hydroxy-3-(pyrrolidin-1-yl)propan-2-yl)-1-(naphthalen-2-yl)pyrrolidine-3-carboxamide;
(R)-1-(4-chloro-3-(pyridin-2-yloxy)phenyl)-N-((1R,2R)-1-(2,3-dihydrobenzo[b][1,4]dioxin-6-yl)-1-hydroxy-3-(pyrrolidin-1-yl)propan-2-yl)pyrrolidine-3-carboxamide;
(R)—N-((1R,2R)-1-(3-chloro-4-(oxetan-3-yloxy)phenyl)-1-hydroxy-3-(pyrrolidin-1-yl)propan-2-yl)-1-(6-fluoronaphthalen-2-yl)pyrrolidine-3-carboxamide;
(R)—N-((1R,2R)-1-(3-chloro-4-cyclopropoxyphenyl)-1-hydroxy-3-(pyrrolidin-1-yl)propan-2-yl)-1-(2-chloro-5-(pyridin-2-yloxy)phenyl)pyrrolidine-3-carboxamide;
(R)—N-((1R,2R)-3-(azetidin-1-yl)-1-(3-chloro-4-(oxetan-3-yloxy)phenyl)-1-hydroxypropan-2-yl)-1-(6-fluoronaphthalen-2-yl)pyrrolidine-3-carboxamide;
(R)-1-(4-chloro-3-(4-fluorophenoxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;
(R)-1-(4-chlorophenyl)-N-((1R,2R)-1-(5-fluoro-2,3-dihydrobenzo[b][1,4]dioxin-6-yl)-1-hydroxy-3-(pyrrolidin-1-yl)propan-2-yl)pyrrolidine-3-carboxamide;
(R)-1-(4-chloro-3-((6-methylpyridin-2-yl)oxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;
(R)—N-((1R,2R)-1-(4-(tert-butoxy)-3-chlorophenyl)-1-hydroxy-3-(pyrrolidin-1-yl)propan-2-yl)-1-(4-chlorophenyl)pyrrolidine-3-carboxamide;
(R)-1-(4-chloro-3-(cyclohexyloxy)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;
(R)-1-(4-chlorophenyl)-N-((1R,2R)-1-hydroxy-3-(pyrrolidin-1-yl)-1-(8-(trifluoromethyl)-2,3-dihydrobenzo[b][1,4]dioxin-6-yl)propan-2-yl)pyrrolidine-3-carboxamide;
(R)-1-(6-chloro-4'-fluoro-[1,1'-biphenyl]-3-yl)-N-((1R,2R)-1-(3-chloro-4-cyclopropoxyphenyl)-1-hydroxy-3-(pyrrolidin-1-yl)propan-2-yl)pyrrolidine-3-carboxamide;
(R)-1-(4-(tert-butyl)phenyl)-N-((1R,2R)-1-(3-chloro-4-cyclopropoxyphenyl)-1-hydroxy-3-(pyrrolidin-1-yl)propan-2-yl)pyrrolidine-3-carboxamide;
(R)—N-((1R,2R)-1-(3-chloro-4-cyclobutoxyphenyl)-1-hydroxy-3-(pyrrolidin-1-yl)propan-2-yl)-1-(4-chlorophenyl)pyrrolidine-3-carboxamide;
(R)—N-((1R,2R)-1-(3-chloro-4-(cyclopentyloxy)phenyl)-1-hydroxy-3-(pyrrolidin-1-yl)propan-2-yl)-1-(4-chlorophenyl)pyrrolidine-3-carboxamide;
(R)-1-(4-(tert-butyl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)pyrrolidine-3-carboxamide;

(R)—N-((1R,2R)-1-(benzo[b][1,4]dioxin-6-yl)-1-hydroxy-3-(pyrrolidin-1-yl)propan-2-yl)-1-(4-chlorophenyl)pyrrolidine-3-carboxamide;
(R)—N-((1R,2R)-1-(3-chloro-4-(cyclopropylthio)phenyl)-1-hydroxy-3-(pyrrolidin-1-yl)propan-2-yl)-1-(4-chlorophenyl)pyrrolidine-3-carboxamide;
(R)—N-((1R,2R)-1-(3-chloro-4-(vinyloxy)phenyl)-1-hydroxy-3-(pyrrolidin-1-yl)propan-2-yl)-1-(4-chlorophenyl)pyrrolidine-3-carboxamide;
(R)—N-((1R,2R)-1-(4-cyclopropoxyphenyl)-1-hydroxy-3-(pyrrolidin-1-yl)propan-2-yl)-1-(4-fluorophenyl)pyrrolidine-3-carboxamide;
(R)—N-((1R,2R)-1-(4-cyclopropoxyphenyl)-1-hydroxy-3-(pyrrolidin-1-yl)propan-2-yl)-1-phenylpyrrolidine-3-carboxamide;
(R)—N-((1R,2R)-1-(3-chloro-4-cyclopropoxyphenyl)-1-hydroxy-3-(pyrrolidin-1-yl)propan-2-yl)-1-phenylpyrrolidine-3-carboxamide;
(R)—N-((1R,2R)-1-(4-cyclopropoxy-3-fluorophenyl)-1-hydroxy-3-(pyrrolidin-1-yl)propan-2-yl)-1-phenylpyrrolidine-3-carboxamide;
(R)—N-((1R,2R)-1-(3-chloro-4-cyclopropoxyphenyl)-1-hydroxy-3-(pyrrolidin-1-yl)propan-2-yl)-1-(4-cyanophenyl)pyrrolidine-3-carboxamide;
(S)—N-((1R,2R)-1-(3-chloro-4-cyclopropoxyphenyl)-1-hydroxy-3-(pyrrolidin-1-yl)propan-2-yl)-1-(4-cyanophenyl)pyrrolidine-3-carboxamide;
(R)—N-((1 R,2R)-1-(3-chloro-4-cyclopropoxyphenyl)-1-hydroxy-3-(pyrrolidin-1-yl)propan-2-yl)-1-(p-tolyl)pyrrolidine-3-carboxamide;
(S)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)-3-hydroxypyrrolidine-3-carboxamide;
(R)-1-(4-chlorophenyl)-N-((1R,2R)-1-(8-fluoro-2,3-dihydrobenzo[b][1,4]dioxin-6-yl)-1-hydroxy-3-(pyrrolidin-1-yl)propan-2-yl)-3-hydroxypyrrolidine-3-carboxamide;
(R)-1-(4-chlorophenyl)-N-((1R,2R)-1-(4-cyclopropoxyphenyl)-1-hydroxy-3-(pyrrolidin-1-yl)propan-2-yl)pyrrolidine-3-carboxamide;
(R)-1-(4-chlorophenyl)-N-((1R,2R)-1-(4-chlorophenyl)-1-hydroxy-3-(pyrrolidin-1-yl)propan-2-yl)pyrrolidine-3-carboxamide;
(R)—N-((1R,2R)-3-(azetidin-1-yl)-1-(4-cyclopropoxyphenyl)-1-hydroxypropan-2-yl)-1-(6-fluoronaphthalen-2-yl)pyrrolidine-3-carboxamide;
(S)—N-((1R,2R)-3-(azetidin-1-yl)-1-(4-cyclopropoxyphenyl)-1-hydroxypropan-2-yl)-1-(6-fluoronaphthalen-2-yl)pyrrolidine-3-carboxamide;
(R)-1-(4-chlorophenyl)-N-((1R,2R)-1-(4-(difluoromethoxy)phenyl)-1-hydroxy-3-(pyrrolidin-1-yl)propan-2-yl)pyrrolidine-3-carboxamide;
(R)—N-((1 R,2R)-1-(4-(difluoromethoxy)phenyl)-1-hydroxy-3-(pyrrolidin-1-yl)propan-2-yl)-1-phenylpyrrolidine-3-carboxamide; and
(R)—N-((1R,2R)-1-(4-cyclopropoxyphenyl)-1-hydroxy-3-(pyrrolidin-1-yl)propan-2-yl)-1-(6-fluoronaphthalen-2-yl)pyrrolidine-3-carboxamide;
and optionally as a tautomer, a single stereoisomer or mixture of stereoisomers thereof and additionally optionally as a pharmaceutically acceptable salt thereof.

16. A pharmaceutical composition comprising the compound of claim 1, optionally as a tautomer, a single stereoisomer or mixture of stereoisomers thereof and additionally optionally as a pharmaceutically acceptable salt thereof, and a pharmaceutically acceptable excipient or carrier.

17. A method of making a compound according to claim 1 where $R^5$ is hydroxy and $R^{5a}$ is hydrogen comprising:
a) treating an intermediate of formula 100

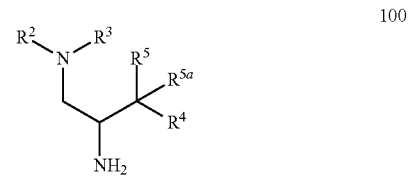

or a salt thereof, where:
$R^2$ and $R^3$ together with the nitrogen to which they are attached form a 4-6 membered heterocycloalkyl ring with 1 or 2 nitrogen atoms, which is optionally substituted with 1 or 2 $R^8$;
$R^4$ is aryl or heteroaryl each of which is optionally substituted with 1, 2, or 3 $R^9$ groups;
$R^5$ is hydroxy and $R^{5a}$ is hydrogen;
each $R^8$, when present, is independently deuterium, amino, alkylamino, dialkylamino, alkyl, hydroxy, alkoxy, halo, haloalkyl, or cycloalkyl;
each $R^9$, when present, is independently cyano, nitro, amino, alkylamino, dialkylamino, halo, haloalkyl, alkyl, —$NR^{11}C(O)NR^{11a}R^{11b}$, hydroxy, alkoxy, haloalkoxy, hydroxyalkoxy, alkenyloxy, cycloalkyloxy, cycloalkylalkyloxy, cycloalkylthio, heterocycloalkyl, heterocycloalkyloxy, heterocycloalkylalkyloxy, or phenyl; where the phenyl is optionally substituted with 1 or 2 $R^{9a}$; where each heterocycloalkyl, either alone or as part of another group, is optionally substituted with 1 or 2 groups independently selected from alkyl, hydroxy, alkylcarbonyl, and alkoxycarbonyl;
each $R^{9a}$, when present, is independently selected from alkyl, hydroxy, alkoxy, halo, haloalkyl, haloalkoxy, alkoxycarbonyl, amino, alkylamino, and dialkylamino; and
$R^{11}$, $R^{11a}$, and $R^{11b}$ are independently hydrogen, alkyl, or cycloalkyl;
with an intermediate of formula $R^6$—$R^1C(O)OH$, using standard amine coupling conditions to yield a compound of Formula I, where:
$R^1$ is N—($R^6$)-azetidinyl, N—($R^6$)-pyrrolidinyl or N—($R^6$)-piperidinyl, each of which is attached to the C(O) group by a carbon atom and is optionally substituted with hydroxy;
$R^6$ is alkyl, alkoxycarbonyl, aryl, arylalkyl, arylcarbonyl, cycloalkyl, cycloalkylalkyl, heterocycloalkyl, heterocycloalkylalkyl, heteroaryl, heteroarylalkyl, or —C(O)$NR^{6a}R^{6b}$;
optionally substituted with 1 or 2 $R^{10}$ groups; and wherein each heterocycloalkyl and cycloalkyl, whether alone or as part of another group, is optionally substituted with 1 or 2 groups independently selected from hydroxy, halo, haloalkyl, alkoxy, alkyl, alkylcarbonyl, and alkoxycarbonyl;
$R^{6a}$ is hydrogen or alkyl, and $R^{6b}$ is aryl or heteroaryl each of which is optionally substituted with 1 or 2 halo; or $R^{6a}$ and $R^{6b}$ together with the nitrogen to which they are attached form a heterocycloalkyl optionally substituted with alkyl, hydroxy, alkylcarbonyl, or alkoxycarbonyl;

each $R^{10}$, when present, is independently cyano, nitro, amino, alkylamino, dialkylamino, halo, haloalkyl, alkyl, alkenyl, alkynyl, —$NR^{11}C(O)NR^{11a}R^{11b}$, alkoxycarbonyl, aminocarbonyl, alkylaminocarbonyl, dialkylaminocarbonyl, cycloalkyl, hydroxy, alkoxy, haloalkoxy, hydroxyalkoxy, alkenyloxy, cycloalkyloxy, cycloalkylalkyloxy, cycloalkylthio, aryl, arylalkyl, aryloxy, heteroaryl, heteroarylalkyl, heteroaryloxy, heterocycloalkyl, heterocycloalkyloxy, or heterocycloalkylalkyloxy; where each aryl or heteroaryl either alone or as part of another group, is independently optionally substituted with 1, 2 or 3 $R^{10a}$; and each heterocycloalkyl, either alone or as part of another group, is optionally substituted with 1 or 2 groups independently selected from alkyl, hydroxy, alkylcarbonyl, and alkoxycarbonyl groups;

each $R^{10a}$, when present, is independently selected from cyano, halo, alkyl, alkenyl, haloalkyl, hydroxyalkyl, and cycloalkyl; and $R^{11}$, $R^{11a}$, and $R^{11b}$ are independently hydrogen, alkyl, or cycloalkyl; and b) optionally separating individual isomers.

\* \* \* \* \*